(12) United States Patent
Foote et al.

(10) Patent No.: US 8,129,391 B2
(45) Date of Patent: Mar. 6, 2012

(54) N-[5-[2-(3,5-DIMETHOXYPHENYL)ETHYL]-1H-PYRAZOL-3-YL]-4-(3,4-DIMETHYLPIPERAZIN-1-YL) BENZAMIDE AND SALTS THEREOF

(75) Inventors: Kevin Michael Foote, Cheshire (GB); Maria-Elena Theoclitou, Cheshire (GB); Andrew Peter Thomas, Cheshire (GB); David Buttar, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 124 days.

(21) Appl. No.: 12/771,661

(22) Filed: Apr. 30, 2010

(65) Prior Publication Data

US 2010/0273811 A1    Oct. 28, 2010

Related U.S. Application Data

(63) Continuation of application No. 11/958,720, filed on Dec. 18, 2007, now Pat. No. 7,737,149.

(60) Provisional application No. 60/985,542, filed on Nov. 5, 2007, provisional application No. 60/871,190, filed on Dec. 21, 2006.

(51) Int. Cl.
    A61K 31/496    (2006.01)
    A61K 31/501    (2006.01)
    C07D 231/38    (2006.01)
    C07D 403/12    (2006.01)

(52) U.S. Cl. .................. 514/254.05; 514/406; 544/371; 548/364.1

(58) Field of Classification Search ............. 514/254.05, 514/406; 544/371; 548/364.1
    See application file for complete search history.

(56) References Cited

U.S. PATENT DOCUMENTS

| | | | |
|---|---|---|---|
| 4,407,941 A | 10/1983 | Suginaka et al. |
| 5,498,630 A | 3/1996 | Phillion et al. |
| 5,514,529 A | 5/1996 | Mihayashi et al. |
| 5,693,667 A | 12/1997 | Phillion et al. |
| 5,705,513 A | 1/1998 | Phillion et al. |
| 5,811,411 A | 9/1998 | Phillion et al. |
| 5,834,447 A | 11/1998 | Phillion et al. |
| 5,849,723 A | 12/1998 | Phillion et al. |
| 5,998,466 A | 12/1999 | Phillion et al. |
| RE36,562 E | 2/2000 | Phillion et al. |
| 6,028,101 A | 2/2000 | Phillion et al. |
| 6,133,252 A | 10/2000 | Phillion et al. |
| 6,166,057 A | 12/2000 | Phillion et al. |
| 6,248,894 B1 | 6/2001 | Phillion et al. |
| 6,252,078 B1 | 6/2001 | Phillion et al. |
| 6,271,237 B1 | 8/2001 | Galemmo, Jr. et al. |
| 6,407,114 B1 | 6/2002 | Bunnage et al. |
| 6,410,558 B1 | 6/2002 | Phillion et al. |
| 6,521,603 B2 | 2/2003 | Phillion et al. |
| 6,548,525 B2 | 4/2003 | Galemmo, Jr. et al. |
| 6,552,008 B1 | 4/2003 | Duffy et al. |
| 7,015,218 B1 | 3/2006 | Ushio et al. |
| 7,034,049 B1 | 4/2006 | Pevarello et al. |
| 7,115,359 B2 | 10/2006 | Usagawa et al. |
| 2001/0046975 A1 | 11/2001 | Phillion et al. |
| 2002/0016326 A1 | 2/2002 | Galemmo, Jr. et al. |
| 2003/0225106 A1 | 12/2003 | Askew et al. |
| 2004/0043904 A1 | 3/2004 | Yamaguchi et al. |
| 2004/0087616 A1 | 5/2004 | Piotrowski et al. |
| 2004/0220170 A1 | 11/2004 | Atkinson et al. |
| 2004/0259877 A1 | 12/2004 | Muto et al. |
| 2005/0020564 A1 | 1/2005 | Atkinson et al. |
| 2005/0037298 A1 | 2/2005 | Usagawa et al. |
| 2005/0070589 A1 | 3/2005 | Ngu et al. |
| 2005/0176965 A1 | 8/2005 | Chen et al. |
| 2005/0209297 A1 | 9/2005 | Sanner et al. |
| 2005/0245518 A1 | 11/2005 | Delorme et al. |
| 2006/0004010 A1 | 1/2006 | Habashita et al. |
| 2006/0019958 A1 | 1/2006 | Muto et al. |
| 2006/0111409 A1 | 5/2006 | Muto et al. |
| 2006/0116395 A1 | 6/2006 | Piotrowski et al. |
| 2006/0122243 A1 | 6/2006 | Muto et al. |

FOREIGN PATENT DOCUMENTS

| | | |
|---|---|---|
| BE | 667399 | 11/1965 |
| EP | 1352650 A1 | 10/2003 |
| EP | 1510207 A1 | 3/2005 |
| EP | 1510210 A1 | 3/2005 |
| EP | 1514544 A1 | 3/2005 |
| EP | 1541563 A1 | 6/2005 |
| GB | 843940 | 8/1960 |
| JP | 3310226 B4 | 11/1933 |

(Continued)

OTHER PUBLICATIONS

Pevarello et al. Journal of Medicinal Chemistry, (2004), 47(13), p. 3367-3380.*
Bogolyubsky et al., "Synthesis of 3-amino-5-oxy-1-(2,4,6-trichlorophenyl)-4-fluoropyrazole and its Acyl Derivatives", UKR. KHIM. ZHURN. (Russian Edition) (1989), vol. 55, No. 4, 420-423.
Cavasotto et al., "In Silico Identifcation of Novel EGFR Inhibitors with Antiproliferative Activity Against Cancer Cells", Bioorganic & Medicinal Chemistry Letters (2006), vol. 16, 1969-1974.
Fu and Shuttleworth, "Synthesis and Purification of 3-N-acylarninopyrazolinones Using a Sequence of Functionalized Polymers", Tetrahedron Letters (2003), vol. 44, 3843-3845.

(Continued)

Primary Examiner — Yong Chu

(57) ABSTRACT

There is provided a compound of formula (I):

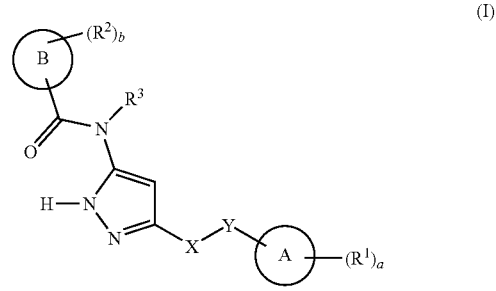

or a pharmaceutically acceptable salt thereof. There are also provided processes for the manufacture of a compound of Formula 1, and the use of a compound of Formula 1 as a medicament and in the treatment of cancer.

3 Claims, No Drawings

FOREIGN PATENT DOCUMENTS

| | | |
|---|---|---|
| JP | 63133152 A | 6/1988 |
| JP | 04184437 A | 7/1992 |
| JP | 07188269 A | 7/1995 |
| JP | 2890065 B2 | 2/1999 |
| JP | 0467645 A | 3/2004 |
| JP | 04292322 A | 10/2004 |
| WO | 9319054 A1 | 9/1993 |
| WO | 9415920 A1 | 7/1994 |
| WO | 9614843 A2 | 5/1996 |
| WO | 9828269 A1 | 7/1998 |
| WO | 9852941 A1 | 11/1998 |
| WO | 9852944 A1 | 11/1998 |
| WO | 0049001 A2 | 8/2000 |
| WO | 0112189 A1 | 2/2001 |
| WO | 0112621 A1 | 2/2001 |
| WO | 02066470 A1 | 8/2002 |
| WO | 02088090 A2 | 11/2002 |
| WO | 2004007458 A1 | 1/2004 |
| WO | 2004071440 A2 | 8/2004 |
| WO | 2004098518 A2 | 11/2004 |
| WO | 2004098528 A2 | 11/2004 |
| WO | 2004099156 A1 | 11/2004 |
| WO | 2005021537 A1 | 3/2005 |
| WO | 2005048948 A2 | 6/2005 |
| WO | 2005051919 A1 | 6/2005 |
| WO | 2005105780 A2 | 11/2005 |
| WO | 2006116713 A1 | 11/2006 |
| WO | 2007016228 A2 | 2/2007 |

OTHER PUBLICATIONS

Hammad et al., "Synthesis of Some New Pyrazolones and Benzimidazol-Acetonitriles Derived from Xanthene", Egyptian Journal of Chemistry (1986), vol. 29, No. 6, 617-622.

Kataeva et al., "Crystal and Molecular Structure of Acylalmino Derivatives of 1-(2,4,6-Trichlorophenyl)-4,5-dihydropyrazol-5-one", Russian Journal of General Chemistry (2003), vol. 73, No. 5, 776-781.

Pevarello et al., "3-Aminopyrazole Inhibitors of CDK2/Cyclin A as Antitumor Agents 1. Lead Finding",J. Med. Chem. (2004), vol. 47, 3367-3380.

Weissberger et al., "Investigation of Pyrazole Compounds. VII. The Reaction of Some Hydrazines with Ethyl Malonate Monoimidoester", Journal of the American Chemical Society (1944), vol. 66, 1851-1855.

* cited by examiner

N-[5-[2-(3,5-DIMETHOXYPHENYL)ETHYL]-1H-PYRAZOL-3-YL]-4-(3,4-DIMETHYLPIPERAZIN-1-YL)BENZAMIDE AND SALTS THEREOF

CROSS-REFERENCE TO RELATED APPLICATIONS

This application is a continuation of U.S. application Ser. No. 11/958,720 filed Dec. 18, 2007, which claims priority under 35 U.S.C. §119(e) to U.S. Provisional Application Ser. No. 60/871,190, filed Dec. 21, 2006 and U.S. Provisional Application Ser. No. 60/985,542, filed Nov. 5, 2007, each of which is incorporated herein by reference in its entirety.

The present invention relates to pyrazole derivatives, a process for their preparation, pharmaceutical compositions containing them, a process for preparing the pharmaceutical compositions, and their use in therapy.

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate (ATP) to tyrosine residues on protein substrates. These kinases play an important part in the propagation of growth factor signal transduction that leads to cellular proliferation, differentiation and migration.

Fibroblast growth factor (FGF) has been recognized as an important mediator of many physiological processes, such as morphogenesis during development and angiogenesis. There are currently over 25 known members of the FGF family. The fibroblast growth factor receptor (FGFR) family consists of four members with each composed of an extracellular ligand binding domain, a single transmembrane domain and an intracellular cytoplasmic protein tyrosine kinase domain. Upon stimulation with FGF, FGFRs undergo dimerisation and transphosphorylation, which results in receptor activation. Receptor activation is sufficient for the recruitment and activation of specific downstream signalling partners that participate in the regulation of diverse process such as cell growth, cell metabolism and cell survival (Reviewed in Eswarakumar, V.P. et. al., Cytokine & Growth Factor Reviews 2005, 16, p139-149). Consequently, FGF and FGFRs have the potential to initiate and/or promote tumorigenesis.

There is now considerable evidence directly linking FGF signalling to human cancer. The elevated expression of various FGFs has been reported in a diverse range of tumour types such as bladder, renal cell and prostate (amongst others). FGF has also been described as a powerful angiogenic factor. The expression of FGFRs in endothelial cells has also been reported. Activating mutations of various FGFRs have been associated with bladder cancer and multiple myeloma (amongst others) whilst receptor expression has also been documented in prostate and bladder cancer amongst others (Reviewed in Grose, R. et. al., Cytokine & Growth Factor Reviews 2005, 16, p179-186 and Kwabi-Addo, B. et. al., Endocrine-Related Cancer 2004, 11, p709-724). For these reasons, the FGF signalling system is an attractive therapeutic target, particularly since therapies targeting FGFRs and/or FGF signalling may affect both the tumour cells directly and tumour angiogenesis.

In accordance with the present invention, there is provided a compound of formula (I):

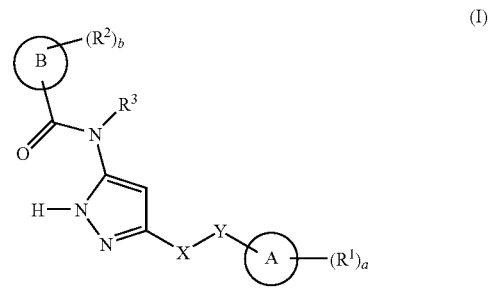

or a pharmaceutically acceptable salt thereof
wherein
  ring A represents a 5- or 6-membered aromatic group optionally comprising at least one ring heteroatom selected from nitrogen, oxygen and sulphur;
  ring B represents a 5- or 6-membered aromatic group optionally comprising at least one ring heteroatom selected from nitrogen, oxygen and sulphur;
  $R^1$ each independently represents
    a halogen,
    a hydroxyl group,
    a cyano group,
    a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
    a $C_{3-5}$cycloalkyl group optionally substituted by one or more substituents selected from $C_1$-$C_3$alkyl, $C_1$-$C_3$alkoxy, $C_3$-cycloalkyl, $C_1$-$C_3$alkylthio, —$NR^6R^7$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
    a $C_2$-$C_3$alkenyl group optionally substituted by one or more substituents selected from $C_1$-$C_3$alkoxy, $C_3$-cycloalkyl, $C_1$-$C_3$alkylthio, —$NR^8R^9$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
    a phenyl group optionally substituted by one or more substituents selected from $C_1$-$C_3$alkoxy, $C_3$-cycloalkyl, $C_1$-$C_3$alkylthio, —$NR^{10}R^{11}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
    a 4- to 6-membered heterocyclyl group optionally substituted by one or more substituents selected from $C_1$-$C_3$alkyl, $C_1$-$C_3$alkoxy, $C_3$-cycloalkyl, $C_1$-$C_3$alkylthio, —$NR^{12}R^{13}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, a —$NR^{16}R^{17}$ group, a —$OCOR^{18}$ group, a —$CO_2R^{19}$ group, a —$CONR^{20}R^{21}$ group, a —$NR^{22}COR^{23}$ group, a —$NR^{24}CO_2R^{25}$ group.

a —$OSO_2R^{26}$ group, or two adjacent $R^1$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{27}R^{28}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^2$ each independently represents a hydroxyl group, a halogen, a cyano group, a —$CO_2R^{29}$ group, a —$CONR^{30}R^{31}$ group, a —$NR^{32}COR^{33}$ group, a —$NR^{34}CO_2R^{35}$ group, a —$NR^{36}R^{37}$ group, a —$SO_2R^{38}$ group, a —$SO_2NR^{39}R^{40}$ group, a —$NR^{41}SO_2R^{42}$ group, a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl, trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl, a $C_3$-$C_6$cycloalkyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{48}R^{49}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{50}R^{51}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_2$-$C_6$alkenyl group optionally substituted by one or more substituents selected from $C_1$-$C_6$alkoxy, $C_3$-$C_6$cycloalkyl, $C_1$-$C_6$alkylthio, —$NR^{52}R^{53}$, (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{54}R^{55}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 7-membered heterocyclyl group optionally fused to a 4- to 7-membered carbocyclyl or heterocyclyl group and optionally substituted by one or more substituents selected from $C_1$-$C_6$alkyl, $C_2$-$C_6$alkenyl, $C_2$-$C_6$alkynyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, cyano, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, oxo, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
- or two adjacent $R^2$ groups together with the atoms to which they are attached form a 4- to 7-membered carbocyclyl or heterocyclyl ring is optionally substituted by one or more substituents selected from $C_1$-$C_3$alkyl, $C_1$-$C_3$alkoxy, $C_3$-cycloalkyl, $C_1$-$C_3$alkylthio, —$NR^{66}R^{67}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen,
- a $C_1$-$C_3$alkyl group optionally substituted by one or more substituents selected from $C_1$-$C_3$alkoxy, $C_3$-cycloalkyl, $C_1$-$C_3$alkylthio, —$NR^{68}R^{69}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

a is 0, 1, 2, 3 or 4;
b is 0, 1, 2, 3 or 4;
$R^4$ and $R^5$ each independently represent hydrogen, $C_1$-$C_4$alkyl or $C_3$-$C_6$cycloalkyl, or $R^4$ and $R^5$ together with the nitrogen atom to which they are attached form a 4- to 6-membered saturated heterocycle;
$R^6$ and $R^7$ each independently represent hydrogen, $C_1$-$C_4$alkyl or $C_3$-$C_6$cycloalkyl, or $R^6$ and $R^7$ together with the nitrogen atom to which they are attached form a 4- to 6-membered saturated heterocycle;
$R^8$ and $R^9$ each independently represent hydrogen, $C_1$-$C_4$alkyl or $C_3$-$C_6$cycloalkyl, or $R^8$ and $R^9$ together with the nitrogen atom to which they are attached form a 4- to 6-membered saturated heterocycle;
$R^{10}$ and $R^{11}$ each independently represent hydrogen, $C_1$-$C_4$alkyl or $C_3$-$C_6$cycloalkyl, or $R^{10}$ and $R^{11}$ together with the nitrogen atom to which they are attached form a 4- to 6-membered saturated heterocycle;
$R^{12}$ and $R^{13}$ each independently represent hydrogen, $C_1$-$C_4$alkyl or $C_3$-$C_6$cycloalkyl, or $R^{12}$ and $R^{13}$ together with the nitrogen atom to which they are attached form a 4- to 6-membered saturated heterocycle;
$R^{14}$ and $R^{15}$ each independently represent hydrogen, $C_1$-$C_4$alkyl or $C_3$-$C_6$cycloalkyl, or $R^{14}$ and $R^{15}$ together with the nitrogen atom to which they are attached form a 4- to 6-membered saturated heterocycle;
$R^{16}$ and $R^{17}$ each independently represent hydrogen, $C_1$-$C_4$alkyl or $C_3$-$C_6$cycloalkyl, or $R^{16}$ and $R^{17}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{18}$ represents $C_1$-$C_4$alkyl, or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{19}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{20}$ and $R^{21}$ each independently represent hydrogen, $C_1$-$C_4$alkyl or $C_3$-$C_6$cycloalkyl, or $R^{20}$ and $R^{21}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{22}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{23}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{24}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{25}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{26}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{27}$ and $R^{28}$ each independently represent hydrogen, $C_1$-$C_4$alkyl or $C_3$-$C_6$cycloalkyl, or $R^{27}$ and $R^{28}$ together with the nitrogen atom to which they are attached form a 4- to 6-membered saturated heterocycle;
$R^{29}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{30}$ and $R^{31}$ each independently represent hydrogen, $C_1$-$C_4$alkyl or $C_3$-$C_6$cycloalkyl, or $R^{30}$ and $R^{31}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{32}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);
$R^{33}$ represents hydrogen, $C_1$-$C_4$alkyl, $C_3$-$C_6$cycloalkyl or a 5- or 6-membered aromatic group optionally comprising at least one ring heteroatom selected from nitrogen, oxygen and sulphur (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{34}$ represents hydrogen, $C_1$-$C_4$alkyl or $C_3$-$C_6$cycloalkyl (each of which may be is optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{35}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{36}$ and $R^{37}$ each independently represent hydrogen, $C_1$-$C_4$alkyl, $C_2$-$C_4$alkynyl, $C_3$-$C_6$cycloalkyl or a 5- or 6-membered aromatic group optionally comprising at least one ring heteroatom selected from nitrogen, oxygen and sulphur, or $R^{36}$ and $R^{37}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl and 4- to 7-membered carbocyclyl or heterocycly group which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl);

$R^{38}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{39}$ and $R^{40}$ each independently represent hydrogen, $C_1$-$C_4$alkyl or $C_3$-$C_6$cycloalkyl, or $R^{39}$ and $R^{40}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{41}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{42}$ K represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{43}$ and $R^{44}$ each independently represent hydrogen, $C_1$-$C_4$alkyl or $C_3$-$C_6$cycloalkyl, or $R^{43}$ and $R^{44}$ together with the nitrogen atom to which they are attached form a 4- to 6-membered saturated heterocycle;

$R^{45}$ and $R^{46}$ each independently represent hydrogen, $C_1$-$C_4$alkyl or $C_3$-$C_6$cycloalkyl, or $R^{45}$ and $R^{46}$ together with the nitrogen atom to which they are attached form a 4- to 6-membered saturated heterocycle;

$R^{47}$ represents hydrogen, $C_1$-$C_4$alkyl or $C_3$-$C_6$cycloalkyl;

$R^{48}$ and $R^{49}$ each independently represent hydrogen, $C_1$-$C_4$alkyl or $C_3$-$C_6$cycloalkyl, or $R^{48}$ and $R^{49}$ together with the nitrogen atom to which they are attached form a 4- to 6-membered saturated heterocycle;

$R^{50}$ and $R^{51}$ each independently represent hydrogen, $C_1$-$C_4$alkyl or $C_3$-$C_6$cycloalkyl, or $R^{50}$ and $R^{51}$ together with the nitrogen atom to which they are attached form a 4- to 6-membered saturated heterocycle;

$R^{52}$ and $R^{53}$ each independently represent hydrogen, $C_1$-$C_4$alkyl or $C_3$-$C_6$cycloalkyl, or $R^{52}$ and $R^{53}$ together with the nitrogen atom to which they are attached form a 4- to 6-membered saturated heterocycle;

$R^{54}$ and $R^{55}$ each independently represent hydrogen, $C_1$-$C_4$alkyl or $C_3$-$C_6$cycloalkyl, or $R^{54}$ and $R^{55}$ together with the nitrogen atom to which they are attached form a 4- to 6-membered saturated heterocycle;

$R^{56}$ and $R^{57}$ each independently represent hydrogen, $C_1$-$C_4$alkyl or $C_3$-$C_6$cycloalkyl, or $R^{56}$ and $R^{57}$ together with the nitrogen atom to which they are attached form a 4- to 6-membered saturated heterocycle;

$R^{58}$ represents $C_1$-$C_4$alkyl or $C_3$-$C_6$cycloalkyl;

$R^{59}$ and $R^{60}$ each independently represent hydrogen, $C_1$-$C_4$alkyl or $C_3$-$C_6$cycloalkyl, or $R^{59}$ and $R^{60}$ together with the nitrogen atom to which they are attached form a 4- to 6-membered saturated heterocycle;

$R^{61}$ represents $C_1$-$C_4$alkyl or $C_3$-$C_6$cycloalkyl;

$R^{62}$ and $R^{63}$ each independently represent hydrogen, $C_1$-$C_4$alkyl or $C_3$-$C_6$cycloalkyl, or $R^{62}$ and $R^{63}$ together with the nitrogen atom to which they are attached form a 4- to 6-membered saturated heterocycle;

$R^{64}$ and $R^{65}$ each independently represent hydrogen, $C_1$-$C_6$alkyl or $C_3$-$C_6$cycloalkyl, or $R^{64}$ and $R^{65}$ together with the nitrogen atom to which they are attached form a 4- to 6-membered saturated heterocycle;

$R^{66}$ and $R^{67}$ each independently represent hydrogen, $C_1$-$C_6$alkyl or $C_3$-$C_6$cycloalkyl, or $R^{66}$ and $R^{67}$ together with the nitrogen atom to which they are attached form a 4- to 6-membered saturated heterocycle;

$R^{68}$ and $R^{69}$ each independently represent hydrogen, $C_1$-$C_6$alkyl or $C_3$-$C_6$cycloalkyl, or $R^{68}$ and $R^{69}$ together with the nitrogen atom to which they are attached form a 4- to 6-membered saturated heterocycle; and where when Y represents $CH_2$, X represents $CH_2$, O, $NR^{70}$ or $S(O)_x$ wherein $R^{70}$ represents hydrogen, $C_1$-$C_4$alkyl or $C_3$-$C_6$cycloalkyl and x is 0, 1 or 2; or when X represents $CH_2$, Y represents $CH_2$, O, $NR^{71}$ or $S(O)_y$ wherein $R^{71}$ represents hydrogen, $C_1$-$C_4$alkyl or $C_3$-$C_6$cycloalkyl and y is 0, 1 or 2.

In accordance with the present invention, there is provided a compound of formula (I):

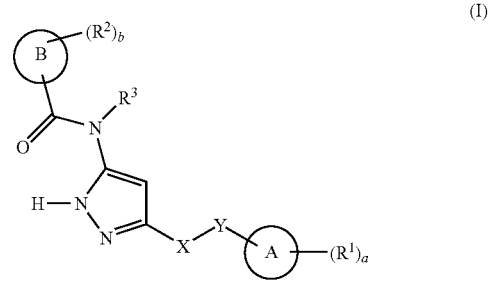

(I)

or a pharmaceutically acceptable salt thereof
wherein
ring A represents a 5- or 6-membered aromatic group optionally comprising at least one ring heteroatom selected from nitrogen, oxygen and sulphur;

ring B represents a 5- or 6-membered aromatic group optionally comprising at least one ring heteroatom selected from nitrogen, oxygen and sulphur;

$R^1$ each independently represents a halogen, a hydroxyl group, a cyano group, a $C_1$-$C_3$alkyl group optionally substituted by one or more substituents selected from $C_1$-$C_3$alkoxy, $C_3$-cyclo alkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_{3-5}$cycloalkyl group optionally substituted by one or more substituents selected from $C_1$-$C_3$alkyl, $C_1$-$C_3$alkoxy, $C_3$-cycloalkyl, $C_1$-$C_3$alkylthio, —$NR^6R^7$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_2$-$C_3$alkenyl group optionally substituted by one or more substituents selected from $C_1$-$C_3$alkoxy, $C_3$-cycloalkyl, $C_1$-$C_3$alkylthio, —$NR^8R^9$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a phenyl group optionally substituted by one or more substituents selected from $C_1$-$C_3$alkoxy, $C_3$-cycloalkyl, $C_1$-$C_3$alkylthio, —$NR^{10}R^{11}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 6-membered heterocyclyl group optionally substituted by one or more substituents selected from $C_1$-$C_3$alkyl, $C_1$-$C_3$alkoxy, $C_3$-cycloalkyl, $C_1$-$C_3$alkylthio, —$NR^{12}R^{13}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, a —$NR^{16}R^{17}$ group, a —$OCOR^{18}$ group, a —$CO_2R^{19}$ group, a —$CONR^{20}R^{21}$ group, a —$NR^{22}COR^{23}$ group, a —$NR^{24}CO_2R^{25}$ group.

a —$OSO_2R^{26}$ group, or two adjacent $R^1$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{27}R^{28}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^2$ each independently represents a hydroxyl group, a halogen, a cyano group, a —$CO_2R^{29}$ group, a —$CONR^{30}R^{31}$ group, a —$NR^{32}COR^{33}$ group, a —$NR^{34}CO_2R^{35}$ group, a —$NR^{36}R^{37}$ group, a —$SO_2R^{38}$ group, a —$SO_2NR^{39}R^{40}$ group, a —$NR^{41}SO_2R^{42}$ group, a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl, trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl, a $C_3$-$C_6$cycloalkyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{48}R^{49}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{50}R^{51}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_2$-$C_6$alkenyl group optionally substituted by one or more substituents selected from $C_1$-$C_6$alkoxy, $C_3$-$C_6$cycloalkyl, $C_1$-$C_6$alkylthio, —$NR^{52}R^{53}$, (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{54}R^{55}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 7-membered heterocyclyl group optionally fused to a 4- to 7-membered carbocyclyl or heterocyclyl group and optionally substituted by one or more substituents selected from $C_1$-$C_6$alkyl, $C_2$-$C_6$alkenyl, $C_2$-$C_6$alkynyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, —$SO_2R^{58}$ (each of which may be optionally substituted by one or more substituents selected from halogen, cyano, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, oxo, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or two adjacent $R^2$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{66}R^{67}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen,
a $C_1$-$C_3$alkyl group optionally substituted by one or more substituents selected from $C_1$-$C_3$alkoxy, $C_3$-cycloalkyl, $C_1$-$C_3$alkylthio, —$NR^{68}R^{69}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

a is 0, 1, 2, 3 or 4;
b is 0, 1, 2, 3 or 4;

$R^4$ and $R^5$ each independently represent hydrogen, $C_1$-$C_4$alkyl or $C_3$-$C_6$cycloalkyl, or $R^4$ and $R^5$ together with the nitrogen atom to which they are attached form a 4- to 6-membered saturated heterocycle;

$R^6$ and $R^7$ each independently represent hydrogen, $C_1$-$C_4$alkyl or $C_3$-$C_6$cycloalkyl, or $R^6$ and $R^7$ together with the nitrogen atom to which they are attached form a 4- to 6-membered saturated heterocycle;

$R^8$ and $R^9$ each independently represent hydrogen, $C_1$-$C_4$alkyl or $C_3$-$C_6$cycloalkyl, or $R^8$ and $R^9$ together with the nitrogen atom to which they are attached form a 4- to 6-membered saturated heterocycle;

$R^{10}$ and $R^{11}$ each independently represent hydrogen, $C_1$-$C_4$alkyl or $C_3$-$C_6$cycloalkyl, or $R^{10}$ and $R^{11}$ together with the nitrogen atom to which they are attached form a 4- to 6-membered saturated heterocycle;

$R^{12}$ and $R^{13}$ each independently represent hydrogen, $C_1$-$C_4$alkyl or $C_3$-$C_6$cycloalkyl, or $R^{12}$ and $R^{13}$ together with the nitrogen atom to which they are attached form a 4- to 6-membered saturated heterocycle;

$R^{14}$ and $R^{15}$ each independently represent hydrogen, $C_1$-$C_4$alkyl or $C_3$-$C_6$cycloalkyl, or $R^{14}$ and $R^{15}$ together with the nitrogen atom to which they are attached form a 4- to 6-membered saturated heterocycle;

$R^{16}$ and $R^{17}$ each independently represent hydrogen, $C_1$-$C_4$alkyl or $C_3$-$C_6$cycloalkyl, or $R^{16}$ and $R^{17}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{18}$ represents $C_1$-$C_4$alkyl, or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{19}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{20}$ and $R^{21}$ each independently represent hydrogen, $C_1$-$C_4$alkyl or $C_3$-$C_6$cycloalkyl, or $R^{20}$ and $R^{21}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{22}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{23}$ represents $C_1$-$C_4$alkyl or $C_3$-$C_6$cycloalkyl(each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{24}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{25}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{26}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{27}$ and $R^{28}$ each independently represent hydrogen, $C_1$-$C_4$alkyl or $C_3$-$C_6$cycloalkyl, or $R^{27}$ and $R^{28}$ together with the nitrogen atom to which they are attached form a 4- to 6-membered saturated heterocycle;

$R^{29}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{30}$ and $R^{31}$ each independently represent hydrogen, $C_1$-$C_4$alkyl or $C_3$-$C_6$cycloalkyl, or $R^{30}$ and $R^{31}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{32}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{33}$ represents hydrogen, $C_1$-$C_4$alkyl, $C_3$-$C_6$cycloalkyl or a 5- or 6-membered aromatic group optionally comprising at least one ring heteroatom selected from nitrogen, oxygen and sulphur (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{34}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{35}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{36}$ and $R^{37}$ each independently represent hydrogen, $C_1$-$C_4$alkyl, $C_2$-$C_4$alkynyl, $C_3$-$C_6$cycloalkyl or a 5- or 6-membered aromatic group optionally comprising at least one ring heteroatom selected from nitrogen, oxygen and sulphur, or $R^{36}$ and $R^{37}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl and 4- to 7-membered carbocyclyl or heterocycly group which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl);

$R^{38}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{39}$ and $R^{40}$ each independently represent hydrogen, $C_1$-$C_4$alkyl or $C_3$-$C_6$cycloalkyl, or $R^{39}$ and $R^{40}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{41}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{42}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{43}$ and $R^{44}$ each independently represent hydrogen, $C_1$-$C_4$alkyl or $C_3$-$C_6$cycloalkyl, or $R^{43}$ and $R^{44}$ together with the nitrogen atom to which they are attached form a 4- to 6-membered saturated heterocycle;

$R^{45}$ and $R^{46}$ each independently represent hydrogen, $C_1$-$C_4$alkyl or $C_3$-$C_6$cycloalkyl, or $R^{45}$ and $R^{46}$ together with the nitrogen atom to which they are attached form a 4- to 6-membered saturated heterocycle;

$R^{47}$ represents hydrogen, $C_1$-$C_4$alkyl or $C_3$-$C_6$cycloalkyl;

$R^{48}$ and $R^{49}$ each independently represent hydrogen, $C_1$-$C_4$alkyl or $C_3$-$C_6$cycloalkyl, or $R^{48}$ and $R^{49}$ together with the nitrogen atom to which they are attached form a 4- to 6-membered saturated heterocycle;

$R^{50}$ and $R^{51}$ each independently represent hydrogen, $C_1$-$C_4$alkyl or $C_3$-$C_6$cycloalkyl, or $R^{50}$ and $R^{51}$ together with the nitrogen atom to which they are attached form a 4- to 6-membered saturated heterocycle;

$R^{52}$ and $R^{53}$ each independently represent hydrogen, $C_1$-$C_4$alkyl or $C_3$-$C_6$cycloalkyl, or $R^{52}$ and $R^{53}$ together with the nitrogen atom to which they are attached form a 4- to 6-membered saturated heterocycle;

$R^{54}$ and $R^{55}$ each independently represent hydrogen, $C_1$-$C_4$alkyl or $C_3$-$C_6$cycloalkyl, or $R^{54}$ and $R^{55}$ together with the nitrogen atom to which they are attached form a 4- to 6-membered saturated heterocycle;

$R^{56}$ and $R^{57}$ each independently represent hydrogen, $C_1$-$C_4$alkyl or $C_3$-$C_6$cycloalkyl, or $R^{56}$ and $R^{57}$ together with the nitrogen atom to which they are attached form a 4- to 6-membered saturated heterocycle;

$R^{58}$ represents $C_1$-$C_4$alkyl or $C_3$-$C_6$cycloalkyl;

$R^{59}$ and $R^{60}$ each independently represent hydrogen, $C_1$-$C_4$alkyl or $C_3$-$C_6$cycloalkyl, or $R^{59}$ and $R^{60}$ together with the nitrogen atom to which they are attached form a 4- to 6-membered saturated heterocycle;

$R^{61}$ represents $C_1$-$C_4$alkyl or $C_3$-$C_6$cycloalkyl;

$R^{62}$ and $R^{63}$ each independently represent hydrogen, $C_1$-$C_4$alkyl or $C_3$-$C_6$cycloalkyl, or $R^{62}$ and $R^{63}$ together with the nitrogen atom to which they are attached form a 4- to 6-membered saturated heterocycle;

$R^{64}$ and $R^{65}$ each independently represent hydrogen, $C_1$-$C_6$alkyl or $C_3$-$C_6$cycloalkyl, or $R^{64}$ and $R^{65}$ together with the nitrogen atom to which they are attached form a 4- to 6-membered saturated heterocycle;

$R^{66}$ and $R^{67}$ each independently represent hydrogen, $C_1$-$C_6$alkyl or $C_3$-$C_6$cycloalkyl, or $R^{66}$ and $R^{67}$ together with the nitrogen atom to which they are attached form a 4- to 6-membered saturated heterocycle;

$R^{68}$ and $R^{69}$ each independently represent hydrogen, $C_1$-$C_6$alkyl or $C_3$-$C_6$cycloalkyl, or $R^{68}$ and $R^{69}$ together with the nitrogen atom to which they are attached form a 4- to 6-membered saturated heterocycle; and where when Y represents $CH_2$, X represents $CH_2$, O, $NR^{70}$ or $S(O)_x$ wherein $R^{70}$ represents hydrogen, $C_1$-$C_4$alkyl or $C_3$-$C_6$cycloalkyl and x is 0, 1 or 2; or when X represents $CH_2$, Y represents $CH_2$, O, $NR^{71}$ or $S(O)_y$, wherein $R^{71}$ represents hydrogen, $C_1$-$C_4$alkyl or $C_3$-$C_6$cycloalkyl and y is 0, 1 or 2; and provided that the compound is not 4-benzamido-N-[5-[2-(3-methoxyphenyl)ethyl]-2H-pyrazol-3-yl]benzamide, 6-anilino-N-[5-[2-(3-methoxyphenyl)ethyl]-2H-pyrazol-3-yl]pyridine-3-carboxamide, prop-2-enyl N-[5-[[5-[2-(3-methoxyphenyl)ethyl]-2H-pyrazol-3-yl]carbamoyl]pyridin-2-yl]carbamate, N-[5-[2-(3-methoxyphenyl)ethyl]-2H-pyrazol-3-yl]-6-pyrazol-1-yl-pyridine-3-carboxamide, or methyl 6-[[5-[2-(3-methoxyphenyl)ethyl]-2H-pyrazol-3-yl]carbamoyl]pyridine-3-carboxylate.

In accordance with a further aspect of the present invention, there is provided a compound of formula (I):

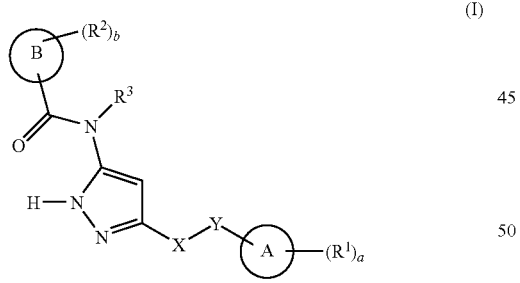

or a pharmaceutically acceptable salt thereof wherein ring A represents a 5- or 6-membered aromatic group optionally comprising at least one ring heteroatom selected from nitrogen, oxygen and sulphur;

ring B represents a 5- or 6-membered aromatic group optionally comprising at least one ring heteroatom selected from nitrogen, oxygen and sulphur;

$R^1$ each independently represents
  a halogen,
  a hydroxyl group,
  a cyano group,
  a $C_1$-$C_3$alkyl group optionally substituted by one or more substituents selected from $C_1$-$C_3$alkoxy, $C_3$-cyclo alkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_{3-5}$cycloalkyl group optionally substituted by one or more substituents selected from $C_1$-$C_3$alkyl, $C_1$-$C_3$alkoxy, $C_3$-cycloalkyl, $C_1$-$C_3$alkylthio, —$NR^6R^7$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_2$-$C_3$alkenyl group optionally substituted by one or more substituents selected from $C_1$-$C_3$alkoxy, $C_3$-cyclo alkyl, $C_1$-$C_3$alkylthio, —$NR^8R^9$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a phenyl group optionally substituted by one or more substituents selected from $C_1$-$C_3$alkoxy, $C_3$-cycloalkyl, $C_1$-$C_3$alkylthio, —$NR^{10}R^{11}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 6-membered heterocyclyl group optionally substituted by one or more substituents selected from $C_1$-$C_3$alkyl, $C_1$-$C_3$alkoxy, $C_3$-cycloalkyl, $C_1$-$C_3$alkylthio, —$NR^{12}R^{13}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, a —$NR^{16}R^{17}$ group,
  a —$OCOR^{18}$ group,
  a —$CO_2R^{19}$ group,
  a —$CONR^{20}R^{21}$ group,
  a —$NR^{22}COR^{23}$ group,
  a —$NR^{24}CO_2R^{25}$ group.
  a —$OSO_2R^{26}$ group, or two adjacent $R^1$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{27}R^{28}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^2$ each independently represents
  a hydroxyl group,
  a halogen, a cyano group,
a —$CO_2R^{29}$ group,
a —$CONR^{30}R^{31}$ group,
a —$NR^{32}COR^{33}$ group,
a —$NR^{34}CO_2R^{35}$ group,
a —$NR^{36}R^{37}$ group,
a —$SO_2R^{38}$ group,
a —$SO_2NR^{39}R^{40}$ group,
a —$NR^{41}SO_2R^{42}$ group,
a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl, trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl,
a $C_3$-$C_6$cycloalkyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{48}R^{49}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{50}R^{51}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
a $C_2$-$C_6$alkenyl group optionally substituted by one or more substituents selected from $C_1$-$C_6$alkoxy, $C_3$-$C_6$cycloalkyl, $C_1$-$C_6$alkylthio, —$NR^{52}R^{53}$, (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{54}R^{55}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
or two adjacent $R^2$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{66}R^{67}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;
$R^3$ represents hydrogen,
a $C_1$-$C_3$alkyl group optionally substituted by one or more substituents selected from $C_1$-$C_3$alkoxy, $C_3$-cycloalkyl, $C_1$-$C_3$alkylthio, —$NR^{68}R^{69}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;
a is 0, 1, 2, 3 or 4;
b is 0, 1, 2, 3 or 4;
$R^4$ and $R^5$ each independently represent hydrogen, $C_1$-$C_4$alkyl or $C_3$-$C_6$cycloalkyl, or $R^4$ and $R^5$ together with the nitrogen atom to which they are attached form a 4- to 6-membered saturated heterocycle;
$R^6$ and $R^7$ each independently represent hydrogen, $C_1$-$C_4$alkyl or $C_3$-$C_6$cycloalkyl, or $R^6$ and $R^7$ together with the nitrogen atom to which they are attached form a 4- to 6-membered saturated heterocycle;

$R^8$ and $R^9$ each independently represent hydrogen, $C_1$-$C_4$alkyl or $C_3$-$C_6$cycloalkyl, or $R^8$ and $R^9$ together with the nitrogen atom to which they are attached form a 4- to 6-membered saturated heterocycle;

$R^{10}$ and $R^{11}$ each independently represent hydrogen, $C_1$-$C_4$alkyl or $C_3$-$C_6$cycloalkyl, or $R^{10}$ and $R^{11}$ together with the nitrogen atom to which they are attached form a 4- to 6-membered saturated heterocycle;

$R^{12}$ and $R^{13}$ each independently represent hydrogen, $C_1$-$C_4$alkyl or $C_3$-$C_6$cycloalkyl, or $R^{12}$ and $R^{13}$ together with the nitrogen atom to which they are attached form a 4- to 6-membered saturated heterocycle;

$R^{14}$ and $R^{15}$ each independently represent hydrogen, $C_1$-$C_4$alkyl or $C_3$-$C_6$cycloalkyl, or $R^{14}$ and $R^{15}$ together with the nitrogen atom to which they are attached form a 4- to 6-membered saturated heterocycle;

$R^{16}$ and $R^{17}$ each independently represent hydrogen, $C_1$-$C_4$alkyl or $C_3$-$C_6$cycloalkyl, or $R^{16}$ and $R^{17}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{18}$ represents $C_1$-$C_4$alkyl, or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{19}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{20}$ and $R^{21}$ each independently represent hydrogen, $C_1$-$C_4$alkyl or $C_3$-$C_6$cycloalkyl, or $R^{20}$ and $R^{21}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{22}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{23}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{24}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{25}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{26}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{27}$ and $R^{28}$ each independently represent hydrogen, $C_1$-$C_4$alkyl or $C_3$-$C_6$cycloalkyl, or $R^{27}$ and $R^{28}$ together with the nitrogen atom to which they are attached form a 4- to 6-membered saturated heterocycle;

$R^{29}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{30}$ and $R^{31}$ each independently represent hydrogen, $C_1$-$C_4$alkyl or $C_3$-$C_6$cycloalkyl, or $R^{30}$ and $R^{31}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{32}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{33}$ represents hydrogen, $C_1$-$C_4$alkyl, $C_3$-$C_6$cycloalkyl or a 5- or 6-membered aromatic group optionally comprising at least one ring heteroatom selected from nitrogen, oxygen and sulphur (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{34}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{35}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{36}$ and $R^{37}$ each independently represent hydrogen, $C_1$-$C_4$alkyl, $C_2$-$C_4$alkynyl, $C_3$-$C_6$cycloalkyl or a 5- or 6-membered aromatic group optionally comprising at least one ring heteroatom selected from nitrogen, oxygen and sulphur, or $R^{36}$ and $R^{37}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl and 4- to 7-membered carbocyclyl or heterocycly group which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl);

$R^{38}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{39}$ and $R^{40}$ each independently represent hydrogen, $C_1$-$C_4$alkyl or $C_3$-$C_6$cycloalkyl, or $R^{39}$ and $R^{40}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{41}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{42}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{43}$ and $R^{44}$ each independently represent hydrogen, $C_1$-$C_4$alkyl or $C_3$-$C_6$cycloalkyl, or $R^{43}$ and $R^{44}$ together with the nitrogen atom to which they are attached form a 4- to 6-membered saturated heterocycle;

$R^{45}$ and $R^{46}$ each independently represent hydrogen, $C_1$-$C_4$alkyl or $C_3$-$C_6$cycloalkyl, or $R^{45}$ and $R^{46}$ together with the nitrogen atom to which they are attached form a 4- to 6-membered saturated heterocycle;

$R^{47}$ represents hydrogen, $C_1$-$C_4$alkyl or $C_3$-$C_6$cycloalkyl;

$R^{48}$ and $R^{49}$ each independently represent hydrogen, $C_1$-$C_4$alkyl or $C_3$-$C_6$cycloalkyl, or $R^{48}$ and $R^{49}$ together with the nitrogen atom to which they are attached form a 4- to 6-membered saturated heterocycle;

$R^{50}$ and $R^{51}$ each independently represent hydrogen, $C_1$-$C_4$alkyl or $C_3$-$C_6$cycloalkyl, or $R^{50}$ and $R^{51}$ together with the nitrogen atom to which they are attached form a 4- to 6-membered saturated heterocycle;

$R^{52}$ and $R^{53}$ each independently represent hydrogen, $C_1$-$C_4$alkyl or $C_3$-$C_6$cycloalkyl, or $R^{52}$ and $R^{53}$ together with the nitrogen atom to which they are attached form a 4- to 6-membered saturated heterocycle;

$R^{54}$ and $R^{55}$ each independently represent hydrogen, $C_1$-$C_4$alkyl or $C_3$-$C_6$cycloalkyl, or $R^{54}$ and $R^{55}$ together with the nitrogen atom to which they are attached form a 4- to 6-membered saturated heterocycle;

$R^{56}$ and $R^{57}$ each independently represent hydrogen, $C_1$-$C_4$alkyl or $C_3$-$C_6$cycloalkyl, or $R^{56}$ and $R^{57}$ together with the nitrogen atom to which they are attached form a 4- to 6-membered saturated heterocycle;

$R^{58}$ represents $C_1$-$C_4$alkyl or $C_3$-$C_6$cycloalkyl;

$R^{59}$ and $R^{60}$ each independently represent hydrogen, $C_1$-$C_4$alkyl or $C_3$-$C_6$cycloalkyl, or $R^{59}$ and $R^{60}$ together with the nitrogen atom to which they are attached form a 4- to 6-membered saturated heterocycle;

$R^{61}$ represents $C_1$-$C_4$alkyl or $C_3$-$C_6$cycloalkyl;

$R^{62}$ and $R^{63}$ each independently represent hydrogen, $C_1$-$C_4$alkyl or $C_3$-$C_6$cycloalkyl, or $R^{62}$ and $R^{63}$ together with the nitrogen atom to which they are attached form a 4- to 6-membered saturated heterocycle;

$R^{64}$ and $R^{65}$ each independently represent hydrogen, $C_1$-$C_6$alkyl or $C_3$-$C_6$cycloalkyl, or $R^{64}$ and $R^{65}$ together with the nitrogen atom to which they are attached form a 4- to 6-membered saturated heterocycle;

$R^{66}$ and $R^{67}$ each independently represent hydrogen, $C_1$-$C_6$alkyl or $C_3$-$C_6$cycloalkyl, or $R^{66}$ and $R^{67}$ together with the nitrogen atom to which they are attached form a 4- to 6-membered saturated heterocycle;

$R^{68}$ and $R^{69}$ each independently represent hydrogen, $C_1$-$C_6$alkyl or $C_3$-$C_6$cycloalkyl, or $R^{68}$ and $R^{69}$ together with the nitrogen atom to which they are attached form a 4- to 6-membered saturated heterocycle; and where when Y represents $CH_2$, X represents $CH_2$, O, $NR^{70}$ or $S(O)_x$ wherein $R^{70}$ represents hydrogen, $C_1$-$C_4$alkyl or $C_3$-$C_6$cycloalkyl and x is 0, 1 or 2; or when X represents $CH_2$, Y represents $CH_2$, O, $NR^{71}$ or $S(O)_y$ wherein $R^{71}$ represents hydrogen, $C_1$-$C_4$alkyl or $C_3$-$C_6$cycloalkyl and y is 0, 1 or 2.

In accordance with a further aspect of the present invention, there is provided a compound of formula (I):

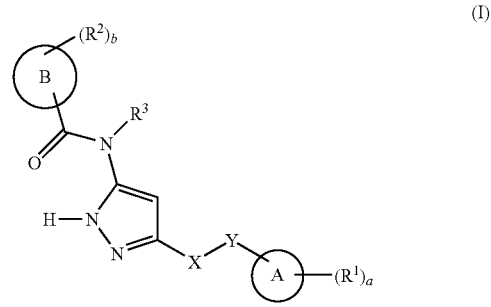

is or a pharmaceutically acceptable salt thereof
wherein
ring A represents a 5- or 6-membered aromatic group optionally comprising at least one ring heteroatom selected from nitrogen, oxygen and sulphur;

ring B represents a 5- or 6-membered aromatic group optionally comprising at least one ring heteroatom selected from nitrogen, oxygen and sulphur;

$R^1$ each independently represents
  a halogen,
  a hydroxyl group,
  a cyano group,
  a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
  a $C_{3-5}$cycloalkyl group optionally substituted by one or more substituents selected from $C_1$-$C_3$alkyl, $C_1$-$C_3$alkoxy, $C_3$-cycloalkyl, $C_1$-$C_3$alkylthio, —$NR^6R^7$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
  a $C_2$-$C_3$alkenyl group optionally substituted by one or more substituents selected from $C_1$-$C_3$alkoxy, $C_3$-cycloalkyl, $C_1$-$C_3$alkylthio, —$NR^8R^9$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a phenyl group optionally substituted by one or more substituents selected from $C_1$-$C_3$alkoxy, $C_3$-cycloalkyl, $C_1$-$C_3$alkylthio, —$NR^{10}R^{11}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 6-membered heterocyclyl group optionally substituted by one or more substituents selected from $C_1$-$C_3$alkyl, $C_1$-$C_3$alkoxy, $C_3$-cycloalkyl, $C_1$-$C_3$alkylthio, —$NR^{12}R^{13}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, a —$NR^{16}R^{17}$ group, a —$OCOR^{18}$ group, a —$CO_2R^{19}$ group, a —$CONR^{20}R^{21}$ group, a —$NR^{22}COR^{23}$ group, a —$NR^{24}CO_2R^{25}$ group.

a —$OSO_2R^{26}$ group, or two adjacent $R^1$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{27}R^{28}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^2$ each independently represents a hydroxyl group, a halogen, a cyano group, a —$CO_2R^{29}$ group, a —$CONR^{30}R^{31}$ group, a —$NR^{32}COR^{33}$ group, a —$NR^{34}CO_2R^{35}$ group, a —$NR^{36}R^{37}$ group, a —$SO_2R^{38}$ group, a —$SO_2NR^{39}R^{40}$ group, a —$NR^{41}SO_2R^{42}$ group, a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_3$-$C_6$cycloalkyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{48}R^{49}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{50}R^{51}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_2$-$C_6$alkenyl group optionally substituted by one or more substituents selected from $C_1$-$C_6$alkoxy, $C_3$-$C_6$cycloalkyl, $C_1$-$C_6$alkylthio, —$NR^{52}R^{53}$, (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl, and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{54}R^{55}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or two adjacent $R^2$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{66}R^{67}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen, a $C_1$-$C_3$alkyl group optionally substituted by one or more substituents selected from $C_1$-$C_3$alkoxy, $C_3$-cycloalkyl, $C_1$-$C_3$alkylthio, —$NR^{68}R^{69}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

a is 0, 1, 2, 3 or 4;
b is 0, 1, 2, 3 or 4;

$R^4$ and $R^5$ each independently represent hydrogen, $C_1$-$C_4$alkyl or $C_3$-$C_6$cycloalkyl, or $R^4$ and $R^5$ together with the nitrogen atom to which they are attached form a 4- to 6-membered saturated heterocycle;

$R^6$ and $R^7$ each independently represent hydrogen, $C_1$-$C_4$alkyl or $C_3$-$C_6$cycloalkyl, or $R^6$ and $R^7$ together with the nitrogen atom to which they are attached form a 4- to 6-membered saturated heterocycle;

$R^8$ and $R^9$ each independently represent hydrogen, $C_1$-$C_4$alkyl or $C_3$-$C_6$cycloalkyl, or $R^8$ and $R^9$ together with the nitrogen atom to which they are attached form a 4- to 6-membered saturated heterocycle;

$R^{10}$ and $R^{11}$ each independently represent hydrogen, $C_1$-$C_4$alkyl or $C_3$-$C_6$cycloalkyl, or $R^{10}$ and $R^{11}$ together with the nitrogen atom to which they are attached form a 4- to 6-membered saturated heterocycle;

$R^{12}$ and $R^{13}$ each independently represent hydrogen, $C_1$-$C_4$alkyl or $C_3$-$C_6$cycloalkyl, or $R^{12}$ and $R^{13}$ together with the nitrogen atom to which they are attached form a 4- to 6-membered saturated heterocycle;

$R^{14}$ and $R^{15}$ each independently represent hydrogen, $C_1$-$C_4$alkyl or $C_3$-$C_6$cycloalkyl, or $R^{14}$ and $R^{15}$ together with the nitrogen atom to which they are attached form a 4- to 6-membered saturated heterocycle;

$R^{16}$ and $R^{17}$ each independently represent hydrogen, $C_1$-$C_4$alkyl or $C_3$-$C_6$cycloalkyl, or $R^{16}$ and $R^{17}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{18}$ represents $C_1$-$C_4$alkyl, or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{19}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{20}$ and $R^{21}$ each independently represent hydrogen, $C_1$-$C_4$alkyl or $C_3$-$C_6$cycloalkyl, or $R^{20}$ and $R^{21}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{22}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{23}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{24}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{25}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{26}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{27}$ and $R^{28}$ each independently represent hydrogen, $C_1$-$C_4$alkyl or $C_3$-$C_6$cycloalkyl, or $R^{27}$ and $R^{28}$ together with the nitrogen atom to which they are attached form a 4- to 6-membered saturated heterocycle;

$R^{29}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{30}$ and $R^{31}$ each independently represent hydrogen, $C_1$-$C_4$alkyl or $C_3$-$C_6$cycloalkyl, or $R^{30}$ and $R^{31}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{32}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{33}$ represents hydrogen, $C_1$-$C_4$alkyl, $C_3$-$C_6$cycloalkyl or a 5- or 6-membered aromatic group optionally comprising at least one ring heteroatom selected from nitrogen, oxygen and sulphur (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{34}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{35}$ represents hydrogen, $C_1$-$C_4$alkyl, $C_2$-$C_4$alkenyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{36}$ and $R^{37}$ each independently represent hydrogen, $C_1$-$C_4$alkyl, $C_2$-$C_4$alkynyl, $C_3$-$C_6$cycloalkyl or a 5- or 6-membered aromatic group optionally comprising at least one ring heteroatom selected from nitrogen, oxygen and sulphur, or $R^{36}$ and $R^{37}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl, trifluoromethyl and 5- or 6-membered aryl group optionally comprising at least one ring heteroatom selected from nitrogen, oxygen and sulphur);

$R^{38}$ represents $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{39}$ and $R^{40}$ each independently represent hydrogen, $C_1$-$C_4$alkyl or $C_3$-$C_6$cycloalkyl, or $R^{39}$ and $R^{40}$ together with the nitrogen atom to which they are attached form a 4- to 6-membered saturated heterocycle (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{41}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{42}$ represents hydrogen, $C_1$-$C_4$alkyl or $C_3$-$C_6$cycloalkyl (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl);

$R^{43}$ and $R^{44}$ each independently represent hydrogen, $C_1$-$C_4$alkyl or $C_3$-$C_6$cycloalkyl, or $R^{43}$ and $R^{44}$ together with the nitrogen atom to which they are attached form a 4- to 6-membered saturated heterocycle;

$R^{45}$ and $R^{46}$ each independently represent hydrogen, $C_1$-$C_4$alkyl or $C_3$-$C_6$cycloalkyl, or $R^{45}$ and $R^{46}$ together with the nitrogen atom to which they are attached form a 4- to 6-membered saturated heterocycle;

$R^{47}$ represents hydrogen, $C_1$-$C_4$alkyl or $C_3$-$C_6$cycloalkyl;

$R^{48}$ and $R^{49}$ each independently represent hydrogen, $C_1$-$C_4$alkyl or $C_3$-$C_6$cycloalkyl, or $R^{48}$ and $R^{49}$ together with the nitrogen atom to which they are attached form a 4- to 6-membered saturated heterocycle;

$R^{50}$ and $R^{51}$ each independently represent hydrogen, $C_1$-$C_4$alkyl or $C_3$-$C_6$cycloalkyl, or $R^{50}$ and $R^{51}$ together with the nitrogen atom to which they are attached form a 4- to 6-membered saturated heterocycle;

$R^{52}$ and $R^{53}$ each independently represent hydrogen, $C_1$-$C_4$alkyl or $C_3$-$C_6$cycloalkyl, or $R^{52}$ and $R^{53}$ together with the nitrogen atom to which they are attached form a 4- to 6-membered saturated heterocycle;

$R^{54}$ and $R^{55}$ each independently represent hydrogen, $C_1$-$C_4$alkyl or $C_3$-$C_6$cycloalkyl, or $R^{54}$ and $R^{55}$ together with the nitrogen atom to which they are attached form a 4- to 6-membered saturated heterocycle;

$R^{56}$ and $R^{57}$ each independently represent hydrogen, $C_1$-$C_4$alkyl or $C_3$-$C_6$cycloalkyl, or $R^{56}$ and $R^{57}$ together with the nitrogen atom to which they are attached form a 4- to 6-membered saturated heterocycle;

$R^{58}$ represents $C_1$-$C_4$alkyl or $C_3$-$C_6$cycloalkyl;

$R^{59}$ and $R^{60}$ each independently represent hydrogen, $C_1$-$C_4$alkyl or $C_3$-$C_6$cycloalkyl, or $R^{59}$ and $R^{60}$ together with the nitrogen atom to which they are attached form a 4- to 6-membered saturated heterocycle;

$R^{61}$ represents $C_1$-$C_4$alkyl or $C_3$-$C_6$cycloalkyl;

$R^{62}$ and $R^{63}$ each independently represent hydrogen, $C_1$-$C_4$alkyl or $C_3$-$C_6$cycloalkyl, or $R^{62}$ and $R^{63}$ together with the nitrogen atom to which they are attached form a 4- to 6-membered saturated heterocycle;

$R^{64}$ and $R^{65}$ each independently represent hydrogen, $C_1$-$C_6$alkyl or $C_3$-$C_6$cycloalkyl, or $R^{64}$ and $R^{65}$ together with the nitrogen atom to which they are attached form a 4- to 6-membered saturated heterocycle;

$R^{66}$ and $R^{67}$ each independently represent hydrogen, $C_1$-$C_6$alkyl or $C_3$-$C_6$cycloalkyl, or $R^{66}$ and $R^{67}$ together with the nitrogen atom to which they are attached form a 4- to 6-membered saturated heterocycle;

$R^{68}$ and $R^{69}$ each independently represent hydrogen, $C_1$-$C_6$alkyl or $C_3$-$C_6$cycloalkyl, or $R^{68}$ and $R^{69}$ together with the nitrogen atom to which they are attached form a 4- to 6-membered saturated heterocycle; and where when Y represents $CH_2$, X represents $CH_2$, O, $NR^{70}$ or $S(O)_x$ wherein $R^{70}$ represents hydrogen, $C_1$-$C_4$alkyl or $C_3$-$C_6$cycloalkyl and x is 0, 1 or 2; or when X represents $CH_2$, Y represents $CH_2$, O, $NR^{71}$ or $S(O)_y$ wherein $R^{71}$ represents hydrogen, $C_1$-$C_4$alkyl or $C_3$-$C_6$cycloalkyl and y is 0, 1 or 2.

In the context of the present specification, unless otherwise indicated, the term "alkyl" includes both linear and branched chain alkyl groups, but references to individual groups such as "n-propyl" are specific for the linear version only, and references to individual branch chained versions, for example "i-propyl", are specific for the branched version only. A similar convention applies to other radicals.

For example, examples of "$C_1$-$C_6$alkyl" and "$C_1$-$C_4$alkyl" include methyl, ethyl, n-propyl, i-propyl, n-butyl, i-butyl and t-butyl. Examples of "$C_1$-$C_6$alkoxy" and "$C_1$-$C_3$alkoxy" include methoxy, ethoxy, n-propoxy and i-propoxy. Examples of "$C_2$-$C_6$alkenyl" include vinyl, allyl and 1-propenyl. Examples of "$C_3$-$C_6$cycloalkyl" include cyclopropyl, cyclopentyl and cyclohexyl. Example of "mono- and di-$C_1$-$C_6$alkylamino" include methylamino, dimethylamino, ethylamino, diethylamino and ethylmethylamino. Examples of "$C_1$-$C_6$alkylthio" include methylthio, ethylthio and propylthio.

Examples of halogen include fluorine, chlorine, bromine and iodine.

A "4- to 7-membered carbocyclyl group", unless otherwise stated, includes saturated and fully or partially unsaturated, monocyclic rings containing 4, 5, 6 or 7 carbon atoms. A "4- to 7-membered carbocyclyl group" includes groups such as $C_4$-$C_7$cycloalkyl, $C_4$-$C_7$cycloalkenyl and $C_6$aryl.

A "5- or 6-membered aromatic group optionally comprising at least one ring heteroatom selected from nitrogen, oxygen and sulphur" or "5- or 6-membered aryl group optionally comprising at least one ring heteroatom selected from nitrogen, oxygen and sulphur" is a fully unsaturated, aromatic monocyclic ring containing 5 or 6 atoms of which at least one is a heteroatom selected from nitrogen, oxygen and sulphur, which may, unless otherwise specified, be carbon or nitrogen linked. Suitably a "5- or 6-membered aromatic ring optionally comprising at least one ring heteroatom selected from nitrogen, oxygen and sulphur" is furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl and triazolyl rings.

A "4- to 7-membered heterocyclyl group", unless otherwise stated, includes saturated and fully or partially unsaturated, monocyclic rings containing 4, 5, 6 or 7 atoms of which at least one is a heteroatom selected from nitrogen, oxygen and sulphur, and which may, unless otherwise specified, be carbon or nitrogen linked. Suitable "4- to 7-membered heterocyclyl group" which may comprise at least one ring heteroatom selected from nitrogen, oxygen and sulphur include azetidine, gamma-butyrolactone, diazepine, dioxolane, dioxane, dihydro-oxazine, dihydrothiophene, dithiolan, furan, hexahydroazepine, imidazole, imidazoline, imidazolidine, isothiazole, isoxazole, morpholine, oxadiazole, oxazine, oxazole, oxetane, piperidine, piperazine, alpha-pyran, gamma-pyran, pyrazine, pyrazolidine, pyrazole, pyrazoline, pyridazine, pyridine, pyrimidine, pyrrole, pyrrolidine, pyrroline, tetrahydrofuran, tetrahydrofuranone, tetrahydropyran, tetrazine, tetrazole, thiadiazole, thiazole, thiolan, thiomorpholine, thiomorpholine S,S-dioxide, thiophene and triazine.

When $R^4$ and $R^5$, or $R^6$ and $R^7$, or $R^8$ and $R^9$, or $R^{10}$ and $R^{11}$, or $R^{12}$ and $R^{13}$, or $R^{14}$ and $R^{15}$, or $R^{27}$ and $R^{28}$, or $R^{43}$ and $R^{44}$, or $R^{45}$ and $R^{46}$, or $R^{48}$ and $R^{49}$, or $R^{50}$ and $R^{51}$, or $R^{52}$ and $R^{53}$, or $R^{54}$ and $R^{55}$, or $R^{56}$ and $R^{57}$, or $R^{59}$ and $R^{60}$, or $R^{62}$ and $R^{63}$, or $R^{64}$ and $R^{65}$, or $R^{66}$ and $R^{67}$, or $R^{68}$ and $R^{69}$ represent a 4- to 6-membered saturated heterocycle, it should be understood that when only one heteroatom is present it is the nitrogen atom to which $R^4$ and $R^5$, or $R^6$ and $R^7$, or $R^8$ and $R^9$, or $R^{10}$ and $R^{11}$, or $R^{12}$ and $R^{13}$, or $R^{14}$ and $R^{15}$, or $R^{27}$ and $R^{28}$, or $R^{43}$ and $R^{44}$, or $R^{45}$ and $R^{46}$, or $R^{48}$ and $R^{49}$, or $R^{50}$ and $R^{51}$, or $R^{52}$ and $R^{53}$, or $R^{54}$ and $R^{55}$, or $R^{56}$ and $R^{57}$, or $R^{59}$ and $R^{60}$, or $R^{62}$ and $R^{63}$, or $R^{64}$ and $R^{65}$, or $R^{66}$ and $R^{67}$, or $R^{68}$ and $R^{69}$ are attached. The "4- to 6-membered saturated heterocycle", unless otherwise stated, includes saturated monocyclic rings containing 4, 5 or 6 atoms wherein at least one atom is nitrogen and the remaining atoms are selected from carbon, nitrogen, oxygen and sulphur. Suitable "4- to 6-membered saturated heterocycle" include pyrrolidine, pyrazolidine, imidazolidine, piperidine, piperazine, morpholine, thiomorpholine and thiomorpholine S,S-dioxide.

A "4- to 7-membered heterocyclyl group optionally fused to a 4- to 7-membered carbocyclyl or heterocyclyl group", unless otherwise stated, includes saturated and fully or partially unsaturated, monocyclic or bicyclic rings, each ring containing 4, 5, 6 or 7 atoms and at least one ring atom of one ring is a heteroatom selected from nitrogen, oxygen and sulphur, and which may, unless otherwise specified, be carbon or nitrogen linked. Suitable "4- to 7-membered heterocyclyl group optionally fused to a 4- to 7-membered carbocyclyl or heterocyclyl group" which may comprise at least one ring heteroatom selected from nitrogen, oxygen and sulphur include azetidine, benzfuran, benzimidazole, benzthiophene, gamma-butyrolactone, diazepine, dioxolane, dioxane, dihydro-oxazine, dihydrothiophene, dithiolan, furan, hexahydroazepine, imidazole, imidazoline, imidazolidine, indazole, indole, isothiazole, isoxazole, morpholine, oxadiazole, oxazine, oxazole, oxetane, piperidine, piperazine, alpha-pyran, gamma-pyran, pyrazine, pyrazolidine, pyrazole, pyrazoline, pyridazine, pyridine, pyrimidine, pyrrole, pyrrolidine, pyrroline, quinazoline, quinoline, tetrahydrofuran, tetrahydrofuranone, tetrahydropyran, tetrahydroquinoline, tetrazine, tetrazole, thiadiazole, thiazole, thiolan, thiomorpholine, thiomorpholine S,S-dioxide, thiophene and triazine.

For the avoidance of doubt, where it is indicated that substituents may carry further substituents for example in definitions of terms such as "a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl)", it is understood that atoms, such as carbon atoms that may be capable of carrying optionally substituents by replacement of hydrogen radicals, in the groups $C_1$-$C_3$alkoxy, $C_3$-cycloalkyl, $C_1$-$C_3$alkylthio and —$NR^4R^5$ (irrespective of any additional substituents defined in the definitions of $R^4$ or $R^5$) may be substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl. For example, $R^4$ or $R^5$ may also be substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess FGFR inhibitory activity.

The invention relates to any and all tautomeric forms of the compounds of the formula (I) that possess FGFR inhibitory activity. For example, the compound of formula (IA) is a tautomer of the compound of formula (I).

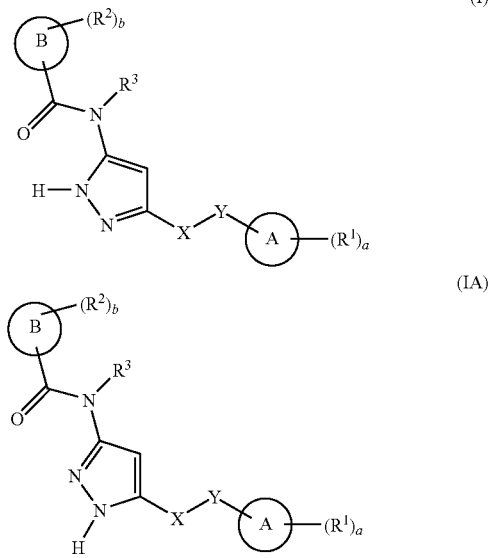

It is also to be understood that certain compounds of the formula (I) can exist in solvated as well as unsolvated forms such as, for example, hydrated forms. It is to be understood that the invention encompasses all such solvated forms that possess FGFR inhibitory activity.

Particular values of variable groups are as follows. Such values may be used where appropriate with any of the definitions, claims or embodiments defined hereinbefore or hereinafter.

In a further embodiment of the invention, A represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring.

In a further embodiment of the invention, A represents a furyl, phenyl, pyrazinyl, pyridazinyl, pyridyl, pyrimidinyl, thienyl or thiazolyl ring.

In a further embodiment of the invention, A represents a furyl, phenyl, pyrazinyl, pyridazinyl, pyridyl, pyrimidinyl or thienyl ring.

In a further embodiment of the invention, A represents a furyl, phenyl, pyrazinyl, pyridazinyl, pyridyl, or pyrimidinyl ring.

In a further aspect of the invention, A represents a furyl, phenyl, pyridyl or pyrimidinyl ring.

In a further aspect of the invention, A represents a furyl, phenyl or pyridyl ring.

In a further aspect of the invention, A represents a furyl or phenyl ring.

In a further aspect of the invention, A represents a phenyl ring.

In a further embodiment of the invention B represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring.

In a further embodiment of the invention B represents a furyl, isothiazolyl, isoxazolyl, oxadiazolyl, phenyl, pyrazinyl, pyrazolyl, pyridazinyl, pyridyl, pyrimidinyl, pyrrolyl or thienyl ring.

In a further embodiment of the invention, B represents a furyl, phenyl, pyrazinyl, pyridazinyl, pyridyl, pyrimidinyl, thienyl or thiazolyl ring.

In a further embodiment of the invention, B represents a furyl, phenyl, pyrazinyl, pyridazinyl, pyridyl, pyrimidinyl or thienyl ring.

In a further embodiment of the invention B represents a phenyl, pyrazinyl, pyrazolyl, pyridazinyl, pyridyl or pyrimidinyl ring.

In a further embodiment of the invention B represents a phenyl, pyrazinyl, pyridyl, thienyl or pyrimidinyl ring.

In a further aspect of the invention B represents a pyridyl, pyrimidinyl or phenyl ring.

In a further embodiment of the invention B represents a phenyl, pyrazinyl, thienyl or pyrimidinyl ring.

In a further aspect of the invention B represents a phenyl ring.

In one embodiment of the invention, each $R^1$ independently represents a halogen; a hydroxyl group; a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl; a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl; or a —$CONR^{20}R^{21}$ group.

In a further embodiment of the invention, each $R^1$ independently represents a halogen; a hydroxyl group; a $C_1$-$C_3$alkyl group optionally substituted by one or more substituents selected from $C_1$-$C_3$alkoxy, $C_3$-cycloalkyl, $C_1$-$C_3$alkylthio, —NR$^4$R$^5$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl; a C$_1$-C$_3$alkoxy group optionally substituted by one or more substituents selected from C$_1$-C$_3$alkoxy, C$_3$-cycloalkyl, —NR$^{14}$R$^{15}$, (each of which may be optionally substituted by one or more substituents selected from halogen, C$_1$-C$_3$alkyl, C$_1$-C$_3$alkoxy, amino (—NH$_2$), mono- and di-C$_1$-C$_3$alkylamino, hydroxyl and trifluoromethyl), halogen and hydroxyl; a —CONR$^{20}$R$^{21}$ group; or two adjacent R$^1$ groups together with the atoms to which they are attached form a 4- to 7-membered carbocyclyl or heterocyclyl ring optionally substituted by one or more substituents selected from C$_1$-C$_3$alkyl, C$_1$-C$_3$alkoxy, C$_3$-cyclo alkyl, C$_1$-C$_3$alkylthio, —NR$^{27}$R$^{28}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further embodiment of the invention, each R$^1$ independently represents a halogen; a hydroxyl group; a C$_1$-C$_3$alkoxy group optionally substituted by one or more substituents selected from C$_1$-C$_3$alkoxy, C$_3$-cycloalkyl, —NR$^{14}$R$^{15}$ (each of which may be optionally substituted by one or more substituents selected from halogen, C$_1$-C$_3$alkyl, C$_1$-C$_3$alkoxy, amino (—NH$_2$), mono- and di-C$_1$-C$_3$alkylamino, hydroxyl and trifluoromethyl), halogen and hydroxyl; or a —CONR$^{20}$R$^{21}$ group.

In a further embodiment of the invention, each R$^1$ independently represents a C$_1$-C$_3$alkoxy group optionally substituted by one or more substituents selected from C$_1$-C$_3$alkoxy, C$_3$-cycloalkyl, —NR$^{14}$R$^{15}$ (each of which may be optionally substituted by one or more substituents selected from halogen, C$_1$-C$_3$alkyl, C$_1$-C$_3$alkoxy, amino (—NH$_2$), mono- and di-C$_1$-C$_3$alkylamino, hydroxyl and trifluoromethyl), halogen and hydroxyl.

In a further embodiment of the invention, each R$^1$ independently represents a C$_1$-C$_3$alkoxy group optionally substituted by one or more substituents selected from methoxy, —N(Me)$_2$ and hydroxyl.

In a further additional aspect of the invention each R$^1$ independently represents a —CONR$^{20}$R$^{21}$ group.

In a further additional aspect of the invention each R$^1$ independently represents a methoxy group; —OCH$_2$CH$_2$OMe; —CH$_2$NMe$_2$ or two adjacent R$^1$ groups together form an —OCH$_2$O— bridge.

In a further additional aspect of the invention each R$^1$ independently represents a hydroxyl group; —CONH$_2$; —CONHMe; —CONMe$_2$ or a methoxy group.

In a further additional aspect of the invention each R$^1$ independently represents —CONHMe or a methoxy group.

In a further additional aspect of the invention R$^1$ represents —CONHMe.

In a further additional aspect of the invention R$^1$ represents methoxy.

In another embodiment of the invention, each R$^2$ independently represents a —NR$^{36}$R$^{37}$ group; a C$_1$-C$_6$alkyl group optionally substituted by one or more substituents selected from C$_1$-C$_6$alkoxy, C$_3$-C$_6$cycloalkyl, C$_1$-C$_6$alkylthio, —NR$^{43}$R$^{44}$, (each of which may be optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl trifluoromethyl and a 4- to 7-membered heterocyclyl group optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{45}$R$^{46}$, —CO$_2$R$^{47}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl; a 4- to 7-membered heterocyclyl group optionally fused to a 4- to 7-membered carbocyclyl or heterocyclyl group and optionally substituted by one or more substituents selected from C$_1$-C$_6$alkyl, C$_2$-C$_6$alkenyl, C$_2$-C$_6$alkynyl, C$_1$-C$_6$alkoxy, C$_1$-C$_6$alkylcarbonyl, C$_3$-C$_6$cycloalkyl, C$_1$-C$_6$alkylthio, —NR$^{56}$R$^{57}$, SO$_2$R$^{58}$ (each of which may be optionally substituted by one or more substituents selected from halogen, cyano, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen, oxo, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{59}$R$^{60}$, —SO$_2$R$^{61}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl; or a C$_1$-C$_6$alkoxy group optionally substituted by one or more substituents selected from C$_1$-C$_6$alkoxy, C$_3$-C$_6$cycloalkyl, —NR$^{62}$R$^{63}$ (each of which may be optionally substituted by one or more substituents selected from halogen, C$_1$-C$_3$alkyl, C$_1$-C$_3$alkoxy, amino (—NH$_2$), mono- and di-C$_1$-C$_3$alkylamino, hydroxyl and trifluoromethyl), halogen, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{64}$R$^{65}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In another embodiment of the invention, each R$^2$ independently represents a —NR$^{36}$R$^{37}$ group; a C$_1$-C$_6$alkyl group optionally substituted by one or more substituents selected from C$_1$-C$_6$alkoxy, C$_3$-C$_6$cycloalkyl, C$_1$-C$_6$alkylthio, —NR$^{43}$R$^{44}$, (each of which may be optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl trifluoromethyl and a 4- to 7-membered heterocyclyl group optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{45}$R$^{46}$, —CO$_2$R$^{47}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl; a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl; or a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl.

In a further aspect of the invention, each $R^2$ independently represents a hydroxyl group; a halogen; a cyano group; a —$CO_2R^{29}$ group; a —$CONR^{30}R^{31}$ group; a —$NR^{32}COR^{33}$ group; a —$NR^{34}CO_2R^{35}$ group; a —$NR^{36}R^{37}$ group; a —$SO_2R^{38}$ group; a —$SO_2NR^{39}R^{40}$ group; a —$NR^{41}SO_2R^{42}$ group; a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl; a 4- to 7-membered heterocyclyl group optionally fused to a 4- to 7-membered carbocyclyl or heterocyclyl group and optionally substituted by one or more substituents selected from $C_1$-$C_6$alkyl, $C_2$-$C_6$alkenyl, $C_2$-$C_6$alkynyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, cyano, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, oxo, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl; or a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl.

In a further aspect of the invention, each $R^2$ independently represents a hydroxyl group; a halogen; a cyano group; a —$CO_2R^{29}$ group; a —$CONR^{30}R^{31}$ group; a —$NR^{32}COR^{33}$ group; a —$NR^{34}CO_2R^{35}$ group; a —$NR^{36}R^{37}$ group; a —$SO_2R^{38}$ group; a —$SO_2NR^{39}R^{40}$ group; a —$NR^{41}SO_2R^{42}$ group; a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl; a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl; or a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{64}$R$^{65}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further aspect of the invention, each R$^2$ independently represents a —NR$^{36}$R$^{37}$ group; a C$_1$-C$_6$alkyl group optionally substituted by one or more substituents selected from —NR$^{43}$R$^{44}$ (which may be optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl, trifluoromethyl and a morpholine, piperidine or piperazine optionally substituted by one or more substituents selected from halogen, C$_1$-C$_3$alkyl, C$_1$-C$_3$alkoxy, C$_1$-C$_3$alkylthio, C$_3$-C$_6$cycloalkyl, amino (—NH$_2$), mono- and di-C$_1$-C$_3$alkylamino, cyano, hydroxyl trifluoromethyl), and a morpholine, piperidine or piperazine optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{45}$R$^{46}$, —CO$_2$R$^{47}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl; or a morpholine, piperidine or piperazine optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{56}$R$^{57}$, SO$_2$R$^{58}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{59}$R$^{60}$, —SO$_2$R$^{61}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further aspect of the invention, each R$^2$ independently represents a methyl or a methoxy group optionally substituted by a morpholine, piperidine or piperazine group each optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{56}$R$^{57}$, SO$_2$R$^{58}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{59}$R$^{60}$, —SO$_2$R$^{61}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further aspect of the invention, each R$^2$ independently represents a morpholine, piperidine or piperazine optionally substituted by one or more substituents selected from C$_1$-C$_6$alkyl, C$_2$-C$_6$alkenyl, C$_2$-C$_6$alkynyl, C$_1$-C$_6$alkoxy, C$_1$-C$_6$alkylcarbonyl, C$_3$-C$_6$cycloalkyl, C$_1$-C$_6$alkylthio, —NR$^{56}$R$^{57}$, SO$_2$R$^{58}$ (each of which may be optionally substituted by one or more substituents selected from halogen, cyano, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen, oxo, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{59}$R$^{60}$, —SO$_2$R$^{61}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further aspect of the invention, each R$^2$ independently represents a morpholine, piperidine or piperazine optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{56}$R$^{57}$, SO$_2$R$^{58}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen, hydroxyl and a 4- to 7-membered heterocyclyl group optionally substituted by one or more substituents selected from C$_1$-C$_6$alkyl, C$_1$-C$_6$alkoxy, C$_3$-C$_6$cycloalkyl, C$_1$-C$_6$alkylthio, —NR$^{59}$R$^{60}$, —SO$_2$R$^{61}$ (each of which may be optionally substituted by one or more substituents selected from halogen, C$_1$-C$_3$alkyl, C$_1$-C$_3$alkoxy, C$_1$-C$_3$alkylthio, amino (—NH$_2$), mono- and di-C$_1$-C$_3$alkylamino, hydroxyl and trifluoromethyl), halogen and hydroxyl.

In a further aspect of the invention, each R$^2$ independently represents a —Cl; —F; —I; —OH; —CN; —CH$_3$; —CH$_2$OH; —CH$_2$N(CH$_3$)$_2$; —CH$_2$CH(CH$_3$)NH$_2$; —OCH$_3$; —OCH$_2$CH$_2$OH; —OCH$_2$CH$_2$OCH$_2$CH$_3$; —SO$_2$CH$_3$; —N(CH$_3$)$_2$; —NHPh; —NHCH$_2$C≡CH; —NHCH$_2$CH$_3$; —NHCH$_2$CH$_2$N(CH$_3$)$_2$; —NHCO$_2$CH$_2$CH═CH$_2$; —NHCOCH$_3$; —NHCOH; —NHCOPh; —CONH$_2$; —NHSO$_2$Me; —SO$_2$N(CH$_3$)$_2$; —CO$_2$H; —CO$_2$CH$_3$; —CO$_2$CH$_2$CH$_3$;

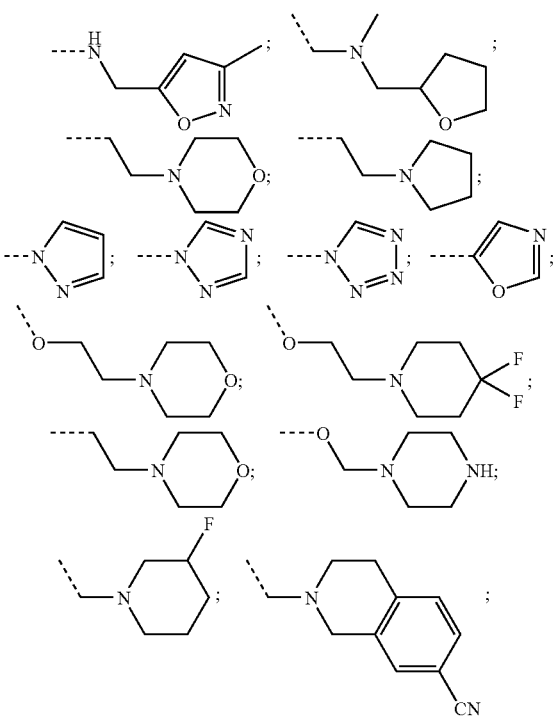

-continued

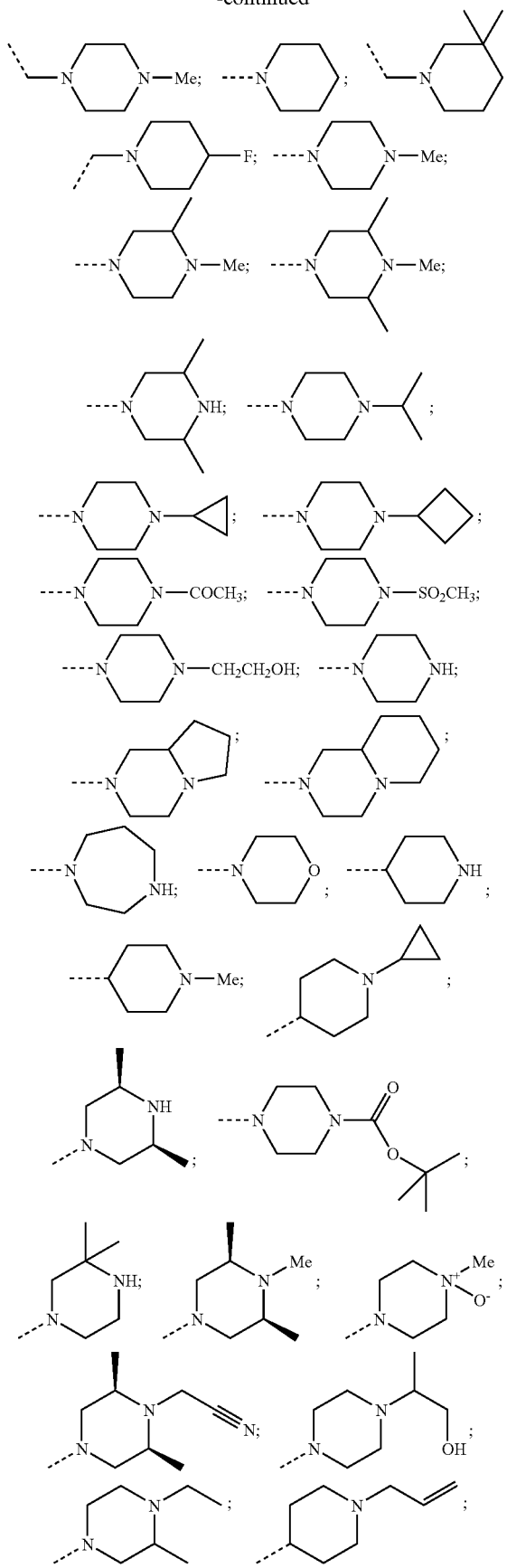

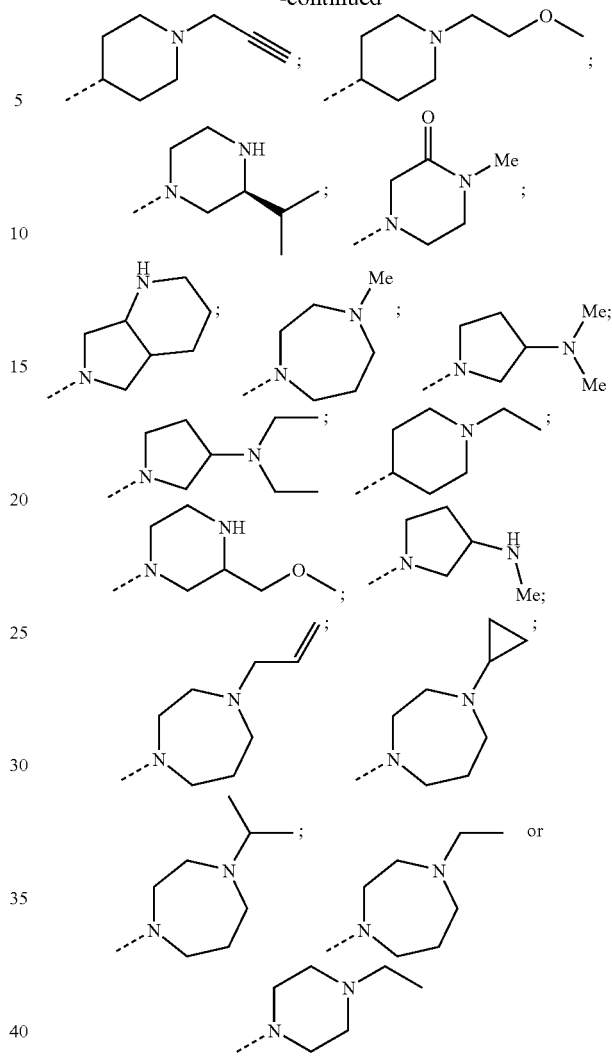

group.

In a further aspect of the invention, each $R^2$ independently represents a —Cl; —F; —I; —OH; —CN; —CH$_3$; —CH$_2$OH; —CH$_2$N(CH$_3$)$_2$; —CH$_2$CH(CH$_3$)NH$_2$; —OCH$_3$; —OCH$_2$CH$_2$OH; —OCH$_2$CH$_2$OCH$_2$CH$_3$; —SO$_2$CH$_3$; —OCH$_2$CH$_2$OH; —N(CH$_3$)$_2$; —NHPh; —NHCH$_2$C≡CH; —NHCH$_2$CH$_3$; —NHCH$_2$CH$_2$N(CH$_3$)$_2$; —NHCO$_2$CH$_2$CH=CH$_2$; —NHCOCH$_3$; —NHCOH; —NHCOPh; —CONH$_2$; —NHSO$_2$Me; —SO$_2$N(CH$_3$)$_2$; —CO$_2$H; —CO$_2$CH$_3$; —CO$_2$CH$_2$CH$_3$;

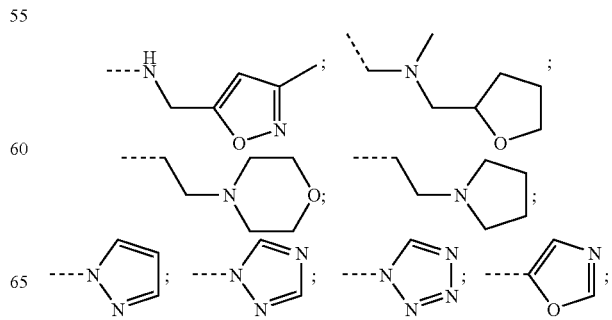

-continued

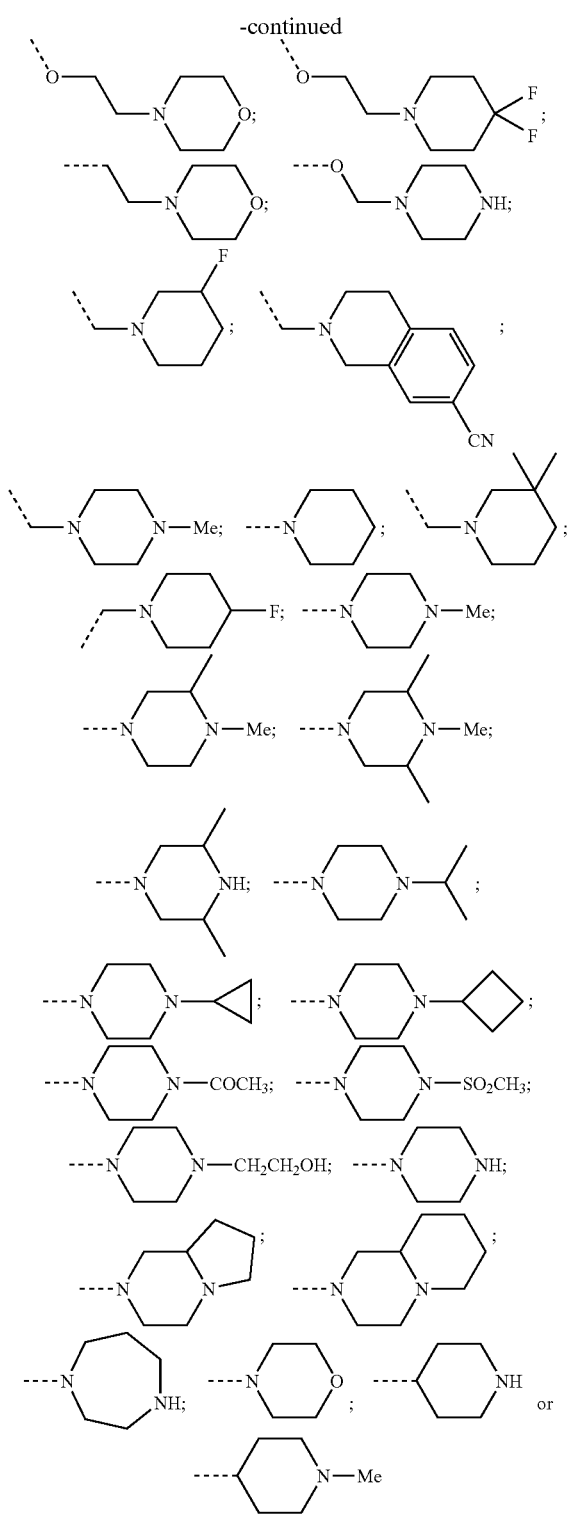

group.

In a further aspect of the invention, each $R^2$ independently represents a —Cl; —F; —I; —OH; —CN; —CH$_3$; —CH$_2$OH; —CH$_2$N(CH$_3$)$_2$; —CH$_2$CH(CH$_3$)NH$_2$; —OCH$_3$; —OCH$_2$CH$_2$OH; —OCH$_2$CH$_2$OCH$_2$CH$_3$; —SO$_2$CH$_3$; —OCH$_2$CH$_2$OH; —N(CH$_3$)$_2$; —NHPh; —NHCH$_2$C≡CH; —NHCH$_2$CH$_3$; —NHCH$_2$CH$_2$N(CH$_3$)$_2$; —NHCO$_2$CH$_2$CH=CH$_2$; —NHCOCH$_3$; —NHCOH;

—NHCOPh; —CONH$_2$; —NHSO$_2$Me; —SO$_2$N(CH$_3$)$_2$; —CO$_2$H; —CO$_2$CH$_3$; —CO$_2$CH$_2$CH$_3$;

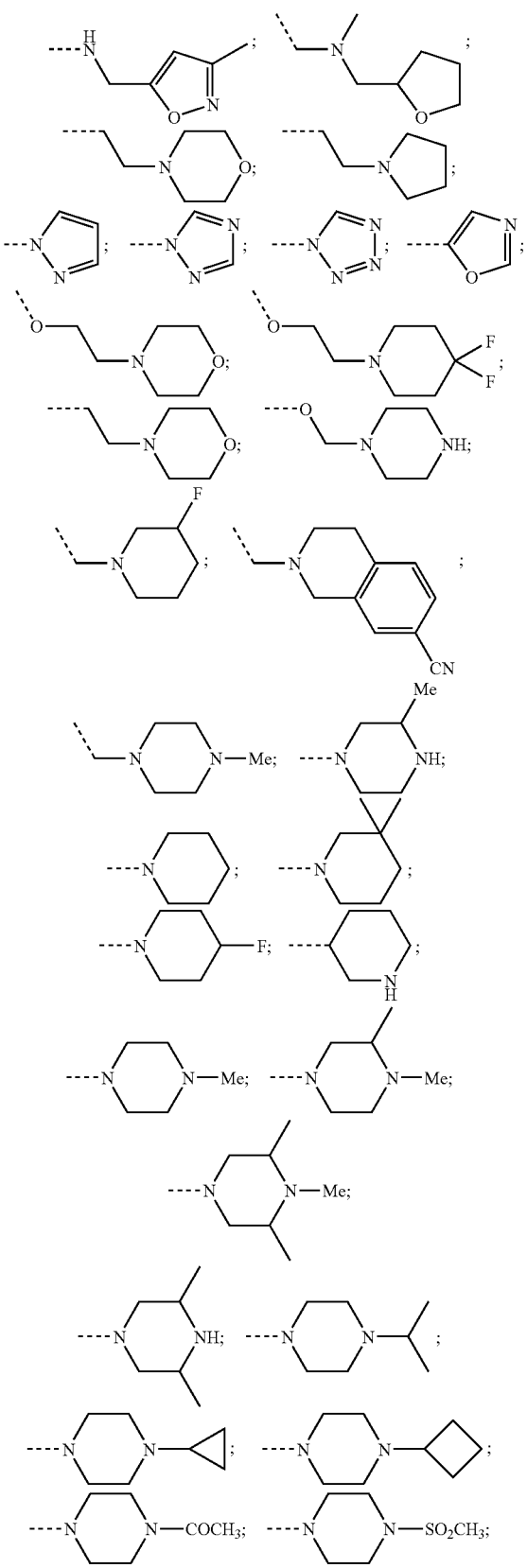

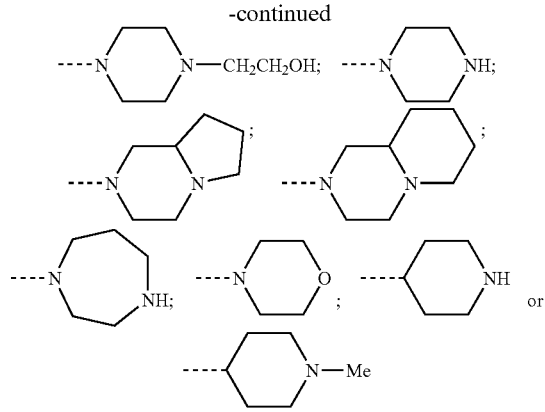
group.
In a further aspect of the invention, each $R^2$ independently represents a —OMe; —OCH$_2$CH$_2$OCH$_3$; —OCH$_2$CH$_2$OH; —CH$_2$N(CH$_3$)$_2$; —NHCH$_2$CH$_2$N(CH$_3$)$_2$;
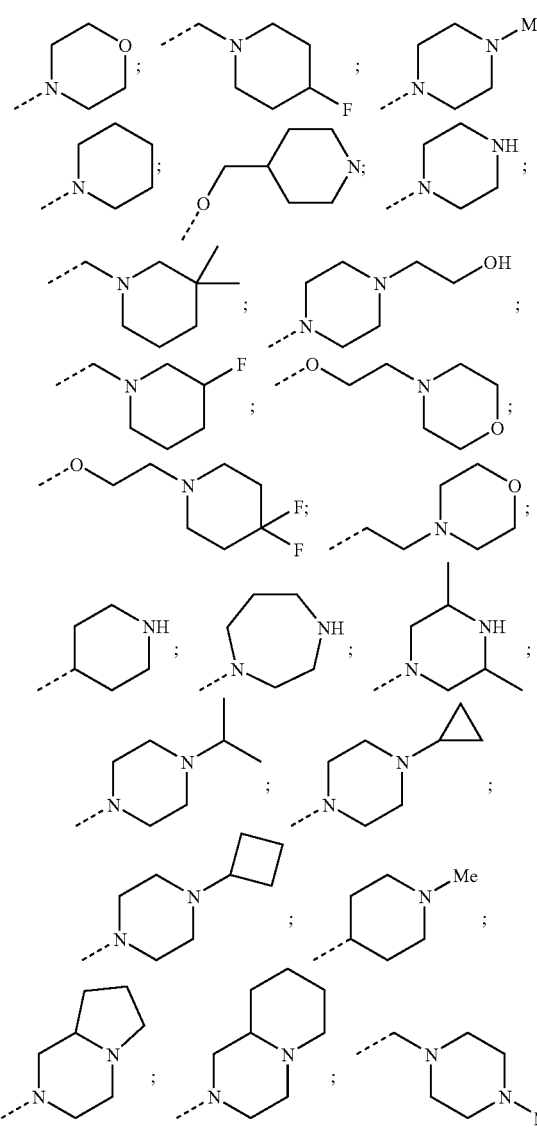
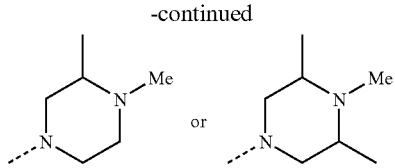
group.
In a further aspect of the invention, each $R^2$ independently represents a —NHCH$_2$CH$_2$N(CH$_3$)$_2$;
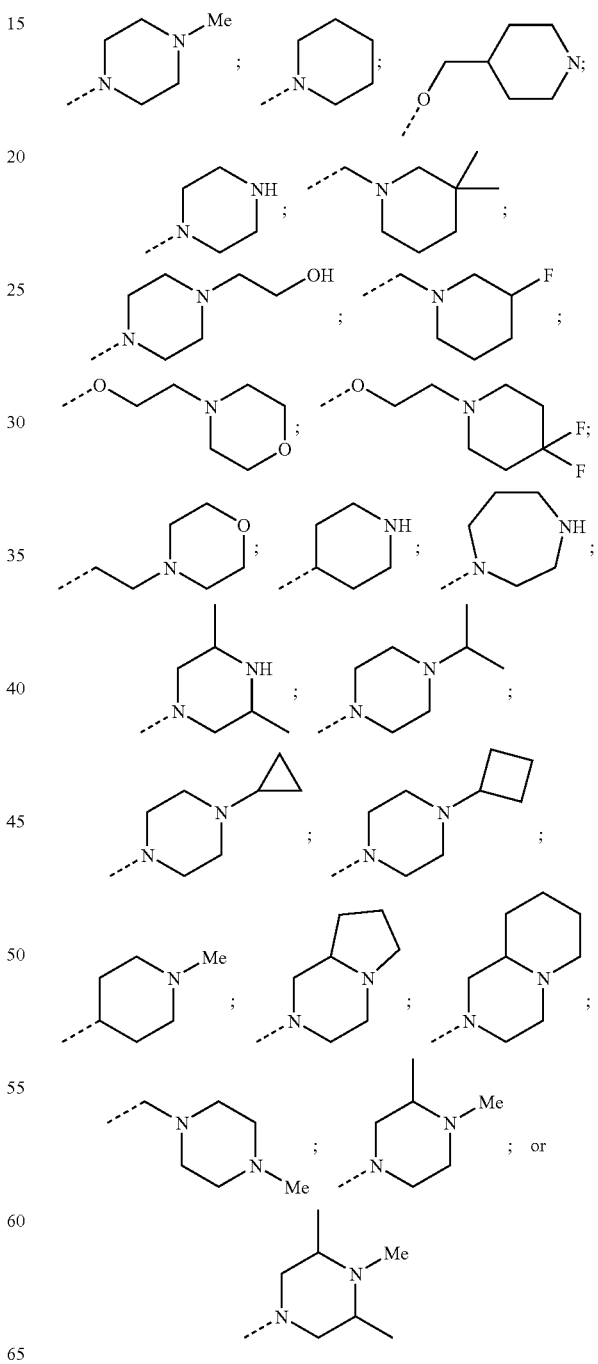
group.

In a further aspect of the invention, each R² independently represents a

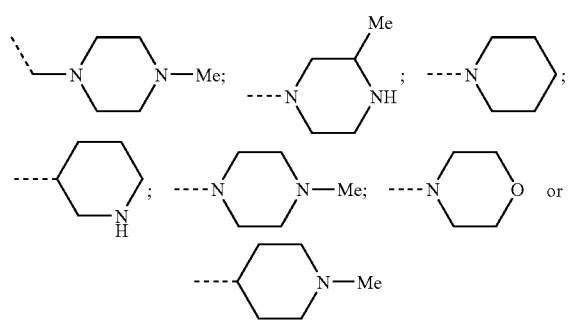

group.

In a further aspect of the invention, each R² independently represents a

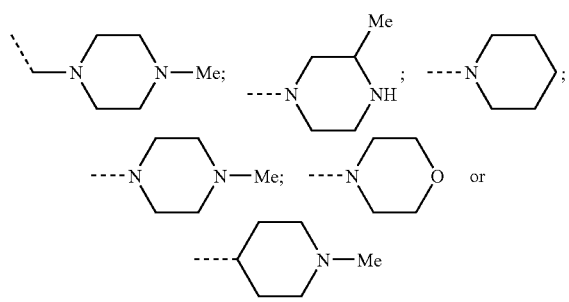

group.

In a further aspect of the invention, each R² independently represents a

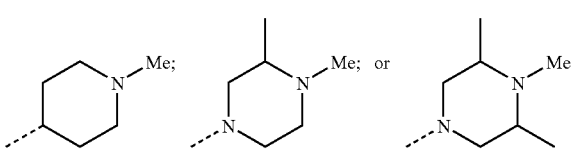

group.

In a further aspect of the invention, R² represents a

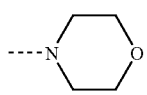

group.

In a further aspect of the invention, R² represents a

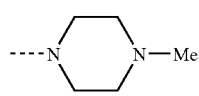

group.

In a further aspect of the invention, R² represents

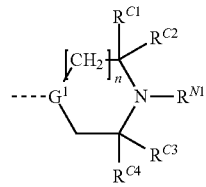

wherein $G^1$ is C or N, n is 1 or 2, $R^{C1}$, $R^{C2}$, $R^{C3}$ and $R^{C4}$ are each independently selected from $C_1$-$C_3$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen, halogen and hydroxyl, or $R^{C1}$ and $R^{C2}$ and/or $R^{C3}$ and $R^{C4}$ together with the atom to which they are attached form a 3- to 6-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, or $R^{C1}$ and $R^{C3}$ together with the atoms to which they are attached and the nitrogen atom to which the $R^{N1}$ group is attached form a 5- to 7-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, and $R^{N1}$ is selected from selected from $C_1$-$C_4$alkyl, $C_2$-$C_4$alkenyl, $C_2$-$C_4$alkynyl, $C_3$-$C_6$cycloalkyl, (each of which may be optionally substituted by one or more substituents selected from cyano, halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen and a 4- to 7-membered heterocyclyl group optionally substituted by one or more substituents selected from $C_1$-$C_3$alkyl, $C_1$-$C_3$alkoxy, $C_3$-$C_5$cycloalkyl, $C_1$-$C_3$alkylthio, —$NR^{59}R^{60}$, —$SO_2R^{61}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen and hydroxyl, or $R^{N1}$ and $R^{C4}$ together with the atoms to which they are attached form a 4- to 7-membered heterocyclyl ring optionally substituted by one or more substituents selected from $C_1$-$C_3$alkyl, $C_2$-$C_3$alkenyl, $C_2$-$C_3$alkynyl, $C_1$-$C_3$alkoxy, $C_3$-$C_5$cycloalkyl, $C_1$-$C_3$alkylthio, —$NR^{56}R^{57}$, $SO_2R^{58}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen, hydroxyl.

In a further aspect of the invention, $R^2$ independently represents

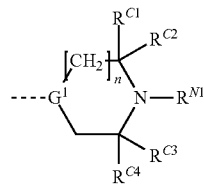

wherein
$G^1$ is C or N,
n is 1 or 2,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or $R^{C3}$ and $R^{C4}$ together with the atom to which they are attached form a 3- to 5-membered carbocyclic ring, and
$R^{N1}$ is selected from selected from $C_1$-$C_2$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl) and hydrogen, or
$R^{N1}$ and $R^{C4}$ together with the atoms to which they are attached form a 4- to 7-membered heterocyclyl ring.

In a further aspect of the invention, $R^2$ independently represents

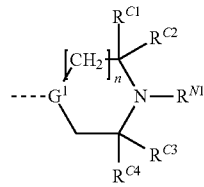

wherein
$G^1$ is C or N,
n is 1 or 2,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or $R^{C3}$ and $R^{C4}$ together with the atom to which they are attached form a cyclopropyl ring, and
$R^{N1}$ is selected from selected from hydrogen, methyl, ethyl, methoxyethyl, ethoxyethyl, hydroxyethyl propenyl, propynyl, propyl, i-propyl, —CH($CH_3$)$CH_2$OH, cyclopropyl, cyclobutyl, cyclopentyl, or
$R^{N1}$ and $R^{C4}$ together with the atoms to which they are attached form a 5- or 6-membered heterocyclyl ring.

In a further aspect of the invention, $R^2$ independently represents

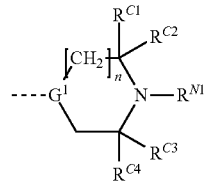

wherein
$G^1$ is C or N,
n is 1 or 2,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or $R^{C3}$ and $R^{C4}$ together with the atom to which they are attached form a cyclopropyl ring, and
$R^{N1}$ is selected from selected from hydrogen, methyl, ethyl, methoxyethyl, ethoxyethyl, hydroxyethyl propenyl, propynyl, i-propyl, —CH($CH_3$)$CH_2$OH, cyclopropyl, cyclobutyl, cyclopentyl, or
$R^{N1}$ and $R^{C4}$ together with the atoms to which they are attached form a 5- or 6-membered heterocyclyl ring.

In a further aspect of the invention $R^3$ represent hydrogen.
In a further embodiment of the invention X represents $CH_2$ or O.
In a further embodiment of the invention Y represents $CH_2$.
In a further embodiment of the invention a is 0, 1 or 2.
In a further embodiment of the invention b is 0, 1 or 2.
In a further aspect of the invention, b is 1.
In a further aspect of the invention, -A-$(R^1)_a$ represents a

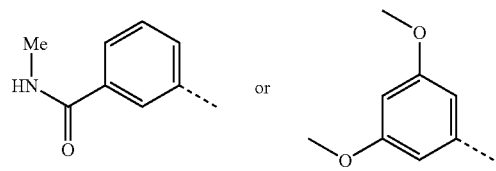

group.
In a further aspect of the invention, -A-$(R^1)_a$ represents a

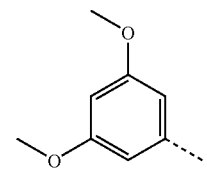

group.
In a further aspect of the invention, —B—$(R^2)_b$ represents a

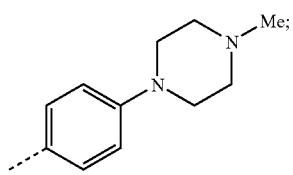

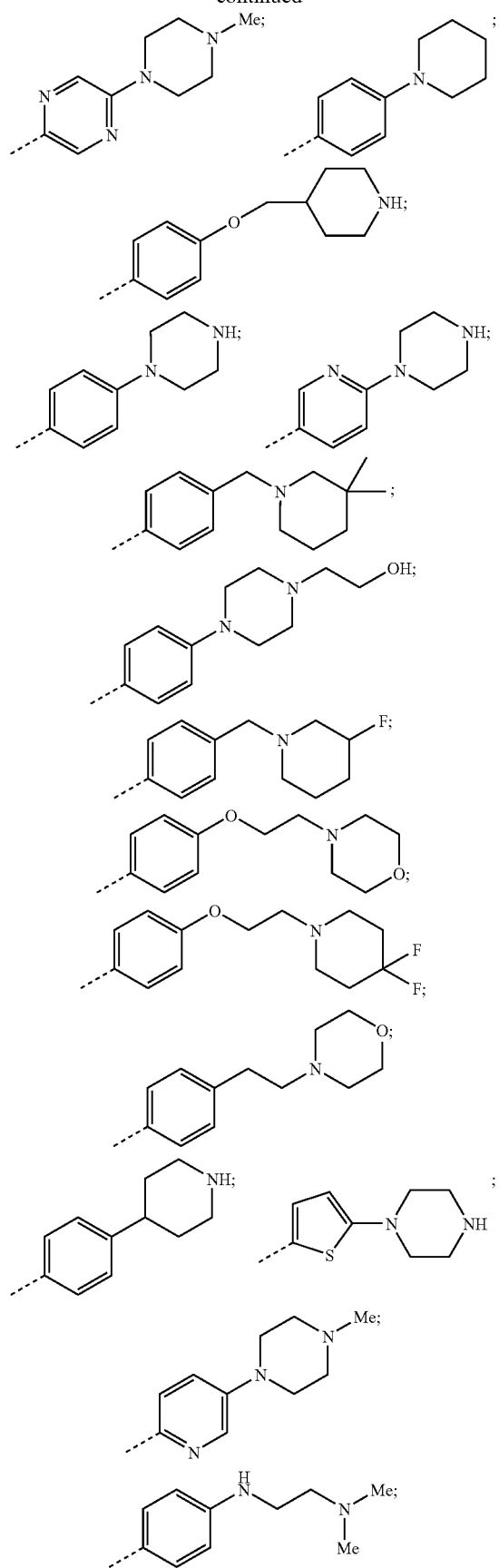
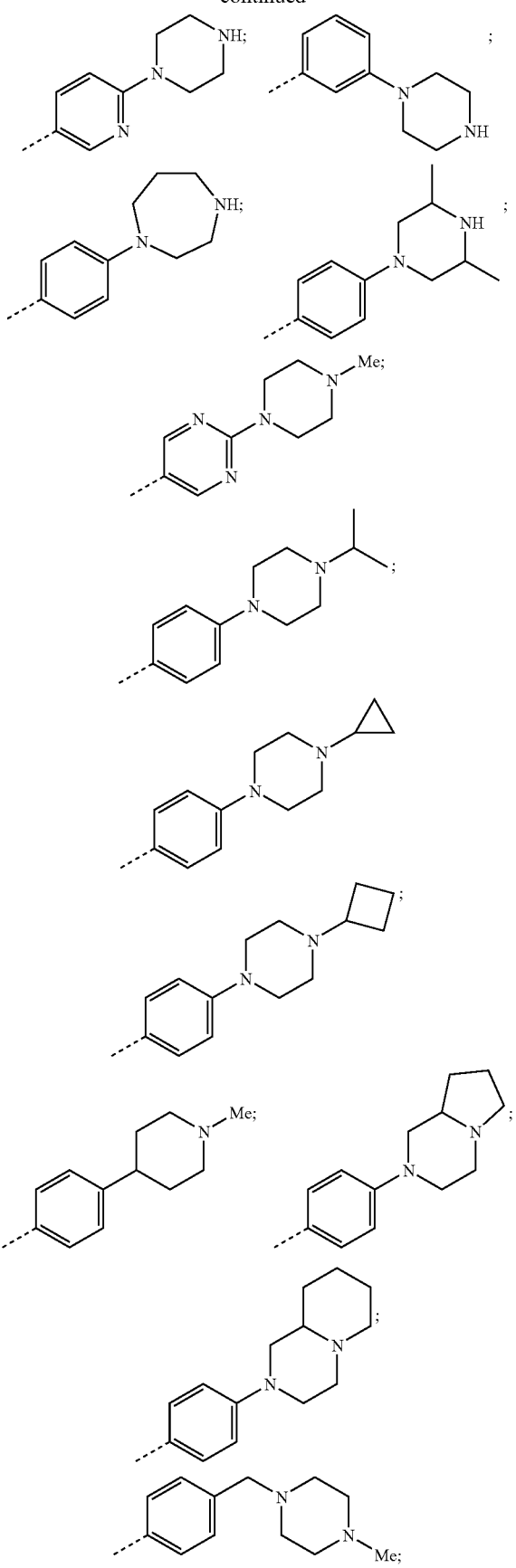

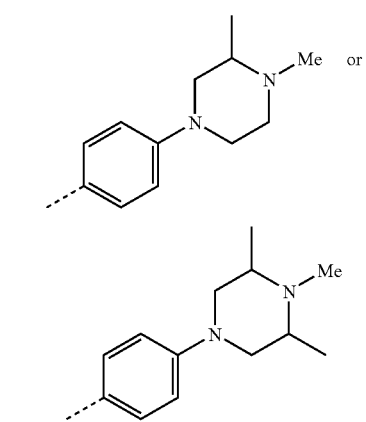
group.
In a further aspect of the invention, —B—$(R^2)_b$ represents a
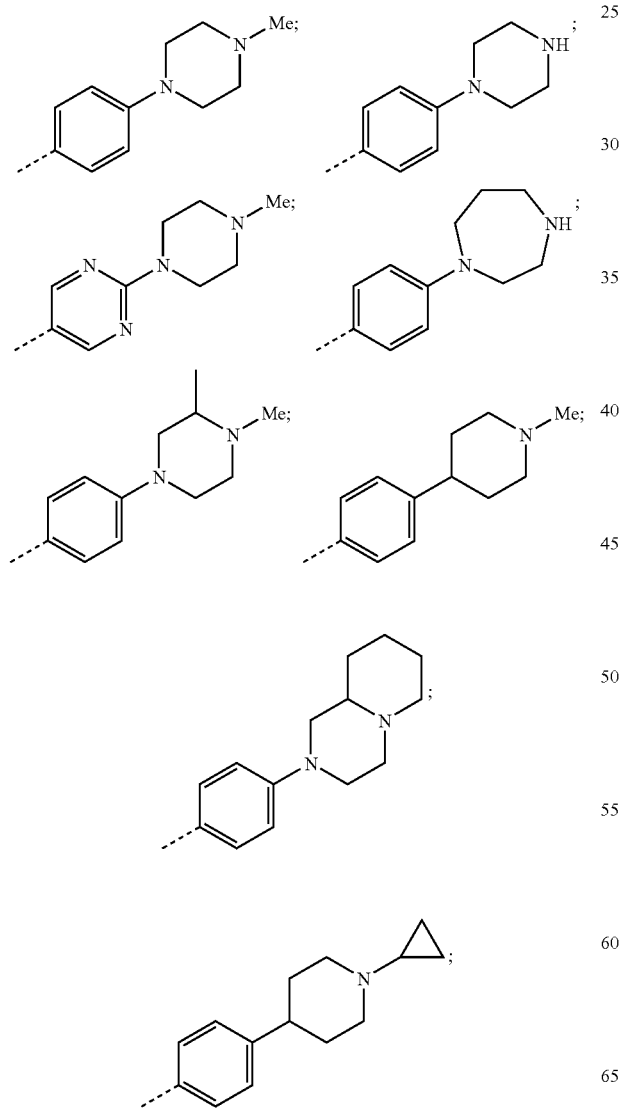
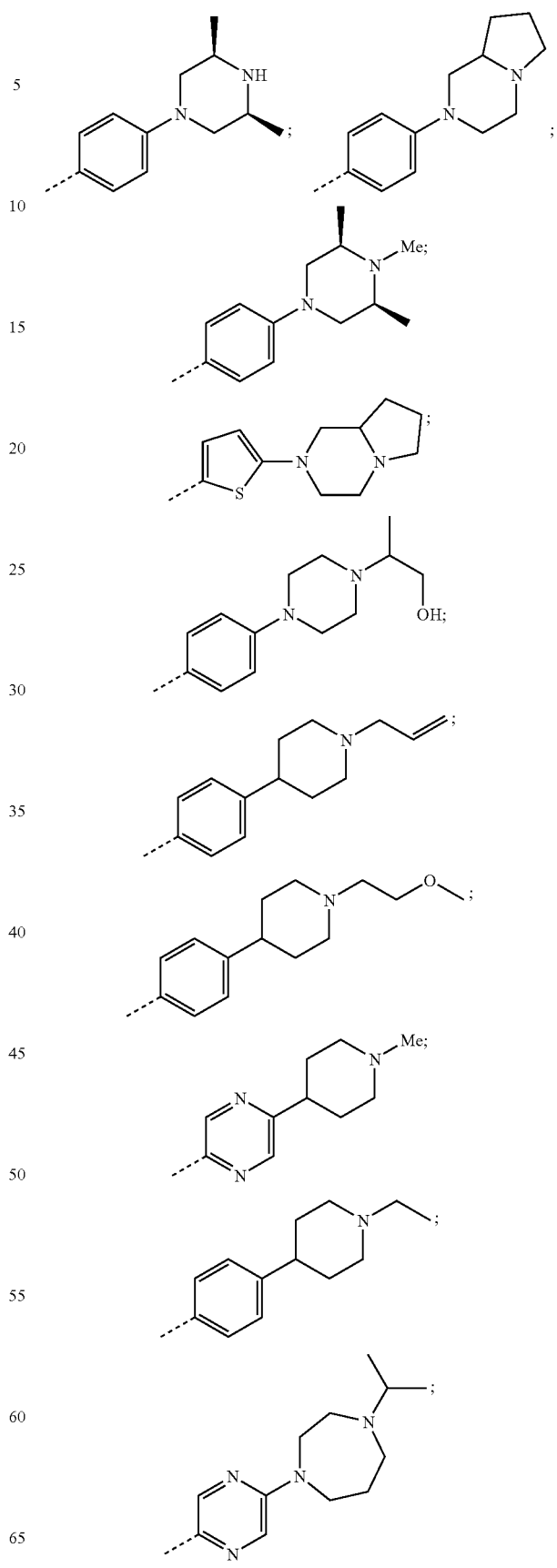

-continued
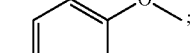
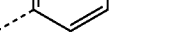
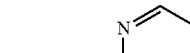
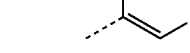
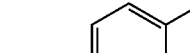
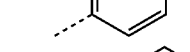
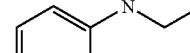
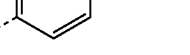
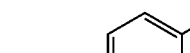
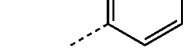
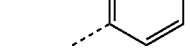
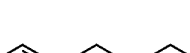
-continued
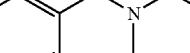
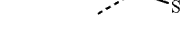

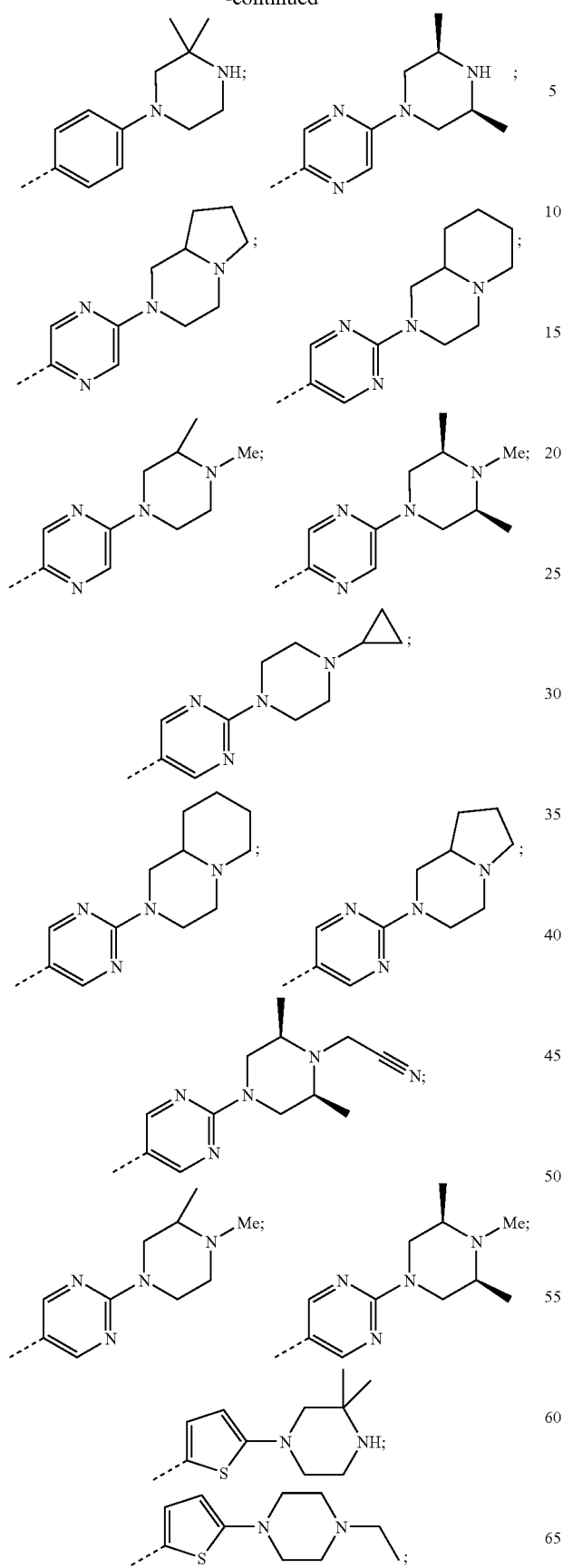
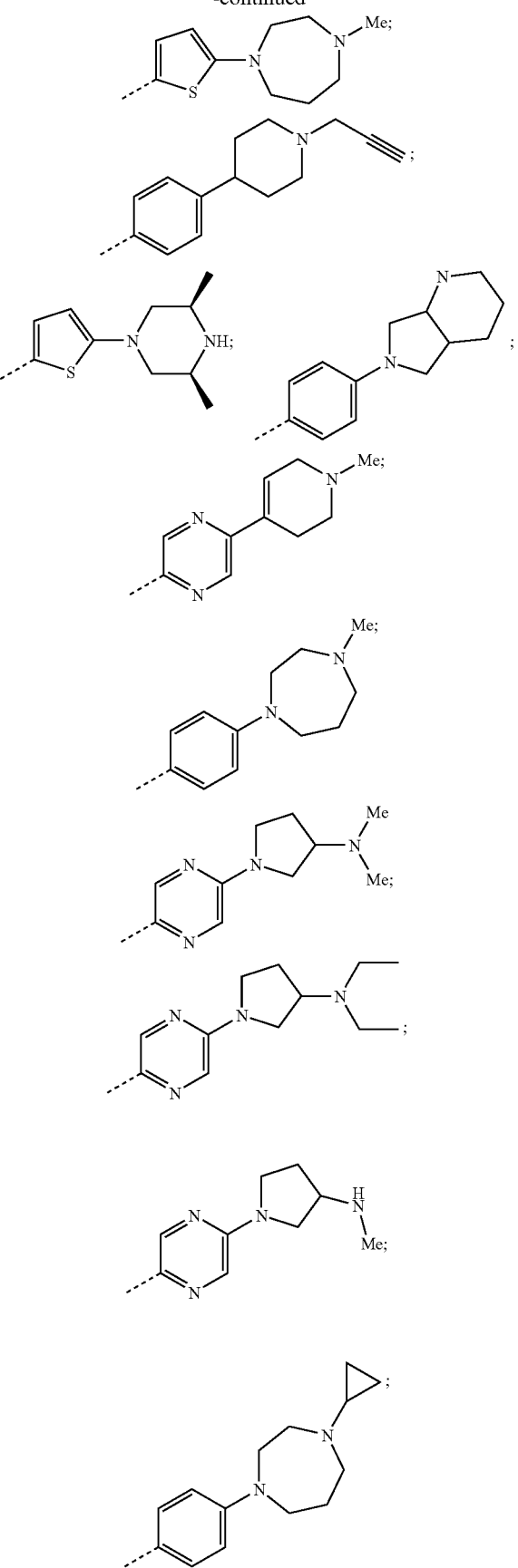

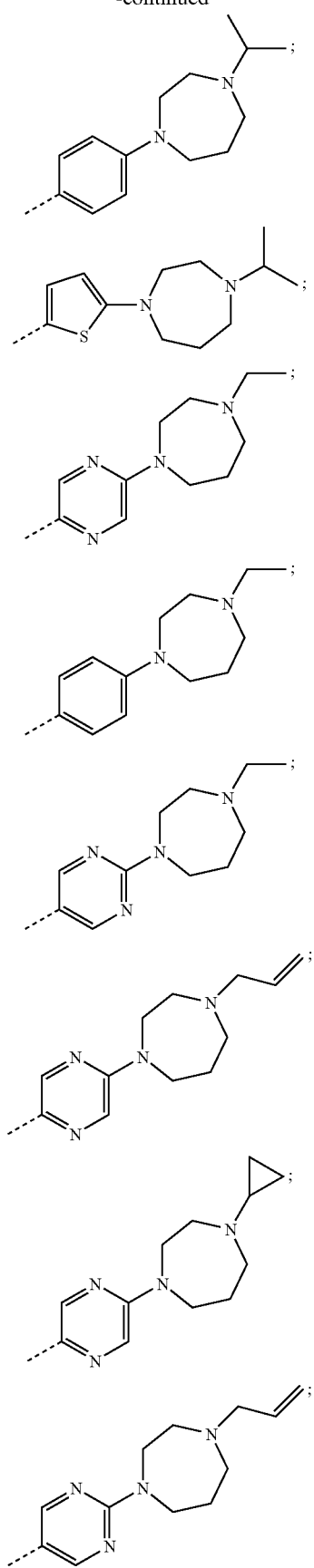
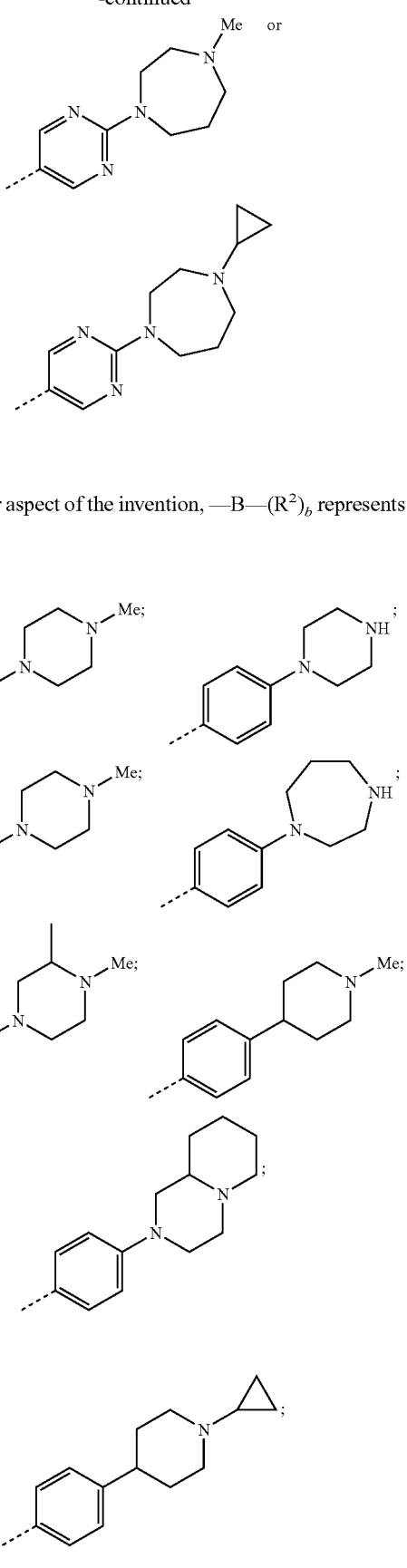
group.
In a further aspect of the invention, —B—(R²)$_b$ represents a

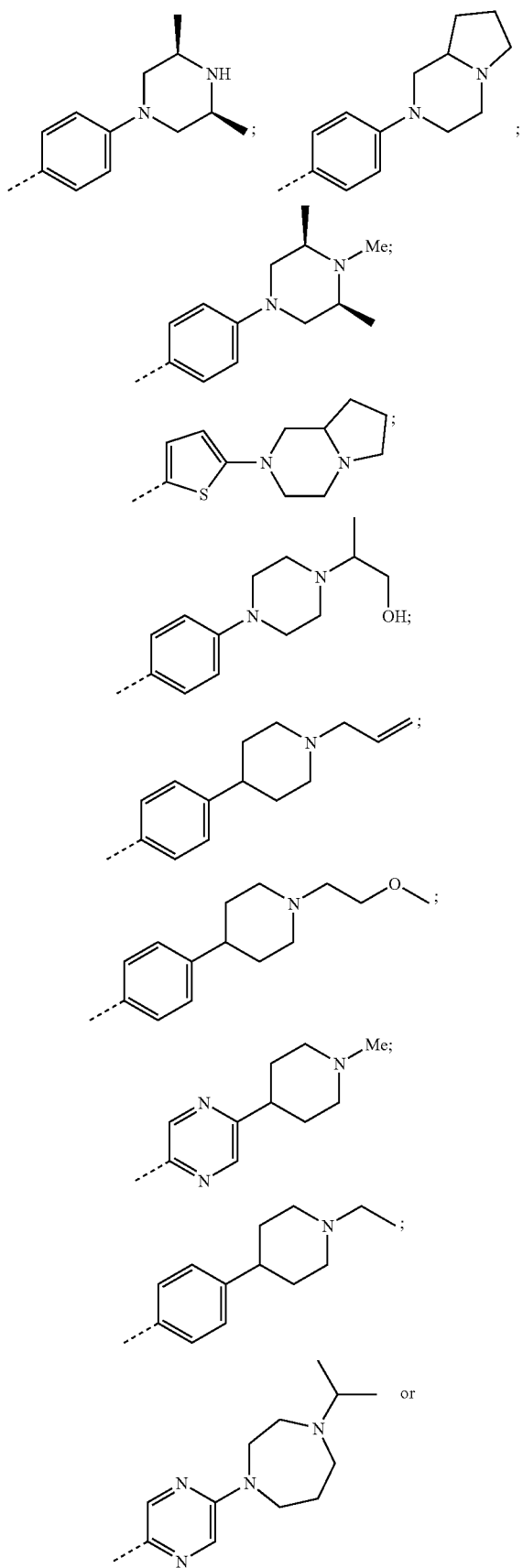

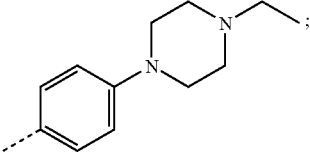

group.

In an embodiment of the invention, there is provided a subset of compounds of formula (I), or pharmaceutically acceptable salts thereof, wherein:

ring A represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

ring B represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

each $R^1$ independently represents a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or a —$CONR^{20}R^{21}$ group;

each $R^2$ independently represents a —$NR^{36}R^{37}$ group, a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$ cyclo alkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

a 4- to 7-membered heterocyclyl group optionally fused to a 4- to 7-membered carbocyclyl or heterocyclyl group and optionally substituted by one or more substituents selected from $C_1$-$C_6$alkyl, $C_2$-$C_6$alkenyl, $C_2$-$C_6$alkynyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, cyano, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, oxo, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen;
X represents $CH_2$ or O;
Y represents $CH_2$;
a is 0, 1 or 2; and
b is 0, 1 or 2.

In an embodiment of the invention, there is provided a subset of compounds of formula (I), or pharmaceutically acceptable salts thereof, wherein:

ring A represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

ring B represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

each $R^1$ independently represents
a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or a —$CONR^{20}R^{21}$ group;

each $R^2$ independently represents
a —$NR^{36}R^{37}$ group, a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen;
X represents $CH_{22}$; or O;
Y represents $CH_2$;
a is 0, 1 or 2; and
b is 0, 1 or 2.

In an embodiment of the invention, there is provided a subset of compounds of formula (I), or pharmaceutically acceptable salts thereof, wherein:

ring A represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

ring B represents a furyl, imidazolyl, isothiazolyl, isoxazolyl, oxadiazolyl, oxazolyl, phenyl, pyrazinyl, pyrazolyl, pyridazinyl, pyridyl, pyrimidinyl, pyrrolyl, tetrazolyl, thiadiazolyl, thiazolyl, thienyl, trazinyl or triazolyl ring;

each $R^1$ independently represents
  a halogen,
  a hydroxyl group,
  a $C_1$-$C_3$alkyl group optionally substituted by one or more substituents selected from $C_1$-$C_3$alkoxy, $C_3$-cycloalkyl, $C_1$-$C_3$alkylthio, —$NR^4R^5$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl,
  a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl,
  a —$CONR^{20}R^{21}$ group, or
  two adjacent $R^1$ groups together with the atoms to which they are attached form a 4- to 7-membered carbocyclyl or heterocyclyl ring optionally substituted by one or more substituents selected from $C_1$-$C_3$alkyl, $C_1$-$C_3$alkoxy, $C_3$-cycloalkyl, $C_1$-$C_3$alkylthio, —$NR^{27}R^{28}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

each $R^2$ independently represents
  a hydroxyl group,
  a halogen,
  a cyano group,
  a —$CO_2R^{29}$ group,
  a —$CONR^{30}R^{31}$ group,
  a —$NR^{32}COR^{33}$ group,
  a —$NR^{34}CO_2R^{35}$ group,
  a —$NR^{36}R^{37}$ group,
  a —$SO_2R^{38}$ group,
  a —$SO_2NR^{39}R^{40}$ group,
  a —$NR^{41}SO_2R^{42}$ group,
  a $C_1$-$C_6$alkyl group optionally substituted by one or more substituents selected from $C_1$-$C_6$alkoxy, $C_3$-$C_6$cycloalkyl, $C_1$-$C_6$alkylthio, —$NR^{43}R^{44}$, (each of which may be optionally substituted from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl and a 4- to 7-membered heterocyclyl group optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), halogen, hydroxyl, and a 4- to 7-membered heterocyclyl group optionally fused to a 4- to 7-membered carbocyclyl or heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), cyano, halogen and hydroxyl,
  a 4- to 7-membered heterocyclyl group optionally fused to a 4- to 7-membered carbocyclyl or heterocyclyl group and optionally substituted by one or more substituents selected from $C_1$-$C_6$alkyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or
  a $C_1$-$C_6$alkoxy group optionally substituted by one or more substituents selected from $C_1$-$C_6$alkoxy, $C_3$-$C_6$cycloalkyl, —$NR^{62}R^{63}$ (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{64}R^{65}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen;
X represents $CH_2$ or O;
Y represents $CH_2$;
a is 0, 1 or 2; and
b is 0, 1 or 2.

In another embodiment of the invention, there is provided a subset of compounds of formula (I), or pharmaceutically acceptable salts thereof, wherein:

ring A represents furyl, phenyl, pyrazinyl, pyridazinyl, pyridyl, pyrimidinyl or thienyl ring;

ring B represents furyl, phenyl, pyrazinyl, pyridazinyl, pyridyl, pyrimidinyl or thienyl ring;

each $R^1$ independently represents
  a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, is hydroxyl and trifluoromethyl), halogen and hydroxyl, or a —$CONR^{20}R^{21}$ group;

each $R^2$ independently represents a —$NR^{36}R^{37}$ group, a $C_1$-$C_6$alkyl group optionally substituted by one or more substituents selected from —$NR^{43}R^{44}$ (which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl, trifluoromethyl and a morpholine, piperidine or piperazine optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), and a morpholine, piperidine or piperazine optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or a morpholine, piperidine or piperazine optionally substituted by one or more substituents selected from $C_1$-$C_6$alkyl, $C_2$-$C_6$alkenyl, $C_2$-$C_6$alkynyl, $C_1$-$C_6$alkoxy, $C_1$-$C_6$alkylcarbonyl, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, cyano, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, oxo, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen;

X represents $CH_2$ or O;

Y represents $CH_2$;

a is 0, 1 or 2; and b is 0, 1 or 2.

In another embodiment of the invention, there is provided a subset of compounds of formula (I), or pharmaceutically acceptable salts thereof, wherein:

ring A represents furyl, phenyl, pyrazinyl, pyridazinyl, pyridyl, pyrimidinyl or thienyl ring;

ring B represents furyl, phenyl, pyrazinyl, pyridazinyl, pyridyl, pyrimidinyl or thienyl ring;

each $R^1$ independently represents a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or a —$CONR^{20}R^{21}$ group;

each $R^2$ independently represents a —$NR^{36}R^{37}$ group, a $C_1$-$C_6$alkyl group optionally substituted by one or more substituents selected from —$NR^{43}R^{44}$ (which may be optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl, is trifluoromethyl and a morpholine, piperidine or piperazine optionally substituted by one or more substituents selected from halogen, $C_1$-$C_3$alkyl, $C_1$-$C_3$alkoxy, $C_1$-$C_3$alkylthio, $C_3$-$C_6$cycloalkyl, amino (—$NH_2$), mono- and di-$C_1$-$C_3$alkylamino, cyano, hydroxyl trifluoromethyl), and a morpholine, piperidine or piperazine optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{45}R^{46}$, —$CO_2R^{47}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl, or a morpholine, piperidine or piperazine optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{56}R^{57}$, $SO_2R^{58}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen, hydroxyl and a 4- to 7-membered heterocyclyl group optionally substituted by one or more substituents selected from $C_1$-$C_6$alkyl, $C_1$-$C_6$alkoxy, $C_3$-$C_6$cycloalkyl, $C_1$-$C_6$alkylthio, —$NR^{59}R^{60}$, —$SO_2R^{61}$ (each of which may be optionally substituted by one or more substituents selected from halogen, $C_1$-$C_3$alkyl, $C_1$-$C_3$alkoxy, $C_1$-$C_3$alkylthio, amino (—$NH_2$), mono- and di-$C_1$-$C_3$alkylamino, hydroxyl and trifluoromethyl), halogen and hydroxyl;

$R^3$ represents hydrogen;

X represents $CH_2$ or O;

Y represents $CH_2$;

a is 0, 1 or 2; and b is 0, 1 or 2.

In another embodiment of the invention, there is provided a subset of compounds of formula (I), or pharmaceutically acceptable salts thereof, wherein:

ring A represents furyl, phenyl or pyridyl ring;

ring B represents phenyl, pyrazinyl, pyridyl, pyrimidinyl or thienyl ring;

each $R^1$ independently represents a methoxy group, —$OCH_2CH_2Ome$, —$CH_2NMe_2$ or two adjacent $R^1$ groups together form an —$OCH_2O$— bridge;

each $R^2$ independently represents a —Cl, —F, —I, —OH, —CN, —$CH_3$, —$CH_2OH$, —$CH_2N(CH_3)_2$, —$CH_2CH(CH_3)NH_2$, —$OCH_3$, —$OCH_2CH_2OH$, —$OCH_2CH_2OCH_2CH_3$, —$SO_2CH_3$, —$N(CH_3)_2$, —NHPh, —$NHCH_2C{\equiv}CH$, —$NHCH_2CH_3$, —$NHCH_2CH_2N(CH_3)_2$, —$NHCO_2CH_2CH{=}CH_2$, —$NHCOCH_3$, —NH- COH, —NHCOPh, —CONH₂, —NHSO₂Me, —SO₂N(CH₃)₂, —CO₂H, —CO₂CH₃, —CO₂CH₂CH₃,

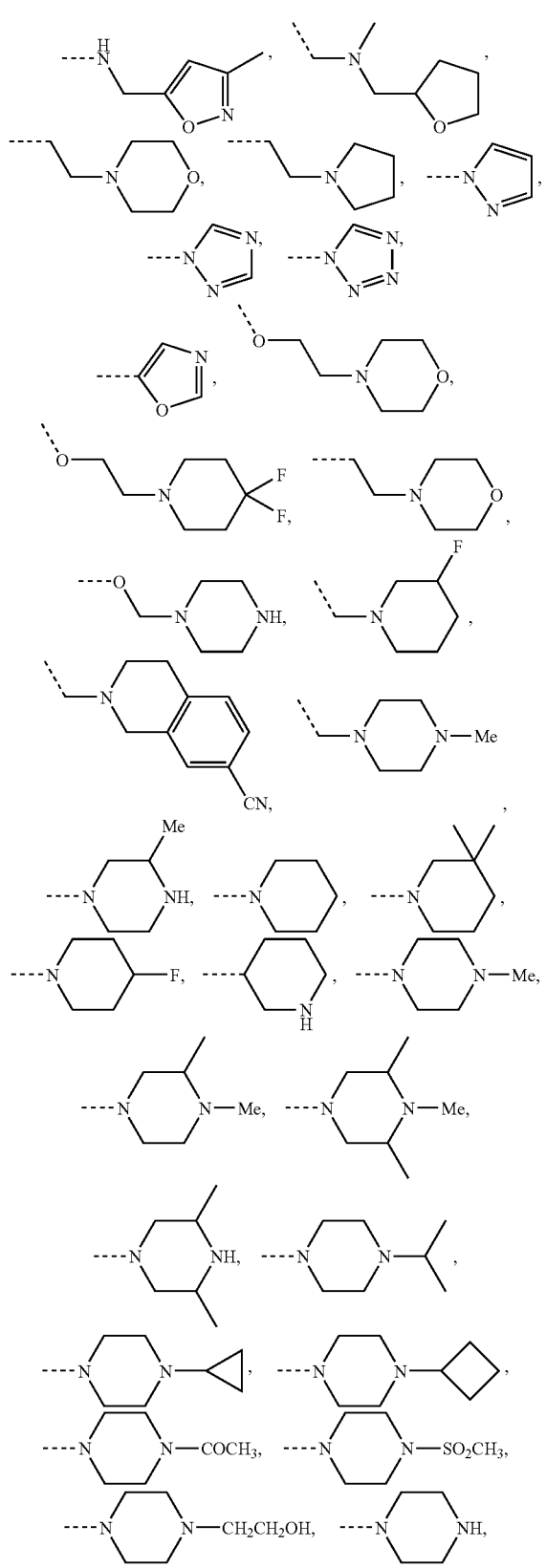

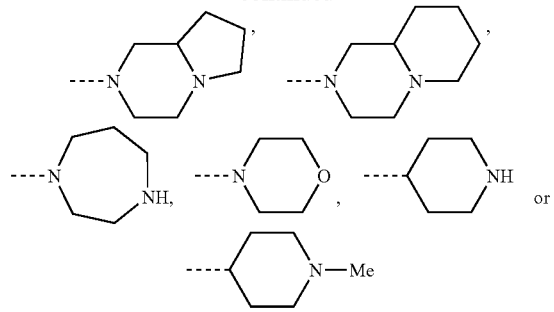

group;
R³ represents hydrogen;
X represents CH₂ or O;
Y represents CH₂;
a is 0, 1 or 2; and
b is 0, 1 or 2.

In a further aspect of the invention, there is provided a compound of formula (I), or pharmaceutically acceptable salts thereof, wherein:
ring A represents a furyl, phenyl, pyridyl or pyrimidinyl ring;
ring B represents a phenyl, pyridyl, pyrimidinyl or thienyl ring;
each R¹ independently represents —CONHMe or a methoxy group;
R² represents a

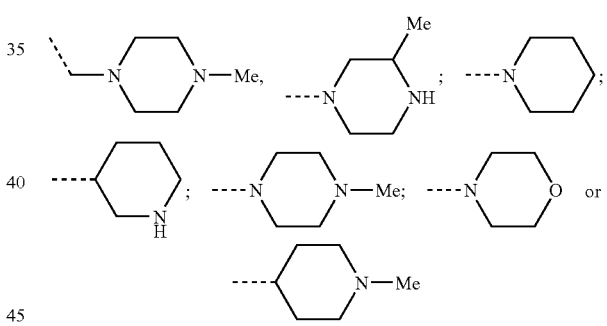

group;
X represents CH₂ or O;
Y represents CH₂;
a is 0, 1 or 2; and
b is 1.

In a further aspect of the invention, there is provided a compound of formula (I), or pharmaceutically acceptable salts thereof, wherein:
ring A represents furyl, phenyl, pyridyl or pyrimidinyl ring;
ring B represents a phenyl, pyridyl or pyrimidinyl ring;
R¹ represents methoxy;
R² represents a

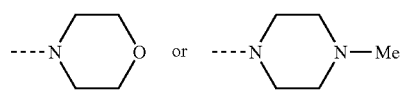

group;

X represents $CH_2$ or O;

a is 0, 1 or 2; and b is 1, or a pharmaceutically acceptable salt thereof.

In another embodiment of the invention, there is provided a subset of compounds of formula (I), or pharmaceutically acceptable salts thereof, wherein:

-A-$(R^1)_a$ represents a

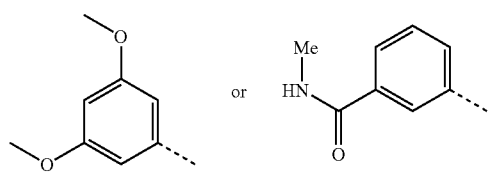

group;

ring B represents phenyl, pyrazinyl, pyridyl, pyrimidinyl or thienyl ring;

each $R^2$ independently represents a —OMe, —$OCH_2CH_2OCH_2CH_3$, —$OCH_2CH_2OH$, —$CH_2N(CH_3)_2$, —$NHCH_2CH_2N(CH_3)_2$,

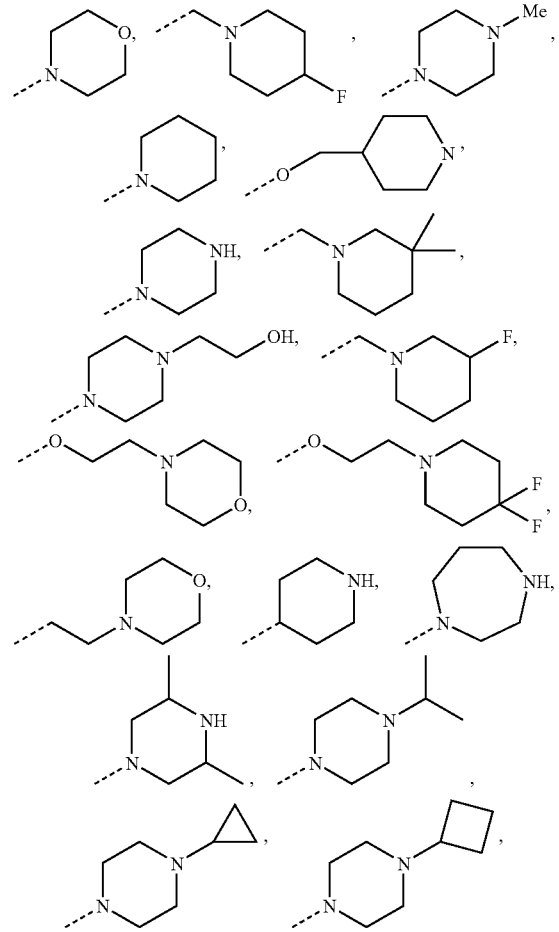

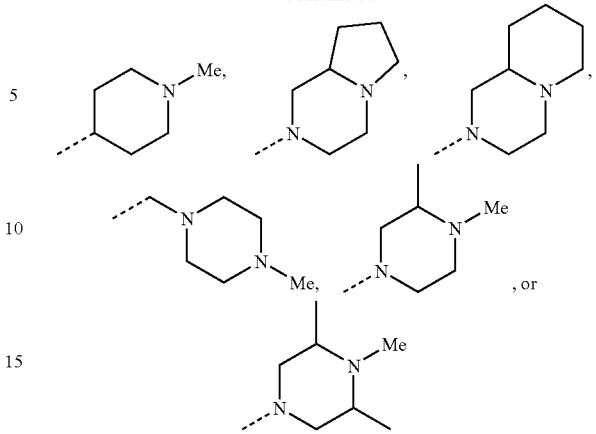

group;

$R^3$ represents hydrogen;

X represents $CH_2$ or O;

Y represents $CH_2$;

b is 1.

In a further aspect of the invention, there is provided a compound of formula (I), or pharmaceutically acceptable salts thereof, wherein:

-A-$(R^1)_a$ represents a group;

—B—$(R^2)_b$ represents a

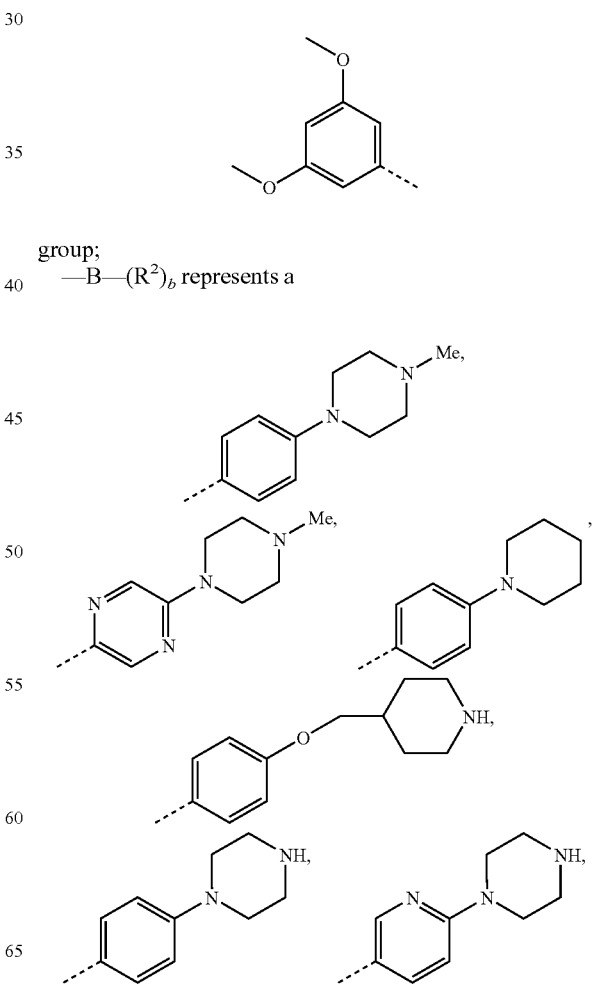

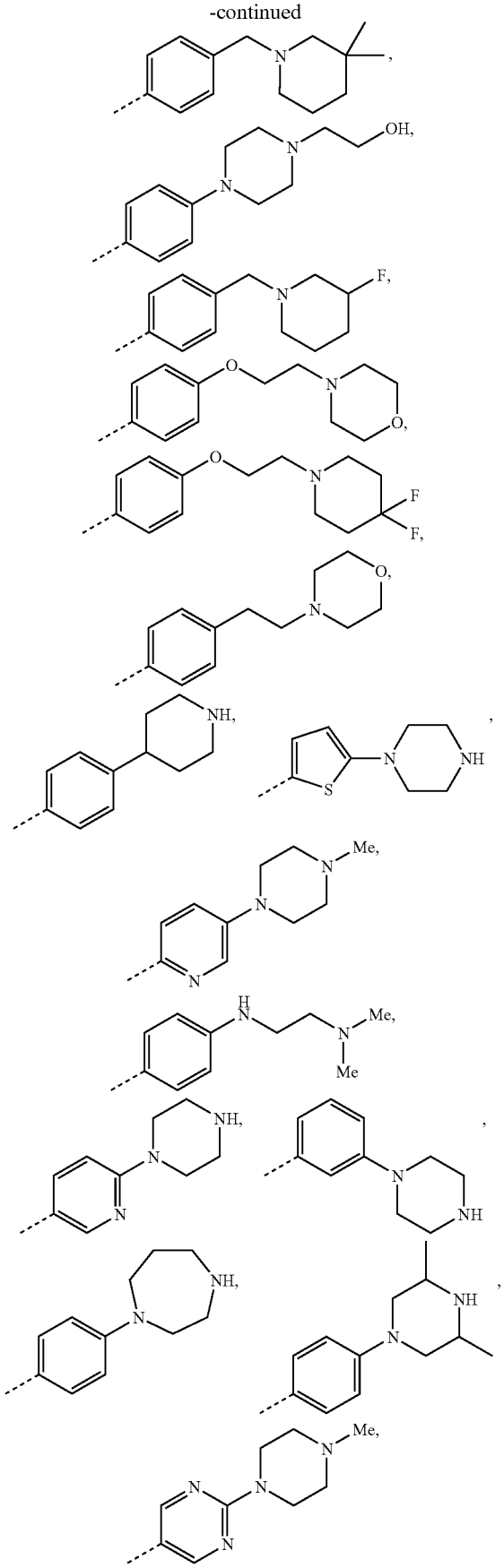
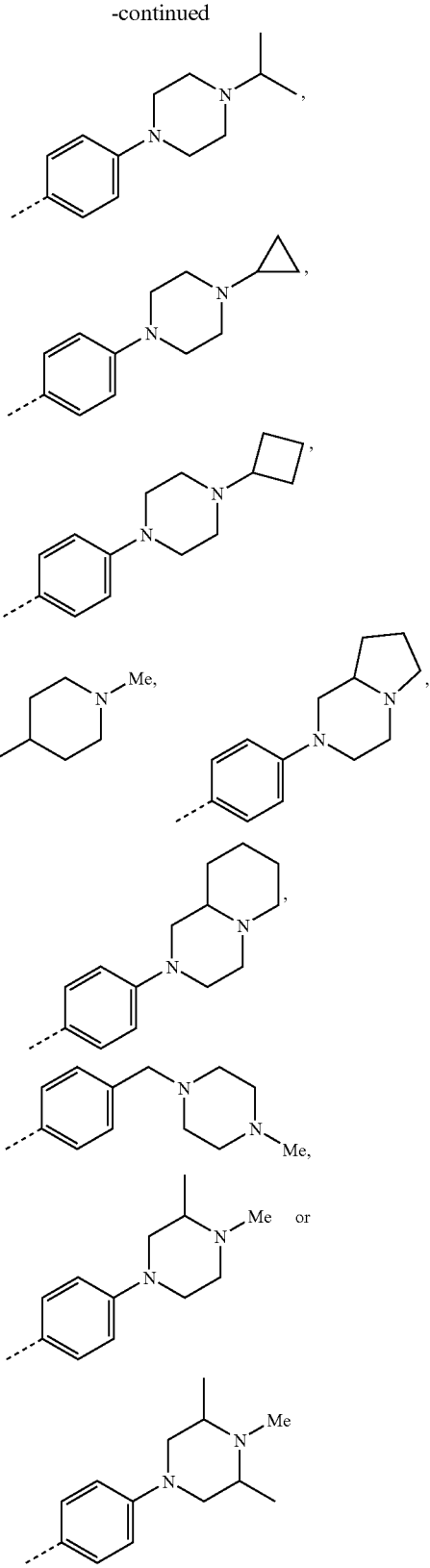
group; and
X represents CH$_2$ or O,
or a pharmaceutically acceptable salt thereof.

In a further aspect of the invention, there is provided a compound of formula (I), or pharmaceutically acceptable salts thereof, wherein:
-A-(R$^1$)$_a$ represents a
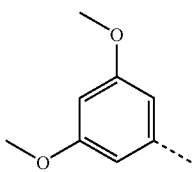
group;
—B—(R$^2$)$_b$ represents a
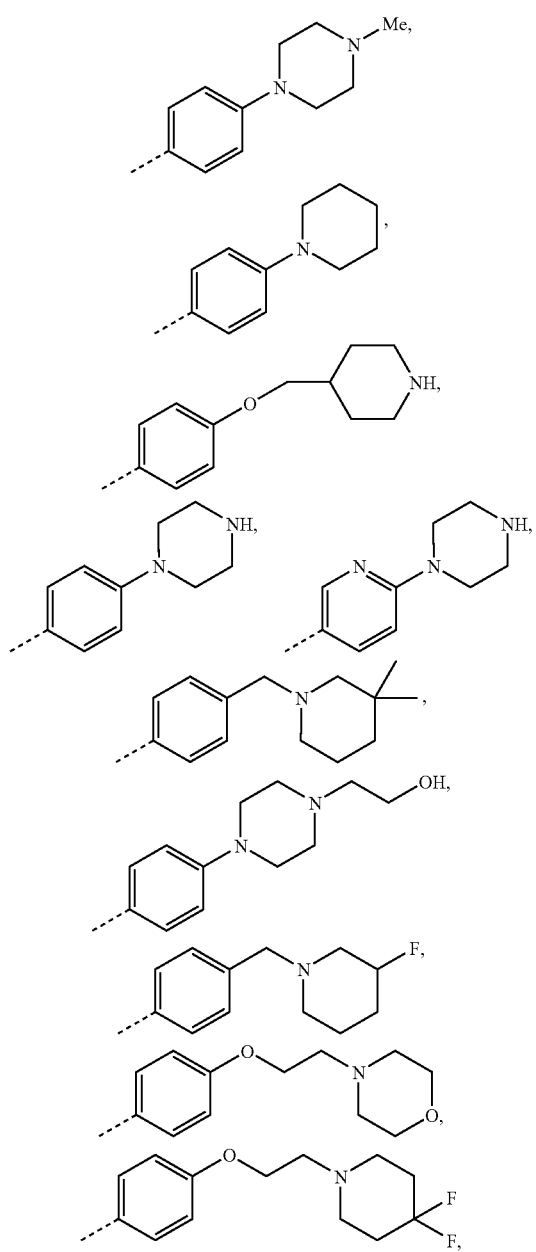
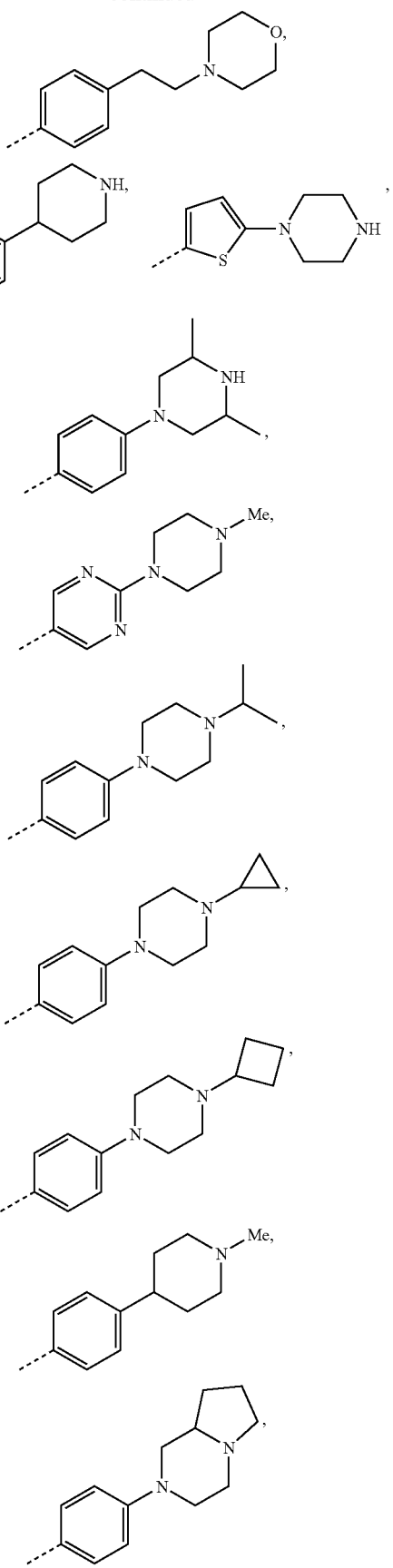

-continued

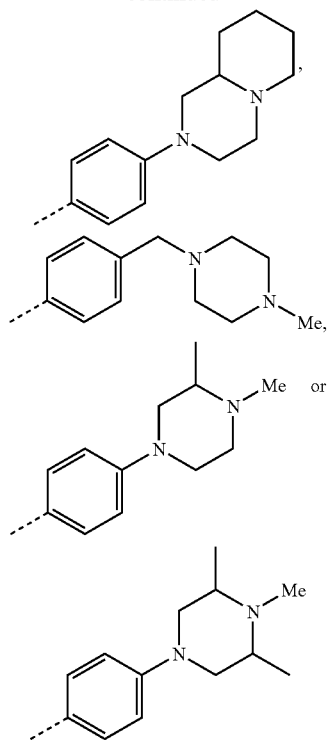

group; and

X represents CH$_2$, or a pharmaceutically acceptable salt thereof.

In a further aspect of the invention, there is provided a compound of formula (I), or pharmaceutically acceptable salts thereof, wherein:

-A-(R$^1$)$_a$ represents a

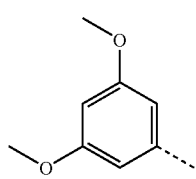

group;

—B—(R$^2$)$_b$ represents a

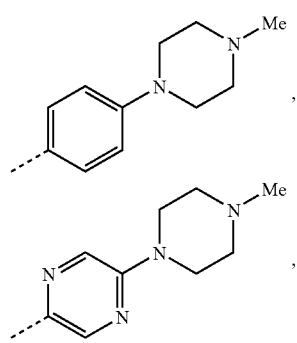

-continued

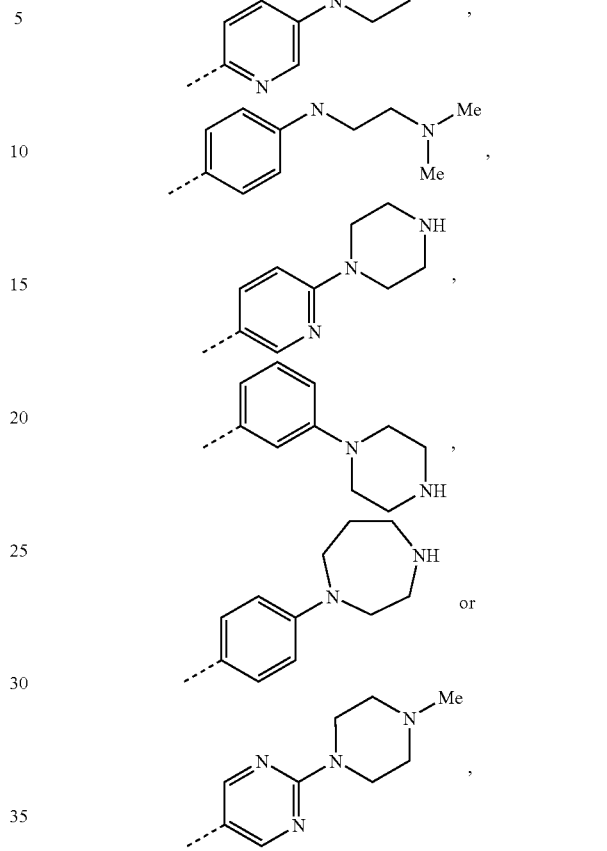

group; and

X represents O, or a pharmaceutically acceptable salt thereof.

In a further aspect of the invention, there is provided a compound of formula (I), or pharmaceutically acceptable salts thereof, wherein:

-A-(R$^1$)$_a$ represents a

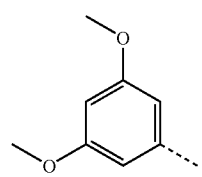

group; and

—B—(R$^2$)$_b$ represents a

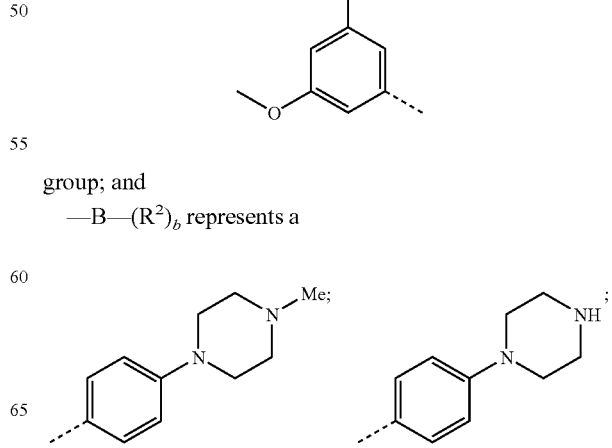

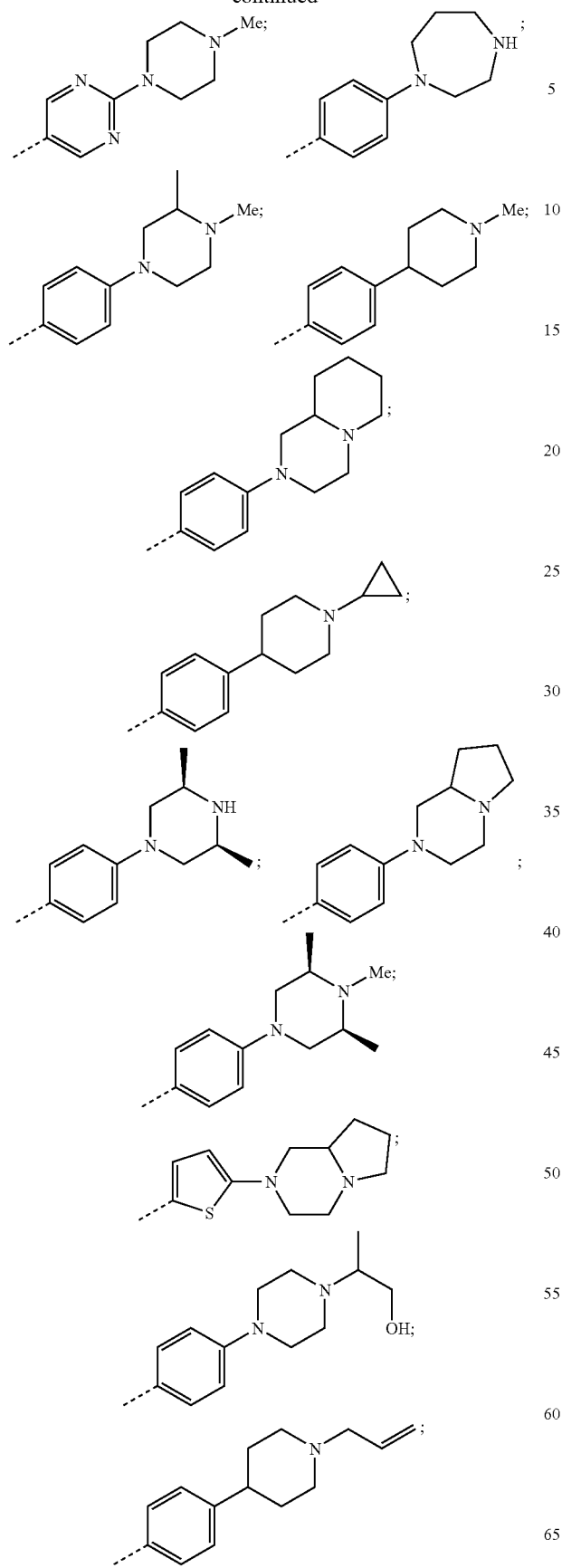
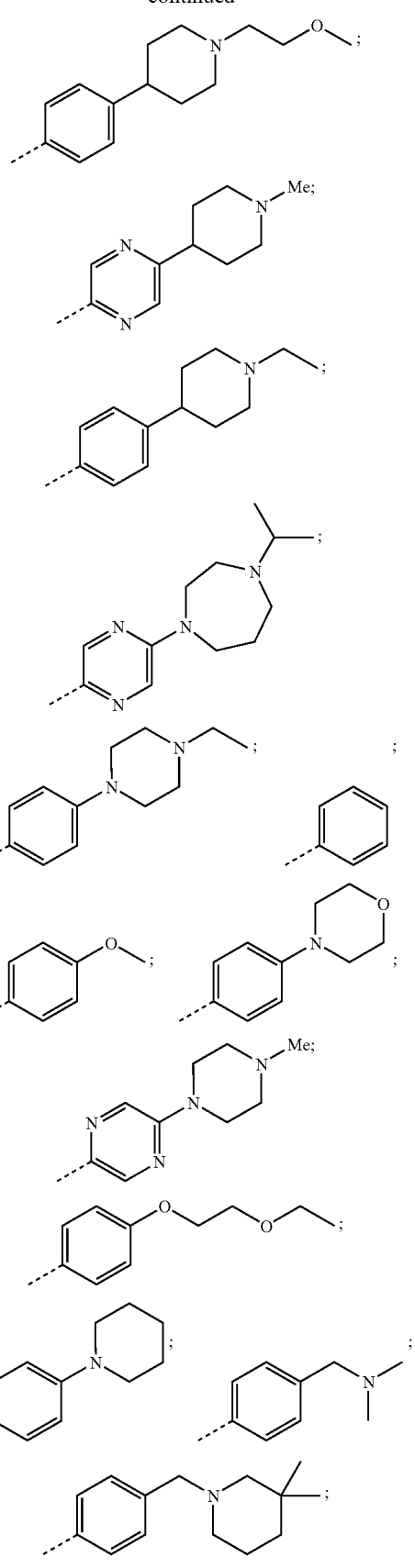

-continued
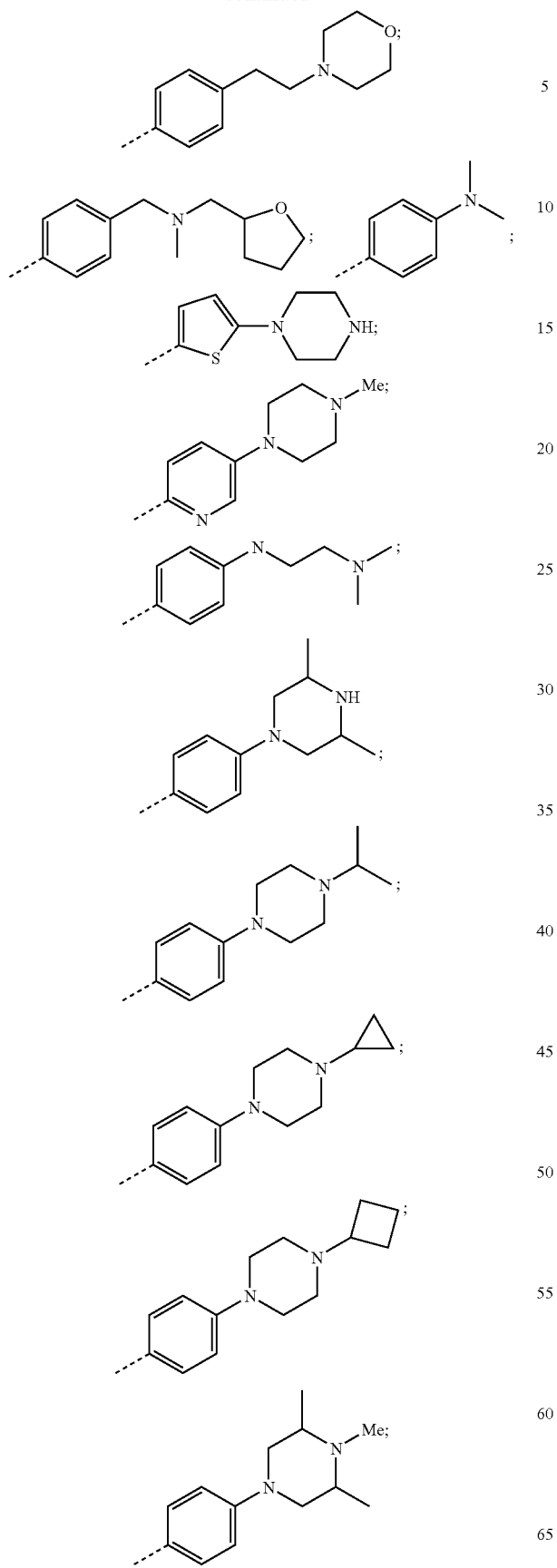
-continued
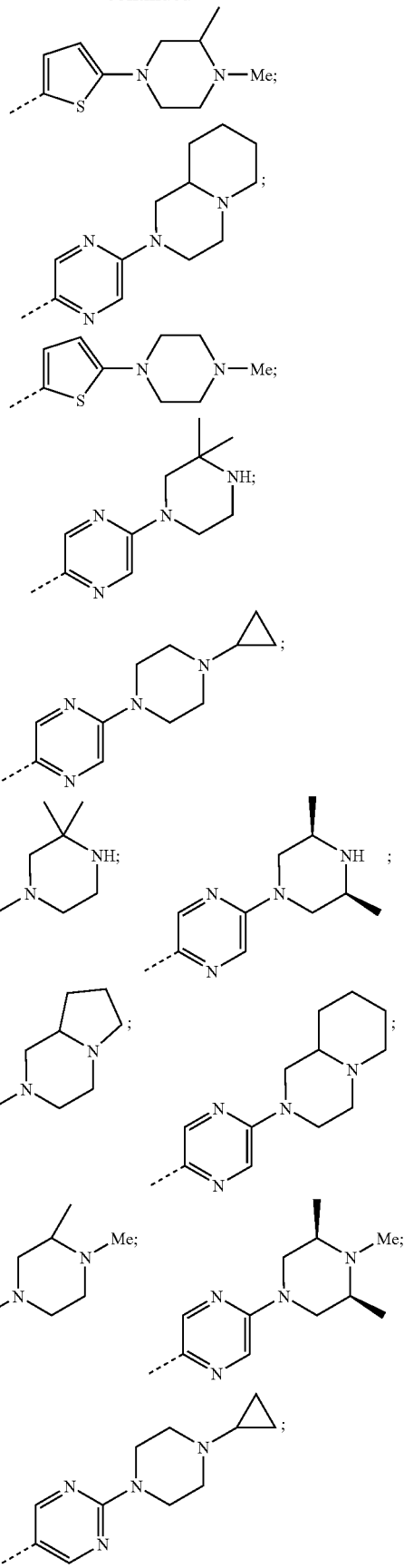

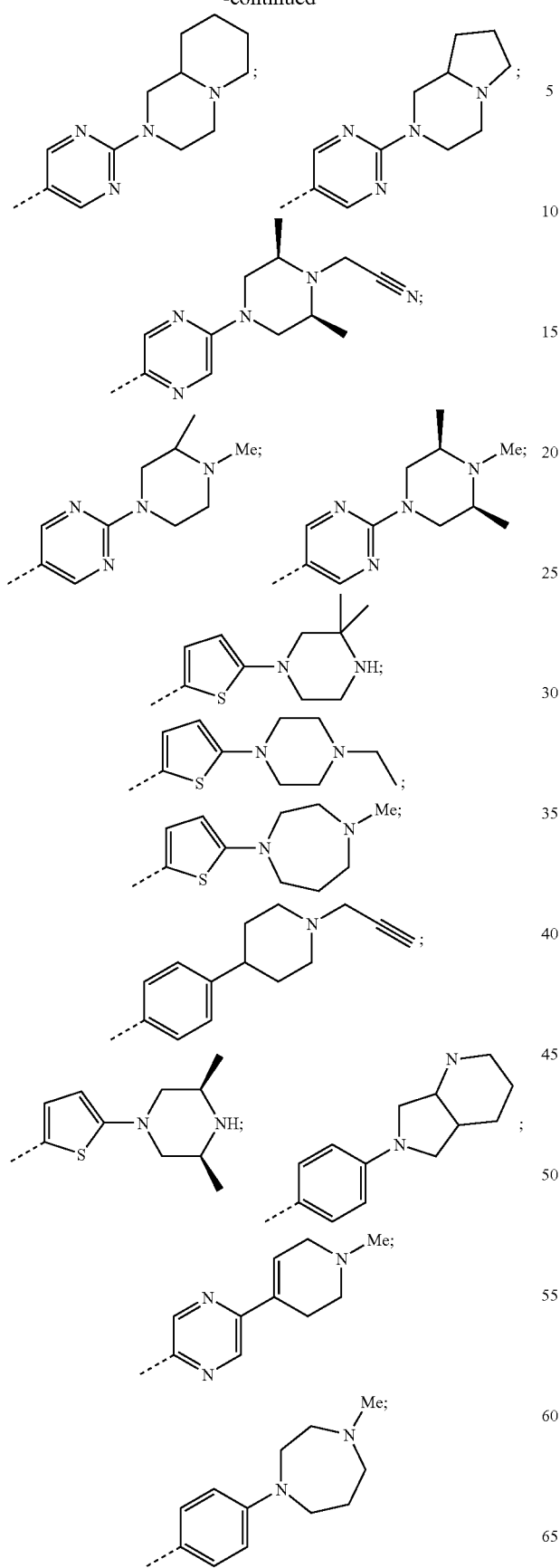
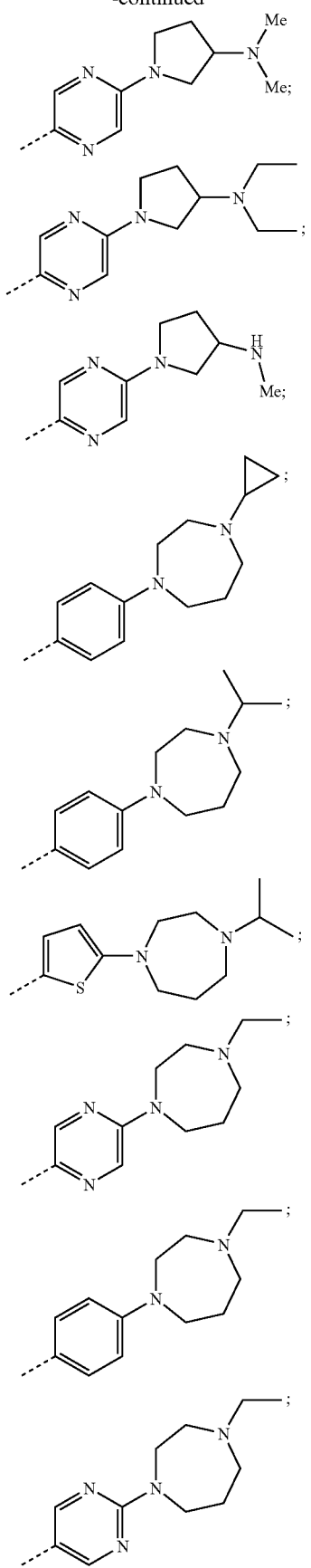

-continued
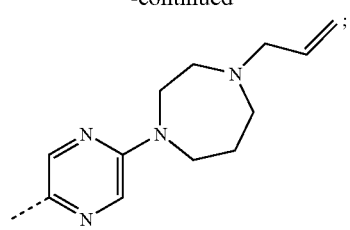
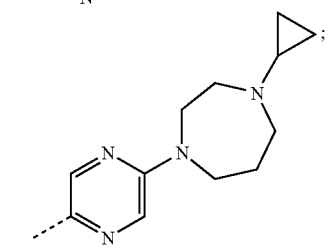
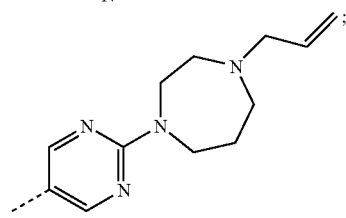
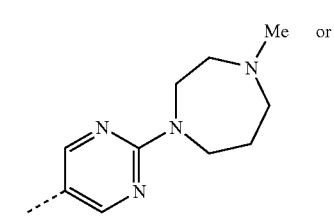
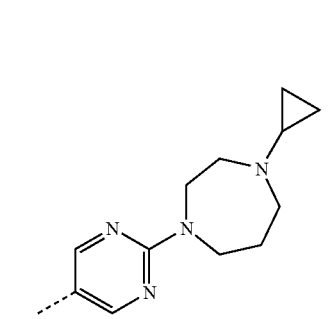
group.
In a further aspect of the invention, there is provided a compound of formula (I), or pharmaceutically acceptable salts thereof, wherein:
-A-(R$^1$)$_a$ represents a
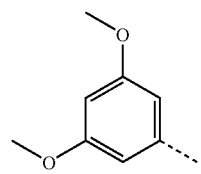
group; and
—B—(R$^2$)$_b$ represents a
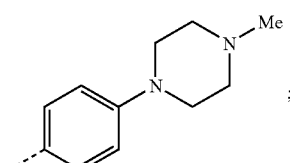
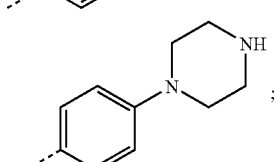
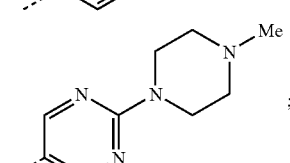
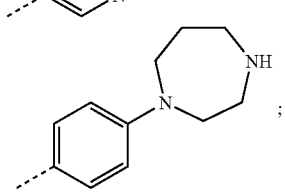
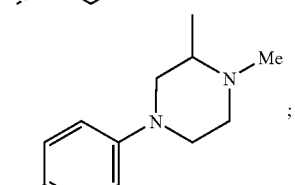
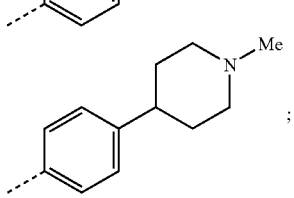
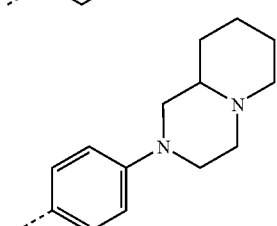
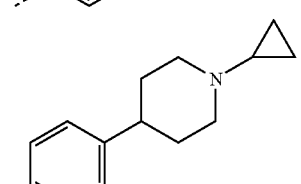
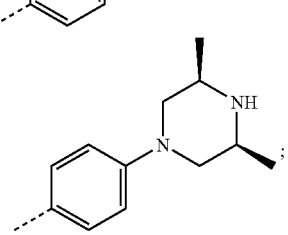

-continued

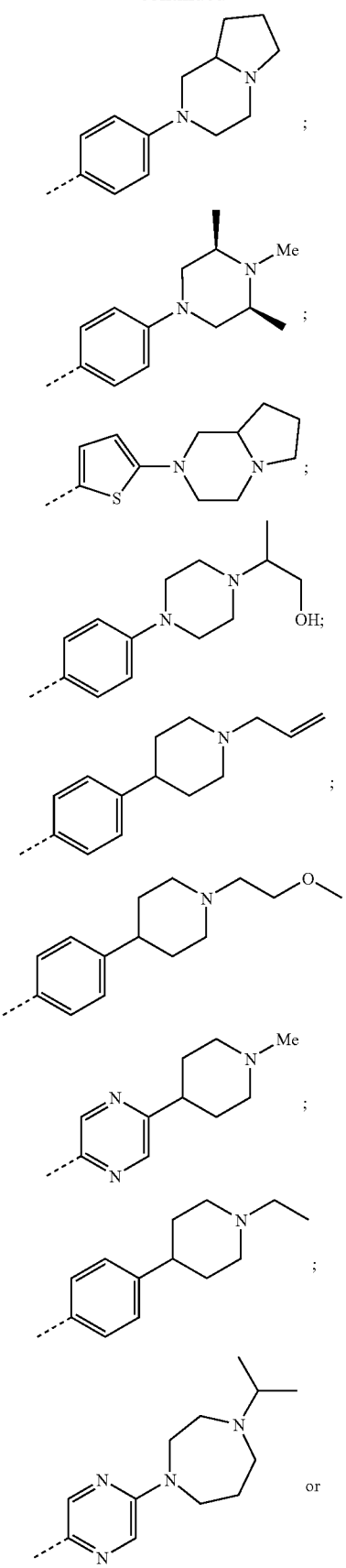

-continued

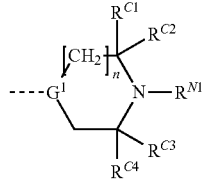

group.

In another embodiment of the invention, there is provided a subset of compounds of formula (I), or pharmaceutically acceptable salts thereof, wherein:

ring A represents furyl, phenyl, pyrazinyl, pyridazinyl, pyridyl, pyrimidinyl, thienyl or thiazolyl ring;

ring B represents furyl, phenyl, pyrazinyl, pyridazinyl, pyridyl, pyrimidinyl, thienyl or thiazolyl ring;

each $R^1$ independently represents
a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or
a —$CONR^{20}R^{21}$ group;

$R^2$ represents $$\text{----}G^1 \underset{\underset{R^{C4}}{R^{C3}}}{\overset{\overset{R^{C1}}{R^{C2}}}{\underset{[CH_2]_n}{\bigg\langle}}} N\text{—}R^{N1}$$

wherein $G^1$ is C or N, n is 1 or 2, $R^{C1}$, $R^{C2}$, $R^{C3}$ and $R^{C4}$ are each independently selected from $C_1$-$C_3$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen, halogen and hydroxyl, or $R^{C1}$ and $R^{C2}$ and/or $R^{C3}$ and $R^{C4}$ together with the atom to which they are attached form a 3- to 6-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, or $R^{C1}$ and $R^{C3}$ together with the atoms to which they are attached and the nitrogen atom to which the $R^{N1}$ group is attached form a 5- to 7-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, and $R^{N1}$ is selected from selected from $C_1$-$C_4$alkyl, $C_2$-$C_4$alkenyl, $C_2$-$C_4$alkynyl, $C_3$-$C_6$cycloalkyl, (each of which may be optionally substituted by one or more substituents selected from cyano, halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen and a 4- to 7-membered heterocyclyl group optionally substituted by one or more substituents selected from $C_1$-$C_3$alkyl, $C_1$-$C_3$alkoxy, $C_3$-$C_5$cycloalkyl, $C_1$-$C_3$alkylthio, —$NR^{59}R^{60}$, —$SO_2R^{61}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen and hydroxyl, or $R^{N1}$ and $R^{C4}$ together with the atoms to which they are attached form a 4- to 7-membered heterocyclyl ring optionally substituted by one or more substituents selected from $C_1$-$C_3$alkyl, $C_2$-$C_3$alkenyl, $C_2$-$C_3$alkynyl, $C_1$-$C_3$alkoxy, $C_3$-$C_5$cycloalkyl, $C_1$-$C_3$alkylthio, —$NR^{56}R^{57}$, $SO_2R^{58}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen, hydroxyl;

$R^3$ represents hydrogen;

X represents $CH_2$ or O;

Y represents $CH_2$;

a is 0, 1 or 2; and b is 1.

In another embodiment of the invention, there is provided a subset of compounds of formula (I), or pharmaceutically acceptable salts thereof, wherein:

ring A represents furyl, phenyl, pyrazinyl, pyridazinyl, pyridyl, pyrimidinyl or thienyl ring;

ring B represents furyl, phenyl, pyrazinyl, pyridazinyl, pyridyl, pyrimidinyl or thienyl ring;

each $R^1$ independently represents a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or a —$CONR^{20}R^{21}$ group;

$R^2$ represents

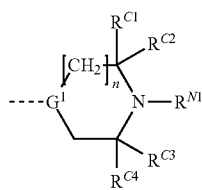

wherein $G^1$ is C or N, n is 1 or 2, $R^{C1}$, $R^{C2}$, $R^{C3}$ and $R^{C4}$ are each independently selected from $C_1$-$C_3$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen, halogen and hydroxyl, or $R^{C1}$ and $R^{C2}$ and/or $R^{C3}$ and $R^{C4}$ together with the atom to which they are attached form a 3- to 6-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, or $R^{C1}$ and $R^{C3}$ together with the atoms to which they are attached and the nitrogen atom to which the $R^{N1}$ group is attached form a 5- to 7-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, and $R^{N1}$ is selected from selected from $C_1$-$C_4$alkyl, $C_2$-$C_4$alkenyl, $C_2$-$C_4$alkynyl, $C_3$-$C_6$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen and a 4- to 7-membered heterocyclyl group optionally substituted by one or more substituents selected from $C_1$-$C_3$alkyl, $C_1$-$C_3$alkoxy, $C_3$-$C_5$cycloalkyl, $C_1$-$C_3$alkylthio, —$NR^{59}R^{60}$, —$SO_2R^{61}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen and hydroxyl, or $R^{N1}$ and $R^{C4}$ together with the atoms to which they are attached form a 4- to 7-membered heterocyclyl ring optionally substituted by one or more substituents selected from $C_1$-$C_3$alkyl, $C_2$-$C_3$alkenyl, $C_2$-$C_3$alkynyl, $C_1$-$C_3$alkoxy, $C_3$-$C_5$cycloalkyl, $C_1$-$C_3$alkylthio, —$NR^{56}R^{57}$, $SO_2R^{58}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen, hydroxyl;

$R^3$ represents hydrogen;

X represents $CH_2$ or O;

Y represents $CH_2$;

a is 0, 1 or 2; and b is 1.

In another embodiment of the invention, there is provided a subset of compounds of formula (I), or pharmaceutically acceptable salts thereof, wherein:

ring A represents furyl, phenyl or pyridyl ring;

ring B represents phenyl, pyrazinyl, pyridyl, pyrimidinyl or thienyl ring;

each $R^1$ independently represents a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or a —$CONR^{20}R^{21}$ group;

$R^2$ represents

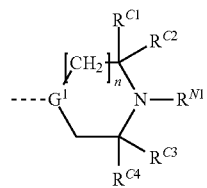

wherein
$G^1$ is C or N,
n is 1 or 2,
$R^{C1}$, $R^{C2}$, $R^{C3}$ and $R^{C4}$ are each independently selected from $C_1$-$C_3$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen, halogen and hydroxyl, or
$R^{C1}$ and $R^{C2}$ and/or $R^{C3}$ and $R^{C4}$ together with the atom to which they are attached form a 3- to 6-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, or
$R^{C1}$ and $R^{C3}$ together with the atoms to which they are attached and the nitrogen atom to which the $R^{N1}$ group is attached form a 5- to 7-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, and
$R^{N1}$ is selected from selected from $C_1$-$C_4$alkyl, $C_2$-$C_4$alkenyl, $C_2$-$C_4$alkynyl, $C_3$-$C_6$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen and a 4- to 7-membered heterocyclyl group optionally substituted by one or more substituents selected from $C_1$-$C_3$alkyl, $C_1$-$C_3$alkoxy, $C_3$-$C_5$cycloalkyl, $C_1$-$C_3$alkylthio, —$NR^{59}R^{60}$, —$SO_2R^{61}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen and hydroxyl, or
$R^{N1}$ and $R^{C4}$ together with the atoms to which they are attached form a 4- to 7-membered heterocyclyl ring optionally substituted by one or more substituents selected from $C_1$-$C_3$alkyl, $C_2$-$C_3$alkenyl, $C_2$-$C_3$alkynyl, $C_1$-$C_3$alkoxy, $C_3$-$C_5$cycloalkyl, $C_1$-$C_3$alkylthio, —$NR^{56}R^{57}$, $SO_2R^{58}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen, hydroxyl;
$R^3$ represents hydrogen;
X represents $CH_2$ or O;
Y represents $CH_2$;
a is 0, 1 or 2; and
b is 1.

In another embodiment of the invention, there is provided a subset of compounds of formula (I), or pharmaceutically acceptable salts thereof, wherein:
ring A represents phenyl ring;
ring B represents phenyl, pyrazinyl, pyridyl, pyrimidinyl or thienyl ring;
each $R^1$ independently represents
a $C_1$-$C_3$alkoxy group optionally substituted by one or more substituents selected from $C_1$-$C_3$alkoxy, $C_3$-cycloalkyl, —$NR^{14}R^{15}$, (each of which may be optionally substituted by one or more substituents selected from halogen, $C_1$-$C_3$alkyl, $C_1$-$C_3$alkoxy, amino (—$NH_2$), mono- and di-$C_1$-$C_3$alkylamino, hydroxyl and trifluoromethyl), halogen and hydroxyl, or
a —$CONR^{20}R^{21}$ group;
$R^2$ represents

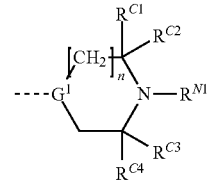

wherein
$G^1$ is C or N,
n is 1 or 2,
$R^{C1}$, $R^{C2}$, $R^{C3}$ and $R^{C4}$ are each independently selected from $C_1$-$C_3$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen, halogen and hydroxyl, or
$R^{C1}$ and $R^{C2}$ and/or $R^{C3}$ and $R^{C4}$ together with the atom to which they are attached form a 3- to 6-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, or
$R^{C1}$ and $R^{C3}$ together with the atoms to which they are attached and the nitrogen atom to which the $R^{N1}$ group is attached form a 5- to 7-membered carbocyclic or heterocyclic ring optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl, and
$R^{N1}$ is selected from selected from $C_1$-$C_4$alkyl, $C_2$-$C_4$alkenyl, $C_2$-$C_4$alkynyl, $C_3$-$C_6$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), hydrogen and a 4- to 7-membered heterocyclyl group optionally substituted by one or more substituents selected from $C_1$-$C_3$alkyl, $C_1$-$C_3$alkoxy, $C_3$-$C_5$cycloalkyl, $C_1$-$C_3$alkylthio, —$NR^{59}R^{60}$, —$SO_2R^{61}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen and hydroxyl, or $R^{N1}$ and $R^{C4}$ together with the atoms to which they are attached form a 4- to 7-membered heterocyclyl ring optionally substituted by one or more substituents selected from $C_1$-$C_3$alkyl, $C_2$-$C_3$alkenyl, $C_2$-$C_3$alkynyl, $C_1$-$C_3$alkoxy, $C3$-$C_5$cycloalkyl, $C_1$-$C_3$alkylthio, —$NR^{56}R^{57}$, $SO_2R^{58}$ (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl), halogen, hydroxyl;

$R^3$ represents hydrogen;
X represents $CH_2$ or O;
Y represents $CH_2$;
a is 0, 1 or 2; and
b is 1 In another embodiment of the invention, there is provided a subset of compounds of formula (I), or pharmaceutically acceptable salts thereof, wherein:
ring A represents phenyl ring;
ring B represents furyl, phenyl, pyrazinyl, pyridazinyl, pyridyl, pyrimidinyl or thienyl ring;
each $R^1$ independently represents
a $C_1$-$C_3$alkoxy group;
$R^2$ represents

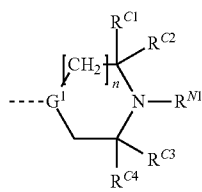

wherein
$G^1$ is C or N,
n is 1 or 2,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or
$R^{C3}$ and $R^{C4}$ together with the atom to which they are attached form a 3- to 5-membered carbocyclic ring, and
$R^{N1}$ is selected from selected from $C_1$-$C_2$alkyl, $C_2$-$C_3$alkenyl, $C_2$-$C_3$alkynyl, $C_3$-$C_5$cycloalkyl, (each of which may be optionally substituted by one or more substituents selected from halogen, $C_1$-$C_2$alkyl, $C_1$-$C_2$alkoxy, $C_1$-$C_2$alkylthio, amino (—$NH_2$), mono- and di-$C_1$-$C_2$alkylamino, hydroxyl and trifluoromethyl) and hydrogen, or
$R^{N1}$ and $R^{C4}$ together with the atoms to which they are attached form a 4- to 7-membered heterocyclyl ring;
$R^3$ represents hydrogen;
X represents $CH_2$ or O;
Y represents $CH_2$;
a is 0, 1 or 2; and
b is 1.

In another embodiment of the invention, there is provided a subset of compounds of formula (I), or pharmaceutically acceptable salts thereof, wherein:
$A(R^1)_a$ represents 3,5-dimethoxyphenyl;
ring B represents phenyl, pyrazinyl, pyrimidinyl or thienyl ring;
$R^2$ represents

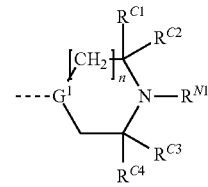

wherein
$G^1$ is C or N,
n is 1 or 2,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or
$R^{C3}$ and $R^{C4}$ together with the atom to which they are attached form a cyclopropyl ring, and
$R^{N1}$ is selected from selected from hydrogen, methyl, ethyl, methoxyethyl, ethoxyethyl, hydroxyethyl, propenyl, propynyl, propyl, i-propyl, —$CH(CH_3)CH_2OH$, cyclopropyl, cyclobutyl, cyclopentyl, or
$R^{N1}$ and $R^{C4}$ together with the atoms to which they are attached form a 5- or 6-membered heterocyclyl ring;
$R^3$ represents hydrogen;
X represents $CH_2$ or O;
Y represents $CH_2$; and
b is 1.

In another embodiment of the invention, there is provided a subset of compounds of formula (I), or pharmaceutically acceptable salts thereof, wherein:
$A(R^1)_a$ represents 3,5-dimethoxyphenyl;
ring B represents phenyl, pyrazinyl, pyrimidinyl or thienyl ring;
$R^2$ represents

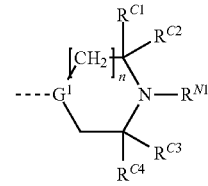

wherein
$G^1$ is C or N,
n is 1,
$R^{C1}$, $R^{C2}$, $R^{C3}$ and $R^{C4}$ are each independently selected from hydrogen, methyl, ethyl, hydroxymethyl, hydroxyethyl, methoxymethyl, methoxyethyl, 2,2,2-trifluoroethyl, or
$R^{C3}$ and $R^{C4}$ together with the atom to which they are attached form a cyclopropyl ring, and
$R^{N1}$ is selected from selected from hydrogen, methyl, ethyl, methoxyethyl, ethoxyethyl, hydroxyethyl, propenyl, propynyl, i-propyl, —$CH(CH_3)CH_2OH$, cyclopropyl, cyclobutyl, cyclopentyl, or R$^{N1}$ and R$^{C4}$ together with the atoms to which they are attached form a 5- or 6-membered heterocyclyl ring;
R$^3$ represents hydrogen;
X represents CH$_2$ or O;
Y represents CH$_2$; and
b is 1.

In a further embodiment of the invention, only one of R$^{C1}$ and R$^{C2}$ or R$^{C1}$ and R$^{C3}$ or R$^{C3}$ and R$^{C4}$ or R$^{N1}$ and R$^{C4}$ together with the atoms to which they are attached form a ring.

In a further embodiment of the invention, R$^{C1}$ and R$^{C2}$ together with the atoms to which they are attached form a ring, and only one of either R$^{C3}$ and R$^{C4}$ or R$^{N1}$ and R$^{C4}$ may together with the atoms to which they are attached form a ring.

In a further embodiment of the invention R$^{C1}$, R$^{C2}$, R$^{C3}$ and R$^{C4}$ are each independently selected from hydrogen and methyl.

Examples of compounds of the invention include:
4-(4-methylpiperazin-1-yl)-N-(5-phenethyl-2H-pyrazol-3-yl)benzamide,
N-[5-[2-(3,5-dimethoxyphenyl)ethyl]-2H-pyrazol-3-y]benzamide,
N-[5-[2-(3,5-dimethoxyphenyl)ethyl]-2H-pyrazol-3-yl]-4-methoxy-benzamide,
N-[5-[2-(3,5-dimethoxyphenyl)ethyl]-2H-pyrazol-3-yl]-4-morpholin-4-yl-benzamide,
N-[5-[2-(3,5-dimethoxyphenyl)ethyl]-2H-pyrazol-3-yl]-4-[(3-fluoro-1-piperidyl)methyl]benzamide,
N-[5-[2-[3-(2-Methoxyethoxy)phenyl]ethyl]-2H-pyrazol-3-yl]-4-(4-methylpiperazin-1-yl)benzamide,
4-(4-Methylpiperazin-1-yl)-N-[5-(2-pyridin-3-ylethyl)-2H-pyrazol-3-yl]benzamide,
N-[5-[2-(2-furyl)ethyl]-2H-pyrazol-3-yl]-4-(4-methylpiperazin-1-yl)benzamide,
N-[5-[2-(3-furyl)ethyl]-2H-pyrazol-3-yl]-4-(4-methylpiperazin-1-yl)benzamide,
N-[5-[2-(3,5-dimethoxyphenyl)ethyl]-2H-pyrazol-3-yl]-4-(4-methylpiperazin-1-yl)benzamide,
N-[5-[2-(3-Methoxyphenyl)ethyl]-2H-pyrazol-3-yl]-4-(4-methylpiperazin-1-yl)benzamide,
N-[5-[(3,5-Dimethoxyphenyl)methoxy]-2H-pyrazol-3-yl]-4-(4-methylpiperazin-1-yl)benzamide,
N-[5-[2-(3-Methoxyphenyl)ethyl]-2H-pyrazol-3-yl]-6-methyl-pyridine-3-carboxamide,
6-Methoxy-N-[5-[2-(3-methoxyphenyl)ethyl]-2H-pyrazol-3-yl]pyridine-3-carboxamide,
N-[5-[2-(3-Methoxyphenyl)ethyl]-2H-pyrazol-3-yl]-4-methylsulfonyl-benzamide,
N-[5-[2-(3-Methoxyphenyl)ethyl]-2H-pyrazol-3-yl]-5-methyl-pyrazine-2-carboxamide,
N-[5-[2-(3-Methoxyphenyl)ethyl]-2H-pyrazol-3-yl]-5-(prop-2-ynylamino)pyridine-2-carboxamide,
6-Ethylamino-N-[5-[2-(3-methoxyphenyl)ethyl]-2H-pyrazol-3-yl]pyridine-3-carboxamide,
4-Acetamido-N-[5-[2-(3-methoxyphenyl)ethyl]-2H-pyrazol-3-yl]benzamide,
N-[5-[(3,5-Dimethoxyphenyl)methoxy]-2H-pyrazol-3-yl]-5-(4-methylpiperazin-1-yl)pyrazine-2-carboxamide,
4-benzamido-N-[5-[2-(3-methoxyphenyl)ethyl]-2H-pyrazol-3-yl]benzamide,
6-(2-methoxyethoxy)-N-[5-[2-(3-methoxyphenyl)ethyl]-2H-pyrazol-3-yl]pyridine-3-carboxamide,
4-cyano-N-[5-[2-(3-methoxyphenyl)ethyl]-2H-pyrazol-3-yl]benzamide,
N-[5-[2-(3-methoxyphenyl)ethyl]-2H-pyrazol-3-yl]benzene-1,4-dicarboxamide,
N-[5-[2-(3-methoxyphenyl)ethyl]-2H-pyrazol-3-yl]-4-pyrazol-1-yl-benzamide,
6-anilino-N-[5-[2-(3-methoxyphenyl)ethyl]-2H-pyrazol-3-yl]pyridine-3-carboxamide,
4-methanesulfonamido-N-[5-[2-(3-methoxyphenyl)ethyl]-2H-pyrazol-3-yl]benzamide,
4-(hydroxymethyl)-N-[5-[2-(3-methoxyphenyl)ethyl]-2H-pyrazol-3-yl]benzamide,
5-formamido-N-[5-[2-(3-methoxyphenyl)ethyl]-2H-pyrazol-3-yl]pyridine-2-carboxamide,
4-(dimethylsulfamoyl)-N-[5-[2-(3-methoxyphenyl)ethyl]-2H-pyrazol-3-yl]benzamide,
6-hydroxy-N-[5-[2-(3-methoxyphenyl)ethyl]-2H-pyrazol-3-yl]pyridine-3-carboxamide,
N-[5-[2-(3-methoxyphenyl)ethyl]-2H-pyrazol-3-yl]-6-morpholin-4-yl-pyridine-3-carboxamide,
N-[5-[2-(3-methoxyphenyl)ethyl]-2H-pyrazol-3-yl]-4-(1,3-oxazol-5-yl)benzamide,
N-[5-[2-(3-methoxyphenyl)ethyl]-2H-pyrazol-3-yl]-4-(tetrazol-1-yl)benzamide,
prop-2-enyl N-[5-[[5-[2-(3-methoxyphenyl)ethyl]-2H-pyrazol-3-yl]carbamoyl]pyridin-2-yl]carbamate,
N-[5-[2-(3-methoxyphenyl)ethyl]-2H-pyrazol-3-yl]-4-(1,2,4-triazol-1-yl)benzamide,
N-[5-[2-(3-methoxyphenyl)ethyl]-2H-pyrazol-3-yl]-6-pyrazol-1-yl-pyridine-3-carboxamide,
N-[5-[2-(3,5-dimethoxyphenyl)ethyl]-2H-pyrazol-3-yl]-4-fluoro-benzamide,
N-[5-[2-(3,5-dimethoxyphenyl)ethyl]-1H-pyrazol-3-yl]-3-methoxy-benzamide,
N-[5-[2-(3,5-dimethoxyphenyl)ethyl]-1H-pyrazol-3-yl]-3-morpholin-4-yl-benzamide,
N-[5-[2-(3,5-dimethoxyphenyl)ethyl]-1H-pyrazol-3-yl]-2-methoxy-benzamide,
N-[5-[2-(3,5-dimethoxyphenyl)ethyl]-1H-pyrazol-3-yl]-4-(2-ethoxyethoxy)benzamide,
N-[5-[2-(3,5-dimethoxyphenyl)ethyl]-1H-pyrazol-3-yl]-4-(1-piperidyl)benzamide,
N-[5-[2-(3,5-dimethoxyphenyl)ethyl]-1H-pyrazol-3-yl]-4-(4-piperidylmethoxy)benzamide,
N-[5-[2-(3,5-dimethoxyphenyl)ethyl]-1H-pyrazol-3-yl]-4-piperazin-1-yl-benzamide,
N-[5-[2-(3,5-dimethoxyphenyl)ethyl]-1H-pyrazol-3-yl]-6-piperazin-1-yl-pyridine-3-carboxamide,
N-[5-[2-(3,5-dimethoxyphenyl)ethyl]-1H-pyrazol-3-yl]-4-(dimethylaminomethyl)benzamide,
N-[5-[2-(3,5-dimethoxyphenyl)ethyl]-1H-pyrazol-3-yl]-4-(2-hydroxyethoxy)benzamide,
4-(2-aminopropyl)-N-[5-[2-(3,5-dimethoxyphenyl)ethyl]-1H-pyrazol-3-yl]benzamide,
N-[5-[2-(3,5-dimethoxyphenyl)ethyl]-1H-pyrazol-3-yl]-4-[(3,3-dimethyl-1-piperidyl)methyl]benzamide,
N-[5-[2-(3,5-dimethoxyphenyl)ethyl]-1H-pyrazol-3-yl]-4-[4-(2-hydroxyethyl)piperazin-1-yl]benzamide,
4-[(7-cyano-3,4-dihydro-1H-isoquinolin-2-yl)methyl]-N-[5-[2-(3,5-dimethoxyphenyl)ethyl]-1H-pyrazol-3-yl]benzamide,
N-[5-[2-(3,5-dimethoxyphenyl)ethyl]-1H-pyrazol-3-yl]-4-[(3-fluoro-1-piperidyl)methyl]benzamide,
N-[5-[2-(3,5-dimethoxyphenyl)ethyl]-1H-pyrazol-3-yl]-4-(2-morpholin-4-ylethoxy)benzamide,
4-[2-(4,4-difluoro-1-piperidyl)ethoxy]-N-[5-[2-(3,5-dimethoxyphenyl)ethyl]-1H-pyrazol-3-yl]benzamide,
N-[5-[2-(3,5-dimethoxyphenyl)ethyl]-1H-pyrazol-3-yl]-4-(2-morpholin-4-ylethyl)benzamide,
N-[5-[2-(3,5-dimethoxyphenyl)ethyl]-1H-pyrazol-3-yl]-4-[(methyl-(oxolan-2-ylmethyl)amino)methyl]benzamide, N-[5-[2-(3,5-dimethoxyphenyl)ethyl]-1H-pyrazol-3-yl]-4-(4-piperidyl)benzamide,
N-[5-[2-(3,5-dimethoxyphenyl)ethyl]-1H-pyrazol-3-yl]-4-dimethylamino-benzamide,
N-[5-[2-(3,5-dimethoxyphenyl)ethyl]-1H-pyrazol-3-yl]-5-piperazin-1-yl-thiophene-2-carboxamide,
methyl 6-[[5-[2-(3-methoxyphenyl)ethyl]-2H-pyrazol-3-yl]carbamoyl]pyridine-3-carboxylate,
6-chloro-N-[5-[2-(3-methoxyphenyl)ethyl]-2H-pyrazol-3-yl]pyridine-3-carboxamide,
6-cyano-N-[5-[2-(3-methoxyphenyl)ethyl]-2H-pyrazol-3-yl]pyridine-3-carboxamide,
4-hydroxy-N-[5-[2-(3-methoxyphenyl)ethyl]-2H-pyrazol-3-yl]pyridine-2-carboxamide,
N-[5-[2-(3-methoxyphenyl)ethyl]-2H-pyrazol-3-yl]-6-(2-pyrrolidin-1-ylethyl)pyridine-3-carboxamide,
5-[[5-[2-(3-methoxyphenyl)ethyl]-2H-pyrazol-3-yl]carbamoyl]pyridine-2-carboxylic acid,
methyl 5-[[5-[2-(3-methoxyphenyl)ethyl]-2H-pyrazol-3-yl]carbamoyl]pyridine-2-carboxylate,
ethyl 5-[[5-[2-(3-methoxyphenyl)ethyl]-2H-pyrazol-3-yl]carbamoyl]pyridine-2-carboxylate,
N-[5-[(3,5-dimethoxyphenyl)methoxy]-2H-pyrazol-3-yl]-5-(4-methylpiperazin-1-yl)pyridine-2-carboxamide,
N-[5-[(3,5-dimethoxyphenyl)methoxy]-2H-pyrazol-3-yl]-4-(2-dimethylaminoethylamino)benzamide,
N-[5-[(3,5-dimethoxyphenyl)methoxy]-2H-pyrazol-3-yl]-4-methoxy-benzamide,
N-[5-[(3,5-dimethoxyphenyl)methoxy]-2H-pyrazol-3-yl]-6-piperazin-1-yl-pyridine-3-carboxamide,
N-[5-[(3,5-dimethoxyphenyl)methoxy]-1H-pyrazol-3-yl]-2-(4-methylpiperazin-1-yl)pyrimidine-5-carboxamide,
N-[5-[(3,5-dimethoxyphenyl)methoxy]-1H-pyrazol-3-yl]-3-piperazin-1-yl-benzamide,
4-(1,4-diazepan-1-yl)-N-[5-[(3,5-dimethoxyphenyl)methoxy]-1H-pyrazol-3-yl]benzamide,
N-[5-[2-[5-(dimethylaminomethyl)-2-furyl]ethyl]-1H-pyrazol-3-yl]-4-(4-methylpiperazin-1-yl)benzamide,
N-[5-(2-benzo[1,3]dioxol-5-ylethyl)-2H-pyrazol-3-yl]-4-(4-methylpiperazin-1-yl)benzamide,
N-[5-[2-(2,5-dimethoxyphenyl)ethyl]-2H-pyrazol-3-yl]-4-(4-methylpiperazin-1-yl)benzamide,
N-[5-[2-(4-methoxy-2-methyl-phenyl)ethyl]-2H-pyrazol-3-yl]-4-(4-methylpiperazin-1-yl)benzamide,
N-[5-[2-(3,5-dimethoxyphenyl)ethyl]-2H-pyrazol-3-yl]-4-(3,5-dimethylpiperazin-1-yl)benzamide,
N-[5-[2-(3,5-dimethoxyphenyl)ethyl]-2H-pyrazol-3-yl]-4-iodo-benzamide,
N-[5-[2-(3,5-dimethoxyphenyl)ethyl]-1H-pyrazol-3-yl]-2-[(3-methyl-1,2-oxazol-5-yl)methylamino]benzamide,
N-[5-[2-(3,5-dimethoxyphenyl)ethyl]-2H-pyrazol-3-yl]-6-(4-methylpiperazin-1-yl)pyridazine-3-carboxamide,
N-[5-[2-(3,5-dimethoxyphenyl)ethyl]-2H-pyrazol-3-yl]-2-(4-methylpiperazin-1-yl)pyrimidine-5-carboxamide,
N-[5-[2-(3,5-dimethoxyphenyl)ethyl]-1H-pyrazol-3-yl]-4-(4-methylpiperazine-1-carbonyl)benzamide,
N-[5-[2-(3,5-dimethoxyphenyl)ethyl]-1H-pyrazol-3-yl]-4-(4-propan-2-ylpiperazin-1-yl)benzamide,
4-(4-cyclopropylpiperazin-1-yl)-N-[5-[2-(3,5-dimethoxyphenyl)ethyl]-1H-pyrazol-3-yl]benzamide,
4-(4-cyclobutylpiperazin-1-yl)-N-[5-[2-(3,5-dimethoxyphenyl)ethyl]-1H-pyrazol-3-yl]benzamide,
4-(4-acetylpiperazin-1-yl)-N-[5-[2-(3,5-dimethoxyphenyl)ethyl]-1H-pyrazol-3-yl]benzamide,
N-[5-[2-(3-methoxyphenyl)ethyl]-1H-pyrazol-3-yl]-4-(4-methylsulfonylpiperazin-1-yl)benzamide,
N-[5-[2-(3,5-dimethoxyphenyl)ethyl]-1H-pyrazol-3-yl]-4-(1-methyl-4-piperidyl)benzamide,
4-(3,4,6,7,8,8a-Hexahydro-1H-pyrrolo[2,1-c]pyrazin-2-yl)-N-[5-[2-(3,5-dimethoxyphenyl)ethyl]-2H-pyrazol-3-yl]benzamide,
4-(1,3,4,6,7,8,9,9a-Octahydropyrido[2,1-c]pyrazin-2-yl)-N-[5-[2-(3,5-dimethoxyphenyl)ethyl]-2H-pyrazol-3-yl]benzamide,
N-[5-[2-(3,5-dimethoxyphenyl)ethyl]-1H-pyrazol-3-yl]-4-[(4-methylpiperazin-1-yl)methyl]benzamide,
N-[5-[2-(3,5-dimethoxyphenyl)ethyl]-1H-pyrazol-3-yl]-4-(3,4-dimethylpiperazin-1-yl)benzamide,
N-[5-[2-(3,5-dimethoxyphenyl)ethyl]-1H-pyrazol-3-yl]-4-(3,4,5-trimethylpiperazin-1-yl)benzamide,
N-[5-[(3,5-dimethoxyphenyl)methoxy]-2H-pyrazol-3-yl]-5-(3,4-dimethylpiperazin-1-yl)thiophene-2-carboxamide,
4-(1,3,4,6,7,8,9,9a-octahydropyrido[2,1-c]pyrazin-2-yl)-N-[5-[(3,5-dimethoxyphenyl)methoxy]-2H-pyrazol-3-yl]benzamide,
4-(1-Cyclopropylpiperidin-4-yl)-N-[5-[2-(3,5-dimethoxyphenyl)ethyl]-2H-pyrazol-3-yl]benzamide,
N-[5-[(3,5-dimethoxyphenyl)methoxy]-2H-pyrazol-3-yl]-4-[(3R,5S)-3,5-dimethylpiperazin-1-yl]benzamide,
N-[5-[(3,5-dimethoxyphenyl)methoxy]-2H-pyrazol-3-yl]-4-(3,4-dimethylpiperazin-1-yl)benzamide,
tert-Butyl 4-[5-[[5-[2-(3,5-dimethoxyphenyl)ethyl]-2H-pyrazol-3-yl]carbamoyl]thiophen-2-yl]piperazine-1-carboxylate,
N-[5-[(3,5-dimethoxyphenyl)methoxy]-2H-pyrazol-3-yl]-4-(1-methylpiperidin-4-yl)benzamide,
4-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]benzamide,
5-(1,3,4,6,7,8,9,9a-Octahydropyrido[2,1-c]pyrazin-2-yl)-N-[5-[2-(3,5-dimethoxyphenyl)ethyl]-2H-pyrazol-3-yl]pyrazine-2-carboxamide,
N-[5-[2-(3,5-dimethoxyphenyl)ethyl]-2H-pyrazol-3-yl]-5-(4-methylpiperazin-1-yl)thiophene-2-carboxamide,
N-[5-[(3,5-dimethoxyphenyl)methoxy]-2H-pyrazol-3-yl]-5-(4-methylpiperazin-1-yl)thiophene-2-carboxamide,
N-[5-[2-(3,5-dimethoxyphenyl)ethyl]-2H-pyrazol-3-yl]-5-(3,3-dimethylpiperazin-1-yl)pyrazine-2-carboxamide,
5-(4-Cyclopropylpiperazin-1-yl)-N-[5-[(3,5-dimethoxyphenyl)methoxy]-2H-pyrazol-3-yl]pyrazine-2-carboxamide,
N-[5-[(3,5-dimethoxyphenyl)methoxy]-2H-pyrazol-3-yl]-4-[(3R,5S)-3,4,5-trimethylpiperazin-1-yl]benzamide,
N-[5-[(3,5-dimethoxyphenyl)methoxy]-2H-pyrazol-3-yl]-4-(3,3-dimethylpiperazin-1-yl)benzamide,
N-[5-[2-(3,5-dimethoxyphenyl)ethyl]-2H-pyrazol-3-yl]-5-[(3R,5S)-3,5-dimethylpiperazin-1-yl]pyrazine-2-carboxamide,
5-(4-Cyclopropylpiperazin-1-yl)-N-[5-[2-(3,5-dimethoxyphenyl)ethyl]-2H-pyrazol-3-yl]pyrazine-2-carboxamide,
5-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]pyrazine-2-carboxamide,
5-(1,3,4,6,7,8,9,9a-Octahydropyrido[2,1-c]pyrazin-2-yl)-N-[5-[(3,5-dimethoxyphenyl)methoxy]-2H-pyrazol-3-yl]pyrazine-2-carboxamide,
4-(4-cyclopropylpiperazin-1-yl)-N-[5-[(3,5-dimethoxyphenyl)methoxy]-2H-pyrazol-3-yl]benzamide,
N-[5-[2-(3,5-Dimethoxyphenyl)ethyl]-2H-pyrazol-3-yl]-4-(4-methyl-4-oxidopiperazin-4-ium-1-yl)benzamide,
4-(4-Cyclobutylpiperazin-1-yl)-N-[5-[(3,5-dimethoxyphenyl)methoxy]-2H-pyrazol-3-yl]benzamide, 2-(1,3,4,6,7,8,9,9a-Octahydropyrido[2,1-c]pyrazin-2-yl)-N-[5-[(3,5-dimethoxyphenyl)methoxy]-2H-pyrazol-3-yl]pyrimidine-5-carboxamide, 5-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]thiophene-2-carboxamide, 5-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]thiophene-2-carboxamide, 5-(3,4,6,7,8,8a-Hexahydro-1H-pyrrolo[2,1-c]pyrazin-2-yl)-N-[5-[(3,5-dimethoxyphenyl)methoxy]-2H-pyrazol-3-yl]pyrazine-2-carboxamide, N-[5-[2-(3,5-Dimethoxyphenyl)ethyl]-2H-pyrazol-3-yl]-5-(3,4-dimethylpiperazin-1-yl)pyrazine-2-carboxamide, N-[5-[(3,5-Dimethoxyphenyl)methoxy]-2H-pyrazol-3-yl]-5-(3,4-dimethylpiperazin-1-yl)pyrazine-2-carboxamide, N-[5-[2-(3,5-dimethoxyphenyl)ethyl]-2H-pyrazol-3-yl]-5-[(3R,5S)-3,4,5-trimethylpiperazin-1-yl]pyrazine-2-carboxamide, 2-(4-cyclopropylpiperazin-1-yl)-N-[5-[2-(3,5-dimethoxyphenyl)ethyl]-2H-pyrazol-3-yl]pyrimidine-5-carboxamide, 2-(1,3,4,6,7,8,9,9a-octahydropyrido[2,1-c]pyrazin-2-yl)-N-[5-[2-(3,5-dimethoxyphenyl)ethyl]-2H-pyrazol-3-yl]pyrimidine-5-carboxamide, 2-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]pyrimidine-5-carboxamide, 5-[(3R,5S)-4-(cyanomethyl)-3,5-dimethylpiperazin-1-yl]-N-[5-[2-(3,5-dimethoxyphenyl)ethyl]-2H-pyrazol-3-yl]pyrazine-2-carboxamide, N-[5-[(3,5-dimethoxyphenyl)methoxy]-2H-pyrazol-3-yl]-5-[(3R,5S)-3,4,5-trimethylpiperazin-1-yl]pyrazine-2-carboxamide, 5-[(3R,5S)-4-(cyanomethyl)-3,5-dimethylpiperazin-1-yl]-N-[5-[(3,5-dimethoxyphenyl)methoxy]-2H-pyrazol-3-yl]pyrazine-2-carboxamide, N-[5-[(3,5-dimethoxyphenyl)methoxy]-2H-pyrazol-3-yl]-2-(3,4-dimethylpiperazin-1-yl)pyrimidine-5-carboxamide, 2-(4-cyclopropylpiperazin-1-yl)-N-[5-[(3,5-dimethoxyphenyl)methoxy]-2H-pyrazol-3-yl]pyrimidine-5-carboxamide, 2-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]pyrimidine-5-carboxamide, N-[5-[2-(3,5-dimethoxyphenyl)ethyl]-2H-pyrazol-3-yl]-2-(3,4-dimethylpiperazin-1-yl)pyrimidine-5-carboxamide, N-[5-[2-(3,5-dimethoxyphenyl)ethyl]-2H-pyrazol-3-yl]-2-[(3R,5S)-3,4,5-trimethylpiperazin-1-yl]pyrimidine-5-carboxamide, N-[5-[2-(3,5-dimethoxyphenyl)ethyl]-2H-pyrazol-3-yl]-4-[4-(1-hydroxypropan-2-yl)piperazin-1-yl]benzamide, N-(3-(3,5-dimethoxybenzyloxy)-1H-pyrazol-5-yl)-2-((3R,5S)-3,4,5-trimethylpiperazin-1-yl)pyrimidine-5-carboxamide, N-[5-[2-(3,5-dimethoxyphenyl)ethyl]-2H-pyrazol-3-yl]-4-(3,3-dimethylpiperazin-1-yl)benzamide, N-[5-[(3,5-dimethoxyphenyl)methoxy]-2H-pyrazol-3-yl]-5-(3,3-dimethylpiperazin-1-yl)thiophene-2-carboxamide, N-[5-[(3,5-dimethoxyphenyl)methoxy]-2H-pyrazol-3-yl]-5-(4-ethylpiperazin-1-yl)thiophene-2-carboxamide, N-[5-[2-(3,5-dimethoxyphenyl)ethyl]-2H-pyrazol-3-yl]-5-(4-methyl-1,4-diazepan-1-yl)thiophene-2-carboxamide, N-[5-[2-(3,5-dimethoxyphenyl)ethyl]-2H-pyrazol-3-yl]-2-(4-ethyl-3-methylpiperazin-1-yl)pyrimidine-5-carboxamide, N-[5-[2-(3,5-dimethoxyphenyl)ethyl]-2H-pyrazol-3-yl]-4-(1-prop-2-enylpiperidin-4-yl)benzamide, 4-(1,4-diazepan-1-yl)-N-[5-[2-(3,5-dimethoxyphenyl)ethyl]-2H-pyrazol-3-yl]benzamide, N-[5-[2-(3,5-dimethoxyphenyl)ethyl]-2H-pyrazol-3-yl]-4-(1-prop-2-ylnylpiperidin-4-yl)benzamide, N-[5-[(3,5-dimethoxyphenyl)methoxy]-2H-pyrazol-3-yl]-5-[(3S,5R)-3,5-dimethylpiperazin-1-yl]thiophene-2-carboxamide, N-[5-[2-(3,5-dimethoxyphenyl)ethyl]-2H-pyrazol-3-yl]-4-[1-(2-methoxyethyl)piperidin-4-yl]benzamide, N-[5-[2-(3,5-dimethoxyphenyl)ethyl]-2H-pyrazol-3-yl]-2-[(3S)-3-propan-2-ylpiperazin-1-yl]pyrimidine-5-carboxamide, N-[5-[2-(3,5-dimethoxyphenyl)ethyl]-2H-pyrazol-3-yl]-2-(4-methyl-3-oxopiperazin-1-yl)pyrimidine-5-carboxamide, 4-(1,2,3,4,4a,5,7,7a-octahydropyrrolo[3,4-b]pyridin-6-yl)-N-[5-[(3,5-dimethoxyphenyl)methoxy]-2H-pyrazol-3-yl]benzamide, N-[5-[2-(3,5-dimethoxyphenyl)ethyl]-2H-pyrazol-3-yl]-5-(1-methylpiperidin-4-yl)pyrazine-2-carboxamide, N-[5-[2-(3,5-dimethoxyphenyl)ethyl]-2H-pyrazol-3-yl]-5-(1-methyl-3,6-dihydro-2H-pyridin-4-yl)pyrazine-2-carboxamide, N-[5-[2-(3,5-dimethoxyphenyl)ethyl]-2H-pyrazol-3-yl]-4-[(3R,5S)-3,5-dimethylpiperazin-1-yl]benzamide, N-[5-[2-(3,5-dimethoxyphenyl)ethyl]-2H-pyrazol-3-yl]-4-[(3R,5S)-3,4,5-trimethylpiperazin-1-yl]benzamide, N-[5-[2-(3,5-dimethoxyphenyl)ethyl]-2H-pyrazol-3-yl]-4-(4-methyl-1,4-diazepan-1-yl)benzamide, N-[5-[2-(3,5-dimethoxyphenyl)ethyl]-2H-pyrazol-3-yl]-5-(3-dimethylaminopyrrolidin-1-yl)pyrazine-2-carboxamide, 5-(3-diethylaminopyrrolidin-1-yl)-N-[5-[2-(3,5-dimethoxyphenyl)ethyl]-2H-pyrazol-3-yl]pyrazine-2-carboxamide, N-[5-[2-(3,5-dimethoxyphenyl)ethyl]-2H-pyrazol-3-yl]-4-(1-ethylpiperidin-4-yl)benzamide, N-[5-[2-(3,5-dimethoxyphenyl)ethyl]-2H-pyrazol-3-yl]-2-[3-(methoxymethyl)piperazin-1-yl]pyrimidine-5-carboxamide, N-[5-[2-(3,5-dimethoxyphenyl)ethyl]-2H-pyrazol-3-yl]-5-(3-methylaminopyrrolidin-1-yl)pyrazine-2-carboxamide, N-[5-[2-(3,5-dimethoxyphenyl)ethyl]-2H-pyrazol-3-yl]-2-(1-methylpiperidin-4-yl)pyrimidine-5-carboxamide, N-[5-[2-(3,5-dimethoxyphenyl)ethyl]-2H-pyrazol-3-yl]-5-(4-methyl-1,4-diazepan-1-yl)pyrazine-2-carboxamide, N-[5-[2-(3,5-dimethoxyphenyl)ethyl]-2H-pyrazol-3-yl]-4-(4-prop-2-enyl-1,4-diazepan-1-yl)benzamide, 4-(4-cyclopropyl-1,4-diazepan-1-yl)-N-[5-[2-(3,5-dimethoxyphenyl)ethyl]-2H-pyrazol-3-yl]benzamide, N-[5-[2-(3,5-dimethoxyphenyl)ethyl]-2H-pyrazol-3-yl]-4-(4-propan-2-yl-1,4-diazepan-1-yl)benzamide, N-[5-[2-(3,5-dimethoxyphenyl)ethyl]-2H-pyrazol-3-yl]-5-(4-propan-2-yl-1,4-diazepan-1-yl)pyrazine-2-carboxamide, N-[5-[2-(3,5-dimethoxyphenyl)ethyl]-2H-pyrazol-3-yl]-5-(4-propan-2-yl-1,4-diazepan-1-yl)thiophene-2-carboxamide, N-[5-[2-(3,5-dimethoxyphenyl)ethyl]-2H-pyrazol-3-yl]-5-(4-ethyl-1,4-diazepan-1-yl)pyrazine-2-carboxamide, N-[5-[2-(3,5-dimethoxyphenyl)ethyl]-2H-pyrazol-3-yl]-4-(4-ethyl-1,4-diazepan-1-yl)benzamide, N-[5-[2-(3,5-dimethoxyphenyl)ethyl]-2H-pyrazol-3-yl]-2-(4-ethyl-1,4-diazepan-1-yl)pyrimidine-5-carboxamide, N-[5-[2-(3,5-dimethoxyphenyl)ethyl]-2H-pyrazol-3-yl]-5-(4-prop-2-enyl-1,4-diazepan-1-yl)pyrazine-2-carboxamide,
N-[5-[2-(3,5-dimethoxyphenyl)ethyl]-2H-pyrazol-3-yl]-2-(4-propan-2-yl-1,4-diazepan-1-yl)pyrimidine-5-carboxamide,
5-(4-cyclopropyl-1,4-diazepan-1-yl)-N-[5-[2-(3,5-dimethoxyphenyl)ethyl]-2H-pyrazol-3-yl]pyrazine-2-carboxamide,
N-[5-[2-(3,5-dimethoxyphenyl)ethyl]-2H-pyrazol-3-yl]-2-(4-prop-2-enyl-1,4-diazepan-1-yl)pyrimidine-5-carboxamide,
N-[5-[2-(3,5-dimethoxyphenyl)ethyl]-2H-pyrazol-3-yl]-2-(4-methyl-1,4-diazepan-1-yl)pyrimidine-5-carboxamide,
2-(4-cyclopropyl-1,4-diazepan-1-yl)-N-[5-[2-(3,5-dimethoxyphenyl)ethyl]-2H-pyrazol-3-yl]pyrimidine-5-carboxamide,
N-[5-[2-[3-(methylcarbamoyl)phenyl]ethyl]-2H-pyrazol-3-yl]-4-(4-methylpiperazin-1-yl)benzamide,
N-[5-[(3,5-dimethoxyphenyl)methoxy]-2H-pyrazol-3-yl]-4-(4-ethylpiperazin-1-yl)benzamide,
N-[5-[2-(3,5-dimethoxyphenyl)ethyl]-2H-pyrazol-3-yl]-4-(4-ethylpiperazin-1-yl)benzamide
and pharmaceutically acceptable salts of any one thereof.

In another aspect of the invention, particular compounds of the invention are any one of the Examples 1 to 20 or pharmaceutically acceptable salts of any one thereof.

In another aspect of the invention, particular compounds of the invention are any one of the Examples or pharmaceutically acceptable salts of any one thereof.

In another aspect of the invention, particular compounds of the invention are any one of Examples 1, 2, 3, 4, 5, 10, 11, 12, 20, 42, 43, 44, 45, 46, 47, 48, 50, 51, 53, 54, 55, 56, 57, 58, 59, 60, 69, 70, 71, 72, 73, 74, 75, 80, 81, 85, 87, 88, 89, 92, 93, 94, 95, or 96, or pharmaceutically acceptable salts of any one thereof.

In another aspect of the invention, particular compounds of the invention are any one of Examples 2, 3, 4, 5, 10, 11, 12, 20, 42, 43, 44, 45, 46, 47, 48, 50, 51, 53, 54, 55, 56, 57, 58, 59, 60, 69, 70, 71, 72, 73, 74, 75, 80, 81, 85, 87, 88, 89, 92, 93, 94, 95, or 96, or pharmaceutically acceptable salts of any one thereof.

In another aspect of the invention, particular compounds of the invention are any one of Examples 10, 11, 12, 20, 43, 44, 45, 46, 50, 51, 53, 54, 55, 56, 57, 58, 59, 60, 69, 70, 72, 73, 74, 75, 80, 81, 85, 87, 88, 89, 92, 93, 94, 95, or 96, or pharmaceutically acceptable salts of any one thereof.

In another aspect of the invention, particular compounds of the invention are any one of Examples 2, 3, 4, 10, 11, 12, 20, 42, 43, 45, 47, 50, 56, 57, 59, 60, 69, 70, 71, 73, 75, 80, 81, 85, 87, 88, 89, 92, 93, 94, 96, 97, 98, 99, 100, 101, 103, 104, 105, 106, 107, 108, 109, 110, 111, 112, 113, 114, 115, 116, 118, 119, 120, 121, 122, 123, 124, 125, 126, 127, 128, 129, 130, 131, 132, 133, 134, 135, 136, 137, 138, 139, 140, 141, 142, 144, 145, 146, 147, 148, 151, 152, 153, 154, 155, 156, 157, 158, 159, 161, 165, 166, 167, 168, 169, 170, 171, 172, 174, 175, 176, 177, 179 or 180, or pharmaceutically acceptable salts of any one thereof.

In another aspect of the invention, particular compounds of the invention are any one of Examples 12, 45, 73, 75, 81, 92, 98, 99, 100, 103, 104, 110, 121, 137, 144, 148, 152, 154, 155, 159, 167, 179 or 180, or pharmaceutically acceptable salts of any one thereof.

The present invention further provides a process for the preparation of a compound of formula (I) as defined herein, or a pharmaceutically acceptable salt thereof, which comprises reacting a compound of formula (II)

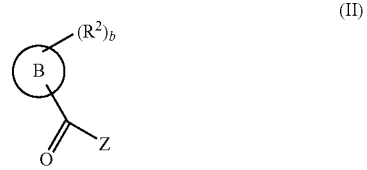

wherein Z represents a leaving group (e.g. halogen, for example chlorine, —CN, —N₃, —OH or a —OR, —OC(O)R, —OCR(NR$^a$R$^b$)₂ or —OC(=NR)NR$^a$R$^b$ group where R is an optionally substituted alkyl, aryl, heteroaryl or alkaryl and each R$^a$, R$^b$ independently is hydrogen or an optionally substituted alkyl, aryl or alkaryl), and B, R² and b are as hereinbefore defined for a compound formula (I), with a compound of formula (III)

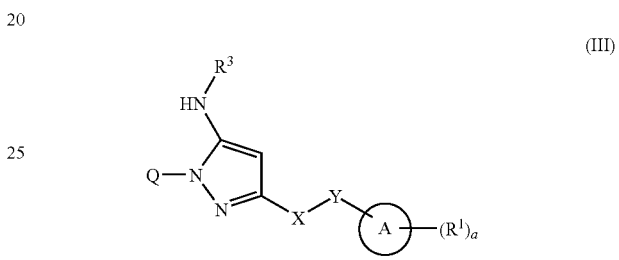

wherein Q is hydrogen or a protecting group (for example t-Bu or BOC group or as described in 'Protective Groups in Organic Synthesis', 2nd edition, T. W. Greene and P. G. M. Wuts, Wiley-Interscience (1991)), and A, R¹, R³, X, Y and a are as defined hereinbefore for a compound of formula (I)

to give a compound of formula (I),
and optionally carrying out one or more of the following:
  converting the compound obtained to a further compound of the invention
  forming a pharmaceutically acceptable salt of the compound.

Suitable compounds of Formula (II) include carboxylic acids or reactive derivatives of a carboxylic acid. Carboxylic acids or reactive derivatives of a carboxylic acid include acyl halides, such as an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of a carboxylic acid with a phenol such as pentafluorophenol, with an ester, such as pentafluorophenyl trifluoroacetate, or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V).

The reaction may conveniently be carried out in the presence of a suitable inert solvent or diluent, for example a halogenated solvent such as methylene chloride, chloroform or carbon tetrachloride, an alcohol or ester such as methanol, ethanol, isopropanol or ethyl acetate, an ether such as tetrahydrofuran or 1,4-dioxan, an aromatic solvent such as toluene. The reaction can also be carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, −20° C. to 100° C., preferably between 0° C. to ambient temperature, dependant upon the reaction being carried out and the nature of the leaving group Z.

The reaction typically can be carried out in the presence of a base. Suitable bases include organic amine bases, such as pyridine, 2,6-lutidine, N,N-diisopropylethylamine, collidine, 4-dimethylaminopyridine, triethylamine, morpholine, N-methylmorpholine or diazabicyclo[5.4.0]undec-7-ene, alkali or alkaline earth metal carbonates or hydroxides, such as sodium carbonate, potassium carbonate, calcium carbonate, sodium hydroxide or potassium hydroxide, alkali metal amides, such as sodium hexamethyldisilazide (NaHMDS), or alkali metal hydrides, such as sodium hydride, dependant upon the reaction being carried out and the nature of the leaving group Z.

The reaction can also be carried out in the presence of a Lewis acid, for example trimethylaluminium, dependant upon the reaction being carried out and the nature of the leaving group Z.

Alternatively, the present invention further provides a process for the preparation of a compound of formula (I) as defined herein, or a pharmaceutically acceptable salt thereof, which comprises reacting a compound of formula (IV)

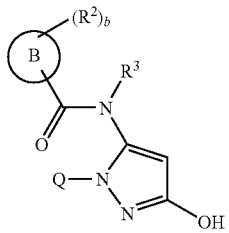

(IV)

wherein Q is hydrogen or a protecting group (for example t-Bu or BOC group or as described in 'Protective Groups in Organic Synthesis', 2nd edition, T. W. Greene and P. G. M. Wuts, Wiley-Interscience (1991)); and B, $R^2$, $R^3$ and b are as defined hereinbefore for a compound of formula (I), with a compound of formula (V)

(V)

wherein $L^1$ represents OH or a leaving group such as halogen or OTs; and A, $R^1$ and a are as defined hereinbefore for a compound of formula (I)

to give a compound of formula (I)

and optionally carrying out one or more of the following:
converting the compound obtained to a further compound of the invention
forming a pharmaceutically acceptable salt of the compound.

The reaction may conveniently be carried out in a suitable solvent such as dichloromethane at temperature in the range from 0° C. to room temperature. When $L^1$ is OH, the reaction typically may be carried out in the presence of diisopropylazidocarboxylate and triphenylphosphine. When $L^1$ is a halogen or OTs, the reaction may conveniently be carried out in a suitable solvent such as N,N-dimethylformamide or acetonitrile at temperature in the range from room temperature to 100° C. The reaction typically may be carried out in the presence of an inorganic base such as potassium carbonate or sodium hydride.

Compounds of formula (II), (III), (IV) or (V) are either commercially available, are known in the literature or may be prepared using known techniques.

Compounds of formula (II), wherein Z is halogen or —OR, may be prepared from compounds of formula (II) wherein Z is —OH by methods known in the literature. For example, methods known for the preparation of acid chlorides or esters from carboxylic acids may be employed.

Compounds of formula (III) where X represents $CH_2$ may be prepared by reacting a compound of formula (VI)

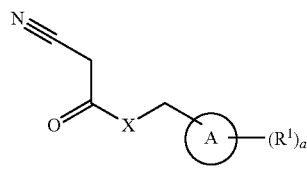

with a hydrazine of formula (VII)

The reaction may be conveniently carried out in a solvent, such as ethanol, at temperature range of 60 to 80° C.

Alternatively, compounds of formula (III) where X represents O may be prepared by reacting a compound of formula (VIII)

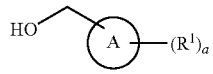

with a compound of formula (IX)

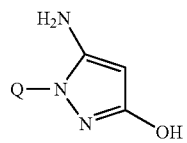

The reaction may be conveniently carried out in a solvent, such as dichloromethane, at temperature range of 0° C. to room temperature. The reaction typically may be carried out in the presence of diisopropylazidocarboxylate and triphenylphosphine.

Compounds of formulae (IV) may be prepared by reacting a compound of formula (X)

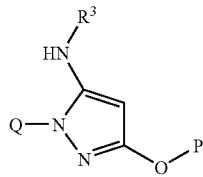

with a compound of formula (II)

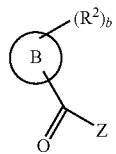

wherein Z represents a leaving group (e.g. halogen, for example chlorine, —CN, —N$_3$, —OH or a —OR, —OC(O)R, —OCR(NR$^a$R$^b$)$_2$ or —OC(=NR)NR$^a$R$^b$ group where R is an optionally substituted alkyl, aryl, heteroaryl or alkaryl and each R$^a$, R$^b$ independently is hydrogen or an optionally substituted alkyl, aryl or alkaryl);

P represents H or a protecting group (for example as described in 'Protective Groups in Organic Synthesis', 2nd edition, T. W. Greene and P. G. M. Wuts, Wiley-Interscience (1991));

Q is hydrogen or a protecting group (for example t-Bu or BOC group or as described in 'Protective Groups in Organic Synthesis', 2nd edition, T. W. Greene and P. G. M. Wuts, Wiley-Interscience (1991)); and B, R$^2$, R$^3$ and b and wherein are as defined hereinbefore for a compound of formula (I), and, when P is a protecting group, removing protecting group P.

Compounds of formula (VI), (VII), (VIII) and (IX) are commercially available compounds, or they are known in the literature, or they are prepared by standard processes known in the art.

Compounds of formula (I) can be converted into further compounds of formula (I) using standard procedures. Examples of the types of conversion reactions that may be used include introduction of a substituent by means of an aromatic substitution reaction, reduction of substituents, alkylation of substituents and oxidation of substituents. The reagents and reaction conditions for such procedures are well known in the chemical art. Examples of aromatic substitution reactions include the introduction of a nitro group using concentrated nitric acid; the introduction of an acyl group using, for example, an acyl halide and Lewis acid (such as aluminum trichloride) under Friedel Crafts conditions; the introduction of an aryl group, for example, using an aryl halide under Suzuki conditions; the introduction of an amino group using, for example, an aryl halide and an amine under Buchwald conditions; the introduction of an alkyl group using an alkyl halide and Lewis acid (such as aluminum trichloride) under Friedel Crafts conditions; and the introduction of a halogen group. Examples of reduction reactions include the reduction of a nitro group to an amino group by catalytic hydrogenation with a nickel catalyst or by treatment with iron in the presence of hydrochloric acid with heating; and particular examples of oxidation reactions include oxidation of alkylthio to alkylsulphinyl or alkylsulphonyl. These reagents and reaction conditions described above are well known in the art.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt, for example an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention.

Certain compounds of formula (I), a pharmaceutically acceptable salt thereof, may be isolated as an amorphous solid or as a crystalline solid. If the compound is in crystalline form, it may exist in a number of different polymorphic forms. Examples of compounds that have been isolated as either amorphous or crystalline solids include: Example 10 isolated as a crystalline form (2-Theta° 3.521 (100%), 7.025 (14.8%), 9.274 (16.9%), 9.654 (15.2%), 10.162 (14.8%), 10.508 (19.3%), 11.628 (49.8%), 12.047 (19.3%), 14.516 (21%), 16.242 (26.3%), 17.682 (18.5%), 18.099 (31.3%), 18.615 (92.6%), 19.315 (56.8%), 20.353 (16%), 20.581 (17.3%), 21.192 (10.3%), 22.467 (23%), 23.057 (88.1%), 23.28 (52.3%), 24.261 (34.2%), 25.363 (10.7%), 27.546 (15.6%), 28.285 (14%) and 29.862 (11.9%); Example 75 isolated as an amorphous solid; Example 81 isolated as an amorphous solid; Example 144 isolated as a crystalline form (2-Theta° 3.62 (100%), 7.247 (4.6%), 10.013 (5.1%), 10.889 (8.1%), 11.294 (7.7%), 12.185 (8.6%), 14.091 (19%), 18.2 (12.7%), 19.102 (8.9%), 19.789 (15.2%) and 20.608 (32.7%); Example 99 isolated as a crystalline form (2-Theta° 4.293 (100%), 8.498 (14%), 10.694 (8.1%), 13.078 (4.5%), 15.056 (49.4%), 16.14 (8.1%), 16.298 (11.1%), 17.425 (34.6%), 17.812 (23.1%), 18.157 (9.6%), 19.224 (15%), 20.931 (20.2%), 21.819 (27.9%), 22.248 (16.2%), 22.593 (23.7%), 23.416 (8.8%), 24.726 (26%), 25.295 (11.6%), 25.859 (5.6%), 27.001 (5.9%), 27.754 (5.3%), 28.442 (4.8%), 29.861 (4.3%), 30.89 (3.8%), 32.264 (5.9%) and 32.896 (5.4%); Example 147 isolated as a crystalline form (2-Theta° 4.492 (91.3%), 12.465 (23.1%), 13.862 (26.3%), 14.56 (14.4%), 15.811 (16.3%), 17.226 (24.4%), 17.886 (20%), 18.3 (15%), 18.9 (100%), 21.328 (20%), 21.705 (28.1%), 23.263 (27.5%), 23.699 (19.4%), 24.005 (53.8%), 24.333 (37.5%), 25.184 (11.9%), 26.114 (11.3%), 26.573 (10.6%) and 27.803 (16.9%); Example 151 isolated as a crystalline form (2-Theta° 3.754 (29.6%), 8.495 (13.9%), 10.235 (19.1%), 10.98 (29.6%), 12.014 (23.5%), 13.38 (18.3%), 14.591 (33%), 15.924 (41.7%), 17.057 (26.1%), 17.379 (30.4%), 18.219 (32.2%), 18.791 (36.5%), 19.201

(100%), 19.577 (47.8%), 20.788 (33%), 21.394 (27%), 22.07 (33%), 23.285 (25.2%), 23.922 (29.6%) and 25.533 (33%); Example 154 isolated as a crystalline form (2-Theta° 5.833 (89.6%), 9.786 (21.9%), 10.784 (32.8%), 12.121 (30.7%), 13.394 (35.4%), 13.709 (45.3%), 14.939 (28.1%), 16.799 (35.4%), 17.664 (25%), 18.223 (21.9%), 18.646 (50%), 19.29 (25.5%), 20.563 (35.4%), 21.32 (100%), 22.747 (37.5%), 24.154 (38.5%), 25.197 (23.4%), 25.704 (15.1%), 26.752 (16.7%) and 31.134 (12%); and Example 155 isolated as an amorphous solid. Unless otherwise stated, the X-ray powder diffraction patterns were determined by mounting a sample of the crystalline material on Siemens single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 Angstroms using a Siemens Diffraktometer 5000. The collimated X-ray source was passed through an automatic variable divergence slit set at V20 and the reflected radiation directed through a 2 mm antiscatter slit and a 0.2 mm detector slit. The sample was exposed for 1 second per 0.02 degree 2-theta increment (continuous scan mode) over the range 2 degrees to 40 degrees 2-theta in theta-theta mode. The instrument was equipped with a scintillation counter as detector. Control and data capture was by means of a Dell Optiplex 686 NT 4.0 Workstation operating with Diffrac+ software.

A person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form is not intended to be limited to the crystals that provide X-ray powder diffraction patterns identical to the X-ray powder diffraction patterns described herein. The present invention also includes any crystals providing X-ray powder diffraction patterns substantially the same as those described herein. A person skilled in the art of X-ray powder diffraction is able to judge the substantial similarity of X-ray powder diffraction patterns and will understand that differences may be the result of various factors for example measurement errors resulting from measurement conditions (such as equipment, sample preparation or the machine used); intensity variations resulting from measurement conditions and sample preparation; relative intensity variations of peaks resulting from variations in size or non-unitary aspect ratios of crystals; and the position of reflections which can be affected by the precise height at which the sample sits in the diffractometer and the zero calibration of the diffractometer, and surface planarity of the sample.

The compounds of formula (I) have activity as pharmaceuticals, in particular as modulators or inhibitors of FGFR activity, and may be used in the treatment of proliferative and hyperproliferative diseases/conditions, examples of which include the following cancers:

(1) carcinoma, including that of the bladder, brain, breast, colon, kidney, liver, lung, ovary, pancreas, prostate, stomach, cervix, colon, thyroid and skin;
(2) hematopoietic tumors of lymphoid lineage, including acute lymphocytic leukaemia, B-cell lymphoma and Burketts lymphoma;
(3) hematopoietic tumours of myeloid lineage, including acute and chronic myelogenous leukaemias and promyelocytic leukaemia;
(4) tumours of mesenchymal origin, including fibrosarcoma and rhabdomyosarcoma; and
(5) other tumours, including melanoma, seminoma, tetratocarcinoma, neuroblastoma and glioma.

In one embodiment the compounds of the invention are useful in the treatment of tumors of the bladder, breast and prostate and multiple myeloma.

Thus, the present invention provides a compound of formula (I), or a pharmaceutically-acceptable salt thereof, as herein defined for use in therapy.

According to a further aspect of the present invention there is provided a compound of the formula (I), or a pharmaceutically acceptable salt thereof, as defined hereinbefore for use in a method of treatment of the human or animal body by therapy.

In a further aspect, the present invention provides the use of a compound of formula (I), or a pharmaceutically acceptable salt, as herein defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating cancer which comprises administering to a patient in need thereof a therapeutically effective amount of a compound of formula (I), or a pharmaceutically acceptable salt thereof, as herein defined.

We have found that the compounds defined in the present invention, or a pharmaceutically acceptable salt thereof, are effective anti-cancer agents which property is believed to arise from modulating or inhibiting FGFR activity. Accordingly the compounds of the present invention are expected to be useful in the treatment of diseases or medical conditions mediated alone or in part by FGFR, i.e. the compounds may be used to produce a FGFR inhibitory effect in a warm-blooded animal in need of such treatment.

Thus the compounds of the present invention provide a method for treating cancer characterised by inhibition of FGFR, i.e. the compounds may be used to produce an anti-cancer effect mediated alone or in part by the inhibition of FGFR.

Such a compound of the invention is expected to possess a wide range of anti-cancer properties as activating mutations in FGFR have been observed in many human cancers, including but not limited to breast, bladder, prostrate and multiple myeloma. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, bladder, prostate, breast and pancreas. In one embodiment compounds of the invention are expected to slow advantageously the growth of primary and recurrent solid tumours of, for example, the skin, colon, thyroid, lungs and ovaries. More particularly such compounds of the invention, or a pharmaceutically acceptable salt thereof, are expected to inhibit the growth of those tumours which are associated with FGFR, especially those tumours which are significantly dependent on FGFR for their growth and spread, including for example, certain tumours of the bladder, prostate, breast and multiple myeloma.

Thus according to this aspect of the invention there is provided a compound of the formula (I), or a pharmaceutically acceptable salt thereof, as defined herein for use as a medicament.

According to a further aspect of the invention there is provided the use of a compound of the formula (I), or a pharmaceutically acceptable salt thereof, as defined herein in the manufacture of a medicament for use in the production of a FGFR inhibitory effect in a warm-blooded animal such as man.

According to this aspect of the invention there is provided the use of a compound of the formula (I), or a pharmaceutically acceptable salt thereof, as defined herein in the manufacture of a medicament for use in the production of an anti-cancer effect in a warm-blooded animal such as man.

According to a further feature of the invention, there is provided the use of a compound of the formula (I), or a pharmaceutically acceptable salt thereof, as defined herein in the manufacture of a medicament for use in the treatment of melanoma, papillary thyroid tumours, cholangiocarcinomas, colon cancer, ovarian cancer, lung cancer, leukemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries.

According to a further aspect of the invention there is provided the use of a compound of the formula (I), or a pharmaceutically acceptable salt thereof, as defined herein in the production of a FGFR inhibitory effect in a warm-blooded animal such as man.

According to this aspect of the invention there is provided the use of a compound of the formula (I), or a pharmaceutically acceptable salt thereof, as defined herein in the production of an anti-cancer effect in a warm-blooded animal such as man.

According to a further feature of the invention, there is provided the use of a compound of the formula (I), or a pharmaceutically acceptable salt thereof, as defined herein in the treatment of melanoma, papillary thyroid tumours, cholangiocarcinomas, colon cancer, ovarian cancer, lung cancer, leukemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries.

According to a further feature of this aspect of the invention there is provided a method for producing a FGFR inhibitory effect in a warm-blooded animal, such as man, in need of such treatment which comprises administering to said animal an effective amount of a compound of formula (I), or a pharmaceutically acceptable salt thereof, as defined herein.

According to a further feature of this aspect of the invention there is provided a method for producing an anti-cancer effect in a warm-blooded animal, such as man, in need of such treatment which comprises administering to said animal an effective amount of a compound of formula (I), or a pharmaceutically acceptable salt thereof, as defined herein.

According to an additional feature of this aspect of the invention there is provided a method of treating melanoma, papillary thyroid tumours, cholangiocarcinomas, colon cancer, ovarian cancer, lung cancer, leukemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries, in a warm-blooded animal, such as man, in need of such treatment which comprises administering to said animal an effective amount of a compound of formula (I) or a pharmaceutically acceptable salt thereof as defined herein.

In a further aspect of the invention there is provided a pharmaceutical composition which comprises a compound of the formula (I), or a pharmaceutically acceptable salt thereof, as defined herein in association with a pharmaceutically-acceptable diluent or carrier for use in the production of a FGFR inhibitory effect in a warm-blooded animal such as man.

In a further aspect of the invention there is provided a pharmaceutical composition which comprises a compound of the formula (I), or a pharmaceutically acceptable salt thereof, as defined herein in association with a pharmaceutically-acceptable diluent or carrier for use in the production of an anti-cancer effect in a warm-blooded animal such as man.

In a further aspect of the invention there is provided a pharmaceutical composition which comprises a compound of the formula (I), or a pharmaceutically acceptable salt thereof, as defined herein in association with a pharmaceutically-acceptable diluent or carrier for use in the treatment of melanoma, papillary thyroid tumours, cholangiocarcinomas, colon cancer, ovarian cancer, lung cancer, leukemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries in a warm-blooded animal such as man.

The compounds of formula (I) and pharmaceutically acceptable salts thereof may be used on their own but will generally be administered in the form of a pharmaceutical composition in which the formula (I) compound or salt (active ingredient) is in association with a pharmaceutically acceptable adjuvant, diluent or carrier. Depending on the mode of administration, the pharmaceutical composition may comprise from 0.01 to 99% w (per cent by weight), from 0.05 to 80% w, from 0.10 to 70% w, and or even from 0.10 to 50% w, of active ingredient, all percentages by weight being based on total composition.

The present invention also provides a pharmaceutical composition comprising a compound of formula (I), or a pharmaceutically acceptable salt thereof, as herein defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt thereof, as herein defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The size of the dose for therapeutic purposes of a compound of the invention will naturally vary according to the nature and severity of the conditions, the age and sex of the animal or patient and the route of administration, according to well known principles of medicine.

In general, a compound of the invention will be administered so that a daily dose in the range, for example, from 0.1 mg to 1000 mg active ingredient per kg body weight is received, given if required in divided doses. However the daily dose will necessarily be varied depending upon the host treated, the particular route of administration, and the severity of the illness being treated. Accordingly the optimum dosage may be determined by the practitioner who is treating any particular patient. In general lower doses will be administered when a parenteral route is employed. Thus, for example, for intravenous administration, a dose in the range, for example, from 0.1 mg to 30 mg active ingredient per kg body weight will generally be used. Similarly, for administration by inhalation, a dose in the range, for example, from 0.1 mg to 25 mg active ingredient per kg body weight will generally be used. Oral administration is however preferred. For example, a formulation intended for oral administration to humans will generally contain, for example, from 0.1 mg to 2 g of active ingredient.

For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of
   5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signaling inhibitors such as farnesyl transferase inhibitors, for example sorafenib (BAY 43-9006)), inhibitors of cell signaling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

EXAMPLES

The invention will now be further described with reference to the following illustrative examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz, in DMSO-$d_6$ unless otherwise indicated;

(viii) chemical symbols have their usual meanings; SI units and symbols are used;

(ix) solvent ratios are given in volume:volume (v/v) terms; and (x) mass spectra (MS) data was generated on an LC/MS system where the HPLC component comprised generally either a Agilent 1100 or Waters Alliance HT (2790 & 2795) equipment and was run on a Phemonenex Gemini C18 5 μm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ spectrometer. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the (M+H)+ for positive ion mode and (M–H)⁻ for negative ion mode;

(xi) Preparative HPLC was performed on C18 reversed-phase silica, for example on a Waters 'Xterra' preparative reversed-phase column (5 microns silica, 19 mm diameter, 100 mm length) using decreasingly polar mixtures as eluent, for example decreasingly polar mixtures of water (containing 1% acetic acid or 1% aqueous ammonium hydroxide (d=0.88) and acetonitrile;

(xii) the following abbreviations have been used:

| | |
|---|---|
| THF | tetrahydrofuran; |
| DMF | N,N-dimethylformamide; |
| EtOAc | ethyl acetate; |
| DCM | dichloromethane; and |
| DMSO | dimethylsulphoxide |
| DIPEA | N,N-diisopropylethylamine (also known as N-ethyl-N-propan-2-yl-propan-2-amine) |
| PBS | phosphate buffered saline |
| HEPES | N-[2-Hydroxyethyl]piperazine-N'-[2-ethanesulfonic acid] |
| DTT | dithiothreitol |
| ATP | Adenosine Triphosphate |
| BSA | bovine serum albumin |
| DMEM | Dulbecco's modified Eagle's Medium |
| MOPS | 3-(N-morpholino)propanesulfonic acid |

(xiii) compounds are named using proprietary naming software: Openeye Lexichem version 1.4, using IUPAC naming convention;

(xiv) unless otherwise specified, starting materials are commercially available.

TABLE 1

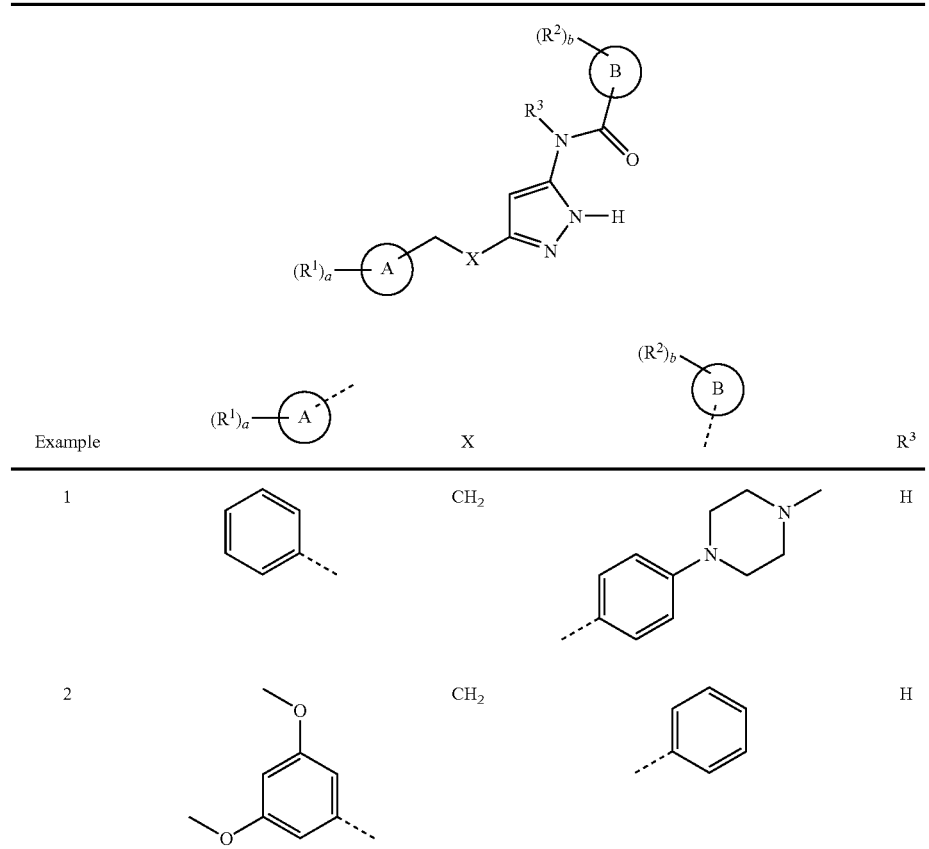

TABLE 1-continued
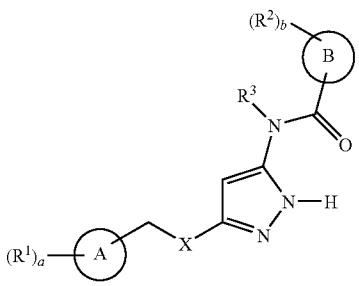
| Example | (R¹)ₐ—⟨A⟩--- | X | (R²)_b—⟨B⟩--- | R³ |
|---|---|---|---|---|
| 3 | 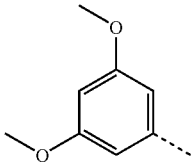 | CH₂ | 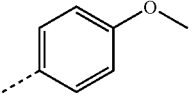 | H |
| 4 | 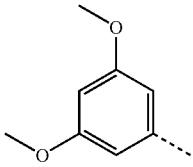 | CH₂ | 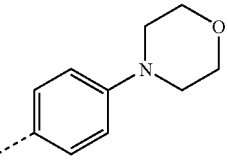 | H |
| 5 | 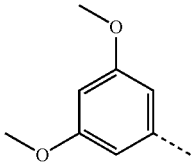 | CH₂ | 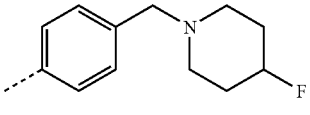 | H |
| 6 | 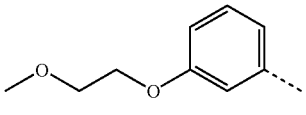 | CH₂ | 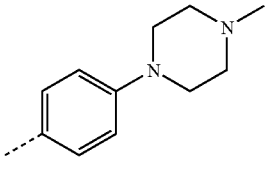 | H |
| 7 | 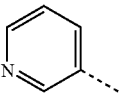 | CH₂ | 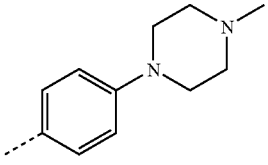 | H |
| 8 | 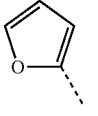 | CH₂ | 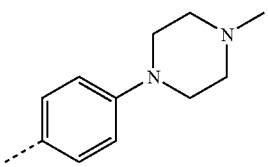 | H |
| 9 | 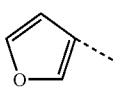 | CH₂ | 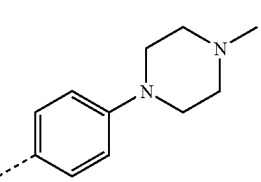 | H |

TABLE 1-continued

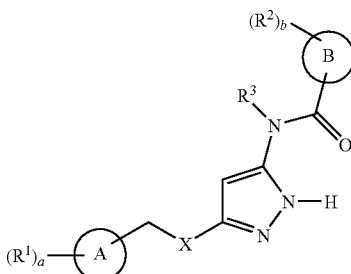

| Example | (R¹)ₐ—A | X | B | R³ |
|---|---|---|---|---|
| 10 | 3,5-dimethoxyphenyl | CH₂ | 4-(4-methylpiperazin-1-yl)phenyl | H |
| 11 | 3-methoxyphenyl | CH₂ | 4-(4-methylpiperazin-1-yl)phenyl | H |
| 12 | 3,5-dimethoxyphenyl | O | 4-(4-methylpiperazin-1-yl)phenyl | H |
| 13 | 3-methoxyphenyl | CH₂ | 6-methylpyridin-3-yl | H |
| 14 | 3-methoxyphenyl | CH₂ | 6-methoxypyridin-3-yl | H |
| 15 | 3-methoxyphenyl | CH₂ | 4-(methylsulfonyl)phenyl | H |
| 16 | 3-methoxyphenyl | CH₂ | 5-methylpyrazin-2-yl | H |
| 17 | 3-methoxyphenyl | CH₂ | 6-(prop-2-yn-1-ylamino)pyridin-3-yl | H |

TABLE 1-continued
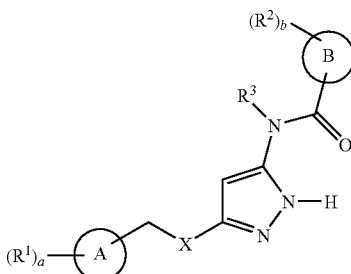
| Example | (R¹)ₐ—A | X | (R²)_b—B | R³ |
|---|---|---|---|---|
| 18 | 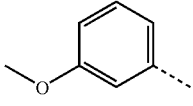 | CH₂ | 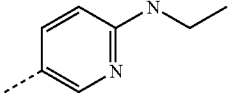 | H |
| 19 | 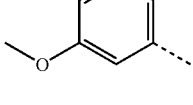 | CH₂ | 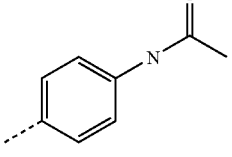 | H |
| 20 | 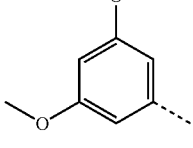 | O | 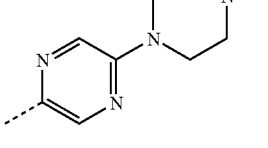 | H |
| 21 | 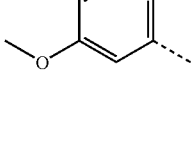 | CH₂ | 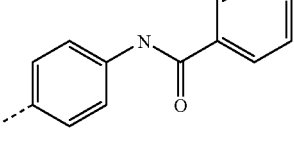 | H |
| 22 | 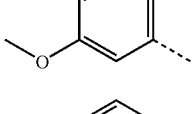 | CH₂ | 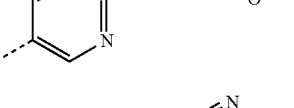 | H |
| 23 | 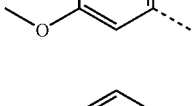 | CH₂ | 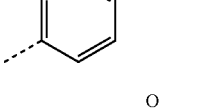 | H |
| 24 | 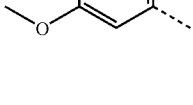 | CH₂ | 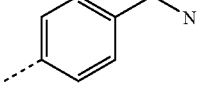 | H |
| 25 | 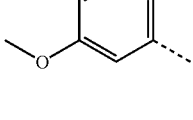 | CH₂ | 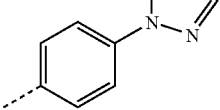 | H |

TABLE 1-continued
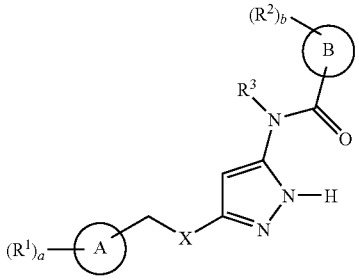
| Example | (R¹)ₐ—A | X | B—(R²)ᵦ | R³ |
|---|---|---|---|---|
| 26 | 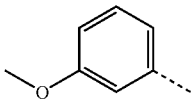 | CH₂ | 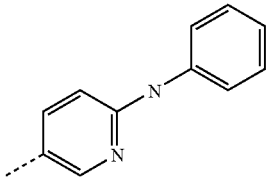 | H |
| 27 | 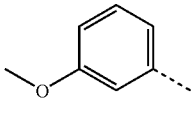 | CH₂ | 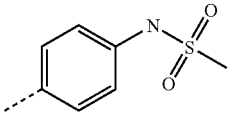 | H |
| 28 | 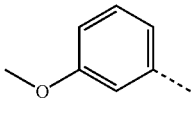 | CH₂ | 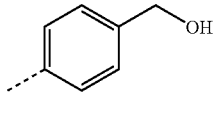 | H |
| 29 | 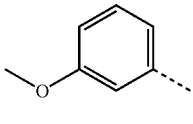 | CH₂ | 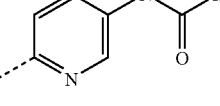 | H |
| 30 | 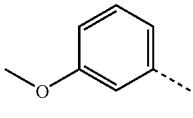 | CH₂ | 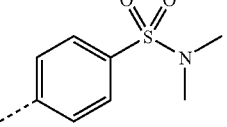 | H |
| 31 | 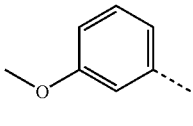 | CH₂ | 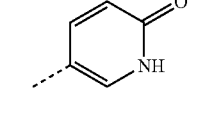 | H |
| 32 | 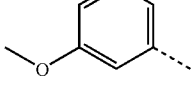 | CH₂ | 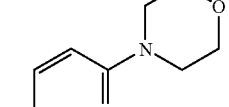 | H |
| 33 | 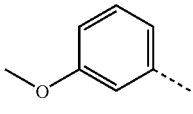 | CH₂ | 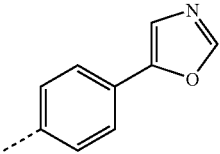 | H |

TABLE 1-continued
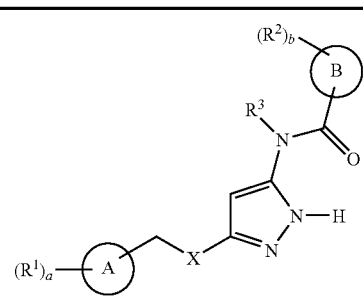
| Example | (R¹)ₐ─A | X | (R²)ᵦ─B | R³ |
|---|---|---|---|---|
| 34 | 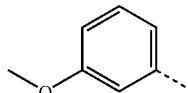 | CH₂ | 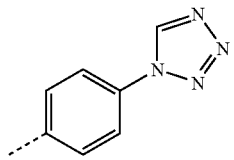 | H |
| 35 | 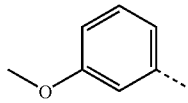 | CH₂ | 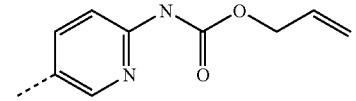 | H |
| 36 | 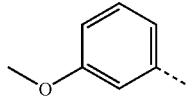 | CH₂ | 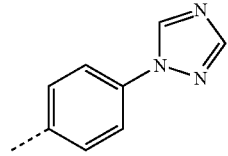 | H |
| 37 | 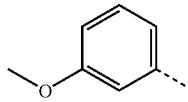 | CH₂ | 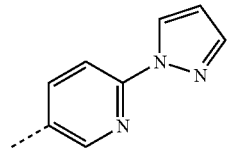 | H |
| 38 | 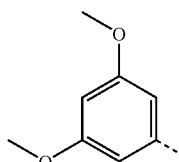 | CH₂ | 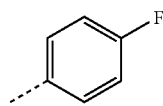 | H |
| 39 | 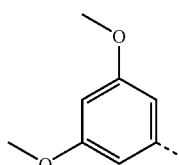 | CH₂ | 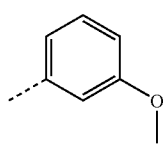 | H |
| 40 | 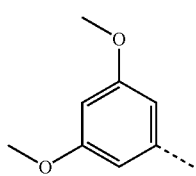 | CH₂ | 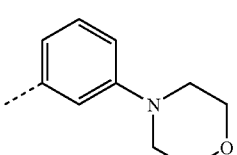 | H |

TABLE 1-continued
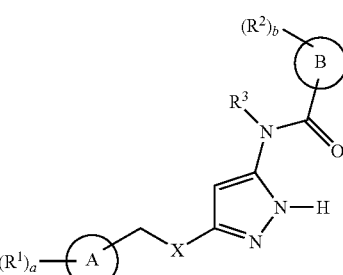
| Example | (R¹)ₐ—A | X | B—(R²)ᵦ | R³ |
|---|---|---|---|---|
| 41 | 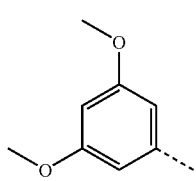 | CH₂ | 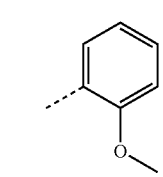 | H |
| 42 | 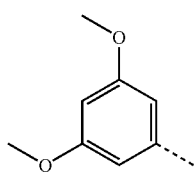 | CH₂ | 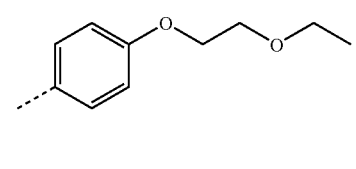 | H |
| 43 | 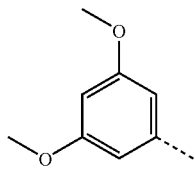 | CH₂ | 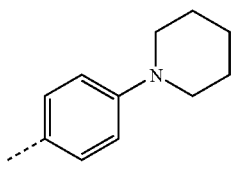 | H |
| 44 | 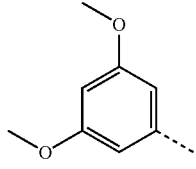 | CH₂ | 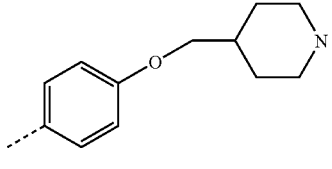 | H |
| 45 | 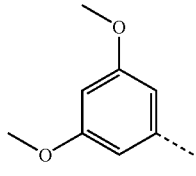 | CH₂ | 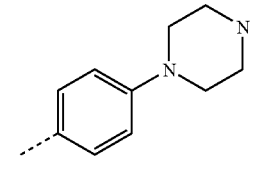 | H |
| 46 | 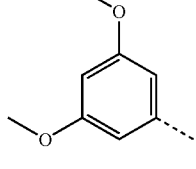 | CH₂ | 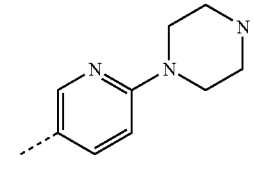 | H |

TABLE 1-continued

| Example | (R¹)ₐ–A | X | B–(R²)_b | R³ |
|---|---|---|---|---|
| 47 | 3,5-dimethoxyphenyl | CH₂ | 4-((dimethylamino)methyl)phenyl | H |
| 48 | 3,5-dimethoxyphenyl | CH₂ | 4-(2-hydroxyethoxy)phenyl | H |
| 49 | 3,5-dimethoxyphenyl | CH₂ | 4-(2-aminopropyl)phenyl | H |
| 50 | 3,5-dimethoxyphenyl | CH₂ | 4-((3,3-dimethylpiperidin-1-yl)methyl)phenyl | H |
| 51 | 3,5-dimethoxyphenyl | CH₂ | 4-(4-(2-hydroxyethyl)piperazin-1-yl)phenyl | H |
| 52 | 3,5-dimethoxyphenyl | CH₂ | 4-((7-cyano-3,4-dihydroisoquinolin-2(1H)-yl)methyl)phenyl | H |

TABLE 1-continued
| Example | (R¹)ₐ—A | X | (R²)ᵦ—B | R³ |
|---|---|---|---|---|
| 53 | 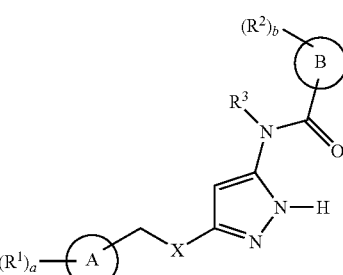 | CH₂ | 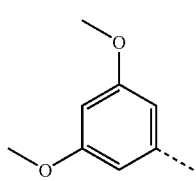 | H |
| 54 | 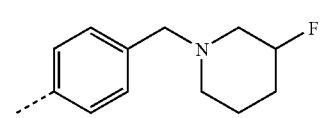 | CH₂ | 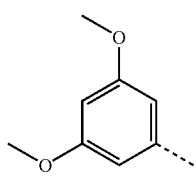 | H |
| 55 | 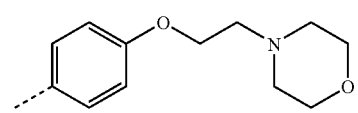 | CH₂ | 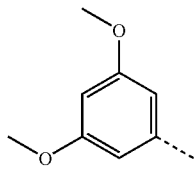 | H |
| 56 | 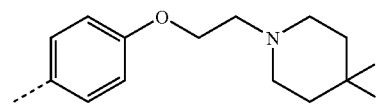 | CH₂ | 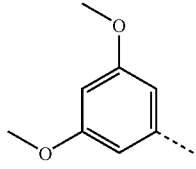 | H |
| 57 | 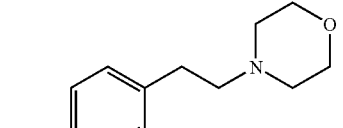 | CH₂ | 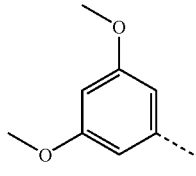 | H |
| 58 | 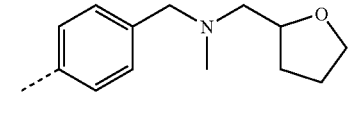 | CH₂ | 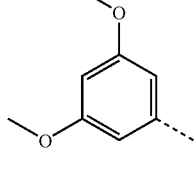 | H |

TABLE 1-continued
| Example | (R¹)ₐ–A | X | B–(R²)ᵦ | R³ |
|---|---|---|---|---|
| 59 | 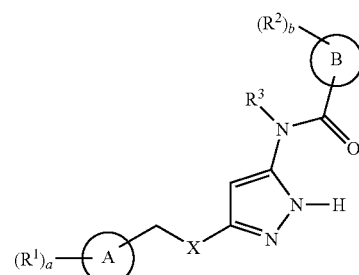 | CH₂ | 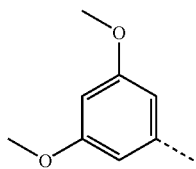 | H |
| 60 | 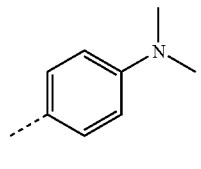 | CH₂ | 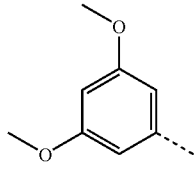 | H |
| 61 | 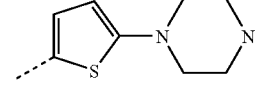 | CH₂ | 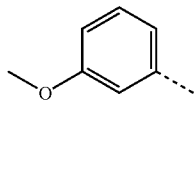 | H |
| 62 | 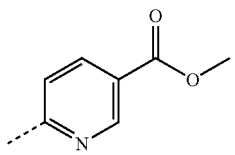 | CH₂ | 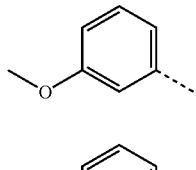 | H |
| 63 | 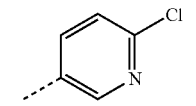 | CH₂ | 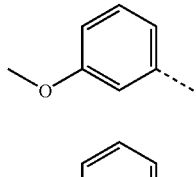 | H |
| 64 | 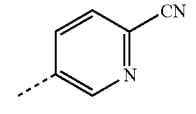 | CH₂ | 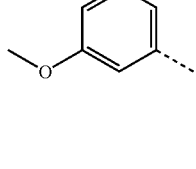 | H |
| 65 | 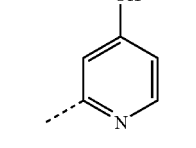 | CH₂ | 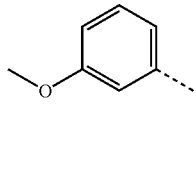 | H |

TABLE 1-continued
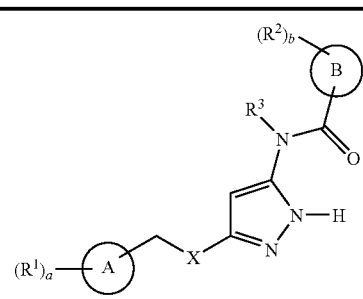
| Example | (R¹)ₐ—A | X | B | R³ |
|---|---|---|---|---|
| 66 |  | CH₂ | 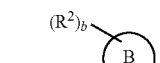 | H |
| 67 |  | CH₂ | 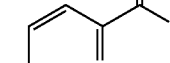 | H |
| 68 |  | CH₂ | 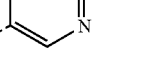 | H |
| 69 |  | O | 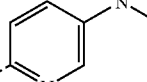 | H |
| 70 |  | O | 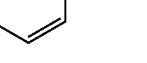 | H |
| 71 |  | O | 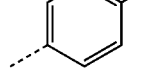 | H |
| 72 |  | O | 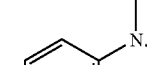 | H |

TABLE 1-continued
| Example | (R¹)ₐ-A | X | (R²)ᵦ-B | R³ |
|---|---|---|---|---|
| 73 | 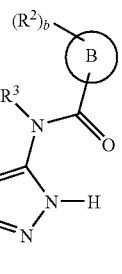 | O | 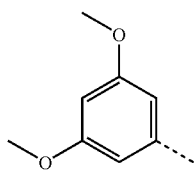 | H |
| 74 | 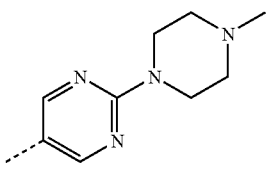 | O | 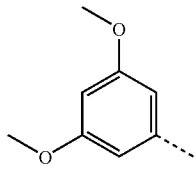 | H |
| 75 | 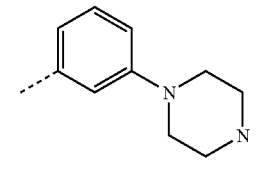 | O | 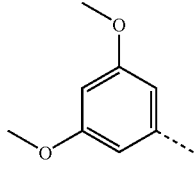 | H |
| 76 | 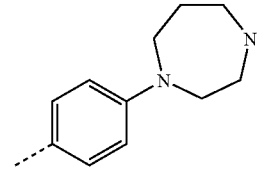 | CH₂ | 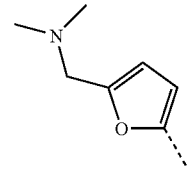 | H |
| 77 | 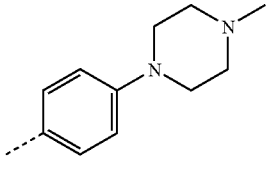 | CH₂ | 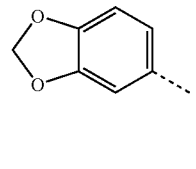 | H |
| 78 | 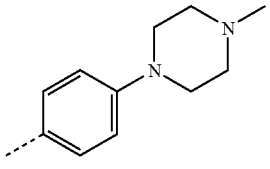 | CH₂ | 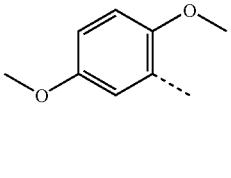 | H |
| 79 | 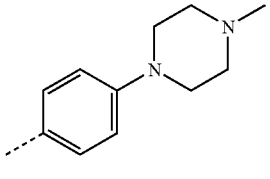 | CH₂ | 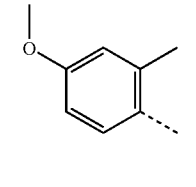 | H |

US 8,129,391 B2
137                                                                                                             138
TABLE 1-continued
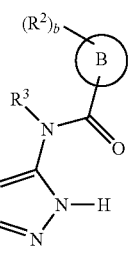
| Example | (R¹)ₐ—A | X | (R²)ᵦ—B | R³ |
|---|---|---|---|---|
| 80 | 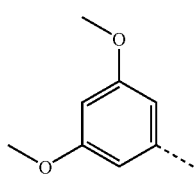 | CH₂ | 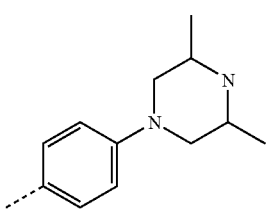 | H |
| 81 | 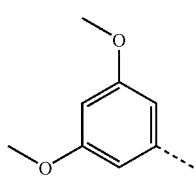 | CH₂ | 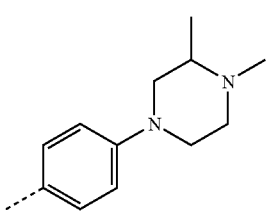 | H |
| 82 | 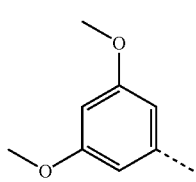 | CH₂ | 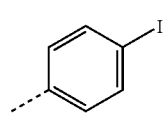 | H |
| 83 | 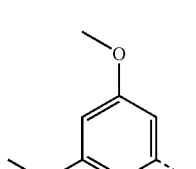 | CH₂ | 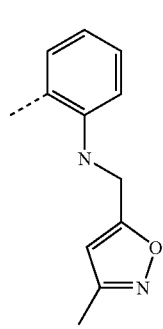 | H |
| 84 | 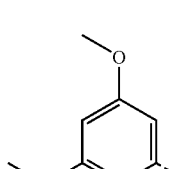 | CH₂ | 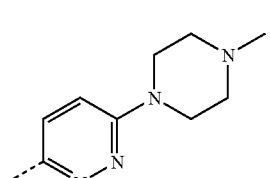 | H |

TABLE 1-continued
| Example | (R¹)ₐ—A | X | B—(R²)ᵦ | R³ |
|---|---|---|---|---|
| 85 | 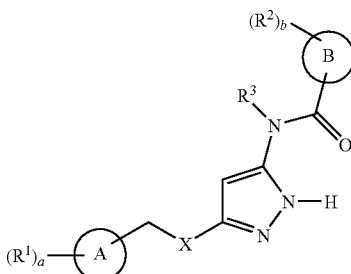 | CH₂ | 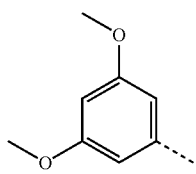 | H |
| 86 | 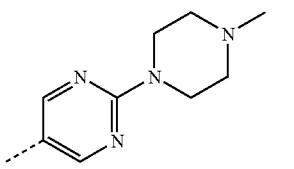 | CH₂ | 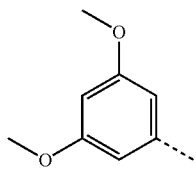 | H |
| 87 | 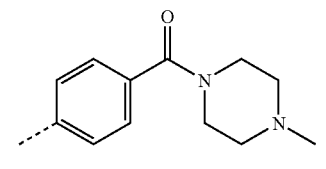 | CH₂ | 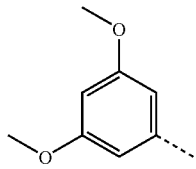 | H |
| 88 | 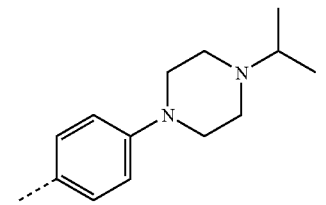 | CH₂ | 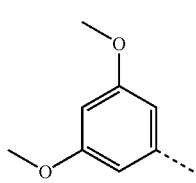 | H |
| 89 | 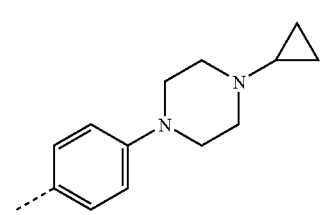 | CH₂ | 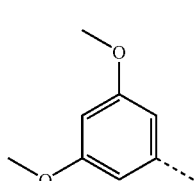 | H |
| 90 | 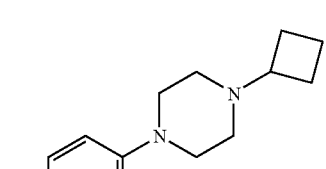 | CH₂ | 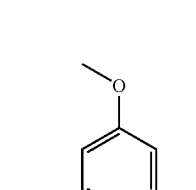 | H |

TABLE 1-continued

| Example | (R¹)ₐ—A | X | B (R²)ᵦ | R³ |
|---|---|---|---|---|
| 91 | 3-methoxyphenyl | CH₂ | 4-(4-methanesulfonylpiperazin-1-yl)phenyl | H |
| 92 | 3,5-dimethoxyphenyl | CH₂ | 4-(1-methylpiperidin-4-yl)phenyl | H |
| 93 | 3,5-dimethoxyphenyl | CH₂ | 4-(hexahydropyrrolo[1,2-a]pyrazin-2-yl)phenyl | H |
| 94 | 3,5-dimethoxyphenyl | CH₂ | 4-(octahydro-2H-pyrido[1,2-a]pyrazin-2-yl)phenyl | H |
| 95 | 3,5-dimethoxyphenyl | CH₂ | 4-((4-methylpiperazin-1-yl)methyl)phenyl | H |
| 96 | 3,5-dimethoxyphenyl | CH₂ | 4-(2,3,4-trimethylpiperazin-1-yl)phenyl | H |

TABLE 1-continued
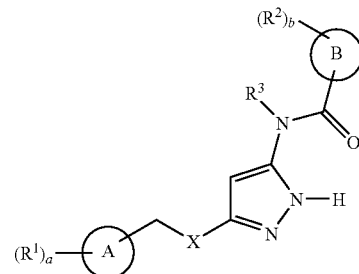
| Example | (R¹)ₐ—A | X | (R²)ᵦ—B | R³ |
|---|---|---|---|---|
| 97 | 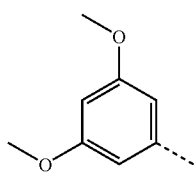 | O | 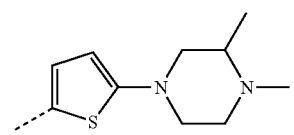 | H |
| 98 | 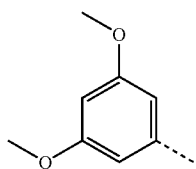 | O | 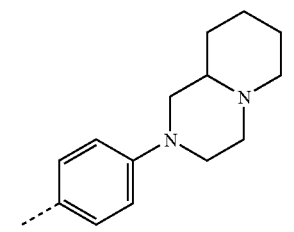 | H |
| 99 | 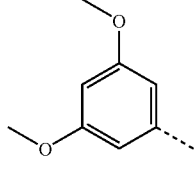 | CH₂ | 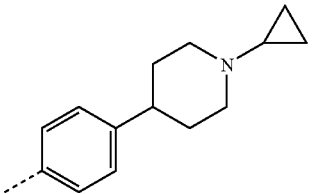 | H |
| 100 | 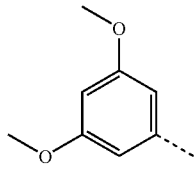 | O | 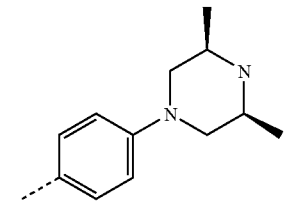 | H |
| 101 | 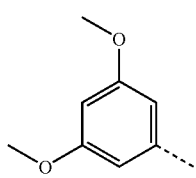 | O | 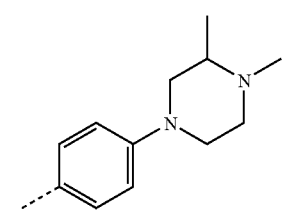 | H |

TABLE 1-continued
| Example | (R¹)ₐ—A | X | B—(R²)ᵦ | R³ |
|---|---|---|---|---|
| 102 | 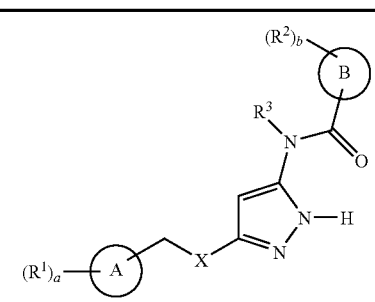 | CH₂ | 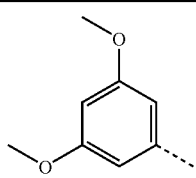 | H |
| 103 |  | O | 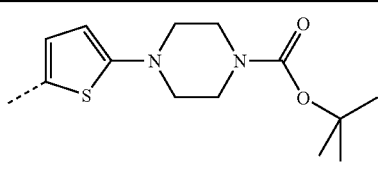 | H |
| 104 | 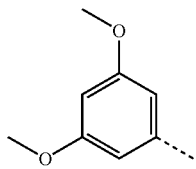 | O |  | H |
| 105 | 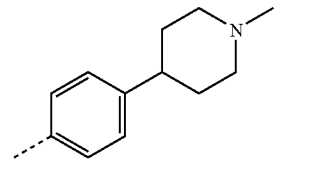 | CH₂ | 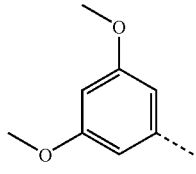 | H |
| 106 |  | CH₂ | 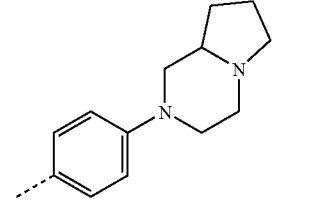 | H |
| 107 | 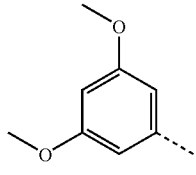 | O |  | H |

TABLE 1-continued

| Example | (R¹)ₐ–A | X | (R²)ᵦ–B | R³ |
|---|---|---|---|---|
| 108 | 3,5-dimethoxyphenyl | CH₂ | 5-(3,3-dimethylpiperazin-1-yl)pyrazin-2-yl | H |
| 109 | 3,5-dimethoxyphenyl | O | 5-(4-cyclopropylpiperazin-1-yl)pyrazin-2-yl | H |
| 110 | 3,5-dimethoxyphenyl | O | 4-((2S,6R)-2,4,6-trimethylpiperazin-1-yl)phenyl | H |
| 111 | 3,5-dimethoxyphenyl | O | 4-(3,3-dimethylpiperazin-1-yl)phenyl | H |
| 112 | 3,5-dimethoxyphenyl | CH₂ | 5-((2R,6S)-2,6-dimethylpiperazin-1-yl)pyrazin-2-yl | H |

TABLE 1-continued
| Example | (R¹)ₐ—A | X | (R²)ᵦ—B | R³ |
|---|---|---|---|---|
| 113 | 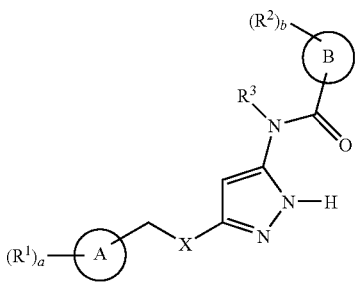 | CH₂ | 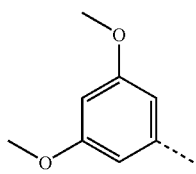 | H |
| 114 | 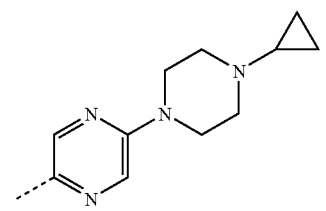 | CH₂ | 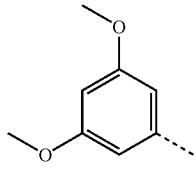 | H |
| 115 | 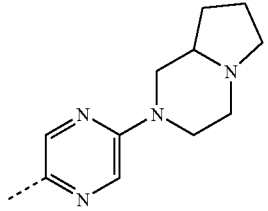 | O | 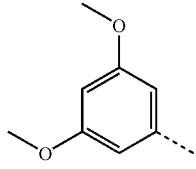 | H |
| 116 | 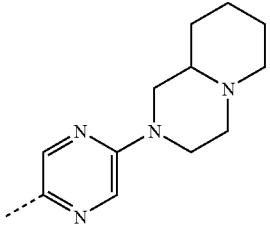 | O | 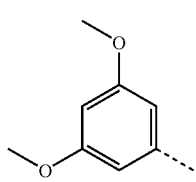 | H |
| 117 | 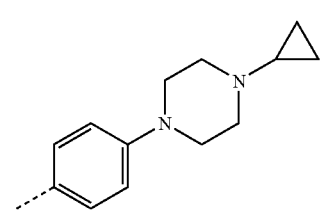 | CH₂ | 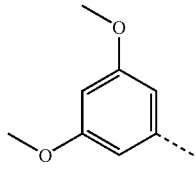 | H |

TABLE 1-continued
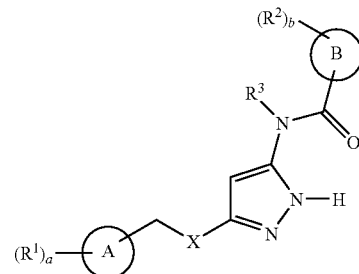
| Example | (R¹)ₐ—A | X | (R²)ᵦ—B | R³ |
|---|---|---|---|---|
| 118 | 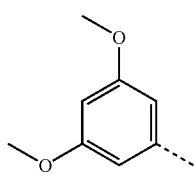 | O | 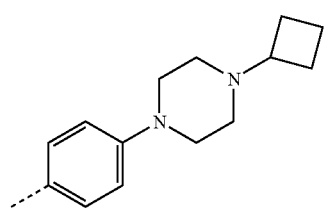 | H |
| 119 | 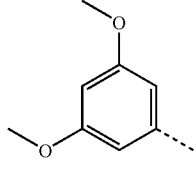 | O | 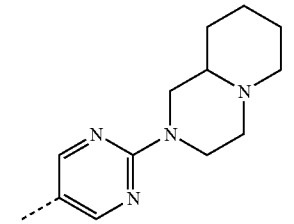 | H |
| 120 | 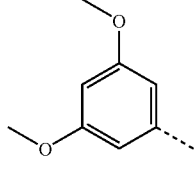 | CH₂ | 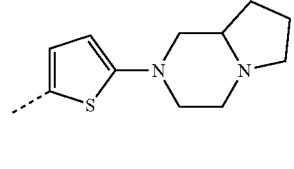 | H |
| 121 | 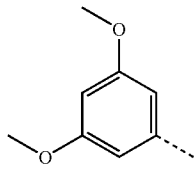 | O | 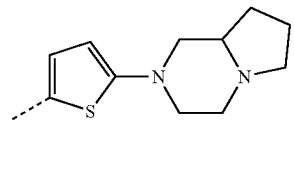 | H |
| 122 | 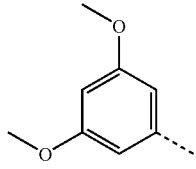 | O | 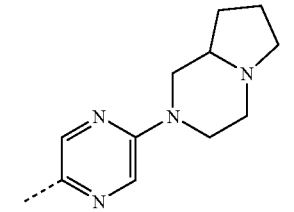 | H |

TABLE 1-continued
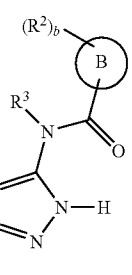
| Example | (R¹)ₐ—A | X | B—(R²)ᵦ | R³ |
|---|---|---|---|---|
| 123 | 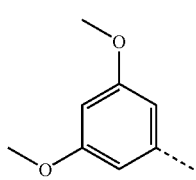 | CH₂ | 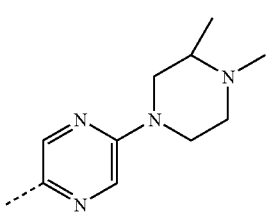 | H |
| 124 | 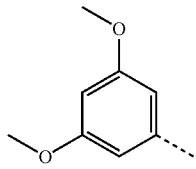 | O | 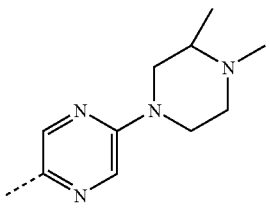 | H |
| 125 | 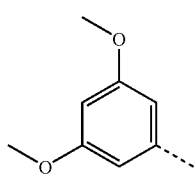 | CH₂ | 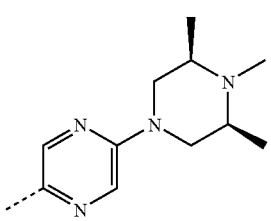 | H |
| 126 | 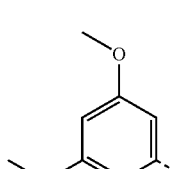 | CH₂ | 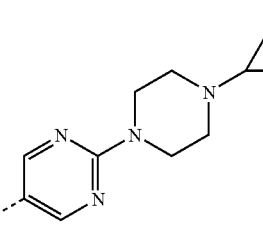 | H |
| 127 | 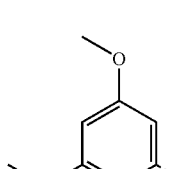 | CH₂ | 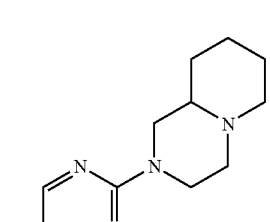 | H |

TABLE 1-continued
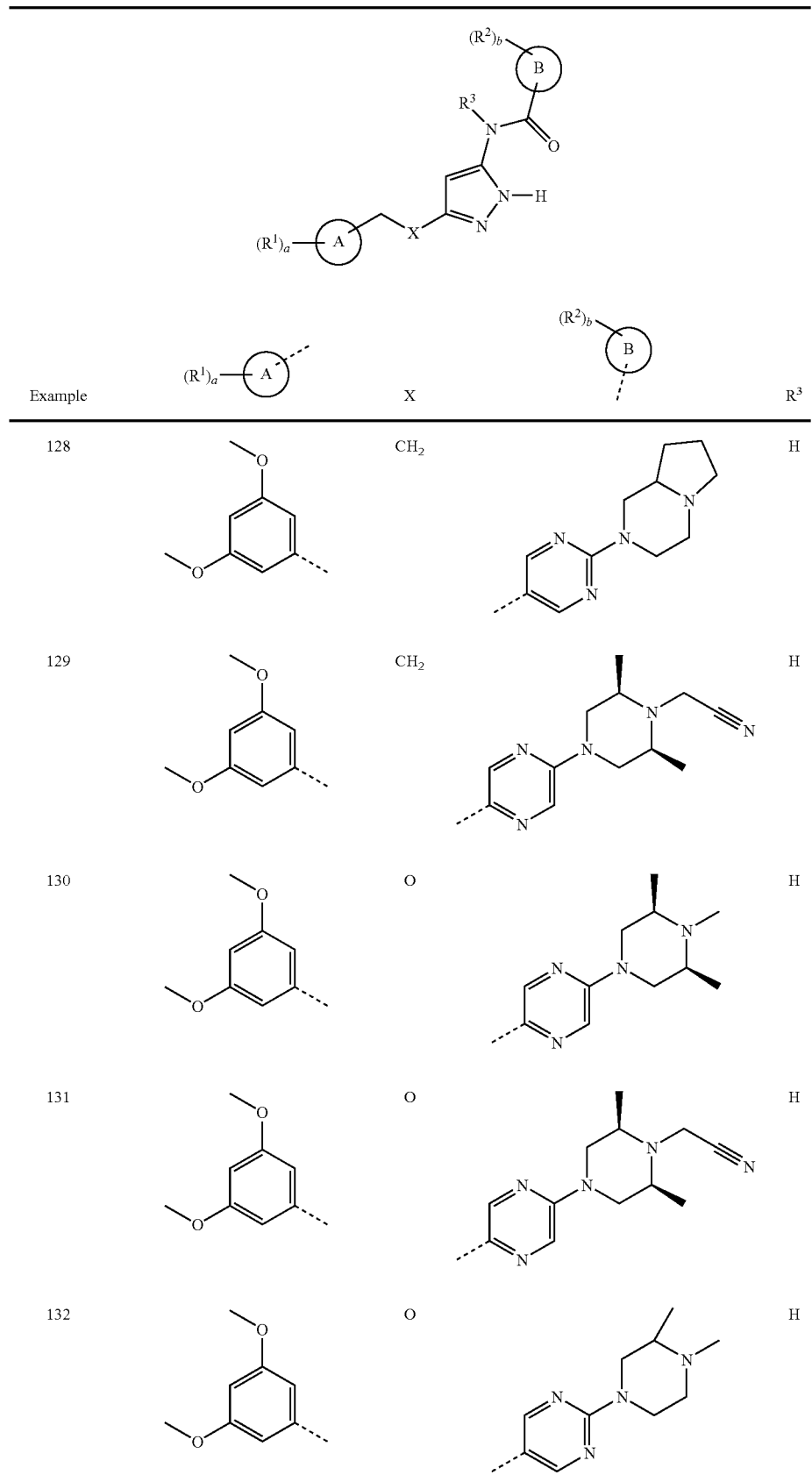

TABLE 1-continued
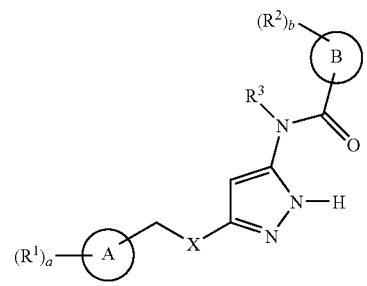
| Example | (R¹)ₐ—A | X | (R²)ᵦ—B | R³ |
|---|---|---|---|---|
| 133 | 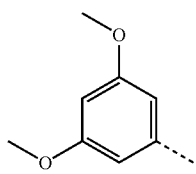 | O | 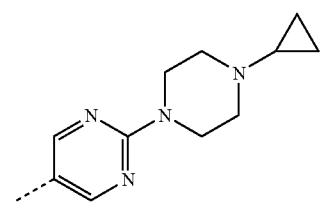 | H |
| 134 | 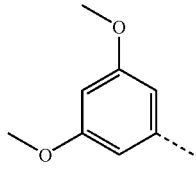 | O | 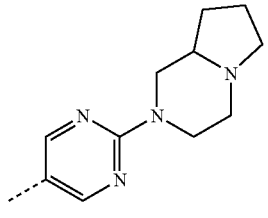 | H |
| 135 | 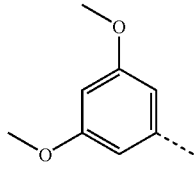 | CH₂ | 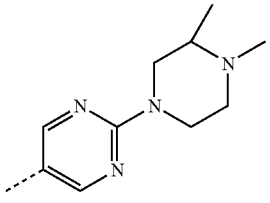 | H |
| 136 | 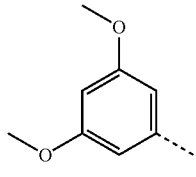 | CH₂ | 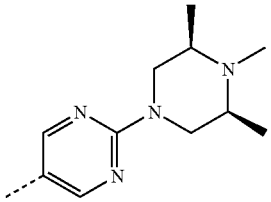 | H |
| 137 | 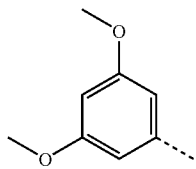 | CH₂ | 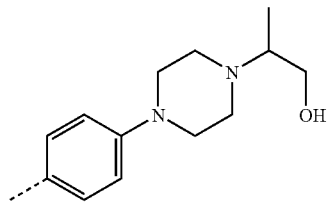 | H |

TABLE 1-continued

| Example | (R¹)ₐ—A | X | (R²)ᵦ—B | R³ |
|---|---|---|---|---|
| 138 | 3,5-dimethoxyphenyl | O | 5-((2S,6S)-2,4,6-trimethylpiperazin-1-yl)pyrimidin-2-yl | H |
| 139 | 3,5-dimethoxyphenyl | CH₂ | 4-(3,3-dimethylpiperazin-1-yl)phenyl | H |
| 140 | 3,5-dimethoxyphenyl | O | 5-(3,3-dimethylpiperazin-1-yl)thiophen-2-yl | H |
| 141 | 3,5-dimethoxyphenyl | O | 5-(4-ethylpiperazin-1-yl)thiophen-2-yl | H |
| 142 | 3,5-dimethoxyphenyl | CH₂ | 5-(4-methyl-1,4-diazepan-1-yl)thiophen-2-yl | H |
| 143 | 3,5-dimethoxyphenyl | CH₂ | 5-(4-ethyl-3-methylpiperazin-1-yl)pyrimidin-2-yl | H |

TABLE 1-continued

| Example | (R¹)ₐ—A | X | B—(R²)ᵦ | R³ |
|---|---|---|---|---|
| 144 | 3,5-dimethoxyphenyl | CH₂ | 4-(1-allylpiperidin-4-yl)phenyl | H |
| 145 | 3,5-dimethoxyphenyl | CH₂ | 4-(1,4-diazepan-1-yl)phenyl | H |
| 146 | 3,5-dimethoxyphenyl | CH₂ | 4-(1-propargylpiperidin-4-yl)phenyl | H |
| 147 | 3,5-dimethoxyphenyl | O | 5-((2R,5S)-2,5-dimethylpiperazin-1-yl)thiophen-2-yl | H |
| 148 | 3,5-dimethoxyphenyl | CH₂ | 4-(1-(2-methoxyethyl)piperidin-4-yl)phenyl | H |
| 149 | 3,5-dimethoxyphenyl | CH₂ | 2-((S)-3-isopropylpiperazin-1-yl)pyrimidin-5-yl | H |

TABLE 1-continued

| Example | (R¹)ₐ—A | X | B—(R²)ᵦ | R³ |
|---|---|---|---|---|
| 150 | 3,5-dimethoxyphenyl | CH₂ | 5-(4-methyl-3-oxopiperazin-1-yl)pyrimidin-2-yl | H |
| 151 | 3,5-dimethoxyphenyl | O | 4-(octahydropyrrolo[3,4-b]pyridin-6-yl)phenyl | H |
| 152 | 3,5-dimethoxyphenyl | CH₂ | 5-(1-methylpiperidin-4-yl)pyrazin-2-yl | H |
| 153 | 3,5-dimethoxyphenyl | CH₂ | 5-(1-methyl-1,2,3,6-tetrahydropyridin-4-yl)pyrazin-2-yl | H |
| 154 | 3,5-dimethoxyphenyl | CH₂ | 4-((2S,6S)-2,6-dimethylpiperazin-1-yl)phenyl | H |
| 155 | 3,5-dimethoxyphenyl | CH₂ | 4-((2S,6S)-2,4,6-trimethylpiperazin-1-yl)phenyl | H |

TABLE 1-continued
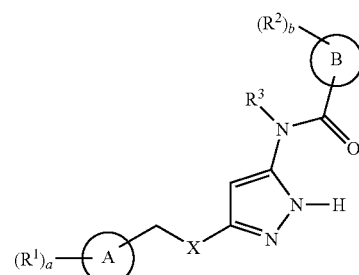
| Example | (R¹)ₐ—A | X | B—(R²)ᵦ | R³ |
|---|---|---|---|---|
| 156 | 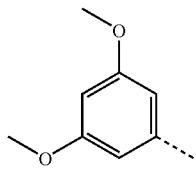 | CH₂ | 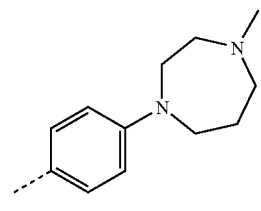 | H |
| 157 | 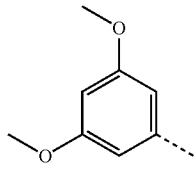 | CH₂ | 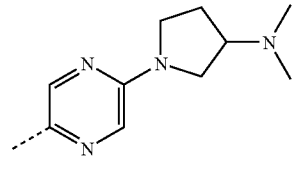 | H |
| 158 | 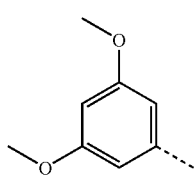 | CH₂ | 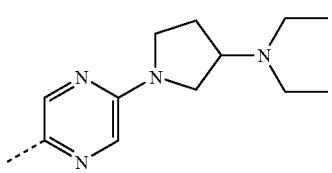 | H |
| 159 | 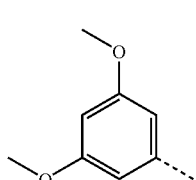 | CH₂ | 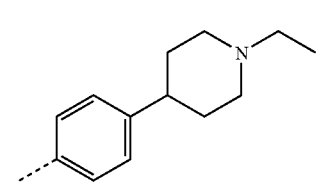 | H |
| 160 | 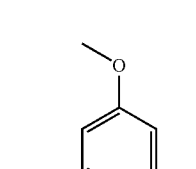 | CH₂ | 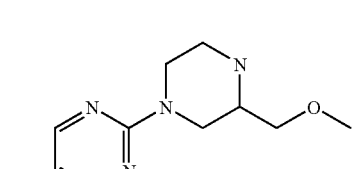 | H |
| 161 | 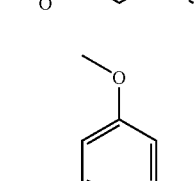 | CH₂ | 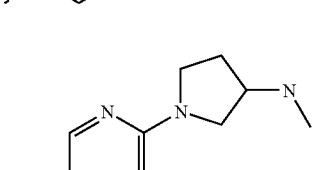 | H |

TABLE 1-continued

| Example | (R¹)ₐ—A | X | (R²)ᵦ—B | R³ |
|---|---|---|---|---|
| 162 | 3,5-dimethoxyphenyl | CH₂ | 2-(1-methylpiperidin-4-yl)pyrimidin-5-yl | H |
| 163 | 3,5-dimethoxyphenyl | CH₂ | 5-(4-methyl-1,4-diazepan-1-yl)pyrazin-2-yl | H |
| 164 | 3,5-dimethoxyphenyl | CH₂ | 4-(4-allyl-1,4-diazepan-1-yl)phenyl | H |
| 165 | 3,5-dimethoxyphenyl | CH₂ | 4-(4-cyclopropyl-1,4-diazepan-1-yl)phenyl | H |
| 166 | 3,5-dimethoxyphenyl | CH₂ | 4-(4-isopropyl-1,4-diazepan-1-yl)phenyl | H |

TABLE 1-continued
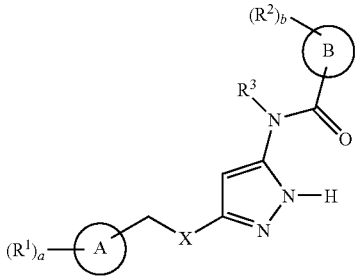
| Example | (R¹)ₐ─A | X | B─(R²)ᵦ | R³ |
|---|---|---|---|---|
| 167 | 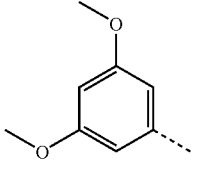 | CH₂ | 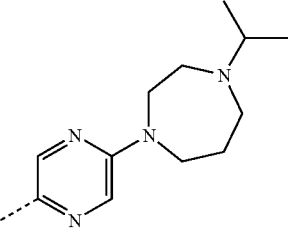 | H |
| 168 | 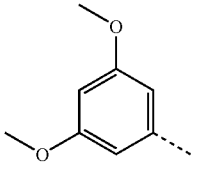 | CH₂ | 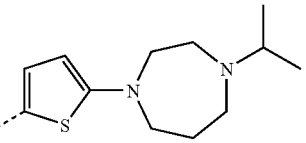 | H |
| 169 | 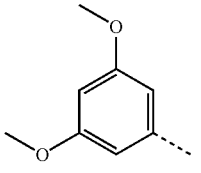 | CH₂ | 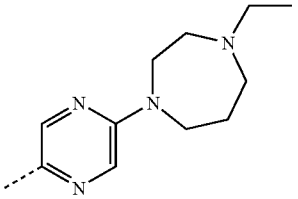 | H |
| 170 | 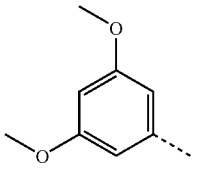 | CH₂ | 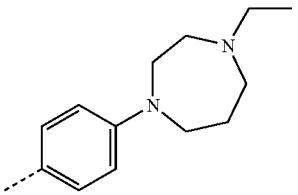 | H |
| 171 | 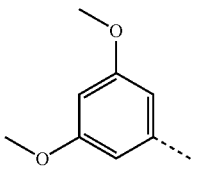 | CH₂ | 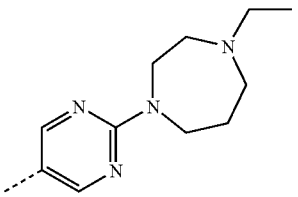 | H |

TABLE 1-continued
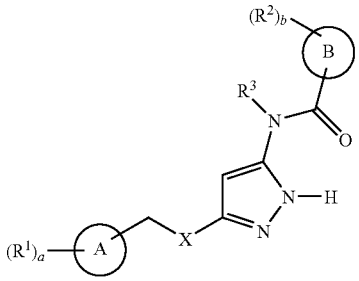
| Example | (R¹)ₐ—A | X | B | R³ |
|---|---|---|---|---|
| 172 | 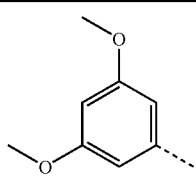 | CH₂ | 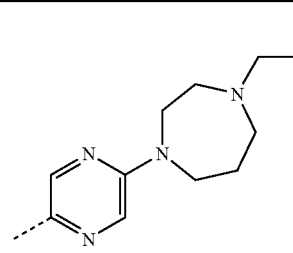 | H |
| 173 | 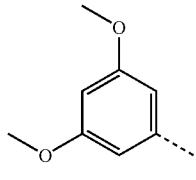 | CH₂ | 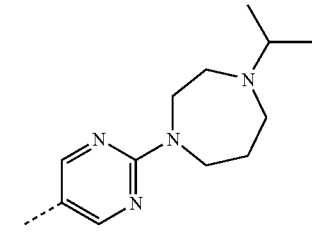 | H |
| 174 | 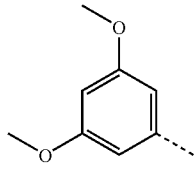 | CH₂ | 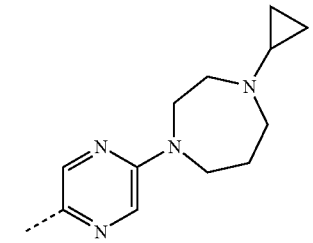 | H |
| 175 | 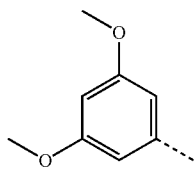 | CH₂ | 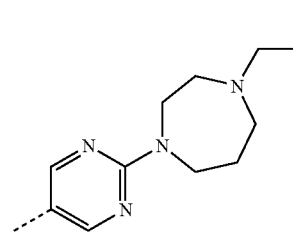 | H |
| 176 | 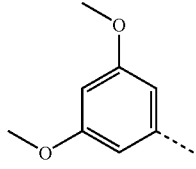 | CH₂ | 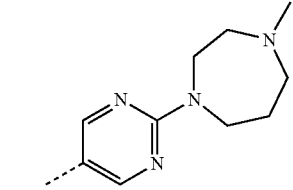 | H |

TABLE 1-continued

| Example | (R¹)ₐ—A— | X | B—(R²)_b (with R³) | R³ |
|---|---|---|---|---|
| 177 | 3,5-dimethoxyphenyl | CH₂ | 2-(4-cyclopropyl-1,4-diazepan-1-yl)pyrimidin-5-yl | H |
| 178 | 3-(N-methylcarbamoyl)phenyl | CH₂ | 4-(4-methylpiperazin-1-yl)phenyl | H |
| 179 | 3,5-dimethoxyphenyl | O | 4-(4-ethylpiperazin-1-yl)phenyl | H |
| 180 | 3,5-dimethoxyphenyl | CH₂ | 4-(4-ethylpiperazin-1-yl)phenyl | H |

Example 1

4-(4-methylpiperazin-1-yl)-N-(5-phenethyl-2H-pyrazol-3-yl)benzamide

Oxalyl chloride (2M in DCM, 250 μl, 0.50 mmol, 1.1 eq) was added dropwise to a mixture of 4-(4-methylpiperazin-1-yl)benzoic acid (100 mg, 0.45 mmol, 1 eq) in DCM (5 ml, containing a few drops of DMF) and DIPEA (171 μl, 0.95 mmol, 2.1 eq) at 0° C. After stirring for 1 h at 0° C., a solution of 5-phenethyl-2H-pyrazol-3-amine (128 mg, 0.68 mmol, 1.5 eq) in DCM (2 ml) was added dropwise. The mixture was maintained at 0° C. for 2 h, then gradually allowed to warm to room temperature overnight. The mixture was diluted with DCM (50 ml), washed with aq. NaHCO₃ solution (50 ml) and the aqueous layer was extracted with DCM (50 ml). The combined organic layers were concentrated. The crude product was purified by reverse-phase prep. HPLC (basic) using a 30-50% gradient of acetonitrile in water (containing 1% ammonium hydroxide) to yield the title compound (8 mg, 3% yield).

¹H NMR (300.132 MHz, DMSO) δ 2.23 (3H, s), 2.44 (4H, t), 2.84-2.95 (4H, m), 3.26-3.30 (4H, m), 6.41 (1H, s), 6.96 (2H, d), 7.15-7.33 (5H, m), 7.89 (2H, d), 10.30 (1H, s), 12.08 (1H, s). MS m/z 390 (MH+)

FGFR Kinase assay—Elisa, IC₅₀ 0.22 μM.

Example 2

N-[5-[2-(3,5-dimethoxyphenyl)ethyl]-2H-pyrazol-3-yl]benzamide

Benzoyl chloride (56 μl, 0.47 mmol, 1.1 eq) was added dropwise to a mixture of tert-butyl 5-amino-3-[2-(3,5- dimethoxyphenyl)ethyl]pyrazole-1-carboxylate (150 mg, 0.43 mmol, 1 eq) and pyridine (104 μl, 1.29 mmol, 3 eq) in DCM (1.5 ml) at ambient temperature. After stirring at ambient temperature for 2 h, a solution of TFA (321 μl, 4.32 mmol, 10 eq) in DCM (2.7 ml) was added dropwise and stirring was continued for a further 1 h. The reaction mixture was concentrated and the crude product was purified by reverse-phase prep. HPLC (basic) using a 33-53% gradient of acetonitrile in water containing 1% ammonium hydroxide solution. The clean fractions were taken and evaporated to afford the title compound as a colourless foamy solid (100 mg, 66% yield).

$^1$H NMR (399.902 MHz, DMSO) δ 2.81 (4H, s), 3.65 (6H, s), 6.26-6.25 (1H, m), 6.35 (2H, d), 6.41 (1H, s), 7.50-7.39 (3H, m), 7.91 (2H, d), 10.56 (1H, s), 12.07 (1H, s). MS m/z 352 (MH+)

Mean of n=1, FGFR Kinase assay—Caliper, IC$_{50}$ 0.140 μM.

tert-butyl 5-amino-3-[2-(3,5-dimethoxyphenyl)ethyl] pyrazole-1-carboxylate, used as starting material was prepared as follows:

A solution of di-tert-butyl dicarbonate (464 mg, 2.12 mmol, 1.05 eq) in DCM (2 ml) was added dropwise to a mixture of 5-[2-(3,5-dimethoxyphenyl)ethyl]-2H-pyrazol-3-amine (500 mg, 2.02 mmol, 1 eq) in DCM (18 ml) containing aq. KOH solution (4.5 N, 3.6 ml, ca. 16 mmol, 8 eq). The reaction mixture was transferred to a separating funnel and the layers separated. The organic layer was washed with water (10 ml), brine (10 ml) and dried over sodium sulfate. After filtering the solvent was evaporated under reduced pressure to yield a pale yellow oil which solidified on standing overnight to afford a cream solid (704 mg, 100% yield).

$^1$H NMR (399.902 MHz, DMSO) δ 1.56 (9H, s), 2.68-2.63 (2H, m), 2.80-2.75 (2H, m), 3.73 (6H, s), 5.22 (1H, s), 6.23 (2H, br.s), 6.32-6.31 (1H, m), 6.44 (2H, d). MS: m/z 370 ([M+Na]+).

5-[2-(3,5-dimethoxyphenyl)ethyl]-2H-pyrazol-3-amine, used as starting material was prepared as follows:

Acetonitrile (2.29 ml, 43.61 mmol, 1.2 eq) was added to a slurry of sodium hydride (1.75 g dispersion in mineral oil, 43.61 mmol, 1.2 eq) in anhydrous toluene (70 ml) and the mixture stirred at room temperature for 30 mins. Ethyl 3-(3,5-dimethoxyphenyl)propanoate (8.66 g, 36.34 mmol, 1 eq) in toluene (60 ml) was added and the reaction was refluxed for 18 h. After cooling, the reaction mixture was quenched with water and the solvent was evaporated under reduced pressure. The residue was dissolved in 2M HCl (50 ml). The acidic solution was extracted with ethyl acetate. The organic extracts were combined and washed with water, brine and dried over magnesium sulphate. After filtering, the solvent was evaporated under reduced pressure to yield the crude product as a yellow oil. The oil was purified by silica column chromatography (eluting with DCM) and the desired fractions were combined and evaporated to yield a cream solid (3.76 g, 44% yield).

To the cream solid (3.72 g, 15.96 mmol, 1 eq) in ethanol (55 ml) was added hydrazine hydrate (852 μl, 17.56 mmol, 1.1 eq). The reaction was refluxed for 24 h before allowing to cool. After evaporation under reduced pressure, the residue was extracted into DCM. The organic layers were washed with water, brine, dried with magnesium sulphate, filtered and evaporated under reduced pressure to afford 5-[2-(3,5-dimethoxyphenyl)ethyl]-2H-pyrazol-3-amine as a pale yellow solid (3.76 g. 42% over 2 steps).

$^1$H NMR (300.132 MHz, DMSO) δ 2.64-2.82 (4H, m), 3.71 (6H, s), 4.07-4.72 (2H, m), 5.20 (1H, s), 6.31 (1H, t), 6.38 (2H, d). MS: m/z 248 (MH+)

Example 3

N-[5-[2-(3,5-dimethoxyphenyl)ethyl]-2H-pyrazol-3-yl]-4-methoxy-benzamide

1-Chloro-N,N,2-trimethylprop-1-en-1-amine (89 μl, 0.63 mmol, 1.05 eq) was added dropwise to 4-methoxybenzoic acid (97 mg, 0.63 mmol, 1 eq) in DCM (1.5 ml) at ambient temperature. After stirring at ambient temperature for 1.5 h, a solution of tert-butyl 5-amino-3-[2-(3,5-dimethoxyphenyl) ethyl]pyrazole-1-carboxylate (199 mg, 0.57 mmol, 0.9 eq) and pyridine (142 μL, 1.74 mmol, 2.75 eq) in DCM (2 ml) was added to the reaction mixture and stirring was continued at ambient temperature for a further 3 h. A solution of TFA (386 μL, 5.2 mmol, 8.25 eq) in DCM (3.5 ml) was then added and stirring was continued at ambient temperature for 18 h. The reaction mixture was concentrated and the crude product was purified by reverse-phase prep. HPLC (basic) using a 33-53% gradient of acetonitrile in water containing 1% ammonium hydroxide solution. The clean fractions were taken and evaporated to afford the title compound as a colourless foamy solid (113 mg, 52% yield).

$^1$H NMR (399.902 MHz, DMSO) δ 2.88 (4H, s), 3.73 (6H, s), 3.84 (3H, s), 6.34-6.32 (1H, m), 6.42 (2H, d), 6.47 (1H, s), 7.01 (2H, d), 7.99 (2H, d), 10.48 (1H, br.s), 12.12 (1H, br.s). MS: m/z 382 (MH+).

Mean of n=1, FGFR Kinase assay—Caliper, IC$_{50}$ 0.132 μM.

tert-butyl 5-amino-3-[2-(3,5-dimethoxyphenyl)ethyl] pyrazole-1-carboxylate, used as starting material was prepared as in Example 2.

Example 4

N-[5-[2-(3,5-dimethoxyphenyl)ethyl]-2H-pyrazol-3-yl]-4-morpholin-4-yl-benzamide

Prepared in an analogous way to Example 3 to give the title compound as a solid (125 mg, 50% yield).

$^1$H NMR (399.902 MHz, DMSO) δ 2.88 (4H, s), 3.26-3.24 (4H, m), 3.76-3.72 (10H, m), 6.34-6.32 (1H, m), 6.46-6.42 (3H, m), 6.98 (2H, d), 7.92 (2H, d), 10.35 (1H, br.s), 12.10 (1H, br.s). MS: m/z 437 (MH+).

Mean of n=1, FGFR Kinase assay—Caliper, IC$_{50}$ 0.068 μM.

Example 5

N-[5-[2-(3,5-dimethoxyphenyl)ethyl]-2H-pyrazol-3-yl]-4-[(4-fluoropiperidin-1-yl)methyl]benzamide A solution of NaHMDS in THF (1 M, 0.65 ml, 0.65 mmol, 1.5 eq) was added dropwise at ambient temperature to a mixture of tert-butyl 5-amino-3-[2-(3,5-dimethoxyphenyl) ethyl]pyrazole-1-carboxylate (150 mg, 0.43 mmol, 1 eq) and methyl 4-[(4-fluoropiperidin-1-yl)methyl]benzoate (131 mg, 0.52 mmol, 1.2 eq) in THF (0.5 ml). The reaction mixture was stirred at ambient temperature for 1 h. It was then concentrated and the crude product was purified by reverse-phase prep. HPLC (basic) using a 39-49% gradient of acetonitrile in water containing 1% ammonium hydroxide solution. The clean fractions were taken and evaporated to afford the title compound as a colourless solid (33 mg, 16% yield).

$^1$H NMR (399.902 MHz, DMSO) δ 1.78-1.67 (2H, m), 1.94-1.80 (2H, m), 2.35-2.29 (2H, m), 2.57-2.55 (2H, m), 2.89 (4H, s), 3.55 (2H, s), 3.73 (6H, s), 4.79-4.61 (1H, m), 6.34-6.33 (1H, m), 6.43 (2H, d), 6.48 (1H, s), 7.40 (2H, d), 7.95 (2H, d), 10.59 (1H, br.s), 12.15 (1H, br.s). MS: m/z 467 (MH+).

Mean of n=1, FGFR Kinase assay—Caliper, $IC_{50}$ 0.063 µM.

tert-butyl 5-amino-3-[2-(3,5-dimethoxyphenyl)ethyl] pyrazole-1-carboxylate, used as starting material was prepared as in Example 2.

Methyl 4-[(4-fluoropiperidin-1-yl)methyl]benzoate, used as starting material was prepared as follows:

4-Fluoropiperidine hydrochloride (366 mg, 2.62 mmol, 1.2 eq) was added in one portion to a mixture of methyl 4-(bromomethyl)benzoate (500 mg, 2.18 mmol, 1 eq) and MP-carbonate (2.74 mmol/g, 1.912 g, 5.24 mmol, 2.4 eq) in MeCN (10 ml). The reaction mixture was stirred at ambient temperature for 18 h. Polymer-supported isocyanate (1 mmol/g, 500 mg, 0.5 mmol, 0.5 eq) was added in one portion and stirring continued for 4 h. The reaction mixture was filtered, the resins washed with MeCN and the combined filtrate was concentrated to afford a clear oil, 478 mg, 87% yield at 80% purity.

$^1$H NMR (399.902 MHz, CDCl3) δ 1.98-1.83 (4H, m), 2.40-2.34 (2H, m), 2.61-2.54 (2H, m), 3.55 (2H, s), 3.91 (3H, s), 4.77-4.60 (1H, m), 7.40 (2H, d), 8.00-7.98 (2H, m). MS: m/z 252 (MH+).

Example 6

N-[5-[2-[3-(2-methoxyethoxy)phenyl]ethyl]-2H-pyrazol-3-yl]-4-(4-methylpiperazin-1-yl)benzamide To 4-(4-methylpiperazin-1-yl)benzoic acid (440 mg, 2 mmol, 1 eq) in dichloromethane (10 ml) at 0° C. was added a few drops of N,N-dimethylformamide followed by the dropwise addition of a 2M solution of oxalyl chloride in dichloromethane (1.1 ml, 2.2 mmol, 1.1 eq). The reaction was maintained at 0° C. for 1 h. 5-[2-[3-(2-Methoxyethoxy)phenyl]ethyl]-2H-pyrazol-3-amine (628 mg, 2.4 mmol, 1.2 eq) in dichloromethane (10 ml) was then added dropwise followed by DIPEA (750 µl, 4.20 mmol, 2.1 eq). The reaction was maintained at 0° C. for a further hour before allowing to warm to room temperature overnight. The mixture was diluted with DCM (50 ml) and washed with aq. NaHCO$_3$ solution (50 ml). The aqueous layer was extracted with DCM (50 ml). The organic extracts were combined, washed with brine, dried with magnesium sulphate and evaporated under reduced pressure. The crude product was purified by acidic reverse-phase prep. HPLC. Fractions containing product were captured onto a SCX-2 column. After washing with methanol, the crude product was released with 10% ammonia in methanol. After evaporation under reduced pressure, the crude product was re-purified on the basic reverse-phase prep. HPLC using a 20-45% gradient of acetonitrile in water containing 1% ammonium hydroxide to yield, after evaporation, a white solid (22.9 mg, 2.5%).

$^1$H NMR (300.132 MHz, DMSO) δ 2.22 (3H, s), 2.44 (4H, t),2.88 (4H, s),3.27 (4H, t),3.30 (3H, s),3.64 (2H, dd),4.06 (2H, dd),6.41 (1H, s),6.72-6.84 (3H, m),6.95 (2H, d),7.18 (1H, t),7.88 (2H, d),10.30 (1H, s),12.06 (1H, s) MS: m/z 464 (MH+).

Mean of n=1, FGFR Kinase assay—Caliper, $IC_{50}$ 0.058 µM.

5-[2-[3-(2-methoxyethoxy)phenyl]ethyl]-2H-pyrazol-3-amine used as starting material was prepared as follows:

To sodium hydride (1.065 g, 26.57 mmol, 1.1 eq) was added anhydrous 1,4-dioxane (40 ml) followed by anhydrous acetonitrile (1.52 ml, 29 mmol, 1.2 eq). 2-Methoxyethyl 3-[3-(2-methoxyethoxy)phenyl]propanoate (6.82 g, 24.16 mmol, 1 eq) in anhydrous 1,4-dioxane (35 ml) was then added. The reaction was refluxed for 18 h. After cooling, the brown solution was quenched with water. The solvent was evaporated under reduced pressure and the aqueous residue was acidified with 2M HCl and extracted with ethyl acetate. The organic layers were combined, washed with 2M HCl, water and brine. After drying (magnesium sulphate), the solution was filtered and evaporated under reduced pressure. The crude product was purified by column chromatography eluting with 0-50% ethyl acetate in hexanes. The desired intermediate was obtained, after evaporation, as a yellow oil (3.24 g, 54%). To this intermediate (3.24 g, 13.10 mmol, 1 eq) in ethanol (65 ml) was added hydrazine.monohydrate (700 ul, 14.41 mmol, 1.1 eq). The reaction was refluxed at 85° C. for 18 h. The solvent was evaporated under reduced pressure. The residue was extracted with ethyl acetate, washed with water and brine, dried (magnesium sulphate), filtered and evaporated under reduced pressure to yield a yellow oil (2.78 g, 81%).

$^1$H NMR (300.132 MHz, DMSO) δ 2.68-2.84 (4H, m),3.31 (3H, s),3.65 (2H, dd),4.06 (2H, dd),4.40 (2H, s),5.19 (1H, s),6.71-6.81 (3H, m),7.17 (1H, t),11.08 (1H, s); MS: m/z 262 (MH+).

2-Methoxyethyl 3-[3-(2-methoxyethoxy)phenyl]propanoate used as starting material was prepared as follows:

To 3-(3-hydroxyphenyl)propionic acid (8.31 g, 50 mmol, 1 eq) in N,N-dimethylformamide (150 ml) was added potassium carbonate (17.28 g, 125 mmol, 3 eq) followed by 2-bromoethyl methyl ether (10.34 ml, 110 mmol, 2.20 eq). The reaction mixture was stirred overnight at room temperature. The reaction mixture was evaporated to dryness. The residue was extracted into ethyl acetate, washed with water and brine, dried with magnesium sulphate, filtered and evaporated to yield a yellow oil ~11.38 g. The reaction mixture was purified by column chromatography using a gradient of 0-30% ethyl acetate in hexanes. To this intermediate (9.82 g, 43.76 mmol, 1 eq) was added N,N-dimethylformamide (50 ml) followed by potassium carbonate (9.1 g, 65.64 mmol, 2.5 eq) and 2-bromoethyl methyl ether (4.94 ml, 52.5 mmol, 1.2 eq). The reaction mixture was heated at 60° C. for 18 h. The reaction mixture was diluted with N,N-dimethylformamide (50 ml) and a further 4.55 g of potassium carbonate was added followed by 2-bromoethyl methyl ether (2.45 ml). The reaction mixture was heated overnight at 60° C. for a further 20 h. After cooling to room temperature, the inorganics were filtered and the solvent was evaporated under reduced pressure. The residue was extracted into ethyl acetate and the organic layers was washed with water, saturated sodium hydrogen carbonate and brine. After drying (magnesium sulphate) and filtration, the organic layers were evaporated under reduced pressure to yield a yellow oil. The crude product was purified by column chromatography, eluting with a gradient of 0-50% ethyl acetate in hexanes. The desired product was obtained as a clear yellow oil (8.755 g, 71%).

$^1$H NMR (300.132 MHz, DMSO) δ 2.63 (2H, t), 2.82 (2H, t), 3.25 (3H, s), 3.31 (3H, s), 3.50 (2H, m), 3.65 (2H, m), 4.06 (2H, m), 4.13 (2H, dd), 6.73-6.82 (3H, m), 7.18 (1H, t); MS: m/z 283 (MH+).

Example 7

4-(4-methylpiperazin-1-yl)-N-[5-(2-pyridin-3-ylethyl)-2H-pyrazol-3-yl]benzamide

Prepared in an analogous way to Example 1 but starting with 5-(2-pyridin-3-ylethyl)-2H-pyrazol-3-amine (189 mg, 1 mmol, 1.5 eq) to give the above titled compound as a white solid (15 mg, 6% yield)

¹H NMR (300.132 MHz, DMSO) δ 2.23 (3H, s), 2.44 (4H, t), 2.89-2.98 (4H, m), 3.28 (4H, t), 6.40 (1H, s), 6.96 (2H, d), 7.28-7.33 (1H, m), 7.65 (1H, dt), 7.89 (2H, d), 8.40 (1H, dd), 8.45 (1H, d), 10.31 (1H, s), 12.09 (1H, s). MS m/z 391 (MH+).

Mean of n=1, FGFR Kinase assay—Caliper, IC$_{50}$ 0.047 µM.

5-(2-pyridin-3-ylethyl)-2H-pyrazol-3-amine, used as starting material was prepared as follows:

Acetonitrile (2.9 ml, 54.8 mmol, 1.3 eq) was added to a slurry of sodium hydride (2.2 g, 54.8 mmol, 1.3 eq) in anhydrous 1,4-dioxane (50 ml). To this was then added a solution of methyl 3-pyridin-3-ylpropanoate (6.96 g, 42 mmol, 1 eq) in anhydrous 1,4-dioxane (50 ml). The reaction was heated under reflux for 18 h. After cooling, ethanol (5 ml) was added, followed by hydrazine. HCl (3181 mg, 46.43 mmol, 1.1 eq). The reaction mixture was heated at 100° C. for 20 h, allowed to cool to room temperature and then evaporated under reduced pressure. The orange residue was dissolved in water (50 ml) and partioned with ethyl acetate (2×75 ml) The organic layers were combined and washed with 2M HCl. The aqueous acidic layers were combined and washed with ethyl acetate. The aqueous layer was separated, basified by the addition of 8N ammonia solution and extracted with ethyl acetate. The organic layer was washed with brine, dried with magnesium sulphate, filtered and evaporated under reduced pressure to yield the title compound as an orange oil. The oil was dissolved in acetonitrile (10 ml) and purified on basic reverse-phase hplc using a 2-20% gradient of acetonitrile in water (containing 1% ammonium hydroxide). Desired fractions were combined and evaporated to yield the title compound (348 mg, 5% yield).

¹H NMR (400.132 MHz, DMSO) δ 2.74 (2H, t), 2.87 (2H, t), 4.43 (2H, s), 5.17 (1H, s), 7.29 (1H, ddd), 7.61 (1H, dddd), 8.39 (1H, dd), 8.42 (1H, d), 11.08 (1H, s). MS; m/z 189 (MH+).

Further product was obtained from the basified aqueous layer by purification using basic to reverse-phase prep. HPLC. After evaporation of the desired fractions under reduced pressure to low volume, the solution was acidified using 2M HCl. The product was captured onto a SCX-2 column. The product was column was eluted using 10% ammonia solution in methanol. After evaporation under reduced pressure a yellow oil was obtained (657 mg, 9% yield).

Example 8

N-[5-[2-(2-furyl)ethyl]-2H-pyrazol-3-yl]-4-(4-methylpiperazin-1-yl)benzamide

Prepared in an analogous way to Example 1 but starting with 5-[2-(2-furyl)ethyl]-2H-pyrazol-3-amine (178 mg, 1 mmol, 1.5 eq) to give the above titled compound as a tan solid (24.8 mg, 10% yield).

¹H NMR (300.132 MHz, DMSO) δ 2.23 (3H, s), 2.44 (4H, t), 2.89-2.98 (4H, m), 3.28 (4H, t), 6.40 (1H, s), 6.96 (2H, d), 7.28-7.33 (1H, m), 7.65 (1H, dt), 7.89 (2H, d), 8.40 (1H, dd), 8.45 (1H, d), 10.31 (1H, s), 12.09 (1H, s). MS; m/z 380 (MH+).

Mean of n=1, FGFR Kinase assay—Elisa, IC$_{50}$ 0.0795 µM.

5-[2-(2-furyl)ethyl]-2H-pyrazol-3-amine, used as starting material was prepared as follows:

a) A mixture of ethyl 2-triphenylphosphoranylideneacetate (34.84 g, 100 mmol, 1 eq) and furan-2-carbaldehyde (9609 mg, 100 mmol, 1 eq) in anhydrous THF (200 ml) was stirred at room temperature for 24 h. The solvent was evaporated under reduced pressure and the residue triturated with ether to produce a brown solution and a precipitate. The solid was filtered, washed and removed. The filtrate was then evaporated. The product was purified by column chromatography on silica eluting with 0-20% ethyl acetate in hexanes. The desired fractions were evaporated to yield a cis/trans mixture of ethyl (E)-3-(2-furyl)prop-2-enoate as a pale yellow oil (NMR suggested mainly trans product) (15.5 g, 93%).

b) A cis/trans mixture of ethyl (E)-3-(2-furyl)prop-2-enoate (15.5 g, 93.27 mmol, 1 eq) was stirred in ethanol (120 ml) containing 10% palladium on charcoal (775 mg, 5% by w). The reaction mixture was stirred under hydrogen for 4 h. A further quantity of 10% Pd/C (775 mg, 5% by w) was added. The reaction was stirred under hydrogen for an additional 95 mins. The reaction was filtered and evaporated under reduced pressure. The crude product was purified by silica column chromatography eluting with 20% ethyl acetate in hexanes. The desired fractions were evaporated under reduced pressure and ethyl 3-(2-furyl)propanoate was obtained as a clear oil (3.69 g, 24% yield).

¹H NMR (300.132 MHz, CDCl3) δ 1.25 (3H, t), 2.64 (2H, t), 2.97 (2H, t), 4.15 (2H, q), 6.02 (1H, td), 6.27 (1H, dd), 7.30 (1H, dd)

5-[2-(2-furyl)ethyl]-2H-pyrazol-3-amine (2.09 g, 54% over 2 steps) was then prepared in an analogous manner to that described for the starting material for example 2 (5-[2-(3-methoxyphenyl)ethyl]-2H-pyrazol-3-amine) using ethyl 3-(2-furyl)propanoate (6.33 g, 37.64 mmol, 1 eq) as starting material.

¹H NMR (300.132 MHz, CDCl3) δ 2.98 (4H, t), 3.45 (2H, s), 6.04 (1H, d), 6.28 (1H, dd), 7.30 (1H, dd). MS m/z 178 (MH+).

Example 9

N-[5-[2-(3-furyl)ethyl]-2H-pyrazol-3-yl]-4-(4-methylpiperazin-1-yl)benzamide

Prepared in an analogous way to Example 1 but starting with 5-[2-(3-furyl)ethyl]-2H-pyrazol-3-amine (178 mg, 1 mmol, 1.5 eq) to give the title compound as a tan solid (17.3 mg, 7% yield).

¹H NMR (300.132 MHz, DMSO) δ 2.23 (3H, s), 2.45 (4H, t), 2.67-2.89 (4H, m), 3.28 (4H, t), 6.39 (1H, d), 6.43 (1H, s), 6.96 (2H, d), 7.45 (1H, t), 7.56 (1H, t), 7.89 (2H, d), 10.29 (1H, s), 12.07 (1H, s). MS m/z 380 (MH+).

Mean of n=1, FGFR Kinase assay—Caliper, IC$_{50}$ 0.137 µM.

5-[2-(3-furyl)ethyl]-2H-pyrazol-3-amine (3.94 g, 59% over final 2 steps), used as starting material was prepared in an analogous manner to the synthesis of 5-[2-(2-furyl)ethyl]-2H-pyrazol-3-amine shown in example 8.

Example 10

N-[5-[2-(3,5-dimethoxyphenyl)ethyl]-2H-pyrazol-3-yl]-4-(4-methylpiperazin-1-yl)benzamide Prepared in an analogous way to Example 1, but starting with 5-[2-(3,5-dimethoxyphenyl)ethyl]-2H-pyrazol-3-amine (566 mg, 2.30 mmol, 1.5 eq) to give the title compound as a beige solid (183.5 mg, 27% yield).

¹H NMR (300.132 MHz, DMSO) δ 2.23 (3H, s), 2.44 (4H, t), 2.86 (4H, s), 3.27 (4H, t), 3.72 (6H, s), 6.32 (2H, t), 6.35-6.42 (3H, m), 6.96 (2H, d), 7.89 (2H, d), 10.31 (1H, s), 12.08 (1H, s). MS: m/z 450 (MH+)

Mean of n=1, FGFR Kinase assay—Caliper Echo Dosing, IC$_{50}$ 0.00085 µM.

5-[2-(3,5-dimethoxyphenyl)ethyl]-2H-pyrazol-3-amine, used as starting material was prepared as indicated in Example 2.

Example 11

N-[5-[2-(3-methoxyphenyl)ethyl]-2H-pyrazol-3-yl]-4-(4-methylpiperazin-1-yl)benzamide Prepared in an analogous way to Example 1, but starting with 5-[2-(3-methoxyphenyl)ethyl]-2H-pyrazol-3-amine (148 mg, 0.68 mmol, 1.5 eq) to give the title compound as a solid (8.2 mg, 4% yield).

$^1$H NMR (300.132 MHz, DMSO) δ 2.23 (3H, s), 2.44 (4H, t), 2.89 (4H, s), 3.26-3.31 (4H, m), 3.73 (3H, s), 6.16 (1H, s), 6.69-6.86 (3H, m), 6.96 (2H, d), 7.20 (1H, t), 7.89 (2H, d), 10.31 (1H, s), 12.08 (1H, s). MS m/z 420 (MH+)

Mean of n=1, FGFR Kinase assay—Elisa, IC$_{50}$ 0.0828 µM.

5-[2-(3-methoxyphenyl)ethyl]-2H-pyrazol-3-amine used as starting material was prepared as follows:

Acetonitrile (3.36 ml, 64.25 mmol, 1 eq) was added to a slurry of sodium hydride (2.57 g dispersion in mineral oil, 64.25 mmol, 1 eq) in anhydrous 1,4-dioxane (50 ml) and the mixture was stirred at room temperature for 20 mins. Methyl 3-(3-methoxyphenyl)propanoate (10.4 g, 53.54 mmol, 1 eq) in 1,4-dioxane (25 ml) was added and the reaction was refluxed for 2 h. The reaction mixture was cooled and quenched with water. The residue was dissolved in 2M HCl and extracted into ethyl acetate. The organic layer was separated, washed with 2M HCl, water and brine and dried over magnesium sulphate. Evaporation under reduced pressure gave yield to a yellow oil, which was purified by silica column chromatography, eluting with a mixture of 0-50% ethyl acetate in hexanes. Fractions containing the product were combined and evaporated to leave 5-(3-methoxyphenyl)-3-oxo-pentanenitrile (5.37 g, 49% yield).

$^1$H NMR (300.132 MHz, CDCl3) δ 2.86 (4H, s), 3.32 (2H, s), 3.73 (3H, s), 6.64-6.72 (3H, m), 7.14 (1H, t)

To 5-(3-methoxyphenyl)-3-oxo-pentanenitrile (5.37 g, 26.42 mmol, 1 eq) in ethanol (80 ml) was added hydrazine hydrate (1.41 ml, 29.06 mmol, 1.1 eq). The reaction was refluxed for 3.5 h then allowed to cool. The mixture was evaporated under reduced pressure. The residue was dissolved in ethyl acetate and the organic layer was washed with water, brine, dried with magnesium sulphate, filtered and evaporated to yield a yellow oil (which solidified on standing). This was acidified and purified by SCX-3 column chromatography. The compound was eluted with 10% ammonia in methanol. After evaporation 5-[2-(3-methoxyphenyl)ethyl]-2H-pyrazol-3-amine was obtained (5.48 g, 96% yield).

$^1$H NMR (300.132 MHz, DMSO): δ 2.64-2.87 (4H, m), 3.73 (3H, s), 4.40 (1H, s), 5.19 (1H, s), 6.71-6.82 (3H, m), 7.18 (1H, t), 11.07 (1H, s). MS; m/z 218 (MH+)

Example 12

N-[5-[(3,5-dimethoxyphenyl)methoxy]-2H-pyrazol-3-yl]-4-(4-methylpiperazin-1-yl)benzamide Prepared in an analogous way to Example 1 but starting with 5-[(3,5-dimethoxyphenyl)methoxy]-2H-pyrazol-3-amine hydrochloride to give the title compound as a beige solid (34 mg, 13% yield).

$^1$H NMR (300.132 MHz, DMSO) δ 2.23 (3H, s), 2.44 (4H, t), 3.27-3.32 (4H, m), 3.75 (6H, s), 5.07 (2H, s), 5.57 (1H, s), 6.44-6.45 (1H, m), 6.59 (2H, d), 7.01 (2H, d), 7.85 (2H, d), 10.64 (1H, s), 11.54 (1H, s). MS m/z 452 (MH+)

Mean of n=3, FGFR Kinase assay—Elisa, IC$_{50}$ 0.06 µM.

5-[(3,5-dimethoxyphenyl)methoxy]-2H-pyrazol-3-amine hydrochloride, used as starting material was prepared as follows:

3-Amino-5-hydroxypyrazole (8 g, 80.74 mmol) and triphenylphosphine (25.45 g, 96.88 mmol) were stirred in DCM (110 ml) under nitrogen and the mixture was cooled in an ice-bath. Diisopropylazodicarboxylate (19.08 ml, 96.88 mmol) was added dropwise (temperature<10° C.) and the reaction mixture was stirred in the ice-bath for 1 h. 3,5-Dimethoxybenzyl alcohol (16.30 g, 96.88 mol) in DCM (35 ml) was added dropwise, the reaction mixture was allowed to warm to room temperature and stirred under nitrogen for 4 days. The mixture was filtered, washed with DCM and the filtrate was extracted with 1M HCl (aq) (3×50 ml). The combined aqueous extracts were washed with DCM (50 ml), resulting in precipitation of the product. The product was collected by filtration, washed with water, DCM and dried under vacuum to afford the title compound as a white solid (358 mg, 1.8% yield). A further crop of product was obtained following precipitation from the initial DCM layer on allowing to stand at room temperature. The solid product was collected by filtration, washed with DCM and dried under vacuum to give an off-white solid (1.127 g, 5.6% yield).

$^1$H NMR (300.132 MHz, DMSO) δ 3.75 (s, 6H), 5.18 (s, 2H), 5.26 (s, 1H), 6.50 (t, 1H), 6.60 (d, 2H). MS:m/z 250 (MH+)

Example 13

N-[5-[2-(3-Methoxyphenyl)ethyl]-2H-pyrazol-3-yl]-6-methyl-pyridine-3-carboxamide 5-[2-(3-methoxyphenyl)ethyl]-2-tert-butyl-pyrazol-3-amine (0.2 g, 0.73 mmol) was dissolved in toluene (10 ml) and to this was added methyl 6-methylpyridine-3-carboxylate (122 mg, 0.73 mmol) and AlMe$_3$ (0.93 ml, 1.8 mmol). The reaction mixture was stirred overnight. The reaction mixture was diluted with DCM (15 ml) and quenched with damp sodium sulfite (care); the reaction was stirred for 20 mins before being filtered and the solvent removed in vacuo to yield a yellow gum. This was dissolved in formic acid (12 ml) and heated at 82° C. overnight. The reaction mixture was evaporated to dryness and the resulting product was passed through a SCX column, eluting initially with methanol followed by 2N ammonia/methanol. After removal of the solvent a yellow solid was obtained which was triturated with hot acetonitrile to afford a white solid. The solid was filtered and dried (117 mg, 48%).

$^1$H NMR (400.132 MHz, DMSO) δ 2.54 (s, 3H), 2.91 (s, 4H), 3.74 (s, 3H), 6.45 (s, 1H), 6.76 (d, 1H), 6.83-6.82 (m, 2H), 7.20 (t, 1H), 7.36 (d, 1H), 8.21 (dd, 1H), 9.01 (s, 1H), 10.81 (s, 1H), 12.21 (s, 1H); MS: m/z 409 (MH+).

Mean of n=1, FGFR Kinase assay—Caliper, IC$_{50}$ 0.95 µM.

5-[2-(3-methoxyphenyl)ethyl]-2-tert-butyl-pyrazol-3-amine, used as starting material was prepared as follows:

The crude 5-(3-methoxy-phenyl)-3-oxo-pentanenitrile (10 g, 0.049 mol), t-butylhydrazine HCl (7.29 g, 0.059 mol) and TEA (8.20 ml, 0.059 mol) were dissolved in ethanol (300 ml) and heated at reflux for 3 h. The reaction mixture was cooled and solvent removed in vacuo to yield a viscous brown oil; this was quenched with water (100 ml), extracted with diethyl ether (3×200 ml), dried (MgSO$_4$) and solvent removed in vacuo to yield a dark orange oil. This was purified via distillation at 165° C. @ 0.40 mbar to afford a clear viscous oil which solidified on standing.

$^1$H NMR (400.132 MHz, CDCl3) δ 1.55 (s, 9H), 2.76-2.71 (m, 2H), 2.85-2.80 (m, 2H), 3.40 (brs, 2H), 3.72 (s, 3H), 5.31 (s, 1H), 6.66 (dd, 1H), 6.71 (s, 1H), 6.76 (d, 1H), 7.11 (t, 1H); MS: m/z 274 (MH+).

5-(3-Methoxy-phenyl)-3-oxo-pentanenitrile, used as starting material was prepared as follows:

LDA (34 ml, 0.068 mol) was added to THF (300 ml) and cooled to −78° C. under a nitrogen atmosphere, to this was slowly added acetonitrile (2.8 g, 0.068 mol) in THF (20 ml). The reaction was stirred for 10 mins at −78° C. before the rapid addition of methyl 3-(3-methoxyphenyl)propanoate (10 g, 0.052 mol). The reaction was stirred for 30 mins before being allowed to warm up to room temperature. The reaction was quenched with 1.0 N HCl (100 ml), extracted with diethyl ether (2×200 ml), dried (MgSO$_4$) and solvent removed in vacuo to yield a yellow gum. This appeared to slowly decompose and was used immediately in the next step.

Example 14

6-Methoxy-N-[5-[2-(3-methoxyphenyl)ethyl]-2H-pyrazol-3-yl]pyridine-3-carboxamide Prepared in an analogous manner to Example 13 except using methyl 6-methoxypyridine-3-carboxylate as a starting material (168 mg, 65%).

$^1$H NMR (400.132 MHz, DMSO) δ 2.90 (s, 4H), 3.74 (s, 3H), 3.93 (s, 3H), 6.45 (s, 1H), 6.77-6.75 (m, 1H), 6.83-6.81 (m, 2H), 6.90 (d, 1H), 7.20 (t, 1H), 8.25 (dd, 1H), 8.81 (d, 1H), 10.70 (s, 1H), 12.17 (s, 1H); MS: m/z 353 (MH+).

Mean of n=1, FGFR Kinase assay—Caliper, IC$_{50}$ 0.61 µM.

Example 15

N-[5-[2-(3-Methoxyphenyl)ethyl]-2H-pyrazol-3-yl]-4-methylsulfonyl-benzamide

Prepared in an analogous manner to Example 13 except using ethyl 4-methylsulfonylbenzoate as a starting material (82 mg, 28%).

$^1$H NMR (400.132 MHz, DMSO) δ 2.91 (s, 4H), 3.28 (s, 3H), 3.74 (s, 3H), 6.49 (s, 1H), 6.78-6.75 (m, 1H), 6.84-6.81 (m, 2H), 7.20 (t, 1H), 8.03 (d, 2H), 8.20 (d, 2H), 10.96 (s, 1H), 12.23 (s, 1H); MS: m/z 400 (MH+).

Mean of n=1, FGFR Kinase assay—Caliper, IC$_{50}$ 0.11 µM.

Example 16

N-[5-[2-(3-Methoxyphenyl)ethyl]-2H-pyrazol-3-yl]-5-methyl-pyrazine-2-carboxamide Prepared in an analogous manner to Example 13 except using methyl 5-methylpyrazine-2-carboxylateas a starting material (63 mg, 26%).

$^1$H NMR (400.132 MHz, DMSO) δ 2.62 (s, 3H), 2.91 (s, 4H), 3.73 (s, 3H), 6.48 (s, 1H), 6.77-6.75 (m, 1H), 6.85-6.80 (m, 2H), 7.20 (t, 1H), 8.67 (s, 1H), 9.13 (s, 1H), 10.26 (s, 1H), 12.28 (s, 1H); MS: m/z 338 (MH+).

Mean of n=1, FGFR Kinase assay—Caliper, IC$_{50}$ 0.75 µM.

Example 17

N-[5-[2-(3-Methoxyphenyl)ethyl]-2H-pyrazol-3-yl]-5-(prop-2-ynylamino)pyridine-2-carboxamide Prepared in an analogous manner Example 13 except using_methyl 5-(prop-2-ynylamino)pyridine-2-carboxylate as a starting material (39 mg, 14%).

$^1$H NMR (400.132 MHz, CDCl3) δ 2.28 (t, 1H), 2.96 (s, 4H), 3.77 (s, 3H), 4.00 (s, 2H), 4.56 (s, 1H), 6.47 (s, 1H), 6.76-6.73 (m, 2H), 6.78 (d, 1H), 7.04 (dd, 1H), 7.21-7.17 (m, 1H), 7.96 (d, 1H), 8.09 (d, 1H), 10.14 (s, 1H), NH missing; MS: m/z 376 (MH+).

Mean of n=1, FGFR Kinase assay—Caliper, IC$_{50}$ 0.66 µM.

Example 18

6-Ethylamino-N-{5-[2-(3-methoxy-phenyl)-ethyl]-2H-pyrazol-3-yl}-nicotinamide Prepared in an analogous manner to Example 13 except using__6-ethylamino-nicotinic acid is methyl ester as a starting material (44 mg, 16%).

$^1$H NMR (400.132 MHz, DMSO) δ 1.15 (t, 3H), 2.89 (s, 4H), 3.35-3.30 (m, 2H), 3.74 (s, 3H), 6.46-6.42 (m, 2H), 6.77-6.75 (m, 1H), 6.82-6.81 (m, 2H), 7.06 (s, 1H), 7.20 (t, 1H), 7.93 (d, 1H), 8.65 (s, 1H), 10.28 (s, 1H), 12.06 (s, 1H); MS: m/z 366 (MH+).

Mean of n=1, FGFR Kinase assay—Caliper, IC$_{50}$ 0.54 µM.

Example 19

4-Acetamido-N-[5-[2-(3-methoxyphenyl)ethyl]-2H-pyrazol-3-yl]benzamide

5-[2-(3-methoxyphenyl)ethyl]-2-tert-butyl-pyrazol-3-amine (0.2 g, 0.73 mmol) was dissolved in THF/pyridine (5 ml/1 ml), to this was added 4-acetamidobenzoyl chloride (190 mg, 0.95 mmol) and the reaction mixture was stirred overnight. The reaction mixture was evaporated to dryness, purified by column chromatography, eluting with 0-5% MeOH in DCM, and evaporated to afford a white foam. The residue was dissolved in formic acid (12 ml) and heated at 82° C. overnight. The reaction mixture was evaporated to dryness and the product was purified by a SCX column. Removal of the solvent gave a yellow solid, which was triturated with hot acetonitrile to afford a white solid. The solid was filtered and dried in vacuo (16 mg, 6%); MS: m/z 378 (MH+).

Mean of n=1, FGFR Kinase assay—Caliper, IC$_{50}$ 0.40 µM.

5-[2-(3-methoxyphenyl)ethyl]-2-tert-butyl-pyrazol-3-amine used as starting material was prepared as indicated in Example 13.

Example 20

N-[5-[(3,5-Dimethoxyphenyl)methoxy]-2H-pyrazol-3-yl]-5-(4-methylpiperazin-1-yl)pyrazine-2-carboxamide NaHMDS (1M solution in THF, 0.645 ml, 0.644 mmol, 1.5 eq) was added dropwise to a stirred suspension of tert-butyl 5-amino-3-[(3,5-dimethoxyphenyl)methoxy]pyrazole-1-carboxylate (150 mg, 0.429 mmol, 1 eq) and methyl 5-(4-methylpiperazin-1-yl)pyrazine-2-carboxylate (122 mg, 0.515 mmol, 1.2 eq) in dry THF (2.5 ml) under nitrogen. The reaction mixture was stirred at room temperature for 50 min, then neutralised with satd aq $NH_4Cl$ and diluted with water (5 ml). The aqueous phase was extracted with ethyl acetate (3×8 ml) and the combined organic extracts were dried over $MgSO_4$, filtered and evaporated. The residual solid was purified by reverse-phase prep. HPLC using a gradient of 31-51% acetonitrile in water containing 1% ammonium hydroxide to afford the product as a white solid (88 mg, 45%).

$^1H$ NMR (399.902 MHz, DMSO) δ 2.24 (s, 3H), 2.41-2.46 (m, 4H), 3.72-3.78 (m, 4H), 3.75 (s, 6H), 5.08 (s, 2H), 5.84 (s, 1H), 6.44 (t, 1H), 6.59 (d, 2H), 8.33 (s, 1H), 8.72 (s, 1H), 10.81 (s, 1H), 11.35 (s, 1H). MS: m/z 454 (MH+).

Mean of n=2, FGFR Kinase assay—Caliper, $IC_{50}$ 0.046 µM.

Methyl 5-(4-methylpiperazin-1-yl)pyrazine-2-carboxylate, used as starting material was prepared as follows:

Methyl 5-chloropyrazine-2-carboxylate (100 mg, 0.579 mmol, 1 eq), 1-methylpiperazine (65 µl, 0579 mmol, 1 eq) and potassium carbonate (161 mg, 1.159 mmol, 2 eq) were heated in DMSO in a microwave reactor at 120° C. for 5 min. The reaction mixture was poured onto an SCX column (10 g), washed with methanol then eluted with 2M ammonia in methanol. The reaction was repeated as above with methyl 5-chloropyrazine-2-carboxylate (150 mg), 1-methylpiperazine (98 µl) and potassium carbonate (241 mg) in DMSO (3 ml). The product fractions from both reactions were combined and evaporated under vacuum to afford the product as a yellow solid (283 mg, 83%).

$^1H$ NMR (399.902 MHz, DMSO) δ 2.23 (s, 3H), 2.42 (t, 4H), 3.73 (t, 4H), 3.82 (s, 3H), 8.38 (d, 1H), 8.66 (d, 1H). MS: m/z 237 (MH+).

Example 21

4-Benzamido-N-[5-[2-(3-methoxyphenyl)ethyl]-2H-pyrazol-3-yl]benzamide

5-[2-(3-Methoxyphenyl)ethyl]-2-tert-butyl-pyrazol-3-amine (0.2 g, 0.73 mmol) was dissolved in toluene (10 ml) and to this was added methyl 4-benzamidobenzoate (200 mg, 0.80 mmol) and $AlMe_3$ (0.93 ml, 1.8 mmol). The reaction was stirred overnight. The reaction was diluted with DCM (15 ml) and quenched with damp sodium sulfite. The reaction mixture was stirred for 20 mins before being filtered and the solvent removed in vacuo to yield a yellow gum. This gum was dissolved in formic acid (12 ml) and heated at 82° C. overnight. The reaction was evaporated to dryness and the resulting product was passed through a SCX column, eluting initially with methanol followed by 2N ammonia/methanol. After removal of the solvent, a yellow solid was obtained which was triturated with hot acetonitrile to afford a white solid. The solid was filtered and dried (66 mg, 21%); 1H NMR (400.132 MHz, DMSO) δ 2.91 (s, 4H), 3.74 (s, 3H), 6.46 (brs, 1H), 6.77 (d, 1H), 6.83 (s, 2H), 7.20 (t, 1H), 7.64-7.54 (m, 3H), 7.90 (d, 2H), 8.02-7.97 (m, 4H), 10.46 (s, 1H), 10.55 (s, 1H), 12.15 (s, 1H); MS: m/z 441 (MH+).

Mean of n=2, FGFR Kinase assay—Caliper, $IC_{50}$ 231 µM.

Example 22

6-(2-Methoxyethoxy)-N-[5-[2-(3-methoxyphenyl)ethyl]-2H-pyrazol-3-yl]pyridine-3-carboxamide 6-Chloro-N-[5-[2-(3-methoxyphenyl)ethyl]-2-tert-butyl-pyrazol-3-yl]pyridine-3-carboxamide (0.15 g, 0.36 mmol) was added to a tube and dissolved in 2-methoxyethanol (15 ml). NaH (51 mg, 1.0 mmol) was added and the reaction was heated at 80° C. overnight. The reaction mixture was evaporated to dryness and passed through a SCX column, eluting initially with methanol followed by 2N ammonia/methanol. The eluant was evaporated to dryness. The obtained gum was then dissolved in formic acid and heated at 80° C. overnight. The reaction was evaporated to dryness and passed through a SCX column, eluting initially with methanol followed by 2N ammonia/methanol. The eluant was evaporated to dryness and the resulting gum was purified by reverse-phase prep. HPLC (basic) using a 30-50% gradient of acetonitrile in water containing 1% ammonium hydroxide solution. The product was obtained as solid (19 mg, 13%); $^1H$ NMR (400.132 MHz, DMSO) δ 2.90 (s, 4H), 3.31 (s, 3H), 3.69-3.67 (m, 2H), 3.74 (s, 3H), 4.47-4.44 (m, 2H), 6.45 (s, 1H), 6.76 (d, 1H), 6.82 (s, 2H), 6.90 (d, 1H), 7.20 (t, 1H), 8.25 (d, 1H), 8.78 (s, 1H), 10.69 (s, 1H), 12.17 (s, 1H); MH+397.

Mean of n=2, FGFR Kinase assay—Caliper, $IC_{50}$ 0.72 µM.

6-Chloro-N-[5-[2-(3-methoxyphenyl)ethyl]-2-tert-butyl-pyrazol-3-yl]pyridine-3-carboxamide, used as starting material was prepared as per Example 21 using methyl 6-chloro-pyridine-3-carboxylate (1.02 g, 33%); $^1H$ NMR (400.132 MHz, CDCl3) δ 1.65 (s, 9H), 2.98-2.88 (m, 4H), 3.79 (s, 3H), 6.20 (brs, 1H), 6.73 (dd, 1H), 6.79 (s, 1H), 6.83 (d, 1H), 7.19 (t, 1H), 7.52-7.47 (m, 2H), 8.12 (brs, 1H), 8.83 (brs, 1H); MS: m/z 413 (MH+).

Example 23

4-Cyano-N-[5-[2-(3-methoxyphenyl)ethyl]-2H-pyrazol-3-yl]benzamide tert-Butyl 5-[(4-cyanobenzoyl)amino]-3-[2-(3-methoxyphenyl)ethyl]pyrazole-1-carboxylate was added to acetonitrile (5 ml) and 6.0 N HCl in propan-2-ol (10 ml). The reaction mixture was stirred overnight to afford a white solid, which was filtered and dissolved in methanol/water. The solution was then passed through a SCX column. On removal of the solvent in vacuo a white solid was obtained (0.29 g, 67%); $^1H$ NMR (400.132 MHz, DMSO) δ 2.91 (s, 4H), 3.74 (s, 3H), 6.48 (s, 1H), 6.76 (d, 1H), 6.83 (s, 2H), 7.20 (t, 1H), 7.97 (d, 2H), 8.12 (d, 2H), 10.95 (s, 1H), 12.24 (s, 1H); MH+347.

Mean of n=2, FGFR Kinase assay—Caliper, $IC_{50}$ 28.6 µM.

tert-Butyl 5-[(4-cyanobenzoyl)amino]-3-[2-(3-methoxyphenyl)ethyl]pyrazole-1-carboxylate, used as starting material was prepared as follows:

tert-Butyl 5-amino-3-[2-(3-methoxyphenyl)ethyl]pyrazole-1-carboxylate (0.4 g, 1.26 mmol) was dissolved in DCM/pyridine (6 ml, 5:1) and to this was added 4-cyanobenzoyl chloride (0.27 g, 0.95 mmol). The reaction mixture was stirred overnight. The reaction mixture was evaporated to dryness to afford a black gum which was used in the next step without any further purification.

tert-butyl 5-amino-3-[2-(3-methoxyphenyl)ethyl]pyrazole-1-carboxylate, used as starting material was prepared as follows:

5-[2-(3-Methoxy-phenyl)-ethyl]-2H-pyrazol-3-ylamine (5 g, 23 mmol) and Boc anhydride (6.5 g, 30 mmol) were dissolved in DCM (200 ml) and stirred overnight at room temperature. The reaction mixture was evaporated to dryness and dissolved in diethyl ether. To this was added iso-hexane and the solvent was slowly removed in vacuo until a solid was visible. The solution was scratched and sonicated to afford tert-butyl 5-amino-3-[2-(3-methoxyphenyl)ethyl]pyrazole-1-carboxylate (6.3 g, 86%) as a white solid; $^1H$ NMR (400.132 MHz, CDCl3) δ 7.20 (t, 1H), 6.82 (d, 1H), 6.79 (s, 1H), 6.74 (d, 1H), 5.22 (s, 1H), 3.79 (s, 3H), 2.93-2.88 (m, 2H), 2.86-2.81 (m, 2H), 1.65 (s, 9H); MH+318.

Example 24

N-[5-[2-(3-Methoxyphenyl)ethyl]-2H-pyrazol-3-yl]benzene-1,4-dicarboxamide

4-Cyano-N-[5-[2-(3-methoxyphenyl)ethyl]-2H-pyrazol-3-yl]benzamide (Example 23) (0.2 g, 0.58 mmol) and NaOH (69 mg, 1.73 mmol) were added to a solution of ethanol/water (20 ml, 3:1) and heated at 80° C. until complete consumption of starting material was observed. Care was required as the amide further hydrolysed to the carboxylic acid. The reaction was extracted with DCM (3×50 ml), dried and the solvent was removed in vacuo to yield a white solid. This was triturated with DCM to afford a white solid (20 mg, 10%); $^1$H NMR (400.132 MHz, DMSO) δ 2.90 (s, 4H), 3.75 (s, 3H), 6.42 (s, 1H), 6.82-6.75 (m, 3H), 7.20 (t, 1H), 7.46 (s, 1H), 7.95 (d, 2H), 8.16-8.03 (m, 3H), 10.82 (s, 1H), 12.18 (s, 1H); MH+366.

Mean of n=1, FGFR Kinase assay—Caliper, $IC_{50}$ 0.43 µM.

Example 25

N-[5-[2-(3-Methoxyphenyl)ethyl]-2H-pyrazol-3-yl]-4-pyrazol-1-yl-benzamide

5-[2-(3-Methoxyphenyl)ethyl]-2-tert-butyl-pyrazol-3-amine (0.2 g, 0.73 mmol) was dissolved in toluene (10 ml) and to this was added methyl 4-pyrazol-1-ylbenzoate (177 mg, 0.88 mmol) and AlMe$_3$ (0.93 ml, 1.8 mmol). The reaction mixture was stirred overnight. The reaction mixture was diluted with DCM (15 ml), quenched with damp sodium sulfite and further stirred for 20 mins before being filtered. The solvent was removed in vacuo to yield a yellow gum. This gum was dissolved in formic acid (12 ml) and heated at 82° C. overnight. The reaction mixture was evaporated to dryness and the resulting product was passed through a SCX column, eluting initially with methanol followed by 2N ammonia/methanol. After solvent removal, a yellow solid was obtained which was triturated with hot acetonitrile to afford a white solid. The solid was filtered and dried (155 mg, 55%); $^1$H NMR (400.132 MHz, DMSO) δ 2.92 (s, 4H), 3.74 (s, 3H), 6.48 (s, 1H), 6.60 (s, 1H), 6.77 (d, 1H), 6.84-6.82 (m, 2H), 7.20 (t, 1H), 7.81 (s, 1H), 7.96 (d, 2H), 8.14 (d, 2H), 8.63 (s, 1H), 10.69 (s, 1H), 12.18 (s, 1H); MS: m/z 388 (MH+).

Mean of n=1, FGFR Kinase assay—Caliper, $IC_{50}$ 0.94 µM.

Example 26

6-Anilino-N-[5-[2-(3-methoxyphenyl)ethyl]-2H-pyrazol-3-yl]pyridine-3-carboxamide Prepared using an analogous method to example 25, but starting with methyl 6-anilinopyridine-3-carboxylate (200 mg, 0.88 mmol) to give the title compound (106 mg, 35%);
$^1$H NMR (400.132 MHz, DMSO) δ 2.90 (s, 4H), 3.74 (s, 3H), 6.44 (s, 1H), 6.76 (d, 1H), 6.87-6.82 (m, 3H), 6.97 (t, 1H), 7.20 (t, 1H), 7.31 (t, 2H), 7.70 (d, 2H), 8.11 (d, 1H), 8.79 (s, 1H), 9.41 (s, 1H), 10.51 (s, 1H), 12.13 (s, 1H); MH+414

Mean of n=2, FGFR Kinase assay—Caliper, $IC_{50}$ 64 µM.

Example 27

4-Methanesulfonamido-N-[5-[2-(3-methoxyphenyl)ethyl]-2H-pyrazol-3-yl]benzamide Prepared using an analogous method to example 25, but starting with methyl 4-methanesulfonamidobenzoate (200 mg, 0.88 mmol) to give the title compound (125 mg, 41%);
$^1$H NMR (400.132 MHz, DMSO) δ 2.90 (s, 4H), 3.06 (s, 3H), 3.74 (s, 3H), 6.42 (s, 1H), 6.76 (d, 1H), 6.83-6.82 (m, 2H), 7.20 (t, 1H), 7.24 (d, 2H), 7.97 (d, 2H), 10.54 (s, 1H), 12.09 (vbrs, 1H); MH+416

Mean of n=1, FGFR Kinase assay—Caliper, $IC_{50}$ 0.26 µM.

Example 28

4-(Hydroxymethyl)-N-[5-[2-(3-methoxyphenyl)ethyl]-2H-pyrazol-3-yl]benzamide Prepared using an analogous method to example 25, but starting with methyl 4-(hydroxymethyl)benzoate (146 mg, 0.88 mmol) to give the title compound (136 mg, 53%); $^1$H NMR (400.132 MHz, DMSO) δ 2.90 (s, 4H), 3.74 (s, 3H), 4.57 (d, 2H), 5.28 (t, 1H), 6.45 (s, 1H), 6.76 (d, 1H), 6.83-6.82 (m, 2H), 7.20 (t, 1H), 7.41 (d, 2H), 7.95 (d, 2H), 10.58 (s, 1H), 12.14 (s, 1H); MH+352.

Mean of n=1, FGFR Kinase assay—Caliper, $IC_{50}$ 0.074 µM.

Example 29

5-Formamido-N-[5-[2-(3-methoxyphenyl)ethyl]-2H-pyrazol-3-yl]pyridine-2-carboxamide Prepared using an analogous method to example 25, but starting with methyl 5-[(2-methylpropan-2-yl)oxycarbonylamino]pyridine-2-carboxylate (222 mg, 0.88 mmol) to give the title compound (72 mg, 27%); $^1$H NMR (400.132 MHz, DMSO) δ 2.91 (s, 4H), 3.73 (s, 3H), 6.47 (s, 1H), 6.76 (d, 1H), 6.83-6.82 (m, 2H), 7.20 (t, 1H), 8.12 (d, 1H), 8.26 (dd, 1H), 8.44 (s, 1H), 8.87 (s, 1H), 10.13 (vbrs, 1H), 10.74 (s, 1H), 12.23 (s, 1H); MH+366

Mean of n=1, FGFR Kinase assay—Caliper, $IC_{50}$ 0.87 µM.

Example 30

4-(Dimethylsulfamoyl)-N-[5-[2-(3-methoxyphenyl)ethyl]-2H-pyrazol-3-yl]benzamide Prepared using an analogous method to example 25, but starting with methyl 4-(dimethylsulfamoyl)benzoate (214 mg, 0.88 mmol) to give the title compound (126 mg, 40%);
$^1$H NMR (400.132 MHz, DMSO) δ 2.66 (s, 6H), 2.91 (s, 4H), 3.74 (s, 3H), 6.49 (s, 1H), 6.77 (d, 1H), 6.83-6.82 (m, 2H), 7.20 (t, 1H), 7.85 (d, 2H), 8.20 (d, 2H), 10.93 (s, 1H), 12.23 (s, 1H); MH+429.

Mean of n=1, FGFR Kinase assay—Caliper, $IC_{50}$ 0.80 µM.

Example 31

6-Hydroxy-N-[5-[2-(3-methoxyphenyl)ethyl]-2H-pyrazol-3-yl]pyridine-3-carboxamide Prepared using an analogous method to example 25, but starting with methyl 6-hydroxypyridine-3-carboxylate (147 mg, 0.88 mmol) to give the title compound (28 mg, 11%);

¹H NMR (400.132 MHz, DMSO) δ 2.89 (s, 4H), 3.73 (s, 3H), 6.37-6.34 (m, 2H), 6.76 (d, 1H), 6.82-6.80 (m, 2H), 7.19 (t, 1H), 7.97 (dd, 1H), 8.18 (d, 1H), 10.44 (s, 1H), 12.03 (vbrs, 1H); MH+339

Mean of n=1, FGFR Kinase assay—Caliper, IC$_{50}$ 1.05 μM.

Example 32

N-[5-[2-(3-Methoxyphenyl)ethyl]-2H-pyrazol-3-yl]-6-morpholin-4-yl-pyridine-3-carboxamide Prepared using an analogous method to example 25, but starting with methyl 6-morpholin-4-ylpyridine-3-carboxylate (195 mg, 0.88 mmol) to give the title compound (140 mg, 47%); ¹H NMR (400.132 MHz, DMSO) δ 2.90 (s, 4H), 3.59-3.57 (m, 4H), 3.71-3.69 (m, 4H), 3.74 (s, 3H), 6.44 (s, 1H), 6.76 (d, 1H), 6.82-6.81 (m, 2H), 6.86 (d, 1H), 7.20 (t, 1H), 8.13 (d, 1H), 8.76 (s, 1H), 10.45 (s, 1H), 12.11 (s, 1H); MH+408

Mean of n=1, FGFR Kinase assay—Caliper, IC$_{50}$ 0.027 μM.

Methyl 6-morpholin-4-ylpyridine-3-carboxylate, used as starting material was prepared as follows:

6-Morpholin-4-ylpyridine-3-carboxylic acid (2.56 g, 13.6 mmol) and potassium carbonate (2.8 g, 20.4 mmol) were added to DMF (40 ml) and to this was added MeI (0.97 ml, 15 mmol). The reaction mixture was heated at 50° C. for 3 h. The solvent was removed in vacuo to yield a dark solid, which was quenched with 2.0N NaOH (100 ml), extracted with DCM (3×100 ml), dried (MgSO$_4$) and solvent removed in vacuo to yield a brown solid. This solid was dissolved in hot acetonitrile and allowed to cool to afford a white solid, which was filtered and the process repeated on the mother liquor to obtain the title compound (1.8 g, 60%); 1H NMR (400.132 MHz, CDCl3) 3.65 (t, 4H), 3.81 (t, 4H), 3.87 (s, 3H), 6.53 (d, 1H), 8.04 (dd, 1H), 8.80 (d, 1H); MH+223.

Example 33

N-[5-[2-(3-Methoxyphenyl)ethyl]-2H-pyrazol-3-yl]-4-(1,3-oxazol-5-yl)benzamide Prepared using an analogous method to example 25, but starting with methyl 4-(1,3-oxazol-5-yl)benzoate (177 mg, 0.88 mmol) to give the title compound (28 mg, 10%); ¹H NMR (400.132 MHz, DMSO) δ 2.91 (s, 4H), 3.74 (s, 3H), 6.48 (s, 1H), 6.77 (d, 1H), 6.82 (m, 2H), 7.20 (t, 1H), 7.87-7.83 (m, 3H), 8.10 (d, 2H), 8.51 (s, 1H), 10.73 (s, 1H), 12.18 (s, 1H); MH+389.

Mean of n=1, FGFR Kinase assay—Caliper, IC$_{50}$ 1.2 μM.

Example 34

N-[5-[2-(3-Methoxyphenyl)ethyl]-2H-pyrazol-3-yl]-4-(tetrazol-1-yl)benzamide Prepared using an analogous method to example 25, but starting with methyl 4-(tetrazol-1-yl)benzoate (179 mg, 0.88 mmol) to give the title compound (16 mg, 6%); ¹H NMR (400.132 MHz, DMSO) δ 2.92 (s, 4H), 3.74 (s, 3H), 6.50 (s, 1H), 6.77 (d, 1H), 6.84-6.82 (m, 2H), 7.21 (t, 1H), 8.06 (d, 2H), 8.25 (d, 2H), 10.19 (s, 1H), 10.89 (s, 1H), 12.22 (s, 1H); MH+390.

Mean of n=1, FGFR Kinase assay—Caliper, IC$_{50}$ 1 μM.

Example 35

Prop-2-enyl N-[5-[[5-[2-(3-methoxyphenyl)ethyl]-2H-pyrazol-3-yl]carbamoyl]pyridin-2-yl]carbamate Prepared using an analogous method to example 25, but starting with methyl 6-(prop-2-enoxycarbonylamino)pyridine-3-carboxylate (208 mg, 0.88 mmol) to give the title compound (38 mg, 12%); ¹H NMR (400.132 MHz, DMSO) δ 2.90 (s, 4H), 3.74 (s, 3H), 4.66 (d, 2H), 5.25 (d, 1H), 5.40 (d, 1H), 6.02-5.95 (m, 1H), 6.46 (s, 1H), 6.76 (d, 1H), 6.84-6.80 (m, 2H), 7.20 (t, 1H), 7.91 (d, 1H), 8.32 (d, 1H), 8.87 (s, 1H), 10.56 (s, 1H), 10.74 (s, 1H), 12.17 (s, 1H); MH+422.

Mean of n=2, FGFR Kinase assay—Caliper, IC$_{50}$ 76 μM.

Methyl 6-(prop-2-enoxycarbonylamino)pyridine-3-carboxylate, used as starting material was prepared in an analogous manner to the synthesis of methyl 6-morpholin-4-ylpyridine-3-carboxylate in Example 32, but starting with 6-(prop-2-enoxycarbonylamino)pyridine-3-carboxylic acid carboxylate (880 mg, 3.96 mmol) to give the title compound (0.35 g, 37%); 1H NMR (400.132 MHz, CDCl3) 3.93 (s, 3H), 4.75 (dt, 2H), 5.32 (dq, 1H), 5.41 (dq, 1H), 6.09-5.99 (m, 1H), 8.07 (d, 1H), 8.30 (dd, 1H), 8.97 (d, 1H), 9.45 (brs, 1H); MH+237.

Example 36

N-[5-[2-(3-Methoxyphenyl)ethyl]-2H-pyrazol-3-yl]-4-(1,2,4-triazol-1-yl)benzamide Prepared using an analogous method to example 25, but starting with methyl 4-(1,2,4-triazol-1-yl)benzoate (177 mg, 0.88 mmol) to give the title compound (83 mg, 29%); ¹H NMR (400.132 MHz, DMSO) δ 2.92 (s, 4H), 3.74 (s, 3H), 6.48 (s, 1H), 6.77 (d, 1H), 6.83-6.82 (m, 2H), 7.20 (t, 1H), 8.00 (d, 2H), 8.19 (d, 2H), 8.29 (s, 1H), 9.42 (s, 1H), 10.79 (s, 1H), 12.20 (s, 1H); MH+389.

Mean of n=1, FGFR Kinase assay—Caliper, IC$_{50}$ 0.66 μM.

Example 37

N-[5-[2-(3-Methoxyphenyl)ethyl]-2H-pyrazol-3-yl]-6-pyrazol-1-yl-pyridine-3-carboxamide Prepared using an analogous method to example 25, but starting with methyl 6-pyrazol-1-ylpyridine-3-carboxylate (177 mg, 0.88 mmol) to give the title compound (151 mg, 54%); ¹H NMR (400.132 MHz, DMSO) δ 2.92 (s, 4H), 3.74 (s, 3H), 6.49 (s, 1H), 6.63 (dd, 1H), 6.77 (d, 1H), 6.83-6.82 (m, 2H), 7.20 (t, 1H), 7.90 (s, 1H), 8.01 (d, 1H), 8.52 (d, 1H), 8.70 (s, 1H), 9.03 (s, 1H), 10.95 (s, 1H), 12.23 (s, 1H); MH+389.

Mean of n=3, FGFR Kinase assay—Caliper, IC$_{50}$ 69 μM.

Methyl 6-pyrazol-1-ylpyridine-3-carboxylate, used as starting material was prepared as follows:

Pyrazole (2.4 g, 35.4 mmol) was added to DMA (100 ml) and to this was slowly added NaH (1.85 g, 38.6 mmol). The reaction mixture was stirred for 10 mins under a nitrogen atmosphere. To the resulting anion was added methyl 6-chloropyridine-3-carboxylate (5.5 g, 32.2 mmol) and the reaction was heated at 95° C. overnight. The reaction mixture was evaporated to dryness, quenched with 2.0 N NaOH (100 ml), extracted with DCM (3×100 ml), dried (MgSO$_4$) and the solvent removed in vacuo to yield a brown solid. This solid was purified via silica column chromatography, eluting with 0-40% diethyl ether in iso-hexane. A white solid was obtained, which was dissolved in hot iso-hexane. On cooling a white solid was obtained which was filtered and dried (2.6 g, 40%); $^1$H NMR (400.132 MHz, CDCl3) δ 3.96 (s, 3H), 6.50 (s, 1H), 7.77 (s, 1H), 8.05 (d, 1H), 8.40 (dd, 1H), 8.62 (d, 1H), 9.02 (d, 1H); MH+203.

Example 38

N-[5-[2-(3,5-Dimethoxyphenyl)ethyl]-2H-pyrazol-3-yl]-4-fluoro-benzamide

Oxalyl chloride (2M in DCM, 1.40 ml, 2.75 mmol, 1.1 eq) was added dropwise to a mixture of 4-fluorobenzoic acid (350 mg, 2.50 mmol, 1 eq) in dichloromethane (15 ml) at 0° C. containing a few drops of DMF (10 ul, 0.12 mmol, 0.05 eq) and DIPEA (937 μl, 5.25 mmol, 2.1 eq). After stirring for 60 mins at 0° C. a solution of 5-[2-(3,5-dimethoxyphenyl)ethyl]-2H-pyrazol-3-amine (742 mg, 3 mmol, 1.2 eq) in DCM (10 ml) was added dropwise over 15 mins. The mixture was maintained at 0° C. for a further 2 h, then gradually allowed to warm to room temperature overnight. The mixture was diluted with DCM (50 ml) and washed with aqueous NaHCO$_3$ solution (50 ml). The aqueous layer was extracted with DCM (50 ml). The combined organic layers were collected and concentrated. The crude product was purified by reverse-phase prep HPLC using a 30-50% gradient of acetonitrile in water containing 1% ammonium hydroxide solution. The desired fractions were evaporated to afford the title compound as a beige solid. (31.5 mg, 3% yield)

$^1$H NMR (300.132 MHz, DMSO) δ 2.87 (4H, s),3.72 (6H, s),6.32 (1H, t),6.42 (2H, d),6.46 (1H, s),7.31 (2H, t),8.06 (2H, m),10.69 (1H, s),12.16 (1H, s). MS: m/z 370 (MH+)

Mean of n=1, FGFR Kinase assay—Caliper, IC$_{50}$ 0.165 μM.

5-[2-(3,5-dimethoxyphenyl)ethyl]-2H-pyrazol-3-amine, used as starting material was prepared as shown in the starting material preparation in Example 2.

Example 39

N-[5-[2-(3,5-Dimethoxyphenyl)ethyl]-1H-pyrazol-3-yl]-3-methoxy-benzamide

1-Chloro-N,N,2-trimethylprop-1-en-1-amine (89 μl, 0.67 mmol, 1.05 eq) was added dropwise to 3-methoxybenzoic acid (97 mg, 0.63 mmol, 1 eq) in DCM (1.5 ml) at ambient temperature. After stirring at ambient temperature for 1.5 h, a solution of tert-butyl 5-amino-3-[2-(3,5-dimethoxyphenyl)ethyl]-1H-pyrazole-1-carboxylate (199 mg, 0.57 mmol, 0.9 eq) and pyridine (142 μL, 1.74 mmol, 2.75 eq) in DCM (2 ml) was added to the reaction mixture and stirring was continued at ambient temperature for a further 3 h. A solution of TFA (386 μL, 5.2 mmol, 8.25 eq) in DCM (3.5 ml) was then added and stirring was continued at ambient temperature for 18 h. The reaction mixture was concentrated and the crude product was purified by reverse-phase prep. HPLC (basic) using a gradient of acetonitrile in water containing 1% ammonium hydroxide solution. The clean fractions were taken and evaporated to afford the title compound as a colourless solid (129 mg, 59% yield). $^1$H NMR (399.902 MHz, DMSO) δ 2.89 (4H, s), 3.73 (6H, s), 3.84 (3H, s), 6.34-6.33 (1H, m), 6.43 (2H, d), 6.48 (1H, s), 7.12-7.10 (1H, m), 7.42-7.37 (1H, m), 7.59-7.56 (2H, m), 10.65 (1H, br.s), 12.16 (1H, br.s). MS: m/z 382 (MH+).

Mean of n=1, FGFR Kinase assay—Caliper, IC$_{50}$ 0.37 μM.

tert-butyl 5-amino-3-[2-(3,5-dimethoxyphenyl)ethyl]-1H-pyrazole-1-carboxylate, used as is starting material was prepared as in Example 2.

Example 40

N-[5-[2-(3,5-Dimethoxyphenyl)ethyl]-1H-pyrazol-3-yl]-3-morpholin-4-yl-benzamide Prepared in an analogous way to Example 39, starting with 3-morpholin-4-ylbenzoic acid (130 mg, 0.63 mmol) to give the title compound as a solid (105 mg, 42% yield); $^1$H NMR (399.902 MHz, DMSO) δ 2.89 (4H, s), 3.21-3.19 (4H, m), 3.73 (6H, s), 3.79-3.76 (4H, m), 6.34-6.33 (1H, m), 6.43 (2H, d), 6.48 (1H, s), 7.12 (1H, d), 7.35-7.31 (1H, m), 7.43 (1H, d), 7.57 (1H, s), 10.62 (1H, br.s), 12.15 (1H, br.s). MS: m/z 437 (MH+)

Mean of n=1, FGFR Kinase assay—Caliper, IC$_{50}$ 0.71 μM.

Example 41

N-[5-[2-(3,5-Dimethoxyphenyl)ethyl]-1H-pyrazol-3-yl]-2-methoxy-benzamide

Prepared in an analogous way to Example 39, starting with 2-methoxybenzoic acid (95.8 mg, 0.63 mmol) to give the title compound as a solid (100 mg, 46% yield); $^1$H NMR (399.902 MHz, DMSO) δ 2.89 (4H, s), 3.73 (6H, s), 3.97 (3H, s), 6.34-6.33 (1H, m), 6.43 (2H, d), 6.49 (1H, s), 7.12-7.07 (1H, m), 7.21 (1H, d), 7.56-7.51 (1H, m), 7.85-7.82 (1H, m), 10.16 (1H, br.s), 12.14 (1H, br.s). MS: m/z 382 (MH+).

Mean of n=1, FGFR Kinase assay—Caliper, IC$_{50}$ 2.61 μM.

Example 42

N-[5-[2-(3,5-Dimethoxyphenyl)ethyl]-1H-pyrazol-3-yl]-4-(2-ethoxyethoxy)benzamide Prepared in an analogous way to Example 39, starting with 4-(2-ethoxyethoxy)benzoic acid (132 mg, 0.63 mmol) to give the title compound as a solid (126 mg, 50% yield); $^1$H NMR (399.902 MHz, DMSO) δ 1.15 (3H, t), 2.88 (4H, s), 3.52 (2H, q), 3.73 (8H, s), 4.19-4.16 (1H, m), 6.34-6.32 (1H, m), 6.43 (2H, d), 6.46 (1H, s), 7.02 (2H, d), 7.98 (2H, d), 10.47 (1H, br.s), 12.11 (1H, br.s). MS: m/z 440 (MH+)

Mean of n=1, FGFR Kinase assay—Caliper, IC$_{50}$ 0.075 μM.

Example 43

N-[5-[2-(3,5-Dimethoxyphenyl)ethyl]-1H-pyrazol-3-yl]-4-(1-piperidyl)benzamide Prepared in an analogous way to Example 39, starting with 4-(1-piperidyl)benzoic acid (129 mg, 0.63 mmol) to give the title compound as a solid (97.5 mg, 39% yield);

$^1$H NMR (399.902 MHz, DMSO) δ 1.60 (6H, s), 2.88 (4H, s), 3.33-3.31 (6H, m), 3.73 (1H, s), 6.33-6.32 (2H, m), 6.42 (1H, d), 6.45 (2H, s), 6.94 (2H, d), 10.26 (1H, br.s), 12.07 (1H, br.s). MS: m/z 435 (MH+)

Mean of n=1, FGFR Kinase assay—Caliper, IC$_{50}$ 0.438 μM.

Example 44

N-[5-[2-(3,5-Dimethoxyphenyl)ethyl]-1H-pyrazol-3-yl]-4-(4-piperidylmethoxy)benzamide Prepared in an analogous way to Example 39, starting with 4-[[1-[(2-methylpropan-2-yl)oxycarbonyl]-4-piperidyl]

methoxy]benzoic acid (211 mg, 0.63 mmol) to give the title compound as a solid (40 mg, 15% yield); $^1$H NMR (399.902 MHz, DMSO) δ1.72-1.67 (2H, m), 1.87-1.79 (2H, m), 2.48-2.45 (1H, m), 2.88 (4H, s), 2.98-2.94 (2H, m), 3.73 (6H, s), 3.88 (2H, d), 6.34 (1H, s), 6.46-6.42 (3H, m), 7.00 (2H, d), 7.97 (2H, d), 10.48 (1H, br.s), 12.14 (1H, br.s). MS: m/z 465 (MH+)

Mean of n=1, FGFR Kinase assay—Caliper, $IC_{50}$ 0.025 μM.

Example 45

N-[5-[2-(3,5-Dimethoxyphenyl)ethyl]-1H-pyrazol-3-yl]-4-piperazin-1-yl-benzamide

Prepared in an analogous way to Example 39, starting with 4-[4-[(2-methylpropan-2-yl)oxycarbonyl]piperazin-1-yl]benzoic acid (193 mg, 0.63 mmol) to give the title compound as a solid (100 mg, 40% yield); $^1$H NMR (399.902 MHz, DMSO) δ 2.84-2.82 (4H, m), 2.88 (4H, s), 3.21-3.15 (4H, m), 3.73 (6H, s), 6.33 (1H, s), 6.46-6.42 (3H, m), 6.94 (2H, d), 7.89 (2H, d), 10.30 (1H, br.s), 12.09 (1H, br.s). MS: m/z 436 (MH+)

Mean of n=2, FGFR Kinase assay—Caliper, $IC_{50}$ 0.026 μM.

Example 46

N-[5-[2-(3,5-Dimethoxyphenyl)ethyl]-1H-pyrazol-3-yl]-6-piperazin-1-yl-pyridine-3-carboxamide Prepared in an analogous way to Example 39, starting with 6-[4-[(2-methylpropan-2-yl)oxycarbonyl]piperazin-1-yl]pyridine-3-carboxylic acid (193 mg, 0.63 mmol) to give the title compound as a solid (96 mg, 39% yield); $^1$H NMR (399.902 MHz, DMSO) δ 2.79-2.76 (4H, m), 2.88 (4H, s), 3.56-3.53 (4H, m), 3.73 (6H, s), 6.34-6.32 (1H, m), 6.45-6.42 (3H, m), 6.82 (1H, d), 8.10-8.07 (1H, m), 8.73 (1H, d), 10.43 (1H, br.s), 12.12 (1H, br.s). MS: m/z 437 (MH+)

Mean of n=2, FGFR Kinase assay—Caliper, $IC_{50}$ 0.040 μM.

Example 47

N-[5-[2-(3,5-Dimethoxyphenyl)ethyl]-1H-pyrazol-3-yl]-4-(dimethylaminomethyl)benzamide Oxalyl chloride (61 μl, 0.69 mmol, 1.1 eq) was added dropwise to 4-(dimethylaminomethyl)benzoic acid (113 mg, 0.63 mmol, 1 eq) in DCM (2.5 ml) containing 1 drop of DMF. After stirring at ambient temperature for 1.5 h, a solution of tert-butyl 5-amino-3-[2-(3,5-dimethoxyphenyl)ethyl]pyrazole-1-carboxylate (196 mg, 0.56 mmol, 0.9 eq) and pyridine (137 μL, 1.69 mmol, 2.70 eq) in DCM (2 ml) was added to the reaction mixture and stirring was continued at ambient temperature for a further 2 h. A solution of TFA (384 μL, 5.16 mmol, 8.25 eq) in DCM (3.5 ml) was then added and stirring was continued at ambient temperature for 18 h. The reaction mixture was concentrated and the crude product was purified by reverse-phase prep. HPLC (basic) using a gradient of acetonitrile in water containing 1% ammonium hydroxide solution. The clean fractions were taken and evaporated to afford the title compound as a colourless solid (65 mg, 25% yield); $^1$H NMR (399.902 MHz, DMSO) δ 2.09 (6H, s), 2.81 (4H, s), 3.38 (2H, s), 3.65 (6H, s), 6.26-6.25 (1H, m), 6.35 (2H, d), 6.40 (1H, s), 7.31 (2H, d), 7.87 (2H, d), 10.51 (1H, br.s), 12.07 (1H, br.s). MS: m/z 409 (MH+)

Mean of n=1, FGFR Kinase assay—Caliper, $IC_{50}$ 0.019 μM.

tert-butyl 5-amino-3-[2-(3,5-dimethoxyphenyl)ethyl]pyrazole-1-carboxylate, used as starting material was prepared as in Example 2.

1H NMR (399.902 MHz, DMSO) δ1.56 (9H, s), 2.68-2.63 (2H, m), 2.80-2.75 (2H, m), 3.73 (6H, s), 5.22 (1H, s), 6.23 (2H, br.s), 6.32-6.31 (1H, m), 6.44 (2H, d). MS: m/z 370 ([M+Na]+).

Example 48

N-[5-[2-(3,5-Dimethoxyphenyl)ethyl]-1H-pyrazol-3-yl]-4-(2-hydroxyethoxy)benzamide A solution of NaHMDS in THF (1 M, 1.15 ml, 1.15 mmol, 2 eq) was added dropwise at ambient temperature to a mixture of tert-butyl-5-amino-3-[2-(3,5-dimethoxyphenyl)ethyl]pyrazole-1-carboxylate (200 mg, 0.58 mmol, 1 eq) and methyl 4-(2-hydroxyethoxy)benzoate (136 mg, 0.69 mmol, 1.2 eq) in THF (1 ml). The reaction mixture was stirred at ambient temperature for 1 h. It was then concentrated and the crude product was purified by reverse-phase prep. HPLC (basic) using a gradient of acetonitrile in water containing 1% ammonium hydroxide solution. The clean fractions were taken and evaporated to afford the title compound as a colourless solid (29 mg, 12% yield); $^1$H NMR (399.902 MHz, DMSO) δ 2.89 (4H, s), 3.77-3.72 (8H, m), 4.07 (2H, t), 4.88 (1H, t), 6.34-6.33 (1H, m), 6.43 (2H, d), 6.46 (1H, s), 7.01 (2H, d), 7.98 (2H, d), 10.46 (1H, br.s), 12.12 (1H, br.s). MS: m/z 412 (MH+)

Mean of n=1, FGFR Kinase assay—Caliper, $IC_{50}$ 0.039 μM.

tert-butyl-5-amino-3-[2-(3,5-dimethoxyphenyl)ethyl]pyrazole-1-carboxylate, used as starting material was prepared as in Example 2.

Example 49

4-(2-Aminopropyl)-N-[5-[2-(3,5-dimethoxyphenyl)ethyl]-1H-pyrazol-3-yl]benzamide

A solution of NaHMDS in THF (1 M, 0.86 ml, 0.86 mmol, 1.5 eq) was added dropwise at ambient temperature to a mixture of tert-butyl-5-amino-3-[2-(3,5-dimethoxyphenyl)ethyl]pyrazole-1-carboxylate (200 mg, 0.58 mmol, 1 eq) and methyl 4-(2-aminopropyl)benzoate (133 mg, 0.69 mmol, 1.2 eq) in THF (1 ml). The reaction mixture was stirred at ambient temperature for 2 h. It was then concentrated and the crude product was purified by reverse-phase prep. HPLC (basic) using a gradient of acetonitrile in water containing 1% ammonium hydroxide solution. The clean fractions were taken and evaporated to afford the title compound as a pale yellow gum (10 mg, 4% yield); $^1$H NMR (399.902 MHz, DMSO) δ 0.89 (3H, d), 2.53-2.47 (2H, m), 2.80 (4H, s), 3.01-2.93 (1H, m), 3.65 (6H, s), 6.25-6.24 (1H, m), 6.34 (2H, d), 6.40 (1H, s), 7.21 (2H, d), 7.84 (2H, d), 10.47 (1H, br.s), 12.06 (1H, br.s). MS: m/z 409 (MH+)

Cell FGFR1, $IC_{50}$ 1.47 μM.

tert-butyl-5-amino-3-[2-(3,5-dimethoxyphenyl)ethyl]pyrazole-1-carboxylate, used as starting material was prepared as in Example 2.

Example 50

N-[5-[2-(3,5-Dimethoxyphenyl)ethyl]-1H-pyrazol-3-yl]-4-[(3,3-dimethyl-1-piperidyl)methyl]benzamide Prepared in an analogous way to Example 49, starting with methyl 4-[(3,3-dimethyl-1-piperidyl)methyl]benzoate (180 mg, 0.69 mmol) to give the title compound as a colourless solid (44 mg, 16% yield); $^1$H NMR (399.902 MHz, DMSO) δ 0.92 (3H, s), 1.23-1.20 (2H, m), 1.59-1.52 (2H, m), 2.01-1.99 (2H, m), 2.35-2.29 (2H, m), 2.89 (4H, s), 3.48 (2H, s), 3.73 (6H, s), 6.34-6.32 (1H, m), 6.43 (2H, d), 6.48 (1H, s), 7.40 (2H, d), 7.94 (2H, d), 10.57 (1H, br.s), 12.14 (1H, br.s). MS: m/z 477 (MH+)

Mean of n=1, FGFR Kinase assay—Caliper, $IC_{50}$ 0.001 µM.

Methyl 4-[(3,3-dimethyl-1-piperidyl)methyl]benzoate, used as starting material was prepared as follows:

3,3-Dimethylpiperidine (170 mg, 1.5 mmol, 1.5 eq) was added in one portion to a mixture of methyl 4-(bromomethyl)benzoate (230 mg, 1 mmol, 1 eq) and MP-carbonate (2.74 mmol/g, 1.46 g, 4 mmol, 4 eq) in MeCN (5 ml). The reaction mixture was stirred at ambient temperature for 18 h. Polymer-supported isocyanate (1 mmol/g, 1 g, 1 mmol, 1 eq) was added in one portion and stirring continued for 4 h. The reaction mixture was filtered, the resins washed with MeCN and the combined filtrate was concentrated to afford a clear liquid (216 mg, 83% yield); $^1$H NMR (399.902 MHz, DMSO) δ 0.91 (6H, s), 1.22-1.19 (2H, m), 1.58-1.52 (2H, m), 1.99 (2H, s), 2.33-2.28 (2H, m), 3.49 (2H, s), 3.85 (3H, s), 7.46 (2H, d), 7.92 (2H, d). MS: m/z 262 (MH+)

Example 51

N-[5-[2-(3,5-Dimethoxyphenyl)ethyl]-1H-pyrazol-3-yl]-4-[4-(2-hydroxyethyl)piperazin-1-yl]benzamide Prepared in an analogous way to Example 49, starting with methyl 4-[4-(2-hydroxyethyl)piperazin-1-yl]benzoate (182 mg, 0.69 mmol) to give the title compound as a colourless solid (11 mg, 4% yield); $^1$H NMR (399.902 MHz, DMSO) δ 2.45 (2H, t), 2.58-2.55 (4H, m), 2.88 (4H, s), 3.29-3.26 (4H, m), 3.58-3.53 (2H, m), 3.73 (6H, s), 4.42 (1H, t), 6.34-6.32 (1H, m), 6.42 (2H, d), 6.45 (1H, s), 6.96 (2H, d), 7.90 (2H, d), 10.30 (1H, br.s), 12.08 (1H, br.s). MS: m/z 480 (MH+)

Mean of n=1, FGFR Kinase assay—Caliper, $IC_{50}$ 0.081 µM.

Methyl 4-[4-(2-hydroxyethyl)piperazin-1-yl]benzoate, used as starting material was prepared as follows:

Trimethylsilyldiazomethane solution (2M in hexanes, 1.2 ml, 2.4 mmol, 1.2 eq) was added dropwise to 4-(4-[2-hydroxyethyl]piperazin-1-yl)benzoic acid (501 mg, 2 mmol, 1 eq) in toluene (14 ml) and methanol (4 ml) at ambient temperature. The reaction mixture was allowed to stir for 5 h, the solvent removed under reduced pressure and the residue dried under high vacuum to afford methyl 4-(2-bromoethoxy)benzoate as a cream solid (342 mg, 65% yield). MS: m/z 265 (MH+)

Example 52

4-[(7-Cyano-3,4-dihydro-1H-isoquinolin-2-yl)methyl]-N-[5-[2-(3,5-dimethoxyphenyl)ethyl]-1H-pyrazol-3-yl]benzamide Prepared in an analogous way to Example 53, starting with methyl 4-[(7-cyano-3,4-dihydro-1H-isoquinolin-2-yl)methyl]benzoate (211 mg, 0.69 mmol) to give the title compound as a pale yellow gum (45 mg, 15% yield); $^1$H NMR (399.902 MHz, DMSO) δ 2.67-2.64 (2H, m), 2.81 (4H, s), 2.86-2.83 (2H, m), 3.54 (2H, s), 3.67-3.64 (8H, m), 6.26-6.24 (1H, m), 6.35 (2H, d), 6.41 (1H, s), 7.26 (1H, d), 7.39 (2H, d), 7.51-7.47 (2H, m), 7.91 (2H, d), 10.53 (1H, br.s), 12.07 (1H, br.s). MS: m/z 522 (MH+)

Mean of n=1, FGFR Kinase assay—Caliper, $IC_{50}$ 0.486 µM.

Methyl 4-[(7-cyano-3,4-dihydro-1H-isoquinolin-2-yl)methyl]benzoate, used as starting material was prepared as follows:

1,2,3,4-tetrahydroisoquinoline-7-carbonitrile hydrochloride (292 mg, 1.5 mmol, 1.5 eq) was added in one portion to a mixture of methyl 4-(bromomethyl)benzoate (230 mg, 1 mmol, 1 eq) and MP-carbonate (2.74 mmol/g, 1.46 g, 4 mmol, 4 eq) in MeCN (5 ml). The reaction mixture was stirred at ambient temperature for 18 h. Polymer-supported isocyanate (1 mmol/g, 1 g, 1 mmol, 1 eq) was added in one portion and stirring continued for 4 h. The reaction mixture was filtered, the resins washed with MeCN and the combined filtrate was concentrated to afford a pale yellow oil which solidified on standing overnight (292 mg, 95% yield); $^1$H NMR (399.902 MHz, DMSO) δ 2.70-2.63 (2H, m), 2.89-2.82 (2H, m), 3.53 (2H, s), 3.68 (2H, s), 3.78 (3H, s), 7.25 (1H, d), 7.51-7.38 (4H, m), 7.89-7.86 (2H, m). MS: m/z 307 (MH+)

Example 53

N-[5-[2-(3,5-Dimethoxyphenyl)ethyl]-1H-pyrazol-3-yl]-4-[(3-fluoro-1-piperidyl)methyl]benzamide A solution of NaHMDS in THF (1 M, 0.86 ml, 0.86 mmol, 1.5 eq) was added dropwise at ambient temperature to a mixture of tert-butyl-5-amino-3-[2-(3,5-dimethoxyphenyl)ethyl]pyrazole-1-carboxylate (200 mg, 0.58 mmol, 1 eq) and methyl 4-[(3-fluoro-1-piperidyl)methyl]benzoate (174 mg, 0.69 mmol, 1.2 eq) in THF (1 ml). The reaction mixture was stirred at ambient temperature for 2 h. The reaction mixture was then concentrated and the crude product was purified by reverse-phase prep. HPLC (acidic) using a gradient of acetonitrile in water containing 0.1% TFA. The clean fractions were taken and evaporated. The residue was dissolved in 3:1 DCM:MeCN mixture (4 ml) and MP-carbonate (2.74 mmol/g, 1 g, 2.74 mmol) was added. The mixture was stirred for 4 h, filtered and the filtrate evaporated to afford the title compound as a pale yellow gum (43 mg, 16% yield); $^1$H NMR (399.902 MHz, DMSO) δ 1.46-1.34 (2H, m), 1.82-1.61 (2H, m), 2.36-2.28 (2H, m), 2.66-2.56 (2H, m), 2.81 (4H, s), 3.50 (2H, s), 3.65 (6H, s), 4.66-4.47 (1H, m), 6.26-6.24 (1H, m), 6.35 (2H, d), 6.40 (1H, s), 7.32 (2H, d), 7.88 (2H, d), 10.51 (1H, br.s), 12.07 (1H, br.s). MS: m/z 467 (MH+)

Mean of n=1, FGFR Kinase assay—Caliper, $IC_{50}$ 0.090 µM.

Methyl 4-[(3-fluoro-1-piperidyl)methyl]benzoate, used as starting material was prepared as follows:

3-Fluoropiperidine hydrochloride (210 mg, 1.5 mmol, 1.5 eq) was added in one portion to a mixture of methyl 4-(bromomethyl)benzoate (230 mg, 1 mmol, 1 eq) and MP-carbonate (2.74 mmol/g, 1.46 g, 4 mmol, 4 eq) in MeCN (5 ml). The reaction mixture was stirred at ambient temperature for 18 h. Polymer-supported isocyanate (1 mmol/g, 1 g, 1 mmol, 1 eq) was added in one portion and stirring continued for 4 h. The reaction mixture was filtered, the resins washed with MeCN and the combined filtrate was concentrated to afford a clear oil, 217 mg, 86% yield.

$^1$H NMR (399.902 MHz, DMSO) δ 1.59-1.42 (2H, m), 1.90-1.67 (2H, m), 2.42-2.36 (2H, m), 2.73-2.63 (2H, m), 3.59 (2H, s), 3.86 (3H, s), 4.73-4.56 (1H, m), 7.46 (2H, d), 7.93 (2H, d). MS: m/z 252 (MH+)

tert-butyl-5-amino-3-[2-(3,5-dimethoxyphenyl)ethyl]pyrazole-1-carboxylate, used as starting material was prepared as in Example 2.

Example 54

N-[5-[2-(3,5-Dimethoxyphenyl)ethyl]-1H-pyrazol-3-yl]-4-(2-morpholin-4-ylethoxy)benzamide Prepared in an analogous way to Example 53, starting with methyl 4-(2-morpholin-4-ylethoxy)benzoate (183 mg, 0.69 mmol) to give the title compound as a pale yellow gum (21 mg, 7.5% yield); $^1$H NMR (399.902 MHz, CDCl3) δ 2.59-2.57 (4H, m), 2.81 (2H, t), 2.99-2.90 (4H, m), 3.75-3.72 (4H, m), 3.77 (6H, s), 4.14 (2H, t), 6.36-6.32 (4H, m), 6.67 (1H, br.s), 6.96 (2H, d), 7.83 (2H, d), 8.53 (1H, br.s). MS: m/z 481 (MH+)

Mean of n=1, FGFR Kinase assay—Caliper, $IC_{50}$ 0.096 μM.

Methyl 4-(2-morpholin-4-ylethoxy)benzoate, used as starting material was prepared as follows:

MP-Carbonate (2.74 mmol/g, 529 mg, 1.45 mmol, 1.5 eq) was added to methyl 4-(2-bromoethoxy)benzoate (250 mg, 0.96 mmol, 1 eq), morpholine (93 μl, 1.06 mmol, 1.1 eq), sodium iodide (150 mg, 1 mmol, 1.05 eq) and MeCN (5 ml) were charged to a microwave reactor vessel and the reaction mixture heated to 120° C. in a microwave reactor for 10 minutes. The reaction mixture was transferred to a SCX-2 cartridge, eluted with MeOH followed by 3.5 N ammonia in MeOH solution. The latter fractions were combined and evaporated to afford a clear oil which solidified on standing to a cream solid (146 mg, 57% yield). $^1$H NMR (400.132 MHz, CDCl3) δ 2.59-2.57 (4H, m), 2.82 (2H, t), 3.74-3.72 (4H, m), 3.88 (3H, s), 4.16 (2H, t), 6.93-6.91 (2H, m), 7.99-7.97 (2H, m). MS: m/z 266 (MH+)

Example 55

4-[2-(4,4-Difluoro-1-piperidyl)ethoxy]-N-[5-[2-(3,5-dimethoxyphenyl)ethyl]-1H-pyrazol-3-yl]benzamide Prepared in an analogous way to Example 53, starting with methyl 4-[2-(4,4-difluoro-1-piperidyl)ethoxy]benzoate (104 mg, 0.35 mmol) to give the title compound as a clear gum (5 mg, 1.7% yield); $^1$H NMR (399.902 MHz, CDCl3) δ 2.06-1.96 (4H, m), 2.70-2.67 (4H, m), 2.88-2.85 (2H, m), 2.97-2.92 (4H, m), 3.77-3.76 (8H, m), 4.12 (2H, t), 6.33-6.32 (2H, m), 6.35-6.35 (2H, m), 6.65 (1H, br.s), 6.95 (2H, d), 7.83 (2H, d), 8.59 (1H, s). MS: m/z 515 (MH+)

Cell FGFR1, $IC_{50}$ 0.46 μM.

Methyl 4-[2-(4,4-difluoro-1-piperidyl)ethoxy]benzoate, used as starting material was prepared as follows:

MP-Carbonate (2.74 mmol/g, 1.234 g, 3.38 mmol, 2.5 eq) was added to methyl 4-(2-bromoethoxy)benzoate (350 mg, 1.35 mmol, 1 eq), 4,4-difluoropiperidine hydrochloride (235 mg, 1.49 mmol, 1.1 eq), sodium iodide (212 mg, 1.42 mmol, 1.05 eq) and MeCN (6 ml) were charged to a microwave reactor vessel and the reaction mixture heated to 120° C. in a microwave reactor for 10 minutes. The reaction mixture was transferred to a SCX-2 cartridge, eluted with MeOH followed by 3.5 N ammonia in MeOH solution. The latter fractions were combined and evaporated to afford a colourless solid (104 mg, 35% yield). $^1$H NMR (400.132 MHz, CDCl3) δ 2.08-1.98 (4H, m), 2.74-2.71 (4H, m), 2.90 (2H, t), 3.89 (3H, s), 4.16 (2H, t), 6.93-6.91 (2H, m), 8.00-7.98 (2H, m). MS: m/z 300 (MH+)

Example 56

N-[5-[2-(3,5-Dimethoxyphenyl)ethyl]-1H-pyrazol-3-yl]-4-(2-morpholin-4-ylethyl)benzamide Prepared in an analogous way to Example 53, starting with methyl 4-(2-morpholin-4-ylethyl)benzoate (172 mg, 0.69 mmol) to give the title compound as a clear gum (42 mg, 15.6% yield); $^1$H NMR (399.902 MHz, DMSO) δ 2.37-2.35 (4H, m), 2.49-2.45 (2H, m), 2.73 (2H, t), 2.80 (4H, s), 3.50 (4H, t), 3.65 (6H, s), 6.26-6.24 (1H, m), 6.34 (2H, d), 6.40 (1H, s), 7.26 (2H, d), 7.83 (2H, d), 10.47 (1H, br.s), 12.06 (1H, br.s). MS: m/z 465 (MH+)

Mean of n=1, FGFR Kinase assay—Caliper, $IC_{50}$ 0.120 μM.

4-(2-Morpholin-4-ylethyl)benzoic acid, used as starting material was prepared as follows: Trimethylsilyldiazomethane solution (2M in hexanes, 1.2 ml, 2.4 mmol, 1.2 eq) was added dropwise to 4-(2-bromoethyl)benzoc acid (459 mg, 2 mmol, 1 eq) in toluene (14 ml) and methanol (4 ml) at ambient temperature. The reaction mixture was allowed to stir for 5 h, the solvent removed under reduced pressure and the residue dried under high vacuum to afford methyl 4-(2-bromoethoxy)benzoate as a pale yellow liquid (487 mg, 100% yield).

$^1$H NMR (399.902 MHz, DMSO) δ 3.20 (2H, t), 3.76 (2H, t), 3.83 (3H, s), 7.42 (2H, d), 7.89 (2H, d).

MP-carbonate (2.74 mmol/g, 270 mg, 0.74 mmol, 0.6 eq) was added to methyl 4-(2-bromoethoxy)benzoate (300 mg, 1.23 mmol, 1 eq), morpholine (0.12 ml, 1.36 mmol, 1.1 eq), sodium iodide (193 mg, 1.29 mmol, 1.05 eq) and MeCN (6 ml) were charged to a microwave reactor vessel and the reaction mixture heated to 120° C. in a microwave reactor for 10 minutes. The reaction mixture was transferred to an SCX-2 cartridge, eluted with MeOH followed by 3.5 N ammonia in MeOH solution. The latter fractions were combined and evaporated to afford a pale yellow solid (130 mg, 52% yield).

$^1$H NMR (399.902 MHz, CDCl3) δ 2.53-2.51 (4H, m), 2.64-2.60 (2H, m), 2.88-2.84 (2H, m), 3.75-3.72 (4H, m), 3.90 (3H, s), 7.28-7.26 (2H, m), 7.97-7.94 (2H, m). MS: m/z 250 (MH+)

Example 57

N-[5-[2-(3,5-Dimethoxyphenyl)ethyl]-1H-pyrazol-3-yl]-4-[(methyl-(oxolan-2-ylmethyl)amino)methyl]benzamide Prepared in an analogous way to Example 53, starting with methyl 4-[(methyl-(oxolan-2-ylmethyl)amino)methyl]benzoate (181 mg, 0.69 mmol) to give the title compound as a clear gum (56 mg, 20% yield); $^1$H NMR (399.902 MHz, DMSO) δ 1.56-1.42 (1H, m), 1.81-1.74 (2H, m), 1.98-1.90 (1H, m), 2.20 (3H, s), 2.44 (2H, d), 3.31 (4H, s), 3.66-3.59 (3H, m), 3.73 (6H, s), 4.01-3.94 (2H, m), 6.34-6.33 (1H, m), 6.43 (2H, d), 6.48 (1H, s), 7.40 (2H, d), 7.95 (2H, d), 10.58 (1H, br.s), 12.15 (1H, br.s). MS: m/z 479 (MH+)

Mean of n=1, FGFR Kinase assay—Caliper Echo Dosing, $IC_{50}$ 0.0053 μM.

Methyl 4-[(methyl-(oxolan-2-ylmethyl)amino)methyl]benzoate, used as starting material was prepared as follows:

MP-carbonate (2.74 mmol/g, 1.44 g, 4 mmol, 2 eq) was added to methyl 4-(bromomethyl)benzoate (500 mg, 2 mmol, 1 eq), N-methyl-1-(oxolan-2-yl)methanamine (231 mg, 2 mmol, 1 eq) and MeCN (10 ml). The reaction mixture was allowed to stir at ambient temperature for 18 h and was then transferred to a SCX-2 cartridge, eluted with MeOH followed by 3.5 N ammonia in MeOH solution. The latter fractions were combined and evaporated to afford a pale yellow solid (355 mg, 64% yield).

1H NMR (399.902 MHz, CDCl3) δ 1.54-1.47 (1H, m), 1.87-1.80 (2H, m), 2.01-1.93 (1H, m), 2.28 (3H, s), 2.46-2.42 (1H, m), 2.55-2.50 (1H, m), 3.68-3.57 (2H, m), 3.76-3.71

(1H, m), 3.87-3.81 (1H, m), 3.91 (3H, s), 4.08-4.01 (1H, m), 7.41 (2H, d), 7.98 (2H, d). MS: m/z 264 (MH+)

Example 58

N-[5-[2-(3,5-Dimethoxyphenyl)ethyl]-1H-pyrazol-3-yl]-4-(4-piperidyl)benzamide

Prepared in an analogous way to Example 53, starting with methyl 4-(4-piperidyl)benzoate hydrochloride (176 mg, 0.69 mmol) to give the title compound as a pale yellow gum (20 mg, 8% yield); $^1$H NMR (399.902 MHz, DMSO) δ 1.69-1.57 (2H, m), 1.84-1.76 (2H, m), 2.76-2.68 (2H, m), 2.93 (4H, s), 3.17-3.12 (2H, m), 3.77-3.76 (7H, m), 6.38-6.37 (1H, m), 6.47 (2H, d), 6.53 (1H, s), 7.38 (2H, d), 7.98 (2H, d), 10.61 (1H, s), 12.20 (1H, s). MS: m/z 435 (MH+)

Mean of n=1, FGFR Kinase assay—Caliper, $IC_{50}$ 0.001 μM.

Example 59

N-[5-[2-(3,5-Dimethoxyphenyl)ethyl]-1H-pyrazol-3-yl]-4-dimethylamino-benzamide

Prepared in an analogous way to Example 39, starting with 4-dimethylaminobenzoic acid (102 mg, 0.63 mmol) to give the title compound as a solid (139 mg, 63% yield); $^1$H NMR (399.902 MHz, DMSO) δ 2.87 (4H, s), 3.00 (6H, s), 3.73 (6H, s), 6.33-6.32 (1H, m), 6.42 (2H, d), 6.45 (1H, s), 6.72 (2H, d), 7.89 (2H, d), 10.21 (1H, brs), 12.06 (1H, br.s). MS: m/z 395 (MH+)

Mean of n=1, FGFR Kinase assay—Caliper, $IC_{50}$ 0.134 μM.

Example 60

N-[5-[2-(3,5-Dimethoxyphenyl)ethyl]-1H-pyrazol-3-yl]-5-piperazin-1-yl-thiophene-2-carboxamide (2,2,2-trifluoroacetic acid salt)

5-[4-[(2-methylpropan-2-yl)oxycarbonyl]piperazin-1-yl]thiophene-2-carboxylic acid (150 mg, mmol) was dissolved in dry THF (10 ml) under nitrogen, 1-chloro-N,N,2-trimethyl-prop-1-en-1-amine (177 μl, mmol) was added and the mixture was stirred at room temperature for 3.5 h. Tert-butyl 5-amino-3-[2-(3,5-dimethoxyphenyl)ethyl]pyrazole-1-carboxylate (167 mg, mmol) and pyridine (47 μl, mmol) were added and the reaction was heated to 65° C. for 18 h. The reaction mixture was then cooled to room temperature and 4M HCl in dioxane (2.0 ml, 2.0 mmol) added. The mixture was stirred overnight at room temperature, evaporated and the residue was purified by acidic prep. HPLC, eluting with a gradient of 24-32% MeCN in 0.1% TFA in water. The clean fractions were taken and evaporated to give the title compound as a pale green solid (28.7 mg, 11%); $^1$H NMR (399.902 MHz, DMSO) δ 2.79 (s, 4H), 3.21 (s, 4H), 3.34 (s, 4H), 3.64 (s, 6H), 6.29 (m, 5H), 7.77 (m, 1H), 8.71 (s, 1H), 10.37 (s, 1H) MS: m/z=442 (MH+)

Mean of n=2, FGFR Kinase assay—Caliper, $IC_{50}$ 0.022 μM.

tert-butyl 5-amino-3-[2-(3,5-dimethoxyphenyl)ethyl]pyrazole-1-carboxylate, used as starting material was prepared as in Example 2.

5-[4-[(2-methylpropan-2-yl)oxycarbonyl]piperazin-1-yl]thiophene-2-carboxylic acid, used as starting material was prepared as follows:

A solution of tert-butyl 4-(5-formylthien-2-yl)piperazine-1-carboxylate (2.51 g, 8.50 mmol) in ethanol (85 ml) was added in one portion to a solution of silver (I) nitrate (10.0 g, 58.8 mmol) and sodium hydroxide (4.83 g, 120.6 mmol) in water (85 ml). This mixture was stirred and heated at 65° C. for 22 h. The mixture was cooled by the addition of ice and then filtered to remove silver salts. The filtrate was carefully evaporated to remove the ethanol and the resulting aqueous solution was filtered again through a glass-fibre pad to remove tarry material. The filtrate was then diluted with water to a total volume of 400 ml and then acidified to pH 5 with acetic acid. The precipitate was filtered off, washed with water and then dried in a vacuum oven at 45° C. overnight to give 5-[4-[(2-methylpropan-2-yl)oxycarbonyl]piperazin-1-yl]thiophene-2-carboxylic acid (1.88 g, 71%).

1H NMR (399.9 MHz, DMSO-$d_6$) δ 1.41 (9H, s), 3.18 (4H, m), 3.45 (4H, m), 6.20 (1H, d), 7.43 (1H, d) MS: m/z 313 (MH+)

tert-Butyl 4-(5-formylthien-2-yl)piperazine-1-carboxylate, used as starting material was prepared as follows:

A mixture of 5-bromothiophene-2-carboxaldehyde (3.82 g, 20.0 mmol), tert-butyl piperazine-1-carboxylate (4.1 g, 22.0 mmol), N-ethyl-N,N-diisopropylamine (7.0 ml, 40.0 mmol) and dimethylsulphoxide (5.0 ml) were stirred at 130° C. under an atmosphere of nitrogen for 18 h. The cooled mixture was partitioned between ethyl acetate and water. The organics were washed with water, brine, dried over magnesium sulphate and evaporated. The resultant dark red solid was purified by silica column chromatography, eluting with dichloromethane followed by ethyl acetate/dichloromethane (15%) to give tert-butyl 4-(5-formylthien-2-yl)piperazine-1-carboxylate (4.3 g, 73%).

1H NMR (399.9 MHz, DMSO-$d_6$) δ 1.41 (9H, s), 3.34 (4H, m), 3.47 (4H, m), 6.36 (1H, d), 7.70 (1H, d), 9.49 (1H, s) MS: m/z 297 (MH+)

Example 61

Methyl 6-[[5-[2-(3-methoxyphenyl)ethyl]-2H-pyrazol-3-yl]carbamoyl]pyridine-3-carboxylate 5-Methoxycarbonylpyridine-2-carboxylic acid (0.285 g, 1.58 mmol) was added to DCM (40 ml), to this was added oxayl chloride (0.165 ml, 1.90 mmol) and a few drops of anhydrous DMF. The reaction mixture was stirred for 30 mins before the addition of tert-butyl 5-amino-3-[2-(3-methoxyphenyl)ethyl]pyrazole-1-carboxylate (0.50 g, 1.58 mmol) and pyridine (2.0 ml). The reaction was stirred overnight. The reaction was evaporated to dryness to give yield to a gum. To this gum was added formic acid. The reaction mixture was stirred for 1 h before being evaporated to dryness. The resulting gum was quenched with saturated potassium carbonate (30 ml), extracted with DCM (3×50 ml), dried (MgSO$_4$) and the solvent removed in vacuo to yield a viscous gum. Trituration with acetonitrile gave the desired product as a slightly yellow solid (24 mg, 4%); $^1$H NMR (400.132 MHz, DMSO) δ 2.92 (s, 4H), 3.74 (s, 3H), 3.95 (s, 3H), 6.50 (s, 1H), 6.76 (d, 1H), 6.83-6.82 (m, 2H), 7.20 (t, 1H), 8.26 (d, 1H), 8.53 (d, 1H), 9.17 (s, 1H), 10.38 (s, 1H), 12.31 (s, 1H); MH+381.

Mean of n=2, FGFR Kinase assay—Caliper, $IC_{50}$ 68 μM.

tert-butyl 5-amino-3-[2-(3-methoxyphenyl)ethyl]pyrazole-1-carboxylate, used as starting material was prepared as in Example 23.

4-(4-Methylpiperazin-1-yl)benzoyl chloride, used as starting material was prepared as follows:

To a suspension of 4-(4-methylpiperazin-1-yl)benzoic acid (500 mg, 2.27 mmol, 1 eq) in DCM (20 ml) was added DMF (1 drop) followed by oxalyl chloride (219 μl, 2.50 mmol, 1.1 eq) added dropwise. The mixture was allowed to stir for 18 hours after which time the mixture was concentrated to dryness and taken through to the next stage with no further purification or characterisation.

Example 62

6-Chloro-N-[5-[2-(3-methoxyphenyl)ethyl]-2H-pyrazol-3-yl]pyridine-3-carboxamide

6-Bromopyridine-3-carboxylic acid (122 mg, 0.82 mmol, 1.3 eq) was dissolved in DCM (5 mL) and oxalyl chloride (72 μL, 0.82 mmol, 1.3 eq) was added dropwise followed by a drop of DMF. The reaction was stirred for 1 h at ambient temperature, then N,N-diethylethanamine (1 mL, 1.89 mmol, 3 eq) was added followed by tert-butyl 5-amino-3-[2-(3-methoxyphenyl)ethyl]pyrazole-1-carboxylate (200 mg, 0.63 mmol, 1 eq). The reaction was stirred for 2 h, then diluted with DCM and washed with water, brine, dried ($MgSO_4$), filtered and evaporated to give the crude Boc-protected compound as a yellow gum. The gum was dissolved in 2-propanol (5 mL) and a solution of 6M HCl in 2-propanol (4 mL) was added. The solution was stirred at ambient temperature overnight and was then evaporated to dryness and loaded onto a SCX-2 column. The column was washed with methanol and the product eluted with 2N ammonia in methanol to give an orange solid. Trituration with a small volume of methanol gave 6-chloro-N-[5-[2-(3-methoxyphenyl)ethyl]-2H-pyrazol-3-yl]pyridine-3-carboxamide (39 mg, 17%) as a white solid; $^1$H NMR (400.13 MHz, DMSO) δ 2.89 (4H, s), 3.74 (3H, s), 6.46 (1H, s), 6.75 (1H, m), 6.81 (2H, m), 7.20 (1H, t), 7.65 (1H, d), 8.35 (1H, m), 8.95 (1H, d), 10.99 (1H, s), 12.23 (1H, s) MS m/z 357 (MH+)

Mean of n=1, FGFR Kinase assay—Caliper, $IC_{50}$ 4.54 μM.

tert-Butyl 5-amino-3-[2-(3-methoxyphenyl)ethyl]pyrazole-1-carboxylate used as starting material was prepared as outlined in Example 23.

Example 63

6-Cyano-N-[5-[2-(3-methoxyphenyl)ethyl]-2H-pyrazol-3-yl]pyridine-3-carboxamide

Preparation was analogous to that described for Example 62, except using 6-cyanopyridine-3-carboxylic acid (122 mg, 0.82 mmol, 1.3 eq) as starting material. After purification by SCX column, the material was further purified by reverse-phase prep. HPLC (basic) using a 30-50% gradient of acetonitrile in water containing 1% ammonium hydroxide solution. The clean fractions were taken and evaporated to afford the title compound as a cream solid. (58 mg, 27% yield); $^1$H NMR (400.13 MHz, DMSO) δ 2.9 (4H, s), 3.74 (3H, s), 6.48 (1H, s), 6.75 (1H, m), 6.8 (2H, m), 7.2 (1H, t), 8.15 (1H, d), 8.52 (1H, m), 9.22 (1H, d), 11.19 (1H, s), 12.26 (1H, s) MS m/z 348 (MH+)

Mean of n=2, FGFR Kinase assay—Caliper, $IC_{50}$ 3.77 μM.

Example 64

4-Hydroxy-N-[5-[2-(3-methoxyphenyl)ethyl]-2H-pyrazol-3-yl]pyridine-2-carboxamide Preparation was analogous to that described for Example 62, except using 4-hydroxypyridine-2-carboxylic acid (114 mg, 0.82 mmol, 1.3 eq) as starting material. After purification by SCX column, the material was further purified by reverse-phase prep. HPLC (basic) using a 30-50% gradient of acetonitrile in water containing 1% ammonium hydroxide solution. The clean fractions were taken and evaporated to afford the title compound as a white solid (10 mg, 5% yield); $^1$H NMR (400.13 MHz, DMSO) δ 2.9 (4H, s), 3.73 (3H, s), 6.47 (1H, s), 6.75 (1H, m), 6.8 (2H, m), 6.92 (1H, s), 7.19 (1H, t), 7.47 (1H, s), 8.32 (1H, s), 10.2 (1H, s), 12.21 (1H, s) MS m/z 339 (MH+)

Mean of n=2, FGFR Kinase assay—Caliper, $IC_{50}$ 5 μM.

Example 65

N-[5-[2-(3-Methoxyphenyl)ethyl]-2H-pyrazol-3-yl]-6-(2-pyrrolidin-1-ylethyl)pyridine-3-carboxamide Preparation was analogous to that described for Example 62, except using 6-(2-pyrrolidin-1-ylethyl)pyridine-3-carboxylic acid (180 mg, 0.82 mmol, 1.3 eq) as starting material. After purification by SCX column, the material was further purified by reverse-phase prep. HPLC (basic) using a 30-50% gradient of acetonitrile in water containing 1% ammonium hydroxide solution. The clean fractions were taken and evaporated to afford the title compound as a white solid (5 mg, 2% yield); $^1$H NMR (400.13 MHz, DMSO) δ 1.66 (4H, m), 2.77 (2H, t), 2.89 (4H, s), 2.94 (2H, t), 3.27 (4H, m), 3.73 (3H, s), 6.46 (1H, s), 6.75 (1H, m), 6.82 (1H, m), 7.19 (1H, t), 7.40 (1H, d), 8.21 (1H, m), 9.01 (1H, d), 10.79 (1H, s), 12.17 (1H, s) MS m/z 420 (MH+)

Mean of n=1, FGFR Kinase assay—Caliper, $IC_{50}$ 0.24 μM.

Example 66

5-[[5-[2-(3-Methoxyphenyl)ethyl]-2H-pyrazol-3-yl]carbamoyl]pyridine-2-carboxylic acid Preparation was analogous to that described for Example 62, except using 6-methoxycarbonylpyridine-3-carboxylic acid (149 mg, 0.82 mmol, 1.3 eq) as starting material. After purification by SCX column, the material was further purified by reverse-phase prep. HPLC (basic) using a 30-50% gradient of acetonitrile in water containing 1% ammonium hydroxide solution. During this purification the ester hydrolysed to the acid product. The clean fractions were taken and evaporated to afford the title compound as a white solid (66 mg, 40% yield); $^1$H NMR (400.13 MHz, DMSO) δ 2.90 (4H, s), 3.74 (3H, s), 6.46 (1H, s), 6.75 (1H, m), 6.83 (2H, m), 7.19 (1H, t), 8.01 (1H, d), 9.12 (1H, d), 11.01 (1H, s), 12.2 (1H, s) MS m/z 367 (MH+)

Mean of n=1, FGFR Kinase assay—Caliper, $IC_{50}$ 1.02 μM.

Example 67

Methyl 5-[[5-[2-(3-methoxyphenyl)ethyl]-2H-pyrazol-3-yl]carbamoyl]pyridine-2-carboxylate To a stirred suspension of 5-[[5-[2-(3-methoxyphenyl)ethyl]-2H-pyrazol-3-yl]carbamoyl]pyridine-2-carboxylic acid (55 mg, 0.15 mmol, 1 eq) in methanol (0.5 mL) was added thionyl chloride (23 uL, 0.32 mmol, 2.1 eq) dropwise. The resulting solution was heated at 50° C. for 3 h. The mixture was concentrated in vacuo to yield an orange solid. This was dissolved in DCM and washed with saturated aqueous sodium hydrogen carbonate and brine. The organic layers were dried over magnesium sulphate, filtered and concentrated to give the crude product as a yellow solid. Trituration with diethyl ether gave the title compound as a white solid 27 mg (47%); $^1$H NMR (400.13 MHz, DMSO) δ 2.92 (4H, s), 3.74 (3H, s), 3.92 (3H, s), 6.49 (1H, s), 6.25 (1H, m), 6.82 (2H, m), 7.19 (1H, t), 8.14 (1H, d), 8.46 (1H, m), 9.20 (1H, d), 11.11 (1H, s), 12.25 (1H, s) MS m/z 381 (MH+)

Mean of n=2, FGFR Kinase assay—Caliper, $IC_{50}$ 2.86 μM.

5-[[5-[2-(3-Methoxyphenyl)ethyl]-2H-pyrazol-3-yl]carbamoyl]pyridine-2-carboxylic acid used as starting material was prepared as outlined in Example 66.

Example 68

Ethyl 5-[[5-[2-(3-methoxyphenyl)ethyl]-2H-pyrazol-3-yl]carbamoyl]pyridine-2-carboxylate Preparation was analogous to that described for Example 67, except using 5-[[5-[2-(3-methoxyphenyl)ethyl]-2H-pyrazol-3-yl]carbamoyl]pyridine-2-carboxylic acid (55 mg, 0.15 mmol, 1 eq) in ethanol (0.5 mL) to give title compound as a white solid (9 mg, 15% yield); $^1$H NMR (400.13 MHz, DMSO) δ 1.40 (3H, t), 2.97 (4H, s), 3.79 (3H, s), 4.44 (2H, q), 6.54 (1H, s), 6.8 (1H, m), 6.87 (2H, m), 7.25 (1H, t), 8.19 (1H, d), 8.52 (1H, m), 9.25 (1H, s), 11.17 (1H, s), 12.3 (1H, s) MS m/z 395 (MH+)

Mean of n=1, FGFR Kinase assay—Caliper, $IC_{50}$ 0.724 μM.

5-[[5-[2-(3-Methoxyphenyl)ethyl]-2H-pyrazol-3-yl]carbamoyl]pyridine-2-carboxylic acid used as starting material was prepared as outlined in Example 66.

Example 69

N-[5-[(3,5-Dimethoxyphenyl)methoxy]-2H-pyrazol-3-yl]-5-(4-methylpiperazin-1-yl)pyridine-2-carboxamide NaHMDS (1M solution in THF, 0.45 ml, 0.451 mmol, 1.5 eq) was added dropwise to a stirred suspension of tert-butyl 5-amino-3-[(3,5-dimethoxyphenyl)methoxy]pyrazole-1-carboxylate (105 mg, 0.301 mmol, 1 eq) and methyl 5-(4-methylpiperazin-1-yl)pyridine-2-carboxylate (85 mg, 0.361 mmol, 1.2 eq) in dry THF (2.5 ml) under nitrogen. The solution was stirred at room temperature for 1 h. The solution was neutralised with satd. aq. NH$_4$Cl and diluted with water (5 ml). The aqueous phase was extracted with ethyl acetate (3×8 ml) and the combined organic extracts were dried over MgSO$_4$, filtered and evaporated. The reaction was repeated as above on a 0.338 mmol scale. The crude extracts were combined with those above and purified on by silica column chromatography, eluting with 0-6% MeOH in DCM, to afford the title compound as a pale brown solid (92 mg, 35% yield); $^1$H NMR (399.902 MHz, DMSO) δ 2.25 (s, 3H), 2.45-2.50 (m, 4H), 3.37-3.43 (m, 4H), 3.75 (s, 6H), 5.08 (s, 2H), 5.88 (bs, 1H), 6.45 (t, 1H), 6.60 (d, 2H), 7.45-7.49 (m, 1H), 7.94 (d, 1H), 8.35 (d, 1H), 10.89 (bs, 1H), 11.36 (bs, 1H) MS: m/z 453 (MH+)

Mean of n=1, FGFR Kinase assay—Caliper, $IC_{50}$ 0.122 μM.

5-(4-Methylpiperazin-1-yl)pyridine-2-carboxylate, used as starting material was prepared as follows:

Methyl 5-bromo 2-carboxylate (250 mg, 1.16 mmol, 1 eq), potassium phosphate (334 mg, 1.62 mmol, 1.4 eq), S-Phos (96 mg, 0.231 mmol, 0.2 eq) and Pd$_2$dba$_3$ (13 mg, 0.058 mmol, 0.05 eq) were stirred in toluene (5 ml) under nitrogen. N-Methylpiperazine (155 μl, 1.39 mmol, 1.2 eq) was added and the mixture was stirred at 100° C. for 48 h, then allowed to cool to room temperature and stirred for a further 48 h. The reaction mixture was poured onto a SCX column and washed through with MeOH, then with 2M NH$_3$ in MeOH to elute the product. Product fractions were evaporated to afford 5-(4-methylpiperazin-1-yl)pyridine-2-carboxylate as an orange oil which crystallized on standing (194 mg, 72% yield).

$^1$H NMR (399.902 MHz, DMSO) δ 2.24 (s, 3H), 2.43-2.48 (m, 4H), 3.35-3.40 (m, 4H), 3.81 (s, 3H), 7.32-7.37 (m, 1H), 7.88 (d, 1H), 8.38 (d, 1H). MS: m/z 236 (MH+)

tert-Butyl 5-amino-3-[(3,5-dimethoxyphenyl)methoxy]pyrazole-1-carboxylate, used as a starting material was prepared as outlined in Example 70.

Example 70

N-[5-[(3,5-Dimethoxyphenyl)methoxy]-2H-pyrazol-3-yl]-4-(2-dimethylaminoethylamino)benzamide hydrochloride tert-butyl 5-amino-3-[(3,5-dimethoxyphenyl)methoxy]pyrazole-1-carboxylate (150 mg, 0.429 mmol) and methyl 4-[2-dimethylaminoethyl-[tert-butoxycarbonyl]amino]benzoate (166 mg, 0.515 mmol) were dissolved in dry THF (2.5 ml). NaHMDS (1 M in THF, 0.645 ml) was added dropwise under nitrogen and the mixture was stirred for 1 h at room temperature. The mixture was neutralised with NH$_4$Cl (aq), diluted with water and extracted with ethyl acetate. The extracts were combined, dried and evaporated. The crude product was purified by silica column chromatography, eluting with a gradient of 0-8% MeOH in DCM. Pure fractions were combined and evaporated to give a brown oil (74 mg). The oil was dissolved in THF (10 ml) and 4 M HCl in dioxane (2 ml) was added. The reaction mixture was stirred at room temperature for 18 h. The solid was collected by filtration, washed (hexane) and dried to give N-[5-[(3,5-dimethoxyphenyl)methoxy]-2H-pyrazol-3-yl]-4-(2-dimethylaminoethylamino)benzamide hydrochloride (38.6 mg, 20% overall yield) as a white solid; $^1$H NMR (399.902 MHz, DMSO) δ 2.84 (d, J=4.0 Hz, 6H), 3.25 (m, 2H), 3.75 (s, 6H), 5.08 (s, 2H), 5.67 (s, 1H), 6.45 (t, J=2.2 Hz, 1H), 6.60 (d, J=2.2 Hz, 2H), 6.72 (d, J=8.8 Hz, 2H), 7.83 (d, J=8.8 Hz, 2H), 9.85 (s, 1H), 10.53 (s, 1H). MS: m/z=440 (MH+)

Mean of n=1, FGFR Kinase assay—Caliper, $IC_{50}$ 0.031 μM.

tert-butyl 5-amino-3-[(3,5-dimethoxyphenyl)methoxy]pyrazole-1-carboxylate, used as starting material, was prepared as follows:

Potassium hydroxide (11.19 g, 199.4 mmol) dissolved in water (44.8 ml) was added to a solution of 5-[(3,5-dimethoxyphenyl)methoxy]-2H-pyrazol-3-amine (7.121 g) dissolved in dichloromethane (40 ml). (2-Methylpropan-2-yl)oxycarbonyl tert-butyl carbonate (6.8 g, 31.2 mmol) dissolved in DCM (35 ml) was added and the reaction mixture was stirred vigorously at room temperature for 4 h. The reaction mixture was separated and the organic layer was washed with water (2×15 ml), brine (2×15 ml), dried over sodium sulphate, filtered, evaporated and dried in vacuo to give tert-butyl 5-amino-3-[(3,5-dimethoxyphenyl)methoxy]pyrazole-1-carboxylate (8.70 g, 99%) as a cream solid.

$^1$H NMR (399.902 MHz, DMSO) δ 1.55 (s, 9H), 3.75 (s, 6H), 4.93 (s, 1H), 5.06 (s, 2H), 6.38 (s, 2H), 6.45 (t, J=2.2 Hz, 1H), 6.60 (d, J=2.3 Hz, 2H). MS: m/z=350 (MH+)

Methyl 4-[2-dimethylaminoethyl-[tert-butoxycarbonyl]amino]benzoate, used as starting material, was prepared as follows:

Methyl 4-(2-[dimethylamino]ethylamino)benzoate (1.00 g, 4.50 mmol) was dissolved in THF (30 ml). (2-Methylpropan-2-yl)oxycarbonyl tert-butyl carbonate (1.035 g, 4.72 mmol) was added and the solution was refluxed for 3 h. The solvent was then evaporated, the residue was dissolved in DCM, washed with sat. aq. ammonium chloride solution, dried over sodium sulphate, filtered and evaporated to give methyl 4-[2-dimethylaminoethyl-[tert-butoxycarbonyl]amino]benzoate (1.07 g, 74%) as a brown oil.

$^1$H NMR (399.902 MHz, DMSO) δ 1.41 (s, 9H), 2.13 (s, 6H), 2.34 (t, J=6.9 Hz, 2H), 3.73 (t, J=6.8 Hz, 2H), 3.86 (s, 3H), 7.43 (d, J=8.5 Hz, 2H), 7.94 (d, J=8.5 Hz, 2H). MS: m/z=323 (MH+)

Methyl 4-(2-[dimethylamino]ethylamino)benzoate, used as starting material, was prepared as follows:

Methyl 4-iodobenzoate (1.19 g, 4.54 mmol, 1.0 eq) was dissolved in dry dimethylformamide (10 ml). N,N-dimethylethane-1,2-diamine (400 mg, 4.54 mmol, 1.0 eq), caesium carbonate (2.69 g, 9.08 mmol, 2.0 eq), 2-acetylcyclohexanone (120 μl, 0.908 mmol, 0.20 eq [20 mol %]) and copper (I) iodide (44 mg, 0.227 mmol, 0.05 eq [5 mol %]) were added and the mixture was stirred under nitrogen at 90° C. for 18 h. The reaction mixture was concentrated, dissolved in methanol and absorbed onto a SCX-2 cation exchange resin column. The column was washed with methanol and the product was eluted with 2M ammonia in methanol. Fractions were evaporated to give methyl 4-(2-[dimethylamino]ethylamino)benzoate (1.00 g, 99%) as a brown gum.

$^1$H NMR (399.902 MHz, DMSO) δ 2.19 (s, 6H), 2.44 (t, J=6.3 Hz, 5H), 3.17 (m, 2H), 3.75 (s, 3H), 6.33 (t, J=5.3 Hz, 1H), 6.62 (d, J=8.9 Hz, 2H), 7.69 (d, J=8.7 Hz, 2H). MS: m/z=223 (MH+)

Example 71

N-[5-[(3,5-Dimethoxyphenyl)methoxy]-2H-pyrazol-3-yl]-4-methoxy-benzamide

4-Methoxybenzoyl chloride (54 mg, 0.315 mmol, 1.1 eq) in THF (2 ml) was added dropwise to a solution of tert-butyl 5-amino-3-[(3,5-dimethoxyphenyl)methoxy]pyrazole-1-carboxylate (100 mg, 0.286 mmol, 1 eq) in THF (3 ml) under nitrogen and the solution was heated at reflux for a total of 14 h, then stirred at room temperature for 16 h. The solvent was evaporated and the residue was purified by prep. HPLC, using a gradient of 55-75% MeCN in H$_2$O (containing 1% ammonium hydroxide). The product fractions were evaporated to dryness and taken up in DCM (4 ml). 4M HCl in dioxane (1 ml) was added and the mixture stirred at room temperature for 1 h, then evaporated to dryness. The residue was partitioned between ethyl acetate (6 ml) and aqueous NaHCO$_3$ (6 ml), the layers were separated and the aqueous layer was re-extracted with ethyl acetate (3×6 ml). The combined organic extracts were dried over Na$_2$SO$_4$, filtered and evaporated to afford the title compound as an off-white solid (22 mg, 20% yield); $^1$H NMR (400.132 MHz, DMSO) δ 3.74 (s, 6H), 3.82 (s, 3H), 5.06 (s, 2H), 5.59 (s, 1H), 6.43 (t, 1H), 6.59 (d, 2H), 7.00 (d, 2H), 7.96 (d, 2H) MS: m/z 384 (MH+)

Mean of n=1, FGFR Kinase assay—Caliper, IC$_{50}$ 0.157 μM.

tert-Butyl 5-amino-3-[(3,5-dimethoxyphenyl)methoxy]pyrazole-1-carboxylate, used as a starting material was prepared as outlined in Example 70.

Example 72

N-[5-[(3,5-Dimethoxyphenyl)methoxy]-2H-pyrazol-3-yl]-6-piperazin-1-yl-pyridine-3-carboxamide

6-[4-[(2-Methylpropan-2-yl)oxycarbonyl]piperazin-1-yl]pyridine-3-carboxylic acid (150 mg, 0.412 mmol) was dissolved in dry THF (10 ml), 1-chloro-N,N,2-trimethyl-prop-1-en-1-amine (65 μl, 0.412 mmol) was added and the mixture was stirred at room temperature under nitrogen overnight. Pyridine (40 μl, 0.412 mmol) and tert-butyl 5-amino-3-[(3,5-dimethoxyphenyl)methoxy]pyrazole-1-carboxylate (142 mg, 0.343 mmol) were added and the mixture was stirred at 65° C. for 18 h. The mixture was then cooled to room temperature and stirred overnight with 4 M HCl in dioxane (1.8 ml, 7.20 mmol). The mixture was then filtered and the solid was washed with hexane. The product was purified on acidic prep. HPLC, eluting with a gradient of 16-26% MeCN in water (containing 0.1% TFA). The product containing fractions were neutralised with aq. NaHCO$_3$ and the acetonitrile removed under vacuum. The product precipitated out and was collected by filtration. This was further washed with water and dried in vacuo to give the title compound (39 mg, 26%) as a white solid; $^1$H NMR (399.902 MHz, DMSO) δ 2.82 (t, J=5.1 Hz, 4H), 3.61 (t, J=4.8 Hz, 4H), 3.80 (s, 6H), 5.13 (s, 2H), 5.62 (bs, 1H), 6.50 (s, 1H), 6.65 (d, J=2.2 Hz, 2H), 6.92 (d, J=8.9 Hz, 1H), 8.09 (d, J=9.3 Hz, 1H), 8.76 (d, J=2.3 Hz, 1H), 10.74 (bs, 1H), 11.64 (bs, 1H). MS: m/z=439 (MH+)

Mean of n=1, FGFR Kinase assay—Caliper, IC$_{50}$ 0.025 μM.

tert-Butyl 5-amino-3-[(3,5-dimethoxyphenyl)methoxy]pyrazole-1-carboxylate, used as starting material, was prepared as follows:

Potassium hydroxide (11.19 g, 199.4 mmol) dissolved in water (44.8 ml) was added to a solution of 5-[(3,5-dimethoxyphenyl)methoxy]-2H-pyrazol-3-amine (7.121 g) dissolved in dichloromethane (40 ml). A solution of (2-methylpropan-2-yl)oxycarbonyl tert-butyl carbonate (6.8 g, 31.2 mmol) in DCM (35 ml) was added and the reaction mixture was stirred vigorously at room temperature for 4 h. The reaction mixture was separated and the organic layer was washed with water (2×15 ml) and brine (2×15 ml), dried over sodium sulphate, filtered, evaporated and dried in vacuo to give tert-butyl 5-amino-3-[(3,5-dimethoxyphenyl)methoxy]pyrazole-1-carboxylate (8.70 g, 99%) as a cream solid.

$^1$H NMR (399.902 MHz, DMSO) δ 1.55 (s, 9H), 3.75 (s, 6H), 4.93 (s, 1H), 5.06 (s, 2H), 6.38 (s, 2H), 6.45 (t, J=2.2 Hz, 1H), 6.60 (d, J=2.3 Hz, 2H). MS: m/z=350 (MH+)

Example 73

N-[5-[(3,5-Dimethoxyphenyl)methoxy]-1H-pyrazol-3-yl]-2-(4-methylpiperazin-1-yl)pyrimidine-5-carboxamide

NaHMDS (1M solution in THF, 0.39 ml, 0.386 mmol, 1.5 eq) was added dropwise to a stirred solution of tert-butyl 5-amino-3-[(3,5-dimethoxyphenyl)methoxy]pyrazole-1-carboxylate (90 mg, 0.258 mmol, 1 eq) and methyl 2-(4-methylpiperazin-1-yl)pyrimidine-5-carboxylate (74 mg, 0.309 mmol, 1.2 eq) in dry THF (5 ml) under nitrogen. The solution was stirred at room is temperature for 1 h, then neutralised with satd. aq. NH$_4$Cl, diluted with water (15 ml) and extracted with ethyl acetate (3×15 ml). The combined organic extracts were dried over MgSO$_4$, filtered and evaporated to give an orange gum. The gum was purified by silica column chromatography, eluting with a gradient of 0-2.5% MeOH in DCM. The crude material, containing starting methyl 2-(4-methylpiperazin-1-yl)pyrimidine-5-carboxylate, was re-dissolved in THF (5 ml) under nitrogen. tert-Butyl 5-amino-3-[(3,5-dimethoxyphenyl)methoxy]pyrazole-1-carboxylate (50 mg, 0.143 mmol) was added followed by dropwise addition of NaHMDS (1M solution in THF, 0.32 ml, 0.32 mmol). The solution was stirred at room temperature for 45 mins, neutralised with satd. aq. NH$_4$Cl, diluted with water (10 ml) and extracted with ethyl acetate (3×10 ml). The combined organic extracts were dried over MgSO$_4$, filtered and evaporated. The gummy residue was purified by silica column chromatography, eluting with a gradient of 0-8% MeOH in DCM, to afford the title compound as a pale brown solid (16 mg, 14% yield); $^1$H NMR (399.9 MHz, DMSO-d$_6$+ d4-AcOD) δ 2.42 (3H, s), 2.67-2.70 (4H, m), 3.75 (6H, s), 3.91-3.94 (4H, m), 5.08 (2H, s), 5.75 (1H, s), 6.45 (1H, t), 6.59 (2H, d), 8.90 (2H, s). MS: m/z 454 (MH+)

Mean of n=1, FGFR Kinase assay—Caliper, IC$_{50}$ 0.044 μM.

tert-Butyl 5-amino-3-[(3,5-dimethoxyphenyl)methoxy]pyrazole-1-carboxylate, used as a starting material was prepared as outlined in Example 70.

Methyl 2-(4-methylpiperazin-1-yl)pyrimidine-5-carboxylate, used as starting material was prepared as follows:

2-Chloropyrimidine 5-carboxylic acid (100 mg, 0.631 mmol, 1 eq) was suspended in a mixture of toluene (3 ml) and methanol (0.8 ml) under nitrogen and cooled in an ice-bath. Trimethylsilyldiazomethane (2M solution in hexanes, 0.347 ml, 0.694 mmol, 1.1 eq) was added dropwise. The solution was stirred at 0° C. for 10 min, then allowed to warm to room temperature and stirred for a further 1 h. 1-Methylpiperazine (70 μl, 0.631 mmol, 1 eq) and triethylamine (88 μl, 0.631 mmol, 1 eq) were added dropwise and stirring continued at room temperature for 2 h. The solvent was evaporated and the residue was taken up in ethyl acetate (20 ml) and water (15 ml). The layers were separated and the aqueous extracted with further portions of ethyl acetate (2×10 ml). The combined extracts were dried over MgSO$_4$, filtered and evaporated. The reaction was repeated as above and the extracts combined with those above to afford methyl 2-(4-methylpiperazin-1-yl)pyrimidine-5-carboxylate as a gummy yellow solid (76 mg, 25% yield).

$^1$H NMR (399.902 MHz, DMSO) δ 2.12 (s, 3H), 2.27 (t, 4H), 3.70 (s, 3H), 3.75 (t, 4H), 8.68 (s, 2H). MS: m/z 237 (MH+)

Example 74

N-[5-[(3,5-Dimethoxyphenyl)methoxy]-1H-pyrazol-3-yl]-3-piperazin-1-yl-benzamide 1-Chloro-N,N-2-trimethyl-1-propenylamine (78 μl, 0.588 mmol, 1.2 eq) was added dropwise to a stirred solution of 3-[4-(tert-butoxycarbonyl)piperazin-1-yl]benzoic acid (150 mg, 0.588 mmol, 1.2 eq) in THF (10 ml) under nitrogen. The mixture was stirred at room temperature overnight. tert-Butyl 5-amino-3-[(3,5-dimethoxyphenyl)methoxy]pyrazole-1-carboxylate (172 mg, 0.490 mmol, 1 eq) and pyridine (48 μl, 0.588 mol, 1.2 eq) were added and the mixture was heated at 65° C. overnight. The mixture was allowed to cool to room temperature and 4M HCl in dioxane (2 ml) was added. Stirring was continued at room temperature overnight. The precipitated yellow solid was collected by filtration and washed with THF. The solid was triturated with aq NaHCO$_3$ (4 ml) and DCM (2 ml). A small amount of a brown gum remained out of solution. The gum was collected by filtration and washed with water and ether. The aqueous filtrate was extracted with ethyl acetate (3×10 ml) and the combined extracts were dried over MgSO$_4$, filtered and evaporated. The extracted product was combined with the gum from filtration and purified by silica column chromatography, eluting with a gradient of 10-12% MeOH in DCM. Product fractions were evaporated to give the title compound as a white solid (27 mg, 10% yield); $^1$H NMR (399.902 MHz, DMSO+d4-AcOD) δ 3.13-3.21 (m, 4H), 3.33-3.40 (m, 4H), 3.68 (s, 6H), 5.02 (s, 2H), 5.71 (s, 1H), 6.38 (t, 1H), 6.52 (d, 2H), 7.12-7.17 (m, 1H), 7.33 (t, 1H), 7.37-7.41 (m, 1H), 7.46-7.49 (m, 1H). MS: m/z 438 (MH+)

Mean of n=1, FGFR Kinase assay—Caliper, IC$_{50}$ 0.130 μM.

Example 75

4-(1,4-Diazepan-1-yl)-N-[5-[(3,5-dimethoxyphenyl)methoxy]-1H-pyrazol-3-yl]benzamide hydrochloride tert-Butyl 5-amino-3-[(3,5-dimethoxyphenyl)methoxy]pyrazole-1-carboxylate (176 mg, 0.50 mmol) and tert-butyl 4-(4-methoxycarbonylphenyl)-1,4-diazepane-1-carboxylate (168 mg, 0.60 mmol) were dissolved in dry THF (5 ml). NaHMDS (1 M in THF, 0.754 ml) was added dropwise under nitrogen and the mixture was stirred for 1 h at room temperature. A further amount of NaHMDS (1M in THF, 0.754 ml) was added and the reaction mixture was stirred under nitrogen for 30 mins. The reaction mixture was neutralised with saturated NH$_4$Cl (aq), diluted with water (20 ml) and extracted with ethyl acetate (3×30 ml). The extracts were combined, dried over MgSO$_4$, filtered and evaporated. The residue was purified by silica column chromatography, eluting with 0-3% MeOH in DCM. The fractions were evaporated to give a brown oil (51 mg) which was repurified by silica column chromatography, eluting with 0-1% MeOH in DCM. The pure fractions were combined, evaporated and the residue was dissolved in THF (10 ml). 4M HCl in dioxan (1.5 ml, 1.5 mmol) was added and the solution was stirred at room temperature overnight. The precipitate was collected by filtration, washed with hexane and dried in vacuo to give the title compound (18.7 mg, 6.5%) as a white solid; $^1$H NMR (399.902 MHz, DMSO) δ 2.01 (m, 2H), 3.08 (m, 2H), 3.20 (m, 2H), 3.53 (m, 2H), 3.68 (s, 6H), 3.72 (t, J=5.2 Hz, 2H), 5.01 (s, 2H), 5.60 (s, 1H), 6.38 (t, J=2.4 Hz, 1H), 6.52 (d, J=2.3 Hz, 2H), 6.81 (d, J=9.2 Hz, 2H), 7.82 (d, J=8.9 Hz, 2H), 8.69 (s, 1H), 10.49 (s, 1H). MS: m/z=452 (MH+)

Mean of n=2, FGFR Kinase assay—Caliper, IC$_{50}$ 0.0085 μM.

tert-Butyl 4-(4-methoxycarbonylphenyl)-1,4-diazepane-1-carboxylate used as starting material was prepared as follows:

Methyl 4-iodobenzoate (1.00 g, 3.82 mmol, 1.0 eq) was dissolved in DMF and tert-butyl 1,4-diazepane-1-carboxylate (765 mg, 3.82 mmol, 1.0 eq), caesium carbonate (2.49 g, 7.63 mmol, 2.0 eq), 2-acetylcyclohexanone (101 μl, 0.76 mmol, 0.20 eq [20 mol %]) and copper iodide (37 mg, 0.19 mmol, 0.05 eq [5 mol %]) were added. The reaction mixture was stirred at 90° C. under nitrogen for 7 h. The reaction mixture was evaporated, dissolved in DCM (50 ml), washed with water (20 ml), saturated ammonium chloride solution (20 ml), dried over MgSO$_4$, filtered and evaporated. The crude product was purified by silica column chromatography, eluting with 0-1% MeOH in DCM. The product containing fractions were combined, evaporated and dried in vacuo to give tert-butyl 4-(4-methoxycarbonylphenyl)-1,4-diazepane-1-carboxylate (168 mg, 13%) as a yellow oil.

$^1$H NMR (399.902 MHz, DMSO) δ 1.12 (s, 5H), 1.24 (s, 4H), 1.72 (m, 2H), 3.12 (m, 1H), 3.42 (m, 1H), 3.49 (m, 3H), 3.59 (m, 2H), 3.69 (s, 3H), 6.72 (d, J=9.1 Hz, 2H), 7.67 (d, J=9.0 Hz, 2H) MS: m/z=335 (MH+)

tert-Butyl 5-amino-3-[(3,5-dimethoxyphenyl)methoxy]pyrazole-1-carboxylate was prepared as follows:

Potassium hydroxide (11.19 g, 199.4 mmol) dissolved in water (44.8 ml) was added to a solution of 5-[(3,5-dimethoxyphenyl)methoxy]-2H-pyrazol-3-amine (7.121 g) dissolved in dichloromethane (40 ml). (2-Methylpropan-2-yl)oxycarbonyl tert-butyl carbonate (6.8 g, 31.2 mmol) dissolved in DCM (35 ml) was added and the reaction mixture was stirred vigorously at room temperature for 4 h. The reaction mixture was separated and the organic layer was washed with water (2×15 ml) and brine (2×15 ml), dried over sodium sulphate, filtered, evaporated and dried in vacuo to give tert-butyl 5-amino-3-[(3,5-dimethoxyphenyl)methoxy]pyrazole-1-carboxylate (8.70 g, 99%) as a cream solid.

$^1$H NMR (399.902 MHz, DMSO) δ 1.55 (s, 9H), 3.75 (s, 6H), 4.93 (s, 1H), 5.06 (s, 2H), 6.38 (s, 2H), 6.45 (t, J=2.2 Hz, 1H), 6.60 (d, J=2.3 Hz, 2H). MS: m/z=350 (MH+)

Example 76

N-[5-[2-[5-(Dimethylaminomethyl)-2-furyl]ethyl]-1H-pyrazol-3-yl]-4-(4-methylpiperazin-1-yl)benzamide A solution of potassium hydroxide (4.5M in water, 1.8 ml, 8.10 mmol, 8.10 eq) was added to a stirred solution of 5-(2-{5-[(dimethylamino)methyl]-2-furyl}ethyl)-1H-pyrazol-3-amine (235 mg, 1.0 mmol, 1.0 eq) in dichloromethane at room temperature. A solution of di-tert-butyl dicarbonate (230 mg, 1.05 mmol, 1.05 eq) in dichloromethane (2.0 ml) was then added and the reaction mixture stirred vigorously for 18 h. The reaction mixture was poured into a separating funnel and the layers were separated. The dichloromethane layer was washed with water (10 ml) and saturated brine (10 ml), dried over anhydrous sodium sulphate, filtered and the solvent removed in vacuo to afford tert-butyl 5-amino-3-(2-{5-[(dimethylamino)methyl]-2-furyl}ethyl)-1H-pyrazole-1-carboxylate as a golden oil, (320 mg).

A portion of this material was used without further purification as follows:

is A solution of sodium bis(trimethylsilyl)amide (1.0 M in tetrahydrofuran, 0.7 ml, 0.69 mmol, 1.50 eq) was added dropwise at room temperature to a stirred solution of tert-butyl 5-amino-3-(2-{5-[(dimethylamino)methyl]-2-furyl}ethyl)-1H-pyrazole-1-carboxylate (crude 154 mg, 0.46 mmol, 1.0 eq) and methyl 4-(4-methylpiperazin-1-yl)benzoate (130 mg, 0.55 mmol, 1.20 eq) in dry tetrahydrofuran (1.0 ml) under nitrogen. The mixture was allowed to stand at room temperature overnight and then the solvent was evaporated under reduced pressure to afford the crude product as a brown gum. This gum was dissolved in methanol (5 ml) and the solution was applied to a SCX-2 column. The column was washed through with methanol containing 10% water. The column was then eluted with 2.0M anhydrous ammonia in methanol. Fractions containing the product were combined and evaporated to give a brown gum, 235 mg. This material was further purified by silica column chromatography, eluting with a 3-10% gradient of methanol (containing ammonia at 2M) in dichloromethane. Pure product fractions were combined and evaporated to give a light brown gum, 32.9 mg. This material was further purified by reverse-phase prep. HPLC (basic) using a 30-50% gradient of acetonitrile in water containing 1% ammonium hydroxide solution. The clean fractions were taken and evaporated to afford the title compound as a solid. (8 mg, 4% yield); $^1$H NMR (500.13 MHz, DMSO-d6) δ 2.17 (6H, d), 2.26 (3H, s), 2.48 (4H, t), 2.88-2.96 (4H, m), 3.30 (4H, t), 3.39 (2H, s), 6.03 (1H, d), 6.12 (1H, d), 6.95 (2H, d), 7.88 (2H, d), 9.95 (1H, broad s), 11.80 (1H, broad s). MS: m/z 437 (MH+)

Mean of n=1, FGFR Kinase assay—Caliper, IC$_{50}$ 0.34 μM.

5-(2-{5-[(dimethylamino)methyl]-2-furyl}ethyl)-1H-pyrazol-3-amine, used as starting material was prepared as follows:

Acetonitrile (0.258 ml, 4.88 mmol) was added to a slurry of sodium hydride (196 mg dispersion in mineral oil, 4.88 mmol) in anhydrous dioxan (15 ml) and the mixture stirred at room temperature under an atmosphere of nitrogen for 5 mins. Ethyl 3-{5-[(dimethylamino)methyl]-2-furyl}propanoate (917 mg, 4.07 mmol) was then added and the reaction was refluxed for 18 h. The mixture was cooled to room temperature and ethanol (1.9 ml) added followed by hydrazine hydrochloride (558 mg, 8.14 mmol). The mixture was refluxed for 1 h. After cooling, the solvent was evaporated under reduced pressure. The residue was dissolved in dichloromethane containing 10% methanol (50 mL) and the insoluble impurities were filtered off. The filtrate was evaporated to give the crude product as a golden oil, 1.07 g. This material was purified by silica column chromatography, eluting with a 0-10% gradient of methanol (containing ammonia at 2M) in dichloromethane. Pure product fractions were combined and evaporated to give a clear oil. (520 mg, 55% yield); $^1$H NMR (399.9 MHz, DMSO-d6) δ2.16 (6H, s), 2.70-2.74 (2H, m), 2.81-2.85 (2H, m), 3.40 (2H, s), 5.20 (1H, s), 6.03 (1H, d), 6.15 (1H, d). MS: m/z 235 (MH+)

Ethyl 3-{5-[(dimethylamino)methyl]-2-furyl}propanoate, used as starting material was prepared as follows:

A mixture of ethyl 3-(2-furanyl)propionate (12.11 g, 72.0 mmol), dimethylammonium chloride (6.76 g, 82.8 mmol), 37% aqueous formaldehyde (6.43 g, 79.2 mmol) in acetic acid (75 ml) was stirred at room temperature until a solution formed. The solution was allowed to stand for 44 h. The mixture was evaporated to an oil. This was suspended in water and extracted with ethyl acetate (2×250 ml). The aqueous layer (containing the product) was basified to pH11 with 4M sodium hydroxide solution and then extracted into ethyl acetate (2×250 ml). These combined extracts were washed with brine, dried over magnesium sulphate and evaporated to give the crude product as a dark brown oil, 6.5 g. This material was purified by silica column chromatography, eluting with a 0-10% gradient of methanol (containing ammonia at 2M) in dichloromethane. Fractions containing the product were combined and evaporated to give a light brown oil (3.44 g). This material was purified by silica column chromatography, eluting with a 0-5% gradient of methanol (containing ammonia at 2M) in dichloromethane. Fractions containing the product were combined and evaporated to give a light brown oil (1.36 g, 8% yield).

1H NMR (399.9 MHz, CDCl3) δ 1.24 (3H, t), 2.29 (6H, s), 2.62-2.65 (2H, m), 2.95 (2H, t), 3.47 (2H, s), 4.11-4.15 (2H, m), 5.95 (1H, d), 6.11 (1H, d). MS: m/z 226 (MH+)

Example 77

N-[5-(2-Benzo[1,3]dioxol-5-ylethyl)-2H-pyrazol-3-yl]-4-(4-methylpiperazin-1-yl)benzamide To a stirred solution of tert-butyl 5-amino-3-(2-benzo[1,3]dioxol-5-ylethyl)pyrazole-1-carboxylate (229 mg, 0.69 mmol, 1.0 eq) in pyridine (5 ml) at 5° C. was added 4-(4-methylpiperazin-1-yl)benzoyl chloride (181 mg, 0.76 mmol, 1.1 eq). The reaction mixture was stirred to 60° C. for 24 h. After this time, the mixture was concentrated and redissolved in DCM (10 ml). Trifluoroacetic acid (464 μl, 6.25 mmol, 8.25 eq) was added and the reaction mixture stirred for 2 h at 25° C. The reaction mixture was then concentrated. The crude product was purified by reverse-phase prep. HPLC (basic)

using a 30-50% gradient of acetonitrile in water containing 1% ammonium hydroxide solution. The clean fractions were combined and evaporated to afford the title compound as a white solid. (12 mg, 4%); $^1$H NMR (300.132 MHz, DMSO) δ 2.28 (s, 3H), 2.49 (t, 2H), 2.89 (s, 2H), 3.31-3.37 (m, 8H), 6.01 (s, 2H), 6.43 (s, 1H), 6.74 (d, 1H), 6.86 (d, 2H), 7.01 (d, 2H), 7.94 (d, 2H), 10.36 (s, 1H), 12.11 (s, 1H); MS: m/z 434 (MH+).

Mean of n=1, FGFR Kinase assay—Caliper, IC$_{50}$ 0.14 μM.

tert-butyl 5-amino-3-(2-benzo[1,3]dioxol-5-ylethyl)pyrazole-1-carboxylate, used as starting material was prepared as follows:

To a stirred solution of 5-(2-benzo[1,3]dioxol-5-ylethyl)-2H-pyrazol-3-amine in DCM (10 ml) was added 4.5M aq. KOH solution (1.9 ml, 8.66 mmol, 8 eq). A solution of BOC$_2$O (464 mg, 2.12 mmol, 1.05 eq) in DCM (2 mL) was then added and the reaction mixture stirred vigorously for 3 h. The reaction mixture was poured into a separating funnel and the layers separated. The organic layer was washed with water (10 mL), brine (10 mL), dried (Na$_2$SO$_4$), filtered and the solvent evaporated to afford the title compound as a white solid. (325 mg, 91%); $^1$H NMR (300.132 MHz, DMSO) δ 1.55 (s, 9H), 2.58-2.64 (m, 2H), 2.73-2.78 (m, 2H), 5.19 (s, 1H), 5.95 (s, 2H), 6.21 (s, 2H), 6.68-6.71 (m, 1H), 6.80 (d, 1H), 6.85 (d, 1H)

5-(2-benzo[1,3]dioxol-5-ylethyl)-2H-pyrazol-3-amine, used as starting material was prepared as follows:

5-(2-Benzo[1,3]dioxol-5-ylethyl)-2H-pyrazol-3-amine used as starting material was prepared in a similar manner to 5-[2-(3-methoxyphenyl)ethyl]-2H-pyrazol-3-amine in example 11. Product was obtained as yellow oil. (3.04 g, 44% yield).

1H NMR (300.132 MHz, DMSO): δ 2.63-2.79 (m, 4H), 4.40 (s, 2H), 5.18 (s, 1H), 5.95 (s, 2H), 6.66 (dd, 1H), 6.77-6.81 (m, 2H). MS: m/z 232 (MH+).

Example 78

N-[5-[2-(2,5-Dimethoxyphenyl)ethyl]-2H-pyrazol-3-yl]-4-(4-methylpiperazin-1-yl)benzamide Made in an analogous way to the compound in example 77, using tert-butyl 5-amino-3-[2-(2,5-dimethoxyphenyl)ethyl]pyrazole-1-carboxylate (240 mg, 0.69 mmol, 1 eq) as starting material to afford the title compound as a white solid. (27 mg, 9%);

$^1$H NMR (300.132 MHz, DMSO) δ 2.23 (s, 3H), 2.43-2.46 (m, 4H), 2.80-2.88 (m, 4H), 3.26-3.29 (m, 4H), 3.68 (s, 3H), 3.76 (s, 3H), 6.43 (s, 1H), 6.72-6.77 (m, 2H), 6.88 (d, 1H), 6.96 (d, 2H), 7.89 (d, 2H), 10.29 (s, 1H), 12.06 (s, 1H)

MS: m/z 450 (MH+)

Mean of n=2, FGFR Kinase assay—Caliper, IC$_{50}$ 0.47 μM.

tert-butyl 5-amino-3-[2-(2,5-dimethoxyphenyl)ethyl]pyrazole-1-carboxylate, used as starting material was made in an analogous way to tert-butyl 5-amino-3-(2-benzo[1,3]dioxol-5-ylethyl)pyrazole-1-carboxylate in Example 77, using 5-[2-(2,5-dimethoxyphenyl)ethyl]-2H-pyrazol-3-amine (200 mg, 0.87 mmol, 1 eq) as starting material to afford the title compound as a white solid. (283 mg, 94%).

1H NMR (300.132 MHz, DMSO) δ 1.60 (s, 9H), 2.61-2.67 (m, 2H), 2.79-2.84 (m, 2H), 3.73 (s, 3H), 3.79 (s, 3H), 5.25 (s, 1H), 6.26 (s, 2H), 6.75-6.79 (m, 2H), 6.84 (d, 1H), 6.92 (d, 1H)

5-[2-(2,5-Dimethoxyphenyl)ethyl]-2H-pyrazol-3-amine, used as starting material, was prepared as follows:

Sodium hydride (60%, 0.240 g, 6 mmol) was added to a stirred solution of methyl 3-(2,5-dimethoxyphenyl)propanoate (1.125 g, 5 mmol) in 1,4 dioxane (25 ml) in dry acetonitrile (0.314 ml, 6 mmol) under nitrogen. The mixture was stirred at r.t for 10 mins then heated at reflux under nitrogen for 18 h. After this time, the mixture was cooled to r.t. upon which a precipitate formed. Ethanol (2 ml) was added, followed by hydrazine monohydrochloride (0.686 g, 10 mmol). The mixture was heated to reflux for 4 h. In this time, the precipitate went into solution and a solid appeared. After filtration, the reaction mixture was concentrated in vacuo and partitioned between 2N HCl and ethyl acetate (25 ml each). The aqueous layer was basified with ammonium hydroxide solution to pH 8, extracted with ethyl acetate and dried with MgSO4. This was filtered, and the solvents were evaporated in vacuo to give an orange oil (0.690 g, 56%).

4-(4-Methylpiperazin-1-yl)benzoyl chloride, used as starting material was prepared as per Example 61.

Example 79

N-[5-[2-(4-Methoxy-2-methyl-phenyl)ethyl]-2H-pyrazol-3-yl]-4-(4-methylpiperazin-1-yl)benzamide Made in an analogous way to the compound in example 77, using tert-butyl 5-amino-3-[2-(4-methoxy-2-methyl-phenyl)ethyl]pyrazole-1-carboxylate (229 mg, 0.69 mmol, 1 eq) as starting material to afford the title compound as a white solid. (15 mg, 5%); $^1$H NMR (300.132 MHz, DMSO) δ 2.26 (s, 3H), 2.72-2.83 (m, 5H), 2.88 (t, 4H), 3.41 (t, 4H), 3.69 (s, 3H), 5.70 (s, 1H), 6.41 (s, 1H), 6.65-6.73 (m, 2H), 6.99 (d, 2H), 7.06 (d, 1H), 7.91 (d, 2H) [NB: With D4-Acetic added]

MS: m/z 434 (MH+)

Mean of n=1, FGFR Kinase assay—Caliper, IC$_{50}$ 0.2 μM.

tert-butyl 5-amino-3-[2-(4-methoxy-2-methyl-phenyl)ethyl]pyrazole-1-carboxylate, used as starting material was made in an analogous way to tert-butyl 5-amino-3-(2-benzo[1,3]dioxol-5-ylethyl)pyrazole-1-carboxylate in Example 77, using 5-[2-(4-methoxy-2-methyl-phenyl)ethyl]-2H-pyrazol-3-amine (214 mg, 0.87 mmol, 1 eq) as starting material to afford the title compound as a white solid. (256 mg, 89%).

1H NMR (300.132 MHz, DMSO) δ 1.60 (s, 9H), 2.30 (s, 3H), 2.58-2.64 (m, 2H), 2.76-2.81 (m, 2H), 3.75 (s, 3H), 5.26 (s, 1H), 6.26 (s, 2H), 6.70-6.74 (m, 1H), 6.77 (d, 1H), 7.13 (d, 1H)

5-[2-(4-methoxy-2-methyl-phenyl)ethyl]-2H-pyrazol-3-amine, used as starting material was prepared as follows:

5-[2-(4-methoxy-2-methyl-phenyl)ethyl]-2H-pyrazol-3-amine, used as starting material, was prepared in a method analogous to that used to synthesize 5-[2-(3-methoxyphenyl)ethyl]-2H-pyrazol-3-amine in example 11 using methyl 3-(4-methoxy-2-methyl-phenyl)propanoate as starting material to give 5-[2-(4-methoxy-2-methyl-phenyl)ethyl]-2H-pyrazol-3-amine as a red solid. MS: m/z 232 (MH+).

4-(4-Methylpiperazin-1-yl)benzoyl chloride, used as starting material was prepared as per example 61.

Example 80

N-[5-[2-(3,5-Dimethoxyphenyl)ethyl]-2H-pyrazol-3-yl]-4-(3,5-dimethylpiperazin-1-yl)benzamide N-[5-[2-(3,5-dimethoxyphenyl)ethyl]-2H-pyrazol-3-yl]-4-(3,5-dimethylpiperazin-1-yl)benzamide was prepared as for Example 94, but starting from methyl 4-(3,5-dimethylpiperazin-1-yl)benzoate (221 mg, 0.84 mmol), tert-butyl 5-amino-3-[2-(3,5-dimethoxyphenyl)ethyl]-1H-pyrazole-1-carboxylate (244 mg, 0.7 mmol) and 1M NaHMDS (1.13 ml, 1.13 mmol) in THF (5 ml). The crude product was purified by reverse phase prep. HPLC (basic) using a 34-54% gradient of acetonitrile in water containing 1% 0.880 ammonia. The clean fractions were taken and evaporated to afford the title compound as a white solid (34 mg, 10%); $^1$H NMR (399.9 MHz, DMSO-d$_6$) δ 1.04 (6H, d), 2.22 (2H, t), 2.53 (2H, d), 2.82 (2H, t), 2.87 (4H, s), 3.71 (1H, s), 3.73 (7H, s), 6.33 (1H, t), 6.42 (2H, d), 6.44 (1H, s), 6.94 (2H, d), 7.89 (2H, d), 10.27 (1H, s), 12.07 (1H, s).

MS: m/z 464 (MH+).

Mean of n=2, FGFR Kinase assay—Caliper, IC$_{50}$ 0.011 μM.

2,6-Dimethylpiperazine (3.43 g, 30.00 mmol) was added to ethyl 4-fluorobenzoate (1.101 mL, 7.5 mmol), in DMSO (10 mL) warmed to 120° C. under nitrogen. The resulting solution was stirred at 120° C. for 20 h. The reaction mixture was cooled and the solvent was evaporated. The crude product was purified by silica column chromatography, eluting with 10% methanol in dichloromethane containing 1% 0.880 ammonia. Pure fractions were evaporated to dryness to afford ethyl 4-(3,5-dimethylpiperazin-1-yl)benzoate (1.490 g, 76%) as a colourless solid. 1H NMR (399.9 MHz, CDCl$_3$) δ 1.15 (6H, d), 1.37 (3H, t), 2.39 (1H, d), 2.42 (1H, d), 2.97-3.05 (2H, m), 3.65-3.69 (2H, m), 4.33 (2H, q), 6.84-6.87 (2H, m), 7.90-7.93 (2H, m)—NH not seen. MS: m/z=264 (MH+).

tert-butyl 5-amino-3-[2-(3,5-dimethoxyphenyl)ethyl]-1H-pyrazole-1-carboxylate, used as starting material was prepared as in Example 2.

Example 81

N-[5-[2-(3,5-Dimethoxyphenyl)ethyl]-1H-pyrazol-3-yl]-4-(3,4-dimethylpiperazin-1-yl)benzamide N-[5-[2-(3,5-Dimethoxyphenyl)ethyl]-2H-pyrazol-3-yl]-4-(3,4-dimethylpiperazin-1-yl)benzamide was prepared as for Example 94, but starting from methyl 4-(3,4-dimethylpiperazin-1-yl)benzoate (221 mg, 0.84 mmol), tert-butyl 5-amino-3-[2-(3,5-dimethoxyphenyl)ethyl]-1H-pyrazole-1-carboxylate (244 mg, 0.7 mmol) and 1M NaHMDS (1.13 ml, 1.13 mmol) in THF (5 ml). The crude product was purified by reverse phase prep. HPLC (basic) using a 38-58% gradient of acetonitrile in water containing 1% 0.880 ammonium hydroxide. The clean fractions were taken and evaporated to afford the title compound as a white solid (63 mg, 19%); $^1$H NMR (500.13 MHz, DMSO-d$_6$) δ 1.12 (3H, d), 1.89-1.90 (3H, m), 2.32 (3H, s), 2.35-2.40 (1H, m), 2.64-2.68 (1H, m), 2.86-2.91 (1H, m), 2.89 (4H, t), 3.00 (1H, s), 3.64-3.68 (2H, m), 3.74 (6H, s), 6.32 (1H, s), 6.33 (1H, t), 6.42 (2H, d), 6.94-6.96 (2H, m), 7.86-7.88 (2H, m). MS: m/z 464 (MH+).

Mean of n=2, FGFR Kinase assay—Caliper, IC$_{50}$ 0.04 μM.

1,2-Dimethyl-piperazine (0.914 g, 8.00 mmol) and ethyl 4-fluorobenzoate (0.587 mL, 4 mmol) were dissolved in DMA (6 mL) and sealed into a microwave tube. The reaction was heated to 150° C. for 90 mins in the microwave reactor and cooled to room temperature. The reaction mixture was evaporated and the crude product was purified by silica column chromatography, eluting with 5% MeOH in DCM (containing 0.1% 0.880 ammonia). Pure fractions were evaporated to dryness to afford ethyl 4-(3,4-dimethylpiperazin-1-yl)benzoate (0.380 g, 36.2%) as a colourless waxy solid.

1H NMR (399.9 MHz, CDCl$_3$) δ 1.15 (3H, d), 1.37 (3H, t), 2.20-2.25 (1H, m), 2.34 (3H, s), 2.37-2.41 (1H, m), 2.61-2.67 (1H, m), 2.87-2.92 (1H, m), 2.99-3.06 (1H, m), 3.58-3.62 (1H, m), 3.65-3.70 (1H, m), 4.33 (2H, q), 6.83-6.87 (2H, m), 7.90-7.94 (2H, m). MS: m/z=263 (MH+).

tert-butyl 5-amino-3-[2-(3,5-dimethoxyphenyl)ethyl]-1H-pyrazole-1-carboxylate, used as starting material was prepared as in Example 2.

Example 82

N-[5-[2-(3,5-Dimethoxyphenyl)ethyl]-2H-pyrazol-3-yl]-4-iodo-benzamide

Trifluoroacetic acid (3.85 mL, 50.02 mmol) was added in one portion to tert-butyl 3-(3,5-dimethoxyphenethyl)-5-(4-iodobenzamido)-1H-pyrazole-1-carboxylate (288 mg, 0.5 mmol) in DCM (10 mL) at room temperature. The resulting solution was stirred for 24 h. The reaction mixture was evaporated to dryness and redissolved in MeOH (5 mL). The crude product was purified by ion exchange chromatography, using a SCX column. The desired product was eluted from the column using 3.5M NH3/Methanol and pure fractions were evaporated to dryness to afford a tan solid. The solid was triturated with DCM to give the title compound (58.0 mg, 24.3%) as a white solid; $^1$H NMR (399.9 MHz, DMSO-d6) δ 2.88 (4H, s), 3.73 (6H, s), 6.33 (1H, t), 6.42 (2H, d), 6.47 (1H, s), 7.77 (2H, d), 7.87 (2H, d), 10.73 (1H, s), 12.17 (1H, s).

MS m/z: 478 (MH+).

Mean of n=1, FGFR Kinase assay—Caliper Echo Dosing, IC$_{50}$ 0.021 μM.

Tert-butyl 3-(3,5-dimethoxyphenethyl)-5-(4-iodobenzamido)-1H-pyrazole-1-carboxylate used as starting material was prepared as follows:

4-Iodobenzoyl chloride (1.332 g, 5.00 mmol) was added to tert-butyl 5-amino-3-[2-(3,5-dimethoxyphenyl)ethyl]-1H-pyrazole-1-carboxylate (1.737 g, 5 mmol) and pyridine (0.445 mL, 5.50 mmol) in DCM (15 mL). The resulting suspension was stirred at 25° C. for 24 h. The reaction mixture was evaporated to dryness and redissolved in EtOAc (25 mL), and washed sequentially with water (10 mL) and saturated brine (10 mL). The organic layer was dried over MgSO4, filtered and evaporated to afford crude product.

The crude product was purified by silica column chromatography, eluting with a gradient of 5-20% EtOAc in isohexane. Pure fractions were evaporated to dryness to afford tert-butyl 3-(3,5-dimethoxyphenethyl)-5-(4-iodobenzamido)-1H-pyrazole-1-carboxylate (1.187 g, 41.1%) as a white solid. 1H NMR (399.9 MHz, CDCl3) δ 1.70 (9H, s), 2.95 (4H, s), 3.78 (6H, s), 6.32 (1H, t), 6.42 (2H, d), 6.91 (1H, s), 7.64-7.67 (2H, m), 7.88-7.90 (2H, m), 11.13 (1H, s). MS m/z: 478 (MH+).

tert-butyl 5-amino-3-[2-(3,5-dimethoxyphenyl)ethyl]-1H-pyrazole-1-carboxylate, used as starting material was prepared as in Example 2.

Example 83

N-[5-[2-(3,5-Dimethoxyphenyl)ethyl]-1H-pyrazol-3-yl]-2-[(3-methyl-1,2-oxazol-5-yl)methylamino]benzamide NaHMDS (1M solution in THF, 0.83 ml, 0.828 mmol, 2.5 eq) was added dropwise to a solution of tert-butyl 5-amino-3-[2-(3,5-dimethoxyphenyl)ethyl]-1H-pyrazole-1-carboxylate (90 mg, 0.364 mmol, 1.1 eq) and methyl 2-{[(3-methylisoxazol-5-yl)methyl]amino}-benzoate (115 mg, 0.331 mmol, 1 eq), stirred in THF (4 ml) under nitrogen. The solution was stirred at room temperature for 50 mins. The solution was quenched with satd. aq. NH$_4$Cl, diluted with water (5 ml) and extracted with ethyl acetate (3×8 ml). The crude product was purified by silica column chromatography, eluting with a gradient of 0-1.5% MeOH in DCM. Fractions containing product were evaporated and further purified by reverse phase prep. HPLC purification, eluting with a gradient of MeCN/H$_2$O+0.1% TFA to afford the title compound as an off-white solid (16 mg, 10% yield); $^1$H NMR (399.902 MHz, DMSO) δ 2.20 (s, 3H), 2.88 (s, 4H), 3.73 (s, 6H), 4.57 (s, 2H), 6.21 (s, 1H), 6.33 (t, 1H), 6.41 (bs, 1H), 6.43 (d, 3H), 6.65 (t, 1H), 6.77 (d, 1H), 7.28-7.34 (m, 1H), 7.75-7.79 (m, 1H), 8.10 (bs, 1H), 10.50 (s, 1H). MS: m/z 462 (MH+)

Mean of n=2, FGFR Kinase assay—Caliper, IC$_{50}$ 1.0 µM.

Methyl 2-{[(3-methylisoxazol-5-yl)methyl]amino}-benzoate, used as starting material was prepared as follows:

1-(3-Methylisoxazol-5-yl)methanamine (155 mg, 1.37 mmol, 1.2 eq), potassium phosphate (341 mg, 1.60 mmol, 1.4 eq), S-Phos (95 mg, 0.230 mmol, 0.2 eq) and Pd$_2$dba$_3$ (13 mg, 0.06 mmol, 0.05 eq) were stirred in toluene (5 ml) under nitrogen. Methyl 2-iodobenzoate (300 mg, 1.14 mmol, 1 eq) was added and the mixture was stirred at room temperature for 3 days, then at 90° C. for 6 h. The reaction mixture was allowed to cool, poured into water (100 ml) and extracted with ethyl acetate (3×60 ml). The combined extracts were washed with brine, dried over MgSO$_4$, filtered and evaporated. The residual gummy oil was triturated with ether resulting in precipitation of a small amount of a yellow solid which was filtered off. The filtrate was evaporated and triturated again with methanol and a second precipitate was removed by filtration. The filtrate was evaporated, then purified by silica column chromatography, eluting with DCM. The product fractions were evaporated to afford methyl 2-{[(3-methyl-isoxazol-5-yl)methyl]amino}-benzoate as a yellow oily gum (128 mg, 45% yield); $^1$H NMR (399.902 MHz, CDCl$_3$) δ 2.25 (s, 3H), 3.88 (s, 3H), 4.53 (d, 2H), 5.99 (s, 1H), 6.62-6.70 (m, 2H), 7.32-7.38 (m, 1H), 7.92-7.96 (m, 1H), 8.19 (t, 1H). MS: m/z 247 (MH+)

tert-butyl 5-amino-3-[2-(3,5-dimethoxyphenyl)ethyl]-1H-pyrazole-1-carboxylate, used as starting material was prepared as in Example 2.

Example 84

N-[5-[2-(3,5-Dimethoxyphenyl)ethyl]-2H-pyrazol-3-yl]-6-(4-methylpiperazin-1-yl)pyridazine-3-carboxamide A solution of NaHMDS (1.500 ml, 1.50 mmol) in THF (1.0M) was added to a stirred solution of tert-butyl 5-amino-3-[2-(3,5-dimethoxyphenyl)ethyl]-1H-pyrazole-1-carboxylate (0.347 g, 1.0 mmol) and methyl 6-(4-methylpiperazin-1-yl)pyridazine-3-carboxylate (0.284 g, 1.20 mmol) in THF (5.00 ml) cooled to 0° C. under nitrogen.

The resulting solution was stirred at ambient temperature for 70 mins. The mixture was then partitioned between ethyl acetate and saturated aqueous ammonium chloride solution diluted with water (1:2). A solid was filtered off to give crude product as a white solid. This was purified by preparative LCMS using decreasingly polar mixtures of water (containing 0.1% TFA) and MeCN as eluents. Fractions containing the desired compound were evaporated to dryness to afford the title compound (0.127 g, 28.1%) as a white solid; $^1$H NMR (500.13 MHz, DMSO-d$_6$, CD$_3$CO$_2$D) δ 2.69 (3H, s), 2.89-2.95 (4H, m), 3.07-3.08 (4H, m), 3.75 (6H, s), 3.92-3.97 (4H, m), 6.34 (1H, s), 6.42 (3H, s), 7.41 (1H, d), 8.00 (1H, d)

MS: m/z 452 (MH+)

Mean of n=2, FGFR Kinase assay—Caliper, IC$_{50}$ 0.39 µM.

Methyl 6-(4-methylpiperazin-1-yl)pyridazine-3-carboxylate, used as starting material was prepared as follows:

A suspension of 6-(4-methylpiperazin-1-yl)pyridazine-3-carboxamide (221 mg, 1.00 mmol) in sodium hydroxide (2.0M aqueous) (10.000 mL, 20.00 mmol), was stirred at reflux for 3 h and then allowed to cool to room temperature. The reaction mixture was adjusted to pH7 by addition of 2M HCl (10 mL) and saturated NaHCO3. The crude product was purified by ion exchange chromatography, using a SCX2 column. The desired product was eluted from the column using methanol and the fractions were evaporated to dryness to afford 6-(4-methylpiperazin-1-yl)pyridazine-3-carboxylic acid as a white solid. This material was suspended in methanol (10.00 ml) at 0° C. and treated with thionyl chloride (0.729 ml, 10.00 mmol), over a period of 5 mins. The resulting suspension was stirred at ambient temperature for 18 h. Sodium bicarbonate solution was added until basic and then the mixture was extracted with ethyl acetate (2×75 mL). The solution was further extracted with 1-butanol (100 mL). The organic extracts were combined and evaporated to dryness to give methyl 6-(4-methylpiperazin-1-yl)pyridazine-3-carboxylate a white solid, 212 mg.

1H NMR (399.9 MHz, DMSO-d$_6$) δ 2.24 (3H, s), 2.43 (4H, t), 3.74 (4H, t), 3.88 (3H, s), 7.30 (1H, d), 7.84 (1H, d)

MS: m/z 237 (MH+)

6-(4-methylpiperazin-1-yl)pyridazine-3-carboxamide, used as starting material was prepared as follows:

6-Chloropyridazine-3-carboxamide (0.315 g, 2 mmol) and 1-methylpiperazine (0.555 ml, 5.00 mmol) were suspended in 2-propanol (2.000 ml) and sealed into a microwave tube. The reaction was heated to 130° C. for 30 mins in the microwave reactor and cooled to ambient temperature. The resulting precipitate was collected by filtration, washed with 2-propanol (10 mL) and dried under vacuum to afford 6-(4-methylpiperazin-1-yl)pyridazine-3-carboxamide (0.333 g, 75%) as a white solid, which was used without further purification. A sample (100 mg) of the crude product was purified by preparative LCMS using decreasingly polar mixtures of water (containing 1% NH3) and MeCN as eluents. Fractions containing the desired compound were evaporated to dryness to afford 6-(4-methylpiperazin-1-yl)pyridazine-3-carboxamide (54 mg) as a white solid.

1H NMR (399.9 MHz, DMSO-d6) δ 2.24 (3H, s), 2.44 (4H, t), 3.71 (4H, t), 7.34 (1H, d), 7.50 (1H, s), 7.84 (1H, d), 8.11 (1H, s)

MS: m/z 222 (MH+)

tert-butyl 5-amino-3-[2-(3,5-dimethoxyphenyl)ethyl]-1H-pyrazole-1-carboxylate, used as starting material was prepared as in Example 2.

Example 85

N-[5-[2-(3,5-Dimethoxyphenyl)ethyl]-2H-pyrazol-3-yl]-2-(4-methylpiperazin-1-yl)pyrimidine-5-carboxamide A solution of NaHMDS (2.100 ml, 2.10 mmol) in THF (1.0M) was added to a stirred solution of tert-butyl 5-amino-3-[2-(3,5-dimethoxyphenyl)ethyl]-1H-pyrazole-1-carboxylate (0.486 g, 1.4 mmol) and methyl 2-(4-methylpiperazin-1-yl)pyrimidine-5-carboxylate (0.397 g, 1.68 mmol) in THF (7.00 ml, cooled to −20° C.), over a period of 5 mins under nitrogen. The resulting solution was stirred at room temperature for 18 h. The mixture was heated to reflux for 90 min, then cooled to room temperature. More NaHMDS (2.100 ml, 2.10 mmol) was added and the mixture stirred for 70 mins. The mixture was allowed to stand for 96 h and then partitioned between ethyl acetate and 2.0M aqueous hydrochloric acid. The aqueous layer was separated and basified with 50% aqueous sodium hydroxide solution and then extracted with ethyl acetate (75 mL). The organic layer was washed with saturated brine (50 mL) and then dried over MgSO4, filtered and evaporated to afford crude product. The crude product was purified by preparative LCMS using decreasingly polar mixtures of water (containing 1% ammonia) and MeCN as eluents. Fractions containing the desired compound were evaporated to dryness to afford the title compound (4.00 mg, 0.633%) as a white solid;

$^1$H NMR (500.13 MHz, DMSO-d$_6$, CD$_3$CO$_2$D) δ 2.34 (3H, s), 2.53 (4H, t), 2.90 (4H, t), 3.74 (6H, s), 3.89 (4H, t), 6.33 (1H, t), 6.35 (1H, s), 6.42 (2H, d), 8.89 (2H, s)

MS: m/z 452 (MH+)

FGFR Kinase assay—Caliper, IC$_{50}$ 0.118 µM.

FGFR Kinase assay—Caliper Echo Dosing, IC$_{50}$ 0.0149 µM.

Methyl 2-(4-methylpiperazin-1-yl)pyrimidine-5-carboxylate, used as starting material was prepared as follows:

Methyl 2-chloropyrimidine-5-carboxylate (0.863 g, 5.0 mmol), N,N-diethylethanamine (0.697 ml, 5.00 mmol) and 1-methylpiperazine (0.565 ml, 5.09 mmol) were suspended in 2-propanol (10.00 ml) and sealed into a microwave tube. The reaction was heated to 100° C. for 10 mins in the microwave reactor and cooled to room temperature. The precipitate was collected by filtration, washed with EtOH (5 mL) and dried under vacuum to afford methyl 2-(4-methylpiperazin-1-yl)pyrimidine-5-carboxylate (0.405 g, 34.3%) as a white solid, which was used without further purification.

MS: m/z 237 (MH+)

tert-butyl 5-amino-3-[2-(3,5-dimethoxyphenyl)ethyl]-1H-pyrazole-1-carboxylate, used as starting material was prepared as in Example 2.

Example 86

N-[5-[2-(3,5-Dimethoxyphenyl)ethyl]-1H-pyrazol-3-yl]-4-(4-methylpiperazine-1-carbonyl)benzamide A solution of NaHMDS (1M in THF) (2.86 mL, 2.86 mmol) was added dropwise to a stirred solution of methyl 4-(4-methylpiperazine-1-carbonyl)benzoate (0.250 g, 0.95 mmol) and tert-butyl 5-amino-3-[2-(3,5-dimethoxyphenyl) ethyl]-1H-pyrazole-1-carboxylate (0.397 g, 1.14 mmol) in THF (2 mL), over a period of 10 mins under nitrogen. The resulting solution was stirred at room temperature for 18 h. The reaction mixture was poured into saturated NH$_4$Cl (25 mL), extracted with EtOAc (2×25 mL), washed with saturated brine and dried over MgSO$_4$, filtered and evaporated to afford the crude product (0.501 g) as a yellow gum. The crude product was purified by preparative HPLC using decreasingly polar mixtures of water (containing 1% ammonium hydroxide) and MeCN as eluents. Fractions containing the desired compound were evaporated to dryness to afford the title compound (0.257 g, 56.5%) as a yellow solid; $^1$H NMR (399.9 MHz, DMSO-d6) δ 2.21 (3H, s), 2.25-2.40 (4H, m), 2.89 (4H, s), 3.16-3.20 (1H, d), 3.32 (4H, s), 3.72 (6H, d), 6.33 (1H, m), 6.42-6.44 (2H, d), 7.46-7.50 (2H, d), 8.02-8.06 (2H, d)

MS: m/z 478 (MH+)

Mean of n=2, FGFR Kinase assay—Caliper, IC$_{50}$ 0.096 µM.

Methyl 4-(4-methylpiperazine-1-carbonyl)benzoate, used as starting material was prepared as follows:

Oxalyl chloride (0.533 mL, 6.11 mmol) was added dropwise to a stirred suspension of 4-(methoxycarbonyl)benzoic acid (1 g, 5.55 mmol) in DCM (20 mL) under nitrogen. The resulting suspension was stirred at room temperature for 30 mins. DMF (0.05 mL) was added dropwise under nitrogen. The resulting suspension was stirred for 90 mins. A solution of 1-methylpiperazine (0.554 mL, 5.00 mmol) and pyridine (1.211 mL, 14.99 mmol) in DCM (15 mL) was added dropwise at 0° C., over a period of 60 mins under nitrogen. The resulting solution was stirred at room temperature for 3 h. The reaction mixture was evaporated to dryness to afford the crude product (1.791 g) as a dark orange solid. The solid was redissolved in DCM and washed with NaHCO$_3$. The organic layer was evaporated to dryness to afford methyl 4-(4-methylpiperazine-1-carbonyl)benzoate (0.890 g, 61.1%) as an orange gum, which solidified on standing. Used without further purification.

1H NMR (399.9 MHz, CDCl3) δ 2.78 (4H, s), 3.43 (4H, s), 7.42-7.45 (2H, m), 8.04-8.06 (2H, m)

MS: m/z 263 (MH+)

tert-butyl 5-amino-3-[2-(3,5-dimethoxyphenyl)ethyl]-1H-pyrazole-1-carboxylate, used as starting material was prepared as in Example 2.

Example 87

N-[5-[2-(3,5-Dimethoxyphenyl)ethyl]-1H-pyrazol-3-yl]-4-(4-propan-2-ylpiperazin-1-yl)benzamide N-[5-[2-(3,5-dimethoxyphenyl)ethyl]-2H-pyrazol-3-yl]-4-(4-propan-2-ylpiperazin-1-yl)benzamide was prepared as for Example 94, but starting from methyl 4-(4-propan-2-yl-piperizin-1-yl)benzoate (263 mg, 0.84 mmol), tert-butyl 5-amino-3-[2-(3,5-dimethoxyphenyl)ethyl]-1H-pyrazole-1-carboxylate (244 mg, 0.7 mmol) and 1M NaHMDS (1.13 ml, 1.13 mmol) in THF (5 ml). The crude product was purified by reverse phase prep. HPLC (basic) using a 38-58% gradient of acetonitrile in water containing 1% 0.880 ammonia. The clean fractions were taken and evaporated to afford the title compound as a white solid (18 mg, 5%); $^1$H NMR (399.9 MHz, DMSO-d$_6$) δ 1.02 (6H, d), 2.55-2.61 (4H, m), 2.65-2.76 (1H, m), 2.89 (2H, s), 3.21-3.28 (4H, s), 3.31 (2H, s), 3.72 (6H, s), 6.33 (1H, t), 6.42 (2H, d), 6.45 (1H, s), 6.95 (2H, d), 7.90 (2H, d), 10.29 (1H, s), 12.07 (1H, s)

MS: m/z 478 (MH+).

Mean of n=5, FGFR Kinase assay—Caliper, IC$_{50}$ 0.0004 µM.

Methyl 4-(4-propan-2-yl-piperizin-1-yl)benzoate used as starting material was prepared as follows:

Tris(dibenzylideneacetone)dipalladium(0) (0.014 g, 0.02 mmol) was added to a deoxygenated suspension of 1-isopropylpiperazine (0.151 g, 1.18 mmol), methyl 4-bromobenzoate (0.215 g, 1 mmol), potassium carbonate (0.193 g, 1.4 mmol) and 2-dicyclohexylphosphino-2'-(N,N-dimethylamino)biphenyl (0.012 g, 0.03 mmol) in DME (4 mL), and sealed into a microwave tube. The reaction was heated to 130° C. for 10 mins in the microwave reactor and cooled to room temperature. The reaction mixture was evaporated to dryness, redissolved in EtOAc (25 mL) and washed sequentially with water (15 mL) and saturated brine (15 mL). The organic layer was dried over MgSO4, filtered and evaporated to afford crude product. The crude product was purified by silica column chromatography, eluting with 5% MeOH in DCM. Pure fractions were evaporated to dryness to afford methyl 4-(4-propan-2-yl-piperizin-1-yl)benzoate (0.170 g, 64.8%) as a tan solid.

1H NMR (399.9 MHz, CDCl3) δ 1.09 (6H, d), 2.66 (4H, t), 2.73 (1H, q), 3.34 (4H, t), 3.86 (3H, s), 6.84-6.88 (2H, m), 7.89-7.93 (2H, m). MS: m/z 264 (MH+).

tert-butyl 5-amino-3-[2-(3,5-dimethoxyphenyl)ethyl]-1H-pyrazole-1-carboxylate, used as starting material was prepared as in Example 2.

Example 88

4-(4-Cyclopropylpiperazin-1-yl)-N-[5-[2-(3,5-dimethoxyphenyl)ethyl]-1H-pyrazol-3-yl]benzamide 4-(4-cyclopropylpiperazin-1-yl)-N-[5-[2-(3,5-dimethoxyphenyl)ethyl]-2H-pyrazol-3-yl]benzamide was prepared as for Example 94, but starting from ethyl 4-(4-cyclopropylpiperazin-1-yl)benzoate (193 mg, 0.7 mmol), tert-butyl 5-amino-3-[2-(3,5-dimethoxyphenyl)ethyl]-1H-pyrazole-1-carboxylate (292 mg, 0.84 mmol) and 1M NaHMDS (1.23 ml, 1.23 mmol) in THF (5 ml). The crude product was purified by reverse phase prep. HPLC (acidic) using a 16-36% gradient of acetonitrile in water containing 0.1% TFA. The clean fractions were neutralised and evaporated to afford the title compound as a white solid (40 mg, 12%); $^1$H NMR (500.13 MHz, DMSO-$d_6$+$d_4$ Acetic Acid) δ 0.46 (2H, d), 0.50 (2H, d), 1.79-1.84 (1H, m), 2.78 (4H, t), 2.90 (4H, s), 3.24-3.31 (4H, m), 3.75 (6H, s), 6.32 (1H, s), 6.33 (1H, t), 6.42 (2H, d), 6.94-6.96 (2H, m), 7.86-7.88 (2H, m).

FGFR Kinase assay—Caliper, $IC_{50}$ 0.156 μM.

FGFR Kinase assay—Caliper Echo Dosing, $IC_{50}$ 0.00077 μM.

tert-butyl 5-amino-3-[2-(3,5-dimethoxyphenyl)ethyl]-1H-pyrazole-1-carboxylate, used as starting material was prepared as in Example 2.

Ethyl 4-(4-cyclopropylpiperazin-1-yl)benzoate used as starting material was prepared as follows:

Ethyl 4-fluorobenzoate (0.153 mL, 1.04 mmol) and 1-cyclopropylpiperazine (0.2637 g, 2.09 mmol) were taken up in DMA (2 mL) and sealed into a microwave tube. The reaction was heated to 150° C. for 90 mins in the microwave reactor and cooled to room temperature. The reaction mixture was evaporated to afford a brown gum, which solidified on standing. The crude product was purified by silica column chromatography, eluting with 10% MeOH (containing 0.1% aqueous ammonia) in DCM. Pure fractions were evaporated to dryness to afford the impure product as a yellow solid. The impure product was purified again by silica column chromatography, eluting with a gradient of 0-2.5% MeOH in DCM. Pure fractions were evaporated to dryness to afford ethyl 4-(4-cyclopropylpiperazin-1-yl)benzoate (0.096 g, 33.6%) as a beige solid.

1H NMR (399.9 MHz, CDCl3) δ 0.45-0.52 (5H, m), 1.36 (3H, t), 2.75 (4H, t), 3.29 (4H, t), 4.32 (2H, q), 6.84-6.88 (2H, m), 7.90-7.93 (2H, m)

m/z (ES+) (M+H)+=275

1-Cyclopropylpiperazine used as starting material was prepared as follows:

A solution of tert-butyl 4-cyclopropylpiperazine-1-carboxylate (0.792 g, 3.50 mmol) in 4M HCl in 1,4-dioxane (4.37 mL, 17.50 mmol) was stirred at room temperature for 3 h under nitrogen. The reaction mixture was filtered and washed with ether to afford crude 1-cyclopropylpiperazine (0.659 g) as a white solid. The crude product was purified by ion exchange chromatography, using a SCX column. The desired product was eluted from the column using 3.5M NH3/MeOH and pure fractions were evaporated to dryness to afford 1-cyclopropylpiperazine (0.264 g, 59.7%) as a yellow oil.

1H NMR (399.9 MHz, DMSO-d6) δ 0.25-0.30 (2H, m), 0.35-0.40 (2H, m), 1.54-1.60 (1H, m), 2.43 (4H, t), 2.60-2.65 (4H, t), 3.30 (1H, s)

tert-Butyl 4-cyclopropylpiperazine-1-carboxylate used as starting material was prepared as follows:

MeOH (0.3 mL), ((1-ethoxycyclopropyl)oxy)trimethylsilane (2 g, 11.47 mmol) and acetic acid (1.051 mL, 18.35 mmol) were added to a stirred solution of tert-butyl piperazine-1-carboxylate (1.068 g, 5.735 mmol) in THF (40 mL) under nitrogen. Sodium cyanoborohydride (0.541 g, 8.60 mmol) was added portionwise over a period of 10 mins. The resulting mixture was stirred at 60° C. for 24 h. The reaction mixture was evaporated to dryness and mixed with water (80 mL) and 1M HCl (25 mL). This solution was washed with EtOAc (2×50 mL), the aqueous layer was basified with $K_2CO_3$, and extracted with EtOAc (2×30 mL). The organic layers were combined, washed with saturated brine (30 mL), dried over MgSO4, filtered and evaporated to afford tert-butyl 4-cyclopropylpiperazine-1-carboxylate (0.792 g, 61.1%) as a colourless oil which crystallised on standing.

1H NMR (399.9 MHz, DMSO-d6) δ 0.30-0.34 (2H, m), 0.40-0.44 (2H, m), 1.41 (9H, s), 1.60-1.65 (1H, m), 2.47 (4H, t), 3.26 (4H, t)

Example 89

4-(4-Cyclobutylpiperazin-1-yl)-N-[5-[2-(3,5-dimethoxyphenyl)ethyl]-1H-pyrazol-3-yl]benzamide 4-(4-cyclobutylpiperazin-1-yl)-N-[5-[2-(3,5-dimethoxyphenyl)ethyl]-2H-pyrazol-3-yl]benzamide was prepared as for Example 94, but starting from ethyl 4-(4-cyclobutyllpiperazin-1-yl)benzoate (202 mg, 0.7 mmol), tert-butyl 5-amino-3-[2-(3,5-dimethoxyphenyl)ethyl]-1H-pyrazole-1-carboxylate (292 mg, 0.84 mmol) and 1M NaHMDS (1.23 ml, 1.23 mmol) in THF (5 ml). The crude product was purified by reverse phase prep. HPLC (basic) using a 39-59% gradient of acetonitrile in water containing 1% 0.880 ammonia. The clean fractions were combined and evaporated to afford the title compound (21 mg, 6%); $^1$H NMR (399.9 MHz, DMSO-$d_6$) δ 1.61-1.71 (2H, m), 1.81-1.86 (2H, m), 1.99-2.02 (2H, m), 2.38 (4H, t), 2.75 (1H, s), 2.85-2.87 (4H, m), 3.26-3.27 (4H, m), 3.72 (6H, d), 6.33 (1H, t), 6.42-6.43 (2H, m), 6.45 (1H, s), 6.95 (2H, d), 7.90 (2H, d), 10.29 (1H, s), 12.07 (1H, s). MS=m/z 490 (MH+).

Mean of n=2, FGFR Kinase assay—Caliper, $IC_{50}$ 0.009 μM.

tert-butyl 5-amino-3-[2-(3,5-dimethoxyphenyl)ethyl]-1H-pyrazole-1-carboxylate, used as starting material was prepared as in Example 2.

Ethyl 4-(4-cyclobutylpiperazin-1-yl)benzoate, used as starting material, was prepared as follows:

Ethyl 4-fluorobenzoate (0.225 mL, 1.53 mmol) and 1-cyclobutylpiperazine (0.430 g, 3.07 mmol) were taken up in DMA (3 mL) and sealed into a microwave tube. The reaction was heated to 150° C. for 90 mins in the microwave reactor and cooled to room temperature. The reaction was not complete, so it was reheated at 150° C. for a further 1 h. The reaction mixture was evaporated to dryness and the crude product purified by silica column chromatography, eluting with a gradient of 0-2.5% MeOH in DCM. Pure fractions were evaporated to dryness to afford ethyl 4-(4-cyclobutylpiperazin-1-yl)benzoate (0.050 g, 11.31%) as a yellow solid.

1H NMR (399.9 MHz, CDCl3) δ 1.29 (3H, t), 1.65-1.70 (2H, m), 1.86 (2H, t), 2.00 (2H, q), 2.41 (4H, d), 2.68-2.75 (1H, m), 3.27 (4H, t), 4.25 (2H, q), 6.79 (2H, d), 7.85 (2H, d). MS=m/z=289 (MH+).

1-Cyclobutylpiperazine, used as starting material, was prepared as follows:

Trifluoroacetic acid (7.84 mL, 101.73 mmol) was added to a stirred solution of tert-butyl 4-cyclobutylpiperazine-1-carboxylate (2.445 g, 10.17 mmol) in DCM (25 mL) cooled to 0° C. under nitrogen and stirred at 20° C. for 24 h. The reaction mixture was evaporated to dryness and diluted with DCM (30 mL). This was then washed with saturated NaHCO3 (2×10 mL) and the organic layers evaporated to dryness. Product was still present in the aqueous layer, so this was basified with 2M NaOH and extracted with DCM (3×10 mL) and EtOAc (1×10 mL). Organic fractions were combined and evaporated to dryness to afford 1-cyclobutylpiperazine (0.430 g, 30.1%). 1H NMR (399.9 MHz, DMSO-d6) δ 1.60-1.67 (2H, m), 1.72-1.80 (2H, m), 1.93-1.97 (2H, m), 2.25 (4H, s), 2.57-2.60 (1H, d), 2.82 (4H, t)

tert-Butyl 4-cyclobutylpiperazine-1-carboxylate, used as starting material, was prepared as follows:

Water (0.3 mL), cyclobutanone (2.000 g, 28.53 mmol) and acetic acid (3.48 mL, 60.86 mmol) were added to a stirred solution of tert-butyl piperazine-1-carboxylate (3.54 g, 19.02 mmol) in THF (40 mL) under nitrogen. Sodium cyanoborohydride (1.793 g, 28.53 mmol) was added portionwise over a period of 10 mins. The resulting mixture was stirred at 60° C. for 19 h. The reaction mixture was evaporated to dryness and mixed with water (80 mL) and 1M HCl (25 mL). The solution was washed with EtOAc (2×50 mL), basified with $K_2CO_3$ and extracted with EtOAc (2×30 mL). The organic layer was washed with saturated brine and dried over MgSO4, filtered and evaporated to afford pure tert-butyl 4-cyclobutylpiperazine-1-carboxylate (2.445 g, 53.5%) as a colourless oil.

1H NMR (399.9 MHz, DMSO-d6) δ 1.40 (9H, s), 1.60-1.65 (2H, m), 1.75-1.80 (1H, m), 1.90-2.00 (2H, m), 2.17 (1H, t), 2.65-2.75 (1H, m), 3.30 (4H, d). MS=m/z 241 (MH+).

Example 90

4-(4-Acetylpiperazin-1-yl)-N-[5-[2-(3,5-dimethoxyphenyl)ethyl]-1H-pyrazol-3-yl]benzamide 4-(4-acetylpiperazin-1-yl)-N-[5-[2-(3,5-dimethoxyphenyl)ethyl]-2H-pyrazol-3-yl]benzamide was prepared as for Example 94, but starting from methyl 4-(4-acetylpiperazin-1-yl)benzoate (221 mg, 0.84 mmol), tert-butyl 5-amino-3-[2-(3,5-dimethoxyphenyl)ethyl]-1H-pyrazole-1-carboxylate (244 mg, 0.7 mmol) and 1M NaHMDS (1.13 ml, 1.13 mmol) in THF (5 ml). The crude product was purified by reverse phase prep. HPLC (basic) using a 31-51% gradient of acetonitrile in water, containing 1% 0.880 ammonia. The clean fractions were taken and evaporated to afford the title compound as a white solid (3 mg, 1.0%); $^1$H NMR (399.9 MHz, DMSO-d$_6$) δ 2.06 (3H, s), 2.78 (4H, s), 3.28 (2H, s) 3.25 (2H, t), 3.49-3.56 (4H, m), 3.73 (6H, s), 6.33 (1H, t), 6.42 (2H, d), 6.45 (1H, s), 6.99 (2H, d), 7.92 (2H, d), 10.32 (1H, s), 12.08 (1H, s).

MS: m/z 478 (MH+).

Mean of n=5, FGFR Kinase assay—Caliper, IC$_{50}$ 0.056 μM.

A deoxygenated suspension of 1-acetylpiperazine (0.308 g, 2.40 mmol), methyl 4-bromobenzoate (0.430 g, 2 mmol), tri-potassium orthophosphate (0.594 g, 2.80 mmol), 2-dicyclohexylphosphino-2',6'-dimethoxy-1,1'-biphenyl (0.164 g, 0.40 mmol) and tris(dibenzylideneacetone)dipaladium(0) (0.092 g, 0.10 mmol) in toluene (10 mL) was stirred at 100° C., over a period of 24 h under nitrogen. The cooled reaction mixture was filtered and evaporated to give crude product. The crude product was purified by silica column chromatography, eluting with a gradient 0-5% MeOH in DCM. Pure fractions were evaporated to dryness to afford methyl 4-(4-acetylpiperazin-1-yl)benzoate (0.295 g, 56.2%) as a yellow solid.

1H NMR (399.9 MHz, CDCl3) δ 2.07 (3H, s), 3.24-3.30 (4H, m), 3.56 (2H, t), 3.70-3.72 (2H, m), 3.80 (3H, s), 6.78-6.81 (2H, m), 7.85-7.89 (2H, m). MS: m/z 263 (MH+).

tert-butyl 5-amino-3-[2-(3,5-dimethoxyphenyl)ethyl]-1H-pyrazole-1-carboxylate, used as starting material was prepared as in Example 2.

Example 91

N-[5-[2-(3-Methoxyphenyl)ethyl]-1H-pyrazol-3-yl]-4-(4-methylsulfonylpiperazin-1-yl)benzamide A solution of formic acid (5 mL, 130.36 mmol) and N-(1-tert-butyl-3-(3-methoxyphenethyl)-1H-pyrazol-5-yl)-4-(4-(methylsulfonyl)piperazin-1-yl)benzamide (255 mg, 0.47 mmol) was stirred at 85° C. for 2 h. The reaction mixture was cooled and evaporated to dryness. The crude product was purified by reverse phase prep. HPLC (basic) using a 36-46% gradient of acetonitrile in water, containing 1% 0.880 ammonia. The clean fractions were combined and evaporated to afford the title compound (43.0 mg, 18.82%) as a white solid; $^1$H NMR (499.9 MHz, DMSO$_{6}$+CD$_3$CO$_2$D) δ 2.87 (3H, s), 2.88-2.92 (4H, m), 3.28-3.32 (4H, m), 3.39-3.42 (4H, m), 3.73 (3H, s), 6.30 (1H, s), 6.71-6.74 (1H, m), 6.77 (1H, s0, 6.80 (2H, d), 6.94-6.98 (2H, m), 7.16 (1H, t), 7.85-7.89 (2H, m).

MS: m/z=484 (MH+).

Mean of n=2, FGFR Kinase assay—Caliper, IC$_{50}$ 0.25 μM.

N-(1-tert-butyl-3-(3-methoxyphenethyl)-1H-pyrazol-5-yl)-4-(4-(methylsulfonyl)piperazin-1-yl)benzamide used as starting material was prepared as follows:

Methanesulphonyl chloride (0.042 mL, 0.55 mmol) was added at 0° C. to a solution of N-(1-tert-butyl-3-(3-methoxyphenethyl)-1H-pyrazol-5-yl)-4-(piperazin-1-yl)benzamide (0.231 g, 0.5 mmol) and N,N-diethylethanamine (0.077 mL, 0.55 mmol) in DCM (4 mL). The resulting solution was stirred at 20° C. for 1 h. The reaction mixture was diluted with saturated sodium hydrogen carbonate (10 ml) filtered and the solid washed with DCM (2×10 ml). The organic layers were combined and washed with water (20 ml) and saturated brine (20 ml). The organics were dried (MgSO4), filtered and evaporated to afford crude product. The crude product was purified by silica column chromatography, eluting with a gradient of 0-5% MeOH in DCM. Pure fractions were evaporated to dryness to afford N-(1-tert-butyl-3-(3-methoxyphenethyl)-1H-pyrazol-5-yl)-4-(4-(methylsulfonyl)piperazin-1-yl)benzamide (0.255 g, 94%) as a white solid. MS: m/z=540 (MH+).

N-(1-tert-butyl-3-(3-methoxyphenethyl)-1H-pyrazol-5-yl)-4-(piperazin-1-yl)benzamide was prepared as follows:

A 2M solution of trimethylaluminium in toluene (6.25 mL, 12.50 mmol) was added dropwise to a stirred solution of and 1-tert-butyl-3-(3-methoxyphenyl)-1H-pyrazol-5-amine (1.367 g, 5.00 mmol) and ethyl 4-(piperazin-1-yl)benzoate (1.171 g, 5 mmol) in toluene (20 mL) at 4° C., over a period of 5 mins under nitrogen. The resulting solution was stirred at 20° C. for 18 h. The reaction mixture was quenched with methanol (20 mL), filtered and evaporated to afford tan solid. The crude product was purified by silica column chromatography, eluting with a gradient of 0 to 10% MeOH in DCM and 0.1% ammonia. Pure fractions were evaporated to dryness to afford N-(1-tert-butyl-3-(3-methoxyphenethyl)-1H-pyrazol-5-yl)-4-(piperazin-1-yl)benzamide (0.520 g, 22.53%) as a white solid.

1H NMR (399.9 MHz, CDCl$_3$) δ 1.59 (9H, s), 2.81-2.91 (4H, m), 2.96-2.99 (4H, m), 3.23 (3H, t), 3.25-3.42 (1H, m), 3.72 (3H, s), 6.17 (1H, s), 6.64-6.68 (1H, m), 6.73 (1H, t), 6.78 (1H, d), 6.84-6.88 (2H, m), 7.12 (1H, t), 7.38 (1H, s), 7.67-7.71 (2H, m).

Piperazine (17.23 g, 200.00 mmol) was added to ethyl 4-fluorobenzoate (7.34 mL, 50 mmol), in DMSO (50 mL) warmed to 120° C. under nitrogen. The resulting solution was stirred at 120° C. for 20 h. The reaction mixture was cooled and the solvent evaporated. The product was partitioned between saturated aq. sodium hydrogen carbonate solution (100 ml) and ethyl acetate (100 ml). This was extracted with ethyl acetate (2×75 ml), washed with brine solution, dried over MgSO4, filtered and evaporated. The crude product was purified by silica column chromatography, eluting with 10% methanol in dichloromethane containing 0.1% 0.880 ammonia. Pure fractions were evaporated to dryness to afford the product as a solid. The insoluble solid was slurried in DCM (500 ml) and stirred for 1 h. This solution was filtered and the organic solution dried over MgSO4, filtered and evaporated to give the bulk of the product as a solid. The solids were combined to give ethyl 4-(piperazin-1-yl)benzoate (9.53 g, 81%). 1H NMR (399.9 MHz, CDCl$_3$) δ 1.28-1.32 (3H, m), 2.94-2.96 (4H, m), 3.20-3.22 (4H, m), 4.26 (2H, q), 6.77-6.81 (2H, m), 7.84-7.87 (2H, m). MS: m/z=236 (MH+)

5-[2-(3-methoxyphenyl)ethyl]-2-tert-butyl-pyrazol-3-amine was prepared as outlined in Example 13.

Example 92

N-[5-[2-(3,5-Dimethoxyphenyl)ethyl]-1H-pyrazol-3-yl]-4-(1-methyl-4-piperidyl)benzamide A solution of NaHMDS (1M in THF) (5.91 mL, 5.91 mmol) was added dropwise to a stirred solution of methyl 4-(1-methylpiperidin-4-yl)benzoate (0.4594 g, 1.97 mmol) and tert-butyl 5-amino-3-[2-(3,5-dimethoxyphenyl)ethyl]-1H-pyrazole-1-carboxylate (0.821 g, 2.36 mmol) in THF (4 mL), over a period of 10 mins under nitrogen. The resulting solution was stirred at room temperature for 18 h. The reaction mixture was poured into saturated NH$_4$Cl (25 mL), extracted with EtOAc (2×25 mL), washed with saturated brine and dried over MgSO$_4$, filtered and evaporated to afford the crude product (1.0719 g) as an orange gum. The crude product was purified by preparative HPLC using decreasingly polar mixtures of water (containing 1% NH3) and MeCN as eluents. Fractions containing the desired compound were evaporated to dryness to afford the title compound (0.142 g, 16.08%) as a white solid;

$^1$H NMR (399.9 MHz, DMSO-d6) δ 1.64-1.78 (4H, m), 1.97-2.01 (2H, m), 2.22 (3H, s), 2.53-2.58 (1H, m), 2.88-2.91 (6H, m), 3.73 (6H, s), 6.33 (1H, t), 6.42-6.44 (3H, m), 7.35 (2H, d), 7.93 (2H, d), 10.57 (1H, s), 12.08 (1H, s)

MS: m/z 449 (MH+)

Mean of n=1, FGFR Kinase assay—Caliper, IC$_{50}$ 0.0079 μM.

Methyl 4-(1-methylpiperidin-4-yl)benzoate, used as starting material, was prepared as follows:

Water (0.2 mL), paraformaldehyde (0.470 g, 15.64 mmol) and acetic acid (0.895 mL, 15.64 mmol) were added to a stirred suspension of 4-(4-(methoxycarbonyl)phenyl)piperidinium chloride (1 g, 3.91 mmol) in THF (20 mL) under nitrogen. Sodium cyanoborohydride (0.369 g, 5.87 mmol) was added portionwise over a period of 10 mins. The resulting mixture was stirred at 60° C. for 19 h. The reaction mixture was evaporated to dryness and mixed with water (20 mL) and 1M HCl (5 mL). The solution was washed with EtOAc (2×15 mL), basified with K$_2$CO$_3$ and extracted with EtOAc (2×15 mL). The organic layer was washed with saturated brine and dried over MgSO4, filtered and evaporated to afford pure methyl 4-(1-methylpiperidin-4-yl)benzoate (0.459 g, 50.4%) as a colourless oil which crystallised on standing.

1H NMR (399.9 MHz, DMSO-d6) δ 1.63-1.72 (2H, m), 1.73-1.77 (2H, m), 1.96-2.03 (2H, m), 2.21 (3H, s), 2.87-2.90 (2H, m), 3.85 (3H, s), 4.30-4.31 (1H, m), 7.40 (2H, d), 7.88-7.91 (2H, m)

tert-butyl 5-amino-3-[2-(3,5-dimethoxyphenyl)ethyl]-1H-pyrazole-1-carboxylate, used as starting material was prepared as in Example 2.

Example 93

4-(3,4,6,7,8,8a-Hexahydro-1H-pyrrolo[2,1-c]pyrazin-2-yl)-N-[5-[2-(3,5-dimethoxyphenyl)ethyl]-2H-pyrazol-3-yl]benzamide 4-(3,4,6,7,8,8a-Hexahydro-1H-pyrrolo[2,1-c]pyrazin-2-yl)-N-[5-[2-(3,5-dimethoxyphenyl)ethyl]-2H-pyrazol-3-yl]benzamide was prepared as for Example 94, but starting from methyl 4-(3,4,6,7,8,8a-hexahydro-1H-pyrrolo[2,1-c]pyrazin-2-yl)benzoate (193 mg, 0.7 mmol), tert-butyl 5-amino-3-[2-(3,5-dimethoxyphenyl)ethyl]-1H-pyrazole-1-carboxylate (292 mg, 0.84 mmol) and 1M NaHMDS (1.23 ml, 1.23 mmol) in THF (5 ml). The crude product was purified by reverse phase prep. HPLC (basic) using a 33-53% gradient of acetonitrile in water, containing 1% 0.880 ammonia. The clean fractions were combined and evaporated to afford the title compound (34 mg, 10%); $^1$H NMR (399.9 MHz, DMSO-d$_6$) δ 1.37-1.41 (1H, m), 1.67-1.77 (2H, m), 1.84-1.88 (1H, m), 1.99-2.06 (1H, m), 2.09 (1H, t), 2.18-2.25 (1H, m), 2.80-2.84 (1H, m), 2.87 (4H, s), 3.01-3.06 (2H, m), 3.73 (6H, s), 3.80-3.83 (1H, m), 3.96-3.98 (1H, m), 6.33 (1H, t), 6.42-6.45 (3H, m), 6.97 (2H, d), 7.90 (2H, d), 10.28 (1H, s), 12.07 (1H, s)

MS=m/z 476 (MH+).

Mean of n=2, FGFR Kinase assay—Caliper, IC$_{50}$ 0.037 μM.

tert-butyl 5-amino-3-[2-(3,5-dimethoxyphenyl)ethyl]-1H-pyrazole-1-carboxylate, used as starting material was prepared as in Example 2.

Methyl 4-(3,4,6,7,8,8a-hexahydro-1H-pyrrolo[2,1-c]pyrazin-2-yl)benzoate, used as starting material was prepared as follows:

Methyl 4-iodobenzoate (2.076 g, 7.92 mmol), cesium carbonate (5.16 g, 15.85 mmol), 2-acetylcyclohexanone (0.209 mL, 1.58 mmol) and copper(I) iodide (0.075 g, 0.40 mmol) were added to a stirred solution 1,2,3,4,6,7,8,8a-octahydropyrrolo[1,2-a]pyrazine (1 g, 7.92 mmol) in DMF (20 mL) under nitrogen. The resulting suspension was stirred at 90° C. for 20 h. The reaction mixture was evaporated to dryness and redissolved in a mixture of methanol and water. The crude product was purified by ion exchange chromatography, using a SCX column. The desired product was eluted from the column using 3.5M NH3/MeOH and pure fractions were evaporated to dryness to afford the desired compound (1.243 g, 60.2%) as a brown gum.

1H NMR (399.9 MHz, DMSO-d6) δ 1.33-1.43 (1H, m), 1.57-1.79 (3H, m), 1.81-1.89 (1H, m), 1.99-2.03 (1H, m), 2.07 (1H, q), 2.16-2.23 (1H, m), 2.56 (1H, t), 2.83-2.95 (2H, m), 3.00-3.05 (2H, m), 3.06-3.09 (1H, m), 3.75-3.78 (3H, m), 3.86 (1H, t), 3.98-4.01 (1H, m), 6.98-7.02 (2H, m), 7.77-7.80 (2H, m).

MS=m/z 261 (MH+).

Example 94

4-(1,3,4,6,7,8,9,9a-Octahydropyrido[2,1-c]pyrazin-2-yl)-N-[5-[2-(3,5-dimethoxyphenyl)ethyl]-2H-pyrazol-3-yl]benzamide A 1M solution of NaHMDS in THF (1.13 ml, 1.05 mmol) was added to a stirred solution of tert-butyl 5-amino-3-[2-(3,5-dimethoxyphenyl)ethyl]-1H-pyrazole-1-carboxylate (244 mg, 0.7 mmol) and methyl 4-(1,3,4,6,7,8,9,9a-octahydropyrido[2,1-c]pyrazin-2-yl)benzoate (231 mg, 0.84 mmol) in THF (5 ml) at 0° C. under nitrogen, over 5 minutes. The reaction mixture was stirred for an additional 5 minutes at 0° C., then stirred at 20° C. for 18 h. An additional amount of tert-butyl 5-amino-3-[2-(3,5-dimethoxyphenyl)ethyl]-1H-pyrazole-1-carboxylate (80 mg, 0.23 mmol) was added with 1M NaHMDS in THF (1.13 ml, 1.13 mmol). The reaction mixture was stirred for an additional 3 h. The reaction mixture was quenched with saturated ammonium chloride (20 ml) and extracted with ethyl acetate (3×20 ml). The extracts were washed with saturated brine solution (15 ml), dried (MgSO4) and evaporated to give crude product. The crude product was purified by reverse phase prep. HPLC (basic) using a 38-58% gradient of acetonitrile in water containing 1% 0.880 ammonium hydroxide. The clean fractions were taken and evaporated to afford the title compound as a white solid (32 mg, 9%); $^1$H NMR (500.13 MHz, DMSO-$d_6$) δ 1.25 (1H, s), 1.62 (2H, t), 1.72 (1H, d), 1.93-1.95 (2H, m), 2.19-2.20 (1H, m), 2.44 (1H, s), 2.81 (3H, q), 2.87 (4H, s), 3.28 (1H, s), 3.69 (1H, s), 3.72 (6H, s), 3.77 (1H, d), 6.33 (1H, t), 6.42 (2H, d), 6.44 (1H, s), 6.96 (2H, d), 7.89 (2H, d), 10.29 (1H, s), 12.07 (1H, s). MS: m/z 490 (MH+).

Mean of n=2, FGFR Kinase assay—Caliper, $IC_{50}$ 0.081 µM.

tert-butyl 5-amino-3-[2-(3,5-dimethoxyphenyl)ethyl]-1H-pyrazole-1-carboxylate, used as starting material was prepared as in Example 2.

Methyl 4-(1,3,4,6,7,8,9,9a-octahydropyrido[2,1-c]pyrazin-2-yl)benzoate, used as starting material, was prepared as follows:

A solution of 2,3,4,6,7,8,9,9a-octahydro-1H-pyrido[1,2-a]pyrazine (5 g) in a mixture of methanol and water (1:1) was converted to the freebase by ion exchange chromatography, using a SCX column. The desired product was eluted from the column using 7M NH3/MeOH and pure fractions were evaporated to dryness to afford the desired compound (1.5224 g, 10.86 mmol) as a yellow solid.

Methyl 4-iodobenzoate (2.84 g, 10.86 mmol), cesium carbonate (7.07 g, 21.71 mmol), 2-acetylcyclohexanone (0.286 mL, 2.17 mmol) and copper(I) iodide (0.103 g, 0.54 mmol) were added to a stirred solution of 2,3,4,6,7,8,9,9a-octahydro-1H-pyrido[1,2-a]pyrazine (1.5224 g, 10.86 mmol) in DMF (30 mL) under nitrogen. The resulting suspension was stirred at 90° C. for 20 h. The reaction mixture was evaporated to dryness and dissolved in methanol. The crude product was purified by ion exchange chromatography, using a SCX column. The desired product was eluted from the column using 3.5M NH3/MeOH and pure fractions were evaporated to dryness to afford a brown gum. This was purified again by silica column chromatography, eluting with 5% MeOH (containing 0.1% ammonium hydroxide) in DCM. Pure fractions were evaporated to dryness to afford the desired compound (0.503 g, 16.8%) as an orange solid $^1$H NMR (399.9 MHz, CDCl$_3$) δ 1.29-1.33 (1H, m), 1.26-1.40 (1H, m), 1.62 (1H, d), 1.64 (1H, d), 1.65-1.68 (1H, m), 1.69 (1H, s), 1.80-1.82 (1H, m), 2.04-2.10 (2H, m), 2.32-2.39 (1H, m), 2.61 (1H, d), 2.89 (2H, d), 3.01-3.08 (1H, m), 3.58-3.63 (1H, m), 3.70-3.75 (1H, m), 3.86 (3H, s), 6.83-6.87 (2H, m), 7.89-7.93 (2H, m). MS m/z=275 (MH+).

Example 95

N-[5-[2-(3,5-Dimethoxyphenyl)ethyl]-1H-pyrazol-3-yl]-4-[(4-methylpiperazin-1-yl)methyl]benzamide A solution of NaHMDS (1M in THF) (2.83 mL, 2.83 mmol) was added dropwise to a stirred solution of methyl 4-((4-methylpiperazin-1-yl)methyl)benzoate (0.351 g, 1.41 mmol) and tert-butyl 5-amino-3-[2-(3,5-dimethoxyphenyl) ethyl]-1H-pyrazole-1-carboxylate (0.589 g, 1.70 mmol) in THF (3 mL), over a period of 10 mins under nitrogen. DMA (3 mL) was added. The resulting solution was stirred at room temperature for 60 h. A further aliquot of NaHMDS (1.415 mL, 1.415 mmol) was added dropwise and the solution was stirred at room temperature for a further 90 mins. The reaction mixture was poured into saturated NH4Cl (25 mL), extracted with EtOAc (2×25 mL), washed with saturated brine and dried over MgSO4, filtered and evaporated to afford the crude product (0.8776 g) as an orange gum. The crude product was purified by preparative HPLC using decreasingly polar mixtures of water (containing 1% NH3) and MeCN as eluents. Fractions containing the desired compound were evaporated to dryness to afford the title compound (0.034 g, 5.19%) as a white solid; $^1$H NMR (500.0 MHz, DMSO-d6) δ 2.18 (3H, s), 2.34-2.37 (2H, m), 3.54 (2H, s), 3.73 (3H, s), 6.32-6.33 (1H, t), 6.41-6.42 (2H, d), 7.38-7.39 (1H, d), 7.90-7.92 (1H, d), 10.02 (1H, s), 11.79 (1H, s)

MS: m/z 464 (MH+)

Mean of n=2, FGFR Kinase assay—Caliper, $IC_{50}$ 0.14 µM.

Methyl 4-((4-methylpiperazin-1-yl)methyl)benzoate, used as starting material was prepared as follows:

A solution of (trimethylsilyl)diazomethane ((0.611 mL, 3.84 mmol) 2.0M in diethyl ether) was added dropwise to a stirred suspension of 4-((4-methylpiperazin-1-yl)methyl) benzoic acid (0.75 g, 3.20 mmol) in toluene (21 mL) and methanol (7 mL) over a period of 10 mins under nitrogen. The resulting suspension was stirred at room temperature for 3 h. A further aliquot of (trimethylsilyl)diazomethane (1.222 mL, 7.68 mmol) was added dropwise and the solution was stirred at room temperature for a further 18 h. The reaction mixture was evaporated to dryness to afford the crude product (0.723 g) as a white solid. This was taken up in DCM and the insolubles were filtered off. The filtrate was evaporated to dryness to afford the crude product. This was taken up in DCM again and more insolubles were filtered off to afford methyl 4-((4-methylpiperazin-1-yl)methyl)benzoate (0.351 g, 44.2%), which was used without purification.

1H NMR (399.9 MHz, CDCl3) δ 2.60-2.61 (3H, m), 2.77 (4H, t), 2.99 (4H, s), 3.58 (1H, s), 3.62 (1H, s), 3.85 (2H, d), 7.29-7.38 (2H, m), 7.92-7.80 (2H, m)

MS: m/z 249 (MH+)

tert-butyl 5-amino-3-[2-(3,5-dimethoxyphenyl)ethyl]-1H-pyrazole-1-carboxylate, used as starting material was prepared as in Example 2.

Example 96

N-[5-[2-(3,5-Dimethoxyphenyl)ethyl]-1H-pyrazol-3-yl]-4-(3,4,5-trimethylpiperazin-1-yl)benzamide N-[5-[2-(3,5-dimethoxyphenyl)ethyl]-1H-pyrazol-3-yl]-4-(3,4,5-trimethylpiperazin-1-yl)benzamide was prepared following the procedure as for Example 94, but starting from ethyl 4-(3,4,5-trimethylpiperazin-1-yl)benzoate (310 mg, 0.86 mmol), tert-butyl 5-amino-3-[2-(3,5-dimethoxyphenyl)ethyl]-1H-pyrazole-1-carboxylate (225 mg, 0.65 mmol) and 1M NaHMDS (2.59 ml, 2.59 mmol) in THF (5 ml). The crude product was purified by reverse phase prep. HPLC (basic) using a 38-58% gradient of acetonitrile in water containing 1% 0.880 ammonia. The clean fractions were taken and evaporated to afford the title compound as a white solid (23 mg, 5.6%); $^1$H NMR (399.99 MHz, CDCl$_3$) δ1.09 (6H, d), 2.17-2.28 (2H, m), 2.22 (3H, s), 2.56 (2H, t), 2.81-2.90 (4H, m), 3.48 (2H, d), 3.68 (6H, s), 6.22 (1H, t), 6.28 (2H, s), 6.56 (1H, s), 6.78 (2H, d), 7.68 (2H, d0, 8.86 (1H, s), 9.65 (1H, s). MS: m/z 464 (MH+).

Mean of n=1, FGFR Kinase assay—Caliper Echo Dosing, IC$_{50}$ 0.00054 μM.

Ethyl 4-(3,4,5-trimethylpiperazin-1-yl)benzoate used as starting material was prepared as follows:

Titanium(IV) isopropoxide (0.598 mL, 2.00 mmol) was added to ethyl 4-(3,5-dimethylpiperazin-1-yl)benzoate (0.262 g, 1 mmol), and paraformaldehyde (0.120 g, 4.00 mmol) in ethanol (5 mL). The resulting solution was stirred at 60° C. under nitrogen for 30 mins. This was cooled to 20° C. and sodium borohydride (0.095 g, 2.5 mmol) was added in one portion. The solution was heated at 60° C. for 24 h. The reaction mixture was quenched with 0.880 ammonia (0.5 mL), filtered, washed with diethyl ether (2×5 mL) and the organic extracts were evaporated. The crude product was purified by silica column chromatography, eluting with a gradient of 0-5% MeOH in DCM containing 0.1% ammonia. Fractions were evaporated to dryness to afford an oil. This was dissolved in acetonitrile (20 ml), polymer supported isocyante resin (1 mmol/g, 2 g) was added and the suspension was stirred overnight. The resin was filtered off and the solution evaporated to dryness to give ethyl 4-(3,4,5-trimethylpiperazin-1-yl)benzoate (0.310 g, 112%) as a white solid. MS: m/z 278 (MH+).

tert-butyl 5-amino-3-[2-(3,5-dimethoxyphenyl)ethyl]-1H-pyrazole-1-carboxylate, used as starting material was prepared as in Example 2.

Example 97

N-[5-[(3,5-dimethoxyphenyl)methoxy]-2H-pyrazol-3-yl]-5-(3,4-dimethylpiperazin-1-yl)thiophene-2-carboxamide 2M Trimethylaluminium (1.250 ml, 2.50 mmol) in toluene, was added dropwise to a stirred solution of ethyl 5-(3,4-dimethylpiperazin-1-yl)thiophene-2-carboxylate (0.268 g, 1 mmol) and 5-[(3,5-dimethoxyphenyl)methoxy]-2H-pyrazol-3-amine hydrochloride (0.286 g, 1.00 mmol) in toluene (7.14 ml) at 80° C. under nitrogen for 4 h and then at 70° C. for 18 h. Ethyl acetate (5 mL) was added to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow gum. The crude product was purified by preparative LCMS, using decreasingly polar mixtures of water (containing 1% NH3) and MeCN as eluents. Fractions containing the desired compound were evaporated to afford the title compound (0.036 g, 7.63%) as a white solid.

1H NMR (500.13 MHz, DMSO-d6) δ 1.07 (3H, d), 2.26-3.12 (4H, m), 3.38-3.47 (3H, m), 3.78 (6H, s), 5.09 (2H, s), 5.55 (1H, s), 6.17 (1H, d), 6.45 (1H, s), 6.61 (2H, d), 7.64 (1H, s). MS: m/z 472 (MH+)

Mean of n=2, FGFR Kinase assay—Caliper Echo Dosing, IC$_{50}$ 0.00046 μM.

5-[(3,5-Dimethoxyphenyl)methoxy]-2H-pyrazol-3-amine hydrochloride, used as starting material was prepared as in Example 12.

Ethyl 5-(3,4-dimethylpiperazin-1-yl)thiophene-2-carboxylate, used as starting material was prepared as follows:

Palladium(II) acetate (0.112 g, 0.50 mmol) was added to a mixture of ethyl 5-bromothiophene-2-carboxylate (0.571 g, 5 mmol), 1,2-dimethyl-piperazine (1.175 g, 5 mmol), rac-2,2'-bis(diphenylphosphino)-1,1'-binaphthyl (0.311 g, 0.50 mmol) and cesium carbonate (2.281 g, 7.00 mmol) in toluene (50.0 ml) at 20° C. under nitrogen. The resulting suspension was stirred at 110° C. for 23 h. The crude product was purified by ion exchange chromatography, using a SCX2 column. The crude material was dissolved in methanol and then applied to the column. The desired product was eluted from the column using 2M NH3 in methanol and pure fractions were evaporated to dryness to afford the crude product as a brown oil. This material was further purified by silica column chromatography, eluting with a gradient of 1 to 5% MeOH in DCM. Pure fractions were evaporated to dryness to afford ethyl 5-(3,4-dimethylpiperazin-1-yl)thiophene-2-carboxylate (0.640 g, 47.7%) as a light brown solid.

1H NMR (399.9 MHz, CDCl3) δ 1.11-1.13 (3H, m), 1.33 (3H, t), 2.24-2.29 (1H, m), 2.33 (3H, s), 2.37-2.44 (1H, m), 2.73 (1H, d), 2.82-2.87 (1H, m), 3.08-3.14 (1H, m), 3.36-3.40 (1H, m), 3.43-3.48 (1H, m), 4.28 (2H, q), 6.01 (1H, d), 7.54 (1H, d)

MS: m/z 269 (MH+)

Example 98

4-(1,3,4,6,7,8,9,9a-octahydropyrido[2,1-c]pyrazin-2-yl)-N-[5-[(3,5-dimethoxyphenyl)methoxy]-2H-pyrazol-3-yl]benzamide A 2M solution of trimethylaluminium in toluene (0.853 mL, 1.71 mmol) was added dropwise to a stirred solution of 5-[(3,5-dimethoxyphenyl)methoxy]-2H-pyrazol-3-amine (0.170 g, 0.68 mmol) and methyl 4-(1,3,4,6,7,8,9,9a-octahydropyrido[2,1-c]pyrazin-2-yl)benzoate (0.187 g, 0.68 mmol) in toluene (10 mL), over a period of 5 mins under nitrogen. The resulting solution was stirred at room temperature for 18 h. The reaction was incomplete, so further trimethylaluminium (0.853 mL, 1.71 mmol) was added dropwise over a period of 5 mins and the solution was stirred at 60° C. for 4 h. The reaction mixture was cooled and poured into acetone (50 mL), quenched with damp sodium sulphite, filtered and evaporated to dryness. The crude product was purified by preparative HPLC, using decreasingly polar mixtures of water (containing 1% NH3) and MeCN as eluents. Fractions containing the desired compound were evaporated to dryness to the title compound (0.105 g, 31.3%) as a white solid.

1H NMR (500.13 MHz, DMSO-d6) δ 1.21-1.26 (1H, m), 1.30-1.33 (1H, m), 1.53-1.57 (1H, m), 1.63 (1H, d), 1.65 (1H, d), 1.76 (1H, d), 1.98 (1H, d), 1.98-2.03 (1H, m), 2.22-2.27 (1H, m), 2.55 (1H, d), 2.79 (1H, t), 2.83 (2H, d), 3.68-3.70 (1H, m), 3.78 (7H, s), 5.10 (2H, s), 5.67 (1H, s), 6.46 (1H, t), 6.61-6.62 (2H, m), 6.97 (2H, d), 7.84 (2H, d), 10.20 (1H, s), 11.15 (1H, s). MS: m/z 492 (MH+).

Mean of n=2, FGFR Kinase assay—Caliper Echo Dosing, IC$_{50}$ 0.003 μM.

Methyl 4-(1,3,4,6,7,8,9,9a-octahydropyrido[2,1-c]pyrazin-2-yl)benzoate used as starting material was prepared as follows:

A solution of 2,3,4,6,7,8,9,9a-octahydro-1H-pyrido[1,2-a]pyrazine dihydrochloride (5 g) in methanol (20 ml) and water (10 ml) was purified by ion exchange chromatography, using a SCX column. The desired product was eluted from the column using 7M NH3/MeOH and pure fractions were evaporated to dryness to afford 2,3,4,6,7,8,9,9a-octahydro-1H-pyrido[1,2-a]pyrazine (1.5224 g, 10.86 mmol) as a yellow solid.

Methyl-4-iodobenzoate (2.84 g, 10.86 mmol), cesium carbonate (7.07 g, 21.71 mmol), 2-acetylcyclohexanone (0.286 mL, 2.17 mmol) and copper(I) iodide (0.103 g, 0.54 mmol) were added to a stirred solution of 2,3,4,6,7,8,9,9a-octahydro-1H-pyrido[1,2-a]pyrazine (1.5224 g, 10.86 mmol) in DMF (30 mL) under nitrogen. The resulting suspension was stirred at 90° C. for 20 h. The reaction mixture was evaporated to dryness. The crude product was purified by ion exchange chromatography, using a SCX column. The desired product was eluted from the column using 3.5M NH3/MeOH and fractions were evaporated to dryness to afford the crude product as an impure brown gum. The crude product was purified by silica column chromatography, eluting with 5% MeOH, 0.1% aqueous ammonia in DCM. Pure fractions were evaporated to dryness to afford the desired compound (0.681 g, 22.87%) as an orange solid.

1H NMR (399.9 MHz, CDCl3) δ 1.29-1.33 (1H, m), 1.26-1.40 (1H, m), 1.62 (1H, d), 1.64 (1H, d), 1.65-1.68 (1H, m), 1.69 (1H, s), 1.80-1.82 (1H, m), 2.04-2.10 (2H, m), 2.32-2.39 (1H, m), 2.61 (1H, d), 2.89 (2H, d), 3.01-3.08 (1H, m), 3.58-3.63 (1H, m), 3.70-3.75 (1H, m), 3.86 (3H, s), 6.83-6.87 (2H, m), 7.89-7.93 (2H, m). MS: m/z 275 (MH+).

Example 99

4-(1-Cyclopropylpiperidin-4-yl)-N-[5-[2-(3,5-dimethoxyphenyl)ethyl]-2H-pyrazol-3-yl]benzamide Methyl 4-(1-cyclopropylpiperidin-4-yl)benzoate (0.259 g, 1 mmol), 5-[2-(3,5-dimethoxyphenyl)ethyl]-2H-pyrazol-3-amine (0.247 g, 1.00 mmol) in toluene (10 ml) was treated with a 2M solution of trimethylaluminium (1.250 ml, 2.50 mmol) in toluene, under nitrogen. The reaction mixture was heated at 60° C. for 18 h. The reaction mixture was cooled and the reaction quenched with methanol (40 ml) and acidified with 2N HCl (1 ml). The crude reaction mixture was purified by ion exchange chromatography, using an SCX column. The crude product was eluted from the column using 7M NH3/MeOH and fractions were evaporated to dryness. The crude product was purified by silica column chromatography, eluting with a gradient of 0 to 5% 2.5M ammonia/methanol in DCM. Pure fractions were evaporated to dryness and the product crystallised from DCM/diethyl ether to give the title compound (0.170 g, 35.8%) as a white solid.

1H NMR (399.9 MHz, DMSO-d6) δ 0.31-0.33 (2H, m), 0.43-0.45 (2H, m), 1.58-1.66 (3H, m), 1.74 (1H, d), 1.77 (1H, s), 2.25-2.30 (2H, m), 2.55 (1H, d), 2.88 (4H, s), 3.05 (2H, d), 3.73 (6H, s), 6.33 (1H, t), 6.42 (2H, d), 6.47 (1H, s), 7.34 (2H, d), 7.92 (2H, d), 10.54 (1H, s), 12.13 (1H, s). MS: m/z 475 (MH+).

Mean of n=3, FGFR Kinase assay—Caliper Echo Dosing, IC$_{50}$ 0.00091 µM.

Methyl 4-(1-cyclopropylpiperidin-4-yl)benzoate used as starting material was prepared as follows:

Methyl 4-piperidin-4-ylbenzoate (1.279 g, 5 mmol) was dissolved in a mixture of THF (15 mL) and methanol (1 mL). [(1-Ethoxycyclopropyl)oxy]trimethylsilane (2.001 mL, 10.00 mmol) added followed by acetic acid (0.916 mL, 16.00 mmol). DCM (15.00 mL) was added to aid solubility. Solid sodium cyanoborohydride (0.471 g, 7.50 mmol) was added in portions over 5 mins. The reaction was stirred at 60° C. for 18 h. This was cooled, quenched with saturated ammonium chloride solution (5 ml), diluted with methanol (20 ml) and partly purified by ion exchange chromatography, using an SCX column. The desired product was eluted from the column using 7M NH3/MeOH and pure fractions were evaporated to dryness to afford an oil. The crude product was purified by silica column chromatography, eluting with 5% MeOH in DCM. Pure fractions were evaporated to dryness to afford the desired compound (0.548 g, 42.3%) as a white solid.

1H NMR (399.9 MHz, CDCl3) δ 0.42-0.50 (4H, m), 1.60-1.65 (2H, m), 1.70-1.75 (1H, m), 1.80-1.85 (2H, m), 2.25-2.32 (2H, m), 2.55-2.61 (1H, m), 3.15-3.18 (2H, m), 3.89 (3H, s), 7.27-7.30 (2H, m), 7.94-7.97 (2H, m). MS: m/z 260 (MH+).

Methyl 4-piperidin-4-ylbenzoate was prepared as follows:

Methyl 4-(piperidin-4-yl)benzoate hydrochloride (5.0 g, 17 mmol) was converted to the freebase by ion exchange chromatography, using an SCX column. The desired product was eluted from the column using 7M NH3/MeOH and pure fractions were evaporated to dryness to afford methyl 4-(piperidin-4-yl)benzoate (4.20 g, 95%) as a white solid. MS: m/z 260 (MH+).

5-[2-(3,5-dimethoxyphenyl)ethyl]-2H-pyrazol-3-amine, used as starting material was prepared as indicated in Example 2.

Example 100

N-[5-[(3,5-dimethoxyphenyl)methoxy]-2H-pyrazol-3-yl]-4-[(3R,5S)-3,5-dimethylpiperazin-1-yl]benzamide A 2M solution of trimethylaluminium in toluene (1.875 mL, 3.75 mmol) was added dropwise to a stirred suspension of ethyl 4-((3R,5S)-3,5-dimethylpiperazin-1-yl)benzoate (0.394 g, 1.50 mmol) and 5-[(3,5-dimethoxyphenyl)methoxy]-2H-pyrazol-3-amine (0.374 g, 1.5 mmol) in toluene (10 mL) at 20° C., over a period of 5 mins under nitrogen. The resulting solution was stirred at 60° C. for 5 h. The reaction mixture was cooled and the reaction quenched by diluting with acetone (100 ml) and excess damp sodium sulphite added in portions. This was stirred for 60 mins. The resulting solid filtered off, washed with 10% methanol in DCM. The filtrate was evaporated to give crude product. The crude product was purified by silica column chromatography, eluting with a gradient of 0 to 5% 2M ammonia/MeOH in DCM. Pure fractions were evaporated to dryness to afford the title compound (0.287 g, 41.1%) as a white solid. 1H NMR (500.13 MHz, DMSO-d6) δ 1.08 (6H, d), 2.31 (2H, t), 3.70-3.73 (2H, m), 3.78 (6H, s), 5.10 (2H, s), 5.64 (1H, s), 6.46 (1H, t), 6.62 (2H, d), 6.95-6.97 (2H, m), 7.83-7.85 (2H, m), 10.21 (1H, s), 11.09 (1H, s). MS: m/z 466 (MH+).

Mean of n=1, FGFR Kinase assay—Caliper Echo Dosing, IC$_{50}$ 0.0014 µM.

Ethyl 4-((3R,5S)-3,5-dimethylpiperazin-1-yl)benzoate used as starting material was prepared as follows.

(2S,6R)-2,6-dimethylpiperazine (6.85 g, 60.00 mmol) was added to ethyl 4-fluorobenzoate (2.201 mL, 15 mmol), in DMSO (40 mL) warmed to 120° C. under nitrogen. The resulting solution was stirred at 120° C. for 20 h. The reaction mixture was cooled and the solvent evaporated. The crude product was purified by silica column chromatography, eluting with a gradient of 0 to 10% methanol in dichloromethane containing 1% 880 ammonia. Pure fractions were evaporated to dryness to afford the desired compound (2.83 g, 71.9%) as a brown oil. 1H NMR (399.9 MHz, CDCl3) δ 1.15 (6H, d), 1.37 (3H, t), 2.38 (1H, d), 2.41 (1H, d), 2.96-3.04 (2H, m), 3.65-3.69 (2H, m), 4.33 (2H, q), 6.84-6.87 (2H, m), 7.89-7.93 (2H, m). MS: m/z 263 (MH+).

5-[(3,5-Dimethoxyphenyl)methoxy]-2H-pyrazol-3-amine was prepared as follows:

MP carbonate (2.74 mmol/g) (12.00 g, 32.88 mmol) was added to 5-[(3,5-dimethoxyphenyl)methoxy]-2H-pyrazol-3-amine hydrochloride (5 g, 17.50 mmol) in methanol (200 mL) and water (20 mL). The resulting suspension was stirred at room temperature for 18 h. The reaction mixture was filtered and MP carbonate was washed with 10% MeOH in DCM. This was evaporated to dryness to afford 5-[(3,5-dimethoxyphenyl)methoxy]-2H-pyrazol-3-amine (2.94 g, 67.5%) as an orange waxy solid.

1H NMR (399.9 MHz, DMSO-d6) δ 3.74 (6H, s), 4.76 (1H, s), 4.97 (2H, s), 6.42 (1H, t), 6.55 (2H, d).

5-[(3,5-Dimethoxyphenyl)methoxy]-2H-pyrazol-3-amine hydrochloride, used as starting material was prepared as in Example 12.

Example 101

N-[5-[(3,5-dimethoxyphenyl)methoxy]-2H-pyrazol-3-yl]-4-(3,4-dimethylpiperazin-1-yl)benzamide N-[5-[(3,5-dimethoxyphenyl)methoxy]-2H-pyrazol-3-yl]-4-(3,4-dimethylpiperazin-1-yl)benzamide was prepared following the procedure for Example 100, but staring from ethyl 4-(3,4-dimethylpiperazin-1-yl)benzoate (0.394 g, 1.50 mmol), 5-[(3,5-dimethoxyphenyl)methoxy]-2H-pyrazol-3-amine (0.374 g, 1.5 mmol) and 2M trimethylaluminium in toluene (1.875 mL, 3.75 mmol). The crude product was purified by silica column chromatography, eluting with a gradient of 0 to 5% 2M ammonia/MeOH in DCM. Pure fractions were evaporated to dryness to afford the title compound (0.301 g, 43.1%) as a white solid.

1H NMR (500.13 MHz, DMSO-d6) δ 1.06-1.10 (3H, m), 2.22-2.30 (1H, m), 2.20-2.63 (4H, m), 2.61-2.65 (1H, m), 2.83-2.86 (1H, m), 2.96-3.02 (1H, m), 3.63-3.70 (2H, m), 3.78 (6H, s), 5.11 (2H, s), 5.66 (1H, s), 6.46 (1H, t), 6.62 (2H, d), 6.96-6.98 (2H, m), 7.83-7.86 (2H, m), 10.15 (1H, s), 11.07 (1H, s). MS: m/z 466 (MH+).

Mean of n=2, FGFR Kinase assay—Caliper Echo Dosing, IC$_{50}$ 0.021 µM.

Ethyl 4-(3,4-dimethylpiperazin-1-yl)benzoate used as starting material was prepared as follows:

1,2-Dimethylpiperazine (2.284 g, 20.00 mmol) and ethyl 4-fluorobenzoate (1.467 mL, 10 mmol) were dissolved in DMA (12 mL) and sealed in a microwave tube. The reaction was heated to 150° C. for 90 mins in the microwave reactor and cooled to room temperature. The reaction mixture was heated for a further 30 mins at 150° C. and cooled to room temperature. The reaction mixture was evaporated and the crude product was purified by silica column chromatography, eluting with 5% MeOH in DCM with 0.1% 0.880 ammonia. Pure fractions were evaporated to dryness to afford ethyl 4-(3,4-dimethylpiperazin-1-yl)benzoate (0.853 g, 32.5%) as a colourless waxy solid.

1H NMR (399.9 MHz, CDCl3) δ 1.14 (3H, d), 1.37 (3H, t), 2.20-2.25 (1H, m), 2.33 (3H, s), 2.34-2.41 (1H, m), 2.62 (1H, t), 2.87-2.91 (1H, m), 2.99-3.05 (1H, m), 3.57-3.62 (1H, m), 3.65-3.70 (1H, m), 4.33 (2H, q), 6.83-6.87 (2H, m), 7.90-7.94 (2H, m). MS: m/z 263.

5-[(3,5-Dimethoxyphenyl)methoxy]-2H-pyrazol-3-amine, used as starting material was prepared as in Example 100.

Example 102 tert-Butyl 4-[5-[[5-[2-(3,5-dimethoxyphenyl)ethyl]-2H-pyrazol-3-yl]carbamoyl]thiophen-2-yl]piperazine-1-carboxylate 2M Trimethylaluminium (1.250 ml, 2.50 mmol) in toluene, was added dropwise to a stirred solution of tert-butyl 4-(5-(methoxycarbonyl)thiophen-2-yl)piperazine-1-carboxylate (0.326 g, 1 mmol) and 5-[2-(3,5-dimethoxyphenyl)ethyl]-2H-pyrazol-3-amine (0.247 g, 1.00 mmol) in toluene (7.14 ml) at 20° C. under nitrogen. The reaction mixture was stirred at 20° C. for 20 h. The temperature was increased to 60° C. and the reaction mixture was stirred for 20 h and then allowed to cool. The reaction mixture was diluted with acetone (10 ml) and quenched with damp solid sodium sulphite. The mixture was stirred for 30 mins, and then a solution of 10% methanol in DCM (10 mL) was added and the mixture stirred for a further 30 mins. The suspension was filtered and the solid washed with 10% methanol in DCM (20 mL); the combined filtrates were evaporated to give a yellow foam. The crude product was purified by silica column chromatography, eluting with a gradient of 1 to 10% 2M ammonia/methanol in DCM. Pure fractions were evaporated to dryness to afford the crude product. This was further purified by preparative HPLC, using decreasingly polar mixtures of water (containing 1% NH3) and MeCN as eluents. Fractions containing the desired compound were evaporated to dryness to afford tert-butyl 4-[5-[[5-[2-(3,5-dimethoxyphenyl)ethyl]-2H-pyrazol-3-yl]carbamoyl]thiophen-2-yl]piperazine-1-carboxylate (0.272 g, 50.2%) as a white dry film.

1H NMR (500.13 MHz, DMSO-d6) δ 1.46 (9H, s), 2.89-2.90 (6H, m), 3.22 (4H, t), 3.52 (4H, t), 3.75 (6H, s), 6.18 (1H, d), 6.27 (1H, s), 6.34 (1H, t), 6.42-6.42 (2H, m), 7.72 (1H, d), 9.81 (1H, s), 11.71 (1H, s); MS: m/z 542 (MH+)

Mean of n=1, FGFR Kinase assay—Caliper Echo Dosing, IC$_{50}$ 0.028 µM.

tert-Butyl 4-(5-(methoxycarbonyl)thiophen-2-yl)piperazine-1-carboxylate, used as starting material was prepared as follows:

2.0M (Trimethylsilyl)diazomethane solution in ether (0.525 ml, 1.05 mmol) was added dropwise to a stirred solution of 5-[4-[(2-methylpropan-2-yl)oxycarbonyl]piperazin-1-yl]thiophene-2-carboxylic acid (0.312 g, 1 mmol) in methanol (2.000 ml) and the mixture was stirred at ambient temperature for 20 h. More 2.0M (Trimethylsilyl)diazomethane solution in ether (0.500 ml, 1.00 mmol) was added and the mixture stirred for 2 h. The mixture was evaporated and the crude product was purified by silica column chromatography, eluting with a gradient of 1 to 3% EtOAc in DCM. Pure fractions were evaporated to dryness to afford the desired compound (0.141 g, 43.2%) as a cream solid.

1H NMR (399.9 MHz, CDCl3) δ 1.48 (9H, s), 3.22 (4H, t), 3.58 (4H, t), 3.82 (3H, s), 6.06 (1H, d), 7.55 (1H, d). MS: m/z 327 (MH+)

5-[4-[(2-methylpropan-2-yl)oxycarbonyl]piperazin-1-yl]thiophene-2-carboxylic acid, used as starting material can be prepared by the method described in the literature (Stokes, Elaine Sophie Elizabeth; Waring, Michael James; Gibson, Keith Hopkinson. Preparation of amides as inhibitors of histone deacetylase. WO2003/092686).

5-[2-(3,5-dimethoxyphenyl)ethyl]-2H-pyrazol-3-amine, used as starting material was prepared as indicated in Example 2.

Example 103

N-[5-[(3,5-dimethoxyphenyl)methoxy]-2H-pyrazol-3-yl]-4-(1-methylpiperidin-4-yl)benzamide N-[5-[(3,5-dimethoxyphenyl)methoxy]-2H-pyrazol-3-yl]-4-(1-methylpiperidin-4-yl)benzamide was prepared following the procedure as for Example 159, but starting from methyl 4-(1-methylpiperidin-4-yl)benzoate (0.25 g, 1.07 mmol), 5-[(3,5-dimethoxyphenyl)methoxy]-2H-pyrazol-3-amine (0.267 g, 1.07 mmol) and 2M trimethylaluminium in toluene (2.14 ml, 4.29 mmol). The crude product was purified by silica column chromatography, eluting with a gradient of 0 to 8% 2.5M NH3/MeOH in DCM. Pure fractions were evaporated to dryness, redissolved in DCM, triturated with ether and evaporated to dryness to afford the title compound (0.225 g, 46.5%) as a white solid. 1H NMR (399.9 MHz, DMSO-d6) δ 1.69 (1H, d), 1.73 (2H, d), 1.77 (1H, s), 1.95-2.02 (2H, m), 2.21 (3H, s), 2.88 (2H, d), 3.76 (6H, s), 5.09 (2H, s), 5.62 (1H, s), 6.45 (1H, s), 6.60 (2H, s), 7.41-7.42 (2H, m), 7.89-7.91 (2H, m), 10.85 (1H, s), 11.58 (1H, s). MS: m/z 451 (MH+).

Mean of n=1, FGFR Kinase assay—Caliper Echo Dosing, $IC_{50}$ 0.00094 µM.

Methyl-4-(1-methylpiperidin-4-yl)benzoate used as starting material was prepared as follows:

Water (0.4 mL), paraformaldehyde (0.742 g, 24.71 mmol) and acetic acid (1.415 mL, 24.71 mmol) were added to a stirred suspension of methyl 4-piperidin-1-ium-4-ylbenzoate chloride (1.58 g, 6.18 mmol) in THF (40 mL) under nitrogen. Sodium cyanoborohydride (0.582 g, 9.27 mmol) was added portion wise over a period of 10 mins. The resulting mixture was stirred at 60° C. for 18 h. The reaction mixture was evaporated to dryness and mixed with water (30 mL) and 1M HCl (10 mL). The solution was washed with ethyl acetate (2×25 mL), basified with solid potassium carbonate and extracted ethyl acetate (2×25 mL). The organic layer was washed with saturated brine and dried over MgSO4, filtered and evaporated to afford pure methyl 4-(1-methylpiperidin-4-yl)benzoate (0.784 g, 54.4%) as a colourless oil which solidified on standing.

1H NMR (399.9 MHz, DMSO-d6) δ 1.62-1.71 (2H, m), 1.72-1.74 (2H, m), 1.95-2.02 (2H, m), 2.21 (3H, s), 2.54-2.59 (1H, m), 2.88 (2H, d), 3.85 (3H, s), 7.39-7.42 (2H, m), 7.88-7.91 (2H, m). MS: m/z 234 (MH+).

Example 104

4-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]benzamide 4-(3,4,6,7,8,8a-hexahydro-1H-pyrrolo[2,1-c]pyrazin-2-yl)-N-[5-[(3,5-dimethoxyphenyl]methoxy]-2H-pyrazol-3-yl)benzamide was prepared following the procedure as for Example 159, but starting from methyl 4-(3,4,6,7,8,8a-hexahydro-1H-pyrrolo[2,1-c]pyrazin-2-yl)benzoate (0.25 g, 0.96 mmol), 5-[(3,5-dimethoxyphenyl)methoxy]-2H-pyrazol-3-amine (0.239 g, 0.96 mmol) and 2M trimethylaluminium in toluene (1.2 ml, 2.4 mmol). The crude product was purified by preparative HPLC, using decreasingly polar mixtures of water (containing 1% NH3) and MeCN as eluents. Fractions containing the desired compound were evaporated to dryness to afford the title compound (0.124 g, 27%) as a white solid.

1H NMR (399.9 MHz, DMSO-d6) δ 1.37-1.44 (1H, m), 1.67-1.74 (2H, m), 1.83-1.89 (1H, m), 1.99-2.04 (1H, m), 2.08 (1H, q), 2.18-2.25 (1H, m), 2.82-2.89 (1H, m), 3.01-3.06 (2H, m), 3.75 (6H, s), 3.85 (1H, d), 3.99-4.02 (1H, m), 5.08 (2H, s), 5.57 (1H, s), 6.44 (1H, s), 6.59-6.60 (2H, m), 7.04 (2H, d), 7.85 (2H, d), 10.61 (1H, s), 11.49 (1H, s). MS: m/z 478 (MH+).

Mean of n=1, FGFR Kinase assay—Caliper Echo Dosing, $IC_{50}$ 0.0013 µM.

Methyl 4-(3,4,6,7,8,8a-hexahydro-1H-pyrrolo[2,1-c]pyrazin-2-yl)benzoate, used as starting material was prepared as follows:

Methyl 4-iodobenzoate (2.076 g, 7.92 mmol), cesium carbonate (5.16 g, 15.85 mmol), 2-acetylcyclohexanone (0.209 mL, 1.58 mmol) and copper(I) iodide (0.075 g, 0.40 mmol) were added to a stirred solution of 1,2,3,4,6,7,8,8a-octahydropyrrolo[1,2-a]pyrazine (1 g, 7.92 mmol) in DMF (20 mL) under nitrogen. The resulting suspension was stirred at 90° C. for 20 h. The reaction mixture was evaporated to dryness and redissolved in a mixture of methanol and water. The crude product was purified by ion exchange chromatography, using a SCX column. The desired product was eluted from the column using 3.5M NH3/MeOH and pure fractions were evaporated to dryness to afford methyl 4-(3,4,6,7,8,8a-hexahydro-1H-pyrrolo[2,1-c]pyrazin-2-yl)benzoate (1.243 g, 60.2%) as a brown gum.

1H NMR (399.9 MHz, DMSO-d6) δ 1.33-1.43 (1H, m), 1.57-1.79 (3H, m), 1.81-1.89 (1H, m), 1.99-2.03 (1H, m), 2.07 (1H, q), 2.16-2.23 (1H, m), 2.56 (1H, t), 2.83-2.95 (2H, m), 3.00-3.05 (2H, m), 3.06-3.09 (1H, m), 3.75-3.78 (3H, m), 3.86 (1H, t), 3.98-4.01 (1H, m), 6.98-7.02 (2H, m), 7.77-7.80 (2H, m). MS: m/z 261 (MH+).

Example 105

5-(1,3,4,6,7,8,9,9a-Octahydropyrido[2,1-c]pyrazin-2-yl)-N-[5-[2-(3,5-dimethoxyphenyl)ethyl]-2H-pyrazol-3-yl]pyrazine-2-carboxamide 2,3,4,6,7,8,9,9a-Octahydro-1H-pyrido[1,2-a]pyrazine (477 mg, 3.40 mmol) was added in one portion to 5-chloro-N-[5-[2-(3,5-dimethoxyphenyl)ethyl]-2H-pyrazol-3-yl]pyrazine-2-carboxamide (659 mg, 1.70 mmol) in anhydrous dimethylsulfoxide (1.70 ml) at 25° C. The resulting solution was stirred at 100° C. for 18 h. The crude product was purified by ion exchange chromatography, using an SCX column. The desired product was eluted from the column using 7M NH3/MeOH to afford impure material. The concentrated eluant was purified by preparative HPLC, using decreasingly polar mixtures of water (containing 1% formic acid) and MeCN as eluents. The sample was then put through a basic HPLC system to obtain the free base. Fractions containing the desired compound were evaporated to dryness to afford the title compound (395 mg, 47%) as a cream solid.

1H NMR (500.133 MHz, DMSO) δ 1.19-1.35 (3H, m), 1.51-1.60 (1H, m), 1.64 (1H, t), 1.73-1.79 (1H, m), 1.93-2.08 (2H, m), 2.17-2.25 (1H, m), 2.73 (1H, dd), 2.81-2.93 (6H, m), 3.13 (1H, td), 3.73 (6H, s), 4.28-4.33 (1H, m), 4.37-4.42 (1H, m), 6.32 (1H, t), 6.38-6.41 (3H, m), 8.26 (1H, d), 8.70 (1H, d), 9.59 (1H, br s), 11.82 (1H, br s). MS: m/z 492 (MH+).

Mean of n=1, FGFR Kinase assay—Caliper Echo Dosing, $IC_{50}$ 0.13 µM.

5-Chloro-N-[5-[2-(3,5-dimethoxyphenyl)ethyl]-2H-pyrazol-3-yl]pyrazine-2-carboxamide used as starting material was prepared as follows:

Trimethylaluminium (2M in toluene, 9.64 ml, 19.28 mmol) was added dropwise to a stirred suspension of 5-[2-(3,5-dimethoxyphenyl)ethyl]-2H-pyrazol-3-amine (1.91 g, 7.71 mmol) and methyl 5-chloropyrazine-2-carboxylate (1.33 g, 7.71 mmol) in anhydrous toluene (38.6 ml) at ambient temperature. The resulting solution was then stirred under nitrogen at ambient temperature for 18 h. The reaction was incomplete so the temperature was increased to 60° C. and the reaction mixture was stirred for a further 3 h. The reaction mixture was quenched with methanol (10 mL) and HCl (2M aqueous solution). The mixture was diluted with EtOAc (100 mL) and water (250 mL) and then acidified with HCl (2N aqueous solution). The organic layer was removed and the aqueous further extracted with EtOAc (2×100 mL). The combined organics were washed with water (200 mL), brine (200 mL) dried over MgSO4 and concentrated under reduced pressure. Upon concentration a precipitate formed. The precipitate was collected by filtration, washed with MeOH (10 mL) and air dried to afford the desired compound (1.88 g, 63%) as a yellow solid, which was used without further purification.

1H NMR (399.9 MHz, DMSO-$d_6$) δ 2.88-2.89 (4H, m), 3.73 (6H, s), 6.33 (1H, t), 6.43 (2H, d), 6.49 (1H, s), 8.93 (1H, s), 9.09 (1H, s), 10.44 (1H, s), 12.31 (1H, s). MS: m/z 388 (MH+).

Example 106

N-[5-[2-(3,5-dimethoxyphenyl)ethyl]-2H-pyrazol-3-yl]-5-(4-methylpiperazin-1-yl)thiophene-2-carboxamide 2M Trimethylaluminium (1.250 ml, 2.50 mmol) in toluene, was added dropwise to a stirred is solution of ethyl 5-(4-methylpiperazin-1-yl)thiophene-2-carboxylate (0.254 g, 1 mmol) and 5-[2-(3,5-dimethoxyphenyl)ethyl]-2H-pyrazol-3-amine (0.247 g, 1.00 mmol) in toluene (7.14 ml) at 20° C. under nitrogen. The reaction mixture was stirred at ambient temperature for 16 h and then heated at 65° C. for 24 h. Ethyl acetate (5 mL) was added to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow solid. The crude product was purified by preparative HPLC, using decreasingly polar mixtures of water (containing 1% NH3) and MeCN as eluents. Fractions containing the desired compound were evaporated to dryness to afford the title compound (0.154 g, 33.8%) as a white solid.

1H NMR (500.13 MHz, DMSO-d6, CD3CO2D) δ 2.32 (3H, d), 2.58 (4H, t), 2.88 (4H, s), 3.26 (4H, t), 3.73 (3H, s), 3.74 (3H, s), 6.13 (1H, d), 6.25 (1H, s), 6.32 (1H, d), 6.40 (2H, d), 7.68-7.69 (1H, m); MS: m/z 456 (MH+)

Mean of n=2, FGFR Kinase assay—Caliper Echo Dosing, $IC_{50}$ 0.001 µM.

Ethyl 5-(4-methylpiperazin-1-yl)thiophene-2-carboxylate, used as starting material was prepared as follows:

Palladium(II) acetate (0.225 g, 1.00 mmol) was added to ethyl 5-bromothiophene-2-carboxylate (2.351 g, 10 mmol), 1-methylpiperazine (1.331 ml, 12.00 mmol), rac-2,2'-Bis(diphenylphosphino)-1,1'-binaphthyl (0.623 g, 1.00 mmol) and cesium carbonate (4.56 g, 14.00 mmol) in toluene (100 ml) at 20° C. under nitrogen. The resulting suspension was stirred at 110° C. for 23 h. The mixture was filtered through celite and the filtrate was evaporated to dryness to give a brown oil. The crude product was purified by ion exchange chromatography, using a SCX column. The desired product was eluted from the column using 7M NH3/MeOH and pure fractions were evaporated to dryness to afford the crude product as a brown gum. This material was further purified by silica column chromatography, eluting with a gradient of 0 to 3% methanol in DCM. Pure fractions were evaporated to dryness to afford the desired compound (1.380 g, 54.3%) as an orange oil.

1H NMR (399.9 MHz, CDCl3) δ 1.33 (3H, t), 2.34 (3H, s), 2.54 (4H, t), 3.28 (4H, t), 4.28 (2H, q), 6.02 (1H, d), 7.55 (1H, d); MS: m/z 255 (MH+)

5-[2-(3,5-dimethoxyphenyl)ethyl]-2H-pyrazol-3-amine, used as starting material was prepared as indicated in Example 2.

Example 107

N-[5-[(3,5-dimethoxyphenyl)methoxy]-2H-pyrazol-3-yl]-5-(4-methylpiperazin-1-yl)thiophene-2-carboxamide 2M Trimethylaluminium (1.250 ml, 2.50 mmol) in toluene, was added dropwise to a stirred solution of ethyl 5-(4-methylpiperazin-1-yl)thiophene-2-carboxylate (0.254 g, 1 mmol) and 5-[(3,5-dimethoxyphenyl)methoxy]-2H-pyrazol-3-amine hydrochloride (0.286 g, 1.00 mmol) in toluene (7.14 ml) at 20° C. under nitrogen. The reaction mixture was stirred at room temperature for 18 h and then heated at 65° C. for 6 h. Ethyl acetate (5 mL) was added to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow solid. The crude product was purified by preparative HPLC, using decreasingly polar mixtures of water (containing 1% NH3) and MeCN as eluents. Fractions containing the desired compound were evaporated to dryness to afford the title compound (0.147 g, 32.1%) as a white solid.

1H NMR (500.13 MHz, DMSO-d6, CD3CO2D) δ 2.29 (3H, s), 2.53-2.55 (4H, m), 3.25-3.28 (4H, m), 3.77 (6H, s), 5.09 (2H, s), 5.63 (1H, s), 6.16 (1H, d), 6.45 (1H, t), 6.60 (2H, d), 7.64 (1H, d); MS: m/z 458 (MH+)

Mean of n=2, FGFR Kinase assay—Caliper Echo Dosing, $IC_{50}$ 0.0011 µM.

Ethyl 5-(4-methylpiperazin-1-yl)thiophene-2-carboxylate, used as starting material was 10 prepared as outlines in Example 106.

5-[(3,5-Dimethoxyphenyl)methoxy]-2H-pyrazol-3-amine hydrochloride, used as starting material was prepared as in Example 12.

Example 108

N-[5-[2-(3,5-dimethoxyphenyl)ethyl]-2H-pyrazol-3-yl]-5-(3,3-dimethylpiperazin-1-yl)pyrazine-2-carboxamide 2,2-Dimethylpiperazine (343 mg, 3.00 mmol) was added in one portion to 5-chloro-N-[5-[2-(3,5-dimethoxyphenyl)ethyl]-2H-pyrazol-3-yl]pyrazine-2-carboxamide (388 mg, 1 mmol) in anhydrous dimethylsulfoxide (1.00 ml) at 25° C. The resulting solution was stirred at 100° C. for 18 h. The crude product was purified by ion exchange chromatography, using a SCX column. The desired product was eluted from the column using 7M NH3/MeOH to afford impure material. The concentrated eluent was purified by preparative HPLC, using decreasingly polar mixtures of water (containing 1% NH3) and MeCN as eluents. Fractions containing the desired compound were evaporated to dryness to afford the title compound (217 mg, 47%) as a yellow solid.

1H NMR (399.9 MHz, DMSO-d6) δ 1.06 (6H, s), 2.04 (1H, s), 2.82-2.88 (6H, m), 3.51 (2H, s), 3.65 (2H, t), 3.72 (6H, s), 6.33 (1H, t), 6.42 (2H, d), 6.46 (1H, s), 8.32 (1H, s), 8.66 (1H, s), 9.71 (1H, s), 12.17 (1H, s). MS: m/z 466 (MH+).

Mean of n=1, FGFR Kinase assay—Caliper Echo Dosing, $IC_{50}$ 0.002 μM.

5-Chloro-N-[5-[2-(3,5-dimethoxyphenyl)ethyl]-2H-pyrazol-3-yl]pyrazine-2-carboxamide was prepared as shown in Example 105.

Example 109

5-(4-Cyclopropylpiperazin-1-yl)-N-[5-[(3,5-dimethoxyphenyl)methoxy]-2H-pyrazol-3-yl]pyrazine-2-carboxamide 5-Chloro-N-[5-[(3,5-dimethoxyphenyl)methoxy]-2H-pyrazol-3-yl]pyrazine-2-carboxamide (390 mg, 1.00 mmol) was added in one portion to 1-cyclopropylpiperazine, 2HCl (398 mg, 2.00 mmol) and N-ethyl-N-propan-2-ylpropan-2-amine (0.52 ml, 3.00 mmol) in anhydrous dimethylsulfoxide (1.00 ml) at 25° C. The resulting solution was stirred at 100° C. for 18 h. The crude product was purified by ion exchange chromatography, using an SCX column. The desired product was eluted from the column using 7M NH₃/MeOH to afford impure material. The concentrated eluent was purified by silica column chromatography, eluting with a gradient of 0 to 10% 7M NH3/MeOH in DCM. Fractions containing desired product were evaporated to dryness to give a yellow solid. The solid was taken up in DCM and triturated with Et₂O to give a solid which was collected by filtration and dried under vacuum to give the title compound (130 mg, 27%) as a yellow solid.

1H NMR (399.9 MHz, DMSO-d6) δ 0.38-0.40 (2H, m), 0.45-0.49 (2H, m), 1.66-1.70 (1H, m), 2.66 (4H, t), 3.71 (4H, t), 3.75 (6H, s), 5.08 (2H, s), 5.84 (1H, s), 6.45 (1H, s), 6.59 (2H, s), 8.33 (1H, s), 8.72 (1H, s), 10.80 (1H, s), 11.35 (1H, s). MS: m/z 480 (MH+).

Mean of n=1, FGFR Kinase assay—Caliper Echo Dosing, $IC_{50}$ 0.003 μM.

5-Chloro-N-[5-[(3,5-dimethoxyphenyl)methoxy]-2H-pyrazol-3-yl]pyrazine-2-carboxamide used as starting material was prepared as follows:

Trimethylaluminium (2M in toluene, 7.44 ml, 14.88 mmol) was added dropwise to a stirred suspension of 5-[(3,5-dimethoxyphenyl)methoxy]-2H-pyrazol-3-amine, HCl (1.70 g, 5.95 mmol) and methyl 5-chloropyrazine-2-carboxylate (1.03 g, 5.95 mmol) in anhydrous toluene (29.8 ml) at ambient temperature. The resulting solution was then stirred under nitrogen at ambient temperature for 18 h. The reaction mixture was quenched with methanol (5 mL) and HCl (2M aqueous solution), diluted with water (200 mL) and extracted with EtOAc (3×150 mL). The organics were washed with water (200 mL), brine (200 mL) dried over MgSO4, filtered and concentrated. On evaporation a precipitate was formed which was collected by filtration, washed with MeOH (20 mL) and air dried to afford the desired compound (1.65 g, 71%) as an orange solid, which was used without further purification.

1H NMR (500.13 MHz, DMSO-d6, 373K) δ 3.78 (6H, s), 5.12 (2H, s), 5.94 (1H, s), 6.46 (1H, s), 6.62 (2H, s), 8.87 (1H, s), 9.09 (1H, s), 10.99 (1H, s), 11.24 (1H, s). MS: m/z 390 (MH+)

Mean of n=1, FGFR Kinase assay—Caliper Echo Dosing, $IC_{50}$ 0.060 μM.

Example 110

N-[5-[(3,5-dimethoxyphenyl)methoxy]-2H-pyrazol-3-yl]-4-[(3R,5S)-3,4,5-trimethylpiperazin-1-yl]benzamide N-[5-[(3,5-Dimethoxyphenyl)methoxy]-2H-pyrazol-3-yl]-4-[(3R,5 S)-3,4,5-trimethylpiperazin-1-yl]benzamide was prepared following the procedure for Example 100, but starting from ethyl 4-((3R,5S)-3,4,5-trimethylpiperazin-1-yl)benzoate (0.276 g, 1.00 mmol) and 5-[(3,5-dimethoxyphenyl)methoxy]-2H-pyrazol-3-amine (0.249 g, 1 mmol) and a 2M solution of trimethylaluminium in toluene (1.25 mL, 2.5 mmol). The crude product was purified by preparative HPLC, using decreasingly polar mixtures of water (containing 1% NH₃) and MeCN as eluents. Fractions containing the desired compound were evaporated to dryness to afford the title compound (0.027 g, 5.63%) as a white solid.

1HNMR (500.133 MHz, DMSO-d6+CD3COOD) δ: 1.13 (6H, d), 2.31 (3H, s), 2.60-2.68 (2H, m), 3.19 (2H, s), 3.70 (1H, s), 3.65 (6H, s), 5.08 (2H, s), 5.68 (1H, s), 6.40-6.44 (1H, m), 6.58 (2H, s), 6.97 (2H, d), 7.82 (2H, d). MS: m/z 480 (MH+).

Mean of n=1, FGFR Kinase assay—Caliper Echo Dosing, $IC_{50}$ 0.00068 μM.

Ethyl 4-((3R,5S)-3,4,5-trimethylpiperazin-1-yl)benzoate used as starting material was prepared as follows:

Titanium (IV) isopropoxide (2.99 mL, 10.00 mmol) was added to ethyl 4-((3R,5S)-3,5-dimethylpiperazin-1-yl)benzoate (1.312 g, 5.00 mmol) and formaldehyde (0.601 g, 20.00 mmol) in ethanol (25 mL) warmed to 60° C. over a period of 45 mins under nitrogen. The resulting solution was cooled to 20° C. and sodium borohydride (0.473 g, 12.50 mmol) was added in one portion and the suspension stirred at 60° C. for 18 h. The reaction was quenched with ammonia (2 ml). The solid filtered off and washed with 10% MeOH in DCM (2×50 ml). The organic layer was evaporated to dryness and the crude product purified by silica column chromatography, eluting with a gradient of 0 to 5% MeOH in DCM containing 0.1% ammonia. Fractions were evaporated to dryness to afford an oil. This was purified by preparative HPLC, using decreasingly polar mixtures of water (containing 1% NH3) and MeCN as eluents. Fractions containing the desired compound were evaporated to dryness to afford the desired compound (0.320 g, 23.16%) as a white crystalline solid.

1H NMR (399.9 MHz, CDCl3) δ 1.11 (6H, d), 1.29 (3H, t), 2.24 (3H, s), 2.25-2.30 (2H, m), 2.59 (1H, d), 2.62 (1H, d), 3.53-3.57 (2H, m), 4.26 (2H, q), 6.75-6.79 (2H, m), 7.82-7.86 (2H, m). MS: m/z 277 (MH+).

5-[(3,5-Dimethoxyphenyl)methoxy]-2H-pyrazol-3-amine, used as starting material was 10 prepared as in Example 100.

Example 111

N-[5-[(3,5-dimethoxyphenyl)methoxy]-2H-pyrazol-3-yl]-4-(3,3-dimethylpiperazin-1-yl)benzamide A 2M solution of trimethylaluminium in toluene (0.691 mL, 1.38 mmol) was added dropwise to a stirred solution of ethyl 4-(3,3-dimethylpiperazin-1-yl)benzoate (145 mg, 0.55 mmol) and 5-[(3,5-dimethoxyphenyl)methoxy]-2H-pyrazol-3-amine (138 mg, 0.55 mmol) in toluene (5 mL) at 20° C., over a period of 5 mins under nitrogen. The resulting solution was stirred at 20° C. for 24 h. This was diluted with acetone (25 ml) and an excess of damp solid sodium sulphite was added. The mixture was stirred for 1 h and the solid filtered off. The solid was washed with 10% MeOH/DCM and the combined organics evaporated to dryness. The crude product was purified by preparative HPLC, using decreasingly polar mixtures of water (containing 1% NH3) and MeCN as eluents. Fractions containing the desired compound were evaporated to dryness to afford the title compound (27.0 mg, 10.49%) as a colourless gum.

1HNMR (500.13 MHz, DMSO-d6 @ 373K) δ: 1.11 (6H, s), 2.85-2.91 (2H, m), 3.03 (2H, s), 3.18-3.22 (2H, m), 3.78 (6H, s), 5.09 (2H, s), 5.62 (1H, s), 6.44 (1H, t), 6.60 (2H, s), 6.92 (2H, d), 7.82 (2H, d), 10.19 (1H, s), 11.12 (1H, s). MS: m/z 466 (MH+).

Mean of n=1, FGFR Kinase assay—Caliper Echo Dosing, $IC_{50}$ 0.00076 μM.

Ethyl 4-(3,3-dimethylpiperazin-1-yl)benzoate used as starting material was prepared as follows:

Ethyl 4-fluorobenzoate (0.151 mL, 1 mmol), 2,2-dimethylpiperazine (0.137 g, 1.20 mmol) and N-ethyl-N-propan-2-ylpropan-2-amine (0.349 mL, 2.00 mmol) were dissolved in DMA (2 mL) and sealed into a microwave tube. The reaction was heated to 200° C. for 4 h in the microwave reactor and cooled to room temperature. The crude mixture was purified by ion exchange chromatography, using an SCX column. The desired product was eluted from the column using 3.5M ammonia in methanol, fractions were evaporated to dryness to afford an oil. The crude product was purified by silica column chromatography, eluting with a gradient of 0 to 10% 2M ammonia/MeOH in DCM. Pure fractions were evaporated to dryness to afford ethyl 4-(3,3-dimethylpiperazin-1-yl)benzoate (0.145 g, 55.3%) as a white solid. 1H NMR (399.9 MHz, CDCl3) δ 1.15 (6H, d), 1.37 (3H, t), 2.38 (1H, d), 2.41 (1H, d), 2.96-3.04 (2H, m), 3.65-3.69 (2H, m), 4.33 (2H, q), 6.84-6.87 (2H, m), 7.89-7.93 (2H, m). MS: m/z 266 (MH+).

5-[(3,5-Dimethoxyphenyl)methoxy]-2H-pyrazol-3-amine, used as starting material was is prepared as in Example 100.

Example 112

N-[5-[2-(3,5-dimethoxyphenyl)ethyl]-2H-pyrazol-3-yl]-5-[(3R,5S)-3,5-dimethylpiperazin-1-yl]pyrazine-2-carboxamide (2S,6R)-2,6-Dimethylpiperazine (228 mg, 2.00 mmol) was added in one portion to 5-chloro-N-[5-[2-(3,5-dimethoxyphenyl)ethyl]-2H-pyrazol-3-yl]pyrazine-2-carboxamide (388 mg, 1.00 mmol) in anhydrous dimethylsulfoxide (1.00 ml) at 25° C. The resulting solution was stirred at 100° C. for 18 h. The crude product was purified by ion exchange chromatography, using an SCX column. The desired product was eluted from the column using 7M NH3/MeOH to afford impure material. The concentrated eluent was purified by preparative HPLC, using decreasingly polar mixtures of water (containing 1% NH3) and MeCN as eluents. Fractions containing the desired compound were evaporated to dryness to afford the title compound (164 mg, 35%) as a cream solid.

1H NMR (399.9 MHz, DMSO-d6) δ 1.05-1.06 (6H, d), 2.43-2.50 (2H, m), 2.72-2.78 (2H, m), 2.88 (4H, s), 3.72 (6H, s), 4.39 (2H, d), 6.33 (1H, t), 6.42 (2H, d), 6.46 (1H, s), 8.34 (1H, d), 8.69 (1H, d), 9.73 (1H, s), 12.18 (1H, s), no NH observed. MS: m/z 466 (MH+).

Mean of n=1, FGFR Kinase assay—Caliper Echo Dosing, $IC_{50}$ 0.0017 μM.

5-Chloro-N-[5-[2-(3,5-dimethoxyphenyl)ethyl]-2H-pyrazol-3-yl]pyrazine-2-carboxamide was prepared as shown in Example 105.

Example 113

5-(4-Cyclopropylpiperazin-1-yl)-N-[5-[2-(3,5-dimethoxyphenyl)ethyl]-2H-pyrazol-3-yl]pyrazine-2-carboxamide 5-Chloro-N-[5-[2-(3,5-dimethoxyphenyl)ethyl]-2H-pyrazol-3-yl]pyrazine-2-carboxamide (388 mg, 1.00 mmol) was added in one portion to 1-cyclopropylpiperazine, 2HCl (398 mg, 2.00 mmol) and N-ethyl-N-propan-2-ylpropan-2-amine (0.52 ml, 3.00 mmol) in anhydrous dimethylsulfoxide (1.00 ml) at 25° C. The resulting solution was stirred at 100° C. for 18 h. The crude product was purified by ion exchange chromatography, using an SCX column. The desired product was eluted from the column using 7M NH3/MeOH to afford impure material. The concentrated eluent was purified by preparative HPLC, using decreasingly polar mixtures of water (containing 1% NH3) and MeCN as eluents. Fractions containing the desired compound were evaporated to dryness to afford the title compound (45 mg, 9%) as a cream solid.

1H NMR (399.9 MHz, DMSO-d6) δ 0.39 (2H, t), 0.46-0.48 (2H, m), 1.67-1.70 (1H, m), 2.66 (4H, q), 2.88 (4H, s), 3.69-3.72 (4H, m), 3.72 (6H, s), 6.33 (1H, t), 6.42 (2H, d), 6.46 (1H, s), 8.35 (1H, d), 8.71 (1H, d), 9.76 (1H, s), 12.18 (1H, s). MS: m/z 478 (MH+).

Mean of n=1, FGFR Kinase assay—Caliper Echo Dosing, $IC_{50}$ 0.0023 μM.

5-Chloro-N-[5-[2-(3,5-dimethoxyphenyl)ethyl]-2H-pyrazol-3-yl]pyrazine-2-carboxamide was prepared as shown in Example 105.

Example 114

5-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]pyrazine-2-carboxamide 1,2,3,4,6,7,8,8a-Octahydropyrrolo[1,2-a]pyrazine (429 mg, 3.40 mmol) was added in one portion to 5-chloro-N-[5-[2-(3,5-dimethoxyphenyl)ethyl]-2H-pyrazol-3-yl]pyrazine-2-carboxamide (659 mg, 1.70 mmol) in anhydrous dimethylsulfoxide (1.70 ml) at 25° C. The resulting solution was stirred at 100° C. for 18 h. The crude product was purified by ion exchange chromatography, using a SCX column. The desired product was eluted from the column using 7M NH3/MeOH to afford impure material. The concentrated eluent was purified by preparative HPLC, using decreasingly polar mixtures of water (containing 1% TFA) and MeCN as eluents. The material was then put through basic HPLC to obtain the free base. Fractions containing the desired compound were evaporated to dryness to afford the title compound (438 mg, 54%) as a cream solid.

1H NMR (399.9 MHz, DMSO-d6) δ 1.35-1.45 (1H, m), 1.63-1.80 (2H, m), 1.82-1.91 (1H, m), 1.93-2.01 (1H, m), 2.09 (1H, q), 2.16-2.20 (1H, m), 2.70-2.76 (1H, m), 2.88 (4H, s), 3.04-3.11 (3H, m), 3.72 (6H, s), 4.47 (1H, d), 4.63 (1H, d), 6.33 (1H, t), 6.42 (2H, d), 6.47 (1H, s), 8.36 (1H, d), 8.71 (1H, d), 9.76 (1H, s), 12.18 (1H, s). MS: m/z 478 (MH+).

Mean of n=1, FGFR Kinase assay—Caliper Echo Dosing, IC$_{50}$ 0.0016 µM.

5-Chloro-N-[5-[2-(3,5-dimethoxyphenyl)ethyl]-2H-pyrazol-3-yl]pyrazine-2-carboxamide was prepared as shown in Example 105.

Example 115

5-(1,3,4,6,7,8,9,9a-Octahydropyrido[2,1-c]pyrazin-2-yl)-N-[5-[(3,5-dimethoxyphenyl)methoxy]-2H-pyrazol-3-yl]pyrazine-2-carboxamide 5-Chloro-N-[5-[(3,5-dimethoxyphenyl)methoxy]-2H-pyrazol-3-yl]pyrazine-2-carboxamide (585 mg, 1.50 mmol) was added in one portion to 2,3,4,6,7,8,9,9a-octahydro-1H-pyrido[1,2-a]pyrazine, HCl (530 mg, 3.00 mmol) and N-ethyl-N-propan-2-ylpropan-2-amine (1.04 ml, 6.00 mmol) in anhydrous dimethylsulfoxide (1.50 ml) at 25° C. The resulting solution was stirred at 100° C. for 18 h. The crude product was purified by ion exchange chromatography, using an SCX column. The desired product was eluted from the column using 7M NH3/MeOH to afford impure material. The concentrated eluent was purified by preparative HPLC, using decreasingly polar mixtures of water (containing 1% NH3) and MeCN as eluents. Fractions containing the desired compound were evaporated to dryness to afford the title compound (302 mg, 41%) as a cream solid.

1H NMR (399.9 MHz, DMSO-d6) δ 1.21-1.29 (2H, m), 1.49-1.67 (1H, m), 1.60-1.64 (2H, m), 1.74 (1H, d), 1.90 (1H, t), 1.93-2.00 (1H, m), 2.10-2.17 (1H, m), 2.67-2.73 (1H, m), 2.82 (2H, d), 3.06-3.13 (1H, m), 3.75 (6H, s), 4.38 (1H, d), 4.46 (1H, d), 5.08 (2H, s), 5.84 (1H, s), 6.44 (1H, s), 6.59 (2H, d), 8.34 (1H, s), 8.71 (1H, s), 10.79 (1H, s), 11.35 (1H, s). MS: m/z 494 (MH+)

Mean of n=1, FGFR Kinase assay—Caliper Echo Dosing, IC$_{50}$ 0.0023 µM.

5-Chloro-N-[5-[(3,5-dimethoxyphenyl)methoxy]-2H-pyrazol-3-yl]pyrazine-2-carboxamide was prepared as outlined in Example 109.

Example 116

4-(4-cyclopropylpiperazin-1-yl)-N-[5-[(3,5-dimethoxyphenyl)methoxy]-2H-pyrazol-3-yl]benzamide 4-(4-Cyclopropylpiperazin-1-yl)-N-[5-[(3,5-dimethoxyphenyl)methoxy]-2H-pyrazol-3-yl]benzamide was prepared following the procedure as outlined for Example 100, starting from ethyl 4-(4-cyclopropylpiperazin-1-yl)benzoate (0.329 g, 1.2 mmol), 5-[(3,5-dimethoxyphenyl)methoxy]-2H-pyrazol-3-amine hydrochloride (0.343 g, 1.20 mmol) and 2M trimethylaluminium in toluene (1.500 mL, 3.00 mmol). The crude product was purified by preparative HPLC, using decreasingly polar mixtures of water (containing 1% NH3) and MeCN as eluents. Fractions containing the desired compound were evaporated to dryness to afford the title compound (0.022 g, 3.84%) as a white solid. 1H NMR (500.13 MHz, DMSOd6) δ 0.34-0.40 (2H, m), 0.45-0.50 (2H, m), 1.67-1.75 (1H, m), 2.67-2.73 (4H, m), 3.24-3.32 (4H, m), 3.78 (6H, s), 5.08 (2H, s), 5.68 (1H, s), 6.42-6.46 (1H, m), 6.58-6.61 (2H, m), 6.95 (2H, d), 7.83 (2H, d), 10.30 (1H, s), 11.01 (1H, s). MS: m/z 478 (MH+).

Mean of n=1, FGFR Kinase assay—Caliper Echo Dosing, IC$_{50}$ 0.00093 µM.

Ethyl 4-(4-cyclopropylpiperazin-1-yl)benzoate used as starting material was prepared following the procedure as outlined for ethyl 4-((3R,5S)-3,5-dimethylpiperazin-1-yl)benzoate (Example 100), starting from ethyl 4-fluorobenzoate (0.880 mL, 6 mmol) and 1-cyclopropylpiperazine (1.666 g, 13.20 mmol) in DMSO (15 mL) The crude product was purified by silica column chromatography, eluting with a gradient of 0 to 8% 2.5M ammonia/MeOH in DCM. Pure fractions were evaporated to dryness to afford the desired compound (1.405 g, 85%) as a beige solid.

1H NMR (399.9 MHz, CDCl3) δ 0.43-0.52 (4H, m), 1.34-1.39 (3H, m), 1.63-1.68 (1H, m), 2.75 (4H, t), 3.29 (4H, t), 4.32 (2H, q), 6.84-6.88 (2H, m), 7.90-7.97 (2H, m). MS: m/z 275 (MH+).

1-Cyclopropylpiperazine used as starting material was prepared as follows:

1-Cyclopropylpiperazine dihydrochloride (1.493 g, 7.5 mmol) was dissolved in water (5.00 mL) and methanol (5.00 mL) and converted to its freebase by ion exchange chromatography, using an SCX column. The desired product was eluted from the column using 3.5M ammonia in methanol and pure fractions were evaporated to dryness to afford 1-cyclopropylpiperazine (0.796 g, 84%) as an oil.

1H NMR (399.9 MHz, CDCl3) δ 0.31-0.39 (4H, m), 1.51-1.56 (1H, m), 1.63-1.67 (1H, m), 2.51 (4H, s), 2.77 (4H, t).

1-Cyclopropylpiperazine dihydrochloride was prepared as follows:

4.0M HCl in dioxane (42.7 mL, 170.78 mmol) was added to a stirred solution of tert-butyl 4-cyclopropylpiperazine-1-carboxylate (7.73 g, 34.16 mmol) in a mixture of methanol (50.0 mL) and ethyl acetate (200 mL). The resulting suspension was stirred at room temperature for 24 h under nitrogen. The white solid filtered off to give 1-cyclopropylpiperazine dihydrochloride (6.30 g, 93%).

1H NMR (399.9 MHz, DMSO-d6) δ 0.73-0.86 (2H, m), 1.07-1.18 (2H, m), 2.85-2.99 (1H, m), 3.30-3.40 (4H, m), 3.52-3.65 (4H, m), 9.89 (2H, s), 11.99 (1H, s).

tert-Butyl 4-cyclopropylpiperazine-1-carboxylate was prepared as follows:

A solution of tert-butyl piperazine-1-carboxylate (9.31 g, 50 mmol), [(1-ethoxycyclopropyl)oxy]trimethylsilane (20.11 mL, 100.00 mmol) and acetic acid(14.31 mL, 250.00 mmol) in tetrahydrofuran (100 mL), methanol (10 mL) was treated with sodium cyanoborohydride (4.71 g, 75.00 mmol) at 20° C. The resulting solution was stirred at 60° C. for 18 h. The reaction mixture was cooled, filtered and evaporated to dryness. 1N HCl (40 ml) and water (60 ml) were added and the solution extracted with ethyl acetate (3×50 ml). The aqueous layer was basified to pH 10 with solid potassium carbonate and extracted with ethyl acetate (4×50 ml). The organic extracts were washed with saturated sodium chloride solution (50 ml) and dried over MgSO$_4$, filtered and evaporated to dryness to give tert-butyl 4-cyclopropylpiperazine-1-carboxylate (7.73 g, 68.3%) as a white waxy solid.

$^1$H NMR (399.9 MHz, CDCl3) δ 0.33-0.40 (4H, m), 1.39 (9H, s), 1.52-1.55 (1H, m), 2.48 (4H, t), 3.31 (4H, t).

5-[(3,5-Dimethoxyphenyl)methoxy]-2H-pyrazol-3-amine hydrochloride, used as starting material was prepared as in Example 12.

Example 117

N-[5-[2-(3,5-Dimethoxyphenyl)ethyl]-2H-pyrazol-3-yl]-4-(4-methyl-4-oxidopiperazin-4-ium-1-yl)benzamide 3-Chloroperoxybenzoic acid (129 mg, 0.53 mmol) was added in one portion to N-[5-[2-(3,5-dimethoxyphenyl)ethyl]-2H-pyrazol-3-yl]-4-(4-methylpiperazin-1-yl)benzamide (225 mg, 0.50 mmol) in acetone (15 mL) at ambient temperature. The resulting solution was stirred at ambient temperature for 2 h. The reaction mixture was concentrated onto silica and the crude product was purified by silica column chromatography, eluting with a gradient of 0 to 10% 7M NH3/MeOH in DCM to 100% methanol. The residue was further purified by ion exchange chromatography, using an SCX column. The desired product was eluted from the column using 7M NH3/MeOH and evaporated to dryness to afford the title compound (183 mg, 79%) as a cream solid.

1H NMR (700.034 MHz, DMSO) δ 2.85 (4H, s), 2.94 (2H, d), 3.09 (3H, s), 3.44 (2H, td), 3.53 (2H, td), 3.65 (2H, d), 3.70 (6H, s), 6.31 (1H, t), 6.37 (1H, s), 6.40 (2H, d), 7.00 (2H, d), 7.90 (2H, d), 10.37 (1H, s), 12.00 (1H, s). MS: m/z 466 (MH+)

Mean of n=1, FGFR Kinase assay—Caliper Echo Dosing, $IC_{50}$ 0.0013 µM.

N-[5-[2-(3,5-dimethoxyphenyl)ethyl]-2H-pyrazol-3-yl]-4-(4-methylpiperazin-1-yl)benzamide was prepared as outlined in Example 10.

Example 118

4-(4-Cyclobutylpiperazin-1-yl)-N-[5-[(3,5-dimethoxyphenyl)methoxy]-2H-pyrazol-3-yl]benzamide 4-(4-Cyclobutylpiperazin-1-yl)-N-[5-[(3,5-dimethoxyphenyl)methoxy]-2H-pyrazol-3-yl]benzamide was prepared following the procedure as outlined for Example 100, starting from 5-[(3,5-dimethoxyphenyl)methoxy]-2H-pyrazol-3-amine (0.173 g, 0.69 mmol), ethyl 4-(4-cyclobutylpiperazin-1-yl)benzoate (0.2 g, 0.69 mmol) and a 2M solution of trimethylaluminium in toluene (1.387 mL, 2.77 mmol) in toluene (10 ml) at room temperature for 20 h. The reaction mixture was poured into acetone (20 mL), quenched with excess damp sodiumsulphite, filtered and evaporated to afford a yellow solid. Acetonitrile (10 ml) was added and this was filtered to afford the title compound (0.079 g, 23.17%) as a white solid.

1H NMR (399.9 MHz, DMSO-d6) δ 1.63-1.66 (1H, m), 1.67-1.70 (1H, m), 1.78-1.89 (2H, m), 1.97-2.03 (2H, m), 2.38 (4H, t), 2.75 (1H, t), 3.75 (6H, s), 5.08 (2H, s), 5.58 (1H, s), 6.45 (1H, s), 6.60-6.60 (2H, m), 7.01 (2H, d), 7.86 (2H, d), 10.61 (1H, s), 11.49 (1H, s). MS: m/z 492 (MH+).

Mean of n=2, FGFR Kinase assay—Caliper Echo Dosing, $IC_{50}$ 0.0011 µM.

Ethyl 4-(4-cyclobutylpiperazin-1-yl)benzoate used as starting material was prepared as follows:

Ethyl 4-fluorobenzoate (0.753 g, 4.48 mmol) was added to a solution of 1-cyclobutylpiperazine (0.571 g, 4.07 mmol) and potassium carbonate (0.563 g, 4.07 mmol) in DMSO (8 mL) under nitrogen. The resulting solution was stirred at 100° C. for 18 h and evaporated to dryness. The residue was triturated with diethyl ether, filtered, and evaporated and the crude product was purified by silica column chromatography, eluting with a gradient of 0 to 2.5% 2.5N MeOH in DCM. Pure fractions were evaporated to dryness to afford ethyl 4-(4-cyclobutylpiperazin-1-yl)benzoate (0.387 g, 32.9%) as a white solid.

1H NMR (399.9 MHz, DMSO-d6) δ 1.28-1.32 (3H, t), 1.62-1.70 (2H, m), 1.77-1.88 (2H, m), 1.95-2.04 (2H, m), 2.35-2.39 (4H, t), 2.70-2.78 (1H, m), 3.28-3.32 (4H, t), 4.22-4.27 (2H, m), 6.96-6.98 (2H, d), 7.66-7.80 (2H, d). MS: m/z 289 (MH+).

1-Cyclobutylpiperazine used as starting material was prepared as follows:

Water (0.15 mL), cyclobutanone (1 g, 14.27 mmol) and acetic acid (1.742 mL, 30.44 mmol) were added to a stirred solution of tert-butyl piperazine-1-carboxylate (1.772 g, 9.51 mmol) in THF (20 mL) under nitrogen. Sodium cyanoborohydride (0.897 g, 14.27 mmol) was added portion wise over a period of 10 mins. The resulting mixture was stirred at 60° C. for 20 h. The reaction mixture was evaporated to dryness and mixed with water (40 mL) and 1M HCl (15 mL). The solution was washed with EtOAc (2×25 mL), basified with solid $K_2CO_3$ and extracted with EtOAc (2×15 mL). The organic layer was washed with saturated brine and dried over MgSO4, filtered and evaporated to afford pure tert-butyl 4-cyclobutylpiperazine-1-carboxylate (1.155 g, 50.5%) as a colourless oil.

1H NMR (399.9 MHz, DMSO-d6) δ 1.40 (9H, s), 1.62-1.65 (2H, m), 1.75-1.80 (2H, m), 1.92-1.98 (2H, m), 2.17 (4H, t), 2.68 (1H, t), 3.28-3.30 (4H, s).

A solution of tert-butyl 4-cyclobutylpiperazine-1-carboxylate (1.1553 g, 4.81 mmol) in ethyl acetate (10 mL) and methanol (10.00 mL) was treated with a 4M-solution hydrogen chloride in dioxane (1.669 mL, 48.07 mmol) was stirred at room temperature for 40 h under nitrogen. The reaction was incomplete so f 4M-solution hydrogen chloride in dioxane (10 mL) was added and the solution was stirred at room temperature for a further 2 h. The reaction mixture was evaporated to dryness to afford a solid. The crude product was purified by ion exchange chromatography, using a SCX column. The desired product was eluted from the column using 3.5M NH3/MeOH and pure fractions were evaporated to dryness to afford 1-cyclobutylpiperazine (0.571 g, 85%) as a yellow oil.

1H NMR (399.9 MHz, DMSO-d6) δ 1.64 (2H, s), 1.74-1.75 (2H, m), 1.92 (2H, s), 2.14 (4H, s), 2.63-2.66 (4H, m), 3.18 (1H, s).

Example 119

2-(1,3,4,6,7,8,9,9a-Octahydropyrido[2,1-c]pyrazin-2-yl)-N-[5-[(3,5-dimethoxyphenyl)methoxy]-2H-pyrazol-3-yl]pyrimidine-5-carboxamide Trimethylaluminium (2M in toluene, 2.15 mL, 4.30 mmol) was added dropwise to a stirred suspension of 5-[(3,5-dimethoxyphenyl)methoxy]-2H-pyrazol-3-amine, HCl (491 mg, 1.72 mmol) and methyl 2-(1,3,4,6,7,8,9,9a-octahydropyrido [2,1-c]pyrazin-2-yl)pyrimidine-5-carboxylate (475 mg, 1.72 mmol) in toluene (8.6 mL) at 25° C. The resulting solution was stirred at ambient temperature for 18 h and then at 60° C. for 2 h. The reaction mixture was cautiously quenched with methanol (20 mL) and treated with HCl (2N aqueous solution, until a freely stirred solution was obtained). The crude product was purified by ion exchange chromatography, using an SCX column. The desired product was eluted from the column using 7M NH3/MeOH and evaporated to dryness to afford crude product. The impure material was purified by preparative HPLC, using decreasingly polar mixtures of water (containing 0.1% NH3) and MeCN as eluents. Fractions containing the desired compound were evaporated to dryness to afford the title compound (361 mg, 43%) as a solid.

1H NMR (500.13 MHz, DMSO-d6, 373K) δ 1.21-1.27 (1H, m), 1.28-1.35 (1H, m), 1.52-1.59 (1H, m), 1.59-1.64 (2H, m), 1.76 (1H, d), 1.85-1.91 (1H, m), 1.98-2.03 (1H, m), 2.10-2.15 (1H, m), 2.68-2.73 (1H, m), 2.80-2.84 (2H, m), 3.08-3.13 (1H, m), 3.78 (6H, s), 4.57-4.61 (1H, m), 4.67-4.71

(1H, m), 5.11 (2H, s), 5.70 (1H, s), 6.46 (1H, t), 6.62 (2H, d), 8.86 (2H, s), 10.30 (1H, s), 11.30 (1H, s). MS: m/z 494 (MH+).

Mean of n=2, FGFR Kinase assay—Caliper Echo Dosing, $IC_{50}$ 0.0033 μM.

Methyl 2-(1,3,4,6,7,8,9,9a-octahydropyrido[2,1-c]pyrazin-2-yl)pyrimidine-5-carboxylate was prepared as outlined in Example 127.

5-[(3,5-Dimethoxyphenyl)methoxy]-2H-pyrazol-3-amine, HCl was prepared as outlined in Example 12.

Example 120

5-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]thiophene-2-carboxamide 2M Trimethylaluminium (1.525 ml, 3.05 mmol) in toluene, was added dropwise to a stirred solution of ethyl 5-(3,4,6,7,8,8a-hexahydro-1H-pyrrolo[2,1-c]pyrazin-2-yl)thiophene-2-carboxylate (0.342 g, 1.22 mmol) and 5-[2-(3,5-dimethoxyphenyl)ethyl]-2H-pyrazol-3-amine (0.302 g, 1.22 mmol) in toluene (8.71 ml) at 20° C. under nitrogen. The reaction mixture was stirred at ambient temperature for 18 h and then stirred and heated at 65° C. for 20 h. Ethyl acetate (5 mL) was added carefully to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow gum, 640 mg. The crude product was purified by preparative HPLC, using decreasingly polar mixtures of water (containing 1% TFA) and MeCN as eluents. Fractions containing the desired compound were evaporated to dryness to afford the TFA salt of the product. This was dissolved in methanol and purified by ion exchange chromatography, using a SCX2 column. The desired product was eluted from the column using 2M NH3 in methanol and pure fractions were evaporated to dryness then triturated with acetonitrile to afford the title compound (0.174 g, 29.6%) as a solid.

1H NMR (500.13 MHz, DMSO-d6, CD3CO2D) δ 1.41-1.43 (1H, m), 1.73-1.78 (2H, m), 1.87-1.91 (2H, m), 2.16-2.23 (2H, m), 2.34-2.38 (1H, m), 2.68-2.72 (1H, m), 2.89 (4H, s), 3.00-3.08 (3H, m), 3.50-3.53 (1H, m), 3.66-3.69 (1H, m), 3.74 (6H, d), 6.12 (1H, d), 6.25 (1H, s), 6.33 (1H, t), 6.41 (2H, d), 7.70 (1H, t); MS: m/z 482 (MH+)

Mean of n=1, FGFR Kinase assay—Caliper Echo Dosing, $IC_{50}$ 0.00098 μM.

Ethyl 5-(3,4,6,7,8,8a-hexahydro-1H-pyrrolo[2,1-c]pyrazin-2-yl)thiophene-2-carboxylate, used as starting material was prepared as follows:

Palladium(II) acetate (0.112 g, 0.50 mmol) was added to ethyl 5-bromothiophene-2-carboxylate (1.175 g, 5 mmol), 1,2,3,4,6,7,8,8a-octahydropyrrolo[1,2-a]pyrazine (0.631 g, 5.00 mmol), rac-2,2'-Bis(diphenylphosphino)-1,1'-binaphthyl (0.311 g, 0.50 mmol) and cesium carbonate (2.281 g, 7.00 mmol) in toluene (50.0 ml) at 20° C. under nitrogen. The resulting suspension was stirred at 110° C. for 23 h. The mixture was filtered through celite washing through with ethyl acetate and the filtrate was evaporated to dryness to give a brown oil. The crude product was purified by ion exchange chromatography, using a SCX2 column. The crude material was dissolved in methanol and then applied to the column. The desired product was eluted from the column using 2M NH3 in methanol and pure fractions were evaporated to dryness to afford the crude product as a brown solid. This material was further purified by silica column chromatography, eluting with a gradient of 0 to 4% MeOH in DCM. Pure fractions were evaporated to dryness to afford the desired compound (0.727 g, 51.9%) as a white solid.

1H NMR (399.9 MHz, CDCl3) δ 1.33 (3H, t), 1.43-1.53 (1H, m), 1.63 (1H, s), 1.73-1.93 (3H, m), 2.10-2.22 (2H, m), 2.33-2.40 (1H, m), 2.74 (1H, t), 3.07-3.16 (3H, m), 3.51-3.55 (1H, m), 3.67-3.71 (1H, m), 4.28 (2H, q), 6.01 (1H, d), 7.55 (1H, d) MS: m/z 281 (MH+)

5-[2-(3,5-dimethoxyphenyl)ethyl]-2H-pyrazol-3-amine, used as starting material was prepared as indicated in Example 2.

Example 121

5-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]thiophene-2-carboxamide 2M Trimethylaluminium (1.525 ml, 3.05 mmol) in toluene, was added dropwise to a stirred solution of ethyl 5-(3,4,6,7,8,8a-hexahydro-1H-pyrrolo[2,1-c]pyrazin-2-yl)thiophene-2-carboxylate (0.342 g, 1.22 mmol) and 5-[(3,5-dimethoxyphenyl)methoxy]-2H-pyrazol-3-amine (0.304 g, 1.22 mmol) in toluene (8.71 ml) at 20° C. under nitrogen. The reaction mixture was stirred at room temperature for 18 h and then heated at 65° C. for 6 h.

Ethyl acetate (5 mL) was added to the reaction mixture followed by a solution of potassium is sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow gum. The crude product was purified by preparative LCMS, using decreasingly polar mixtures of water (containing 1% TFA) and MeCN as eluents. Fractions containing the desired compound were evaporated to dryness to afford the TFA salt of the product. This was dissolved in methanol and purified by ion exchange chromatography, using a SCX2 column. The desired product was eluted from the column using 2M NH3 in methanol and pure fractions were evaporated to dryness then triturated with 25 ethanol to afford the title compound (0.266 g, 45.1%) as a white solid.

1H NMR (500.13 MHz, DMSO-d6, CD3CO2D) δ 1.40-1.44 (1H, m), 1.72-1.80 (2H, m), 1.85-1.90 (2H, m), 2.17-2.22 (2H, m), 2.34-2.39 (1H, m), 2.73 (1H, t), 3.03-3.09 (3H, m), 3.52-3.54 (1H, m), 3.67-3.70 (1H, m), 3.77 (6H, s), 5.09 (2H, s), 5.62 (1H, s), 6.16 (1H, d), 6.45 (1H, t), 6.60 (2H, d), 7.64 (1H, d); MS: m/z 484 (MH+)

Mean of n=1, FGFR Kinase assay—Caliper Echo Dosing, $IC_{50}$ 0.00079 μM.

Ethyl 5-(3,4,6,7,8,8a-hexahydro-1H-pyrrolo[2,1-c]pyrazin-2-yl)thiophene-2-carboxylate is prepared as outlined in Example 120.

5-[(3,5-Dimethoxyphenyl)methoxy]-2H-pyrazol-3-amine, used as starting material was prepared as in Example 100.

Example 122

5-(3,4,6,7,8,8a-Hexahydro-1H-pyrrolo[2,1-c]pyrazin-2-yl)-N-[5-[(3,5-dimethoxyphenyl)methoxy]-2H-pyrazol-3-yl]pyrazine-2-carboxamide 5-Chloro-N-[5-[(3,5-dimethoxyphenyl)methoxy]-2H-pyrazol-3-yl]pyrazine-2-carboxamide (585 mg, 1.50 mmol)

was added in one portion to 1,2,3,4,6,7,8,8a-octahydropyrrolo[1,2-a]pyrazine (379 mg, 3.00 mmol) in anhydrous dimethylsulfoxide (1.50 ml) at 25° C. The resulting solution was stirred at 100° C. for 18 h. The residue was purified by ion exchange chromatography, using an SCX column. The desired product was eluted from the column using 7M NH3/MeOH to afford impure material. The concentrated eluent was purified by preparative HPLC, using decreasingly polar mixtures of water (containing 1% NH3) and MeCN as eluents. Fractions containing the desired compound were evaporated to dryness to afford impure product as a yellow solid. The impure material was then repurified by silica column chromatography, eluting with a gradient of 0 to 5% 7M NH3/MeOH in DCM. Pure fractions were evaporated to dryness to afford the title compound (269 mg, 37%) as a yellow solid.

1H NMR (500.133 MHz, DMSO, 373K) δ 1.38-1.46 (1H, m), 1.67-1.82 (2H, m), 1.85-1.91 (1H, m), 2.04-2.10 (1H, m), 2.17 (1H, q), 2.22-2.29 (1H, m), 2.78 (1H, dd), 3.02-3.16 (3H, m), 3.76 (6H, s), 4.41 (1H, d), 4.57 (1H, d), 5.09 (2H, s), 5.85 (1H, s), 6.44 (1H, s), 6.59 (2H, d), 8.26 (1H, d), 8.71 (1H, s), 10.42 (1H, s), 11.13 (1H, s). MS: m/z 480 (MH+).

Mean of n=1, FGFR Kinase assay—Caliper Echo Dosing, $IC_{50}$ 0.0013 µM.

5-Chloro-N-[5-[(3,5-dimethoxyphenyl)methoxy]-2H-pyrazol-3-yl]pyrazine-2-carboxamide was prepared as shown in Example 109.

Example 123

N-[5-[2-(3,5-Dimethoxyphenyl)ethyl]-2H-pyrazol-3-yl]-5-(3,4-dimethylpiperazin-1-yl)pyrazine-2-carboxamide 5-Chloro-N-[5-[2-(3,5-dimethoxyphenyl)ethyl]-2H-pyrazol-3-yl]pyrazine-2-carboxamide (388 mg, 1.00 mmol) was added in one portion to 1,2-dimethyl-piperazine (228 mg, 2.00 mmol) in anhydrous dimethylsulfoxide (2.00 ml) at 25° C. The resulting solution was stirred at ambient temperature for 2 h. The residue was purified by ion exchange chromatography, using an SCX column. The desired product was eluted from the column using 7M NH3/MeOH to afford impure material. The concentrated eluent was purified by silica column chromatography, eluting with a gradient of 0 to 10% 7M NH3/MeOH in DCM. Pure fractions were evaporated to dryness to afford the title compound (375 mg, 81%) as a yellow solid.

1H NMR (399.9 MHz, DMSO-d6) δ 1.07-1.09 (3H, d), 2.06-2.20 (2H, m), 2.23 (3H, s), 2.76-2.86 (2H, m), 2.87 (4H, s), 3.13-3.19 (1H, m), 3.72 (6H, s), 4.27-4.30 (2H, m), 6.33 (1H, t), 6.42 (2H, d), 6.46 (1H, s), 8.35 (1H, d), 8.70 (1H, d), 9.75 (1H, s), 12.18 (1H, s). MS: m/z 466 (MH+).

Mean of n=1, FGFR Kinase assay—Caliper Echo Dosing, $IC_{50}$ 0.0022 µM.

5-Chloro-N-[5-[2-(3,5-dimethoxyphenyl)ethyl]-2H-pyrazol-3-yl]pyrazine-2-carboxamide was prepared as shown in Example 105.

Example 124

N-[5-[(3,5-Dimethoxyphenyl)methoxy]-2H-pyrazol-3-yl]-5-(3,4-dimethylpiperazin-1-yl)pyrazine-2-carboxamide 5-Chloro-N-[5-[(3,5-dimethoxyphenyl)methoxy]-2H-pyrazol-3-yl]pyrazine-2-carboxamide (390 mg, 1.00 mmol) was added in one portion to 1,2-dimethyl-piperazine (228 mg, 2.00 mmol) in anhydrous dimethylsulfoxide (2.00 ml) at 25° C. The resulting solution was stirred at ambient temperature for 2 h. The residue was purified by ion exchange chromatography, using an SCX column. The desired product was eluted from the column using 7M NH3/MeOH to afford impure material. The concentrated eluent was purified by silica column chromatography, eluting with a gradient of 0 to 10% 7M NH3/MeOH in DCM. Pure fractions were evaporated to dryness to afford the title compound (392 mg, 84%) as a yellow solid.

1H NMR (399.902 MHz, DMSO) δ 1.08 (3H, d), 2.06-2.12 (1H, m), 2.18 (1H, td), 2.23 (3H, s), 2.77-2.88 (2H, m), 3.14-3.21 (1H, m), 3.75 (6H, s), 4.32 (2H, t), 5.08 (2H, s), 5.84 (1H, s), 6.44 (1H, t), 6.59 (2H, d), 8.34 (1H, s), 8.71 (1H, s), 10.79 (1H, s), 11.35 (1H, s). MS: m/z 468 (MH+).

Mean of n=1, FGFR Kinase assay—Caliper Echo Dosing, $IC_{50}$ 0.0015 µM.

5-Chloro-N-[5-[(3,5-dimethoxyphenyl)methoxy]-2H-pyrazol-3-yl]pyrazine-2-carboxamide was prepared as outlined in Example 109.

Example 125

N-[5-[2-(3,5-dimethoxyphenyl)ethyl]-2H-pyrazol-3-yl]-5-[(3R,5S)-3,4,5-trimethylpiperazin-1-yl]pyrazine-2-carboxamide 5-Chloro-N-[5-[2-(3,5-dimethoxyphenyl)ethyl]-2H-pyrazol-3-yl]pyrazine-2-carboxamide (271 mg, 0.70 mmol) was added in one portion to a 3:1 mixture of (2R,6S)-1,2,6-trimethylpiperazine and 2-[(2S,6R)-2,6-dimethylpiperazin-1-yl]acetonitrile (180 mg, 1.40 mmol) in anhydrous dimethylsulfoxide (1.40 ml) at 25° C. The resulting solution was stirred at ambient temperature for 2 h. The reaction was incomplete and N-ethyl-N-propan-2-ylpropan-2-amine (0.24 ml, 1.40 mmol) was added and the solution was stirred at 60° C. for a further 2 h. The reaction mixture was diluted with methanol (20 mL) and purified by ion exchange chromatography, using an SCX column. The desired product was eluted from the column using 7M NH3/MeOH to afford impure material. The concentrated eluent was purified by silica column chromatography, eluting with a gradient of 0 to 5% 7M NH3/MeOH in DCM. Pure fractions were evaporated to dryness to afford the title compound (246 mg, 73%) as a yellow solid.

1H NMR (399.9 MHz, DMSO-d6) δ 1.10-1.12 (6H, d), 2.15-2.21 (2H, m), 2.20 (3H, s), 2.75 (2H, t), 2.88 (4H, s), 3.72 (6H, s), 4.37 (2H, d), 6.33 (1H, s), 6.42-6.43 (2H, m), 6.46 (1H, s), 8.37 (1H, s), 8.70 (1H, s), 9.75 (1H, s), 12.18 (1H, s). MS: m/z 480 (MH+).

Mean of n=1, FGFR Kinase assay—Caliper Echo Dosing, $IC_{50}$ 0.0017 µM.

5-Chloro-N-[5-[2-(3,5-dimethoxyphenyl)ethyl]-2H-pyrazol-3-yl]pyrazine-2-carboxamide was prepared as shown in Example 105.

3:1 mixture of (2R,6S)-1,2,6-trimethylpiperazine and 2-[(2S,6R)-2,6-dimethylpiperazin-1-yl]acetonitrile used as starting material was prepared as follows;

Macroporous triethylammonium methylpolystyrene cyanoborohydride (2.31 mmol/g, 5.05 g, 11.67 mmol) was added to cis-3,5-dimethyl-piperazine-1-carboxylic acid tert-butyl ester (1.00 g, 4.67 mmol), 37% aqueous formaldehyde (6.99 ml, 93.33 mmol) and acetic acid (0.53 ml, 9.33 mmol) in methanol (9.33 ml) at 25° C. The resulting suspension was stirred under nitrogen at ambient temperature for 24 h. The macroporous triethylammonium methylpolystyrene cyanoborohydride was removed by filtration, washing with methanol (50 mL). The filtrate was purified by ion exchange chromatography, using an SCX column. The desired product was eluted from the column using 7M NH3/MeOH and evaporated to dryness.

The residue was taken up in ethyl acetate (21.00 mL) and methanol (10.00 mL) and treated with hydrogen chloride (4M in 1,4-dioxane, 4.21 ml, 16.84 mmol) at 25° C. under nitrogen. The resulting solution was stirred at ambient temperature for 3 days. The crude product was purified by ion exchange chromatography, using an SCX column. The desired product was eluted from the column using 7M NH3/MeOH and evaporated to dryness to afford a 3:1 mixture of (2R,6S)-1,2,6-trimethylpiperazine and 2-[(2S,6R)-2,6-dimethylpiperazin-1-yl]acetonitrile (645 mg, quant.) as a colourless oil. This was used directly with no further purification.

Example 126

2-(4-cyclopropylpiperazin-1-yl)-N-[5-[2-(3,5-dimethoxyphenyl)ethyl]-2H-pyrazol-3-yl]pyrimidine-5-carboxamide Trimethylaluminium (2M in toluene, 1.92 mL, 3.85 mmol) was added dropwise to a stirred suspension of 5-[2-(3,5-dimethoxyphenyl)ethyl]-2H-pyrazol-3-amine (381 mg, 1.54 mmol) and methyl 2-(4-cyclopropylpiperazin-1-yl)pyrimidine-5-carboxylate (404 mg, 1.54 mmol) in toluene (7.7 mL) at 25° C. The resulting solution was stirred at ambient temperature for 18 h and then heated at 60° C. for 2 h. The reaction mixture was quenched with methanol (20 mL) and treated with HCl (2N aqueous solution). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 0.1% NH3) and MeCN as eluents. Fractions containing the desired compound were evaporated to dryness to afford the title compound (100 mg, 14%) as a solid.

1H NMR (399.9 MHz, DMSO-d6) δ 0.36-0.41 (2H, m), 0.45-0.47 (2H, m), 1.65-1.68 (1H, m), 2.61 (4H, t), 2.88 (4H, s), 3.72 (6H, s), 3.80 (4H, t), 6.33 (1H, t), 6.42 (2H, d), 6.44 (1H, s), 8.90 (2H, s), 10.60 (1H, s), 12.14 (1H, s). MS: m/z 478 (MH+).

Mean of n=1, FGFR Kinase assay—Caliper Echo Dosing, IC$_{50}$ 0.0036 µM.

Methyl 2-(4-cyclopropylpiperazin-1-yl)pyrimidine-5-carboxylate used as starting material was prepared as follows;

A solution of methyl-2-chloropyrimidine-5-carboxylate (900 mg, 5.22 mmol) in dichloromethane (7.50 ml) was added to a stirred suspension of 1-cyclopropylpiperazine, 2HCl (1038 mg, 5.22 mmol) and N-ethyl-N-propan-2-ylpropan-2-amine (4.10 mL, 23.47 mmol) in dichloromethane (13 mL) at room temperature under nitrogen. The resulting solution was stirred at ambient temperature for 18 h. The reaction mixture was poured onto ice (100 mL), extracted with dichloromethane (3×75 mL), the organic layer was dried over MgSO4, filtered and evaporated to afford white solid. The crude product was purified by ion exchange chromatography, using an SCX column. The desired product was eluted from the column using 7M NH3/MeOH and pure fractions were evaporated to dryness to afford the desired compound (880 mg, 64%) as a white solid. This was used directly with no further purification.

1H NMR (399.9 MHz, DMSO-d6) δ 0.36-0.39 (2H, m), 0.45-0.47 (2H, m), 1.65-1.68 (1H, m), 2.61 (4H, t), 3.81 (3H, s), 3.81-3.84 (4H, t), 8.79 (2H, s). MS: m/z 263 (MH+).

5-[2-(3,5-dimethoxyphenyl)ethyl]-2H-pyrazol-3-amine, used as starting material was 25 prepared as indicated in Example 2.

Example 127

2-(1,3,4,6,7,8,9,9a-octahydropyrido[2,1-c]pyrazin-2-yl)-N-[5-[2-(3,5-dimethoxyphenyl)ethyl]-2H-pyrazol-3-yl]pyrimidine-5-carboxamide Trimethylaluminium (2M in toluene, 1.45 mL, 2.90 mmol) was added dropwise to a stirred suspension of 5-[2-(3,5-dimethoxyphenyl)ethyl]-2H-pyrazol-3-amine (286 mg, 1.16 mmol) and methyl 2-(1,3,4,6,7,8,9,9a-octahydropyrido [2,1-c]pyrazin-2-yl)pyrimidine-5-carboxylate (320 mg, 1.16 mmol) in toluene (5.8 mL) at 25° C. The resulting solution was stirred at ambient temperature for 18 h and then at 60° C. for 2 h. The reaction mixture was quenched with methanol (20 mL) and treated with HCl (2N aqueous solution, until a freely stirred solution was obtained). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 0.1% NH3) and MeCN as eluents. Fractions containing the desired compound were evaporated to dryness to afford the title compound (238 mg, 42%) as a solid.

1H NMR (399.9 MHz, DMSO-d6) δ 1.14-1.32 (2H, m), 1.46-1.55 (1H, m), 1.61 (2H, d), 1.73 (1H, d), 1.80-1.83 (1H, m), 1.92-1.99 (1H, m), 2.03-2.10 (1H, m), 2.64-2.70 (1H, m), 2.79 (2H, d), 2.88 (4H, s), 3.02-3.09 (1H, m), 3.72 (6H, s), 4.55-4.59 (1H, m), 4.65-4.68 (1H, m), 6.33 (1H, t), 6.42 (2H, d), 6.44 (1H, s), 8.89 (2H, s), 10.59 (1H, s), 12.15 (1H, s). MS: m/z 492 (MH+).

Mean of n=1, FGFR Kinase assay—Caliper Echo Dosing, IC$_{50}$ 0.0029 µM.

Methyl 2-(1,3,4,6,7,8,9,9a-octahydropyrido[2,1-c] pyrazin-2-yl)pyrimidine-5-carboxylate used as starting material was prepared as follows;

A solution of methyl 2-chloropyrimidine-5-carboxylate (900 mg, 5.22 mmol) in dichloromethane (7.50 ml) was added to a stirred suspension of 2,3,4,6,7,8,9,9a-octahydro-1H-pyrido[1,2-a]pyrazine, HCl (1106 mg, 6.26 mmol) and N-ethyl-N-propan-2-ylpropan-2-amine (3.19 mL, 18.25 mmol) in dichloromethane (13.00 mL) at room temperature under nitrogen. The resulting solution was stirred at ambient temperature for 18 h. The reaction mixture was poured onto ice (50 mL), extracted with DCM (3×50 mL), the organic layer was dried over MgSO4, filtered and evaporated to afford yellow solid. The crude product was purified by crystallisation from IPA to afford the title compound (591 mg, 41%) as a white solid. The filtrate still contained some product and was purified by silica column chromatography, eluting with a gradient of 0 to 10% 7M NH3/MeOH in dichloromethane. Pure fractions were evaporated to dryness to afford a further sample of the title compound (402 mg, 28%) as a white solid.

1H NMR (399.9 MHz, DMSO-d6) δ 1.14-1.30 (2H, m), 1.46-1.55 (1H, m), 1.61 (2H, d), 1.72 (1H, d), 1.81 (1H, t), 1.95 (1H, m), 2.06 (1H, m), 2.67-2.70 (1H, m), 2.80 (2H, d), 3.05-3.12 (1H, m), 3.81 (3H, s), 4.59 (1H, m), 4.68 (1H, d), 8.79 (2H, s). MS: m/z 277 (MH+).

5-[2-(3,5-dimethoxyphenyl)ethyl]-2H-pyrazol-3-amine, used as starting material was prepared as indicated in Example 2.

Example 128

2-(3,4,6,7,8,8a-hexahydro-1H-pyrrolo[2,1-c]pyrazin-2-yl)-N-[5-[2-(3,5-dimethoxyphenyl)ethyl]-2H-pyrazol-3-yl]pyrimidine-5-carboxamide Trimethylaluminium (2M in toluene, 2.55 ml, 5.10 mmol) was added dropwise to a stirred suspension of 5-[2-(3,5-dimethoxyphenyl)ethyl]-2H-pyrazol-3-amine (504 mg, 2.04 mmol) and methyl 2-(3,4,6,7,8,8a-hexahydro-1H-pyrrolo[2,1-c]pyrazin-2-yl)pyrimidine-5-carboxylate (535 mg, 2.04 mmol) in toluene (10.20 ml) at 25° C. The resulting solution was stirred at ambient temperature for 18 h and then at 60° C. for 2 h. The reaction mixture was quenched with methanol (20 mL) and treated with HCl (2N aqueous solution, until a freely stirred solution was obtained). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 0.1% NH3) and MeCN as eluents. Fractions containing the desired compound were evaporated to dryness to afford the title compound (288 mg, 30%) as a solid.

1H NMR (399.9 MHz, DMSO-d6) δ 1.36-1.40 (1H, m), 1.68-1.75 (2H, m), 1.83-1.90 (2H, m), 2.07 (2H, q), 2.67-2.72 (1H, m), 2.88 (4H, s), 3.01-3.08 (3H, m), 3.72 (6H, s), 4.71-4.75 (1H, m), 4.87 (1H, d), 6.33 (1H, t), 6.42 (2H, d), 6.44 (1H, s), 8.90 (2H, s), 10.59 (1H, s), 12.15 (1H, s). MS: m/z 478 (MH+).

Mean of n=1, FGFR Kinase assay—Caliper Echo Dosing, $IC_{50}$ 0.003 μM.

5-[2-(3,5-dimethoxyphenyl)ethyl]-2H-pyrazol-3-amine, used as starting material was 30 prepared as indicated in Example 2.

Methyl 2-(3,4,6,7,8,8a-hexahydro-1H-pyrrolo[2,1-c]pyrazin-2-yl)pyrimidine-5-carboxylate used as starting material was prepared as follows;

A solution of methyl 2-chloropyrimidine-5-carboxylate (1.56 g, 9.04 mmol) in dichloromethane (7.50 ml) was added to a stirred suspension of 1,2,3,4,6,7,8,8a-octahydropyrrolo[1,2-a]pyrazine (1.37 g, 10.85 mmol) and N-ethyl-N-propan-2-ylpropan-2-amine (3.95 ml, 22.60 mmol) in dichloromethane (22.60 ml) at room temperature under nitrogen. The resulting solution was stirred at ambient temperature for 18 h. The reaction mixture was poured onto ice (100 mL), extracted with dichloromethane (3×100 mL), the organic layer was dried over MgSO4, filtered and evaporated to afford a yellow solid. The aqueous layer was purified by ion exchange chromatography, using an SCX column. The desired product was eluted from the column using 7M NH3/MeOH and evaporated to dryness to afford crude product. The combined crude product was purified by silica column chromatography, eluting with a gradient of 0 to 10% 7M NH3/MeOH in dichloromethane. Pure fractions were evaporated to dryness to afford the desired compound (1.36 g, 57%) as a yellow solid.

1H NMR (399.902 MHz, DMSO) δ 1.33-1.44 (1H, m), 1.63-1.78 (2H, m), 1.80-1.93 (2H, m), 2.04-2.11 (2H, m), 2.72 (1H, dd), 3.00-3.09 (3H, m), 3.81 (3H, s), 4.74 (1H, d), 4.88 (1H, d), 8.79 (2H, s). MS: m/z 263 (MH+).

Example 129

5-[(3R,5S)-4-(cyanomethyl)-3,5-dimethylpiperazin-1-yl]-N-[5-[2-(3,5-dimethoxyphenyl)ethyl]-2H-pyrazol-3-yl]pyrazine-2-carboxamide 5-Chloro-N-[5-[2-(3,5-dimethoxyphenyl)ethyl]-2H-pyrazol-3-yl]pyrazine-2-carboxamide (271 mg, 0.70 mmol) was added in one portion to a 3:1 mixture of (2R,6S)-1,2,6-trimethylpiperazine and 2-[(2S,6R)-2,6-dimethylpiperazin-1-yl]acetonitrile (180 mg, 1.40 mmol) in anhydrous dimethylsulfoxide (1.40 ml) at 25° C. The resulting solution was stirred at ambient temperature for 2 h. The reaction was incomplete and N-ethyl-N-propan-2-ylpropan-2-amine (0.24 ml, 1.40 mmol) was added and the solution was stirred at 60° C. for a further 2 h. The reaction mixture was diluted with methanol (20 mL) and purified by ion exchange chromatography, using an SCX column. The desired product was eluted from the column using 7M NH3/MeOH to afford impure material. The concentrated eluent was purified by silica column chromatography, eluting with a gradient of 0 to 5% 7M NH3/MeOH in DCM. Pure fractions were evaporated to dryness to afford the title compound (77 mg, 22%) as a yellow solid.

1H NMR (399.9 MHz, CDCl3) δ 1.22 (6H, d), 2.71-2.79 (2H, m), 2.84 (1H, d), 2.87 (1H, d), 2.90-3.00 (4H, m), 3.77 (6H, s), 3.83 (2H, s), 4.32-4.35 (2H, m), 6.33 (1H, t), 6.36 (2H, d), 6.55 (1H, s), 8.01 (1H, d), 8.92 (1H, d), 9.73 (1H, s), One NH not observed. MS: m/z 505 (MH+).

Mean of n=1, FGFR Kinase assay—Caliper Echo Dosing, $IC_{50}$ 0.0035 μM.

5-Chloro-N-[5-[2-(3,5-dimethoxyphenyl)ethyl]-2H-pyrazol-3-yl]pyrazine-2-carboxamide was prepared as shown in Example 105.

Example 130

N-[5-[(3,5-dimethoxyphenyl)methoxy]-2H-pyrazol-3-yl]-5-[(3R,5S)-3,4,5-trimethylpiperazin-1-yl]pyrazine-2-carboxamide 5-Chloro-N-[5-[(3,5-dimethoxyphenyl)methoxy]-2H-pyrazol-3-yl]pyrazine-2-carboxamide (273 mg, 0.70 mmol) was added in one portion to a 3:1 mixture of (2R,6S)-1,2,6-trimethylpiperazine and 2-[(2S,6R)-2,6-dimethylpiperazin-1-yl]acetonitrile (180 mg, 1.40 mmol) in anhydrous dimethylsulfoxide (1.40 ml) at 25° C. The resulting solution was stirred at ambient temperature for 2 h. The reaction was incomplete and N-ethyl-N-propan-2-ylpropan-2-amine (0.24 ml, 1.40 mmol) was added and the solution was stirred at 60° C. for a further 2 h. The reaction mixture was diluted with methanol (20 mL) and purified by ion exchange chromatography, using an SCX column. The desired product was eluted from the column using 7M NH3/MeOH to afford impure material. The concentrated eluent was purified by silica column chromatography, eluting with a gradient of 0 to 5% 7M NH3/MeOH in DCM. Pure fractions were evaporated to dryness to afford the title compound (248 mg, 74%) as a yellow solid.

1H NMR (500.13 MHz, DMSO-d6, 373K) δ 1.13-1.14 (6H, m), 2.24 (3H, s), 2.25-2.31 (2H, m), 2.81 (1H, d), 2.83 (1H, d), 3.78 (6H, s), 4.30-4.33 (2H, m), 5.11 (2H, s), 5.90 (1H, s), 6.46 (1H, t), 6.62 (2H, d), 8.27 (1H, d), 8.72 (1H, d), 10.3 (1H, s), 11.1 (1H, s). MS: m/z 482 (MH+).

Mean of n=1, FGFR Kinase assay—Caliper Echo Dosing, $IC_{50}$ 0.00059 μM.

5-Chloro-N-[5-[(3,5-dimethoxyphenyl)methoxy]-2H-pyrazol-3-yl]pyrazine-2-carboxamide was prepared as outlined in Example 109.

Example 131

5-[(3R,5S)-4-(cyanomethyl)-3,5-dimethylpiperazin-1-yl]-N-[5-[(3,5-dimethoxyphenyl)methoxy]-2H-pyrazol-3-yl]pyrazine-2-carboxamide 5-Chloro-N-[5-[(3,5-dimethoxyphenyl)methoxy]-2H-pyrazol-3-yl]pyrazine-2-carboxamide (273 mg, 0.70 mmol)

was added in one portion to a 3:1 mixture of (2R,6S)-1,2,6-trimethylpiperazine and 2-[(2S,6R)-2,6-dimethylpiperazin-1-yl]acetonitrile (180 mg, 1.40 mmol) in anhydrous dimethylsulfoxide (1.40 ml) at 25° C. The resulting solution was stirred at ambient temperature for 2 h. The reaction was incomplete and N-ethyldiisopropylamine (0.24 ml, 1.40 mmol) was added and the solution was stirred at 60° C. for a further 2 h. The reaction mixture was diluted with methanol (20 mL) and purified by ion exchange chromatography, using an SCX column. The desired product was eluted from the column using 7M NH3/MeOH to afford impure material. The concentrated eluent was purified by silica column chromatography, eluting with a gradient of 0 to 5% 7M NH3/MeOH in DCM. Pure fractions were evaporated to dryness to afford the title compound (65 mg, 18%) as a yellow solid.

1H NMR (399.9 MHz, CDCl3) δ 1.22 (6H, t), 2.72-2.77 (2H, m), 2.86 (1H, d), 2.89 (1H, d), 3.80 (6H, s), 3.83 (2H, s), 4.33-4.37 (2H, m), 5.18 (2H, s), 5.50 (1H, s), 6.41 (1H, t), 6.61 (2H, d), 7.99 (1H, d), 8.88 (1H, d), 9.62 (1H, s), 10.7 (1H, s). MS: m/z 507 (MH+).

Mean of n=1, FGFR Kinase assay—Caliper Echo Dosing, IC$_{50}$ 0.0035 μM.

5-Chloro-N-[5-[(3,5-dimethoxyphenyl)methoxy]-2H-pyrazol-3-yl]pyrazine-2-carboxamide was prepared as outlined in Example 109.

Example 132

N-[5-[(3,5-dimethoxyphenyl)methoxy]-2H-pyrazol-3-yl]-2-(3,4-dimethylpiperazin-1-yl)pyrimidine-5-carboxamide Trimethylaluminium (2M in toluene, 1.29 ml, 2.58 mmol) was added dropwise to a suspension of 5-[(3,5-dimethoxyphenyl)methoxy]-2H-pyrazol-3-amine, HCl (295 mg, 1.03 mmol) and methyl 2-(3,4-dimethylpiperazin-1-yl)pyrimidine-5-carboxylate (258 mg, 1.03 mmol) in toluene (5.16 ml) at 25° C. The resulting solution was stirred at 60° C. for 5 h. The reaction mixture was poured into methanol (50 mL) and acidified with HCl (2M aqueous solution). The crude product was purified by ion exchange chromatography, using an SCX column. The desired product was eluted from the column using 7M NH3/MeOH and evaporated to dryness to afford impure product. The impure material was purified by silica column chromatography, eluting with a gradient of 0 to 5% 7M NH3/MeOH in dichloromethane. Pure fractions were evaporated to dryness to afford the title compound (298 mg, 62%) as a white crystalline solid.

1H NMR (500.133 MHz, DMSO, 373K) δ 1.05 (3H, d), 2.10-2.20 (2H, m), 2.24 (3H, s), 2.81 (1H, dt), 2.91 (1H, dd), 3.24-3.29 (1H, m), 3.76 (6H, s), 4.39-4.47 (2H, m), 5.09 (2H, s), 5.71 (1H, s), 6.44 (1H, t), 6.60 (2H, d), 8.84 (2H, s), 10.30 (1H, s), 11.28 (1H, s). MS: m/z 468 (MH+).

Mean of n=1, FGFR Kinase assay—Caliper Echo Dosing, IC$_{50}$ 0.0036 μM.

5-[(3,5-Dimethoxyphenyl)methoxy]-2H-pyrazol-3-amine, HCl was prepared as outlined in Example 12.

Methyl 2-(3,4-dimethylpiperazin-1-yl)pyrimidine-5-carboxylate used as starting material was prepared as follows:

A solution of methyl 2-chloropyrimidine-5-carboxylate (500 mg, 2.90 mmol) in dichloromethane (7.50 ml) was added to a stirred solution of 1,2-dimethylpiperazine (331 mg, 2.90 mmol) and N-ethyl-N-propan-2-ylpropan-2-amine (1.26 mL, 7.24 mmol) in dichloromethane (7.25 ml) at room temperature under nitrogen. The resulting solution was stirred at ambient temperature for 5 h. The reaction mixture was concentrated under reduced pressure and the crude product was purified by ion exchange chromatography, using an SCX column. The desired product was eluted from the column using 7M NH3/MeOH and evaporated to dryness to afford impure product. The impure material was purified by silica column chromatography, eluting with a gradient of 0 to 5% 7M NH3/MeOH in dichloromethane. Pure fractions were evaporated to dryness to afford the desired compound (713 mg, 98%) as a yellow solid.

1H NMR (399.9 MHz, DMSO-d6) δ 1.04-1.06 (3H, m), 1.98-2.05 (1H, m), 2.06-2.13 (1H, m), 2.21 (3H, s), 2.78-2.84 (2H, m), 3.14-3.21 (1H, m), 3.81 (3H, s), 4.46-4.55 (2H, m), 8.78 (2H, s). MS: m/z 251 (MH+).

Example 133

2-(4-cyclopropylpiperazin-1-yl)-N-[5-[(3,5-dimethoxyphenyl)methoxy]-2H-pyrazol-3-yl]pyrimidine-5-carboxamide Trimethylaluminium (2M in toluene, 2.00 mL, 4.00 mmol) was added dropwise to a stirred suspension of 5-[(3,5-dimethoxyphenyl)methoxy]-2H-pyrazol-3-amine, HCl (459 mg, 1.60 mmol) and methyl 2-(4-cyclopropylpiperazin-1-yl)pyrimidine-5-carboxylate (421 mg, 1.60 mmol) in toluene (8.0 mL) at 25° C. The resulting solution was stirred at ambient temperature for 18 h and then at 60° C. for 2 h. The reaction mixture was quenched with methanol (20 mL) and treated with HCl (2N aqueous solution, until a freely stirred solution was obtained). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 0.1% NH3) and MeCN as eluents. Fractions containing the desired compound were evaporated to dryness to afford the title compound (94 mg, 12%) as a solid.

1H NMR (500.13 MHz, DMSO-d6, 373K) δ 0.40-0.43 (2H, m), 0.44-0.49 (2H, m), 1.71-1.75 (1H, m), 2.65 (4H, t), 3.78 (6H, s), 3.84 (4H, t), 5.11 (2H, s), 5.71 (1H, s), 6.46 (1H, t), 6.62 (2H, d), 8.86 (2H, s), 10.3 (1H, s), 11.3 (1H, s). MS: m/z 480 (MH+).

Mean of n=1, FGFR Kinase assay—Caliper Echo Dosing, IC$_{50}$ 0.0039 μM.

Methyl 2-(4-cyclopropylpiperazin-1-yl)pyrimidine-5-carboxylate was prepared as outlined in Example 126.

5-[(3,5-Dimethoxyphenyl)methoxy]-2H-pyrazol-3-amine, HCl was prepared as outlined in Example 12.

Example 134

2-(3,4,6,7,8,8a-hexahydro-1H-pyrrolo[2,1-c]pyrazin-2-yl)-N-[5-[(3,5-dimethoxyphenyl)methoxy]-2H-pyrazol-3-yl]pyrimidine-5-carboxamide Trimethylaluminium (2M in toluene, 2.50 ml, 5.00 mmol) was added dropwise to a stirred suspension 5-[(3,5-dimethoxyphenyl)methoxy]-2H-pyrazol-3-amine, HCl (572 mg, 2.00 mmol) and methyl 2-(3,4,6,7,8,8a-hexahydro-1H-pyrrolo [2,1-c]pyrazin-2-yl)pyrimidine-5-carboxylate (525 mg, 2.00 mmol) in toluene (10.00 ml) at 25° C. The resulting solution was stirred at ambient temperature for 18 h and then at 60° C. for 2 h. The reaction mixture was cautiously quenched with methanol (20 mL) and treated with HCl (2N aqueous solution, until a freely stirred solution was obtained). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 0.1% NH3) and MeCN as eluents. Fractions containing the desired compound were evaporated to dryness to afford the title compound (269 mg, 28%) as a solid.

1H NMR (500.13 MHz, DMSO-d6, 373K) δ 1.39-1.47 (1H, m), 1.69-1.75 (1H, m), 1.76-1.82 (1H, m), 1.84-1.90 (1H, m), 1.99-2.03 (1H, m), 2.13-2.21 (2H, m), 2.72-2.78 (1H, m), 3.04-3.13 (3H, m), 3.78 (6H, s), 4.70-4.75 (1H, m), 4.85-4.88 (1H, m), 5.11 (2H, s), 5.72 (1H, s), 6.46 (1H, t), 6.62 (2H, d), 8.87 (2H, s), 10.30 (1H, s), 11.30 (1H, s). MS: m/z 480 (MH+).

Mean of n=1, FGFR Kinase assay—Caliper Echo Dosing, $IC_{50}$ 0.0024 μM.

5-[(3,5-Dimethoxyphenyl)methoxy]-2H-pyrazol-3-amine, HCl was prepared as outlined in Example 12.

Methyl 2-(3,4,6,7,8,8a-hexahydro-1H-pyrrolo[2,1-c]pyrazin-2-yl)pyrimidine-5-carboxylate used as starting material was prepared as outlined in Example 128.

Example 135

N-[5-[2-(3,5-dimethoxyphenyl)ethyl]-2H-pyrazol-3-yl]-2-(3,4-dimethylpiperazin-1-yl)pyrimidine-5-carboxamide Trimethylaluminium (2M in toluene, 1.31 ml, 2.62 mmol) was added dropwise to a suspension of 5-[2-(3,5-dimethoxyphenyl)ethyl]-2H-pyrazol-3-amine (260 mg, 1.05 mmol) and methyl 2-(3,4-dimethylpiperazin-1-yl)pyrimidine-5-carboxylate (263 mg, 1.05 mmol) in toluene (5.26 ml) at 25° C. The resulting solution was stirred at 60° C. for 18 h. The reaction mixture was poured into methanol (50 mL) and acidified with HCl (2M aqueous solution, to obtain a clear freely stirring solution). The crude product was purified by ion exchange chromatography, using an SCX column. The desired product was eluted from the column using 7M NH3/MeOH and evaporated to dryness to afford impure product. The impure material was purified by silica column chromatography, eluting with a gradient of 0 to 5% 7M NH3/MeOH in dichloromethane. Fractions containing product were evaporated to dryness to give material that was still impure. The residue was repurified by preparative HPLC, using decreasingly polar mixtures of water (containing 1% NH3) and MeCN as eluents. Fractions containing the desired compound were evaporated to dryness to afford the title compound (175 mg, 36%) as a white solid.

1H NMR (399.9 MHz, DMSO-d6) δ 1.05-1.07 (3H, m), 1.99-2.05 (1H, m), 2.07-2.13 (1H, m), 2.22 (3H, s), 2.76-2.84 (2H, m), 2.88 (4H, s), 3.12-3.19 (1H, m), 3.72 (6H, s), 4.46-4.55 (2H, m), 6.33 (1H, t), 6.42 (3H, m), 8.89 (2H, s), 10.60 (1H, s), 12.12 (1H, s). MS: m/z 466 (MH+).

Mean of n=1, FGFR Kinase assay—Caliper Echo Dosing, $IC_{50}$ 0.0026 μM.

5-[2-(3,5-Dimethoxyphenyl)ethyl]-2H-pyrazol-3-amine, used as starting material was prepared as indicated in Example 2.

Methyl 2-(3,4-dimethylpiperazin-1-yl)pyrimidine-5-carboxylate used as starting material was prepared as outlined in Example 132.

Example 136

N-[5-[2-(3,5-dimethoxyphenyl)ethyl]-2H-pyrazol-3-yl]-2-[(3R,5S)-3,4,5-trimethylpiperazin-1-yl]pyrimidine-5-carboxamide Trimethylaluminium (2M in toluene, 1.04 ml, 2.08 mmol) was added dropwise to a suspension of 5-[2-(3,5-dimethoxyphenyl)ethyl]-2H-pyrazol-3-amine (205 mg, 0.83 mmol) and methyl 2-((3R,5S)-3,4,5-trimethylpiperazin-1-yl)pyrimidine-5-carboxylate (220 mg, 0.83 mmol) in toluene (5.257 ml) at 25° C. The resulting solution was stirred at 60° C. for 18 h. The reaction mixture was poured into methanol (50 mL) and acidified with HCl (2M aqueous solution, to obtain a clear freely stirring solution). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 1% NH3) and MeCN as eluents. Fractions containing the desired compound were evaporated to dryness to afford the title compound (157 mg, 39%) as a white solid.

1H NMR (399.9 MHz, DMSO-d6) δ 1.09-1.10 (6H, m), 2.08-2.14 (2H, m), 2.20 (3H, s), 2.71 (1H, d), 2.74 (1H, d), 2.87 (4H, s), 3.72 (6H, s), 4.55-4.59 (2H, m), 6.33 (1H, t), 6.42 (3H, m), 8.89 (2H, s), 10.61 (1H, s), 12.15 (1H, s). MS: m/z 480 (MH+).

Mean of n=1, FGFR Kinase assay—Caliper Echo Dosing, $IC_{50}$ 0.0019 μM.

5-[2-(3,5-dimethoxyphenyl)ethyl]-2H-pyrazol-3-amine, used as starting material was prepared as indicated in Example 2.

Methyl 2-((3R,5S)-3,4,5-trimethylpiperazin-1-yl)pyrimidine-5-carboxylate used as starting material was prepared as follows:

Macroporous triethylammonium methylpolystyrene cyanoborohydride (2.31 mmol/g, 3.15 g, 7.29 mmol) was added to methyl 2-((3R,5S)-3,5-dimethylpiperazin-1-yl)pyrimidine-5-carboxylate (730 mg, 2.92 mmol), formaldehyde (37% aqueous solution, 4.43 ml, 59.13 mmol) and acetic acid (0.334 ml, 5.83 mmol) in methanol (5.83 ml) at 25° C. The resulting suspension was stirred at ambient temperature for 5 h. The macroporous triethylammonium methylpolystyrene cyanoborohydride was removed by filtration, washing with methanol (50 mL). The filtrate was purified by ion exchange chromatography, using an SCX column. The desired product was eluted from the column using 7M NH3/MeOH and evaporated to dryness to afford impure product. The impure material was purified by silica column chromatography, eluting with a gradient of 0 to 6% 7M NH3/MeOH in dichloromethane. Pure fractions were evaporated to dryness to afford the desired compound (474 mg, 62%) as a white oil which solidified on standing.

1H NMR (399.9 MHz, DMSO-d6) δ 1.09 (6H, d), 2.07-2.15 (2H, m), 2.19 (3H, s), 2.73-2.76 (2H, m), 3.81 (3H, s), 4.56-4.60 (2H, m), 8.79 (2H, s). MS: m/z 265 (MH+).

Methyl 2-((3R,5S)-3,5-dimethylpiperazin-1-yl)pyrimidine-5-carboxylate used as starting material was prepared as follows:

A solution of methyl 2-chloropyrimidine-5-carboxylate (535 mg, 3.10 mmol) in dichloromethane (7.50 ml) was added to a stirred solution of (2S,6R)-2,6-dimethylpiperazine (354 mg, 3.10 mmol) and N-ethyl-N-propan-2-ylpropan-2-amine (1.35 ml, 7.75 mmol) in dichloromethane (7.24 ml) at room temperature under nitrogen. The resulting solution was stirred at ambient temperature for 3 h. The reaction mixture was concentrated under reduced pressure and the crude product was purified by ion exchange chromatography, using an SCX column. The desired product was eluted from the column using 7M NH3/MeOH and evaporated to dryness to afford impure product. The impure material was purified by silica column chromatography, eluting with a gradient of 0 to 5% 7M NH3/MeOH in dichloromethane. Pure fractions were evaporated to dryness to afford the desired compound (740 mg, 95%) as a white solid.

1H NMR (399.9 MHz, DMSO-d6) δ 1.02-1.04 (6H, m), 2.33 (1H, s), 2.43-2.46 (2H, m), 2.64-2.69 (2H, m), 3.81 (3H, s), 4.62-4.66 (2H, m), 8.77 (2H, s). MS: m/z 251 (MH+).

Example 137

N-[5-[2-(3,5-dimethoxyphenyl)ethyl]-2H-pyrazol-3-yl]-4-[4-(1-hydroxypropan-2-yl)piperazin-1-yl]benzamide 2-(Piperazin-1-yl)propan-1-ol 2HCl (0.274 g, 1.26 mmol) was added to N-ethyl-N-propan-2-ylpropan-2-amine (0.330 mL, 1.89 mmol) in DMSO (5 mL). The reaction mixture was stirred at room temperature for 10 mins. N-[5-[2-(3,5-dimethoxyphenyl)ethyl]-2H-pyrazol-3-yl]-4-fluorobenzamide (0.233 g, 0.63 mmol) was added and the mixture heated at 110° C. for 18 h under nitrogen. Heating was continued for 12 additional days. The reaction was cooled and the crude mixture was purified by ion exchange chromatography, using a SCX column. The desired product was eluted from the column using 7M NH3/MeOH and pure fractions were evaporated to dryness to afford crude product. The crude product was purified by preparative HPLC, using decreasingly polar mixtures of water (containing 1% NH3) and MeCN as eluents. Fractions containing the desired compound were evaporated to dryness to afford the title compound (0.048 g, 15.44%) as a cream solid.

1H NMR (500.13 MHz-DMSO-d6+CD3COOD @ 373K): 1.02 (3H, d), 2.70-2.81 (5H, m), 2.89 (4H, s), 3.28-3.34 (4H, m), 3.37-3.44 (1H, m), 3.50-3.55 (1H, m), 3.73 (6H, s), 6.27-6.32 (2H, m), 6.40 (2H, s0, 6.92 (2H, d), 7.82-7.88 (2H, m). MS: m/z (MH+).

Mean of n=1, FGFR Kinase assay—Caliper Echo Dosing, $IC_{50}$ 0.00057 µM.

2-(Piperazin-1-yl)propan-1-ol. 2HCl used as starting material was prepared as follows:

A 1M solution of borane tetrahydrofuran complex (12.00 mL, 12.00 mmol) in THF, was added dropwise to a stirred suspension of 2-(1-tert-butoxycarbonylpiperazin-4-yl)propionic acid (2.58 g, 10 mmol) in tetrahydrofuran (50 mL) at 0° C., over a period of 10 mins under nitrogen. The resulting solution was stirred at 60° C. for 8 h. This was quenched with acetic acid/water (10 ml, 1:2 mixture) and evaporated to dryness. The residue was dissolved in ethyl acetate (50 ml), washed with saturated sodium bicarbonate (25 ml) and water, dried over MgSO4, filtered and evaporated to dryness to give tert-butyl 4-(1-hydroxypropan-2-yl)piperazine-1-carboxylate (0.810 g, 33.2%)

1H NMR (399.9 MHz, CDCl3) δ 0.83 (3H, d), 1.39 (9H, s), 2.30 (2H, t), 2.51-2.57 (3H, m), 2.71-2.82 (1H, m), 3.34-3.40 (2H, m), 3.35-3.39 (4H, m).

A suspension of tert-butyl 4-(1-hydroxypropan-2-yl)piperazine-1-carboxylate (0.782 g, 3.2 mmol) in a mixture of ethyl acetate (10 ml) and methanol (10.00 mL), was treated drop-wise with 4.0M HCl in dioxane (12.00 ml, 48.00 mmol) at room temperature. The reaction mixture was stirred for 18 h. The reaction mixture was diluted with ether and the white solid filtered off, washed with ether and air dried to give 2-(piperazin-1-yl)propan-1-ol (0.525 g, 76%), as its dihydrochloride salt.

N-[5-[2-(3,5-dimethoxyphenyl)ethyl]-2H-pyrazol-3-yl]-4-fluorobenzamide used as starting material was prepared as follows:

A 2M solution of trimethylaluminium in toluene (3.00 mL, 3.00 mmol) was added drop-wise to a stirred solution of ethyl 4-fluorobenzoate (0.440 mL, 3.00 mmol) and 5-[2-(3,5-dimethoxyphenyl)ethyl]-2H-pyrazol-3-amine (0.742 g, 3 mmol) in toluene (10 mL) at room temperature. The reaction was stirred at room temperature for 18 h. The reaction mixture was poured into acetone (50 mL) and treated with an excess of damp sodium sulphite. The reaction mixture was purified by ion exchange chromatography, using a SCX column. The desired product was eluted from the column using 7M NH3/MeOH and fractions were evaporated to dryness to afford a yellow gum. The crude product was purified by silica column chromatography, eluting with a gradient of 0 to 5% 2.5M ammonia/MeOH in DCM. Pure fractions were evaporated to dryness to afford the desired compound (0.245 g, 22.11%) as a white solid.

1H NMR (399.9 MHz, DMSO-d6) δ 2.88 (4H, s), 3.73 (6H, s), 6.33 (1H, t), 6.42 (2H, d), 6.47 (1H, s), 7.32 (2H, t), 8.05-8.09 (2H, m), 10.69 (1H, s), 12.16 (1H, s). MS: m/z 370 (MH+).

Example 138

N-(3-(3,5-dimethoxybenzyloxy)-1H-pyrazol-5-yl)-2-((3R,5S)-3,4,5-trimethylpiperazin-1-yl)pyrimidine-5-carboxamide Trimethylaluminium (2M in toluene, 1.04 mL, 2.07 mmol) was added dropwise to a suspension of 5-[(3,5-dimethoxyphenyl)methoxy]-2H-pyrazol-3-amine, HCl (237 mg, 0.83 mmol) and methyl 2-((3R,5S)-3,4,5-trimethylpiperazin-1-yl)pyrimidine-5-carboxylate (219 mg, 0.83 mmol) in toluene (4.2 mL) at 25° C. The resulting solution was stirred at 60° C. for 2 h. The reaction mixture was poured into methanol (50 mL) and acidified with HCl (2M aqueous solution). The crude product was purified by ion exchange chromatography, using an SCX column. The desired product was eluted from the column using 7M NH3/MeOH and evaporated to dryness to afford impure product. The impure material was purified by preparative HPLC, using decreasingly polar mixtures of water (containing 1% NH3) and MeCN as eluents. Fractions containing the desired compound were evaporated to dryness to afford the title compound (158 mg, 40%) as a white solid.

1H NMR (500.133 MHz, DMSO, 373K) δ 1.10 (6H, d), 2.14-2.20 (2H, m), 2.22 (3H, s), 2.74-2.79 (2H, m), 3.76 (6H, s), 4.53-4.57 (2H, m), 5.08 (2H, s), 5.71 (1H, s), 6.44 (1H, t), 6.59 (2H, d), 8.84 (2H, s), 10.32 (1H, s), 11.31 (1H, s). MS: m/z 482 (MH+).

Mean of n=1, FGFR Kinase assay—Caliper Echo Dosing, $IC_{50}$ 0.0026 µM.

5-[(3,5-Dimethoxyphenyl)methoxy]-2H-pyrazol-3-amine, HCl was prepared as outlined in Example 12.

Methyl 2-((3R,5S)-3,4,5-trimethylpiperazin-1-yl)pyrimidine-5-carboxylate was prepared as outlined in Example 136.

Example 139

N-[5-[2-(3,5-dimethoxyphenyl)ethyl]-2H-pyrazol-3-yl]-4-(3,3-dimethylpiperazin-1-yl)benzamide N-[5-[2-(3,5-dimethoxyphenyl)ethyl]-2H-pyrazol-3-yl]-4-fluorobenzamide (0.1 g, 0.27 mmol) and 2,2-dimethylpiperazine (0.124 g, 1.04 mmol) were stirred at 60° C. for 20 mins. Potassium carbonate (0.033 ml, 0.54 mmol) and DMSO (1 ml) were added and the reaction stirred at 120° C. in a sealed tube for 16 days. The reaction mixture was cooled and evaporated. The crude product was purified by preparative HPLC, using decreasingly polar mixtures of water (containing 1% $NH_3$) and MeCN as eluents. Fractions containing the desired compound were evaporated to dryness to afford the title compound (6.00 mg, 2.000%) as a colourless gum.

1H NMR (399.9 MHz, CDCl3) δ 1.19 (6H, s), 2.92-2.95 (4H, m), 3.02 (4H, d), 3.04 (1H, s), 3.17 (2H, t), 3.75 (6H, s), 6.32-6.35 (3H, m), 6.84 (2H, d), 7.77 (2H, d), 8.73 (1H, s). MS: m/z 465 (MH+).

Mean of n=1, FGFR Kinase assay—Caliper Echo Dosing, IC$_{50}$ 0.00047 µM.

N-[5-[2-(3,5-dimethoxyphenyl)ethyl]-2H-pyrazol-3-yl]-4-fluorobenzamide used as starting material was prepared as follows: A 2M solution of trimethylaluminium (3.54 ml, 7.08 mmol) in toluene was added dropwise to 5-[2-(3,5-dimethoxyphenyl)ethyl]-2H-pyrazol-3-amine (0.7 g, 2.83 mmol) in toluene (35 ml). Methyl 4-fluorobenzoate (0.366 ml, 2.83 mmol) was then added and the resulting solution was stirred at room temperature for 18 h. An additional amount of methyl 4-fluorobenzoate (0.183 ml, 1.42 mmol) was added and the solution was stirred at room temperature for a further 20 h. The reaction mixture was poured into acetone (40 ml), and treated with an excess of damp sodium sulfite solution. The suspension was stirred for 2 h, filtered and the filtrate was purified by silica column chromatography, eluting with a gradient 2.5 to 5% 2.5N NH$_3$/MeOH in DCM. Pure fractions were evaporated to dryness to afford the desired compound as a beige oil which solidified on standing (0.147 g, 14.06%) to a white solid.

1H NMR (399.9 MHz, DMSO-d6) δ 2.88 (4H, s), 3.73 (6H, s), 6.33 (1H, t), 6.43 (2H, d), 6.47 (1H, s), 7.31 (2H, t), 8.05-8.09 (2H, m), 10.69 (1H, s), 12.16 (1H, s). MS: m/z 370 (MH+).

Example 140

N-[5-[(3,5-dimethoxyphenyl)methoxy]-2H-pyrazol-3-yl]-5-(3,3-dimethylpiperazin-1-yl)thiophene-2-carboxamide 2M Trimethylaluminium (1.250 ml, 2.50 mmol) in toluene, was added dropwise to a stirred solution of ethyl 5-(3,3-dimethylpiperazin-1-yl)thiophene-2-carboxylate (0.268 g, 1 mmol) and 5-[(3,5-dimethoxyphenyl)methoxy]-2H-pyrazol-3-amine hydrochloride (0.286 g, 1.00 mmol) in toluene (7.14 ml) at 65° C. under nitrogen. The reaction mixture was stirred and heated at 65° C. for 4 h then 50° C. for 18 h followed by 80° C. for 5 h. Ethyl acetate (5 mL) was added to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow gum. The crude product was purified by preparative LCMS, using decreasingly polar mixtures of water (containing 1% NH3) and MeCN as eluents. Fractions containing the desired compound were evaporated to dryness to afford the title compound (0.073 g, 15.48%) as a white solid.

1H NMR (500.13 MHz, DMSO-d6, CD3CO2D) δ 1.36 (6H, s), 3.24 (4H, s), 3.40 (2H, t), 3.74 (6H, s), 5.06 (2H, s), 5.64 (1H, s), 6.24 (1H, d), 6.41 (1H, s), 6.57 (2H, s), 7.62-7.63 (1H, m); MS: m/z 472 (MH+)

Mean of n=1, FGFR Kinase assay—Caliper Echo Dosing, IC$_{50}$ 0.00098 µM.

Ethyl 5-(3,3-dimethylpiperazin-1-yl)thiophene-2-carboxylate, used as starting material was prepared as follows:

Palladium(II) acetate (0.112 g, 0.50 mmol) was added to ethyl 5-bromothiophene-2-carboxylate (1.175 g, 5 mmol), 2,2-dimethyl-piperazine (0.571 g, 5.00 mmol), rac-2,2'-bis(diphenylphosphino)-1,1'-binaphthyl (0.311 g, 0.50 mmol) and cesium carbonate (2.281 g, 7.00 mmol) in toluene (50.0 ml) at 20° C. under nitrogen. The resulting suspension was stirred at 110° C. for 23 h. The crude product was purified by ion exchange chromatography, using a SCX2 column. The crude material was dissolved in methanol and then applied to the column. The desired product was eluted from the column using 2M NH3 in methanol and pure fractions were evaporated to dryness to afford the crude product as a brown solid. This material was further purified by silica column chromatography, eluting with a gradient of 0 to 4% MeOH in DCM. Pure fractions were evaporated to dryness to afford ethyl 5-(3,3-dimethylpiperazin-1-yl)thiophene-2-carboxylate (0.484 g, 36.1%) as a brown gum.

1H NMR (399.9 MHz, CDCl3) δ 1.20 (6H, s), 1.33 (3H, t), 2.98 (2H, s), 3.05 (2H, d), 3.16-3.19 (2H, m), 4.28 (2H, q), 6.00 (1H, d), 7.54 (1H, d) MS: m/z 269 (MH+)

5-[(3,5-Dimethoxyphenyl)methoxy]-2H-pyrazol-3-amine hydrochloride, used as starting material was prepared as in Example 12.

Example 141

N-[5-[(3,5-dimethoxyphenyl)methoxy]-2H-pyrazol-3-yl]-5-(4-ethylpiperazin-1-yl)thiophene-2-carboxamide Trimethylaluminium (2M solution in toluene, 1.40 mL, 2.79 mmol) was added dropwise to a stirred suspension of 5-[(3,5-dimethoxyphenyl)methoxy]-2H-pyrazol-3-amine, HCl (319 mg, 1.12 mmol) and ethyl 5-(4-ethylpiperazin-1-yl)thiophene-2-carboxylate (300 mg, 1.12 mmol) in toluene (5.60 mL) at 25° C. The resulting solution was then stirred at 60° C. under nitrogen for 5 h. The reaction mixture was cautiously quenched into methanol (100 mL), acidified with HCl (2M aqueous solution) and the mixture was purified by ion exchange chromatography, using an SCX column. The desired product was eluted from the column using 7M NH3/MeOH and evaporated to dryness to afford impure material. The crude product was purified by silica column chromatography, eluting with a gradient of 0 to 5% 7M NH3/MeOH in DCM. Fractions were evaporated to dryness to afford impure N-[5-[(3,5-dimethoxyphenyl)methoxy]-2H-pyrazol-3-yl]-5-(4-ethylpiperazin-1-yl)thiophene-2-carboxamide as a cream solid. The residue was repurified by preparative HPLC, using decreasingly polar mixtures of water (containing 1% NH3) and MeCN as eluents. Fractions containing the desired compound were evaporated to dryness to afford the title compound (72 mg, 14%) as a white solid.

1H NMR (500.133 MHz, DMSO, 373K) δ 1.04 (3H, t), 2.43 (2H, q), 2.53-2.54 (4H, m), 3.23-3.25 (4H, m), 3.76 (6H, s), 5.07 (2H, s), 5.60 (1H, s), 6.14 (1H, d), 6.44 (1H, t), 6.59 (2H, d), 7.63 (1H, d), 10.05 (1H, s), 11.09 (1H, s). MS: m/z 472 (MH+).

Mean of n=1, FGFR Kinase assay—Caliper Echo Dosing, IC$_{50}$ 0.00086 µM.

Ethyl 5-(4-ethylpiperazin-1-yl)thiophene-2-carboxylate used as starting material was prepared as follows:

Tris(dibenzylideneacetone)dipalladium(0) (183 mg, 0.20 mmol) followed by sodium tert-butoxide (538 mg, 5.60 mmol) was added to ethyl 5-bromothiophene-2-carboxylate (1.034 g, 4.40 mmol), 1-ethylpiperazine (0.51 ml, 4.00 mmol) and (rac)-(−)-2,2'-bis(diphenylphosphino)-1,1'-binaphthyl (249 mg, 0.40 mmol) in toluene (20.00 ml) at 25° C. under nitrogen. The resulting suspension was stirred at 110° C. for 18 h. The cooled reaction mixture was diluted with methanol and purified by ion exchange chromatography, using an SCX column. The desired product was eluted from the column using 7M NH3/MeOH and evaporated to dryness to afford crude product. The residue was purified by silica column chromatography, eluting with a gradient of 0 to 3% 7M NH3/MeOH in DCM. Fractions containing desired product were evaporated to dryness to give impure orange oil. The impure material was further purified by preparative HPLC, using decreasingly polar mixtures of water (containing 1% NH3) and MeCN as eluents. Fractions containing the desired compound were evaporated to dryness to afford ethyl 5-(4-ethylpiperazin-1-yl)thiophene-2-carboxylate (339 mg, 32%) as a yellow oil.

1H NMR (399.902 MHz, DMSO) δ 1.03 (3H, t), 1.25 (3H, t), 2.38 (2H, q), 2.49 (4H, m), 3.24 (4H, m), 4.19 (2H, q), 6.21 (1H, d), 7.51 (1H, d). MS: m/z 269 (MH+)

5-[(3,5-Dimethoxyphenyl)methoxy]-2H-pyrazol-3-amine, HCl was prepared as outlined in Example 12.

Example 142

N-[5-[2-(3,5-dimethoxyphenyl)ethyl]-2H-pyrazol-3-yl]-5-(4-methyl-1,4-diazepan-1-yl)thiophene-2-carboxamide Ethyl 5-(4-methyl-1,4-diazepan-1-yl)thiophene-2-carboxylate (0.201 g, 0.75 mmol) and 5-[2-(3,5-dimethoxyphenyl)ethyl]-2H-pyrazol-3-amine (0.185 g, 0.75 mmol) in toluene (10 mL) were stirred at 20° C. and a 2M solution of trimethylaluminium in toluene (0.938 mL, 1.88 mmol) was added drop-wise. The reaction stirred under nitrogen at 60° C. for 18 h. The reaction mixture was cooled and quenched by pouring into methanol (50 ml), acidified with few drops of 2N hydrochloric acid. The crude product was purified by ion exchange chromatography, using a SCX column. The desired product was eluted from the column using 7M NH3/MeOH and fractions were evaporated to dryness to afford crude product. The crude product was purified by preparative HPLC, using decreasingly polar mixtures of water (containing 1% NH3) and MeCN as eluents. Fractions containing the desired compound were evaporated to dryness to afford the title compound (0.162 g, 46.0%) as a tan solid.

1H NMR (399.9 MHz, DMSO-d6) δ 1.89-1.93 (2H, m), 2.28 (3H, s), 2.50-2.54 (2H, m), 2.63 (1H, d), 2.64-2.65 (1H, m), 2.85 (4H, s), 3.43 (2H, t), 3.50 (2H, t), 3.72 (6H, s), 5.86 (1H, d), 6.32-6.34 (2H, m), 6.41 (2H, d), 7.79 (1H, d), 10.15 (1H, s), 12.00 (1H, s). MS: m/z 470 (MH+).

Mean of n=1, FGFR Kinase assay—Caliper Echo Dosing, IC$_{50}$ 0.0021 μM.

Ethyl 5-(4-methyl-1,4-diazepan-1-yl)thiophene-2-carboxylate was prepared as follows:

Palladium(II)acetate (0.135 g, 0.60 mmol) was added to ethyl 5-bromothiophene-2-carboxylate (1.411 g, 6 mmol), 1-methyl-1,4-diazepane (0.822 g, 7.20 mmol), BINAP (0.374 g, 0.60 mmol) and cesium carbonate (2.74 g, 8.40 mmol) in dioxane (40 mL) warmed to 80° C. for 18 h under nitrogen. The crude reaction mixture was purified by ion exchange chromatography, using a SCX column. The desired product was eluted from the column using 7M NH3/MeOH. Fractions were evaporated to dryness to afford the crude product. The crude product was purified by silica column chromatography, eluting with a gradient of 0 to 5% 3M ammonia/MeOH in DCM. Pure fractions were evaporated to dryness to afford ethyl 5-(4-methyl-1,4-diazepan-1-yl)thiophene-2-carboxylate (0.204 g, 12.67%) as a yellow gum.

1H NMR (399.9 MHz, CDCl3) δ: 1.34 (3H, t), 1.97-2.04 (2H, m), 2.38 (3H, s), 2.55-2.61 (2H, m), 2.67 (2H, m), 3.48 (2H, t), 3.54-3.57 (2H, m), 4.28 (4H, q), 5.79 (1H, d), 7.55 (1H, d). MS: m/z 269 (MH+).

Example 143

N-[5-[2-(3,5-dimethoxyphenyl)ethyl]-2H-pyrazol-3-yl]-2-(4-ethyl-3-methylpiperazin-1-yl)pyrimidine-5-carboxamide Trimethylaluminium (2M in toluene, 1.65 ml, 3.31 mmol) was added dropwise to a stirred suspension of methyl 2-(4-ethyl-3-methylpiperazin-1-yl)pyrimidine-5-carboxylate (303 mg, 1.15 mmol) and 5-[2-(3,5-dimethoxyphenyl)ethyl]-2H-pyrazol-3-amine (283 mg, 1.15 mmol) in toluene (5.73 ml) at room temperature. The resulting solution was stirred at 60° C. overnight. The reaction mixture was quenched into methanol (100 mL) and treated with HCl (2N aqueous solution, until the pH was 7 or lower). The crude product was purified by ion exchange chromatography, using a SCX column. The desired product was eluted from the column using 7M NH3/MeOH and fractions were evaporated to dryness to afford impure product as a yellow dry film. The crude product was purified by preparative HPLC, using decreasingly polar mixtures of water (containing 1% NH3) and MeCN as eluents. Fractions containing the desired compound were evaporated to dryness to afford the title compound (269 mg, 49%) as a cream solid.

1H NMR (399.9 MHz, DMSO-d$_6$) δ 0.99 (3H, d), 1.03 (3H, d), 2.20-2.26 (1H, m), 2.35-2.43 (2H, m), 2.74-2.79 (1H, m), 2.83 (1H, m), 2.88 (4H, s), 3.02-3.07 (1H, m), 3.30-3.38 (1H, m), 3.72 (6H, s), 4.27-4.31 (2H, m), 6.33 (1H, t), 6.42 (2H, d), 6.44 (1H, s), 8.89 (2H, s), 10.58 (1H, s), 12.15 (1H, s). MS: m/z 480 (MH+)

Mean of n=1, FGFR Kinase assay—Caliper Echo Dosing, IC$_{50}$ 0.0027 μM.

Methyl 2-(4-ethyl-3-methylpiperazin-1-yl)pyrimidine-5-carboxylate, used as starting material, was prepared as follows:

A solution of methyl 2-chloropyrimidine-5-carboxylate (300 mg, 1.74 mmol) in dichloromethane (4.30 ml) was added to a stirred solution of 1-ethyl-2-methylpiperazine (223 mg, 1.74 mmol) and N-ethyl-N-propan-2-ylpropan-2-amine (0.75 ml, 4.35 mmol) in dichloromethane (4.40 ml) at 25° C. under nitrogen. The resulting solution was stirred at room temperature for 4 h. The reaction mixture was concentrated under reduced pressure and diluted with MeOH (10 mL). The crude product was purified by ion exchange chromatography, using a SCX column. The desired product was eluted from the column using 7M NH3/MeOH and was evaporated to dryness to afford impure product. The crude product was purified by silica column chromatography, eluting with a gradient of 0 to 3% 7M NH$_3$/MeOH in dichloromethane. Pure fractions were evaporated to dryness to afford the desired compound (382 mg, 83%) as a colourless oil.

1H NMR (399.9 MHz, DMSO-d$_6$) δ 0.98 (3H, t), 1.02 (3H, d), 2.20-2.27 (1H, m), 2.33-2.38 (1H, m), 2.40-2.45 (1H, m), 2.71-2.79 (1H, m), 2.81-2.85 (1H, m), 3.06-3.11 (1H, m), 3.35-3.42 (1H, m), 3.81 (3H, s), 4.28-4.35 (2H, m), 8.78 (2H, s). MS: m/z 265 (MH+)

Example 144

N-[5-[2-(3,5-dimethoxyphenyl)ethyl]-2H-pyrazol-3-yl]-4-(1-prop-2-enylpiperidin-4-yl)benzamide N-[5-[2-(3,5-dimethoxyphenyl)ethyl]-2H-pyrazol-3-yl]-4-(1-prop-2-enylpiperidin-4-yl)benzamide was prepared following the procedure as outlined for Example 99, starting from methyl 4-(1-prop-2-enylpiperidin-4-yl)benzoate (0.259 g, 1.00 mmol) and 5-[2-(3,5-dimethoxyphenyl)ethyl]-2H-pyrazol-3-amine (0.247 g, 1 mmol) and 2M trimethylaluminium (1.250 mL, 2.50 mmol) in toluene (10 ml). The crude product was purified by silica column chromatography, eluting with a gradient of 0 to 5% 2.5M ammonia/methanol in DCM. Pure fractions were evaporated to dryness and the product was crystallised from DCM/diethyl ether to give on filtration the title compound (0.182 g, 38.3%) as a white solid.

1H NMR (399.9 MHz, DMSO-$d_6$) δ 1.66-1.70 (2H, m), 1.73-1.79 (2H, m), 1.99-2.05 (2H, m), 2.55 (1H, d), 2.88 (4H, s), 2.95 (1H, s), 2.99 (3H, d), 3.73 (6H, s), 5.12-5.18 (1H, m), 5.22 (1H, t), 5.83-5.89 (1H, m), 6.33 (1H, t), 6.43 (2H, d), 6.47 (1H, s), 7.35 (2H, d), 7.93 (2H, d), 10.55 (1H, s), 12.13 (1H, s). MS: m/z 475 (MH+).

Mean of n=1, FGFR Kinase assay—Caliper Echo Dosing, $IC_{50}$ 0.000041 µM.

Methyl 4-(1-prop-2-enylpiperidin-4-yl)benzoate used as starting material was prepared as follows:

3-Bromoprop-1-ene (0.433 mL, 5.00 mmol) was added dropwise over 5 mins under nitrogen to a stirred solution of methyl 4-piperidin-4-ylbenzoate (1.096 g, 5 mmol) and N-ethyl-N-isopropylpropan-2-amine (2.066 mL, 12.50 mmol) in DCM (10 mL) at room temperature. The reaction mixture was stirred for 1 h at room temperature. This was evaporated to dryness and partially purified on a SCX column, eluting with 3.5N ammonia in methanol. Fractions containing product were combined and evaporated to dryness. The crude product was purified by silica column chromatography, eluting with 5% MeOH in DCM. Pure fractions were evaporated to dryness to afford the desired compound (1.004 g, 77%) as a white solid.

1H NMR (399.9 MHz, CDCl3) δ 1.78-1.86 (4H, m), 2.02-2.08 (2H, m), 2.53-2.57 (1H, m), 3.03-3.05 (3H, m), 3.07 (1H, t), 3.90 (3H, s), 5.14-5.23 (2H, m), 5.85-5.97 (1H, m), 7.28-7.31 (2H, m), 7.95-7.98 (2H, m). MS: m/z 260 (MH+).

Methyl 4-piperidin-4-ylbenzoate was prepared as outlined in Example 99.

5-[2-(3,5-dimethoxyphenyl)ethyl]-2H-pyrazol-3-amine, used as starting material was prepared as indicated in Example 2.

Example 145

4-(1,4-diazepan-1-yl)-N-[5-[2-(3,5-dimethoxyphenyl)ethyl]-2H-pyrazol-3-yl]benzamide 4-(1,4-diazepan-1-yl)-N-[5-[2-(3,5-dimethoxyphenyl)ethyl]-2H-pyrazol-3-yl]benzamide was prepared following the procedure as outlined for Example 99, starting from ethyl 4-(1,4-diazepan-1-yl)benzoate (0.497 g, 2 mmol) and 5-[2-(3,5-dimethoxyphenyl)ethyl]-2H-pyrazol-3-amine (0.495 g, 2.00 mmol) and 2M trimethylaluminium (2.50 mL, 5.0 mmol) in toluene (10 ml). The crude product was purified by silica column chromatography, eluting with a gradient of 0 to 10% 2.5 M ammonia MeOH in DCM. Fractions containing the product were evaporated to dryness and further purified by preparative HPLC, using decreasingly polar mixtures of water (containing 1% NH3) and MeCN as eluents. Fractions containing the desired compound were evaporated to dryness to afford the title compound (0.024 g, 2.67%) as a white solid.

1H NMR (500.13 MHz, DMSO-d6+d4HOAc) δ 2.07 (2H, t), 2.90 (4H, s), 3.10 (2H, t), 3.24 (2H, t), 3.62 (2H, t), 3.74-3.76 (8H, m), 6.33 (2H, t), 6.42 (2H, d), 6.81-6.83 (2H, m), 7.88-7.89 (2H, m). MS: m/z 450 (MH+).

Mean of n=2, FGFR Kinase assay—Caliper Echo Dosing, $IC_{50}$ 0.0007 µM.

Ethyl 4-(1,4-diazepan-1-yl)benzoate used as starting material was prepared as follows: Ethyl 4-fluorobenzoate (11.01 mL, 75 mmol) and 1,4-diazepane (30.0 g, 300.00 mmol) in DMSO (150 mL) warmed to 100° C. under nitrogen. The resulting solution was stirred at 100° C. for 24 h. The reaction mixture was cooled and evaporated to dryness. The reaction mixture was quenched with 2M NaOH (150 mL), extracted with EtOAc (3×75 mL), the organic layer was washed with saturated brine (100 ml), dried over MgSO4, filtered and evaporated to afford ethyl 4-(1,4-diazepan-1-yl)benzoate (17.43 g, 94%) as a colourless oil.

1H NMR (399.9 MHz, CDCl3) δ 1.27-1.31 (3H, m), 1.71 (1H, s), 1.79-1.85 (2H, m), 2.74 (1H, d), 2.74 (1H, d), 2.95 (1H, d), 2.96 (1H, d), 3.51 (2H, t), 3.56 (2H, t), 4.21-4.27 (2H, m), 6.56-6.60 (2H, m), 7.80-7.83 (2H, m). MS: m/z 249 (MH+).

5-[2-(3,5-Dimethoxyphenyl)ethyl]-2H-pyrazol-3-amine, used as starting material was prepared as indicated in Example 2.

Example 146

N-[5-[2-(3,5-dimethoxyphenyl)ethyl]-2H-pyrazol-3-yl]-4-(1-prop-2-ynylpiperidin-4-yl)benzamide N-[5-[2-(3,5-dimethoxyphenyl)ethyl]-2H-pyrazol-3-yl]-4-(1-prop-2-ynylpiperidin-4-yl)benzamide was prepared following the procedure as outlined for Example 99, starting from methyl 4-(1-prop-2-ynylpiperidin-4-yl)benzoate (0.257 g, 1.00 mmol) and 5-[2-(3,5-dimethoxyphenyl)ethyl]-2H-pyrazol-3-amine (0.247 g, 1 mmol) in dry toluene (10 mL) with 2M trimethylaluminium (1.250 mL, 2.50 mmol). The crude product was purified by silica column chromatography, eluting with a gradient of 0 to 5% 2.5M ammonia/methanol in DCM. Pure fractions were evaporated to dryness and the product crystallised from DCM/diethyl ether to give the title compound (0.245 g, 51.8%) as a white solid.

1H NMR (399.9 MHz, DMSO-d6+d4HOAc) δ 1.64-1.73 (2H, m), 1.79 (2H, d), 2.24-2.29 (2H, m), 2.49-2.54 (1H, m), 2.88 (4H, s), 2.90 (1H, s), 2.93 (1H, s), 3.15 (1H, t), 3.73 (6H, s), 6.33 (1H, t), 6.42 (2H, d), 6.44 (1H, s), 7.36 (2H, d), 7.93 (2H, d), 10.57 (1H, s), 11.95 (4H, s). MS: m/z 473 (MH+).

Mean of n=1, FGFR Kinase assay—Caliper Echo Dosing, $IC_{50}$ 0.0011 µM.

Methyl 4-(1-prop-2-ynylpiperidin-4-yl)benzoate used as starting material was prepared following the procedure as for methyl 4-(1-prop-2-enylpiperidin-4-yl)benzoate (Example 144), but starting from 3-bromoprop-1-yne (0.356 mL, 4.00 mmol) (80% solution in toluene), methyl 4-piperidin-4-ylbenzoate (0.877 g, 4 mmol) and N-ethyl-N-isopropylpropan-2-amine (1.653 mL, 10.00 mmol) in DCM (5 mL). The crude product was purified by silica column chromatography, eluting with 5% MeOH in DCM. Pure fractions were evaporated to dryness to afford the desired compound (0.748 g, 72.7%) as a white solid. 1H NMR (399.9 MHz, CDCl3) δ 1.81-1.90 (4H, m), 2.27 (1H, t), 2.32-2.38 (2H, m), 2.54-2.59 (1H, m), 3.00-3.04 (2H, m), 3.36 (2H, d), 3.90 (3H, s), 7.27-7.30 (2H, m), 7.95-7.98 (2H, m). MS: m/z 258 (MH+).

Methyl 4-piperidin-4-ylbenzoate was prepared as outlined in Example 144.

5-[2-(3,5-dimethoxyphenyl)ethyl]-2H-pyrazol-3-amine, used as starting material was prepared as indicated in Example 2.

Example 147

N-[5-[(3,5-dimethoxyphenyl)methoxy]-2H-pyrazol-3-yl]-5-[(3S,5R)-3,5-dimethylpiperazin-1-yl]thiophene-2-carboxamide 2M Trimethylaluminium (1.250 ml, 2.50 mmol) in toluene, was added dropwise to a stirred solution of ethyl 5-((3R,5S)-3,5-dimethylpiperazin-1-yl)thiophene-2-carboxylate (0.268 g, 1 mmol) and 5-[(3,5-dimethoxyphenyl)methoxy]-2H-pyrazol-3-amine hydrochloride (0.286 g, 1.00 mmol) in toluene (7.14 ml) at room temperature and then the mixture was heated at 80° C. under nitrogen for 4 h and then at 70° C. for 18 h. Ethyl acetate (5 mL) was added to the reaction mixture followed by a solution of potassium sodium tartrate (5 mL, 20% aqueous). More ethyl acetate (50 mL) and water (25 mL) was added and the mixture was filtered through celite. The filtrate was transferred to a separating funnel and the aqueous layer removed. The ethyl acetate layer was washed with saturated brine and then dried over magnesium sulphate. After filtration the solvent was evaporated to give the crude product as a yellow gum. The crude product was purified by preparative HPLC, using decreasingly polar mixtures of water (containing 1% NH3) and MeCN as eluents. Fractions containing the desired compound were evaporated to dryness to afford the title compound (0.154 g, 32.7%) as a white solid.

1H NMR (500.13 MHz, DMSO-d6, CD3CO2D) δ 1.23 (6H, d), 2.79 (2H, t), 3.26-3.34 (2H, m), 3.63-3.66 (2H, m), 3.76 (6H, s), 5.08 (2H, s), 5.63 (1H, s), 6.25 (1H, d), 6.43 (1H, t), 6.59 (2H, d), 7.66 (1H, d), 11.08 (1H, s) MS: m/z 472 (MH+)

Mean of n=1, FGFR Kinase assay—Caliper Echo Dosing, $IC_{50}$ 0.0018 µM.

5-[(3,5-Dimethoxyphenyl)methoxy]-2H-pyrazol-3-amine hydrochloride, used as starting material was prepared as in Example 12.

Ethyl 5-((3R,5S)-3,5-dimethylpiperazin-1-yl)thiophene-2-carboxylate, used as starting material was prepared as follows:

Palladium(II) acetate (0.225 g, 1.00 mmol) was added to ethyl 5-bromothiophene-2-carboxylate (2.351 g, 10 mmol), (2S,6R)-2,6-dimethylpiperazine (1.142 g, 10.00 mmol), rac-2,2'-bis(diphenylphosphino)-1,1'-binaphthyl (0.623 g, 1.00 mmol) and cesium carbonate (4.56 g, 14.00 mmol) in dioxane (100 ml) at 20° C. under nitrogen. The resulting suspension was stirred at 105° C. for 23 h. The mixture was evaporated to dryness to give a brown oil. This crude product was purified by ion exchange chromatography, using a SCX2 column. The crude material was dissolved in methanol and then applied to the column. The desired product was eluted from the column using 2M NH3 in methanol and pure fractions were evaporated to dryness to afford the crude product as a brown solid.

This material was further purified by silica column chromatography, eluting with a gradient of 0 to 5% MeOH in DCM. Pure fractions were evaporated to dryness to afford ethyl 5-((3S,5R)-3,5-dimethylpiperazin-1-yl)thiophene-2-carboxylate (1.600 g, 59.6%) as a white solid.

1H NMR (399.9 MHz, CDCl3) δ 1.12-1.14 (6H, m), 1.33 (3H, t), 2.46-2.56 (2H, m), 2.98-3.07 (2H, m), 3.42-3.46 (2H, m), 4.28 (2H, q), 6.00 (1H, d), 7.55 (1H, d) MS: m/z 269 (MH+)

Example 148

N-[5-[2-(3,5-dimethoxyphenyl)ethyl]-2H-pyrazol-3-yl]-4-[1-(2-methoxyethyl)piperidin-4-yl]benzamide N-[5-[2-(3,5-dimethoxyphenyl)ethyl]-2H-pyrazol-3-yl]-4-[1-(2-methoxyethyl)piperidin-4-yl]benzamide was prepared following the procedure as outlined for Example 99, starting from methyl 4-(1-(2-methoxyethyl)piperidin-4-yl)benzoate (0.428 g, 1.25 mmol) and 5-[2-(3,5-dimethoxyphenyl)ethyl]-2H-pyrazol-3-amine (0.309 g, 1.25 mmol) and 2M trimethylaluminium (1.56 mL, 3.13 mmol) in toluene (10 ml). The crude product was purified by silica column chromatography, eluting with a gradient of 0 to 5% 2.5M ammonia/methanol in DCM. Pure fractions were evaporated to dryness and the product was crystallised from DCM/diethyl ether to afford the title compound (0.215 g, 34.9%) as an off white solid.

1H NMR (399.9 MHz, CDCl3) δ 1.76-1.91 (4H, m), 2.10-2.17 (2H, m), 2.54-2.58 (1H, m), 2.63 (2H, t), 2.92-2.96 (4H, m), 3.10 (2H, d), 3.37 (3H, s), 3.56 (2H, t), 3.76 (6H, s), 6.33-6.35 (3H, m), 6.68 (1H, s), 7.32 (2H, d), 7.80 (2H, d), 8.65 (1H, s), 9.28 (1H, s). MS: m/z 493 (MH+).

Mean of n=2, FGFR Kinase assay—Caliper Echo Dosing, $IC_{50}$ 0.00087 µM.

Methyl 4-(1-(2-methoxyethyl)piperidin-4-yl)benzoate used as starting material was prepared as follows:

A solution of methyl 4-(piperidin-4-yl)benzoate, HCl (1.279 g, 5 mmol), N-ethyl-N-propan-2-ylpropan-2-amine (3.49 mL, 20.00 mmol) and 1-bromo-2-methoxyethane (0.470 mL, 5.00 mmol) in dichloromethane (10 mL) was heated at 40° C. or 18 h. A few drops of DMF were added to aid solubility. The reaction mixture was cooled, diluted with DCM (30 ml) and washed with water (2×30 ml) and saturated sodium chloride solution (30 ml). This was dried over MgSO4, filtered and evaporated to dryness. The crude product was purified by silica column chromatography, eluting with a gradient of 0 to 5% MeOH in DCM. Pure fractions were evaporated to dryness to afford methyl 4-(1-(2-methoxyethyl)piperidin-4-yl)benzoate (0.723 g, 52.1%) as a colourless oil.

1H NMR (399.9 MHz, CDCl3) δ 1.75 (1H, t), 1.81-1.90 (3H, m), 2.09-2.15 (2H, m), 2.55 (1H, q), 2.60-2.63 (2H, m), 3.08-3.11 (2H, m), 3.37 (3H, s), 3.53-3.56 (2H, m), 3.89-3.90 (3H, m), 7.27-7.31 (2H, m), 7.95-7.98 (2H, m). MS: m/z 278 (MH+).

5-[2-(3,5-dimethoxyphenyl)ethyl]-2H-pyrazol-3-amine, used as starting material was prepared as indicated in Example 2.

Example 149

N-[5-[2-(3,5-dimethoxyphenyl)ethyl]-2H-pyrazol-3-yl]-2-[(3S)-3-propan-2-ylpiperazin-1-yl]pyrimidine-5-carboxamide Trimethylaluminium (2M in toluene, 1.23 mL, 2.46 mmol) was added dropwise to a stirred suspension of (S)-methyl 2-(3-propan-2-ylpiperazin-1-yl)pyrimidine-5-carboxylate (260 mg, 0.98 mmol) and 5-[2-(3,5-dimethoxyphenyl)ethyl]-2H-pyrazol-3-amine (243 mg, 0.98 mmol) in toluene (8.38 mL) at room temperature. The reaction was then stirred at 60° C. for 18 h under a nitrogen atmosphere. The reaction mixture was quenched into methanol (100 mL) and treated with HCl (2N aqueous solution, until the pH was 7 or lower). The crude product was purified by ion exchange chromatography, using a SCX column. The desired product was eluted from the column using 7M NH3/MeOH and fractions were evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (292 mg, 62%) as a white solid.

1H NMR (399.9 MHz, DMSO-d$_6$) δ 0.95-0.97 (6H, d), 1.63 (1H, m), 2.26-2.31 (1H, m), 2.57-2.64 (1H, m), 2.68 (1H, d), 2.88 (4H, s), 2.89-2.97 (1H, m) 2.98-3.02 (1H, m), 3.72 (6H, s), 4.57 (1H, d), 4.66 (1H, d), 6.33 (1H, t), 6.41-6.44 (3H, m), 8.88 (2H, s), 10.56 (1H, s), 12.14 (1H, s). MS: m/z 480 (MH+)

Mean of n=1, FGFR Kinase assay—Caliper Echo Dosing, IC$_{50}$ 0.0044 µM.

5-[2-(3,5-dimethoxyphenyl)ethyl]-2H-pyrazol-3-amine, used as starting material was prepared as indicated in Example 2.

(S)-methyl 2-(3-propan-2-ylpiperazin-1-yl)pyrimidine-5-carboxylate, used as starting material was prepared as follows:

A solution of (2S)-2-propan-2-ylpiperazine (223 mg, 1.74 mmol) in dichloromethane (4.40 mL) was added to a stirred solution of methyl 2-chloropyrimidine-5-carboxylate (300 mg, 1.74 mmol) in dichloromethane (4.30 mL) at 25° C. N-Ethyl-N-propan-2-ylpropan-2-amine (0.752 mL, 4.35 mmol) was added. The resulting solution was stirred at room temperature for 18 h under a nitrogen atmosphere. The reaction mixture was concentrated and diluted with methanol. The crude product was purified by ion exchange chromatography, using a SCX column. The desired product was eluted from the column using 7M NH3/MeOH and fractions were evaporated to dryness to afford the desired compound (456.1 mg, 99%) as a yellow oil. This was used directly with no further purification.

1H NMR (399.9 MHz, DMSO-d$_6$) δ 0.94-0.96 (6H, m), 1.58-1.66 (1H, m), 2.25-2.30 (1H, m), 2.56-2.63 (1H, m), 2.68-2.74 (1H, m), 2.95-3.02 (2H, m), 3.81 (3H, s), 4.56-4.60 (1H, m), 4.64-4.68 (1H, m), 8.78 (2H, s). MS: m/z 265 (MH+)

(2S)-2-propan-2-ylpiperazine, used as starting material was prepared as follows:

A solution of tert-butyl (2S)-2-propan-2-ylpiperazine-1-carboxylate (2 g, 8.76 mmol) in a mixture of ethyl acetate (20 mL) and methanol (20.00 mL) was stirred at room temperature with 4M HCl in dioxane (30 mL) for 40 h under nitrogen. The reaction mixture was evaporated to dryness. The crude product was purified by ion exchange chromatography, using a SCX column. The desired product was eluted from the column using 3.5M NH3/MeOH and pure fractions were evaporated to dryness to afford (2S)-2-propan-2-ylpiperazine (1.052 g, 94%) as a white solid.

1H NMR (399.9 MHz, DMSO-d6) δ 0.83-0.87 (6H, m), 1.39-1.47 (1H, m), 2.15-2.22 (2H, m), 2.41-2.47 (1H, m), 2.53-2.59 (1H, m), 2.67 (1H, d), 2.75-2.80 (2H, m)—2 protons not seen.

Example 150

N-[5-[2-(3,5-dimethoxyphenyl)ethyl]-2H-pyrazol-3-yl]-2-(4-methyl-3-oxopiperazin-1-yl)pyrimidine-5-carboxamide Trimethylaluminium (2M in toluene, 1.23 mL, 2.46 mmol) was added dropwise to a stirred suspension of 5-[2-(3,5-dimethoxyphenyl)ethyl]-2H-pyrazol-3-amine (243 mg, 0.98 mmol) and methyl 2-(4-methyl-3-oxopiperazin-1-yl)pyrimidine-5-carboxylate (246 mg, 0.98 mmol) in toluene (5.00 mL) at 25° C. The resulting solution was stirred at 60° C. for 24 h. The reaction mixture was added to methanol (100 mL), then treated with HCl (2N aqueous solution, until pH was 7 or lower). The crude product was purified by ion exchange chromatography, using a SCX column. The desired product was eluted from the column using 7M NH3/MeOH and fractions were evaporated to dryness to afford impure product. The crude product was purified by preparative HPLC, using decreasingly polar mixtures of water (containing 0.1% TFA) and MeCN as eluents. Fractions containing the desired compound were evaporated to dryness to afford the title compound (204 mg, 45%) as a white solid.

1H NMR (399.9 MHz, DMSO-d$_6$) δ 2.88-2.91 (7H, m), 3.44 (2H, t), 3.72 (6H, s), 4.08 (2H, t), 4.33 (2H, s), 6.33 (1H, t), 6.40-6.47 (3H, m), 8.95 (2H, s), 10.66 (1H, s), 12.16 (1H, s). MS: m/z 466 (MH+)

Mean of n=1, FGFR Kinase assay—Caliper Echo Dosing, IC$_{50}$ 0.012 µM.

5-[2-(3,5-dimethoxyphenyl)ethyl]-2H-pyrazol-3-amine, used as starting material was prepared as indicated in Example 2.

Methyl 2-(4-methyl-3-oxopiperazin-1-yl)pyrimidine-5-carboxylate, used as starting material was prepared as follows:

A solution of 1-methylpiperazin-2-one (198 mg, 1.74 mmol) in dichloromethane (4.00 mL) was added to a stirred solution of methyl 2-chloropyrimidine-5-carboxylate (300 mg, 1.74 mmol) in dichloromethane (4.70 mL) at 25° C. The resulting solution was stirred at room temperature for 4 h under nitrogen. The reaction mixture was concentrated and dissolved in ethyl acetate (25 ml) and NaOH (50 ml, 1M aqueous solution). The organic layer was washed with ethyl acetate (25 ml). The organic layers were combined and washed with brine (50 ml), dried using MgSO4, filtered and evaporated to dryness to afford methyl 2-(4-methyl-3-oxopiperazin-1-yl)pyrimidine-5-carboxylate (246 mg, 57%) as a cream solid.

1H NMR (399.9 MHz, DMSO-d$_6$) δ 2.91 (3H, s), 3.44 (2H, t), 3.83 (3H, s), 4.09 (2H, t), 4.35 (2H, s), 8.86 (2H, s). MS: m/z 501 (2MH+)

Example 151

4-(1,2,3,4,4a,5,7,7a-octahydropyrrolo[3,4-b]pyridin-6-yl)-N-[5-[(3,5-dimethoxyphenyl)methoxy]-2H-pyrazol-3-yl]benzamide 4-(1,2,3,4,4a,5,7,7a-octahydropyrrolo[3,4-b]pyridin-6-yl)-N-[5-[(3,5-dimethoxyphenyl)methoxy]-2H-pyrazol-3-yl]benzamide was prepared following the procedure as for Example 115, but starting from methyl 4-(1,2,3,4,4a,5,7,7a-octahydropyrrolo[3,4-b]pyridin-6-yl)benzoate (0.221 g, 0.85 mmol) and 5-[(3,5-dimethoxyphenyl)methoxy]-2H-pyrazol-3-amine HCl (0.243 g, 0.85 mmol) and 2M trimethylaluminium in toluene (1.06 ml, 2.13 mmol). The crude product was purified by preparative HPLC, using decreasingly polar mixtures of water (containing 1% NH3) and MeCN as eluents. Fractions containing the desired compound were evaporated to dryness to afford the title compound (0.124 g, 30.5%) as a white solid.

1H NMR (399.9 MHz, DMSO-d$_6$) δ 1.36-1.45 (1H, m), 1.50-1.60 (1H, m), 1.63-1.75 (2H, m), 2.12 (1H, s), 2.27-2.38 (1H, m), 2.83 (1H, d), 3.16 (1H, d), 3.26-3.36 (2H, m), 3.37-3.45 (2H, m), 3.85 (6H, s), 5.08 (2H, s), 5.54 (1H, s), 6.44 (1H, s), 6.52 (2H, d), 6.57 (2H, s), 7.82 (2H, d), 10.46 (1H, s0, 11.45 (1H, s). 1 proton not seen. MS: m/z 478 (MH+).

Mean of n=3, FGFR Kinase assay—Caliper Echo Dosing, IC$_{50}$ 0.0013 µM.

Methyl 4-(1,2,3,4,4a,5,7,7a-octahydropyrrolo[3,4-b]pyridin-6-yl)benzoate used as starting material was prepared as follows:

2,3,4,4a,5,6,7,7a-Octahydro-1H-pyrrolo[3,4-b]pyridine. 2HCl (0.813 g, 5 mmol) was dissolved in water (10 ml) and placed on a SCX2 column (50 g). This was washed through with methanol and released the freebase from the column with 7N ammonia in methanol. The freebase and methyl 4-fluorobenzoate (0.291 mL, 2.25 mmol) were dissolved in DMSO (10 mL) and heated at 120° C. for 12 h. The crude reaction mixture was partly purified by ion exchange chromatography, using a SCX column. The desired product was eluted from the column using 7M NH3/MeOH and fractions were evaporated to dryness. The crude product was purified by silica column chromatography, eluting with a gradient of 0 to 10% 3M ammonia/MeOH in DCM. Pure fractions were evaporated to dryness to afford the desired compound (0.230 g, 17.67%) as a white solid.

1HNMR (700.03 MHz, CDCl3) δ: 1.48-1.53 (1H, m), 1.57-1.68 (2H, m), 1.74-1.83 (1H, m), 2.34-2.40 (1H, m), 2.66-2.70 (1H, m), 2.97-3.02 (1H, m), 3.23-3.27 (1H, m), 3.83-3.87 (1H, m), 3.46-3.50 (3H, m), 3.85 (3H, s), 6.49 (2H, d), 7.89 (2H, d). MS: m/z 261 (MH+).

Example 152

N-[5-[2-(3,5-dimethoxyphenyl)ethyl]-2H-pyrazol-3-yl]-5-(1-methylpiperidin-4-yl)pyrazine-2-carboxamide Trimethylaluminium (2 M in toluene, 1.73 ml, 3.46 mmol) was added dropwise to a stirred suspension of 5-[2-(3,5-dimethoxyphenyl)ethyl]-2H-pyrazol-3-amine (247 mg, 1.00 mmol) and methyl 5-(1-methylpiperidin-4-yl)pyrazine-2-carboxylate (235 mg, 1.00 mmol) in anhydrous toluene (5.00 ml) at room temperature. The resulting solution was stirred at 60° C. for 18 h. The reaction mixture was quenched into methanol (100 mL) and treated with HCl (2M aqueous solution, to pH7 or lower) and the crude product was purified by ion exchange chromatography, using a SCX column. The desired product was eluted from the column using 7M NH3/MeOH. At this point a white solid precipitated from the eluent. The precipitate was collected by suction filtration and dried under vacuum to afford the product (90 mg, 20%) as a cream solid. The filtrate was concentrated and a second sample of product was obtained by crystallisation from methanol to afford the title compound (93 mg, 21%) as a cream solid.

1H NMR (399.9 MHz, DMSO-d6) δ 1.80-1.89 (4H, m), 1.98-2.04 (2H, m), 2.22 (3H, s), 2.83-2.90 (7H, m), 3.73 (6H, s), 6.33 (1H, t), 6.43 (2H, d), 6.50 (1H, d), 8.73 (1H, d), 9.18 (1H, d), 10.27 (1H, s), 12.27 (1H, s). MS: m/z 451 (MH+).

Mean of n=2, FGFR Kinase assay—Caliper Echo Dosing, IC$_{50}$ 0.0013 μM.

Methyl 5-(1-methylpiperidin-4-yl)pyrazine-2-carboxylate used as starting material was prepared as follows:

Sodium triacetoxyborohydride (530 mg, 2.50 mmol) was added to methyl 5-(piperidin-4-yl)pyrazine-2-carboxylate (221 mg, 1.00 mmol), formaldehyde (37% aqueous solution, 1.50 ml, 20.00 mmol) and acetic acid (0.11 ml, 2.00 mmol) in methanol (5.00 ml) at 25° C. The resulting solution was stirred at ambient temperature for 18 h. The reaction mixture was quenched with water (5 mL) and the crude product was purified by ion exchange chromatography, using a SCX column. The desired product was eluted from the column using 7M NH3/MeOH and evaporated to dryness to afford methyl 5-(1-methylpiperidin-4-yl)pyrazine-2-carboxylate (239 mg, 100%) as a yellow waxy solid. This was used directly with no further purification.

1H NMR (399.9 MHz, CDCl3) δ 1.92-1.99 (4H, m), 2.07-2.13 (2H, m), 2.34 (3H, s), 2.79-2.87 (1H, m), 2.99-3.03 (2H, m), 4.03 (3H, s), 8.61 (1H, d), 9.21 (1H, d). MS: m/z 236 (MH+).

Methyl 5-(piperidin-4-yl)pyrazine-2-carboxylate used as starting material was prepared as follows:

Hydrogen chloride (4M in 1,4-dioxane, 0.37 ml, 1.48 mmol) was added to methyl 5-[1-[(2-methylpropan-2-yl)oxycarbonyl]piperidin-4-yl]pyrazine-2-carboxylate (120 mg, 0.37 mmol) in MeOH (3.70 ml). The resulting solution was stirred at ambient temperature for 24 h. The crude product was purified by ion exchange chromatography, using a SCX column. The desired product was eluted from the column using 7M NH3/MeOH and evaporated to dryness to afford methyl 5-(piperidin-4-yl)pyrazine-2-carboxylate (83 mg, 100%) as a pale yellow solid. This was used directly with no further purification.

1H NMR (399.9 MHz, CDCl3) δ 1.76-1.86 (2H, m), 1.92-1.97 (2H, m), 2.80 (2H, d), 2.97-3.05 (1H, m), 3.23-3.27 (2H, m), 4.04 (3H, s), 8.61 (1H, d), 9.22 (1H, d), NH not observed. MS: m/z 222 (MH+).

Methyl 5-[1-[(2-methylpropan-2-yl)oxycarbonyl]piperidin-4-yl]pyrazine-2-carboxylate used as starting material was prepared as follows:

Palladium, 10% on carbon (21 mg, 0.20 mmol) and methyl 5-[1-[(2-methylpropan-2-yl)oxycarbonyl]-3,6-dihydro-2H-pyridin-4-yl]pyrazine-2-carboxylate (183 mg, 0.57 mmol) in ethanol (5.73 mL) was stirred under an atmosphere of hydrogen at ambient temperature and atmospheric pressure for 6 h. The reaction mixture was filtered through celite and concentrated under reduced pressure to give a yellow oil. The crude product was purified by silica column chromatography, eluting with a gradient of 0 to 50% EtOAc in isohexane. Pure fractions were evaporated to dryness to afford methyl 5-[1-[(2-methylpropan-2-yl)oxycarbonyl]piperidin-4-yl]pyrazine-2-carboxylate (126 mg, 68%) as a yellow oil.

1H NMR (DMSO, 399.99 MHz) δ1.43 (9H, s), 1.58-1.68 (2H, m), 1.89 (2H, d), 2.88 (2H, s), 3.07-3.14 (1H, m), 3.92 (3H, s), 4.07-4.11 (2H, m), 8.78 (1H, d), 9.13 (1H, d). MS: m/z 322 (MH+).

Methyl 5-[1-[(2-methylpropan-2-yl)oxycarbonyl]-3,6-dihydro-2H-pyridin-4-yl]pyrazine-2-carboxylate used as starting material was prepared as follows:

Saturated aqueous sodium hydrogen carbonate solution (5.00 ml) was added to methyl 5-chloropyrazine-2-carboxylate (173 mg, 1.00 mmol), tert-butyl 4-(4,4,5,5-tetramethyl-1,3,2-dioxaborolan-2-yl)-3,6-dihydro-2H-pyridine-1-carboxylate (371 mg, 1.20 mmol), palladium(II) acetate (11 mg, 0.05 mmol) and triphenylphosphine (52 mg, 0.20 mmol) in 1,2-dimethoxyethane (5.00 ml) at 25° C. under nitrogen. The resulting mixture was stirred at 80° C. for 4 h. The reaction mixture was diluted with water (50 mL) and washed with EtOAc (50 mL). The aqueous layer was adjusted to pH 1 using HCl (2M aqueous solution) and extracted with EtOAc (2×50 mL). The combined organics were dried over MgSO4 and concentrated under reduced pressure to afford 5-[1-[(2-methylpropan-2-yl)oxycarbonyl]-3,6-dihydro-2H-pyridin-4-yl]pyrazine-2-carboxylic acid (305 mg, 100%) as a yellow solid. This was used directly in the next reaction, with no further purification.

1H NMR (DMSO, 399.9 MHz) δ1.45 (9H, s), 2.64 (2H, d), 3.58 (2H, t), 4.13 (2H, d), 7.02 (1H, s), 9.01 (1H, d), 9.12 (1H, d), 13.40 (1H, br s). MS: m/z 306 (MH+).

Example 153

N-[5-[2-(3,5-dimethoxyphenyl)ethyl]-2H-pyrazol-3-yl]-5-(1-methyl-3,6-dihydro-2H-pyridin-4-yl)pyrazine-2-carboxamide Trimethylaluminium (2M in toluene, 1.74 ml, 3.48 mmol) was added dropwise to a stirred suspension of 5-[2-(3,5- dimethoxyphenyl)ethyl]-2H-pyrazol-3-amine (343 mg, 1.39 mmol) and methyl 5-(1-methyl-3,6-dihydro-2H-pyridin-4-yl)pyrazine-2-carboxylate (324 mg, 1.39 mmol) in anhydrous toluene (6.94 ml) at ambient temperature. The resulting solution was then stirred at 60° C. for 18 h. The reaction mixture was quenched into methanol (100 mL) and treated with HCl (2M aqueous solution, to pH7 or lower) and purified by ion exchange chromatography, using a SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (152 mg, 24%) as a white solid.

1H NMR (399.9 MHz, DMSO-d6) δ 2.33 (3H, s), 2.63-2.64 (4H, m), 2.86-2.89 (4H, m), 3.16 (2H, s), 3.73 (6H, s), 6.33 (1H, s), 6.43-6.43 (2H, m), 6.50 (1H, s), 7.04 (1H, s), 8.96 (1H, s), 9.17 (1H, s), 10.26 (1H, s), 12.28 (1H, s). MS: m/z 449 (MH+).

Mean of n=1, FGFR Kinase assay—Caliper Echo Dosing, $IC_{50}$ 0.00082 μM.

Methyl 5-(1-methyl-3,6-dihydro-2H-pyridin-4-yl)pyrazine-2-carboxylate used as starting material was prepared as follows:

Sodium triacetoxyborohydride (749 mg, 3.53 mmol) was added to methyl 5-(1,2,3,6-tetrahydropyridin-4-yl)pyrazine-2-carboxylate (310 mg, 1.41 mmol), formaldehyde (37% aqueous solution, 2.10 ml, 28.30 mmol) and acetic acid (0.16 ml, 2.83 mmol) in methanol (7.00 ml) at 25° C. The resulting solution was stirred at ambient temperature for 18 h. The reaction mixture was quenched with saturated aqueous NaHCO3 solution (5 mL), diluted with methanol (10 mL) and the crude product was purified by ion exchange chromatography, using a SCX column. The desired product was eluted from the column using 7M NH3/MeOH and evaporated to dryness to afford the desired compound (324 mg, 98%) as a tan waxy solid. This was used directly with no further purification.

1H NMR (399.9 MHz, CDCl3) δ 2.44 (3H, s), 2.69-2.75 (4H, m), 3.23-3.25 (2H, m), 4.03 (3H, s), 6.89-6.91 (1H, m), 8.79 (1H, d), 9.20 (1H, d). MS: m/z 234 (MH+).

Methyl 5-(1,2,3,6-tetrahydropyridin-4-yl)pyrazine-2-carboxylate used as starting material was prepared as follows:

Hydrogen chloride (4M in 1,4-dioxane, 1.57 ml, 6.29 mmol) was added to methyl 5-[1-[(2-methylpropan-2-yl)oxycarbonyl]-3,6-dihydro-2H-pyridin-4-yl]pyrazine-2-carboxylate (502 mg, 1.57 mmol) in methanol (15.70 ml) at room temperature The resulting solution was stirred at ambient temperature for 18 h. The reaction mixture was diluted with water (20 mL) and the crude product purified by ion exchange chromatography, using a SCX column. The desired product was eluted from the column using 7M NH3/MeOH and evaporated to dryness to afford the desired compound (316 mg, 92%) as a yellow solid. This was used directly with no further purification.

1H NMR (399.9 MHz, DMSO-d6) δ 2.47-2.54 (2H, m, partially obscured by solvent peak), 2.94 (2H, t), 3.49 (2H, q), 3.92 (3H, s), 7.09-7.11 (1H, m), 9.00 (1H, d), 9.12 (1H, d), NH not observed. MS: m/z 261 (M+MeCN+H+).

Methyl 5-[1-[(2-methylpropan-2-yl)oxycarbonyl]-3,6-dihydro-2H-pyridin-4-yl]pyrazine-2-carboxylate used as starting material was prepared as outlined in Example 152.

Example 154

N-[5-[2-(3,5-dimethoxyphenyl)ethyl]-2H-pyrazol-3-yl]-4-[(3R,5S)-3,5-dimethylpiperazin-1-yl]benzamide N-[5-[2-(3,5-dimethoxyphenyl)ethyl]-2H-pyrazol-3-yl]-4-[(3R,5S)-3,5-dimethylpiperazin-1-yl]benzamide was prepared following the procedure as for Example 155, but starting with ethyl 4-((3R,5S)-3,5-dimethylpiperazin-1-yl)benzoate (0.525 g, 2 mmol), 5-[2-(3,5-dimethoxyphenyl)ethyl]-2H-pyrazol-3-amine (0.495 g, 2.00 mmol) and 2M trimethylaluminium (2.5 ml, 5.0 mmol in toluene). The crude mixture was chromatographed on a SCX column, eluting with 7N ammonia in methanol. Fractions containing product were combined and evaporated to give an oil. The oil was suspended in dichloromethane (20 ml) and product slowly crystallised out. This was filtered to give the title compound (0.465 g, 50.2%).

1H NMR (399.9 MHz, DMSO-d6) δ 1.04-1.05 (6H, m), 1.92 (2H, s), 2.20-2.25 (2H, m), 2.80-2.82 (1H, m), 2.81-2.84 (1H, m), 2.87 (4H, s), 3.71-3.74 (2H, m), 3.73 (6H, s), 6.33 (1H, t), 6.40 (1H, s), 6.42 (2H, d), 6.95 (2H, d), 7.89 (2H, d), 10.30 (1H, s). MS: m/z 464 (MH+).

Mean of n=1, FGFR Kinase assay—Caliper Echo Dosing, $IC_{50}$ 0.00075 μM.

5-[2-(3,5-dimethoxyphenyl)ethyl]-2H-pyrazol-3-amine, used as starting material was prepared as indicated in Example 2.

Example 155

N-[5-[2-(3,5-dimethoxyphenyl)ethyl]-2H-pyrazol-3-yl]-4-[(3R,5S)-3,4,5-trimethylpiperazin-1-yl]benzamide A 2M solution of trimethylaluminium (2.500 mL, 5.00 mmol) in toluene, was added dropwise to a stirred suspension of ethyl 4-((3R,5S)-3,4,5-trimethylpiperazin-1-yl)benzoate (0.643 g, 2 mmol) and 5-[2-(3,5-dimethoxyphenyl)ethyl]-2H-pyrazol-3-amine (0.495 g, 2.00 mmol) in toluene (10 mL) at room temperature. The solution was then heated at 60° C. for 18 h. The reaction mixture was cooled and quenched with methanol (15 ml) and 2N hydrochloric acid (5 ml). The crude reaction mixture was purified by ion exchange chromatography on a SCX column, eluting with 7N ammonia in methanol. The appropriate fractions were evaporated to give an oil. The crude product was purified by silica column chromatography, eluting with a gradient of 0 to 10% 2.5N ammonia/MeOH in DCM. Pure fractions were evaporated to dryness to afford, on crystallisation from DCM/diethyl ether, the title compound (0.322 g, 33.7%) as a cream solid.

1HNMR (500.13 MHz, DMSOd+CD3COOD @ 373K) δ: 1.16 (6H, d), 2.34 (3H, s), 2.48-2.55 (2H, m), 2.66 (2H, t), 2.88 (4H, s), 3.69-3.75 (2H, m), 3.73 (3H, s), 6.28-6.92 (2H, m), 6.47-6.49 (2H, m), 6.92 (2H, d), 7.85 (2H, d). MS: m/z 478 (MH+).

Mean of n=2, FGFR Kinase assay—Caliper Echo Dosing, $IC_{50}$ 0.00045 μM.

Ethyl 4-((3R,5S)-3,4,5-trimethylpiperazin-1-yl)benzoate used as starting material was prepared as follows:

Sodium triacetoxyborohydride (5.30 g, 25.00 mmol) was added to ethyl 4-((3R,5S)-3,5-dimethylpiperazin-1-yl)benzoate (2.62 g, 10 mmol), and acetic acid (1.145 mL, 20.00 mmol) in methanol (15 mL) at 25° C. The resulting solution was stirred at ambient temperature for 18 h. The reaction mixture was quenched with saturated NaHCO3 (15 mL) to pH7 and the crude product was purified by ion exchange chromatography, using a SCX column. The desired product was eluted from the column using 7M NH3/MeOH and evaporated to dryness to afford an oil. The crude product was purified by silica column chromatography, eluting with a gradient of 0 to 5% MeOH in DCM. Pure fractions were evaporated to dryness to afford ethyl 4-((3R,5S)-3,4,5-trimethylpiperazin-1-yl)benzoate (1.960 g, 70.9%) as a yellow oil. MS: m/z 277 (MH+).

Ethyl 4-((3R,5S)-3,5-dimethylpiperazin-1-yl)benzoate used as starting material was prepared as follows:

(2S,6R)-2,6-dimethylpiperazine (6.85 g, 60.00 mmol) was added to ethyl-4-fluorobenzoate (2.20 mL, 15 mmol), in DMSO (40 mL) and warmed to 120° C. under nitrogen. The resulting solution was stirred at 120° C. for 20 h. The reaction mixture was cooled and the solvent evaporated. The crude product was purified by silica column chromatography, eluting with a gradient of 0 to 10% methanol in dichloromethane containing 1% 0.880 ammonia. Pure fractions were evaporated to dryness to afford ethyl 4-((3R,5S)-3,5-dimethylpiperazin-1-yl)benzoate (2.83 g, 71.9%) as a brown oil, which solidified on standing.

1H NMR (399.9 MHz, CDCl3) δ 1.15 (6H, d), 1.37 (3H, t), 2.38 (1H, d), 2.41 (1H, d), 2.96-3.04 (2H, m), 3.65-3.69 (2H, m), 4.33 (2H, q), 6.84-6.87 (2H, m), 7.89-7.93 (2H, m). MS: m/z 263 (MH+).

5-[2-(3,5-dimethoxyphenyl)ethyl]-2H-pyrazol-3-amine, used as starting material was prepared as indicated in Example 2.

Example 156

N-[5-[2-(3,5-dimethoxyphenyl)ethyl]-2H-pyrazol-3-yl]-4-(4-methyl-1,4-diazepan-1-yl)benzamide N-[5-[2-(3,5-dimethoxyphenyl)ethyl]-2H-pyrazol-3-yl]-4-(4-methyl-1,4-diazepan-1-yl)benzamide was prepared following the procedure as for Example 115, but starting from of methyl 4-(4-methyl-1,4-diazepan-1-yl)benzoate (0.372 g, 1.5 mmol) and 5-[2-(3,5-dimethoxyphenyl)ethyl]-2H-pyrazol-3-amine (0.371 g, 1.5 mmol) and 2M trimethylaluminium in toluene (1.875 ml, 3.75 mmol). The crude product was purified by silica column chromatography, eluting with a gradient of 0 to 10% 2.5M ammonia/MeOH in DCM. Pure fractions were evaporated to dryness and the residual oil crystallised from DCM/diethyl ether to afford the title compound (0.142 g, 20.42%) as a white solid. 1HNMR (500.13 MHz, DMSOd6+CD3COOD @ 373K) δ: 2.08-2.15 (2H, m), 2.69 (3H, s), 2.88 (4H, s), 3.11 (2H, t), 3.19-3.24 (2H, m), 3.56 (2H, t), 3.72 (3H, s), 3.74 (2H, t), 6.30 (1H, d), 3.32 (1H,$), 6.49 (2H, s), 6.79 (2H, d), 7.86 (2H, d). MS: m/z 464 (MH+).

Mean of n=2, FGFR Kinase assay—Caliper Echo Dosing, IC$_{50}$ 0.00081 μM.

Methyl 4-(4-methyl-1,4-diazepan-1-yl)benzoate used as starting material was prepared as follows:

1-Methyl-1,4-diazepane (15.07 g, 132.00 mmol) was added to methyl 4-fluorobenzoate (7.76 mL, 60 mmol) in DMA (150 mL). The resulting solution was stirred at 100° C. for 40 h. The reaction mixture was evaporated and quenched with 2M sodium hydroxide (50 ml). This was extracted with DCM (3×50 ml). The combined organic extracts were washed with saturated brine (50 ml), dried over MgSO4, filtered and evaporated to dryness. The crude product was purified by silica column chromatography, eluting with a gradient of 0 to 10% MeOH in DCM. Pure fractions were evaporated to dryness to afford methyl 4-(4-methyl-1,4-diazepan-1-yl)benzoate (3.59 g, 24.10%) as a tan waxy solid.

1H NMR (399.9 MHz, CDCl3) δ 1.95 (2H, q), 2.31 (3H, s), 2.48 (2H, d), 2.63-2.65 (2H, m), 3.47 (2H, t), 3.54-3.56 (2H, m), 3.78 (3H, s), 6.56-6.59 (2H, m), 7.79-7.83 (2H, m).

Example 157

N-[5-[2-(3,5-dimethoxyphenyl)ethyl]-2H-pyrazol-3-yl]-5-(3-dimethylaminopyrrolidin-1-yl)pyrazine-2-carboxamide N,N-dimethylpyrrolidin-3-amine (114 mg, 1.00 mmol) was added to 5-chloro-N-[5-[2-(3,5-dimethoxyphenyl)ethyl]-2H-pyrazol-3-yl]pyrazine-2-carboxamide (136 mg, 0.35 mmol) in anhydrous dimethylsulfoxide (1.75 ml) at 25° C. The resulting solution was stirred at room temperature for 20 mins. The reaction mixture was diluted with methanol (5.00 ml) and the crude product was purified by ion exchange chromatography, using a SCX column. The desired product was eluted from the column using 7M NH3/MeOH and fractions were evaporated to dryness to afford impure product as a brown oil. The crude product was purified by preparative HPLC, using decreasingly polar mixtures of water (containing 1% NH3) and MeCN as eluents. Fractions containing the desired compound were evaporated to dryness to afford the title compound (130 mg, 80%) as a white solid.

1H NMR (399.9 MHz, DMSO-d$_6$) δ 1.86 (1H, t), 2.16-2.21 (1H, m) 2.23 (6H, s), 2.83-2.85 (1H, m), 2.88 (4H, s), 3.25-3.29 (1H, m), 3.45-3.54 (1H, m), 3.72 (6H, s), 3.73-3.79 (1H, m), 3.81-3.86 (1H, m), 6.33 (1H, t), 6.42 (2H, d), 6.46 (1H, s), 8.01 (1H, d), 8.71 (1H, d), 9.73 (1H, s), 12.17 (1H, s). MS: m/z 466 (MH+)

Mean of n=2, FGFR Kinase assay—Caliper Echo Dosing, IC$_{50}$ 0.0024 μM.

5-Chloro-N-[5-[2-(3,5-dimethoxyphenyl)ethyl]-2H-pyrazol-3-yl]pyrazine-2-carboxamide was prepared as shown in Example 105.

Example 158

5-(3-diethylaminopyrrolidin-1-yl)-N-[5-[2-(3,5-dimethoxyphenyl)ethyl]-2H-pyrazol-3-yl]pyrazine-2-carboxamide N,N-diethylpyrrolidin-3-amine (142 mg, 1.00 mmol) was added to 5-chloro-N-[5-[2-(3,5-dimethoxyphenyl)ethyl]-2H-pyrazol-3-yl]pyrazine-2-carboxamide (136 mg, 0.35 mmol) in anhydrous dimethylsulfoxide (1.75 ml) at 25° C. The resulting solution was stirred at room temperature for 50 mins. The reaction mixture was diluted with methanol (5.00 ml) and the crude product was purified by ion exchange chromatography, using a SCX column. The desired product was eluted from the column using 7M NH3/MeOH and fractions were evaporated to dryness to afford impure product as a brown dry film. The crude product was purified by preparative HPLC, using decreasingly polar mixtures of water (containing 1% NH3) and MeCN as eluents. Fractions containing the desired compound were evaporated to dryness to afford the title compound (141 mg, 82%) as a white solid.

1H NMR (399.9 MHz, DMSO-d$_6$) δ 0.99 (6H, t), 1.80-1.90 (1H, m), 2.17-2.23 (1H, m), 2.56-2.68 (4H, m), 2.88 (4H, s), 3.20-3.26 (1H, m), 3.34-3.41 (1H, m), 3.43-3.50 (1H, m), 3.72 (6H, s), 3.73-3.78 (1H, m) 3.82-3.87 (1H, m), 6.33 (1H, t), 6.42 (2H, d), 6.46 (1H, s), 8.01 (1H, d), 8.71 (1H, d), 9.73 (1H, s), 12.17 (1H, s). MS: m/z 494 (MH+)

Mean of n=2, FGFR Kinase assay—Caliper Echo Dosing, $IC_{50}$ 0.0029 µM.

5-Chloro-N-[5-[2-(3,5-dimethoxyphenyl)ethyl]-2H-pyrazol-3-yl]pyrazine-2-carboxamide was 25 prepared as shown in Example 105.

Example 159

N-[5-[2-(3,5-dimethoxyphenyl)ethyl]-2H-pyrazol-3-yl]-4-(1-ethylpiperidin-4-yl)benzamide A 2M solution of trimethylaluminium in toluene (0.413 mL, 0.83 mmol), was added drop-wise to a suspension of methyl 4-(1-ethylpiperidin-4-yl)benzoate (0.082 g, 0.33 mmol) and 5-[2-(3,5-dimethoxyphenyl)ethyl]-2H-pyrazol-3-amine (0.082 g, 0.33 mmol) in toluene (2 mL) at room temperature. The solution was then heated at 60° C. for 18 h. The reaction mixture was cooled, quenched with methanol (2 ml) and 2N hydrochloric acid (1 ml). The reaction mixture was purified by ion exchange chromatography, using a SCX column. The desired product was eluted from the column using 7M NH3/MeOH and fractions were evaporated to dryness. The crude product was purified by preparative HPLC, using decreasingly polar mixtures of water (containing 1% NH3) and MeCN as eluents. Fractions containing the desired compound were evaporated to dryness to afford the title compound (0.058 g, 38.0%) as a white solid.

1H NMR (500.13 MHz, DH4OAcDMSO-d6) δ 1.21 (3H, t), 1.26 (2H, s), 1.84-1.93 (1H, m), 1.95-2.04 (2H, m), 2.77 (2H, t), 2.89 (4H, s), 2.94 (2H, q), 3.34-3.40 (2H, m), 3.72 (6H, s), 6.30 (1H, d), 6.35 (1H, d), 6.41 (2H, d), 7.34 (2H, d), 7.89 (2H, d). MS: m/z 463 (MH+).

Mean of n=1, FGFR Kinase assay—Caliper Echo Dosing, $IC_{50}$ 0.00097 µM.

5-[2-(3,5-dimethoxyphenyl)ethyl]-2H-pyrazol-3-amine, used as starting material was prepared as indicated in Example 2.

Methyl 4-(1-ethylpiperidin-4-yl)benzoate used as starting material was prepared as follows:

Sodium triacetoxyborohydride (0.397 g, 1.88 mmol) was added portion-wise to acetaldehyde (0.168 mL, 3.00 mmol), methyl 4-(piperidin-4-yl)benzoate, HCl (0.192 g, 0.75 mmol) and sodium acetate (0.062 g, 0.75 mmol) in methanol (5 mL) at room temperature. The resulting solution was stirred at room temperature for 18 h. The reaction mixture was quenched with saturated NaHCO₃ (3 mL) to pH7 and the crude product was purified by ion exchange chromatography, using a SCX column. The desired product was eluted from the column using 7M NH3/MeOH and evaporated to dryness to afford an oil. The crude product was purified by silica column chromatography, eluting with a gradient of 0 to 5% MeOH in DCM. Pure fractions were evaporated to dryness to afford methyl 4-(1-ethylpiperidin-4-yl)benzoate (0.082 g, 44.2%) as a colourless oil. MS: m/z 248 (MH+).

Example 160

N-[5-[2-(3,5-dimethoxyphenyl)ethyl]-2H-pyrazol-3-yl]-2-[3-(methoxymethyl)piperazin-1-yl]pyrimidine-5-carboxamide Trimethylaluminium (2M in toluene, 1.596 mL, 3.19 mmol) was added dropwise to a solution of 5-[2-(3,5-dimethoxyphenyl)ethyl]-2H-pyrazol-3-amine (314 mg, 1.27 mmol) and methyl 2-(3-(methoxymethyl)piperazin-1-yl)pyrimidine-5-carboxylate (338 mg, 1.27 mmol) in toluene (6.35 mL) at 25° C. The resulting mixture was stirred at 60° C. for 18 h under nitrogen. The reaction mixture was added to methanol (100 mL) and treated with HCl (2N aqueous solution, until pH was 7 or lower). The crude product was purified by ion exchange chromatography, using a SCX column. The desired product was eluted from the column using 7M NH3/MeOH and fractions were evaporated to dryness to afford the crude product as a yellow dry film. The crude product was purified by preparative HPLC, using decreasingly polar mixtures of water (containing 1% NH3) and MeCN as eluents. Fractions containing the desired compound were evaporated to dryness to afford the title compound (348 mg, 57%) as a white solid.

1H NMR (399.9 MHz, CDCl₃) δ 2.72-2.77 (2H, m), 2.82-2.92 (5H, m), 2.97-3.04 (2H, m), 3.24-3.28 (1H, m), 3.30 (3H, s), 3.35-3.38 (1H, m), 3.69 (6H, s), 4.61 (2H, d), 6.25-6.28 (3H, m), 6.61 (1H, s), 8.73 (1H, s), 8.76 (2H, s), 9.6 (1H, s). MS: m/z 482 (MH+).

Mean of n=2, FGFR Kinase assay—Caliper Echo Dosing, $IC_{50}$ 0.0043 µM.

5-[2-(3,5-dimethoxyphenyl)ethyl]-2H-pyrazol-3-amine, used as starting material was prepared as indicated in Example 2.

Methyl 2-(3-(methoxymethyl)piperazin-1-yl)pyrimidine-5-carboxylate used as starting material was prepared as follows:

A solution of methyl 2-chloropyrimidine-5-carboxylate (300 mg, 1.74 mmol) in DCM (4.70 mL) was added to a stirred solution of 2-(methoxymethyl)piperazine (226 mg, 1.74 mmol) and N-ethyl-N-propan-2-ylpropan-2-amine (0.752 mL, 4.35 mmol) in DCM (4.00 mL) at 25° C. under nitrogen. The resulting solution was stirred at room temperature for 6 h. The reaction mixture was concentrated and diluted with MeOH. The resulting mixture was filtered. The filtrate was purified by ion exchange chromatography, using a SCX column. The desired product was eluted from the column using 7M NH3/MeOH and fractions were evaporated to dryness to afford methyl 2-(3-(methoxymethyl)piperazin-1-yl)pyrimidine-5-carboxylate (346 mg, 75%) as a yellow solid. This was used directly with no further purification.

1H NMR (399.9 MHz, CDCl₃) δ 2.72-2.79 (2H, m), 2.84-2.90 (1H, m), 2.99-3.07 (2H, m), 3.25-3.30 (1H, m), 3.31 (3H, s), 3.38-3.42 (1H, m), 3.80 (3H, s), 4.61-4.68 (2H, m), 8.76 (2H, s). MS: m/z 267 (MH+)

2-(Methoxymethyl)piperazine used as starting material was prepared as follows:

1,4-Dibenzyl-2-(methoxymethyl)piperazine (1.578 g, 5.08 mmol) and palladium (10% on carbon, 0.163 g, 1.53 mmol) in ethanol (50.8 ml) were stirred under an atmosphere of hydrogen at room temperature for 3 days. The reaction mixture was filtered through celite, washing with ethanol. The resulting mixture was evaporated to dryness to afford crude product. The crude product was purified by ion exchange chromatography, using a SCX column. The desired product was eluted from the column using 7M NH3/MeOH and fractions were evaporated to dryness to afford 2-(methoxymethyl)piperazine (0.559 g, 84%) as a yellow oil. This was used directly without further purification.

1H NMR (399.9 MHz, CDCl₃) δ 2.37-2.43 (1H, m), 2.65-2.76 (2H, m), 2.78-2.86 (3H, m), 2.89-2.92 (1H, m), 3.14-3.18 (1H, m), 3.24-3.27 (1H, m), 3.27 (3H, s).

1,4-Dibenzyl-2-(methoxymethyl)piperazine used as starting material was prepared as follows: Sodium hydride (0.857 g, 21.42 mmol) was added portionwise to stirred Et₂O (23.0 ml) at 25° C. under nitrogen. A solution of (1,4-dibenzylpiperazin-2-yl)methanol (1.411 g, 4.76 mmol) in DMF (8.0 ml) was added portionwise under nitrogen. The resulting suspension was stirred at room temperature for 1 h. A solution of methyl iodide (0.454 ml, 7.28 mmol) in Et$_2$O (7.0 ml) was added dropwise to the reaction mixture at 10° C., under nitrogen. The resulting mixture was stirred at room temperature for 21 h. The reaction mixture was quenched with water (35 mL and extracted with Et$_2$O (3×50 mL). The organic layers were combined and washed with water (50 mL), dried over MgSO4, filtered and evaporated to afford 1,4-dibenzyl-2-(methoxymethyl)piperazine (1.580 g, 107%) as a yellow oil. This was used directly without further purification.

1H NMR (399.9 MHz, DMSO-d$_6$) δ 2.10-2.23 (3H, m), 2.44-2.48 (1H, m), 2.57-2.63 (3H, m), 3.21 (3H, s), 3.35-3.39 (1H, m), 3.44 (2H, d), 3.60-3.63 (1H, m), 3.95-3.99 (1H, m), 7.20-7.34 (10H, m). 1H obscured by water peak. MS: m/z 311 (MH+)

Example 161

N-[5-[2-(3,5-dimethoxyphenyl)ethyl]-2H-pyrazol-3-yl]-5-(3-methylaminopyrrolidin-1-yl)pyrazine-2-carboxamide Hydrogen chloride (4M in dioxane, 0.57 mL, 2.26 mmol) was added to tert-butyl N-[1-[5-[[5-[2-(3,5-dimethoxyphenyl)ethyl]-2H-pyrazol-3-yl]carbamoyl]pyrazin-2-yl]pyrrolidin-3-yl]-N-methylcarbamate (312 mg, 0.57 mmol) in methanol (2.80 mL) at 25° C. The resulting solution was stirred at room temperature for 48 h. The reaction was incomplete and further hydrogen chloride (4M in dioxane, 0.28 mL, 1.12 mmol) was added and the solution was stirred at room temperature for a further 16 h. The reaction mixture was diluted with MeOH (5 ml) and the crude product was purified by ion exchange chromatography, using a SCX column. The desired product was eluted from the column using 7M NH3/MeOH and fractions were evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (101 mg, 39%) as a white solid.

1H NMR (399.9 MHz, CDCl$_3$) δ 1.85-1.93 (1H, m), 2.14-2.22 (1H, m), 2.43 (3H, s), 2.84-2.92 (4H, m), 3.39-3.42 (2H, m), 3.51-3.57 (1H, m), 3.63-3.68 (2H, m), 3.70 (6H, s), 6.25-6.26 (1H, m), 6.30 (2H, d), 6.43 (1H, s), 7.69 (1H, d), 8.85 (1H, d), 9.65 (1H, s). MS: m/z 452 (MH+)

Mean of n=2, FGFR Kinase assay—Caliper Echo Dosing, IC$_{50}$ 0.003 μM.

tert-butyl N-[1-[5-[[5-[2-(3,5-dimethoxyphenyl)ethyl]-2H-pyrazol-3-yl]carbamoyl]pyrazin-2-yl]pyrrolidin-3-yl]-N-methylcarbamate used as starting material was prepared as follows:

A solution of tert-butyl N-methyl-N-pyrrolidin-3-ylcarbamate (200 mg, 1.00 mmol) in dioxane (0.75 ml) was added to a stirred solution of 5-chloro-N-[5-[2-(3,5-dimethoxyphenyl)ethyl]-2H-pyrazol-3-yl]pyrazine-2-carboxamide (136 mg, 0.35 mmol) in dioxane (0.75 ml) and NMP (0.25 ml) at 25° C. The resulting solution was stirred at room temperature for 24 h. The reaction was incomplete so N-ethyl-N-propan-2-ylpropan-2-amine (0.06 ml, 0.35 mmol) was added and the solution was stirred at room temperature for a further 17 h. The reaction mixture was diluted with MeOH (5 ml) and the crude product was purified by ion exchange chromatography, using a SCX column. The desired product was eluted from the column using 7M NH3/MeOH and fractions were evaporated to dryness to afford impure product (312 mg, 162%) as a yellow oil. This was used directly with no further purification. MS: m/z 552 (MH+)

5-Chloro-N-[5-[2-(3,5-dimethoxyphenyl)ethyl]-2H-pyrazol-3-yl]pyrazine-2-carboxamide was prepared as shown in Example 105.

Example 162

N-[5-[2-(3,5-dimethoxyphenyl)ethyl]-2H-pyrazol-3-yl]-2-(1-methylpiperidin-4-yl)pyrimidine-5-carboxamide Trimethylaluminium (2 M in toluene, 1.168 ml, 2.34 mmol) was added dropwise to a suspension of 5-[2-(3,5-dimethoxyphenyl)ethyl]-2H-pyrazol-3-amine (231 mg, 0.93 mmol) and methyl 2-(1-methylpiperidin-4-yl)pyrimidine-5-carboxylate (220 mg, 0.93 mmol) in anhydrous toluene (4.671 ml) at 25° C. The resulting solution was stirred at 60° C. for 2 h. The reaction mixture was poured into methanol (100 mL), acidified with 2M HCl and the crude product was purified by ion exchange chromatography, using a SCX column. The desired product was eluted from the column using 7M NH3/MeOH. The crude product was purified by preparative HPLC, using decreasingly polar mixtures of water (containing 1% NH3) and MeCN as eluents. Fractions containing the desired compound were evaporated to dryness to afford the title compound (166 mg, 39%) as a white solid.

1H NMR (399.9 MHz, DMSO-d6) δ 1.80-1.88 (2H, m), 1.94 (2H, d), 1.98-2.03 (2H, m), 2.21 (3H, s), 2.80-2.85 (3H, m), 2.89 (4H, s), 3.73 (6H, s), 6.33 (1H, t), 6.42 (2H, d), 6.49 (1H, s), 9.20 (2H, s), 11.04 (1H, s), 12.24 (1H, s). MS: m/z 451 (MH+).

Mean of n=4, FGFR Kinase assay—Caliper Echo Dosing, IC$_{50}$ 0.036 μM.

Methyl 2-(1-methylpiperidin-4-yl)pyrimidine-5-carboxylate used as starting material was prepared as follows:

Sodium triacetoxyborohydride (532 mg, 2.51 mmol) was added to methyl 2-(piperidin-4-yl)pyrimidine-5-carboxylate (222 mg, 1.00 mmol), formaldehyde (37% aqueous solution, 1.50 ml, 20.07 mmol) and acetic acid (0.115 ml, 2.01 mmol) in methanol (4.994 ml) at 25° C. The resulting solution was stirred at ambient temperature for 3 days. The reaction mixture was diluted with methanol (20 mL) and the crude product was purified by ion exchange chromatography, using an SCX column. The desired product was eluted from the column using 7M NH3/MeOH and evaporated to dryness to afford methyl 2-(1-methylpiperidin-4-yl)pyrimidine-5-carboxylate (223 mg, 94%) as a cream waxy solid. This was used directly with no further purification.

1H NMR (399.9 MHz, DMSO-d6) δ 1.77-1.88 (2H, m), 1.95 (2H, d), 2.00-2.07 (2H, m), 2.22 (3H, s), 2.83-2.90 (3H, m), 3.91 (3H, s), 9.19 (2H, s). MS: m/z 236 (MH+).

Methyl 2-piperidin-4-ylpyrimidine-5-carboxylate used as starting material was prepared as follows:

Hydrogen chloride (4M in 1,4-dioxane, 3.04 ml, 12.15 mmol) was added to a stirred suspension of methyl 2-(1-(tert-butoxycarbonyl)piperidin-4-yl)pyrimidine-5-carboxylate (976 mg, 3.04 mmol) in methanol (15.20 ml) at 25° C. The resulting solution was stirred at ambient temperature for 18 hours. The reaction mixture was purified by ion exchange chromatography, using an SCX column. The desired product was eluted from the column using 7M NH3/MeOH and evaporated to dryness to afford methyl 2-(piperidin-4-yl)pyrimidine-5-carboxylate (600 mg, 89%) as a yellow solid. This was used directly with no further purification.

1H NMR (399.9 MHz, DMSO-d6) δ 1.63-1.73 (2H, m), 1.86-1.89 (2H, m), 2.58-2.65 (2H, m), 2.96-3.07 (3H, m), 3.91 (3H, s), 9.19 (2H, s), NH not observed. MS: m/z 222 (MH+).

Methyl 2-[1-[(2-methylpropan-2-yl)oxycarbonyl]piperidin-4-yl]pyrimidine-5-carboxylate used as starting material was prepared as follows:

Methyl 2-(1-(tert-butoxycarbonyl)-1,2,3,6-tetrahydropyridin-4-yl)pyrimidine-5-carboxylate (960 mg, 3.01 mmol) and palladium, 10% on carbon (96 mg, 0.09 mmol) in ethanol (10 ml) and ethyl acetate (40.0 ml) were stirred under an atmosphere of hydrogen at atmospheric pressure and ambient temperature for 18 h. The reaction mixture was filtered through celite, washing with methanol, ethyl acetate and dichloromethane and concentrated under reduced pressure to give methyl 2-(1-(tert-butoxycarbonyl)piperidin-4-yl)pyrimidine-5-carboxylate (966 mg, 100%) as a yellow oil, which crystallised on standing. This was used directly with no further purification.

1H NMR (399.9 MHz, DMSO-d6) δ 1.42 (9H, s), 1.61-1.70 (2H, m), 1.97 (2H, d), 2.91 (2H, s), 3.10-3.16 (1H, m), 3.91 (3H, s), 4.03 (2H, d), 9.20 (2H, s). MS: 322 m/z (MH+).

Methyl 2-[1-[(2-methylpropan-2-yl)oxycarbonyl]-3,6-dihydro-2H-pyridin-4-yl]pyrimidine-5-carboxylate used as starting material was prepared as follows:

(Trimethylsilyl)diazomethane, 2M in hexanes (4.19 ml, 8.38 mmol) was added dropwise to 2-(1-(tert-butoxycarbonyl)-1,2,3,6-tetrahydropyridin-4-yl)pyrimidine-5-carboxylic acid (1.28 g, 4.19 mmol) in toluene (12 ml) and methanol (3.00 ml) at 25° C. over a period of 2 mins under nitrogen. The resulting solution was stirred at ambient temperature for 2 hours. The reaction mixture was quenched with the dropwise addition of acetic acid until bubbling ceased, then the reaction mixture was diluted with EtOAc (100 mL) and water (100 mL). The organic layer was removed and the aqueous further extracted with EtOAc (2×50 mL). The combined organics were washed with sodium hydrogen carbonate solution (100 mL), water (100 mL), brine (100 mL) and dried over MgSO4, filtered and evaporated to afford methyl 2-(1-(tert-butoxycarbonyl)-1,2,3,6-tetrahydropyridin-4-yl)pyrimidine-5-carboxylate (1.182 g, 88%) as a yellow solid. This was used directly with no further purification.

1H NMR (399.9 MHz, DMSO-d6) δ 1.44 (9H, s), 2.63-2.66 (2H, m), 3.56 (2H, t), 3.92 (3H, s), 4.16 (2H, d), 7.38 (1H, s), 9.21 (2H, s). MS: m/z 320 (MH+).

2-[1-[(2-Methylpropan-2-yl)oxycarbonyl]-3,6-dihydro-2H-pyridin-4-yl]pyrimidine-5-carboxylic acid used as starting material was prepared as follows:

Saturated aqueous sodium hydrogen carbonate solution (25.00 ml) was added to methyl 2-chloropyrimidine-5-carboxylate (0.863 g, 5 mmol), tert-butyl 4-(4,4,5,5-tetramethyl-1,3,2-dioxaborolan-2-yl)-5,6-dihydropyridine-1 (2H)-carboxylate (1.855 g, 6.00 mmol), palladium(II) acetate (0.056 g, 0.25 mmol) and triphenylphosphine (0.262 g, 1.00 mmol) in 1,2-dimethoxyethane (25.00 ml) at 25° C. under nitrogen. The resulting mixture was stirred at 80° C. for 4 h. The cooled reaction mixture was taken up in water (50 mL), washed with EtOAc (50 mL) and then the aqueous layer was acidified to pH1 with 2N HCl. The aqueous layer was extracted with EtOAc (3×25 mL) and the combined organics washed with brine, dried over MgSO4 and concentrated under reduced pressure to afford 2-(1-(tert-butoxycarbonyl)-1,2,3,6-tetrahydropyridin-4-yl)pyrimidine-5-carboxylic acid (1.280 g, 84%) as a yellow solid. This was used directly with no further purification.

1H NMR (399.9 MHz, DMSO-d6) δ 1.44 (9H, s), 2.65 (2H, q), 3.56 (2H, t), 4.15 (2H, m), 7.36 (1H, s), 9.18 (2H, s), 13.6 (1H, s). MS: m/z 304 (M−H).

5-[2-(3,5-Dimethoxyphenyl)ethyl]-2H-pyrazol-3-amine, used as starting material was prepared as indicated in Example 2.

Example 163

N-[5-[2-(3,5-dimethoxyphenyl)ethyl]-2H-pyrazol-3-yl]-5-(4-methyl-1,4-diazepan-1-yl)pyrazine-2-carboxamide 1-methyl-1,4-diazepane (0.20 ml, 1.60 mmol) was added to 5-chloro-N-[5-[2-(3,5-dimethoxyphenyl)ethyl]-2H-pyrazol-3-yl]pyrazine-2-carboxamide (310 mg, 0.80 mmol) in DMSO (4.00 ml) at 25° C. The resulting solution was stirred at room temperature for 1 h. The reaction mixture was diluted with MeOH (5 ml) and the crude product was purified by ion exchange chromatography, using a SCX column. The desired product was eluted from the column using 7M NH3/MeOH and fractions were evaporated to dryness to afford crude product as an orange dry film. The crude product was purified by preparative HPLC, using decreasingly polar mixtures of water (containing 1% NH3) and MeCN as eluents. Fractions containing the desired compound were evaporated to dryness to afford the title compound (296 mg, 79%) as a white solid.

1H NMR (399.9 MHz, CDCl$_3$) δ 1.95-2.01 (2H, m), 2.32 (3H, s), 2.53 (2H, t), 2.66 (2H, t), 2.84-2.92 (4H, m), 3.65-3.75 (2H, m), 3.70 (6H, s), 3.81-3.86 (2H, m), 6.26 (1H, t), 6.29 (2H, d), 6.45 (1H, s), 7.82 (1H, d), 8.83 (1H, d), 9.65 (1H, s). One NH peak not observed. MS: m/z 466 (MH+).

Mean of n=2, FGFR Kinase assay—Caliper Echo Dosing, IC$_{50}$ 0.0018 μM.

5-Chloro-N-[5-[2-(3,5-dimethoxyphenyl)ethyl]-2H-pyrazol-3-yl]pyrazine-2-carboxamide was prepared as shown in Example 105.

Example 164

N-[5-[2-(3,5-dimethoxyphenyl)ethyl]-2H-pyrazol-3-yl]-4-(4-prop-2-enyl-1,4-diazepan-1-yl)benzamide N-[5-[2-(3,5-dimethoxyphenyl)ethyl]-2H-pyrazol-3-yl]-4-(4-prop-2-enyl-1,4-diazepan-1-yl)benzamide was prepared using the same procedure as for Example 159, but starting from ethyl 4-(4-allyl-1,4-diazepan-1-yl)benzoate (0.288 g, 1 mmol, 5-[2-(3,5-dimethoxyphenyl)ethyl]-2H-pyrazol-3-amine (0.247 g, 1 mmol) and a 2M solution of trimethylaluminium (1.250 mL, 2.50 mmol) in toluene. The crude product was purified by preparative HPLC, using decreasingly polar mixtures of water (containing 1% NH3) and MeCN as eluents. Fractions containing the desired compound were evaporated to dryness to afford a gum, which solidified on trituration with DCM/Ether to afford the title compound (0.071 g, 14.50%).

1H NMR (399.9 MHz, CDCl$_3$) δ 1.87-1.93 (2H, m), 2.53 (2H, t), 2.68 (2H, t), 2.86-2.91 (4H, m), 3.07 (2H, d), 3.43 (2H, t), 3.48 (1H, t), 3.50 (1H, d), 3.71 (6H, s), 5.11-5.13 (1H, m), 5.12-5.17 (1H, m), 5.79-5.86 (1H, m), 6.28 (1H, t), 6.33 (2H, d), 6.59 (2H, d), 7.75 (2H, d), 9.26 (1H, s). MS: m/z 490 (MH+).

Mean of n=2, FGFR Kinase assay—Caliper Echo Dosing, IC$_{50}$ 0.00078 μM.

5-[2-(3,5-dimethoxyphenyl)ethyl]-2H-pyrazol-3-amine, used as starting material was prepared as indicated in Example 2.

Ethyl 4-(4-allyl-1,4-diazepan-1-yl)benzoate used as starting material was prepared as follows:

3-Bromoprop-1-ene (0.433 mL, 5.00 mmol) was added to a stirred solution of ethyl 4-(1,4-diazepan-1-yl)benzoate (1.242 g, 5 mmol) and DIPEA (2.183 mL, 12.50 mmol) in dichloromethane (20 mL). The reaction mixture was stirred under nitrogen at room temperature for 24 h. This was diluted with dichloromethane (20 mL), washed with water (2×25 ml) and saturated sodium chloride solution (20 ml), dried over MgSO$_4$, filtered and evaporated to dryness. The crude product was purified by silica column chromatography, eluting with a gradient of 0 to 5% 2.5M ammonia/MeOH in DCM. Pure fractions were evaporated to dryness to afford ethyl 4-(4-allyl-1,4-diazepan-1-yl)benzoate (0.700 g, 48.5%) as a yellow oil.

1H NMR (399.9 MHz, CDCl$_3$) δ 1.36 (3H, t), 1.94-2.00 (2H, m), 2.57-2.60 (2H, m), 2.75 (1H, d), 2.77-2.77 (1H, m), 3.10-3.12 (2H, m), 3.54-3.64 (4H, m), 4.31 (2H, q), 5.11-5.15 (1H, m), 5.11-5.19 (1H, m), 5.78-5.91 (1H, m), 6.62-6.66 (2H, m), 7.87-7.90 (2H, m). MS: m/z 289 (MH+).

Ethyl 4-(1,4-diazepan-1-yl)benzoate used as starting material was prepared as follows:

Ethyl 4-fluorobenzoate (11.01 mL, 75 mmol) and 1,4-diazepane (30.0 g, 300.00 mmol) in DMSO (150 mL) warmed to 100° C. under nitrogen. The resulting solution was stirred at 100° C. for 24 h. The reaction mixture was cooled and evaporated to dryness. The reaction mixture was quenched with 2M NaOH (150 mL), extracted with EtOAc (3×75 mL), the organic layer was washed with saturated brine (100 ml), dried over MgSO4, filtered and evaporated to afford ethyl 4-(1,4-diazepan-1-yl)benzoate (17.43 g, 94%) as a colourless oil.

1H NMR (399.9 MHz, CDCl3) δ 1.27-1.31 (3H, m), 1.71 (1H, s), 1.79-1.85 (2H, m), 2.74 (1H, d), 2.74 (1H, d), 2.95 (1H, d), 2.96 (1H, d), 3.51 (2H, t), 3.56 (2H, t), 4.21-4.27 (2H, m), 6.56-6.60 (2H, m), 7.80-7.83 (2H, m). MS: m/z 249 (MH+).

Example 165

4-(4-cyclopropyl-1,4-diazepan-1-yl)-N-[5-[2-(3,5-dimethoxyphenyl)ethyl]-2H-pyrazol-3-yl]benzamide 4-(4-cyclopropyl-1,4-diazepan-1-yl)-N-[5-[2-(3,5-dimethoxyphenyl)ethyl]-2H-pyrazol-3-yl]benzamide was prepared using the same procedure as for Example 159, but starting from ethyl 4-(4-cyclopropyl-1,4-diazepan-1-yl)benzoate (0.288 g, 1 mmol, 5-[2-(3,5-dimethoxyphenyl)ethyl]-2H-pyrazol-3-amine (0.247 g, 1 mmol) and a 2M solution of trimethylaluminium (1.250 mL, 2.50 mmol) in toluene. The crude product was purified by preparative HPLC, using decreasingly polar mixtures of water (containing 1% NH3) and MeCN as eluents. Fractions containing the desired compound were evaporated to dryness to afford a gum which solidified on trituration with DCM/Ether to afford the title compound (0.165 g, 33.7%).

1H NMR (500.13 MHz, DMSOd6+CD3COOD @ 373K) δ 0.32-0.36 (2H, m), 0.41-0.47 (2H, m), 1.84-1.90 (2H, m), 2.93-2.98 (1H, m), 2.76 (2H, t), 2.87 (4H, s), 2.93 (2H, t), 3.50-3.58 (4H, m), 3.72 (6H, s), 6.29 (1H, s), 6.30-6.32 (1H, m), 6.39 (2H, d), 6.72 (2H, d), 7.81 (2H, d). MS: m/z 490 (MH+).

Mean of n=1, FGFR Kinase assay—Caliper Echo Dosing, IC$_{50}$ 0.000064 μM.

5-[2-(3,5-dimethoxyphenyl)ethyl]-2H-pyrazol-3-amine, used as starting material was prepared as indicated in Example 2.

Ethyl 4-(4-cyclopropyl-1,4-diazepan-1-yl)benzoate used as starting material was prepared as follows:

A solution of ethyl 4-(1,4-diazepan-1-yl)benzoate (0.621 g, 2.5 mmol), (1-ethoxycyclopropoxy)trimethylsilane (2.51 mL, 12.50 mmol) and acetic acid (0.286 mL, 5.00 mmol) in tetrahydrofuran (50 mL), methanol (5 mL) was treated with sodium cyanoborohydride (0.393 g, 6.25 mmol) at 20° C. The resulting solution was stirred at 60° C. for 18 h. The reaction mixture was cooled, filtered and evaporated to dryness. 1N HCl (40 ml) and water (60 ml) were added and the solution extracted with ethyl acetate (3×50 ml). The aqueous layer was basified to pH 10 with solid potassium carbonate and extracted with ethyl acetate (4×50 ml). The organic extracts washed with saturated NaCl (50 ml) and dried over MgSO$_4$, filtered and evaporated to dryness. The crude product was purified by silica column chromatography, eluting with a gradient of 0 to 5% MeOH in DCM. Pure fractions were evaporated to dryness to afford ethyl 4-(4-cyclopropyl-1,4-diazepan-1-yl)benzoate (0.849 g, 118%) as a colourless oil.

1H NMR (399.9 MHz, CDCl$_3$) δ 0.33 (1H, t), 0.34-0.35 (1H, m), 0.36-0.41 (1H, m), 0.37-0.40 (1H, m), 1.29 (3H, t), 1.74-1.79 (1H, m), 1.84-1.90 (2H, m), 2.69 (2H, t), 2.86 (2H, t), 3.47 (2H, t), 3.49 (2H, t), 4.24 (2H, q), 6.58 (1H, d), 6.60 (1H, s), 7.81-7.84 (2H, m). MS: m/z 289 (MH+) (ESI+).

Example 166

N-[5-[2-(3,5-dimethoxyphenyl)ethyl]-2H-pyrazol-3-yl]-4-(4-propan-2-yl-1,4-diazepan-1-yl)benzamide N-[5-[2-(3,5-dimethoxyphenyl)ethyl]-2H-pyrazol-3-yl]-4-(4-propan-2-yl-1,4-diazepan-1-yl)benzamide was prepared using the same procedure as for Example 159, but starting from ethyl 4-(4-isopropyl-1,4-diazepan-1-yl)benzoate (0.212 g, 0.73 mmol), 5-[2-(3,5-dimethoxyphenyl)ethyl]-2H-pyrazol-3-amine (0.181 g, 0.73 mmol) and a 2M solution of trimethylaluminium (0.913 ml, 1.83 mmol) in toluene. The crude product was purified by preparative HPLC, using decreasingly polar mixtures of water (containing 1% NH3) and MeCN as eluents. Fractions containing the desired compound were evaporated to dryness to afford a gum which solidified on trituration with DCM/Ether to afford the title compound (0.154 g, 42.9%) as a cream solid.

1H NMR (500.13 MHz, DMSOd6+CD3COOD @ 373K) δ 1.00 (6H, s), 1.85-1.90 (2H, m), 2.64 (2H, t) 2.80-2.85 (2H, m), 2.88 (4H, s), 2.94-3.01 (1H, m), 3.53-3.59 (4H, m), 3.72 (6H, s), 6.29 (1H, s), 6.30-6.32 (1H, m), 6.40 (2H, d), 6.73 (2H, d), 7.81 (2H, d). MS: m/z 492 (MH+).

Mean of n=1, FGFR Kinase assay—Caliper Echo Dosing, IC$_{50}$ 0.0007 μM.

5-[2-(3,5-dimethoxyphenyl)ethyl]-2H-pyrazol-3-amine, used as starting material was prepared as indicated in Example 2.

Ethyl 4-(4-isopropyl-1,4-diazepan-1-yl)benzoate used as starting material was prepared as follows:

A solution of ethyl 4-fluorobenzoate (0.293 mL, 2 mmol) and 1-isopropyl-1,4-diazepane (0.539 mL, 4.00 mmol) in dimethylsulfoxide (10 mL), was heated at 120° C. for 18 h. The reaction mixture was diluted with water (75 ml) and extracted with ethyl acetate (3×25 ml). The extracts were washed with saturated sodium chloride solution (50 ml), dried over MgSO4, filtered and evaporated to dryness. The crude product was purified by silica column chromatography, eluting with a gradient of 0 to 5% MeOH in DCM. Pure fractions were evaporated to dryness to afford ethyl 4-(4-isopropyl-1,4-diazepan-1-yl)benzoate (0.212 g, 36.5%) as a yellow oil.

1H NMR (399.9 MHz, CDCl3) δ 0.92 (6H, d), 1.28 (3H, t), 1.80-1.86 (2H, m), 2.46 (2H, t), 2.69 (2H, t), 2.81-2.89 (1H, m), 3.51 (4H, t), 4.24 (2H, q), 6.58 (2H, d), 7.81 (2H, d). MS: m/z 291 (MH+) (ESI+).

Example 167

N-[5-[2-(3,5-dimethoxyphenyl)ethyl]-2H-pyrazol-3-yl]-5-(4-propan-2-yl-1,4-diazepan-1-yl)pyrazine-2-carboxamide 1-isopropyl-1,4-diazepane (228 mg, 1.60 mmol) was added to 5-chloro-N-[5-[2-(3,5-dimethoxyphenyl)ethyl]-2H-pyrazol-3-yl]pyrazine-2-carboxamide (310 mg, 0.80 mmol) in DMSO (4.00 ml) at 25° C. The resulting solution was stirred at room temperature for 2 hours. The reaction was incomplete so the temperature was increased to 60° C. and the reaction mixture was stirred for a further 2 h. The reaction was still incomplete so the reaction mixture was stirred for a further 18 h at room temperature. The reaction mixture was diluted with MeOH (5 ml) and the crude product was purified by ion exchange chromatography, using a SCX column. The desired product was eluted from the column using 7M NH3/MeOH and fractions were evaporated to dryness to afford crude product as an orange dry film. The crude product was purified by preparative HPLC, using decreasingly polar mixtures of water (containing 1% NH3) and MeCN as eluents. Fractions containing the desired compound were evaporated to dryness to afford the title compound (167 mg, 42%) as a pale yellow solid.

1H NMR (399.9 MHz, CDCl$_3$) δ 0.93 (6H, d), 1.83-1.89 (2H, m), 2.54 (2H, t), 2.72 (2H, t), 2.82-2.92 (5H, m), 3.70 (6H, s), 3.73-3.76 (4H, m), 6.26 (1H, d), 6.29 (2H, d), 6.43 (1H, s), 7.81 (1H, d), 8.82 (1H, d), 9.64 (1H, s). One NH signal not observed. MS: m/z 494 (MH+).

Mean of n=2, FGFR Kinase assay—Caliper Echo Dosing, IC$_{50}$ 0.00063 µM.

5-Chloro-N-[5-[2-(3,5-dimethoxyphenyl)ethyl]-2H-pyrazol-3-yl]pyrazine-2-carboxamide was prepared as shown in Example 105.

Example 168

N-[5-[2-(3,5-dimethoxyphenyl)ethyl]-2H-pyrazol-3-yl]-5-(4-propan-2-yl-1,4-diazepan-1-yl)thiophene-2-carboxamide Trimethylaluminium (0.751 ml, 1.50 mmol) was added dropwise to a stirred suspension of 5-[2-(3,5-dimethoxyphenyl)ethyl]-2H-pyrazol-3-amine (148 mg, 0.60 mmol) and ethyl 5-(4-propan-2-yl-1,4-diazepan-1-yl)thiophene-2-carboxylate (178 mg, 0.60 mmol) in toluene (3.002 ml) at 25° C. The resulting solution was stirred at 60° C. for 18 h. The cooled reaction mixture was added to methanol (50 mL) and treated with HCL (2M aqueous solution, to pH7 or below) and purified by ion exchange chromatography, using a SCX column. The desired product was eluted from the column using 7M NH3/MeOH and evaporated to dryness to afford impure material. The crude product was purified by preparative HPLC, using decreasingly polar mixtures of water (containing 1% NH3) and MeCN as eluents. Fractions containing the desired compound were evaporated to dryness to afford the title compound (123 mg, 41%) as a yellow solid.

1H NMR (399.9 MHz, DMSO-d6) δ 0.95-0.96 (6H, m), 1.79-1.85 (2H, m), 2.54-2.56 (2H, m), 2.72 (2H, m), 2.85 (4H, s), 2.88 (1H, m), 3.42-3.48 (4H, m), 3.72 (6H, s), 5.86 (1H, d), 6.33 (1H, s), 6.34 (1H, s), 6.41 (2H, d), 7.78 (1H, d), 10.14 (1H, s), 12.00 (1H, s). MS: m/z 498 (MH+).

Mean of n=2, FGFR Kinase assay—Caliper Echo Dosing, IC$_{50}$ 0.0015 µM.

Ethyl 5-(4-propan-2-yl-1,4-diazepan-1-yl)thiophene-2-carboxylate used as starting material was prepared as follows:

Sodium triacetoxyborohydride (396 mg, 1.87 mmol) was added portionwise to ethyl 5-(1,4-diazepan-1-yl)thiophene-2-carboxylate (190 mg, 0.75 mmol) and acetic acid (0.086 ml, 1.49 mmol) in acetone (1.917 ml) at room temperature. The resulting solution was stirred at ambient temperature for 18 h under nitrogen. The reaction mixture was concentrated and diluted with water (200 mL) and basified with 2M NaOH. The aqueous was extracted with diethyl ether (3×100 mL) and washed sequentially with water (200 mL) and saturated brine (200 mL). The organic layer was dried over MgSO4, filtered and evaporated to afford desired product ethyl 5-(4-isopropyl-1,4-diazepan-1-yl)thiophene-2-carboxylate (181 mg, 82%). This was used directly with no further purification.

1H NMR (399.9 MHz, CDCl$_3$) δ 0.99-1.01 (6H, m), 1.33 (3H, t), 1.89-1.95 (2H, m), 2.59-2.62 (2H, m), 2.75-2.77 (2H, m), 2.88-2.95 (1H, m), 3.48-3.52 (4H, m), 4.27 (2H, q), 5.77-5.78 (1H, d), 7.54 (1H, d). MS: m/z 297 (MH+).

Ethyl 5-(1,4-diazepan-1-yl)thiophene-2-carboxylate used as starting material was prepared as follows:

Palladium(II) acetate (52.1 mg, 0.23 mmol) followed by sodium tert-butoxide (624 mg, 6.49 mmol) was added to a stirred solution of ethyl 5-bromothiophene-2-carboxylate (1090 mg, 4.64 mmol), homopiperazine (511 mg, 5.10 mmol) and (rac)-(−)-2,2'-bis(diphenylphosphino)-1,1'-binaphthyl (289 mg, 0.46 mmol) in toluene (20 mL) at 25° C. under nitrogen. The resulting suspension was stirred at 110° C. for 3 h. The cooled reaction mixture was diluted with MeOH and the crude product was purified by ion exchange chromatography, using an SCX column. The desired product was eluted from the column using 7M NH3/MeOH and fractions containing the desired product were evaporated to dryness to afford impure product as a brown oil. The crude product was purified by silica column chromatography, eluting with a gradient of 0 to 5% 7N NH3/MeOH in DCM and then 0 to 3% NH3/MeOH in DCM. Pure fractions were evaporated to dryness to afford ethyl 5-(4-ethylpiperazin-1-yl)thiophene-2-carboxylate (195 mg, 17%) as a yellow oil.

1H NMR (399.9 MHz, CDCl$_3$) δ 1.33 (3H, t), 1.89-1.95 (2H, m), 2.88 (2H, t), 3.03-3.06 (2H, m), 3.49-3.54 (2H, m), 3.57 (2H, t), 4.27 (2H, q), 5.80 (1H, d), 7.54 (1H, d) NH not observed. MS: m/z 255 (MH+).

5-[2-(3,5-dimethoxyphenyl)ethyl]-2H-pyrazol-3-amine, used as starting material was 10 prepared as indicated in Example 2.

Example 169

N-[5-[2-(3,5-dimethoxyphenyl)ethyl]-2H-pyrazol-3-yl]-5-(4-ethyl-1,4-diazepan-1-yl)pyrazine-2-carboxamide 1-ethyl-1,4-diazepane (205 mg, 1.60 mmol) was added to 5-chloro-N-[5-[2-(3,5-dimethoxyphenyl)ethyl]-2H-pyrazol-3-yl]pyrazine-2-carboxamide (310 mg, 0.80 mmol) in DMSO (4.00 ml) at 25° C. The resulting solution was stirred at room temperature for 2 h. The reaction was incomplete so the temperature was increased to 60° C. and the reaction mixture was stirred for a further 15 mins. The reaction mixture was diluted with MeOH (5 ml) and the crude product was purified by ion exchange chromatography, using a SCX column. The desired product was eluted from the column using 7M NH3/MeOH and fractions were evaporated to dryness to afford crude product as an orange dry film. The crude product was purified by preparative HPLC, using decreasingly polar mixtures of water (containing 1% NH3) and MeCN as eluents. Fractions containing the desired compound were evaporated to dryness to afford the title compound (228 mg, 59%) as a white solid.

1H NMR (399.9 MHz, CDCl$_3$) δ 1.00 (3H, t), 1.91-1.97 (2H, m), 2.50 (2H, q), 2.56 (2H, t), 2.72 (2H, t), 2.84-2.91 (4H, m), 3.69 (6H, s), 3.67-3.71 (2H, m), 3.79-3.82 (2H, m), 6.25 (1H, t), 6.29 (2H, d), 6.45 (1H, s), 7.81 (1H, d), 8.83 (1H, d), 9.68 (1H, s). MS: m/z 480 (MH+).

Mean of n=2, FGFR Kinase assay—Caliper Echo Dosing, IC$_{50}$ 0.0027 μM.

5-Chloro-N-[5-[2-(3,5-dimethoxyphenyl)ethyl]-2H-pyrazol-3-yl]pyrazine-2-carboxamide was prepared as shown in Example 105.

Example 170

N-[5-[2-(3,5-dimethoxyphenyl)ethyl]-2H-pyrazol-3-yl]-4-(4-ethyl-1,4-diazepan-1-yl)benzamide N-[5-[2-(3,5-dimethoxyphenyl)ethyl]-2H-pyrazol-3-yl]-4-(4-ethyl-1,4-diazepan-1 was prepared using the same procedure as for Example 159, but starting from ethyl 4-(4-ethyl-1,4-diazepan-1-yl)benzoate (0.502 g, 1.4 mmol), 5-[2-(3,5-dimethoxyphenyl)ethyl]-2H-pyrazol-3-amine (0.346 g, 1.40 mmol) and A 2M solution of trimethylaluminium (1.750 mL, 3.50 mmol) in toluene. The crude product was purified by preparative HPLC, using decreasingly polar mixtures of water (containing 1% NH3) and MeCN as eluents. Fractions containing the desired compound were evaporated to dryness to afford a gum which solidified on trituration with DCM/Ether to afford the title compound (0.171 g, 25.6%) as a white solid.

1H NMR (399.9 MHz, DMSO-d$_6$) δ 1.00 (3H, t), 1.89 (2H, d), 2.53 (2H, d), 2.73 (4H, s), 2.87 (4H, s), 3.49-3.54 (2H, m), 3.54-3.58 (2H, m), 3.73 (6H, s), 6.33 (1H, t), 6.42 (3H, d), 6.73 (2H, d), 7.87 (2H, d), 10.17 (1H, s), 12.04 (1H, s). MS: m/z 478 (MH+) (ESI+).

Mean of n=1, FGFR Kinase assay—Caliper Echo Dosing, IC$_{50}$ 0.00071 μM.

Ethyl 4-(4-ethyl-1,4-diazepan-1-yl)benzoate used as starting material was prepared as follows:

A solution of ethyl 4-(1,4-diazepan-1-yl)benzoate (0.621 g, 2.5 mmol), acetaldehyde (0.701 mL, 12.50 mmol) and acetic acid (0.286 mL, 5.00 mmol) in tetrahydrofuran (30 mL), methanol (3 mL) was treated with sodium cyanoborohydride (0.393 g, 6.25 mmol) at 20° C. The resulting solution was stirred at 60° C. for 18 h. The reaction mixture was cooled and extra amount of acetaldehyde (2.146 mL, 38 mmol) and sodium triacetoxyborohydride (1.060 g, 5.00 mmol) were added. The reaction was stirred at room temperature for 18 h. The reaction mixture was filtered and evaporated to dryness. The residue was dissolved in 2N HCl (5 ml) and methanol (20 ml). The solution of crude product was purified by ion exchange chromatography, using a SCX column. The desired product was eluted from the column using 7M NH3/MeOH and pure fractions were evaporated to dryness to afford ethyl 4-(4-ethyl-1,4-diazepan-1-yl)benzoate (0.526 g, 76%)

1H NMR (399.9 MHz, CDCl$_3$) δ 1.07 (3H, t), 1.36 (3H, t), 1.90-2.05 (2H, m), 2.52-2.61 (2H, m), 2.70-2.77 (2H, m), 3.54 (2H, t), 3.57 (2H, t), 4.29-4.34 (2H, m), 6.63-6.67 (2H, m), 7.86-7.90 (2H, m). MS: m/z 277 (MH+).

5-[2-(3,5-dimethoxyphenyl)ethyl]-2H-pyrazol-3-amine, used as starting material was prepared as indicated in Example 2.

Example 171

N-[5-[2-(3,5-dimethoxyphenyl)ethyl]-2H-pyrazol-3-yl]-2-(4-ethyl-1,4-diazepan-1-yl)pyrimidine-5-carboxamide Trimethylaluminium (1.25 ml, 2.50 mmol) was added dropwise to a stirred suspension of methyl 2-(4-ethyl-1,4-diazepan-1-yl)pyrimidine-5-carboxylate (265 mg, 1.00 mmol) and 5-[2-(3,5-dimethoxyphenyl)ethyl]-2H-pyrazol-3-amine (248 mg, 1.00 mmol) in toluene (5.01 ml) at 25° C. The resulting solution was stirred at 60° C. for 18 h. The cooled reaction mixture was quenched into methanol (50 mL) and treated with HCl (2M aqueous solution, to pH7 or lower) and purified by ion exchange chromatography, using an SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing desired product still contained an impurity, so they were concentrated to dryness and purified by crystallisation from MeCN to afford the title compound (104 mg, 22%) as a cream solid.

1H NMR (399.9 MHz, DMSO-d6) δ 0.99 (3H, t), 1.82-1.87 (2H, m), 2.48 (2H, q, partially obscured by DMSO peak), 2.52-2.57 (2H, m, partially obscured by DMSO peak), 2.71 (2H, m), 2.87 (4H, s), 3.72 (6H, s), 3.82 (2H, t), 3.87 (2H, t), 6.33 (1H, t), 6.42 (2H, d), 6.44 (1H, s), 8.88 (2H, s), 10.56 (1H, s), 12.13 (1H, s). MS: m/z 480 (MH+).

Mean of n=1, FGFR Kinase assay—Caliper Echo Dosing, IC$_{50}$ 0.0092 μM.

Methyl 2-(4-ethyl-1,4-diazepan-1-yl)pyrimidine-5-carboxylate used as starting material was prepared as follows:

A solution of methyl 2-chloropyrimidine-5-carboxylate (200 mg, 1.16 mmol) in dichloromethane (4.00 mL) was added to a stirred solution of 1-ethyl-1,4-diazepane (149 mg, 1.16 mmol) and N-ethyl-N-propan-2-ylpropan-2-amine (0.902 mL, 5.22 mmol) in dichloromethane (4.00 mL) at 25° C. The resulting solution was stirred at ambient temperature for 18 h. The reaction mixture was evaporated to dryness and redissolved in MeOH (20 mL) and the crude product was purified by ion exchange chromatography, using an SCX column. The desired product was eluted from the column using 7M NH3/MeOH and evaporated to dryness to afford methyl 2-(4-ethyl-1,4-diazepan-1-yl)pyrimidine-5-carboxylate (268 mg, 87%) as a cream oil which crystallised on standing. This was used directly with no further purification.

1H NMR (399.9 MHz, DMSO-d6) δ 0.98 (3H, t), 1.81-1.87 (2H, m), 2.45-2.50 (2H, m), 2.55 (2H, m), 2.70-2.72 (2H, m), 3.81 (3H, s), 3.82 (2H, q), 3.86-3.89 (2H, m), 8.79 (2H, s). MS: m/z 265 (MH+).

1-Ethyl-1,4-diazepane used as starting material was prepared as follows:

Lithium aluminum hydride (38.2 ml, 38.19 mmol) was added to 1-(1,4-diazepan-1-yl)ethanone (1.697 g, 11.93 mmol) in THF (59.7 ml) at 0° C. under nitrogen. The resulting solution was stirred at ambient temperature for 1 h and then at 60° C. for 1 h. The cooled reaction mixture was poured onto ice (500 mL), acidified with HCl (2M aqueous solution) and purified by ion exchange chromatography, using an SCX column. The desired product was eluted from the column using 7M NH3/MeOH and evaporated to dryness to afford 1-ethyl-1,4-diazepane (0.610 g, 40%) as a yellow liquid. This was used directly with no further purification.

1H NMR (399.9 MHz, CDCl3) δ 1.07 (3H, t), 1.74-1.80 (2H, m), 2.58 (2H, q), 2.64-2.70 (4H, m), 2.89-2.95 (4H, m).

Example 172

N-[5-[2-(3,5-dimethoxyphenyl)ethyl]-2H-pyrazol-3-yl]-5-(4-prop-2-enyl-1,4-diazepan-1-yl)pyrazine-2-carboxamide 1-Prop-2-enyl-1,4-diazepane (224 mg, 1.60 mmol) was added to 5-chloro-N-[5-[2-(3,5-dimethoxyphenyl)ethyl]-2H-pyrazol-3-yl]pyrazine-2-carboxamide (310 mg, 0.80 mmol) in DMSO (4.00 ml) at 25° C. The resulting solution was stirred at room temperature for 3 h. The reaction mixture was diluted with MeOH (5 ml) and the crude product was purified by ion exchange chromatography, using a SCX column. The desired product was eluted from the column using 7M NH3/MeOH and fractions were evaporated to dryness to afford crude product as an orange oil. The crude product was purified by preparative HPLC, using decreasingly polar mixtures of water (containing 1% NH3) and MeCN as eluents. Fractions containing the desired compound were evaporated to dryness to afford the title compound (271 mg, 69%) as a yellow solid.

1H NMR (399.9 MHz, $CDCl_3$) δ 1.91-1.97 (2H, m), 2.57 (2H, t), 2.72 (2H, t), 2.84-2.91 (4H, m), 3.06 (2H, d), 3.70 (6H, s), 3.74-3.83 (4H, m), 5.07-5.13 (2H, m), 5.73-5.83 (1H, m), 6.25 (1H, t), 6.29 (2H, d), 6.43 (1H, s), 7.82 (1H, d), 8.83 (1H, d), 9.64 (1H, s). MS: m/z 492 (MH+).

Mean of n=1, FGFR Kinase assay—Caliper Echo Dosing, $IC_{50}$ 0.0034 µM.

5-Chloro-N-[5-[2-(3,5-dimethoxyphenyl)ethyl]-2H-pyrazol-3-yl]pyrazine-2-carboxamide was prepared as shown in Example 105.

Example 173

N-[5-[2-(3,5-dimethoxyphenyl)ethyl]-2H-pyrazol-3-yl]-2-(4-propan-2-yl-1,4-diazepan-1-yl)pyrimidine-5-carboxamide Trimethylaluminium (1.19 ml, 2.38 mmol) was added dropwise to a stirred suspension of methyl 2-(4-propan-2-yl-1,4-diazepan-1-yl)pyrimidine-5-carboxylate (265 mg, 0.95 mmol) and 5-[2-(3,5-dimethoxyphenyl)ethyl]-2H-pyrazol-3-amine (235 mg, 0.95 mmol) in toluene (4.76 ml) at 25° C. The resulting solution was stirred at 60° C. for 18 h. The cooled reaction mixture was quenched into methanol (50 mL) and treated with HCl (2M aqueous solution, to pH7 or lower) and purified by ion exchange chromatography, using an SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (81 mg, 17%) as a cream solid.

1H NMR (399.9 MHz, DMSO-d6) δ 0.94-0.95 (6H, m), 1.78 (2H, m), 2.51-2.54 (2H, m, partially obscured by DMSO peak), 2.67-2.74 (3H, m), 2.87 (4H, s), 3.73 (6H, s), 3.82 (4H, t), 6.33 (1H, t), 6.42 (2H, d), 6.44 (1H, s), 8.88 (2H, s), 10.55 (1H, s), 12.13 (1H, s). MS: m/z 494 (MH+).

Mean of n=1, FGFR Kinase assay—Caliper Echo Dosing, $IC_{50}$ 0.018 µM.

Methyl 2-(4-propan-2-yl-1,4-diazepan-1-yl)pyrimidine-5-carboxylate used as starting material was prepared as follows:

A solution of methyl 2-chloropyrimidine-5-carboxylate (209 mg, 1.21 mmol) in dichloromethane (4.00 ml) was added to a stirred solution of 1-propan-2-yl-1,4-diazepane (172 mg, 1.21 mmol) and N-ethyl-N-propan-2-ylpropan-2-amine (0.523 ml, 3.02 mmol) in dichloromethane (4.00 ml) at 25° C. The resulting solution was stirred at ambient temperature for 18 h. The reaction mixture was evaporated to dryness and redissolved in MeOH (20 mL) and the crude product was purified by ion exchange chromatography, using an SCX column. The desired product was eluted from the column using 7M NH3/MeOH and evaporated to dryness to afford methyl 2-(4-propan-2-yl-1,4-diazepan-1-yl)pyrimidine-5-carboxylate (267 mg, 79%) as a cream oil which crystallised on standing. This was used directly with no further purification.

1H NMR (399.9 MHz, DMSO-d6) δ 0.92-0.94 (6H, m), 1.74-1.80 (2H, m), 2.71 (2H, t), 2.82-2.89 (1H, m), 3.81 (3H, s), 3.80-3.85 (4H, m), 8.78-8.78 (2H, m), 1× (2H, m) obscured by DMSO peak. MS: m/z 279 (MH+).

1-Propan-2-yl-1,4-diazepane used as starting material was prepared as follows:

Benzyl 4-propan-2-yl-1,4-diazepane-1-carboxylate (3.00 g, 10.85 mmol) and palladium, 10% on carbon (0.289 g, 2.71 mmol) in ethanol (54.3 ml) were stirred under an atmosphere of hydrogen at atmospheric pressure and ambient temperature for 18 h. The reaction mixture was filtered through celite, washing with ethanol, methanol and dichloromethane and the filtrate concentrated under reduced pressure to afford 1-propan-2-yl-1,4-diazepane (1.54 g, 100%) as a yellow liquid. This was used directly with no further purification.

1H NMR (399.9 MHz, CDCl3) δ 1.00-1.02 (6H, m), 1.69-1.74 (2H, m), 1.94 (1H, br s), 2.63-2.68 (4H, m), 2.87-2.94 (5H, m).

Benzyl 4-propan-2-yl-1,4-diazepane-1-carboxylate used as starting material was prepared as follows:

Sodium triacetoxyborohydride (5.79 g, 27.32 mmol) was added portionwise to benzyl 1,4-diazepane-1-carboxylate (2.56 g, 10.93 mmol) and acetic acid (1.251 mL, 21.85 mmol) in acetone (5.00 mL) at room temperature. The resulting solution was stirred at ambient temperature for 18 h under nitrogen. The reaction mixture was concentrated and diluted with water (200 mL) and basified with 2M NaOH. The aqueous was extracted with diethyl ether (3×100 mL) and washed sequentially with water (200 mL) and saturated brine (200 mL). The organic layer was dried over MgSO4, filtered and evaporated to afford the desired product (3.00 g, 99%). This was used directly with no further purification.

1H NMR (399.9 MHz, DMSO-d6) δ 0.92-0.95 (6H, m), 1.63-1.69 (2H, m), 2.60 (2H, t), 2.80-2.88 (1H, m), 3.38-3.45 (4H, m), 5.09 (2H, s), 7.29-7.40 (5H, m), one (2H, m) obscured by solvent peak. MS: m/z 277 (MH+).

Example 174

5-(4-cyclopropyl-1,4-diazepan-1-yl)-N-[5-[2-(3,5-dimethoxyphenyl)ethyl]-2H-pyrazol-3-yl]pyrazine-2-carboxamide 1-Cyclopropyl-1,4-diazepane, 2HCl (205 mg, 0.96 mmol) was added to 5-chloro-N-[5-[2-(3,5-dimethoxyphenyl)ethyl]-2H-pyrazol-3-yl]pyrazine-2-carboxamide (310 mg, 0.80 mmol) and N-ethyl-N-propan-2-ylpropan-2-amine (0.48 ml, 2.80 mmol) in DMSO (4.00 ml) at 25° C. The resulting solution was stirred at room temperature for 24 h. The reaction was incomplete so the temperature was increased to 80° C. and the reaction mixture was stirred for a further 3 h. The reaction mixture was diluted with MeOH (5 ml). The crude product was purified by ion exchange chromatography, using a SCX column. The desired product was eluted from the column using 7M NH3/MeOH and fractions were evaporated to dryness to afford crude product as a brown oil. The crude product was purified by preparative HPLC, using decreasingly polar mixtures of water (containing 1% NH3) and MeCN as eluents. Fractions containing the desired compound were evaporated to dryness to afford the title compound (277 mg, 70%) as a yellow solid.

1H NMR (399.9 MHz, CDCl$_3$) δ 0.32-0.37 (2H, m), 0.38-0.43 (2H, m), 1.75-1.80 (1H, m), 1.86-1.92 (2H, m), 2.74 (2H, t), 2.83-2.92 (6H, m), 3.70 (6H, s), 3.70-3.77 (4H, m), 6.26 (1H, t), 6.29 (2H, d), 6.42 (1H, s), 7.82 (1H, d), 8.83 (1H, d), 9.64 (1H, s). MS: m/z 492 (MH+).

Mean of n=1, FGFR Kinase assay—Caliper Echo Dosing, IC$_{50}$ 0.0037 µM.

5-Chloro-N-[5-[2-(3,5-dimethoxyphenyl)ethyl]-2H-pyrazol-3-yl]pyrazine-2-carboxamide was prepared as shown in Example 105.

Example 175

N-[5-[2-(3,5-dimethoxyphenyl)ethyl]-2H-pyrazol-3-yl]-2-(4-prop-2-enyl-1,4-diazepan-1-yl)pyrimidine-5-carboxamide Trimethylaluminium (1.35 ml, 2.70 mmol) was added dropwise to a stirred suspension of methyl 2-(4-prop-2-enyl-1,4-diazepan-1-yl)pyrimidine-5-carboxylate (300 mg, 1.09 mmol) and 5-[2-(3,5-dimethoxyphenyl)ethyl]-2H-pyrazol-3-amine (268 mg, 1.09 mmol) in toluene (5.43 ml) at 25° C. The resulting solution was stirred at 60° C. for 18 h. The cooled reaction mixture was quenched into methanol (50 mL) and treated with HCl (2M aqueous solution, to pH7 or lower) and purified by ion exchange chromatography, using a SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (220 mg, 41%) as a cream solid.

1H NMR (399.9 MHz, DMSO-d6) δ 1.82-1.88 (2H, m), 2.53-2.57 (2H, m, partially obscured by DMSO peak), 2.71 (2H, t), 2.88 (4H, s), 3.08 (2H, d), 3.73 (6H, s), 3.83 (2H, t), 3.86-3.88 (2H, m), 5.10-5.13 (1H, m), 5.17 (1H, d), 5.77-5.87 (1H, m), 6.33 (1H, t), 6.42 (2H, d), 6.44 (1H, s), 8.89 (2H, s), 10.56 (1H, s), 12.13 (1H, s). MS: m/z 492 (MH+).

Mean of n=1, FGFR Kinase assay—Caliper Echo Dosing, IC$_{50}$ 0.007 µM.

5-[2-(3,5-dimethoxyphenyl)ethyl]-2H-pyrazol-3-amine, used as starting material was prepared as indicated in Example 2.

Methyl 2-(4-prop-2-enyl-1,4-diazepan-1-yl)pyrimidine-5-carboxylate used as starting material was prepared as follows:

A solution of methyl 2-chloropyrimidine-5-carboxylate (200 mg, 1.16 mmol) in dichloromethane (4.00 mL) was added to a stirred solution of 1-prop-2-enyl-1,4-diazepane (163 mg, 1.16 mmol) and N-ethyl-N-propan-2-ylpropan-2-amine (0.501 mL, 2.90 mmol) in dichloromethane (4.00 mL) at 25° C. The resulting solution was stirred at ambient temperature for 18 h. The reaction mixture was evaporated to dryness and redissolved in MeCN (20 mL) and the crude product was purified by ion exchange chromatography, using an SCX column. The desired product was eluted from the column using 7M NH3/MeOH and evaporated to dryness to afford the desired compound (304 mg, 95%) as a cream oil which crystallised on standing. This was used directly with no further purification.

1H NMR (399.9 MHz, DMSO-d6) δ 1.81-1.87 (2H, m), 2.55 (2H, m), 2.70-2.72 (2H, m), 3.06-3.09 (2H, m), 3.81 (3H, s), 3.80-3.89 (4H, m), 5.09-5.13 (1H, m), 5.13-5.19 (1H, m), 5.76-5.86 (1H, m), 8.79 (2H, d). MS: m/z 277 (MH+).

1-Prop-2-enyl-1,4-diazepane used as starting material was prepared as follows:

To a solution of tert-butyl 1-homopiperazinecarboxylate (9.73 mL, 50 mmol) in dichloromethane (250 mL) was added PS-TBD resin (40 g, 100 mmol) and 3-bromoprop-1-ene (4.33 mL, 50 mmol) dropwise at 25° C. The mixture was stirred for 2 h. The PS-TBD was filtered off and the filtrate evaporated to dryness, redissolved in MeOH/EtOAc (1:9) and then filtered through a short silica column. The filtrate obtained was evaporated to dryness, treated with TFA (20 ml) and then stirred at room temperature for 1 h. The reaction mixture was evaporated to dryness and redissolved in MeOH (50 mL) and the crude product was purified by ion exchange chromatography, using an SCX column. The desired product was eluted from the column using 7M NH3/MeOH and evaporated to dryness to afford 1-prop-2-enyl-1,4-diazepane (4.07 g, 58.0%) as a pale yellow oil.

1H NMR (399.902 MHz, CDCl3) δ 1.70 (m, 2H), 1.98 (s, 1H), 2.59 (m, 4H), 2.85 (m, 4H), 3.06 (m, 2H), 5.07 (m, 2H), 5.81 (m, 1H)

Example 176

N-[5-[2-(3,5-dimethoxyphenyl)ethyl]-2H-pyrazol-3-yl]-2-(4-methyl-1,4-diazepan-1-yl)pyrimidine-5-carboxamide Trimethylaluminium (1.35 ml, 2.70 mmol) was added dropwise to a stirred suspension of methyl 2-(4-methyl-1,4-diazepan-1-yl)pyrimidine-5-carboxylate (270 mg, 1.08 mmol) and 5-[2-(3,5-dimethoxyphenyl)ethyl]-2H-pyrazol-3-amine (267 mg, 1.08 mmol) in toluene (5.39 ml) at 25° C. The resulting solution was stirred at 60° C. for 18 h. The cooled reaction mixture was quenched into methanol (50 mL) and treated with HCl (2M aqueous solution, to pH7 or lower) and purified by ion exchange chromatography, using a SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing pure desired compound were evaporated to dryness to afford the title compound (136 mg, 27%) as a cream solid. The fractions containing impure product were concentrated and purified by crystallisation from MeCN to afford the title compound (56.0 mg, 11%) as a beige solid.

1H NMR (399.9 MHz, DMSO-d6) δ 1.86-1.92 (2H, m), 2.27 (3H, s), 2.64 (2H, t), 2.88 (4H, s), 3.73 (6H, s), 3.81 (2H, t), 3.89 (2H, t), 6.33 (1H, t), 6.41-6.45 (3H, m), 8.89 (2H, s), 10.57 (1H, s), 12.13 (1H, s). 2H obscured by DMSO peak. MS: m/z 466 (MH+).

Mean of n=1, FGFR Kinase assay—Caliper Echo Dosing, IC$_{50}$ 0.0058 µM.

5-[2-(3,5-dimethoxyphenyl)ethyl]-2H-pyrazol-3-amine, used as starting material was prepared as indicated in Example 2.

Methyl 2-(4-methyl-1,4-diazepan-1-yl)pyrimidine-5-carboxylate used as starting material was prepared as follows:

A solution of methyl 2-chloropyrimidine-5-carboxylate (200 mg, 1.16 mmol) in dichloromethane (4.00 mL) was added to a stirred solution of 1-methyl-1,4-diazepane (0.144 mL, 1.16 mmol) and N-ethyl-N-propan-2-ylpropan-2-amine (0.902 mL, 5.22 mmol) in dichloromethane (4.00 mL) at 25°

C. The resulting solution was stirred at ambient temperature for 18 h. The reaction mixture was evaporated to dryness and redissolved in MeOH (20 mL) and the crude product was purified by ion exchange chromatography, using an SCX column. The desired product was eluted from the column using 7M NH3/MeOH and evaporated to dryness to afford methyl 2-(4-methyl-1,4-diazepan-1-yl)pyrimidine-5-carboxylate (274 mg, 94%) as a white solid. This was used directly with no further purification.

1H NMR (399.9 MHz, DMSO-d6) δ 1.86-1.89 (2H, m), 2.26 (3H, s), 2.49-2.54 (2H, m, partially obscured by DMSO peak), 2.62-2.64 (2H, m), 3.81 (3H, s), 3.80-3.84 (2H, m), 3.89-3.91 (2H, m), 8.79 (2H, d). MS: m/z 251 (MH+)

Example 177

2-(4-cyclopropyl-1,4-diazepan-1-yl)-N-[5-[2-(3,5-dimethoxyphenyl)ethyl]-2H-pyrazol-3-yl]pyrimidine-5-carboxamide Trimethylaluminium (1.402 ml, 2.80 mmol) was added dropwise to a stirred suspension of methyl 2-(4-cyclopropyl-1,4-diazepan-1-yl)pyrimidine-5-carboxylate (310 mg, 1.12 mmol) and 5-[2-(3,5-dimethoxyphenyl)ethyl]-2H-pyrazol-3-amine (277 mg, 1.12 mmol) in toluene (5.61 ml) at 25° C. The resulting solution was stirred at 60° C. for 18 h. The cooled reaction mixture was quenched into methanol (50 mL) and treated with HCl (2M aqueous solution, to pH7 or lower) and purified by ion exchange chromatography, using a SCX column. The desired product was eluted from the column using 7M NH3/MeOH and evaporated to dryness to afford impure product. The crude product was purified by preparative HPLC, using decreasingly polar mixtures of water (containing 1% NH3) and MeCN as eluents. Fractions containing the desired compound were evaporated to dryness to afford the title compound (8.00 mg, 1%) as a cream solid. Some impure fractions were combined and concentrated to dryness and purified by crystallisation from MeCN to afford the title compound (51 mg, 9%) as a cream solid.

1H NMR (399.9 MHz, DMSO-d6) δ 0.31 (2H, m), 0.41-0.44 (2H, m), 1.84-1.89 (3H, m), 2.71 (2H, t), 2.88 (4H, s), 3.73 (6H, s), 3.81-3.87 (4H, m), 6.33 (1H, t), 6.42 (2H, d), 6.44 (1H, d), 8.89 (2H, s), 10.55 (1H, s), 12.14 (1H, s), 2H obscured by DMSO peak. MS: m/z 492 (MH+)

Mean of n=2, FGFR Kinase assay—Caliper Echo Dosing, IC$_{50}$ 0.0073 μM.

5-[2-(3,5-dimethoxyphenyl)ethyl]-2H-pyrazol-3-amine, used as starting material was prepared as indicated in Example 2.

Methyl 2-(4-cyclopropyl-1,4-diazepan-1-yl)pyrimidine-5-carboxylate used as starting material was prepared as follows:

A solution of methyl 2-chloropyrimidine-5-carboxylate (200 mg, 1.16 mmol) in dichloromethane (4.00 mL) was added to a stirred solution of 1-cyclopropyl-1,4-diazepane (247 mg, 1.16 mmol) and N-ethyl-N-propan-2-ylpropan-2-amine (0.902 mL, 5.22 mmol) in dichloromethane (4.00 mL) at 25° C. The resulting solution was stirred at ambient temperature for 18 h. The reaction mixture was evaporated to dryness and redissolved in MeOH (20 mL) and the crude product was purified by ion exchange chromatography, using an SCX column. The desired product was eluted from the column using 7M NH3/MeOH and evaporated to dryness to afford methyl 2-(4-cyclopropyl-1,4-diazepan-1-yl)pyrimidine-5-carboxylate (312 mg, 97%) as a cream solid. This was used directly with no further purification.

1H NMR (399.9 MHz, DMSO-d6) δ 0.28-0.31 (2H, m), 0.40-0.45 (2H, m), 1.80-1.84 (2H, m), 1.85-1.89 (1H, m), 2.71 (2H, m), 2.85-2.88 (2H, m), 3.81 (3H, s), 3.82-3.88 (4H, m), 8.79 (2H, s). MS: m/z 277 (MH+)

Example 178

N-[5-[2-[3-(methylcarbamoyl)phenyl]ethyl]-2H-pyrazol-3-yl]-4-(4-methylpiperazin-1-yl)benzamide A 2M solution of trimethylaluminium (0.936 mL, 1.87 mmol) in toluene, was added drop-wise to a stirred suspension of 3-(2-(5-amino-1H-pyrazol-3-yl)ethyl)-N-methylbenzamide (0.183 g, 0.75 mmol) and methyl 4-(4-methylpiperazin-1-yl)benzoate (0.176 g, 0.75 mmol) in toluene (5 mL) at room temperature. The solution was then stirred at 60° C. for 18 h. The reaction mixture was cooled, poured into methanol (5 ml) and acidified with 2N HCl (15 ml). The crude product was purified by ion exchange chromatography, using a SCX column. The desired product was eluted from the column using 7M NH3/MeOH and pure fractions were evaporated to dryness to afford an oil. The crude product was purified by preparative HPLC, using decreasingly polar mixtures of water (containing 1% NH3) and MeCN as eluents. Fractions containing the desired compound were evaporated to dryness to afford the title compound (0.109 g, 32.6%) as a white solid.

1H NMR (399.9 MHz, DMSO-d6) δ 1.88 (3H, s), 2.23 (3H, s), 2.45 (4H, t), 2.87-3.02 (4H, m), 3.40 (4H, t), 6.39 (1H, s), 6.97 (2H, d), 7.37 (1H, s), 7.38 (2H, t), 7.65-7.67 (1H, m), 7.75 (1H, s), 7.90 (2H, d), 8.36 (1H, d), 10.36 (1H, s). MS: m/z 447 (MH+).

Mean of n=2, FGFR Kinase assay—Caliper Echo Dosing, IC$_{50}$ 0.0011 μM.

3-(2-(5-Amino-1H-pyrazol-3-yl)ethyl)-N-methylbenzamide used as starting material was prepared as follows:

1.8M LDA in THF (30.0 mL, 54.00 mmol) was added to tetrahydrofuran (60 mL) and cooled to −78° C. Acetonitrile (2.82 mL, 54.00 mmol) was added drop-wise over 15 mins. A solution of methyl 3-(3-(methylcarbamoyl)phenyl)propanoate (2.99 g, 13.5 mmol) in tetrahydrofuran (10 ml) was added. The resulting mixture stirred at −78° C. for 10 mins. The reaction mixture was warmed to 5° C. and stirred for 30 mins, hydrazine hydrochloride (3.70 g, 54.00 mmol) and ethanol (60.0 mL) were added and the reaction mixture heated at 80° C. for 18 h. The reaction mixture was cooled and evaporated to dryness. The residue was dissolved in methanol (50 ml) and the crude product was purified by ion exchange chromatography, using a SCX column. The desired product was eluted from the column using 7M NH3/MeOH fractions were evaporated to dryness to afford an oil. The crude product was purified by silica column chromatography, eluting with a gradient of 0 to 10% MeOH in DCM. Pure fractions were evaporated to dryness to afford 3-(2-(5-amino-1H-pyrazol-3-yl)ethyl)-N-methylbenzamide (0.450 g, 13.64%) as a yellow oil.

1H NMR (399.9 MHz, DMSO-d$_6$) δ 2.73-2.79 (4H, m), 2.89 (1H, d), 3.18 (3H, d), 4.09 (1H, d), 5.19 (1H, s), 7.35 (1H, s), 7.35-7.37 (1H, m), 7.63-7.66 (1H, m), 7.72 (1H, s), 8.38 (1H, d)—1 proton not seen. MS: m/z 245 (MH+).

Methyl 3-(3-(methylcarbamoyl)phenyl)propanoate used as starting material was prepared as follows:

A solution of (E)-methyl 3-[3-(methylcarbamoyl)phenyl]prop-2-enoate (3.77 g, 17.20 mmol) and 10% palladium on carbon (0.458 g, 0.43 mmol) in a mixture of ethanol (100 mL) and DMF (10.00 mL) was stirred at room temperature for 18 h under a balloon of hydrogen. The 20 reaction mixture was filtered through celite and evaporated to dryness to afford methyl 3-(3-(methylcarbamoyl)phenyl)propanoate (3.05 g, 80%) as a white solid. MS: m/z 222 (MH+).

(E)-methyl 3-[3-(methylcarbamoyl)phenyl]prop-2-enoate used as starting material was prepared as follows:

A solution of 3-formyl-N-methylbenzamide (2.9 g, 17.77 mmol) and methyl 2-triphenylphosphoranylideneacetate (8.91 g, 26.66 mmol) in dichloromethane (85 mL), was stirred at room temperature for 18 h. The reaction mixture was evaporated to dryness. The crude product was purified by silica column chromatography, eluting with a gradient of 0 to 10% MeOH in DCM. Pure fractions were evaporated to dryness to afford impure product. Re-purified by silica column chromatography, eluting with a gradient of 50 to 100% EtOAc in hexanes. Pure fractions were evaporated to dryness to afford (E)-methyl 3-[3-(methylcarbamoyl)phenyl]prop-2-enoate (3.77 g, 97%).

1H NMR (399.9 MHz, CDCl$_3$) δ 3.02-3.03 (3H, m), 3.81 (3H, s), 6.34 (1H, s), 6.51 (1H, s), 7.42-7.48 (2H, m), 7.61-7.66 (1H, m), 7.67 (1H, d), 7.74-7.76 (1H, m), 7.93 (1H, t).

3-Formyl-N-methylbenzamide used as starting material was prepared as follows:

A 2M solution of methylamine in THF (44 mL, 5 eq, 87.5 mmol) was added to methyl 3-formylbenzoate (2.875 g, 1 eq, 17.5 mmol) in dry THF (65 ml). The reaction mixture was cooled to −50° C. under nitrogen and a 2M solution of trimethylaluminium in toluene (22 ml, 2.5 eq, 43.75 mmol) was added slowly over 15 mins. The reaction mixture was allowed to warm slowly to room temperature and stirred for 18 h. The reaction mixture was quenched with a 20% w/v solution of potassium sodium tartrate in water (50 ml). This was extracted with ethyl acetate (2×100 ml) and washed with water (50 ml), saturated sodium chloride solution (50 ml), dried over MgSO$_4$ and evaporated under reduced pressure to give a gum. The crude product was purified by silica column chromatography, eluting with a gradient of 0 to 2.5% methanol in DCM. Pure fractions were combined and evaporated to afford 3-formyl-N-methylbenzamide (1.6502 g, 58%) as an off-white solid.

1H NMR (399.9 MHz, DMSO-d$_6$) δ 2.78-2.85 (3H, m), 7.70-7.75 (1H, t), 8.05-8.08 (1H, m), 8.04-8.09 (1H, m), 8.37-8.39 (1H, d), 8.63-8.70 (1H, s), 10.08 (1H, s). MS: m/z 164 (MH+).

Example 179

N-[5-[(3,5-dimethoxyphenyl)methoxy]-2H-pyrazol-3-yl]-4-(4-ethylpiperazin-1-yl)benzamide Trimethylaluminium (2M in toluene, 1.51 mL, 3.02 mmol) was added dropwise to 5-[(3,5-dimethoxyphenyl)methoxy]-2H-pyrazol-3-amine, HCl (345 mg, 1.21 mmol) and methyl 4-(4-ethylpiperazin-1-yl)benzoate (300 mg, 1.21 mmol) in toluene (6.0 mL) at 25° C. The resulting solution was stirred at 60° C. for 19 h under nitrogen. The reaction was incomplete and further trimethylaluminium (0.50 mL, 3.02 mmol) was added and the solution was stirred at 60° C. for a further 4 h. The reaction mixture was added to methanol (100 ml) and treated with HCl (2N aqueous solution, until pH was 7 or lower). The crude product was purified by ion exchange chromatography, using a SCX column. Some product crystallised out of the pure fractions and was collected by vacuum filtration to give the title compound (95 mg, 17%) as a white solid. The filtrate was evaporated to dryness to give a further sample of the title compound (115 mg, 20%) as a white solid. Impure fractions containing the desired product were repurified by preparative HPLC, using decreasingly polar mixtures of water (containing 1% NH3) and MeCN as eluents, to afford a third sample of the title compound (27 mg, 5%) as a white solid.

1H NMR (399.9 MHz, DMSO-d$_6$) δ 1.05 (3H, t), 2.38 (2H, q), 3.75 (6H, s), 5.08 (2H, s), 5.67 (1H, s), 6.45 (1H, t), 6.60 (2H, d), 7.01 (2H, d), 7.86 (2H, d). At approximately δ 2.5, 4H peak obscured by DMSO. At approximately δ 3.3, 4H peak obscured by H$_2$O. MS: m/z 466 (MH+)

Mean of n=2, FGFR Kinase assay—Caliper Echo Dosing, IC$_{50}$ 0.00068 μM.

5-[(3,5-Dimethoxyphenyl)methoxy]-2H-pyrazol-3-amine hydrochloride, used as starting material was prepared as in Example 12.

Methyl 4-(4-ethylpiperazin-1-yl)benzoate, used as starting material, was prepared as follows:

1-Ethylpiperazine (3.68 mL, 29.0 mmol) was added to methyl 4-fluorobenzoate (1.50 mL, 11.6 mmol) in dimethylsulfoxide (29.0 mL) at 25° C. The resulting solution was stirred at 120° C. for 18 h. The reaction mixture was concentrated and diluted with EtOAc (50 mL) and water (20 mL). NaOH (2N aqueous solution, 20 mL) was added and the layers were separated and washed with EtOAc (40 mL). The organic layers were combined and washed with water (40 mL) and saturated brine (40 mL). The organic layer was dried over magnesium sulphate, filtered and evaporated to afford the desired product (1.960 g, 68%). This was used without further purification.

1H NMR (399.9 MHz, CDCl$_3$) δ 1.06 (3H, t), 2.40 (2H, q), 2.52 (4H, t), 3.29 (4H, t), 3.79 (3H, s), 6.78-6.81 (2H, m), 7.83-7.86 (2H, m). MS: m/z 249 (MH+)

Example 180

N-[5-[2-(3,5-dimethoxyphenyl)ethyl]-2H-pyrazol-3-yl]-4-(4-ethylpiperazin-1-yl)benzamide Trimethylaluminium (2M in toluene, 1.51 mL, 3.02 mmol) was added dropwise to 5-[2-(3,5-dimethoxyphenyl)ethyl]-2H-pyrazol-3-amine (299 mg, 1.21 mmol) and methyl 4-(4-ethylpiperazin-1-yl)benzoate (300 mg, 1.21 mmol) in toluene (6.0 mL) at 25° C. The resulting suspension was stirred at 60° C. for 24 h under nitrogen. The reaction mixture was added to methanol (100 mL) and was treated with HCl (2N aqueous solution, until the pH was 7 or lower). The crude product was purified by ion exchange chromatography, using a SCX column. The desired product was eluted from the column using 7M NH3/MeOH and fractions were evaporated to dryness to afford impure product. The crude product was purified by silica column chromatography, eluting with a gradient of 0 to 5% 7M NH3/MeOH in DCM. Pure fractions were evaporated to dryness to afford the title compound (288 mg, 51%) as a cream solid.

1H NMR (399.9 MHz, DMSO-d$_6$) δ 1.05 (3H, t), 2.38 (2H, q), 2.50 (4H, peak obscured by DMSO), 2.87 (4H, s), 3.26-3.29 (4H, m), 3.73 (6H, s), 6.33 (1H, t), 6.42 (2H, d), 6.45 (1H, s), 6.96 (2H, d), 7.90 (2H, d), 10.29 (1H, s), 12.07 (1H, s). MS: m/z 464 (MH+).

Mean of n=2, FGFR Kinase assay—Caliper Echo Dosing, IC$_{50}$ 0.0017 μM.

5-[2-(3,5-dimethoxyphenyl)ethyl]-2H-pyrazol-3-amine, used as starting material was prepared as indicated in Example 2.

Methyl 4-(4-ethylpiperazin-1-yl)benzoate, used as starting material, was prepared as outlined in Example 179.

Enzyme Assays
FGFR Kinase Assay—Caliper

To determine inhibition of FGFR activity, kinase assays were conducted using Caliper technology.

Kinase activity assays were performed in Greiner 384-well low volume plates, with a total reaction volume of 12 ul per well. Final concentration of FGFR1 active kinase in each reaction well was 7.2 nM. The substrate for each assay was a custom peptide with fluorescent tag (13 amino acids in length, KKSRGDYMTMQIG with the fluorescene tag on the first K).

Compounds were serially diluted in 5% (v/v) DMSO, before being added to assay plates. The Enzyme (at 7.2 nM [final]) and Substrate (at 3.6 uM [final]) were added separately to the compound plates, in reaction buffer [comprising: 50 mM MOPS (Sigma, Catalogue No. M1254)—pH 6.5, 0.004% Triton (Sigma, Catalogue No. X-100), 2.4 mM DTT, 12 mM $MgCl_2$, 408 uM ATP] resulting in a final DMSO concentration in the reaction mix of 0.8%.

Assay plates were incubated at room temperature for 1.5 h, before the reaction was stopped with the addition of buffer [comprising: 100 mM HEPES—pH7.5, 0.033% Brij-35 (Sigma Catalogue No. B4184), 0.22% Caliper Coating Reagent #3 (Caliper Life Sciences Catalogue No. 760050), 88 mM EDTA, 5% DMSO]. Stopped assay plates were then read using the Caliper LabChip® LC3000 (which uses microfludics to measure a shift in mobility between fluorescent labelled peptide and the FGFR1 kinase—phosphorylated form of this peptide).

In the assay, compounds were tested at a range of concentrations. The mean data values for each concentration, along with untreated control wells and 100% inhibition control wells were used to derive a plot of inhibition against concentration. From this data, the IC50 value or a percentage inhibition value at fixed concentration may be determined.

Percentage inhibition at 1 uM, as expressed herein, is a calculated value based on the curve fit that was generated experimentally. From the fitted curve plot, the effect of compound at a concentration of 1 uM was calculated as a percentage inhibition. The $IC_{50}$ is the concentration of compound, which inhibits FGFR1 kinase activity by 50% in the context of this assay.

Results of FGFR Inhibition Tests for Examples

| Example | Activity class |
|---------|----------------|
| 3 | A |
| 4 | A |
| 5 | A |
| 6 | A |
| 7 | A |
| 8 | A |
| 9 | A |
| 13 | B |
| 14 | B |
| 15 | A |
| 16 | B |
| 17 | B |
| 18 | B |
| 19 | B |
| 20 | A |

Activity:
A less than 0.3 μM
B greater than 0.3 μM and less than 1 μM
C greater than 1 μM and less than 30 μM
Eg. Example 14 is 612 nM.

FGFR Kinase Assay—Caliper Echo Dosing

To determine inhibition of FGFR activity, kinase assays were conducted using Caliper technology.

Kinase activity assays were performed in Greiner 384-well low volume plates, with a total reaction volume of 12 ul per well. Final concentration of FGFR1 active kinase in each reaction well was 7.2 nM. The substrate for each assay was a custom peptide with fluorescent tag (13 amino acids in length, KKSRGDYMTMQIG with the fluorescene tag on the first K).

Compounds were dispensed directly in to assay plates using a Labcyte Echo 550 acoustic droplet ejection unit. Each well received 120 nl of DMSO containing compound such that the final concentration of compound in the assay prior to the addition of the stop solution ranged between 30 uM and 30 pM. In addition to compounds each plate carried maximum and minimum control wells, the max wells contained 120 nl of DMSO and the min wells contained 120 nl of 10 mM staurosporine (LC Laboratories, MA 01801, USA Catalogue No. S-9300). The Enzyme (at 7.2 nM [final]) and Substrate (at 3.6 uM [final]) were added separately to the compound plates, in reaction buffer [comprising: 50 mM MOPS (Sigma, Catalogue No. M1254)—pH 6.5, 0.004% Triton (Sigma, Catalogue No. X-100), 2.4 mM DTT, 12 mM $MgCl_2$, 408 uM ATP] resulting in a final DMSO concentration in the reaction mix of 1%.

Assay plates were incubated at room temperature for 1.5 h, before the reaction was stopped with the addition of buffer [comprising: 100 mM HEPES—pH7.5, 0.033% Brij-35 (Sigma Catalogue No. B4184), 0.22% Caliper Coating Reagent #3 (Caliper Life Sciences Catalogue No. 760050), 88 mM EDTA, 5% DMSO]. Stopped assay plates were then read using the Caliper LabChip® LC3000 (which uses microfludics to measure a shift in mobility between fluorescent labelled peptide and the FGFR1 kinase—phosphorylated form of this peptide).

In the assay, compounds were tested at a range of concentrations. The mean data values for each concentration, along with untreated control wells and 100% inhibition control wells were used to derive a plot of inhibition against concentration. From this data, the IC50 value or a percentage inhibition value at fixed concentration may be determined.

Percentage inhibition at 1 uM, as expressed herein, is a calculated value based on the curve fit that was generated experimentally. From the fitted curve plot, the effect of compound at a concentration of 1 uM was calculated as a percentage inhibition. The $IC_{50}$ is the concentration of compound, which inhibits FGFR1 kinase activity by 50% in the context of this assay. This value is calculated using a standard curve fitting software package Origin™. Where compounds have been tested on more than one occasion the $IC_{50}$ value is sited as a geometric mean.

FGFR Kinase Assay—Elisa

To determine inhibition of FGFR activity, kinase assays were conducted using ELISA (Enzyme-Linked Immunosorbent Assay) technology.

Kinase activity assays were performed in 384-well polypropylene plates (Matrix, Catalogue No. 4311. Matrix are part of Thermo Fisher Scientific, 22 Friars Drive, Hudson, N.H. 03051, USA) with a total volume of 40 μl in each well. Each well was coated with 2 μg of polyEAY substrate (Sigma, Catalogue No. P3899) at 4° C. overnight. The plates were then washed once with 100 μl PBS and once with 100 μl 50 mM HEPES (pH 7.4) prior to the addition of the kinase assay reagents. Reactions contained $His_6$-tagged FGFR kinase domain (FGFR kinase domain (amino acids 458-765, C488A, C584S) N-terminally fused to a $His_6$-tag and TEV cleavage site encoded by the following sequence; [MHHH-HHHEFKGSTSLYKKAGSSENLYFQGA]. The final alanine denotes the start of the FGFR protein sequence. The resultant protein was expressed and purified based on Mohammadi et al, Cell Vol 86, 577-587 (1996). Each kinase reaction contained 0.1 ng $His_6$-tagged FGFR kinase domain, 50 mM HEPES (pH 7.4), 0.1 mM $Na_3VO_4$, 0.1 mM DTT, 0.05% (v/v) Triton X100, 20 mM $MgCl_2$, 160 μM ATP. Various concentrations of test compounds were each added in 5% (v/v) DMSO to yield a final assay DMSO concentration of 1.25% (v/v). The kinase reactions were incubated at room temperature for 45 minutes and stopped by washing the plate three times with 100 μl PBS plus 0.05% Tween. 40 μl of a one in 10000 dilution of 4G10-HRP antibody (Upstate Biotechnology, UBI 16-105. Upstate are part of Millipore Corporation, 290 Concord Road, Billerca Mass. 01821 USA) made up in 0.5% (w/v) BSA/PBS was then added to each well and the plates incubated at room temperature for one hour. Following this, the plates were then washed repeatedly with 100 μl PBS plus 0.05% Tween to remove all traces of the antibody solution. 40 μl of 50 m/ml 3,3',5,5'-Tetramethylbenzidine (Sigma, Catalogue No. T2885), 0.05M phosphate-citrate buffer, containing 0.03% sodium perborate was added to each well and the plates incubated at room temperature for twelve minutes. The colour reaction was stopped by the addition of 20 μl 2M $H_2SO_4$ and the plates read at 450 nm on a Spectrafluor Plus (Tecan Trading AG, Switzerland). In the assay, compounds were tested at a range of concentrations. The mean data values for each concentration, along with untreated control wells and 100% inhibition control wells were used to derive a plot of inhibition against concentration. From this data, the IC50 value or a percentage inhibition value at fixed concentration may be determined.

Percentage inhibition at 1 uM, as expressed herein, is a calculated value based on the curve fit that was generated experimentally. From the fitted curve plot, the effect of compound at a concentration of 1 uM was calculated as a percentage inhibition. The $IC_{50}$ value is the concentration of test compound that inhibits 50% of FGFR kinase activity.

Results of FGFR Inhibition Tests for Examples

| Example | Activity class |
| --- | --- |
| 1 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | B |
| 14 | B |
| 15 | A |
| 16 | B |
| 17 | B |
| 18 | B |
| 19 | A |
| 20 | A |

Activity:
A less than 0.3 μM
B greater than 0.3 μM and less than 1 μM
C greater than 1 μM and less than 30 μM
Eg Example 14 is 732 nM.

Cell Assays
Cell pErk—Growth Factor Stimulated Erk Phosphorylation

These and other assays were used to evaluate the ability of a test compound to inhibit growth factor stimulated cellular signalling in mammalian cell lines. This was achieved by measuring the amount of receptor tyrosine kinase regulated Erk phosphorylation within a cell following compound treatment.

NIH 3T3 (ECACC, 93061524) cells were routinely passaged in DMEM (Gibco BRL, 41966) plus 10% foetal calf serum (FCS), 1% L-glutamine (Gibco BRL, 25030) to a confluence not greater than 80%. To undertake the assay, NIH 3T3's were seeded at $1\times10^4$ cells/well in DMEM plus 10% foetal calf serum, 1% L-glutamine in 96 well plates (Costar, 3904) and incubated at 37° C. (+5% $CO_2$) in a humidified incubator. Once the cells had fully adhered (typically following 4-5 hours incubation) the media was removed from each well and the cells gently washed with 100 μl warm serum free media. 90 μl of serum free DMEM plus 1% L-glutamine was then added to each well and the plates were returned to a humidified 37° C. (+5% $CO_2$) incubator. The following day, the plates were dosed with 10 nl compound (diluted from 10 mM stock in DMSO using serum free DMEM) and the plates were returned to a humidified 37° C. (+5% $CO_2$) incubator for one hour. NIH 3T3 cells were then stimulated with a final concentration of 3 ng/ml bFGF (Sigma, F0291) for 20 minutes at 37° C. Following stimulation the cells were fixed by adding formaldehyde (4% v/v final concentration) and incubating at room temperature for 20 minutes. The fixative solution was then removed and the wells were washed twice with 100 μl phosphate buffered saline (PBS/A) before permeabilising the cells by the addition of 50 μl/well 0.1% triton/PBS/A for 10 minutes at room temperature. The permeabilisation solution was then removed and the cells washed twice more with 100 μl/well PBS/A before the addition of 50 μl/well anti-phospho p44/42 antibody (Cell Signalling Technology, 9106), diluted 1/500 with PBS/A plus 10% FCS. The anti-phospho p44/42 antibody recognises Erk phosphorylated at threonine 202 and tyrosine 204. Following incubation at room temperature for 2 hours, the antibody solution was removed and the wells were washed twice with 100 μl/well PBS/A. 50 μl/well 1/250 goat anti-mouse alexa fluor 488 secondary antibody (Molecular Probes, A11001) and 1/10000 Hoescht (Molecular Probes, H-3570) diluted with PBS/A plus 10% FCS was added and the plate incubated in the dark at room temperature for one hour. Finally, the plates were washed three times with 100 μl/well PBS/A, leaving the final wash in the wells before sealing the is plates. The plates were read at 350 nm and 488 nm using an Arrayscan (Cellomics). The mean average intensity fluorescence values for each test compound concentration, untreated control wells and 100% inhibition control wells were used to determine the test compounds $IC_{50}$ value. $IC_{50}$ value is the concentration of test compound that inhibits 50% of Erk phosphorylation.

Results of FGFR Inhibition Tests for Examples

| Example | Activity class |
| --- | --- |
| 1 | B |
| 2 | A |
| 7 | C |
| 8 | A |
| 9 | B |
| 10 | A |
| 11 | A |
| 18 | B |

Activity:
A less than 0.3 μM
B greater than 0.3 μM and less than 1 μM
C greater than 1 μM and less than 30 μM
Eg Example 18 is 877 nM.

Cell FGFR1—Cell Based Inhibition of Transiently Expressed FGFR1 IIIc Phosphorylation (Measured Using Phospho-Specific Primary and Fluorescent Secondary Antibodies).

This assay is designed to detect inhibitors of transiently expressed FGFR1 phosphorylation by antibody staining of fixed cells detected using ArrayScan technology. (For a description of ArrayScan technology see http://www.cellomics.com/content/menu/Arrayscan/)

Cos-1 cells were routinely passaged in DMEM (Gibco BRL, 41966) plus 3% foetal calf serum (FCS), 1% L-glutamine (Gibco BRL, 25030) to a confluence of 80%. To undertake the assay, Cos-1 cells were harvested at 90-95% confluence for cell transfection. For each 96-well plate, 24 ul Lipofectamine 2000 (Invitrogen, Catalogue No. 11668-019) was added to 809 ul OptiMEM (Invitrogen, Catalogue No. 11058-021) and incubated at room temperature for 5 minutes. For each 96 well plate, 20 ug 3' FLAG tagged FGFR1/pcDNA3.1 (In-house clone 15, MSD 4793) was diluted with OptiMEM to a total volume of 833 ul. Equal volumes of DNA and Lipofectamine 2000 were combined (DNA:Lipid=1:1.2 ratio) and incubated at room temperature for 20 minutes. The "FLAG-tag" was a purification/detection tag which comprises the amino sequence: N-DYKDDDDK-C. The "FLAG-tag" was cloned at the N-terminus of FGFR1. The clone was full-length, wild-type FGFR1 Inc isoform.

The harvested Cos-1 cells are counted using a coulter counter and diluted further with 1% FCS/DMEM to $2.5 \times 10^5$ cells/ml. For each 96-well, 8.33 ml cells were required. The complexed transfection solution was added to the cell solution and the cells were seeded at $2.5 \times 10^5$ cells/well in DMEM plus 1% foetal calf serum, 1% L-glutamine in 96 well plates (Costar, 3904) and incubated at 37° C. (+5% $CO_2$) in a humidified incubator overnight (24 hrs). The following day, the plates were dosed with 25 µl compound (diluted from 10 mM stock in DMSO using serum free DMEM) and the plates were returned to a humidified 37° C. (+5% $CO_2$) incubator for one hour. Media was removed from the wells using vacuum aspiration; cells were fixed by adding 50 µl of 100% methanol to each well and incubated at room temperature for 20 minutes. The fixative solution was then removed and the wells were washed once with 200 µl phosphate buffered saline (PBS/A) before permeabilising the cells by the addition of 50 ul/well 0.1% triton/PBS/A for 20 minutes at room temperature. The permeabilisation solution was then removed and the cells washed once more with 200 u/well PBS/A before the addition of 40 µl 1/1000 primary antibody solution (Cell Signalling Technologies #CS3476; mouse anti-phospho FGFR1 diluted in PBS/A with 10% FCS+0.1% Tween20) to each well.

Following incubation at room temperature for 1 hour, the antibody solution was removed and the wells were washed once with 200 ul/well PBS/A. Then 40 µl 1/500 secondary antibody (A11005; goat anti-mouse 594) solution and 1/10000 Hoechst (diluted together in PBS/A with 10% FCS+0.1% Tween 20) were added and the plate incubated in the dark at room temperature for one hour. Finally, the plates were washed once with 200 µl/well PBS/A, leaving the final wash in the wells before sealing the plates. The plates were read on an Arrayscan (Cellomics). The Channel 2 (594 nm) values obtained from undosed (max) and reference compound (min) wells within a plate are used to set boundaries for 0% and 100% compound inhibition. Compound data was normalized against these values to determine the dilution range of a test compound that gives 50% inhibition of phosphorylated FGFR1.

Cell FGFR1 (ECHO)—Cell Based Inhibition of Transiently Expressed FGFR1 IIIc Phosphorylation Via Use of ECHO Technology (Measured Using Phospho-Specific Primary and Fluorescent Secondary Antibodies).

This assay is designed to detect inhibitors of transiently expressed FGFR1 phosphorylation by antibody staining of fixed cells detected using ArrayScan technology.

Cos-1 cells were routinely passaged in DMEM (Gibco BRL, 41966) plus 3% foetal calf serum (FCS), 1% L-glutamine (Gibco BRL, 25030) to a confluence of 80%. To undertake the assay, Cos-1 cells were harvested at 90-95% confluence for cell transfection. For each 96-well plate, 24 µl Lipofectamine 2000 was added to 809 ul OptiMEM and incubated at room temperature for 5 minutes. For each 96 well plate, 20 ug 3' FLAG tagged FGFR1/pcDNA3.1 (In-house clone15, MSD 4793) was diluted with OptiMEM to a total volume of 833 µl. Equal volumes of DNA and Lipofectamine 2000 were combined (DNA:Lipid=1:1.2 ratio) and incubated at room temperature for 20 minutes.

The harvested Cos-1 cells are counted using a coulter counter and diluted further with 1% FCS/DMEM to $2.5 \times 10^5$ cells/ml. For each 96-well, 8.33 ml cells were required. The complexed transfection solution was added to the cell solution and the cells were seeded at $2.5 \times 10^5$ cells/well in DMEM plus 1% foetal calf serum, 1% L-glutamine in 96 well plates (Costar, 3904) and incubated at 37° C. (+5% $CO_2$) in a humidified incubator overnight (24 hrs).

The following day, compounds from dry weight samples were dissolved in 100% DMSO to give 10 mM concentration. 40 µl of the compound was dispensed into the wells of each quadrant across the 384 Labcyte plate (Labcyte Catalogue No. P-05525) (inclusive of a positive control (100% DMSO), a negative control (10 µM) and a reference compound (250 nM)). The 384 Labcyte plate was then transferred to the Hydra to dilute the compounds 1:100 into the remaining wells of the quadrant. 70 µl of media was aspirated from the assay plate using the Quadra before the plate was transferred onto the ECHO 550. The 384 Labcyte compound plate was also transferred onto the ECHO 550. Compound transfer to the assay plate on the ECHO 550 was at concentration ranges 1) 10 µM, 2) 3 µM, 3) 1 µM, 4) 0.3 µM, 5) 0.1 µM, 6) 0.01.

The plates were gently tapped to mix compound in with the cell media and left to incubate at 37° C. with 5% $CO_2$ for 1 hour.

Media was removed from the wells using vacuum aspiration; cells were fixed by adding 50 µl of 100% methanol to each well and incubated at room temperature for 20 minutes. The fixative solution was then removed and the wells were washed once with 200 µl phosphate buffered saline (PBS/A) before permeabilising the cells by the addition of 50 ul/well 0.1% triton/PBS/A for 20 minutes at room temperature. The permeabilisation solution was then removed and the cells washed once more with 200 µl/well PBS/A before the addition of 40 µl 1/1000 primary antibody solution (Cell Signalling Technologies #C53476; mouse anti-phospho FGFR1 diluted in PBS/A with 10% FCS+0.1% Tween20) to each well. Following incubation at room temperature for 1 hour, the antibody solution was removed and the wells were washed once with 200 ul/well PBS/A. Then 40 µl 1/500 secondary antibody (A11005; goat anti-mouse 594) solution and 1/10000 Hoechst (diluted together in PBS/A with 10% FCS+0.1% Tween 20) were added and the plate incubated in the dark at room temperature for one hour. Finally, the plates were washed once with 200 µl/well PBS/A, leaving the final wash in the wells before sealing the plates. The plates were read on an Arrayscan (Cellomics). The Channel 2 (594 nm) values obtained from undosed (max) and reference compound (min) wells within a plate are used to set boundaries for 0% and 100% compound inhibition. Compound data was normalized against these values to determine the dilution range of a test compound that gives 50% inhibition of phosphorylated FGFR1.

The invention claimed is:

1. A pharmaceutical composition comprising a compound of formula

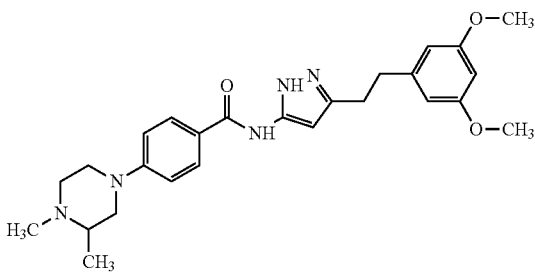

or a pharmaceutically acceptable salt thereof, in association with a pharmaceutically acceptable adjuvant, diluent or carrier.

2. A process for the preparation of a pharmaceutical composition of the invention which comprises mixing a compound of formula
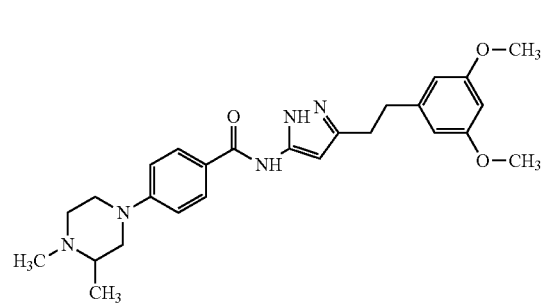
or a pharmaceutically acceptable salt thereof, with a pharmaceutically acceptable adjuvant, diluent or carrier.
3. The compound
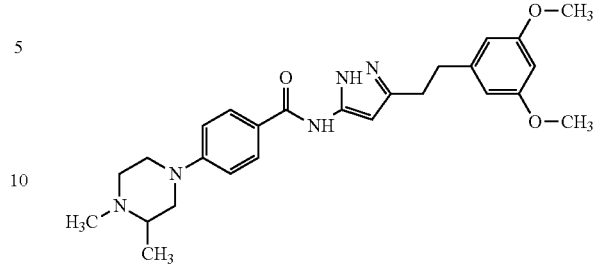
or a pharmaceutically acceptable salt thereof.
* * * * *